US007741040B2

(12) United States Patent
Markowitz

(10) Patent No.: US 7,741,040 B2
(45) Date of Patent: Jun. 22, 2010

(54) METHODS AND COMPOSITIONS FOR DETECTING CANCERS

(75) Inventor: Sanford D. Markowitz, Pepper Pike, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 11/484,025

(22) Filed: Jul. 7, 2006

(65) Prior Publication Data

US 2007/0021599 A1 Jan. 25, 2007

Related U.S. Application Data

(63) Continuation of application No. 10/456,930, filed on Jun. 5, 2003, now abandoned.

(60) Provisional application No. 60/386,653, filed on Jun. 5, 2002.

(51) Int. Cl.
*C12Q 1/68* (2006.01)
(52) U.S. Cl. .......................................................... 435/6
(58) Field of Classification Search ....................... None
See application file for complete search history.

(56) References Cited

U.S. PATENT DOCUMENTS

| 5,786,146 | A | 7/1998 | Herman et al. |
| 6,017,704 | A | 1/2000 | Herman et al. |
| 6,200,756 | B1 | 3/2001 | Herman et al. |
| 6,265,171 | B1 | 7/2001 | Herman et al. |
| 7,214,485 | B2 * | 5/2007 | Belinsky et al. ................. 435/6 |
| 2002/0127674 | A1 | 9/2002 | Yu et al. |
| 2002/0156002 | A1 | 10/2002 | Curtis et al. |

FOREIGN PATENT DOCUMENTS

| EP | 1 130 094 A2 | 9/2001 |
| WO | WO 01/73030 A2 | 10/2001 |
| WO | WO 02/18632 A2 | 3/2002 |
| WO | WO 02/46415 A2 | 6/2002 |
| WO | WO 02/50105 A1 | 6/2002 |
| WO | WO 02/063002 A2 | 8/2002 |
| WO | WO 02/079449 A2 | 10/2002 |
| WO | WO 03/091448 A2 | 11/2003 |
| WO | WO 03091448 A2 * | 11/2003 |

OTHER PUBLICATIONS

Filetti, S. et al. Sodium/iodide symporter: a key transport system in thyroid cancer cell metabolism. Eur. J. Endocrinol. 141, 443-457 (1999).
Reizer, J. et al. A functional superfamily of sodium/solute symporters. Bichem. Biophys. Acta. 1197, 133-166 (1994).
Swick, A.G. et al. Promoter-cDNA-directed heterologous protein expression in *Xenopus laevis* oocytes. PNAS 89, 1812-1816 (1992).
Romero, M.F. et al. Cloning and Characterization of a Na+ -driven. J. Biol. Chem. 275, 24552-24559 (2000).
Sciortino, C.M. et al. Cation and voltage dependence of rat kidney electrogenic Na+ -HCO3-cotransporter, rkNBC, expressed in oocytes. Am. J. Physiol. 277, F611-623 (1999).
Herman, J.G. et al. Methylation-specific PCR: A novel PCR assay for methylation status of CpG islands. PNAS 93, 9821-9826 (1996).
Kane, M.F. et al. Methylation of the hMLH1 Promoter Correlates with Lack of Expression of hMLH1 in Sporadic Colon Tumors and Mismatch Repair-defective Human Tumor Cell Lines. Cancer Res. 57, 808-11 (1997).
Gonzalgo, M.L. and Jones, P.A. Rapid quantitation of methylation differences at specific sites using methylation-sensitive single nucleotide primer extension (Ms-SNuPE). Nucleic Acids Res. 25, 2529-31 (1997).
Xiong, Z. and Laird, P.W. COBRA: a sensitive and quantitative DNA methylation assay. Nucleic Acids Res. 25, 2532-4 (1997).
Hibi, K. et al. Molecular Detection of Genetic Alterations in the Serum of Colorectal Cancer Patients. Cancer Res. 58, 1405-7 (1998).
Baylin, S.B. et al. Alterations in DNA Methylation: A Fundamental Aspect of Neoplasia. Adv. Cancer Res., 72, 141-96 (1998).
Jones, P.A. et al. The DNA methylation paradox. Trends Genet. 15, 34-7 (1999).
Baylin, S. et al. Altered methylation patterns in cancer cell genomes: Cause or consequence? Cancer Cell 1, 299-305 (2002).
Feinberg, A.P. and Vogelstein, B. Hypomethylation distinguishes genes of some human cancers from their normal counterparts. Nature 301, 89-92 (1983).
Veigl, M.L. et al. Biallelic inactivation of hMLH1 by epigenetic gene silencing, a novel mechanism causing human MSI cancers. PNAS 95, 8698-702 (1998).
Grady, W.M. et al. Detection of Aberrantly Methylated hMLH1 Promoter DNA in the Serum of Patients with Microsatellite Unstable Colon Cancer. Cancer Res. 61, 900-2 (2001).
Usadel, H. et al. Quantitative Adenomatous Polyposis Coli Promoter Methylation Analysis in Tumor Tissue, Serum, and Plasma DNA of Patients with Lung Cancer. Cancer Res. 62, 371-5 (2002).
Costello, J.F. et al. Aberrant CpG-island methylation has non-random and tumour-type-specific patterns. Nat. Genet. 24, 132-8 (2000).

(Continued)

*Primary Examiner*—Christopher H Yaen
*Assistant Examiner*—Hong Sang
(74) *Attorney, Agent, or Firm*—Ropes & Gray LLP

(57) ABSTRACT

In certain aspects, the invention provides isolated SLC5A8 (also referred to as Hui1) nucleic acid molecules, which encode novel sodium solute symporter members. The invention also provides antisense nucleic acid molecules, recombinant expression vectors containing SLC5A8 nucleic acid molecules, host cells into which the expression vectors have been introduced, and nonhuman transgenic animals in which a SLC5A8 gene has been introduced or disrupted. The invention still further provides isolated SLC5A8 proteins, fusion proteins, antigenic peptides, and anti-SLC5A8 antibodies. Diagnostic methods utilizing compositions of the invention are also provided. In other aspects, the invention provides methods and compositions for detecting and treating SLC5A8-associated cancer. Differential methylation of the SLC5A8 nucleotide sequences has been observed in SLC5A8-associated cancer, such as colon cancer, breast cancer, thyroid cancer, or stomach cancer.

18 Claims, 107 Drawing Sheets

OTHER PUBLICATIONS

Attwood, J.T. et al. DNA methylation and the regulation of gene transcription. Cell Mol. Life Sci. 59, 241-257 (2002).

Moinova, H.R. et al. HLTF gene silencing in human colon cancer. PNAS 99, 4562-7 (2002).

Siu, I.-M. et al. The Identification of Monoclonality in Human Aberrant Crypt Foci. Cancer Res. 59, 63-66 (1999).

Bird, R.P. Observation and Quantification of Aberrant Crypts in the Murine Colon Treated with a Colon Carcinogen: Preliminary Findings. Cancer Lett. 37, 147-51 (1987).

Pretlow, T.P. et al. Aberrant Crypts: Putative Preneoplastic Foci in Human Colonic Mucosa. Cancer Res. 51, 1564-7 (1991).

Herman, J.G. et al. Inactivation of the CDKN2/p16/MTS1 Gene is Frequently Associated with Aberrant DNA Methylation in all Common Human Cancers. Cancer Res. 55, 4525-4530 (1995).

Gonzalez-Zulueta, M. et al. Methylation of the 5' CpG Island of the p16/CDKN2 Tumor Suppressor Gene in Normal and Transformed Human Tissues Correlates with Gene Silencing. Res. 55, 4531-4535 (Oct. 15, 1995).

Jeronimo, C. et al. Quantitation of GSTP1 Methylation in Nonneoplastic Prostatic Tissue and Organ-Confined Prostate Adenocarcinoma. J. Natl. Cancer Inst. 93, 1747-1752 (2001).

Smanik, P.A. et al. Cloning of the Human Sodium Iodide Symporter. Biochem. Biophys. Res. Commun. 226, 339-345 (1996).

Prasad, P.D. et al. Cloning and Functional Expression of a cDNA Encoding a Mammalian Sodium-dependent Vitamin Transporter Mediating the Uptake of Pantothenate, Biotin, and Lipoate. J. Biol. Chem. 273, 7501-7506 (1998).

Wright, E.M. et al. 'Active' Sugar Transport in Eukaryotes. J. Exp. Biol. 196, 197-212 (1994).

Bird, R.P. A novel methodological approach to study the level of specific protein and gene expression in aberrant crypt foci putative preneoplastic colonic lesions by Western blotting and RT-PCR. Cancer Lett. 116, 15-19 (1997).

Markowitz, S. et al. Inactivation of the Type II Tgf-$\beta$ Receptor in Colon Cancer Cells with Microsatellite Instability. Science 268, 1336-1338 (1995).

Willson, J.K.V. et al. Cell Culture of Human Colon Adenomas and Carcinomas. Cancer Res. 47, 2704-2713 (1987).

Li, H. et al. SLC5A8, a sodium transporter, is a tumor suppressor gene silenced by methylation in human colon aberrant crypt foci and cancers. PNAS 100(14), 6412-7 (2003).

Rodriguez, A.-M. et al. Identification and Characterization of a Putative Human Iodide Transporter Located at the Apical Membrane of Thyrocytes. J. Clin. Endocrinol. Metab. 87, 3500-3 (2002).

Chung, "Sodium Iodide Symporter: Its Role in Nuclear Medicine," J. Nucl. Med., 43, 1188-200 (2002).

Jung, H. The sodium/substrate symporter family: structural and functional features. FEBS Letters 529, 73-77 (2002).

Rodriguez, et al., J. Clin. Endocrinol. Metab., 87, 3500-3 (2002).

Riedel, C. et al., "Journey of the iodide transporter NIS: from its molecular identification to its clinical role in cancer", TIBS Trends in Biochemical Sciences, 26(8), pp. 490-496 (1002).

Ishikawa, N. et al., "SGLT gene expression in primary lung cancers and their metastatic lesions", Japanese Journal of Cancer Research: Gann., 92(8), pp. 874-879 (2002).

Miyauchi, Seiji et al., "Functional identification of SLC5A8, a tumor suppressor down-regulated in colon cancer, as a Na+-coupled transporter for short-chain fatty acids", Journal of Biological Chemistry, 279(14), pp. 13293-13296 (2004).

Ueno, Masako et al., "Aberrant methylation and histone deacetylation associated with silencing of SLC5A8 in gastric cancer", Tumor Biology, 25(3), pp. 134-140 (2004).

Fleisher, A. S. et al., "Microsatellite instability in inflammatory bowel disease-associated neoplastic lesions is associated with hypermethylation and diminished expression of the DNA mismatch repair gene, hMLH1", Cancer Research, 60(17), pp. 4864-4868 (2000).

Jubb, A. M. et al, "Methylation and colorectal cancer", The Journal of Pathology, 195 (1) pp. 111-134 (2001).

Boehringer Mannheim Catalog pp. 557 (1991).

Bowie et al., "Deciphering the Message in Protein Sequences: Tolerance to Amino Acid Substitutions," Science 247:1306-1310 (1990).

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology 111:2129-2138 (1990).

Cameron, Mol. Biol. 7:253-268 (1997).

Hammer et al., "Spontaneous Inflammatory Disears in Transgenic Rats Expressing HLA-B27 and Human $\beta_2$m: An Animal Model of HLA-B27-Associated Human Disorders," Cell 63:1099-1112 (1990).

Houdebine, "Production of Pharmaceutical Proteins from Transgenic Animals," Journal of Biotechnology 34:269-287 (1994).

Kappell, Current Opinions in Biotechnology 3:548-553 (1992).

Lazar et al., "Transforming Growth Factor α: Mutation of Aspartic Acid 47 and leucine 48 Results in Different Biological Activities," Molecular and Cellular Biology 6(3):1247-1252 (1988).

Mullins et al., "Expression of the DBA/23 Ron-2 Gene in the Adrenal Gland of Transgenic Mice," The Embo Journal 8(13):4065-4072 (1989).

Mullins et al., "Perspective Series: Molecular Medicine in Genetically Engineered Animals," J. Clin. Invest. 98(11):S37-S40 (1996).

Mullins, Hypotension 22:630-633 (1993).

Mullins, Nature 344:541-544 (1990).

NCBI AC063951 Partial Report pp. 1-8.

Ngo et al., "Computational Complexity, Protein Structure Prediction, and the Levinthal Paradox." The Protein Folding Problem and Tertiary Structure Prediction Merz et al., Ed. Birkhauser, Boston, MA pp. 433 and 492-495 (1994).

Niemann, Transg. Res. 7:73-75 (1997).

Overbeek et al., "Factors Affecting Transgenic Animal Production," Transgenic Animal Technology—A Laboratory Handbook ed. Pinkert pp. 96-98 (1994).

Skolnick el al., "From Genes to Protein Structure and Function: Novel Applications of Computational Approaches in the Genomic Era," TIBTECH 18:34-39 (2000).

Taurog et al., "HLA-B27 in Inbred and Non-inbred Transgenic Mice—Cell Surface Expression and Recognition as an Alloantigen in the Absence of Human $\beta_2$-Microglobulin," The Journal of Immunology 141(11):4020-4023 (1988).

Wall, "Transgenlc Evaluation and Mapping Laboratory. Agricultural Research Service," Theriogenology 45:57-68 (1996.

* cited by examiner

NCBI GenBank Accession Number AC063951
Human Genomic Sequence that covers 15 exons of the Hui 1 Gene and the promoter region.
Base Pairs 82200-83267 are underlined on page 32.

```
GAATTCTTTCAGGGTCCTCCACTAATGCAGGATAAAACCCAACCTAACTTTTCAAAGCCA
AGCCAGAGCTTTGCTGATATCATGTCATATCATGTGTCCATGCGCTCAGACTGCAAACAT
TTATGAACACACGTCTTTTCTGTTCCCTCTCTTAGTATTTTTAACCCCGCTTCTGACTGG
CAGACTGCTTTTCAACCTTCAAGGACTATCCCAAATACAAGTCCTTTGAAAAGCTTTCTC
TGTTCCTCAACCCCAGGCAGAATTAATAGTTATAATTCAATATATCTCCAACAGACAAAT
TCGCTAGACTATAACTACTCGGTTCCAGGCTCCATTTCTCCAACAACTATCAAAACCTGC
AGGCATCACTGTTTACCCTGGAATAGCCAGCTCATACCCAGCACACAGTAAGCTCTACTG
CTTACTGCAATATGTGCTTACATATATTGCAGAATATGTATAGATTTAGCTTTTGCCACA
CTTTATTTTGCTTATTTGCTATATAAATTAAGCTTTTATCACACTTTATTTGTTTATTT
ACATTACTGCATGCAATTCCCATTTCCTTAACAAGATTATAAATTCCTTGAGGGCAGAGC
CTTTGTCACACTTCACTTGTATTCCTCAGAAGGTTACTCAATGCTAAACATATTATTAAC
TGCTCAATTAATATTTGTTGAAGTAAATTACTTTTTCTATGGTTTCTTTGATGAGGGTCT
CCGGCAAGGAAACATTTTCACCCAGGATCAAAGCAGAAATTACATCCAAGAGGGTCTCCC
AGCAAGATGTGGAGAGACTGGCTACTTGCAGTGTTTGAGATAACACCTGCAAAAAGAAAA
AACAATGCATACTCAGCAATCAGCTTTTAAAAACCAGACTCTCGAGCATATTAAGTTGGG
AACTCACCTTACAGACATCAGCAGGCGTGGGTATCTTTGTCCCACTTCCATGTTTTACAA
GTATAAGGTATGTTTCCAACAACCTTTTAATCTGTTCAGAACTTTCACAACAGTTAGTTT
TTGTTACTTTTGTGTGTAGATCCAAGAGCGATTCCTGCAAACAAAGAATTTAACAGAGAG
AATATAAAGTATCAAACTCAACTGTTAATCCAACAATAAAAACTGTGGGACAGTTCAACT
TTTCCCATTCTCTTGCTTTGGAAGAAAAGATACATTTACCAGGACTCACTAACGATAAC
AGCTAACATTGGCTGAGTGCATTGTTCTAAGTCTTTTTTTTTTTTTTTTTTTGAGAT
GGAGTTTCACTCTTATTGCCCAGGCTGGAGTGCAATGGCGCAATCTTTGCTCACCGCAAC
CTCTGCCTCCCAGGTTCAAGCGATTCTCCTGCCTCACCCTCCCAAGTAGCTGGGATTGCA
GGCATGCGCCATTTTGTATTTTTAGTAGAGACAGCGTTTCTCCATGTTGTTCAGGCTGGT
CTCGAACTCCCAACCTCAGGTGATCCACCCACCTCGGCCTCCCAAAGTGCTGGGATTACA
GGTGTGAGCCACTGTGCCCGGCCCATTCTAAGTTTTTTACAAGTATTCACTCATCATCCT
CACAGCAACCCTGAGGGAGAGAATATTACTACCCCATTTATTATCTGAAGAGACTGGGG
AATCGAGATTTCAAATAATTTTCCCAGGTTACACTAGCAGTAAGTGGAAGGGTCAAGATT
CAAACAGGCAGTCTGGCTCCAGAGCCTTCTACTGCATCTCAAGATAACATATCAAATAAA
AAATAGCACAGGGGGGCAGAGGGAAGGAAAATTTTAATATGTGTACAGAAGTATAAATAA
AACAATTATAAAATATAACTTCTAGGAGTGATTTGCAAAACTGAGAGCAGAAACAGTAAA
TTCTTAGACTCCTTATCAAAAACCCATCCTTAAAGATTAGAACTCACTTGCAAACATTCA
AAAAATGTACCAAAATGTTCCTTGGAGATGTAGGATACAGTGGATTTGACCATGTTTTTG
AGTGTTTCTCCAATTAACATCCATGGTAGTTGAGTTTCTGTTTCAGTGACTGGTCCTAGC
TTTCGCAAAATTAGCTTCACTGCCTGTGGGAATACAAGTCATTAACATTAATATATAAAC
TCTTATTTTCAAGTATTGCTCTGGGAGTCACCACTCTGATTACATTAGCTACCTTAAAAA
TCAGGTCTGGAATAGTCAAGGATATGGCAACTTTGATGGTTAATAACGTGTCCCAAAAGG
AACTTCTAAACTAGGATGGAATTTTATCATTACAACTGTTCCCTCCCACCTGCCCTTG
CCCATTAATCAATTTATCTTACCCCCTAGCATCCAAAATAAAGAAGACATCAATGGCTCT
GTAAGTAACATCTCACTGTCCAAGGCCTACATTGGGTAAGCATTGTTACTGAACACCCAA
CACTCCTCATCTAGTGCTATGTACTCTAGGCTGTCTTCCCTCCACATCATTTGCCTCATT
CTTTTCTACTTTCTGTTTCATCCATCCACATAGACTCTAAGCACCCCTCCCATTATGTA
CCTGGCCTGTACAGGAGTGAAACATATTTCTAACTCCTTTGCACATTTCAAAGAGCAACT
GTCCAACACCTTCAACTTTTTCTGGATGTTTATCAAGATCAAGAAACATTAAATTGAAAA
```

```
AAGGAACTTCTAAACTAGGATGGGAATTTTATCATTACAACTGTTCCCTCCCC
ACCTGCCCTTGCCCATTAATCAATTTATCTTACCCCCTAGCATCCAAAATAAA
GAAGACATCAATGGCTCTGTAAGTAACATCTCACTGTCCAAGGCCTACATTG
GGTAAGCATTGTTACTGAACACCCAACACTCCTCATCTAGTGCTATGTACTCT
AGGCTGTCTTCCCTCCACATCATTTGCCTCATTCTTTTCTACTTTCTGTTTCATC
CATCCACATAGACTCTAAGCACCCCTCCCCATTATGTACCTGGCCTGTACAGG
AGTGAAACATATTTCTAACTCCTTTGCACATTTCAAAGAGCAACTGTCCAACA
CCTTCAACTTTTTCTGGATGTTTATCAAGATCAAGAAACATTAAATTGAAAAG
TGCGTTTTTATCAGAGACCTAAAATATAAAGTAGAAATGGAAAATTATATTC
ACAAACATAAACATATCCAAATGAAGAACTCTCATTTGCTATTCTATATATTG
TTATTTAAATATACTTAGGAAAAAATTGTGAAAAGAACAGACATTTGTAATG
ATTTCAAACTACTCTAATAGTGTGTTCTCACTTGGAATGTCACACAAAAGAGT
GAATTCATTGGTATTACAGGAAGATATGTACTACAAAAAAAACTACAGAAGT
CAACATTCTATCTTTTAAAGTAAATACATTTGTATTTTGTATTGTATACAGTAA
AATATTTGTATTTTATGAAATAAAAAATTTAATATTAATGTTTTTGTTTTATTA
CAAAAACCCTCTAAAATTTACTATGAATATTTTATACAAACACAAATGACAC
CATGCTACCAGTTACTTCCAGGAAACTATTAGAAAAGTTCTTGTTAATGTCAC
AGTTCATGTATTTACTGACTTGAATTAGAGAGCATTTTTGATATATACACACT
GAAAGCTATCACAAACCTAAATAACAATACAATAGTGACCCAAATTAGATCA
CATCAATTTGTGAGCAACAAATAAGTCTTACTGTGAGATAAATTCAAAATAG
TAACAGATTTCTGTTAAGTATATATATAGATACATAGAAAAAATTAGCCCAT
AATAACCACATTTTTAAAAGATATCTACTTCTATTCATCAGATTATTATTATTA
TTATTATTACTAGTGTGTGTGTGTATGTGTGTGTGTGTGATATGGAGTCTTG
CTCTGTCGCCTAGGCTGGAGTGCAGTGGTGTGATCTCAGCTCACTGCAACTTC
CACCTCCTGGGCTCAAGCAATTCTCATGTCTCAGCCTCCCAAGTAGCTGAGGA
TACAGGTGCGCGCCACCACGCCCAGCTAATTTTTGCATTTTTAGTAGAGACGG
GGTTTTGCCATGTTGGTCAGGCTGGTCTCCAATTCCTGACCTCAGGTGATCCA
CCTGCCTCGGCCTCCCAAGGTGTTGGGATTACAGGCATGAGCCACCACGCCT
GGCCTATTCATCAGATTCTTGATGATTAGCAACAAACAGATAAAATACCAGA
CTAACCTTTCTCATCAAAAAGTAAAACTTTCAGCAGCAAAATTTCTTATATG
TAGTTTTTTATGAGCCAGGAGTGTGCTGTACATGCTATACATGAAAAAAATA
AGATACATTTCATTAATCATATAATTGTAATAAATACATACTACATGTCAACA
ATATGGGCAACAATGTGCTGGGTATGCAAGGAATACACAGCAGGTATCAAAC
AAATTTAAAATCTCATTCATTTATGGAGACACCCACATGTTGAAAGGAAGAC
TTGACCACAGACATGAAGAGTCCTAGGACTGGTGGTACTGGTTTTACAAACA
AGACTCCAGGAAAAGTTGAAATTTGTAATGAGCTCTGAATGAAAGAAGAATT
AGGTGGGGACTGCAGTCCATATTATTGGTATAAAAGCAAGAGCAAAGATGAG
GCAGGTGGAAATGATCATGGTCATGACAAGGAGGCTGGTCCATCTAAAAGAG
GAAAGATGATACAGTAGAGGAGAGCAGCTATGGATAAAGTTGGTCAGGTAG
ACAGGTCTAGCTTACATCTGTATAAGCACTTACTCTGTGTTACGCCATTTAAT
CAGCACAATAACTCTATGGGATGGGTACTATTATAATCCTCCCATTCTACAGA
TAATGAAAGTGAGGCAGAAAGCATAAGCAACTTGCTCAAGGTCAAGCAGCC
ATGCATCTATAACTAAATAATTACTTATATATAATCACATTGTTAAATTTGGT
CTCCCTAATGATAGAAGGGTATGGAATATATCTCTCCAATTTTCTCATAACCC
CAGTACCTAATAGTTCCTTGCTGACAGCAGGTACTAATAAATGTTGGCTGAAT
GAGAAATGACCATTTTCAGAAAGACTAATTTGGCAGCAATATACAGGATAAA
```

```
GTGTTGAGTTCAGTTTCAGTAATACAAGTGAAAATAGCCAGGCTACTGAAGTTGTCACAC
CGAAAGCAAATAAATTTAGAACTGAAGAGCCTGACTTAGGAGACATAAAAGTGGCAGCTT
TTATGACAGCTGAAGTCATAAAACTAAATCAATTATTCCCCAAAGACCTTGTTGGTTGTT
TAATGAAATAATATTGGTTTCTAACATATTTGACCAAAAGCTTCATAGGGAACTAGTAAA
GGCTGGAAAAGATTTCTTTCTCTTTCTTCATTCAAAGTTCCTAAAAGAGAACGGTGGGC
TGAGTGAAACGGGTGGCATAAAACAAAGTCTATTGTCCCATACCATGCATACACCATTTA
CTGTGGGGTAAGGGGCTGATGACTGATATTAAACACTCCTGTGGCAATTATAGAACATGA
AAACAACCGGAAGACCAAGTGGAAAATCCCACCAAACCCCAGACTTAAACAGATAATAAG
ACAATTTATGCTTACTTTAAACAAAAGGTTACTACAAAATTCATTCTCTTTCCTTGTCCA
CATTTACTCACAAATACTGAGTGTCTCTTTCACCTTAGTAAGTATTAGTGGCTGGGGAAA
TGTCAGTGTTTAAAACAGGGCTCTTAACCTGTCTTAAACCTCCCTTATACCAGGTGTAGA
GAGGACAGCAATACATTATAACCAAACAATTCTGGTAAAAGTTGTGTGACATAGGTGGTT
AAAAAATGCCAAGAGGATAGAGAGTACAAAATTTTATTAATACTTCTGGCAAAGGTGCCT
GTTTGTGGAGGCTGTAGGGACCGAGTCAGGCCTTCTTGGGTGGGTATACTTCCAGTAGCT
GGAGAGGAGAGATGGTCATGGCAACTCAGACTGGCAGACTAGATTGTGGACCACTTTGGC
TGGAGAATCAACTTTGTACATGGAAACAATTAGGCACTGAGCTGGCAAAGTGGTTTGGAG
TCATAAAGAAGCCAGGGAAAAGAAGCAGGCAATTAAAAAACATACTAGAGAGAGAAAGG
GGTTACCTGTATATACTGGACATGTCCTTCACCATCAGTCTCCACAGGTACTTATAAAGA
TATGATAACGAGGTGAAAGCCCATTCTAACAACTCTGTGTCCTGAGTCTCCAGGATCGAG
GTGATAGTCAAAAAAACTCTGGAAAGTGTGGGTAGAAATCCATCTGCAGATCTCGTGCC
AACTGTACAACCAAACTGGATTAAAAAAAGAAGCAACTGATCATGTGGATTTTTTAAAA
GGCTACAAATCTACTTAACGATAGTAGGTGGCCTATGATCATAGGATTAATTAAATAAAA
ATACTTCTAAATCAAGTCTGAAAAATTATAAAATTCTTTAAATCTTAAGATCTCAGCAAA
GAAATCAGGCAAGAAGTTACATTCCATCATAAGTTGTAGCCAACTGTTCCTATAGTGTCA
AAGAAAAATGAGATTATCTTAGTATATAACAAATGCGAAATTATACCCCAAGATTCCACT
TTATGGTAATGCACTTATTCCTAACAGAAAAGGAAAATCCTCCTTGTTTCTAAATTATGA
GCACCTGATCTGCGGTATATGTAGCTTTGAAACACAATCTTTCTTAAAATTCAGGCAAAT
ATAGTTGTGAGCTTTCTCTCAAGATGCTACTTACTCCAAAAGGGGTTGATAGGCAAAACT
GTTCTTAACTTGCAGGTGAGTCTTCAAACTCTGAACTATCTCGTTTTGGTGATACACCAA
CTGATTGAATGATTGGCATTTGTCAATAACTTCTTTGTAAAATTTTCCTGAGTGGGGGAA
AAAAAAATATGTTCTTTTCTATCACACCACTATTCAGCTGTATGGAACATATAAAGTGCA
AACTATGGGTGAATAAAATAGAAACGAAATAGAAAATACCGAAGTGTTCTGTGAGGTTTA
ATTCTCTCCATTTCAGCAGACCCTCAAAAAGTAGGTTTCAACCTCCTGTCAAGATTAAA
GCAGTCCATTAATCAAATAACTCTAAGAAAGCAATGATCAAGGTAAATAGAATAATGATA
TATTAATATCTTAAGACAATGATACTGAAGAGTTTAAGAACTCCTTTTAGTTTTTTAAAA
CAGGCCATTAAGTAACACACTAAAAAGCAATCAGAAGTTATCAATAGGCCACTTATAAAA
TGCTGTTTTGTTGATTTGGTTTCAGCAAATAATTTTCTGGGCCTATATATATTGTCCAC
TAAGGGAAAATTATTTTCTGTGTTTTTTTATAATTTTAGGCAAAGAATAAGGTGTTGGTT
CTTTACAGTTCCTTCATTCTGCTTTTAGAAATATGAATTACTACAACCTTATAAAGAAGT
AATATGGCATTCCTGTTAAAATTCAAAATAGTTACGCTCTTTGACCCAGGTAGTTCTTAT
AAAGTTTGCAAGCCTTTAAGTAAAGATGTTTATTCAGCTTAACTACAGTGTGGGGAAAC
ATTAAACAGGCTAAAATATCCGACAATAGGAAATGGTTGGAATAGCCCATGGTCTATAT
ATACTAAGGTATATTATGTGGCTACTAAAAGAGCTATATCTCTATTGAACTAGAACTAC
ACTGAAGATATGCCCCCAAAATGATAAAAGTTATGCAGTGAGAGGGTATGGCAGGATTCA
```

```
TTTCCTGAGTGGGGGAAAAAAAAATATGTTCTTTTCTATCACACCACTATTCA
GCTGTATGGAACATATAAAGTGCAAACTATGGGTGAATAAAATAGAAACGA
AATAGAAAATACCGAAGTGTTCTGTGAGGTTTAATTCTCTCCATTTCAGCAGA
CCCTCAAAAAGTAGGTTTCAACCTCCTGTCAAGATTAAAGCAGTCCATTAAT
CAAATAACTCTAAGAAAGCAATGATCAAGGTAAATAGAATAATGATATATTA
ATATCTTAAGACAATGATACTGAAGAGTTTAAGAACTCCTTTTAGTTTTTTAA
AACAGGCCATTAAGTAACACACTAAAAAGCAATCAGAAGTTATCAATAGGCC
ACTTATAAAATGCTGTTTTGTTGATTTGGTTTCAGCAAATAATTTTCTGGGGC
CTATATATATTGTCCACTAAGGGAAAATTATTTTCTGTGTTTTTTATAATTTT
AGGCAAAGAATAAGGTGTTGGTTCTTTACAGTTCCTTCATTCTGCTTTTAGAA
ATATGAATTACTACAACCTTATAAAGAAGTAATATGGCATTCCTGTTAAAATT
CAAAATAGTTACGCTCTTTGACCCAGGTAGTTCTTATAAAGTTTGCAAGCCTT
TAAGTAAAAGATGTTTATTCAGCTTAACTACAGTGTGGGGAAACATTAAACA
GGCTAAAATATCCGACAATAGGAAAATGGTTGGAATAGCCCATGGTCTATAT
ATACTAAGGTATATTATGTGGCTACTAAAAAGAGCTATATCTCTATTGAACTA
GAACTACACTGAAGATATGCCCCCAAAATGATAAAAGTTATGCAGTGAGAGG
GTATGGCAGGATTCAATTTTCCTTAAAAAACAAAAATAAAAAACCCTCTATA
AATGTTTGTACATACGAACATGAGAGGACAGTATGGAAGAATACAACTATAC
TGAACTGTCAGTGTTGGCTTCCTTGGGAATTAGGGGTGGGAGGAGTGAGATA
ATGGGCTTTTCGTAAGTTTACCACTATGTTACTTAACTTGTTAACATGGTATC
AATTACTTTGTACTTTGAAAGGTAAAGCCAATAAATTATCATACATGTATGAC
ATGTATGTATACATGTACGTATGTGTGTATATAGATGTATAAATAAATGCATA
CCCCCCCAAAACAATCATTCTACCAAAAGATACATGCCTTCGTATGTTTATC
TCTACACTATCCACAATAGCAAGACATTGAATTGTCCCAGGTGTCCATCAAC
AGTAGATTGGATAAAGAAAATATAGTACATATACACCATGGAATATTATATG
CCTTAAAAAAGAATGAAATCGTGTCCTTTGCAGCAACATGGATACAGCTGGA
GTCCATAATACTAAGCAAATTAACATAGGAACAGAAAACCAAAAACTGCATG
TTCTGACTTATAAGTGGGAGCTAAATATTGAGTACACATAGACATAAATATA
AGAACAATGAACACTGTGGATTACTAGAGGGTGGAGGAAGTGGGGATGGGT
TAAAAAAAACTACCTGTGGGGTACTATGCTCACTACCTGGGTGACAGGATCC
ATACTCCAAACCTCAGCATCACACAATATTCCCATGTAACAAACCTGCACAG
GTACCCCTGTATCTAAAATCAAAGTTGAAATAAAAATAAAAATAAATACAA
ATATGTGTTTATAGAGAGAGAAAAAAGAGAGAATAAACACATAAGCACA
CATGCAAACAGCATGCCAAATCTACAATATCAAAAAAAAAAAATCCTTAAACT
GTTCTTTGGAAATCTTTAAAATCAATAGTTAGGCAGAATAGATACTATGTAAC
CACAAATATTAAAAACTAAAAATTAAAAAAAAAGGCAGAAAAGAAAGAGAA
TCCCATTAAATTTTGTTTTAGGCTGGGGACAATGGCTCATGCCTGTAATCCCA
ACAGTGGGAGGCTGAGGCAGGAAGAGCATTTGAGCCCAGGAGTTTGAGACT
AGCCTAGGCAACAACACGAGATCCTATCTCTATTTTTCAAAAGTAAAAATATT
AAAATTTTTTGTTGTTGTTTTCATGTCCTTTAAGGCATTTTCATGTCCTTTAA
GGCAGAAAGAAAATATGCAACACAGTTTAAAACTTAAATGCAGAACGCATTT
CTAGCCTAGCACAGACCTGGCGTATGTCAGCTATGTGTGAGAGACCATGTCA
CGTCCTTTTGCAAGGTAACTCTGGAGCTCCTTTCACCAAGAGACGGAGTCTGT
TTCCTCACCCTTTGAATCTGGCCTGGCCTCCTGACTTGCTTTGACTAATAACAT
GCGATGAAAGTGACTCTCATGACCAAAGCAAAACTTTATGAGGTCTTGACAG
CTTCTGCCTTCACTCTATTGAAAAGATTCTGCCACCATGAAAAGAAGCCTAGT
```

```
AGGTTAGGTTCCCTTTACTATGAGTTCTCAAAGCACAATGTGCTCACCTAGACGACATCA
TTTAACACATTGAATTTACACAGTGGAGATAATGCATTCAAAGACCCAGCGAGTGGAGTC
TGATTATAGTAAAGAAGAATATTACGAACTGAGATTGGATCGCCAAGGTATAGGCATGTT
ACGTACGACCTTAAAATGCTAGGAGGAATAACGACATGATGCAGAAAAAGACTTCTGCAT
AAAAGGATGACAAGGCCGGGCGTGGTGGCTCACACCTGTAATCCCAGCACTTTCGGAGGC
CAAGGCGAGCAGATCACGAGGTCAGGAGATTGAGACCATCCTGGCCAACATGTCAAAACC
CCGTCTCTACTAAAAATGCAAAATTAGCTGGGTGTGGTGGCACGTACCTGTAATCCCAG
CTACTCGGGAGGCTGAGGCAGGAGAATCGCTTAAACCTGGGAGGTGGAGATTGCAGTGAG
CCAAGATCACGCCACTGCACTCCAACCTGGAGACGGAGCGAGACTCCATCTCAAAAAAAT
GAATAAATAAATAAAAGTAAAATAAAGGGATGACAGAGTCAGAGTATGGTTAAAACTGGA
AAATATTATGTAGTCTAGCCCCTTTATTTTTATAAAGGAGAAAATTAAGCCCCGGGAAAA
GGGCTTCCTCAAAATCACTTTAAAGTTATAGCTTCAGGAATATGGATCTGCAGCAGTGCT
TGGAATGCATAAGGGAAAGGGAGAGGCTAGAATCACAAAGACAGCTGAAAGTCAAGTCAA
TTGTCTAATAGAGCTTCACCCAACAGAACTTTCTGCAAAGATGAAAATGTTCCAATTCTA
TATTTATTCAATATGTTAGCAACTAGCCACATTTGGGCACCCAAATTTTAATTTACTTT
AAATCCAATTTGTCATATGTGGCTACTGTATGAAACAGCACAGGTCTAAAGCATTTCATG
TCCAAAAAGGAATACCTTGAAAAACAATTCACTTCTACTAACAGAAGAAACTAAAACACC
ATGAACACTTGAAGATTGACTAGTATCACATTCTCTTACCTCCTCATAGCTTGCAGTTCT
ATCAATCCGGTGAATAATATCAATATTAACATTCCCCAGTCGTTCAGCAAATGTAAGAAA
CTGGAAGGGAAAGTATATTTAAGATACATAATTAATTAAAATTTATCAGATCTTTAATAT
CTATTTGAATGCTGCATGTAGGCATCTCTAATCACAAAGGATAAGTGGAAAAATAAACTG
AAAAACATACGGCCGTAAACAAATTTACTGCATCACTGTTCAAAGATAATGAATACTTCT
ATGTTTGCATAATTTCTCTCAGCTATGTCATTTCAAATAAAATTTCCATTGCCAGACTGG
TGAGCCTAGGTGGATGCTGGCAATTAGTCTCGCTAGATCTATTAGGTTTCATACCCTCCC
ATAAGCATGGGGACCTAGCAAAGTCGCTGCAATAAAAGTGTTTTAAACATATACAGACC
TATGATTGTATCCTAAGGAAGACCTGGAAACAATCTATCAAGGGGCAAACAGAGAAAGCG
CTGTATATTTGCCCTTAGCTGGGAATCACTCACCGCCAGCCGACTCGCCCAATTCGGTCT
TTAAAGATAAAGAGCAGGGGAGAATTGGTCCTAAGCAATCTCCTGGAATAGTGAATTTA
ATTCTGGACTACAGGAAATTCCCAGGACTGGCCAGACCCCATAAAACATGGGTGAAACTT
GCTGTCCACACTTCTTTCCTCCTCCAACCCATGTTTACTACATCCAGTGTCTCCCTCTTT
CGCCGGAGCCTCCAGGAAAGTGACACACTCGGCCCAGAAGTCTGAGGCCCCTGGAGTCTC
GCTCAGAGCCTGTCTCACGACTGAGGCAGCGGAGACCCGCGGCTCCCTGCCTAAGCTCCC
GCGCTCACCCGGTAGGTGTTCTCGGTCTTGTGGGAAACGGGCTTTGTCTTCATGGCTGCA
GAGGGCCAGTGGCCCGCGACGGCCTCGGGAGTGTCGAAGGGATGCAACCGACAGTAAGGA
GGGGAAAGCGGCTCACAGGCTATACTCTCCGATTCCCAGATGCCCAGACTTTCTCACGTG
CGGCTTGAGCCCCTGGGCGCCGCCATGTTGGAGACAAGGAGGAGCCTGAGTGGGTCACGT
GGACGGAAAAAGAACGGCGCAGGCGCACCCTTTGGTGGGGTGGGGCCTACAGGAGGCGG
GGCTGCGCACATAAGGGCGGGCGTTTGGGTGAGGTGTTCTTTTCACTCCCTTCGGTAAAG
GTTTAGAAGACAAATGTATTTTCATTATAAAATAAACATACCTGTAATCGTTATCAACT
AACATTACTGTCCCTCACTACGTACCTGCATCGTGCAAAGATCCTTTCATCCATAATTTC
ACAGTAAAGCTTATTAGGGATGTTAATACAAAGGAGGTACTGCGTCTATCTATATATCTA
TATATAGATATATACTTTTTTTTTTTTTTTTGAGACGGAGTCTCACTCTGTCTCCCAG
GCTGGAGGGCAGTGGCGCGATCTCGGCTCACTACAATCTCCGCCTCCGGGTTCAAGCAG
TTCTCCTGCCTCAGCGTCCAAAGTAGCTGGGACTACAGGCACCCGCCGCCACGCCCGGCT
```

Fig. 1-5

```
AATTCTTTTGTATTTTAGTAGAGACGGGGTTTCACCTTGTTGCCCAGGCTGGTCGCGAAC
TCCTGAGCTCAGGCAATCCGCCCGCCTCGGTTTTCCAAAGTGCTGGGATTACAGGTGTGA
GCCACCGCGCCTGGCCGGTACTGTGTATATTTTAAGCCAATTTGACACAAGAGGAAACC
AAGGTTGTGCAGCTGGTAACTGGCAGTCTTCACTCAGACTCTAAATTTTGGTATTCTTAA
CCACTACGCTGTAAATAAAATTGAAAATAGAGAAGGAGTTTTAAGAAAAATCTTTTAAT
TTCATGCACAACCGCTGTTAATGTTTGGTGTTTTTCCCATCACTTTAATGTCTACACATA
GCATGTTGTTAAATTGTACAGTTATATATACATATGTACAATTTTAAAAAATAATTTA
AAAATATAATTATTTACCCCATTTTACATTCATTCATTCATTCAGCAACTATTTCTTGAG
AGTCCTCTGTGGACCAGGTACTGTTCTGGGAGCCAAACGAGAAAGGCAATAATAGTATTA
ATTAATTATTTGAAAATATTCACAGCCTTCAATTCCTGGGCTAAAGTGAGCCTCCCACCT
CAGCCTCCCAAGTAGCTAGGGCTACAGGCATGCACCACCACACCCAGCTCTTTTATTATT
ATTATTATTATTATTATTATTATTATTTGTAGAGATGGGATCTTGCTATATTGC
CCAGGCTGGTATCAAACTTCTGGACTCAAGCAGTCCTCTTGGCTTGGCCTCCCAAAGTGC
TGGGATTACAGGGGTGAGCCACCATGCCCAGACTGGAAATACTTGGTCTGAGATGCTTAC
ATTTTAGTCAAGGAGTGATGTTAAGTAGACAATTGGATATATTGTTGTACAGAGCTCACT
GTAGCAGTCTGGGCTGCAGACGTGACTTAAATACACCTAAATACCTCAAGTGTGAGGCAT
TTGCGACTGGGAAAGAGAGCCAGTAAGGTAGAAACAGACTAGTTATGGCATGGAAGCAGA
GCTGGTGGCCAACTATACTGCAAATTCGAGGATAGAGAAGTGGTTGCTGGATCTGACAAG
GTGAAGGTCACTGGTGACCTTGCTAAGTACAGTCTAGTTGGAAGAAAGGAAGTGAAATAT
GCATGGATTGAGGAGGTAATCAGAGTTGAGAAAGTGAACATAACACTTTCAAATTGTTAT
TGGCATTATCACATCAACATTTTCTGTGTCACCACAGGGTTGTTCTAAATATTTTAATGC
CTCCATAGCATTTATAGATTTTTTATAATAAAATATTGACGTGCCTAATGTTCCATTGG
CTTTCAGTAGGCTAATAATTGGTCTTTTTTTTTAAAAGCCTTTTATGGGTCACAGGGAA
ATCTAAGAAAGCTGTAGAACTTCTCCCAGAAAGATGCAAAGAAGCTCATCCACACTAAAA
TGTGCACGTTTCAGAGAGTTAGAAGCCTGCAGTTAACTGAGGGTAGAAGCCCCACTCAA
AGCAATATTTTCCCAACCTGTTGCCAAAATCACCCCCACATCATTGTGCCATTTCCTTC
TCTGCAATTTATTTTGGTAATGGAGTTAACTGGACAATAAGGAGTGAAGAGAAAAATCA
AAGAAACTGAAAGAACTGACACAAGTTATATTGACCATTTATTGTTTGCATTGTTCTTCA
TTACATGACCCTCACACACTGACTTGACTCTGACTGGCTTAACAATATGTCAATAGAACA
TGGTGGTTGAGAGCATAGATGCTGGAACCAGGTTGTCTGGAGGTAATCCTGGTTCTGCCA
TTTATTAGTAGGGTCAGTTACCCTTTCAGAATGACATTTCCGTATATGTAAATGAAGCTA
ACAAAGTAGCTACCTCACGGGTGGTGATTATGCAGAGTAAATAAGCTAATGGATAAAAG
ATGCTTAGAATGTGCCAGACACCATAATTGCGCAAGCTCAGAAATTACTTAACCTTTCTG
AGACCCAATTTCCTCATCTATAAAATAGAGATGACAATAATACCAGTCTTTCAAGATACT
GTGTTGGTGCATAGAGCATGAAATAAATGTTTGCTAAGTGGATAAATAAATGACCATTTA
TTCTCTACTACCTGGCTACCTGACAAGTTCCTTAAGGGCTGACACCTTATACTTTTTCAA
CTTTGTGTCATCAGTTCCCTTGAACATAAGAGTTGTTTAATGAATGTCTGTTGAATTAAC
AAAGCTTATAATACTTACATTGACCCGGACAAATTTAAGAGTAATATAGTTCCAGCATTG
GATGTGAATTGCACCACATGATTTTGGTATCTCTCAAAACTAAGTTTCTAAGCTTTAAT
GGAATACCGAAAGCATCCGTGAAGAGCACGAGTGTTTCTTATAAACATTTCCTTGCTTCC
AGCGTTTGTCCTCTGTCAAGGTATAGGATGAATATCCTATACCATCCTTTATATCCTTTT
TCCATTAGGGCTCTGCCTGTCCTAACTACTCCAGCCAGTAAATAACATACATTATTTTTT
CATTCTTTTATTCTTAAGCTTTATAGGGCGCTCCTGGAAGTTTTGCTTTTAATTTTTGT
TTCCTTATTGCTTAGCGTGCTGCAATTTCAAGCCAAGAAACTTTAAGAGCATGTAAGAGC
```

Fig. 1-6

```
TAGGCCCAGTGGCTCATGCCTGTAATCCCAGAGCTTTGGGAGGTCAAGGTGAGAGGATTG
CTTGAACCCAGAAATTTGAGACCAGTCTTGGGCAACAAGGCGAAATCCCATCTCTACAAA
AAATACAAAAATTAGCCAGACATGGGGATGTGCACCTGTAGTCCCAGCTACTCAGGAGGC
TGAGGTGGGAGGAACACTTGATCCAGGAGGTCAAGGCTCCAGTGCTGTGATCCTGCGACT
GCACTCCAGCTTGGGTAACAGAGTGAGACCCTGTCTTGAAAGAAAAAAAGGAAGGAAGG
AGAGGGAGAAAGAAGGGAAAGTAAAGGAAGGAAGGGAGGGGAGAGGAGGGAAAGGAAGG
GAAGAAAGCACATGAGGAGTTTACCCAGCCTAGACAAGAAAGTGGAATCCAGAGAAGGCT
TCTTGGGGAAGTGACATCTAAGCTGAGACCTGGAAAATGAATAGGAATTAGCCAGGCAA
GGAATGGACATGAATGGTGTTATCTAGGTAGAGGGAGGAGTATAGGCATTTGTCTCAAAA
TGGTTGAGACAAATTTGGTTACTTTTAGTTTCCAAGGCAAAGCCACACCCTGTCAAATTA
GCATTGGCCATGGGTATCATCTTTAGCATCCTTGGACTAATAATAGGAAGAATAGGGAC
AAGATGAAGCTCAGAGGTAAGAAGAGCCTTGGTTTTCTCATCTGTAAAGTGAGATAGACA
TATGAGAAAGTCAACAGTCATATGAGACAGTTGAAAGATTAACACATTGTATCACTTCTC
ACAGTCATATGAGACCGTTGAAAGATTAATTAATACATTGTATCGCTTCTCAGCCTTTTG
GCTAAGATCAAGTCTAGTAATTAACACATTGTATGTGGTGATCTGGAAGGGGGCAAGTCG
ACCTAGTGGCATGGTCTTGTTTAGAAAGCAGTTCAAGGAGTGCTGTGTATCAGGGCAGAG
AGGATTTGACTCAGAACAAGGGACCAAGGAAGTGAATGTAAAAAAAGAAAGAGAAGAGA
AAGTTTTAGTAATTCTTTGTTGGTTTTTCTTAAATAGAGACAGGGGTCTCACTACATTG
CCCAGGCTGGTCTTGAACTCCTGGGCTCAAGCGATCCTCCTGCCCAGCCGAGTAGTTCTT
GACTGTGGTAGTAAGGAAAGCTGATCCACGTATCTCTTCTTGAGAAACTGTGTATTGTT
GACAGTGTGTGTAAATCAGGAAGCAGTGAGAGCATGGAGTTTGGATTTGGGACAACTGGG
TCCCAGTTCTAGCATTTTTCATGTATTAGCCAGTAACTGGGCAACTGACTTAACCTTTCA
GCCTCAGTTTCCTCATCTTTAAAACAGGCATAATAACTAGTTCTGCCTTTTCCCTTAACG
GTTGCTAAGAAGACCATTCGATATAAAGCAGGCAAAGTCCCTGTAACCAATACAGAGGA
GTTACAGAAACACTAAGTATTGTTTCCTTTGCATTGTGTGATCATGTTCAGCCCTGATA
CCACAGAGCTTCTATTCTCCTTTCCTTATTTGAAGCTCAGGCATTAGAAACATTAGACC
AGAAATTGCGGATTTGTGGGGCCTATAAGCTCAGGTAGCCCACAGATAAGTTTTGTTTAC
CAAACATATTCTTCTTCTTCTTTTTTTTTAAGAGAGTGTCTCGCTCCGTTGTCCAGGC
TGGAGTACAGTGGCACGATCGTCACTTACTGCCAACCTCAAGCTCCTTGGCTCAAGCGAT
CCTCCCACCCCAGCCTCCCTGGTAGCTACAGATACTACAGGTGTGCATCACCATGTCCAG
CTAATTTTAAAAACATTTTAGAGGTGAGTCTTGCTGTGTTGCCCAGGCTGATCTCGAAC
TACTGGGCTCAAGTGATCTTCCTATTCCAGCTTCCCAAAGTGCTGGCATTACAGACATGA
GCTGCCATGCCCAGCATACCAGATGATATTCTTGAAATTTATTTTTATTTTTATAATCA
GATACTCTCTCAGCAGAATCACAAATGTTTAATTTGTTAAAAATCTGAAAATTTTAGGT
AAAACTCTAGATTTTCAACTTCTCTTGAAAAGTAAAAAAAAGAAAACTGCAATACTGGG
CCCATATTTTGAGAAGCAACAACCAGCTGGAGTTGAGTAGTAGTGGCTCTTTGATGCCAC
CACTTTGTCTCTGTGCACACCACTCCTTCCTTTTTGTCCTACCCCAGGCCCATGTCATGA
CTTAAGGTGGATACCTGGCCCTGTGGAAAGCTCAGTGTGTAGCCTCTGCCTCAGAATAT
TCCTCAGGCAGAAGGCTGTTCTCGTCTTTGGTTTTAAACATGCCTCATAGGCAGCAGATT
ATTTTTCTGTTGCTTCTGCAGCTGCTTTTATTGTTTAATGCAGTGAGTGACTCAACTTGT
TGTTGCTGTTGTTGTTTCTGTTGTTTGAGACAGACTCTCACTCTGTCTTCCAGGCTGGAG
TGCACTGGCGTGATCTCGGCTCACTGCAACCTCCACCTCTCAGGTTCAAGTGATTCTCCT
GCCTCAGCCTCCCACATAGCTGGGATTACAGGCACCCGCCACCATACCTGGCTAATTTTT
GTATTTTTAGTAGAGACGGAATTTCGCCATGTTGTCCAGGCTGGTCTCGAACTCCTGACC
```

```
GTGATCTGGAAGGGGGCAAGTCGACCTAGTGGCATGGTCTTGTTTAGAAAGC
AGTTCAAGGAGTGCTGTGTATCAGGGCAGAGAGGATTTGACTCAGAACAAGG
GACCAAGGAAGTGAATGTAAAAAAAAGAAAGAGAAGAGAAAGTTTTAGTAA
TTCTTTGTTGGTTTTTTCTTAAATAGAGACAGGGGTCTCACTACATTGCCCAG
GCTGGTCTTGAACTCCTGGGCTCAAGCGATCCTCCTGCCCAGCCGAGTAGTTC
TTGACTGTGGTAGTAAGGAAAGCTGATCCACGTATCTCTTCTTGAGAAAACTG
TGTATTGTTGACAGTGTGTGTAAATCAGGAAGCAGTGAGAGCATGGAGTTTG
GATTTGGGACAACTGGGTCCCAGTTCTAGCATTTTTCATGTATTAGCCAGTAA
CTGGGCAACTGACTTAACCTTTCAGCCTCAGTTTCCTCATCTTTAAAACAGGC
ATAATAACTAGTTCTGCCTTTTCCCTTAACGGTTGCTAAGAAGACCATTCGAT
ATAAAGCAGGCAAAGTCCCTGTAACCAATACAGAGGAGTTACAGAAACACT
AAGTATTGTTTCCCTTTGCATTGTGTGATCATGTTCAGCCCTGATACCACAGA
GCTTCTATTCTCCTTTCCTTATTTTGAAGCTCAGGCATTAGAAACATTAGACC
AGAAATTGCGGATTTGTGGGGCCTATAAGCTCAGGTAGCCCACAGATAAGTT
TTGTTTACCAAACATATTCTTCTTCTTCTTTTTTTTTTTAAGAGAGTGTCTCGCT
CCGTTGTCCAGGCTGGAGTACAGTGGCACGATCGTCACTTACTGCCAACCTCA
AGCTCCTTGGCTCAAGCGATCCTCCCACCCCAGCCTCCTGGTAGCTACAGAT
ACTACAGGTGTGCATCACCATGTCCAGCTAATTTTAAAAACATTTTTAGAGGT
GAGTCTTGCTGTGTTGCCCAGGCTGATCTCGAACTACTGGGCTCAAGTGATCT
TCCTATTCCAGCTTCCCAAAGTGCTGGCATTACAGACATGAGCTGCCATGCCC
AGCATACCAGATGATATTCTTGAAATTTATTTTTATTTTTATAATCAGATACT
CTCTCAGCAGAATCACAAATGTTTTAATTTGTTAAAAATCTGAAAATTTTAGG
TAAAACTCTAGATTTTCAACTTCTCTTGAAAAGTAAAAAAAAAGAAAACTGC
AATACTGGGCCCATATTTTGAGAAGCAACAACCAGCTGGAGTTGAGTAGTAG
TGGCTCTTTGATGCCACCACTTTGTCTCTGTGCACACCACTCCTTCCTTTTTGT
CCTACCCCAGGCCCATGTCATGACTTAAGGTGGATACCTGGCCCCTGTGGAA
AGCTCAGTGTGTAGCCTCTGCCTCAGAATATTCCTCAGGCAGAAGGCTGTTCT
CGTCTTTGGTTTTAAACATGCCTCATAGGCAGCAGATTATTTTTCTGTTGCTTC
TGCAGCTGCTTTTATTGTTAATGCAGTGAGTGACTCAACTTGTTGTTGCTGTT
GTTGTTTCTGTTGTTTGAGACAGACTCTCACTCTGTCTTCCAGGCTGGAGTGC
ACTGGCGTGATCTCGGCTCACTGCAACCTCCACCTCTCAGGTTCAAGTGATTC
TCCTGCCTCAGCCTCCCACATAGCTGGGATTACAGGCACCCGCCACCATACCT
GGCTAATTTTTGTATTTTTAGTAGAGACGGAATTTCGCCATGTTGTCCAGGCT
GGTCTCGAACTCCTGACCTCAAGTGATCCACCTGCCTCGGCCTCCCAAAGTGC
TGGGATTACAGGCATGAGCCACCCCGCCCAGTTGAGTGACTCAACTTTTTATA
AGGGAGTCAGTGCAGTTTTTCAGTTGGTATTCAAATATTTGTAACACCTTCCC
TATCCCTGAACACACACACACACACACACACACACACACACACACACCAC
TGTGGTCTGTATTCATCTTGTTTTCCTTCCTCACTTTCGCTCACCATTTGCATTT
CTGTCATGGACTTTAATTTCCTTATTCTTTAAAGTAAGCTATCTCAGAGGATA
ATCTAAATTAACCTGCTTTTAGAACAATTTAAACATCCACATACTTTTACCTA
CCCCTGTTTATGATTTTTATCCTTTCTTTTGATCATTAGCTAAACTGTTGGCAT
CATGTTTAGGAAGGATGAGTAGTCTCACCACTGGGTTGTATCTCCCCTTTATT
TTCTCACCTTTCTCTTGGTTTGGTTTTGGTTTCCATTGTTACAGTGTGATTGCTT
CTTTGAACACAAGGCGCTACATCACAGTACAAGGAGCTTGGACTCTGCACC
CAGCCCTCCCAGGCTCACACACTTGGGCTGCCACTGCTCTAGGAGCTTCCATT
TACTCATCAATACGGGGGATACTAGTGCCCCTCATGGGGTGGTTATGAGGAG
```

Figure 1 Cont.

```
GCAATGACCTCATACATTGCTTCTCAAGTGTGGTCCCTGACCAGCAGTATCAG
CACCTCATGAGAACTTGGTTAGCACTGTAAATTCTCAGACCCTGCTCCAACCC
TCCTGAATCAAGAACTCTGGGGATGGGGCCCAGCAAACTGCTTTCATAAGCC
TTCCAGGTGATTCTGAGGCAGGCTCTAGTATGGGAATCACTGACTTAACATAC
ACTACAGCACCTAGAACATTGTCCAACACATACCATGTGCTACAGAAAGTGT
TTATTCTTATTACTGTCTAGTCTTTACATAAATGTTTGCATCATCATTATTTAA
TTCTTCTATTCATCTCTCTGATATAGTAGTATGATACTGTTAGCCTTTTTATTTT
TTATTTTTATGGATACATAACAATTATATATTTATGGGCTACATGTGATATT
TTGATACAAGTATACAATGTGTAATGGTCAAATTAGGGTAATTGGGATATTC
ATCACCTCAAGCTTTTATTATTTTTTGTTAGAAACAATCCAGCTCCCGTCTTC
TAGTTATTTTGAGATGTGCAATAAATTATTGTTAACTACAGTTGCTCTATTAT
GCTACCAAACACTGGATCTTATTCCTTCAATCTCATTGTATTTTGTATCCAAT
AACCACCCCCTTTTTATGCTTCCTCCACTACCCTTCCCAGCTTCTGGTAGCCAT
CATTCTACATTCTATCTCCATGAGATCAATTTTTTTAGCTCCCACATATGAGTG
AGAACACTCATATTATTTGTTTTTCTGTGCCTGGCTTACTTCATTTTACATAAC
ATCCTCCAGTTCCATCCATGCTGTTGCAAATGATAGGATTTCATATTTTTTATG
GCTGAATAATATTCCATTGTGTATATTACTACATTTTCTTTACCCATGCATCC
ATTAATGAACACTTAGATTGAGTCTATGTTGATTATTATGAATAGTACTGCAA
TAAATATTGGAATGCAGATATCTCTTTGATATGCTGATTTCCTTTTCTTTTGAT
ATATACCCAGCAGTGAGATTGCTGGATCATATCATAGGTCTAATTTTAGTTTT
TTGAGGACCCTCTATACTGTTCTCCATAGCCATTGTACTAATTTACATTTCCAC
CAACAACATATGAGAGTTCCCTTTCTCCACATTATCACCAGCACCCATTATTG
CCTGTCTTTTTATAAAAGTCATTTTAACTGGAGTGAGATGATACCTCATTGT
AGTTGTTTGTGGGGCTTTTTAAAATTTTGTTTTGTTTGTCAGACTTGAGCATTT
CCCAGGCTGGAGTGCAGTGGCATGATCATAACTCACTGCAGCCTTGAACTCC
TAGGCTCAGGCATCCTCCTGCCTCAGCATCCAAAGTAGCTGGGACTACTTGTA
GTTTTGATTTGCATTTCTCTGATGATAAGTGATGTTGAGCACCTTTTTACATGC
CTATTTGCCATTTGTATGTCTTCTTTTCAGAAATGTCTATCCAAATATTTTGCC
CATTTTTTAAATCACATTTATTTTTACTATTGAGCTTCTTCTATATTCTGGTTAT
TAATCCCTTGCCAGATGGGCTTTGAAAATATTTTCTCCCCATGGATTGTTTCTT
CACTTTGTTGGTTGTTTCCTTTGCTGTGCAGAAGCTTTTTAGTTTGATGTAAT
CTCATTTGTCCATTTTTGCCCTTGGCTGCCTATGCTTTTGAGGTCTTACTCAGG
AAATCTTTGTCCAGACTAATGTCCTTGAGCATTTCCTCAATGTTTCTTCTAGT
ATTTCATAGTTTGGGGTCTCAGATTTAAGTATTTAAGTCATTTTGATTTGATTT
GATTTTTGTATATGATGAGAGAAAGGAGTCTAGTTTCATTCTTCTGCATGTGG
ATATCCAGTTTTCCCAGCATCATTTATTGAAGACACTGTCCTTTCCCCAATGT
ATGTTTTGATGCTTTTGTTAAAAAGAATTGACTGGCTGGGCACAGTGGCTC
TTGCCTGTAACCCAGCACTTTGGGAGGCCGAGGTGGGAGGATCATTTGAGGT
CAGGAGTTTGAGACCAGCCTGGCCAACATAGTGAAACCCCATCTCTACTAAA
AATACAAAAAATTAGCCAGATGTGGTGGCACACGCTTGTAATCCCAGCTATT
CCAGAGGCCGAGGTGAGAGAATCACTGGAATCCAGGAGGCGGAGGTTGCAG
TGAGCCAAAATCATGCCACTGCACTCCAGCTTGGGCAACAAAGTGAGACTCA
TCTCAAAAAAAAAAAAAAAAAGGAGGGGGAGTTGACTGTAAACATGTGGA
TTTATTTCTAGGTTCTCCATCTTGTTCCATTGTTTTATGTGTCTATTTTATGCC
AGTATATTATGTTTTGGTTACTATAGTTTTGCAATATAATTCGAAGTCAGGT
AATGTGATGCCTCTAGCTTTGTTCTTTATAAGTAGCCTCATTTTAAATGAGGG
```

Figure 1 Cont.

```
ATCTGAGGCTCAGAGAACTGCTAAATGGTAGAAAGAGTTGAAGCTGGGTCTT
CTAACTTCATGTTCAGTGCTCTGTTTCATGTCCCCACACTATCCCACATCTTAA
GAGTGTAAACTAATAGGGGCAAATTTAGATAAATTGGCCAGGCATGGTGGCT
CACGCCTGTAATCCCAGCACTTTGGGAGGCTGAGGTGGGTGGATCACTTGAG
GTCAGAGTTTGAGACCAGCCTGGCCAACATGATGAAACCCTGTCTCTACTAA
AAATACAAAATTAGCCAGGTGTGGTGGCTCATGCCTGTAGTCCCACTTACTCA
GGAGGCTGAGTCAGGAGAATTGCTAGAACCCAGGAAGCAGAGATTGCTGTG
AGCTGAGACCATGCCACTGCACTCCAGCCTGGGAGACAGAGCGAGACTCCGT
CTCAAAAAAGGAAAAAAGATAAATAAATGCTTGGCTGTTGTAGATATTTG
TAGATTTCCTTGTCCTCTCTTTTCAGCAGCAGTCCCCAACCTTGTTGGCACCAG
GGGCTGGTTTCGTGGAAGACAATTTTTCCACAGACTGGGGGCTGCGAGTGAG
GGGGTGGTTTCAGGATGAAACTGTTCTGCCTCAGATCATCAAGCATTAGTTAG
ATTCTCATAAGAAGCACTGCAAGCTGGATCCTGTATGCGCAGTTCACAATG
GGGTTCCACTCCTATGAGAATCTAATGCCGCCGCTGATCTGACAGGAGGCGA
AGCTCAGATTGTAATGCTCTTTTGCCTATCTCTCACCTCCTGTTGCGCAGCCCA
GTTCCTAACAGGCCATGAACCGGTACCGGTCCGCGGCTCAGGGGTTGGGGAC
CCCTTTTCAGGAAACAGCATCCTGATTTTCCTTTGAAGAATCAATCTGCCTTC
ACTCTTAGTGTCTGAGGTTCGAGCTAGGGTCCAGGGAAGGTCTGTGTCCTAG
GCTGCATTTCTTTGACAACATCATTGGCTTAGAGATGGGCAGGTACCCCAAGC
TGGGCCAAGCCCCTGAGCTGAACTTTTACTAGAGCTAAGCCATAGGTAAGAA
GGTGCTTCTTTTTCTTAGATTTGCCAGGATGCTAGGAGCCTGAAGTTTTTGGT
GGTCCTCGTTGTCACTTCATGGAGAGGTCGGCCTGAGAATGAAGCCTATGCA
AAGGAAAACAGAGGGGACAGGGAGAGAGAAATTGATAATAAGTATTGATTA
GCTTATTGGATCCATCCAGTCCTTGGACTTTCAGTAACCTTAGTTCACTAATTC
CCTCTTTTGTGTTTAAGCCAATTTGAGTTGGGTTCTGTCATTTGCAACCAAAA
CAATATAGAATTTATGCCGATAATTTAAGATTTGTATGTTGCTCATAAGATTG
GAAACCTAAGCCTTCCTCCGAACACAAATATGTGAGTAAGAATAAAAAAAGT
CAAATACAAAGTCTTGATGATAACAGTCAATGGGATGGATTTGGAAAGTGTC
TCAGACTAGGAGTCAGAAAACCTGGGTGCTGATCCTAGGAGGTTCACTTAGC
CATGTGACTTTGTAAAATGTGTGAAACTAACGCTGTAAAATATGAAAAATTA
ACCCTGCAACAAAAAGTAATGTACACATACATATTTTGAATGTTGCATGAT
ATAAAGTCAAGTAAGTAATTTATTAGAGTTGCTCCCAGAACTTTTTCTGTATA
TCCAATAATTAGTTTTCAATAATAGTGAAGGAAAGACCTAGGAGTGGACATT
TCTCAGTCTCTCATACACCATATGCACTGATCTGGGTGACAGAATACCTTTAA
AGATACACTTAAAAATGCATCTTAAGAGAATAAGACAAGCCACAGACTGGG
AAAAATATCTGCAAAACACTTATCTAATAAAGTTTTGTATTCAAAATATGCAA
ACACCCTTAAAACTCCACAATAAAAAACAAATAGCCCAATTAAAAAATGAAT
GAGAGATCTGAACAGACACCTCACTGCAGAATATATACAGTATGAAAGATG
CTCAACATCATATGTCATTAGAGAATTGAAATTTAAAATAACAAGATACCAC
TACACACCTATTACAGTGGCTCCACTCCAAAATACTGACAACACTAAATGCT
GGAAAGGACGTGGAGCAGCAGAAATTCTCATTCATTGCTGGTGAGAATACAA
AATGGCACAGCCACTTTAGGAGACACCTATTTCTTAGAAAGTGAAACATAGG
CTTACCATATGGTCCAGCGATTGTGCTCTTAAGTACTCATCCAAATGAACTGA
AAACTTATAGCCACACAAAACCAGCACACAAATATTTATAGCAGCTTTATT
CATAATTGCCAAAAATTGGAAGTGACCAAGATGTTCTTCAATGGATAAACAA
ACCATGGAACATTTAGACAATGGAATATTATTCCAGGATAAAAAGAAACCAA
```

Figure 1 Cont.

```
CTATCAGGCTATTGCAAAGTGAAAGAAACCAATCTGAAAAGGCTACATAGGC
TTCATCTTTAAGACTCCAAATATGACATTCTAGAAAAGTTAAAACTGTAGAG
ACAATAAAAATATCAGTGGTACTAGAGTGAGTGGGGGAAAGAAGGGAGGGA
TCATTAGGTGGAACACAGGGCATTCTTAGGTCAGTGACACTACTTTTATGACA
CTGTAATTATAGATACATGACTAATGCAACATATTACTAATGAAGAAAATTG
TGCGGGGAGGGAAAGTAGGCATATGGAAACTCTCTGTACTTTCTGTTCAATTT
TTCTATAAACCTAAAACCACTATAAAAATAAAGTCTATTAATTTTTTTTAAAA
AATGTGTCTCTGTAATTCCTTCTGCCTCTCATCCTGAAGTCCTCTATGAAAT
GGAATCAGGAAAGACAACACCTTACTCTTGAATCCTGGGAGCCCCAAGAAGA
AGTAGGACTGGAATCTCAGGAGTACTAGAAACCAGGAAAATTTGGATCCACT
GACATCCAAAGTGGATCAGAAAGAAAAGTGAGTGCCTCAGACACCAATTGG
AAAAGAAAAATTTATTTACTTTCTCAATGAATATTTATTGAGTGCCTCCTGTG
TAAGGCACTGGTCTAAGAGCTGAAGATACAACAGTAAACAAAGTTTCTCCCG
TCACGAGGCTCAGGTTCTAGTTTGGAGGGACAAAAAGAAAAAAACATGTGA
ATTTATAGACTGTCAGATGCAATAAGTGCCATGGAGATAATATAGCTGGTGA
GTAGTGTGTGGCAGAAGCTGTTAATTGTTCCGTAGAATTAATTGTTCCATTCA
TCTTTTAGAAAAAGAAGCCTCATCTCAAAGTTTACTTGGTTATGCATCTGTAC
ATTACAATCTTCATTTCCCCAGATCCATTCTACTCTCCTGCCCCCTTGCACCTA
GATACAGCCTTGTGACCAAGGTCAGCCCCATGGGAAGTGCTCTGCGTAACTT
CCAGGTCATTTGCTAAAAGATAAAGCTACTTGCCTTGGATTCTTTCTTTCTCTC
TCCTATTGACTGGGAAATAATGATTGAAGAATCCTTGGAAGCCAAAAGTGGA
AGACAGCAGAGCCCCCAGTTGTAGTCTGTTCGATTCTTAGCTGTTACATGAGA
GGAAATTTTTTTTTTGAGACTTCCCCAATGCCTGGACTTTTCAGTAACATAA
GGCAATATATCCCCTTGTGTGTATAGGCAAGGCTGAGTCAGCTTTCTGTCACT
TGTAACCTAGATTAATTTTTTCTGATTAATTAATTGTTCCAATTAGTACAAGA
ATAATTTATATACTAGACTTTCTGCCTCACCTTGAAACCTGGAAGCTCACTGT
ATCAGTTCTCTCTTGCCACAATGAAGTTGCTTGTAAAACAACCACAGTGGCAA
GCAACAAGTCTACAGTTGGCTGAGTGGCTCTGCTATTCTGTATTGGTCTTGGC
TGATCTTGGCTGGGCTCATTCATGTGTCTGTGGTCAGCTGGCAGACTGGCTGG
GGGCTGGCTAATCTAGCACAGTTTTGGCTTAAATGACCCAACTACCTGGCTCT
GCTTCACAGCATCTCTCATCATCCATTAGGCTATCCTGAGCTTTTTTCATGGTA
AAGCAGGGTTCTGAGACAGACAGGCAGAATGCAAGGTCTAAGCTCATAATG
GTCACAGTACCACTCCCACAGCATTTTGTTGGGTACAGTAAGTCACAAGGAA
GGTCCATATTTAAGGATGGAGGAAATAGTCTCTACTCCGAAGAGCTGCAAAT
TCCTATTGCAAAGGGCATGGCTACTACAGGGAGGGGTGGAGAATTGGAGACA
TTTTTGCAATCAGTCTACCACATTTATCATAATTATTCCCATAATTAAACAGT
GGTGGTAGAGAGAAAAGGAGCAACTGGATACTGGAGCTTAACCAGGTGCCT
ACTAAGCACAAATTCCTCAGTACATGCAGGGGATGAAGCTATCCTATTCTGA
TTCCACCCATTTAGCATATGTGATTTTTTTTTAAGTTGGAAATAGGCAGAGA
GACCCTGTTTTGAAAGAGAACTTAAGGGTCATCCGGCCCAATCTCCATATTGT
TTCAGAAAAAAGAACCAGGCACCAAAGTTAGGGACTTGCCCAGGGCCACA
CAGTGAGTGAGGGACACACGTGGGTCTAGATGTTTGCCTGCTGACTCCCCGC
ACAGCAGACCTTCCACGGTCCTGTGCTGTTCTCTTCTCACGCCAAGGCAGAAC
ACAGCAGTGGCCACGTGCTTGCACTTTGGAGGCAGTTAGCCTGGGTTGTCTTT
CTTCCTTCCTTTCTTTTTTTTGAGACGGAGTTTTGCTCTTGTTGCTCAGGCTG
GAGTGCAATGGTGTGATCTCCGCTCACTGCAACCTCCACCTCCCAGATTCAAG
```

Figure 1 Cont.

```
CTATTCTCCTGCCTCAGCCTCCCGAGTAGCTGGGATTACAGGCATGCACCACC
ACGCCCAGCTAATTTTGTATTTTTAGTAGAGACAGGGTTTCTCCATGTTGGTC
AGGCTGCTCTCGAACTCCTGACCTGAGATGATCCACCCACCTCGGCCTCCCAA
AGTGCTGGGATTACAGGCGTGAGCCACCATGCCCAGCCAGCCTGGGTTTTCA
ACCTGGCCTCTTGCTTATTACTTATGAGACTTTGGACAAATTATTTAACCCCTC
TATCAATGATTGTAATAGTACTGGGCCTCATAGGGTTGTTGGGCAGATTAAAT
GAAAGAAAGGAAATAAAGCACATAGCAAGTGCTCAATAAATTTTAGCTATTA
TATTTTCTCTAAAAATACAGCATTTTCCTATTTGGTTTGTTCTTGTGTGCATTT
AGTCTGGGTTTAGGCATTCAAGAGAGCTGAAAATATCATAATACTAAATATT
TAGATGGCAAAGAATGAATTCAACTTATAAAAGTACCTGGAGTATAAATTCA
CATTTTCTTGTAAGAAGAGATATTTATAATCTGGTTTATTTGTTTACTTACTAA
CAAACATTTACTGAGAGTCTACTGCGAGTCAGGCATTGTAGTAGTTTGCTCTT
GCTGCAACATATTACCACAAACTTAGTGCCTTAAAACAACATATGTTCTGGA
AGTCAGAAGTCTGAAATGGATCATCTGGGCTGTTCCTTATGGAAGCCCCAGG
GGACAATCTGTTTCTTTGGTTTTTCCAGCTTCTGGAGGCTGCCAGAATTCCTTG
GATCATGGCCTGTTTCACTCCAATCTCTGCTTCCACCATCACCTCTTCTCTCCC
TTGACTCCATTGTCTCATTGCCTTCTCTGACACTCTTGCCTGTCCATTATCAGC
CTCTCCATATGGATTGTGCTTTCTTACAGCATGGTGGCCTCAGGGTAGTCAGA
CATGGTGGCTCAAGGCTCCAAAAATGAGTATTTTCAGCAAGCAAAACAAAAG
CTCCATGCTCTTTCATGAATTCACATTAGAAGTCACATAGCTTTGTATTCCAT
GTGGGAGTTGAAGAATGAGAAGTCATGGACACAGGGAGGGGAACAACACAC
TCTGGGTCCTGTTGTGGGATGAGGGATGAGGGGAGGGACAAATACCTAATGC
ATGCAGGGCTTAAAACCTAGATGACGAGGCTAGGAAGAAACTGCATCAACTA
ACGAGCAAAATAACCAGCTAACATCATAATGACAGGACCAAATTCACATATA
ACAATATTAACTTTAAATGTAAATGGGCTAAATGCTCCAATTAAAAGACACA
GACTGGCAAATTGGATAAAGAGTCAAGACCCATCAGTGTGCTGTATTTAGGA
AACCCATCTCACGTGCAGAGACACACATAGGCTCAAAATAAAGGGATGGAG
GAAGATCTACCAAGCAAATGGAAAACAAAAAAAGGCAGGGGTTGCAATCCT
AGTCTCGGATAAAACAGACTTTAAATCAACAAAGATCAAAAGAGACAAAGA
AGGCCACTACATAATGGTAAAGGGATCAATTCAACAAGAAGAGCTAACTATC
CTAAATATATATGCACCCAATACAGGAGCACCCAGATTCATAAAGCAAGTCC
TTAGTGACCTACAAAGAGACTTAGACTCCCACACAATAATAATGGGAGACTT
TAACATCCCACTGTCAACATTAGACAGATCAATGATACAGAAAGTTAAAAAG
GATACCCAGGAATTGAACTCAGCTCTGCACCAAGTGGACCTAAAAGACATCT
ACAGAACTCTCCACCCCAAATCAACAGAATATACATTTTTTTTCAGCACCACA
CCACACCTATTCCAAAATTGACCACATAGTTGGAAGGAAAGCACTCCTCAGC
AAATGTGAAAGAACAGAAATGATAACAAACTGTCTCTCAGACCACAGTGCAA
TCAAACTAGAACTCAGGATTAAGAAACTCACTCAAAACTGCTCAACTACATG
GAAACTGAACAACCTGCTCCTGAATGACTACTGGGTACATAACGAAATGAAG
GCAGATATAAAGATGTTCTTTGAAACCAACGAGAACAAAGACACAACATACC
AGAATCTCTGGGACACATTCAAAGCAGTGTGTAGAGGGAAATTTATAGCACT
AAATGGCCACAAAAGAAAGCAGGAAAGATCCAAAATTGACACCCTAACATC
ACAATTAAAAGAACTAGAAAAGCAAGAGCAAACACATTCAAAAGCTAGCAG
AAGGCAAGAAATAACTAAAATCAGAGCAGAACTGAAGGAAATAGAGACACA
AAAAACCCTTCAAAAAATTAATGAATCCAGGAGCTGGTTTTTTGAAAGGATC
AACAAAATTGATAGAGCGCTAGCAAGACTAATAAAGAAGAAAAGAGAGAAG
```

Figure 1 Cont.

```
AATCAAATAGATGCAATAAAAAATGATAAAGGGGATATCACCACCGATCCCA
CAGAAATACAAACTACCATTGGAGAATACTACAAACATCTCTATGCAAATAA
ACTAGAAAATCTAGAAGAAATGGAAAAATTCCTTGACACATACACTCTCCCA
AGACTAAACCAGGAAGAAGTTGAATCTCTGAATAGACCAATAACAGGAGCT
GAAATTGTGGCAATAATCAATAGCTTACCAACCAAAAAAAGTCCAGGACCAG
ATGGATTCACAGCCGAATTCTACCAGAGGTACAAGGAGGAGATGGTACCATT
CTTCCTGAAACTATTCCAATTAATAGAAAAAGAGGGAATCCTCCCCAACTCA
TTTTATGAGGCCAGCATCATCCTGATACCAAAGCCTGGCAGAGACACAACCA
AAAAAGAGAATTTTAGACCAATATCCTTGATGAACATTGATGCAAAAATCCT
CAATAAAATACTGGCAAACCGAATCCAGCAGCACATCAAAAAGCTTATCCAC
CATGATCAAGTTGGCTTCATCCCTGGGATGCAAGGCTGGTTCAACATACACA
AATCAATAAACGCAATCCATCACATAAACAGAACCAATGACAAAAACCACAT
GATTATCTCAATAGATGCAGAAAAGGCCTTTGACAAAATTCAACAACCCTTC
ATGCTAAAAACTCTCAATAAATTAGGTATTGATGGGACATATCTCAAAATAA
TAAGAGCTGTCTATGACAAACCCACAGCCAATATCATACTGAATGGGCAAAA
ACTGGAAGCATTCCCTTGAAAACTGGCACAAGACAGGGATGCCCTCTCTCAC
CACTCCTATTCAACATAGTGTTGGAAGTTCTGGCCAGGGCAATTAGGCAGGA
GAAGGAAATAAAGGGTATTCAATTAGGAAAAGAGGAAGTCAAATTGTCCCT
GTTTGCAGATGACATGATTGTATATCTAGAAAACCCCATTGTCTCAGCTCAAA
ATCTCCTTAAGCTGATAAGCAACTTCAGCGAAGTCTCAGGATACAAAATCAA
TGTACCAAAATCACAAGCATTCTTATACACCAATAACAGACAAACAGAGAGC
CAAATCATGAGTGAACTCCCATTCACAATTGCTTCAAAGAGAATAAAATACC
TAGGAATCCAACTTACAAGGGACGTGAAGTACCTCTTCAAGGAGAACTACAA
ACCACTGCTCAGTGAAATAAAAGAGGATATAAACAAATGGAAGAACATTCC
ATGCTCATGGGTAGGAAGAATCAATATCGTGAAAATGGCCATACTGCCTAAA
GTAATTTATAGATTCAATGCCATCCCCATCAAGCTACCAATGACTTTCTTCAC
AGAATTGGAAAAAACTACTTTAAAGTTCATATGGAACCAAAAAAGAGCCCGC
ATCGCCAAGGCAATCCTAAGCCAAAAGAACAAAGCTGGAGGCATCACGCTA
CCTGACTTCAAACTATACTACAAGGCTACAGTAACCAAAACAGCATGGTACT
GGTACCAAAACAGAGATATAGATCAATGGAACAGAACAGAGCCCTCAGAAA
TAACGCCTCATATCTACAACTATCTGATCTTTGACAAACCTGAGAAAAACAA
GCAATGGGGAAAGGATTCCCTATTTAATAAATGGTGCTGGGAAAACTGGCTA
GCCATTTGTAGAAAGCTGAAACCGGATCCCTTCCTTACACCTTATACAAAAAT
TAATTCAAGATGGATTAAAGACTTAACATGTTAGACCTAAAACCATAAAAAT
CCTAGAAGAAAACCTAGGCAATACTATCCAGGACATAGGCATGGGCAAGGA
CTTCATGTCTAAAACACCAAAAGCAATGGCAACAAAAGACAAAATTGACAA
ATGGGATCTAATTAAACTAAAGAGCTTCTGCACAGCAAAAGAAACTACCATC
AGAGTGAACAGGCAACCTGCAAAATGGGAGAAAATTTTCGCAACCTACTCAT
CTGACAAAGGGCTAATATCCAGAATCTACAATGAACTCAAACAATTCACAAG
AAAAAAACAAACAACCCCATCAAAAAGTGGGCAAAGGATATGAACAGACAC
TTCTCAAAAGAAGACATTTATGCAGCCAAAAAATACATGAAAAAATGCTCAT
CATCACTGGCCATCAGAGAAATACAAATCAAAACCACAATGAGATACCATCT
CACACCAGTTAGAATGGCCATCATTAAAAAGTCAGGAAACAACAGGTGCTGG
AGAGGATGTGGAGAAATAGGAACACTTTTACACTGTTGGTGGGACTGTAAAC
TAGTTTAACCATTGTGGAAGTCAGTGTGGCGATTCCTCAGGGATCTAGAACTA
GAAATACCATTTGACCCAGCCATCCCATTACTGGGTATATACCCAAAGGATT
```

Figure 1 Cont.

```
ATAAATCATGCTACTATAAAGACACATGCACACGTATGTTTATTGCAGCACTA
TTCACAATAGCAAAGACTATTGTCTTTTGCTATTTGGAACCAACCCAAATGTC
TAACAATGATAGACTGGATTAAGAAAATGTGGCACATATACACCATGGAATA
CTATGCAGCCATAAAAAATGATGAGTTCATGTCCTTTGTAGGGACATGGATG
AAGCTGGAAATCATCATTCTCAGTAAACTATCACAAGGACAAAAAACCAAAC
GCCGCATATTCTCACTCATAAGTGGGAATTGAACAATGAGAACACATGGACA
CAGGAAGGGGAACATCACACTCCGGGGACTCTTGTGGGGTGGGGGAAGGGG
GGAGAGAGAGCATTAGGAGATATACCTAATGCTAAATGACGAGTTAATGGGT
GCAGCACACCAACATGGACATGTATGCGTATGTAACAAACCTGCACATTGT
GCGCATGTACCCTAAAACTTAAAGTATAATAAAAAAAAAAAACCTAGATGAC
GGGTTGAGAGGTGCAGCAAACCACCATGGCACATGTATAGCTATGTAAGAAA
CCTGCATGTTCTTCACATGTATCCCAGATCTTAAAATAAATAAAAAATAAAA
ATAAATAAATAAAAATAAAAATTATATTAAAAAAGAAGTCACATAGCTTTAT
TTCCATACCCCATGGGTTGAAGCAGTCACAGCCCATTCAGATTCCAGGGAAA
GGGACACAGGCCACATCTCTTGATGAAAAGAACATGAAAGAATGTGCAGTTA
TGTTTTAAAAACATCCCAGTAGAGTTCACGAACATGAGTTTTTACAGCAGAC
ACTACATTTCCCTGCCAGTTTACCTGCCTTGGGATGGTGGAGGTCTCTGAAGT
TGGCAGTCGTTTCCTGCAGGATTCTAAGTTGGATGGCAGCAGCTCTCCAGCTC
TGAGGCAACGAAACTGAAAGCTAGTGGAGAGTTGCCTGAATTTTGCCTTCTC
AGGTCTTTCCATAAGTTCTGTGAACACTCAATTTCCTGTATCAAATTCCTTCTT
CTTGAAAATGCTTAGAGTGATACCTGTTTTTTCTACTGGAGTCTGACTGATTC
AAGCTCCAAAGTCTGCCCTCCTAACTGCCTCTCGCGTTGTTCTAAACCTTTCT
GGTGCTCCTGGCCTGCTCCTTTGCAACCCACACACACTCACACATCCAGCATA
CCCTAAGAAGATGACACTGCCTCTTAGTGCTCACAAAAGGAGTGCAAGTTAT
ATGAACCTCAACTATCCTTTCTATCCAACTGGAACTGTATCTGTCTGTTTTCC
CCCTTCTGCTCCGTCTTAGAAGAAAAGTTCATCAATACTTTTGGGAAAAAGGT
AAACTTTTAAACACGATGCATGGCACCCTTCATTTATCTTTTCAACCTGATTTT
CTGCCATCTTTTTATATGTGCCCATGTTAATTATGGTAGACTAACTGCTTTACC
AAATAGACTCATAAAATTGGTGGAATTATTGCTGCAACAGAAAGACCCAAAG
GTCTACAATGGCCTAAACCCTGTAAAAGTTTATTTCTTGCTCAAATAACAATT
ATAGGCAAGCAAATAATCAGTGGCATATGCCCTTCTCTATGTAGGGACTTAA
ACTAATAGAGAGACAACCATTTCCTTCCCTCCCTCCCTCCCTCTCTCTCTCT
TTCTTTCTTTCTTTTTTTTTTTTTTTTTTTTGATGGAGTCTTGCTCTGTCACC
CAGGCTGGAGTGCAGTGGCGCGATCTAGGCTCACTGCAACCTCCGCCTCCCG
GGTTCAAGCGATTCTCCTGCCTCAGCCTCCTGAGCACCTGGGATTATAGGCGC
CCACCACCACGCTCGACTAATTTTTGTATTTTTAGTAGAGACAGGGTTTCGCC
ACGTTGGCCAGGCTGGTCTCAAAGTCCTAACCTCAGGTGATCAGCCCGCCTTG
GCTTCCCAAAGTGCTGGGATTACAGGCGTGAGCCACTGCGCCTAGCCTGAGA
CAACCATTTTCAACATTTGCTTTCCAAGGTCACCCTTTCCAGACATCCAGAAG
AGAATGTAAACTAAAAATAAAATCCTAAGCCCCCCAACCAACTGAACAGACC
CCCTCTTGGCCAAGAAGACCTCAAGAAAAACTTAAAAACTGAATTCCTGGCC
ATCACAAGAAGGGAAGGTCCAATATGCTTTGTTATCCTCCCTCCCTTTTGGAG
TTAGGCACAACTGAACAGCATTAGTGTTAAAATAGAGATCGTAAAGCTAAC
AAAATGGACTTATTGTCACAATAAGATGCCAAATTACAAATAGGACCTAACA
CGACACAAGAAGGGTTGAGTCACACATTCTTATAATTCACTGTAACCCAGTG
TACTGGAAAACAATATCTTAATATGAAATATTCCTTTTTTGCTGCCTCCGAAT
```

```
GTCTGGAAGGTATGGCACTGTTCAAAGACAGTGTAATGAAATATTTATTATAAGGTTTAA
TTGCTTGAACAGCCAGATATAGAAAGGACTGCAGACAGATAGTCAGGAGACTTAACTTCT
GGTCCCACTTTTAGTATTTAAAATCCTATGTGACCTTTGACACGCTTCTCCTTGGGCCTC
AGTTTCTTCATCTCCAAATTCTTGGCTGCTACTCTGCTAAGATCAAGTGTACAAAATTAG
GAGGTTAGGCTAGATTTTGCTTTTACCAGTTGTTCTATTGCAGCAGGTGCAGTTATACAT
GATGGGCAAAGGCTTGTGGGGTGTCAGGGGCCTTGTCCCTTCCTAGCGCCACTAGGGTTA
ATAGGCCTGGTGGCCTGTTTCATGTCCATTTCACTAGTTGAGCACATATTGAAGAAAGAT
TTTATATATGGGTCATAGTGGACCATGAAGAACTCCCAACTTATTTCCCTGACAACATTC
TTTTTTTTCCTTTGAGACAGCCTTGCTTTGTTGCCCAGGCTGTAGTGCAGTGGCATGATT
TCGGCTCACTGCAACCTCCGCCTCCCTGGTTCAAACAGTTCTCCTGCTTCAGCCTCCCAA
GTAGCTGGGACTACAGGCATGTGCCACCATGCCTGGCTATTTTTTTTTTGTATTTTAGT
AGAGATGGGGTTTCACCATGTTGACCAGGCTGGTCTCGAACTCCTGACCTCAAGCGATCC
ACCCACCTCCGCCTCCCAGAGTGCTGAGATTACAGGCATGAACCACTGCACCCAGACCCC
TGACAAGATTCTCGAGATTTAACAATCTCAAATCTTCTTTCCGCAGTGCCAACTAGACAA
GATATCAGGGCCAAAAATATTTGGCTCTGAGATGTAAGAAAGGTCTTTCTAATTACTGTA
GAACTTGAGGTCATGATCATCACAGCCAGTGGTGTGCTGCTCCTACCTGCTTGTAAAAGC
CAGTTGCTAAATATTCAGGAATGTTTCAAGCCAAACAACCACTGGTAGCTTGAAATCAGT
CATGGGGAGAGTATTGACACCACAGAAGTTGACAGATGCTACAAATCCATGTTCTCTCCA
CATCCACCCCTCCCTGAGCCAGTTTACCAGCAATTCCCGCATCCAGCTCTTAACACTGG
AAGTTTTATCCAGGACTATGGCTAAATTAAATATGTGTGTCTTAAAAGAATTTTTTC
CCTGCTTTTTGGTTTGTGGATACAAAGAGCTGAATCATTAAAACTTGTTTTCTCTCCAC
CTCAACAGTGGCTTTCTTTATAGATTCTATGAATCTGAAAGATACAAGTTCCACCAGAGG
TCTTGGTAGGGTTCCACAGCCCCAAGCTCTGCAGGTTCTGACAAAGGATAGGCTGGGCCC
TGCCAGGAAAACTCACAGAACCACATCAAGGTGTTTGTGCTGCTGCTTTAAGAGTTTGTC
CTCAAGACAAATAAGAGTTTGCCTATTTGGGGCTTTGGAAATTTTTTTTAGGATTTTG
GAAGCCTGTTCTGTTACTTGCTAGTTGTGTTACTGGACAAGTTAGTTAACCTTGCTGATC
CTGGGAAGTAATCTCAGGAAAGCAGGGAAAGGCAAAACAGCGTGTGTTATTAAGCTGTGG
GAAACTGGGACTTGATGCCCCTGGGACTCTCTAAGCAGTCCTGCAAATTGCATTTCGGAA
TTAGGATAACCAACAGCAACACGGGATTTCCATGCTAAACCAGGGAAAACTCAGGTCCCT
GGAAAGCCAGGATGAGTTCGTCACCCATTCAGAATCATCTGCCTAAGAGTCAGAAGAGGG
GAACATTTATCCACTAGTTCATGCCCTGTAGTGGTTAAGTTGCCCCATGAGATGCCAACT
CCCTTGCACTTGCATACTTGTATATGTTCAAGTATGGTGCACATGCTTGAGACAGGATCT
CGCTCTGTTGCCCAGGCTGGAGTGCTCTGGCTTATCACGGCTCACTGCAGCCTCAACCAC
CCGGGCTCAAGTGATCCTTCCACCTCAGCCTCCTGAGTAGCTGGGACCACAGGCATGCAT
CACCATGCCTGGCTAACTTAAAAAATTTTTTGTAGAGATGGAGTCTCACTATGTTGCCC
AGCCTGGCCTCAAACTCCTGAACTCAAATGATTCTCCTACGTTGGCCTCCCAAAGTGCTG
GGATTGCAGGAATAAGCCACTGTGCCCAGCCAACCTTGCTGAGCTTCACTTATATGTGGA
ATGGATGAGACCACTTCAGAGGGTTTATGGGTTTGTCATGAAGCTCAGGGAGCTTAAGGC
TCAAGACACCTCACTTGTACAAGCTTCTCACAGGAGGGCTTTAGGTACACTGTATTTGTA
ATTTTCTAGTCTAAAGACCCCTGCCCTCTTCCCAAAATGTGTCATCTTCAGAGCTGCACA
AACCTTGGATCTGATCCTGCTTGTGAGGATGAATCACGTGTAAAACACTTATTCTTGAGT
CTGGCCCATTGTAAAAGCCTCAGAAATAGTCCTTGCTGTTGTCAGTGGAAGTACTTTCCC
TCCATTATCACATATCCACATATTCTTTCTCCCACTGCCTAAATGTCAATGCCCATCCAC
GTCTGCTCAGAGTTTGCTTCTTTTCCTATAATGTCAGTTTCTTGCCAATCACTCCCCACT
```

```
AAGCAATCGGACAGCCTCGGCCTCACAAAGTGCTGGGATTACAGGCATGAGC
CACTGCGCCTGGCCAAGTCTCCCCCTTTAAAATCCCTTCCTTCAGTCTAACAC
TTGAAATGGTCTTTTGGAGGCACAAGCCTGGCCATTTCCCAATTGCTAGCATT
TGAATAAAGTTGCTTTCCTTTTACTCGCTTCTCATATTTTGGCTCTCAAGTCAT
GAGCAGCCAGACTTGCATTCAGTCACAACGTGGCTGCCCTGCATCTCATTCTG
CCCTGGGGTTGCTCTTGCTCAACTTCCTTGGACATTGTTAGAAATGTATTTTG
ACTGTCACATATGCAAGTATGCAAGTGCAAGGGAGTTGGCATCTCATGGGGC
AATGTAACCACTGCAGGACATGAACTAGTTGATAAATATTCGTCTCTTCTGAC
TCTTGAGCAGATGATTCTGAAAGGGTGATGAACTCATCCTGGCTTTCCACGGA
TCTGAGTTTTCTCTGAGTTAGCACTGGAAATCCCATGTTGCTGTTGGTTACCTT
AATTCTGAAATGCATTATGCAGGACTCCTTAGGGGGTCCCAGTGAGATCAAG
TTCCAGTTTCCCACAGCTTAATAACACAGATTGTTTTGCCTTTTCCTGCATTTC
TGGGATTACTTCCCAATATATACTGCCTTCACACAAGCTTGTGTCTTCGGCTC
TGTTTTCTATGGGGAATCTAGCTGGTCTTTGAATTGGGCAATGCTTAGCTTAT
CTGTGCAGTGATGAGTGTTTCCAACTTTAGGAAACTTAAAAAGACAGAGGCA
AGTGAAATAAGTCAGGGCCCCAAACAGCCAAATTATCACTTTCCTGACGTTG
TTACAAAATTAGTCTGGAAGGTATGGCACTGTTCAAAGACAGTGTAATGAAA
TATTTATTATAAGGTTTAATTGCTTGAACAGCCAGATATAGAAAGGACTGCA
GACAGATAGTCAGGAGACTTAACTTCTGGTCCCACTTTTAGTATTTAAAATCC
TATGTGACCTTTGACACGCTTCTCCTTGGGCCTCAGTTTCTTCATCTCCAAATT
CTTGGCTGCTACTCTGCTAAGATCAAGTGTACAAAATTAGGAGGTTAGGCTA
GATTTTGCTTTTACCAGTTGTTCTATTGCAGCAGGTGCAGTTATACATGATGG
GCAAAGGCTTGTGGGGTGTCAGGGGCCTTGTCCCTTCCTAGCGCCACTAGGG
TTAATAGGCCTGGTGGCCTGTTTCATGTCCATTTCACTAGTTGAGCACATATT
GAAGAAAGATTTTATATATGGGTCATAGTGGACCATGAAGAACTCCCAACTT
ATTTCCCTGACAACATTCTTTTTTTCCTTTGAGACAGCCTTGCTTTGTTGCCC
AGGCTGTAGTGCAGTGGCATGATTTCGGCTCACTGCAACCTCCGCCTCCCTGG
TTCAAACAGTTCTCCTGCTTCAGCCTCCCAAGTAGCTGGGACTACAGGCATGT
GCCACCATGCCTGGCTATTTTTTTTTTGTATTTAGTAGAGATGGGGTTTCAC
CATGTTGACCAGGCTGGTCTCGAACTCCTGACCTCAAGCGATCCACCCACCTC
CGCCTCCCAGAGTGCTGAGATTACAGGCATGAACCACTGCACCCAGACCCCT
GACAAGATTCTCGAGATTTAACAATCTCAAATCTTCTTTCCGCAGTGCCAACT
AGACAAGATATCAGGGCCAAAAATATTTGGCTCTGAGATGTAAGAAAGGTCT
TTCTAATTACTGTAGAACTTGAGGTCATGATCATCACAGCCAGTGGTGTGCTG
CTCCTACCTGCTTGTAAAAGCCAGTTGCTAAATATTCAGGAATGTTTCAAGCC
AAACAACCACTGGTAGCTTGAAATCAGTCATGGGGAGAGTATTGACACCACA
GAAGTTGACAGATGCTACAAATCCATGTTCTCTCCACATCCACCCCTCCCTGA
GCCAGTTACCAGCAATTCCCCGCATCCAGCTCTTAACACTGGAAGTTTTTAT
CCAGGACTATGGCTAAATTAAATATGTGTGTCTTAAAAAGAATTTTTTTCCCT
GCTTTTTGGTTTGTGGATACAAAGAGCTGAATCATTAAAACTTGTTTTTCTCTC
CACCTCAACAGTGGCTTTCTTTATAGATTCTATGAATCTGAAAGATACAAGTT
CCACCAGAGGTCTTGGTAGGGTTCCACAGCCCAAGCTCTGCAGGTTCTGAC
AAAGGATAGGCTGGGCCCTGCCAGGAAAACTCACAGAACCACATCAAGGTG
TTTGTGCTGCTGCTTTAAGAGTTTGTCCTCAAGACAAATAAGAGTTTGCCTAT
TTGGGGGCTTTGGAAATTTTTTTTAGGATTTTGGAAGCCTGTTCTGTTACTTG
CTAGTTGTGTTACTGGACAAGTTAGTTAACCTTGCTGATCCTGGGAAGTAATC
```

Figure 1 Cont.

```
TCAGGAAAGCAGGGAAAGGCAAAACAGCGTGTGTTATTAAGCTGTGGGAAA
CTGGGACTTGATGCCCCTGGGACTCTCTAAGCAGTCCTGCAAATTGCATTTCG
GAATTAGGATAACCAACAGCAACACGGGATTTCCATGCTAAACCAGGGAAA
ACTCAGGTCCCTGGAAAGCCAGGATGAGTTCGTCACCCATTCAGAATCATCT
GCCTAAGAGTCAGAAGAGGGGAACATTTATCCACTAGTTCATGCCCTGTAGT
GGTTAAGTTGCCCCATGAGATGCCAACTCCCTTGCACTTGCATACTTGTATAT
GTTCAAGTATGGTGCACATGCTTGAGACAGGATCTCGCTCTGTTGCCCAGGCT
GGAGTGCTCTGGCTTATCACGGCTCACTGCAGCCTCAACCACCCGGGCTCAA
GTGATCCTTCCACCTCAGCCTCCTGAGTAGCTGGGACCACAGGCATGCATCAC
CATGCCTGGCTAACTTAAAAAATTTTTTGTAGAGATGGAGTCTCACTATGTT
GCCCAGCCTGGCCTCAAACTCCTGAACTCAAATGATTCTCCTACGTTGGCCTC
CCAAAGTGCTGGGATTGCAGGAATAAGCCACTGTGCCCAGCCAACCTTGCTG
AGCTTCACTTATATGTGGAATGGATGAGACCACTTCAGAGGGTTTATGGGTTT
GTCATGAAGCTCAGGGAGCTTAAGGCTCAAGACACCTCACTTGTACAAGCTT
CTCACAGGAGGGCTTTAGGTACACTGTATTTGTAATTTTCTAGTCTAAAGACC
CCTGCCCTCTTCCCAAAATGTGTCATCTTCAGAGCTGCACAAACCTTGGATCT
GATCCTGCTTGTGAGGATGAATCACGTGTAAAACACTTATTCTTGAGTCTGGC
CCATTGTAAAAGCCTCAGAAATAGTCCTTGCTGTTGTCAGTGGAAGTACTTTC
CCTCCATTATCACATATCCACATATTCTTTCTCCCACTGCCTAAATGTCAATGC
CCATCCACGTCTGCTCAGAGTTTGCTTCTTTTCCTATAATGTCAGTTTCTTGCC
AATCACTCCCCACTTGCCATTTGCCAGTCTTATTCCATAAGGTGCATCTGCA
CTTCCTCACTGCGTCCTTTTTCATAATGGGAAAACAATGTCCAGCGATTATAT
TCTTCACAGAAGTGATGTGACAGCAAAGAGAGATCATAAATGAATCGCCTGA
AGCTTGTTGGTGTGAGGGGGAAACCAAAGTCATATTAATACTTAACAAAACA
AGCAACAGGACAGGAAAACAAAAGGTAATTAAGGCAAAGCTGTGATGTTTT
GCCAGTTGTTAACATAAGAGGCCAATTGTCAGCTGACTGTGATGTAAAGACG
CTTCCTTTAAGAGCATGTGTAATATGTATCTCAGAATCATCAAAGGGCTCTAA
GTCACCCTAATAATGGGTCTGTACCACAAACAGAGAGAATGCAAACCACATT
TTGTCTTAAAAGACACAGCAAATTGCACTGCAGCTGTAACAAGAATCTCAGA
GTCATTTGCATTAACTGGGGATGAGTGAAGGGGCTAAGTGGAGTGTCTGTGT
GCAACATGGCACTTCTTCCTTGACCTGTGAGAAAGGAACTTGACAGCCAGGC
TCAGTGGCTCATGCCTGTAATCCCAGCACTCTGGGAGGCTGAGGCAGGTGGA
TCACGAGGTCAAGAGTTCAAGATCAGCCTGGCCAACACAGTGAAACCCCGTT
TCTACTAAAAGTAAAAGAAAAAAAATTAGCCGGGCATGGTGGCGGACGCC
TGTAGTTCCAGCTACTTGGGAGGCTGAGGCAGGAGAATGGCATGAACCCGGG
AGGCAGAGGTTGCAGCGAGCTGAGATCGTGCCACTGCACTCCAGCCTGGGAG
ACACAGCGAAACTCTGTCTCAAAAAACAAAAAAGGAAAGAAAAGAAAGGAA
CTTGACTTATATACACTTAGGTGCAGCCATCATTGAGGGCTTGTTGTGCAAGG
TGCTATGGATGGTGATGAGTAAAACCAGGTGTCCTTTCTATTATGCTGTGCTG
GAAGCTTCTTTGGCAAGTGAAGGGAGTGTGGCCTTTGGGATCAGATGAATCT
GGTGGAATCCTGGCTCTGTGCTCAGCATATGATTTAGACATTTATGTAACCTT
CTTGAGCCTCAAGTTTCCTCATCTGTAAAATGGTAACAATACTACCCATCTTA
CAGAATCACAGAGAGGATTAAATGGGAAAAAAAGACAAAGTGTCTGAAAT
ATAGCAAGTTCTTAATAAATATTAACTTTCTTACCCCCTTCTGGAGGCATAGA
ATCTTAGTGCAATCTTGGTACTCTCAGAAACTGTTTATGTAGCTCATCTGAAT
CTTATTTTTTAGTAGTTGAAACATTTTGTCTTAATACAGAAGCAATACATATT
```

Figure 1 Cont.

```
TGTAGCACAAGAATTAGAATATTTATTTATATATATTTATTTATTTTTGAGA
CCAAGTCTCACTCTGTTGCACAGGCTGGAGTTCAGTGGTGCAATCTCAGCTCA
CTGCAACCTCCACCTCCTGGGTTCAAGGGATTCTCCTGCCTCAGCCTCCTGAA
TAGCTGAGATTACAGGCGTGCACCACCATGCCCGGCTAATTTTGTATATTTT
AATAGAGCCAGGGTTTCACCATGTTGGCCAGGCTGGTCTTGAACTCCTGACCT
CAAGTGATCCACCCGCCTCAGCCTCCCAAAGTGCTGGGATTACAGGGGTGAG
CCACCGCGCCCGGCAAGAATTAGAATATTTAGATAAGAAAAAAATTCAAAAT
TACAAATAATTCTAATACGTTAACACCCTTGGGTGTATCCTTCCAGGACACTT
TTATGCCTGTTAATACATACGTATTATTAAAAATATAATTATACAATACATAT
TATTTTATAACCTGCTTTGTTTTCATACGTTACGTCATTATGGGAAATCTTTGA
AAAAATCTCTCCCATGAAAAGGCCAGCTAACAATTATGGGAAGTATGGGAAG
TGGTTTCGATTAACATACTGTGACAACTATCTATTATTAAGAAAGTCACGACA
AAATTTTGGTGCCCCTTTCCCAGATGAAGGCCACATAGCTGCTATAAGGGAC
AAGGACCAGTAATATCTTCAAATCCTCTTTTTGAAGTGCCTTCATTTAAAAAT
CATGCATTTTCTTTTAAGAGTTTTATAAAATCTAGGAGGAAACTTATCCCTTT
GTGTTTAGAACAAGGCAAAAGAAATTTCTGATTGGATATTGTTATGGGCCCA
TGACTTCTGTTGCAGAGAAGGTAATAGAAAAAGGTAAAATACTTCTACGCTC
TATAATTCACCTTGCTGGAAAAAAAACAACTGGATTGGCTTGACAGGGCTT
AGACGGGTGACCAGGTTACTGTTTGGTTGGTTGAGAGACGGAAGCAGTACAG
AATGACAAAAGTGTGTGGTGGGCCACCGGCCACTGGTTCATCATAGCAGGAC
CTCAAACCAATGTCTAGTCCATGAATGTTTATATATGGGTTGGTATATGAAGG
TGGATATTTGCAAACAAATGCTTAGTTTTAGTGTCAGGATTTTCTTCCTAATT
AATGAAAAGAGACTGTATGTTTTCAAGTTCTGTAGGCCTAACTAGAAAGAAA
AGAGTTCAGGATTTCAGATTGTGCTACTTTCACAAGATGTAGGTATATCTTTA
CCAAAACACACATGGCTATGCACATGTTCAAGTATCTTGTTATAAGAAGGGT
GTGGTGTAAGTGGAAAAATTGCTTCTGTTATTCTTGTGAGGCAGTGTAACTTA
GTGGTTAGAAGCACTGATTGAAGAGCAAGACTACCTAGTCTTGAATTCAGCT
TCACCAACTGTTAGCTGGGCAATCTTGGGCAAGTTAGTTACTCTTTCTGAGTC
TCTATTTTTCTTGACCTGTAAGAAAGGAAATTGATGGCCAGGAGTGGTGGCTC
ATGCCTGTAATCCCAGCACTTTGGGAGGTTTAGGCAGGCGGATCACAAGTTC
AAGATCAGCCTGGCCAACACAGTGAAACCCCATCTCTACTGAAAGTAAAAGT
AAAAAACAAAAAAAAACAAAAAAAGAAAAAACAAATTAGCTGGGCATGATG
GTGGGTGCTGGGAGGCTGAGGCAGGAGAATGGCGTGAACCCGGGAGGCAGA
GGTTGCAGTGAGCCGAGATCGTGCCACTGTCTTCTAGCTTTGAGACAGCGAA
ACTCTGTCTCAAAAAAAAAAAAAAAGAAAAAGAAAAGAAAGGAACATGACT
TATGTATATTTAGGTGCAGCCATGATTGAGGGCTTGTTGTGCAAGCTGCTATG
GATGGTCATGAGTAAAACTAGGTCTCCTTACTATTATGCTGTGCTGGAAGCTT
CCTTATGGGTATAATAATAGTTGCTCCTATTAATGAGTATATCCACCTCATAG
GGTTGTTGAAGGATTTGAAAAATATTTTAGAAAGTAACAACTTTCAGCATTTA
GAACAGTGCCTAGTATATAATAGGAAGTATGTGTTAGCTATTGCCATTTTATT
AGAGTTTTAACAGGTCAGTCCAACAGAACTGGCAATTTCCTGAGTGATACTTT
TTTTTTTTCCTGGGACAGAGTGTTGCTCTGTTGCCCAGGCTGGAGTGTAGTGG
TGTGATCTTGGCTAACTGCAACTTCTTCCTCCTGGGTTCAAGCCATTCTCCTGC
CTCAGCCTCCAGGGTAGCTGGAATTATGAGAACGCACCAACACGCCCAGCTA
ATTATTGTATTTTAGTAGAGACGGGGGTTTCACTGTGTTGTCCAGGCTGGTCT
CCAACTCCTGACCTCAAGTGATCTGCCCACCTCAGCCTCCCACAGTGCTGGGA
```

Figure 1 Cont.

```
TTACAGGCGTGAGCTACTTTTAATTCATTCATTACTCAAACAACACGGTATCC
TGGATGTCTATATATGGTTAGGCACTATGCTAGGCTCTGGGCAACTGAAAAA
AAAATGCCAATATTCTATATCTTTGAAAAGTAAAAACTGACTACTCGTGTCTT
CTCAAGAAGCTTTGTGACTGAGGTTATGCAGGTCTTTTTATCTAGAGTAGGCT
TCCTGGAAGGAGGACAAGACTAGCTCACCTGCAAAGAACTCAGTCACTTATC
AGGAATGAATGAAGTGCAGAGCGTATTGGGATTCCCTAACACCAACTCTTCC
TGAACATGCACCTTTGTCAAACCTGCCACTGTCAGAGCTGCCGACACAGGCA
ATGGATGGGGACATCAGGACAGGGCTTGGGGTGGGAGCCTGCAGTTCCTGGA
ATTTGCCCTGCTGACCTCACACTAGGTGATTTTATCCTACTTCCCAGAAACTTT
CCCCCAGTTAGTCTAAAGTTGGGATGAAGCTACAAATTATTTGCTCTGAAAAT
TCTGAGTCTATTCTAGAGTTAATTTCCTGTACATGTTACATGGTTTGCATTATT
AGAAGGGCCAAGGGGCCCCGGCAGTGCATTCCTTTTCATTTTCTGTAAAAGG
GATCTGTGGGACTCTTTCATCTTCCATTAATGATGAGAATGTGGAAAGGGGA
GGGTGGGGTAAGAGAACTAACAATTATTGAGCACTTACTCTGTGCCAGGTAC
TTTGTACATGTTCCTGGCACAGAGTCAGTGCTCAATAATTATCGGTTTTTGGG
GGAACTGAAACGAAAATCTGAGAGGCCAGGGGCCATGTTTTGTCAATACGT
CTATTTGGCAATGAGCACATTACCATGTATATTGTCAGTGGTCCATGTTGTT
GAATGATATGATTATACACATGTTATGTGTGCATATCCACCACCTATCTATGT
ATCATCACTTGTCTATCACTTATTGAATCTTAGCTAAAGCTCATGCTATTTAA
AATTACAATTGCCTTGGTCTCAGTTGAATACCATCCCATAATTTCTATGTGAA
ACAATTGATTTTGTGATTTCTATTTCATAATTGCAGAATTAACTAATTTATTAT
TCAAGTCCTTTGAACTTAAAGATGTTTTCAGTAGTGTGGATTGAATATATCTA
TGGGTTTGATGAAATTAACTTTTTTTTTTTTATGAGACGGAGTTTCACTCTTG
TTTCCCAGGCTGGAGTGCAGTGGCGCAATCTTGGCTCACTGCAACCTCTGCCT
CCTGGGTTCGAGCAATTCTCCTGCCTCAGCCTCCTAAGTAGCTGGGATTACAG
GCGCCCGCCACCATGCTCGGCTAATTTTTTGTATTTTAGTAGAGACGGGATT
TCATCATGTTGGCCAGGCTGGTCTCGAAGTCCCGACCTCAGGTGATCCCCTA
CCTCGGCCTCCCAAAGTGCAGGGATTACAGGCATAAGCCACTGTGCTCGGCC
GAAAGTAACTTTTAATTGTGATAATTACATTGCCCTTATTTCCATTACGCATG
AAACAGAACTCCTCTGTCTTCTTATGGTAAAATTTTGGCACTGAAGACCAGTT
GAAGATGAAGGATGCATCTTGGTAAGTTGAAAGAGGAGAGAGAGTGGGCC
AGGGAAGCCACAGTGGGCAACAGATTGGCATCCCAGCTTTCACCCCTCTCTA
TCATTCTTAGGTATTTCAGGTCAGAATTAAGAGGAACTAATTGGAGATATCAT
CTTCTTGGAATTGTTTGTGCCTCATAACACTTTAAAAATGCATTGACGCAGTG
ATTTCTGAAGTTCAGTCATTTGTGTATTGCCTTCACGAATTTTGCTATACCTTT
GAATCACCTGTACTCATACTGACTTGAGTTTTTAATCATCTCACTTTCTTAAAA
TTAAATACTTTTCTTTTTGGGAAGAGGATCTCATATTATTACTTTTTAAAAAA
TCTCTTTTTCCACACGTTCTAGTTATATCATTACTATAAAATTGAAGACAGGC
TTCACTTGTTAAAAACTGAATGTAACTATAAAATTCAATCCAAGAAAAACAA
AGAAAATGTTAGACAAAATTTTAGCTAAGCCTTATTTTCTTGGACTTGAAGC
CTAAGTTTTGCTCCCTGTCAGAGGGTTGCTAAAAGACCAGCAGCAAACTGAG
AGTTTACCTTGGAGGTAATCAGAAAGAAAAAATAATTTTAAGGGGAATAACT
TTCTCCCCCATATAATTCGGTGTATTTTAATGCCTGGTTGAGCCACTGTAATA
CTATGGAAGATTATGTCATCTTCCGTAATACACATTATCTCACACATGGCAAA
ACACTTCATGAGAAGAGAAACTGACATCTCATGATTTTGACCTTCACCACATA
TACAAGTTTTTTGTTAGAAATATCACTCACGAAAAATGGATGAAGTAGTCTT
```

Figure 1 Cont.

```
CCATGCAGAAGTTTGGACATTTCAATTTAATGTCTCTGGTAAAGATTTTCCAG
TTAAAAGCACATTGACCACAATGTTTCGTCTTCTCTTTAACACTGAAAAGGGG
AGGAACGGCCTTATTAGCAGTCAATACTATCAAAGTCAATGGAGGCAAGGGA
CCAATGGCCCATCATAGTCCTAATATCACTTACTGTTTTCGAAGGAGGACATC
TTTCATAGTGGTATCTACCATCTCTTGGGGAGAAGAGCAGGAATGGATAGAT
TAACCTCTTCCAGACATCTGCTCACAGTCCCGATGCGGTTTCTGACTTAGAGG
GTTTTTCTTAGAGATCTTCTCTGCTGTCCTCTGCAGCTGTCAGGGCATTCTCCA
GATGGGGCCTGGTAGGAGTCCTTGAATTGACTCAGGTCCCACATCTCCCTGCA
GTTCATTTATGCTTCAGGTCAAGGGTCACAAATATTCACTTGATAAGGGATGA
CAGATTAGTCACAGCTAGCTGCTGAAAGTGGAGTTGCATGAAGTGCACATTT
AGCTTGCATGAGGGAGAGCACAAATTGGAAACTTATCAAAATTGCCTTGGTG
GGTCTCTTTCAAGGCTTCTTTGGAGGCTGCTCTCAGATCTATTACCTCTGGAA
ATTCTTGAGGACTTTTAAAAATACAATGACATCTCATCTCTTCTTAAATTCTGT
CTAGTGGACAATTTGTGAGGGGTGTATGTGGAATCTGCAATTGAATTCTTCC
TCAGGTACGGTGAGTTGGGCCTCATTCCAGCTCCACCGCCATCATCATCAGAA
TCCTAGTGGGAATTTCCCTTCCTCAGAAGACTGAAACTCCACCTGTGCTGGTA
ATGCCAGGCCCCCTACATAGCTCCAGTCTATTACCTCAAGGGAACACAAAGG
CACACTCTTACAATATATTTACACCTGAGCTTGTAAATATGACAGCTAAGA
ATCAGAAATGTTGTTTTACTTAAATGGGCTTGTCAGTAGATTGGGAGTATATT
GTATTCCAAGGAAATGCTTTTAGATGTAATTTAGGTACAAACTCTGGATTT
TCCTTCACGTACAAAAATTAAAACTTTGATTACACACTAGCAGAAATGACAG
CAGTAAGAGTTTTTTATTTTAATTGTATTTATTAAACAATTAGGAAACACTG
TATACTTTCTAATTGTTCTAAGTTGCTTTATAATTCTTAATTCATTTCAACTCT
ATTACAACCTTATGATCACCTACTATGTGACTGTAAAGCACTGTACTTATTA
CATTAGCTCTAATTCTTACAATCATCCTTGAAGGTAGTTAGTACTCCCATTGTT
ATGAATGACCACTCTTCAGAAGCAGGAGGGACCCTCATCCAAATTTGATTTG
GATGTCAAAACTGATGATGCCACACATCCACCTCACATAGGTATGAAAACTA
TTATTCACATAATGAGGCTTTCTGGGGATAGCAGTGTGGTTTCCAAGCAGATA
AAAAAAAATGGCTTGAGAGAGAGCACAGAAAGGAGACTGGCTTAGGGTTTG
TTTTGTTGGTGGTTGAGGTGGGGCCAGGGTGAGGGTTCCCACACATGGTTTGA
AGTTGCCATGCAGCTTCCTAGTAGCAAAGGAGGGAATATCCTGGTTTTCTTAT
CAGTTCTCCTGGATATGGGCAGATGAGGAAGAGGGAGGGGTAAGGCTTAAA
AGCTGGCAGTAGTCAAAAGTCAAAAAATGGAGTCAGATTCCTTATTATACCC
ATTTTACCAATGAAGAAACTGCGATTCTAGGATATCATGCATTGTGTCAGGCA
TGACTTTAGTGCAGTAATTCTCTGTGAAACTTAGCCCCACACTGCACTGTACT
GTGGTCTTGGAGAAGTAGAAGCAATAGGAAATACACACACACACACACACA
CACACACACACACACACACACACACAGTGATTTACTATAAGGAATTAG
CTCACATGATTAAGGAGCCTGAGAAGTCCAAGATCTGCATTCAGCAAGACAG
AGACCCAGGGGAGTTAATGGTATAAGTTCCAGTCAGAGTCTAAAGGCAGGAG
AAAATTGATGATGTCTCAGCTTGAAGACAGTCAGGCAAAGAGAAATAATTCT
TTCTTACTCAATCTTTTAATCTATTCGGGCCTTCAATGAATTGGATGAGGCCC
ACCCACATTGGGGATGGCCATCTGCTTTACTCAGTCTACCTATTCAAGTGTTA
ATCTCATCCAGAAACACCCTCACAGACACACTCAGCAGTAATATTCAGCCAA
ATATCTGGCTATTTCATGACCCATACAAGTTGATATATGCAGATAACCATCAC
AGTATCCACCTTGAAAATGCACATCCCTTATTATTGAAGGGGAGTGGGAGGC
AGAGGAAATCCTAAACACCATTGCAAATCTATATATTCTAGAGAGACTATGA
```

Figure 1 Cont.

AAGCAATGTAGCTTGGCATGGTGGAAGGAGCATGGTCTTTGGGATCAGAAGA
TTTGGTTATAATTTGGCTTTGCCATTTATTGGCTGTGTTATCTTGAAAATTGCT
TAGCCTTACTGAGTTTTAGTGATACAGAACATCTCCAGTGACATGCAAATTTA
TAAAACATCCCATTCTATTTTGGGGGTCTCCATTGGAAAGCTCTTTCTTAAAT
AATGGCATTTCCCTATATTAGGTTTGGGGTGCATACATAGTCTCTACTGGTAT
ATCAAGGCAAGTTACCAGGAATTCCAATGTATAAGGACACAGCTGGCCATCT
GGAACAAATATTGGAAGGGATTTTGGAGAACAGAGGTTAGATCCAGGGGCA
ATAAGGTCCAGACTCTTCACAAGAGATGAGATGAAGGCCATGCTCTGCCTAT
TTAGGAATCCACAGGACACTGAGAGTTACCCCAAGACAAGAGAAAGTTCAA
ATACCCAAGACATTGATTGACTACTGGCAATAGTTTTGGCACAACCCTGGG
ATTTGCTGCCCAAATGTTGTTTCAGTCTTGTCCCAGGAGAGCTCAGTTCTCAG
GCTGGCTCCACAGCCTACCATGTTAGCAAGCCCAAAAGTGAATATGTCTTTTG
TAATTTTTCCAGCAAAAATTCCAGGGCTGACTCTCATTGATCCAAATTTGGTC
ACAGGCCCATCCATGAATCAATTGCTGTGACCAATTTACTAGGCCTGAGTCAC
TGGTCTGTCCACCCCAGGTGTCTTGTGGTCAGCTCACCTGAACAGCACGGACT
GAGACCCAAGAAAAACTGATGCACTGTTACTAAAAAAGTGAGGAAGTGAGG
CTGAGTAGGCAAAACAGCAGATGTCCATTACAGGAAAGATCTCCAAAATGTA
ACCTCACTCATTTTTCTGTATGTGTAACTCTGTGTGAACTTAGCGCCTGCCCC
AAGGGTGGCATTTACTTAGACTGTGATGAAAATAGAGACCCTGGATTTGTGC
AGTGCTCTGTCTTCCCCCCTCTCTTTCTGCTACCACGATTTCTCCAACTTCTGG
TTGTATCAGGTTTCAGCTAAGGGAGGGAAGACATGACTTAACGCATAGGCTT
CCATAGAGATTCCATACTGGGACTTCAAATAGGTCACACTACTGGTGAGTCC
CAGCACACAGATCCTAGTGCCAAGATACTCATGCTGTTGATTCAGAACTTCCA
GACATACATGTGCTTCCTCTGACAGGGAAGGCTGCTACTACCTATATCTTCTG
AATTGGTTCATATTAATCATAGGTCATGTGTACCACTGGTAACAATAGTCATC
GTTTAGTGAATGTTTACAAGTGAGAACACTGCCTATTCATAAGCTTGAAATTA
TCTGTGAATTTGGGAATGTGTGCCAGCCGTAAGCTGACCAGACATACTTACTG
GTCATTAATCAACAGGGTTTTGTTTCCTTATCCCTATGTTTGACTGAGACAAA
TTCCTCTCCCTACATCACTCAAATGTGGATACAGAAGTCTTCTCCCCTTCCTAT
TTATAACCTCAAAAGGTTGCAATTTGGACTGGAGGTAAGGAGGAGATAAAGT
ACTTACAAACTACTTGTGGAATTCCCCCAGTCCCCTCCACCCCCTGCTTTTTCC
CTGTGTCTTGACCAAAAATCACAGAGTACCTTGATCACACTATGACACAACC
AGCAGCAGGCTTTTCCCAGCAGGCTTGACACCAGGGCTTTGAACATTCCCAG
GCCCTCATACAGGTATCAAGGTTTACGAGGAAGAAACTGGTCCTAGCCTTAG
CCCAAATCCTTAAACCTTTATATAAACTCCATGCCCTGACCTCCTCACAGCAG
ACATAACTAGATAGAACACCGTTGTCTCTTGCTGTTTGTTGCAAAGATTGCTA
CAGCCTTCTCTGTGCCTAAGTTTTTCTAATCAATGCTTTGGATGGATCAAAAA
GAAAAAAAAGAATTTATAACTAAAAGGAAAATATTGTGTACTATATATTATA
TATAGCATATATAATATATAATCTGTATAAAATACATGTAACATATAATCCAT
TGTATGTTATATGTAATTTTTATGGAAATACAACAAATTATAAGTATAATAAT
TATGTATGTTACATATATATATTTTTCACGTTTTAACTTGAGGTTTAAGT
ACCTGTGATCTTTTTTTTTTTTTTTTTTGAGACAGAATCTAGCTCTGTCAT
CCAGGCTGCAGGGCAGTGGCTTGATCTCGGCTCACTGCAAGCTCCACCCCCT
GGGTTCACGCCATTCTCCTGCCTCAGCCTCCAGAATAGCTGGGACTCTAGGCG
CCCGCCACCACGCCCGGCTAATTTTTTGTGTTTTAGTAGAGATGGGGTTTCA
CCATGTTAGCCAGGATGGTCTCGATCTCCTGACCTTGTGATCCGCCTGCCTCG

Figure 1 Cont.

```
GCCTCCCATAGTGCTGGGATTACAGGCATGAGCCACCGCGCCCAGCCTATCT
GTGATCTTAACCAATTTATCTTGCCTTTTCTGATGCATGACTAAGAACTTATG
GGGAATTCAAATAGATCACTAATATAAAGACAATTTAAAGTGCTTGACTTGC
CAGTGTTCTTATAGCAAAACTTTCATAAAGTTTATGACACTTCTTTGATTTCTA
AGGTTTTAGGGGTACAGGCATATCTTATTATAGAGTATTTTCCTCTTTCATTT
AAAGATTTAATTTACTACGCATCATTTCCAAGCTCCTTGACCTTTTCTGGATCC
CCACCACCACCTGCCCTAATGGATACTGACACCAGCTGTGAATATGTATAAT
ATAAACTGGCCAAAACACATGGCCTGGGCAGGTTAATAACTTGCTGCCCCTT
CAAACTGATATTATTTAAATTTGTATTTAACACTTGAACACTGTCATAGGCTG
ATCCTAAAATGAACCCCAATAATCCATGCCTCTTGGTAGTTATGCCCTGTGTA
ATCTCCTCCCATGAGTGTGGGCTGACCTAGCAACTTGCTTTTAACTACTATA
AAATAGCAACAGTGATGGGCTGTCATTTCTGTGATGGTGTTACATAAGAGTTT
TACTTCTGTTTTATTAACAGACCCTCTCAATGCCTTCTCAGCTTGCATACTTTG
ATGAAACAAGCAGCTGGGTTAAGAGATGTCCATGTCGCAAGGAAATGAGGG
CAGCCTCCATCAACAGCCAGCAAACAACTGAGGCTCTCAGTCTGACAGCCCA
TGAGTAACTGAATCCTGCCAACAAGCATGCAAGCTTGGAAGCAGATCCTTCC
CCAGTCAAGCTTTTGAATGCAACCTCAGCCCCTGCTGACACTTAATGGTGCCT
TGTGAGGGCCCTGTAGGCAGTGGAGCAAGCTAAGCTGTACCTGGATTCATGA
CCCACACAAACTGGGAGGCAACAAATGTGTGTTGTTTTACACCACAAAATTT
GTGGTAATTTGTTACACAGTGACAGATTAATACAAGTACTGAGTGGGGAAGG
TTGCATATACCATTCAGCCAAAGCTCTCTTGTTAACTGGAACCACCCTAATTA
CAAGATAATTTAATGAATGACTGTGTTACCTGAACACACCCTTCAGAGACCC
CATCACTTGCATGAGTCAGAGCTCTATGGGCTTCAAGTGACAGAAATCCATTC
TAATTAGCTTAAGTAAAAAGGGATTTGTTGATTTACATACCTGAGAGGCCA
AGGGTGTACCAAGCACCCTCAATTTCAGATCTACTAAAAAGGACTCTGACTG
GCCCTTTTTAGATACATGCCAATCATTAAAGATTTAATGTATCTATAATAAGA
TACTATATAATAAGATATTAGGACCAATCATTGTGTCTAGTTGGATAGAGTTC
TCTGAGTGGTTGGCTTGGGTTTCATGCCTACCCTTGCGGTGGAGAAGGGGAG
AAGAACATTACATTTGAAAGCCTTATCATGTAATATACAGATAGTTACCCAA
AGAAATTTTTTTTTTTTTTGCTCTAAAAAGGCGAGAATGTACACAGGGCAGG
CAGGCAAAACAACAGCTGTCTACTATACTGCCTACTACCCAGCTGGGAGGCA
AAGTGACTCCATCTTGGATGCTAACCTGCCATGTTGACTTCTGATTAGCCACA
ATCCTGTGAATATCTCCTGATTCCTACTTTATTTACTGTTTGTGTATAAGAACA
TGTCAACCTTGATGTTATCACACACATTTTGCCTGTTTGGGAGGGTCGCCTTT
AATTGTCTTGCTGGAGCATGTATACCATTTTCCTGTCATATTCATATATAAGC
CTTGGGTCAGCAGAGTAACAGTGCAAAGATTTACCTGTCTTGTGGCTGCCTAA
GACCACACTTCTATCTGTAAGTTCCCCCAATAAAACACTCTTTGCCAACAAAC
TGGATTTGTCTGTCTTGTTCTTTGGTTTCTCAGCTCCTTTGGCACTTGAGGGCC
AATTTGTATATATGGCCCTTTCACAGAACATCAGCATCTCATGAAAATATTGC
TTCCCATCACATACAAACTTCTCTTCCAAAGACATTCTGGTAAATGTGGAATA
TTGGGTCTCTTTAGAATTCCAGTGATTTAGACATTTTTATTGAATTATATAA
TATTCACATATCCTAAGAGTACAAATAGATGAATTTTCACGAACTGAGTTCAT
CTTAAACCACCATCCAGATGAAGGCACATTACCGTTATGGGATCTTTGGGAT
GTCGCTTTTCTGGCTGGAAACCTCTGTGGCCGTTGGTGCCTTTGCCTGAGTTCT
TGTCCTGCATCCAGGAAGAATGAAGTATGCAGACAAGTGGAGGGTGAACAA
GATAAAGAGGAGCTTTATTGAGTGTGAGAATAGCTCAGAGGAGACCTGCAGT
```

```
GTGTATATGTGTGTGAAGGTAGGGAAAGGAGGGGGCTAGGTAAGAGAGCTAAATTTCCCT
AGCAGGAAATTAACAGAAAATACCTAAGCTTTAAAACATCAGGAAATAGCTATCATACAT
AGCTACGTAGACATATAGTGGTCAATATTAAAAGAAACAACTAAAATAATATAATGTAC
TTTTTTTTTTTTTTTTTTTTTGCTGGTGAGTGGAAATCAGAGGTAGGGACACTATTGC
TGTTTTGGTTAAAAGCCTTATAGCCTTATTTGGCTGTTTTGCTGATATACACGTATTAGC
CTAATACAATTAAAATTTTAATAAAATCAGAGACCCTTCCAAGAAACTAATATTCAAAAA
AACAAATATCAAAAGTAAAAAAAATAATAAAACAAGAGGAAACAATTGTCTGGGGCCAGG
GTAGGGTACTACTCCTAGTTCCAAGCCAGTTTTTAAATAAATGGACTTTAGGAACATAAC
CTGTTCATAAGGATGGACTTTCCACATTTCAAACCCAGTAATGGTAGAATAACTGCCTTA
GGAGATTCTAGATACAGCCTTTCTTTCCGCCAACTTGCCCCACTGTTCGACTGTTTCTCA
TCATGCTGGGGGTGAACAGCATCCTCTCGGATGCTTGTAAAGCAATGGCCTGAACAGAGC
TAATGTTTTAGGTCCATGTAACTCCATTTTCCTAGACATAAAGTTGAGAGTTAAGTTTT
GAGGCCTAATGGTCCCTTTCCTAATCTGAGAATGAGTTGGAAAGCTCAGCTCTCCTTCCT
TTCTCTGGGCTGCTCCTTTCCAGGTGAAGGGGTTTGTGATGTTGTAAGCGAGGAGATTTG
TCAGATTAAGCACACAGGGTGCCATGGAAGGTAAATTAAATTGACGATAGATTCAGCTTA
ATAAGACTTTGCAAACTTTCCAAATTCTTCAGTCAAGCTTCAAATTTCCAGGGAAAAGTG
AAAGCTCTTAATTTACTGGGTTTAGGTTGGTCTGCCCAAGTTTTCCACTTGAGTAGTAAA
ATCCCTCCAACTTCTAGAATTCGAAGAGCAGCCAGGGCTGAGCTGGGAGCATTTCTCCCA
TCTGTGATAGGCCAAGCTTCTCAGGAATCAATTATCCTTCTTTTGGCATCAAACTCCCAT
TAGCCAATGACAGTTCCAACATAACCACCTGGTCCAGGTGGCTACACTTAGGAGAAGAAA
GTAGGGGGTAGGGGGAAAGACCCCCACAGTGCCTTTGAGCAGAGCTCTTGCAATGTGAAG
AGATACTTCTTGCACCTTTAGAGGAAAGGAAATTCCGAACATTTGCTTTCTGCTGTTGTT
CCTTCTTCTCATCTTAGGGGTTCTGAGCCCATTTGCTTCAGTATAAAGATAGTTCTATGC
TAGTTCAGTCACAGAGAGGGCTGGACCAGACCCTTGCCAGAATCTCCAGAGACAAGTGCC
CATGCCATACAGAGCCCAAGAGTTAAGAATACCCTTGCTACTCTGGTGCCACATTGGTAT
GACATCTCCCTTAGGCATTCCTTAGTCCTTGCAGTAGAAGAAGCCCACCTTATCTTAAAC
CTGACATGCAAAAACTGAGTGATAAAGTAAATTAAAGAATGAGTATCTGTTTTGAAGTAT
GATCTTTACAAAAGGGTTCACCAAAGACTGCTTAGATTATTAGATTGATCAAAAAATCAA
TTTATGATACATCTTTTTCAGATGCGTATTATATAAAACAAAAGTGCTAAGACTGGGTAT
AACTGCTAGCAACAACAATACAAGTAGCTAGAACCAAAAGCATGCACCACCATGCCCAGC
TGATTTTTTAATTTTATTTTAGAGATGGGGTCTCACTATGTTGCCCAGGCTGGTCTCAAA
CTTCTGGACTCAAGTGATCCTCCTACCTCAAGCATCCCAAAGTGCTGGGATTACAGCTAT
TTTATATATATATATATATATATATATATATATATATATATATATATACACACATATA
TACACACATATATATACACATACACATATATATGTATATATATACATATATATATA
CACACACATAATTTACTTTTCTCATGAGCCTTGTCTGCGTGATTAGAATATAAGATCCAT
GAAGTCAAGACTGGTGTGACACATTTCTTTTATCTTAGTCCCTGATATAGTTTGGATGT
TATCCCACCCAAATCTCATATTGAAATGTAATCCCCAATGTTGAAGGTGGGGCCTGTTGG
GAGGTGATTGGATGAATGATGGGGCCGATCTCTCAGGAATGATTTAGTACTTTCCCCTT
TGTACTGTTCTCGTGATAGTGAGTAAGTGCTCACAAGATCTGGTTGTTAAAAGTGAGTG
GCATCTCTCTCCAACTCTCTTGGTCCTGATTTCCTCATGTGATATGCCTGCTTCCATTTT
GCGTTCCGCCATGATTCTAACTTTCCTGAAGCCTTCCCAGAAGCTATGCTTCCTGTATTT
GCCTTCTGCCATGATTGTAAGTTTCCTGAAGCTTTCCCAGAAGCTGATGCAGAAGCTATG
CTTTCTGTACAGCCTGCAGAAGCATGAGCCCATTAAACCTCTTTTCTTCTTAATTACTCA
GTCTCAATTATTTATATTAGCAATGCAAGAACAGACTAATACAGTCCTTAGCCCAGATCT
```

```
CAGAGATTAACTCTTTTGATTATCTCTGGAGAAGTGTTCCTTCTTGTACCATTC
TTCCAAAGCACAGCCAAAGGCTTTATAAGTTTATATGCAAATAATAAAATCA
CACAACCAAATCTGTAAAGATTCAGCAGGTGAATGTCAATCTTTAATATGA
TACTAACATTTATACTGTACACAAACCTATGGCTCTGTTTTGTTAGTTCCTGCT
CAGAATCTGACTACCTTTTTCACTGAATATTTTGGAAAGCTAACTACTCTTTC
AAATCCTGCCTTTTGACCAGGTACAGTGGCTCATGCCTGTTATCTCACCTACT
CTGGAGGCTGAGGTGGGAGGATCACTTGAGCCCAGGAGACTGCAGTGAGCTA
GGATTGCACTACTGCCCTCCAGCCTGGGCAACAGAGTGAGAGTCTGTCTCAA
AATAAAAATAAAAATAATAAAATTCTGCCACTGATTAAACCCATTTTCAAAA
ATTCTTTAAGCATTTCTGTGAGAGACAGTTTACAAGACCCATGAGAAAACCT
GTCTGTTTACTTTATAGTGTTATTTTTAACCAAAAGTGGCATTATCCTTCTTGA
CATCAGACTTCACTTTGAAAGACTTTAGACTGTGTCTAAAATCACAGCCACCA
TCCAAGCAAGGTTGGCATCAGTCAAGTTGTTTACATACAAGTGCACAGACAT
AGGGTTTCTGGAGTTAAAAAAAAAAACCAACCAACCAACCAAATCATCCCCC
TCTTCCACCAAATTCCAGGACACCCAGTTAAATTTGAATTTCAGATAAACAGT
GAATAATTTTTCATTATAATTTATGTCCCATGCTTATAACAAATTCAAATTAA
CTGGGCACTTGTATTTTGTCTGGCAGCCCGACCCAGGGCTGAAAATAATTCTA
GAAGAAGAGTTTCTGAAACTGCTTTGTTAATGGCAGCATTATGAGACTAGAA
TATAGTCTCTCAAGGCAACAGCCCTCATTTACACATCTAAATTATGAGATCCT
TTTTTAAGAAAGGGGATCACCTGATCTTTCTGTAAGACTTCATTACATTGTAG
TCAAGAAAAGGACACATTAGCAGGTAGCAAGCAAAAAGTATGTGAATTTC
ATTAGTGTTCATTGTTTGTTACACCTTGACCAGGCTCTTAAATTAGCAAATAA
GCAGTTCCTTATAACCTTTCCAAAATCTACCTATGTTTATTTAAGTTGAGTCA
GATCAACTGGTTTTACTCAAATATTGTAAGGAATAATGAATAAAACAAATAG
AAAAGTTATGCTACCACAACAACAAACAAAAAGGGAAATTCCCCATTGAAG
ATTGGTCTGTGAGGACCACTTCCTGGTCTTAACTTTGCTTCCTCTGACTCCATT
GGTAGAGAGGTACGCAAATTTCTAAGGGAGCACCCTAGTGCCTCATAACTCT
TTGGTTTAACCATCATCTAGTAATAGCCACCTGTCATTAAAAAACCCAAGCAG
TGAAACACTGCCAACACATGGAAGGCGTATAGAACTGAGAGGGCTGAGGCT
GTCAGGCATGGAACAGGTATTTTTGTATCCTTTCAAATATTTCAGTAGTGCT
TATTATATAGTCAGTGTCTTCCTGACACAGTATGCCTTCTATTCTCAACATGA
ATTTCCTTAGAGTCACTTTTCTTTGTGCTTTCGATAGTTTCCAGTTTTATTTTTA
TTTATTTATTTATATATATATATTTATTTATTTTCTATTTATTTTATTATTATTA
TACTTTAAGTTTTAGGGTACATGTGCACAATGTGCAGGTTAGTTACATATGTA
TACATGTGCCATGCTGGTGTGCTGCACCCATTAACTCGTCATTTAGCATTAGG
TATATCTCCTAATGTTATCCCTCCCCCTTCCCCCCACCCCACAACAGTCCCCA
GAGTGTGCTGTTCCCCTTCCTGTTTTATTTTTAAAAGGGAGAACTCACCTTTCT
GTAAAAGAACATCAATAGAAGAATTTTGCCAGAAAGAAAGAAAGGCAATAC
AGAGTCTTTTCTAATTCTGTCAATGGAAATGTCTTTTTTAAAAAATACACAGG
CTTTCTTTGATTAGTCAATTTTTTTCCCCAAGAGTTGTATCTCACTGAGTACAG
TTTTTTTATTCAAGAGTTGTATCTCACAGTGAGAAAGAAAGAAAGAAAGAAA
GAAAGAAAGAAAGAAAGAAAGAAAGAAAAAAAAAACTTGAAATAA
AGAAACTTGAAAGAAGGTTGAGAATTGTTACTTATTTGCAAATCTTGAGTTTT
GGCCTGAGAGTGGAGAGTAATTGGAACATTGAAGATGAAAAAATTTCTAAGA
GATTAAAAAAAAAAACAAGAAAAGAAAAAGAAAAGAAAGAGAAACAACT
ATTAATTCTAAGAAAAGCACAAGGTTACATAAAAAAGCCAATTTCTTCTTAG
```

```
GTGATTTTGGCTTACTGCAACCTCGGACTCTCAGGTTCAACGGGTTCAAGCAATTCTCCT
GTCTCAGCCTCCCGAGTAGTCGGGACTACAGGCGCCTACCACCATGCCTGGCTAATTTTT
GTATTTTTAGCAGAGACGAGATTTCACCATATTGCTCAGACCGGTCTCAAACTCCTGACC
AAAACGAAGTGTTTTTTAACCTACAATTTAAGTAAATGTTTAATGTTTATTTATAATTT
ATTTATTAAATGTTTACATTCACCAGGCACTATTCTAAATAAAACAATGTTGCTGTCCTC
ACATAATGAAGATTCTGGAGGGGTCAACATAGAATACGTACATAACCAAGTAATGTACAA
CATTCCACCATGATGAAGATAATTTGTTCCTAAATAAAGGTCCTCGTGGGTGAATTCTCA
TAGGCTGAAAATGTACCTAACATTCATTTTGACAGAAAGACACTCTTTTCTCTTAAGCC
CCCAAATTAACACCTATTTATGTTAAAATAACATCAATCCCATTAAAACAGGTACAATTA
TCTCAAAGGTAAATGGTTATCATAGGACTGATGTCTGTGCTCATAAAGCATCAAAGCAAC
CATATGATTCTCTGCGTTTATGTAATTAAATGTTTAATGAAAAACAAAAACAAAAACAT
GAGCTCTTTTTTGTGGCACCTTGGAGGCAATTAGCTGCTTCAGGATGAAGCTAAATATCT
CCTCCCCAGCCACTGGCTGACAGACACTCATTGGATTGGACAACGAATGGCAATTTGTA
CTTATGAGAAGCATATGGCACAGAGGTTGCTGCCGACGCTCTGGAAGAGTTATGTGGTCC
GAGTCAGTGGTGGGACCAACGAACAAGGTTTCCTCATGAAGCAGTGTGTCCTGACCCATG
GCTGGGTCTGCCTACTGCTACTGAGTAGGGCATTCCTGTTATAGACCAAGGAGAACTGG
AGAAAGAAAGTGCGAATCTGTTTGGGGTTTCATTGTGCATGCCAATCTGAGCATTCTCCA
GTTGGTTATCTTAAAAAAAAAAAAAAAAAGGAGGGAAGGATACTCCTGGACTGACTGAT
ACTATGGTGTCATGTTGCTGGGGCCCAAAAGAGCTAACAGAAATGCAAACTTTTCAGTC
TCTCTAAAGAAGACAATGCCCCCCACCCATATGTTGCCAGAAAGCCCTTAAACAAAGAGA
GTAAGATACTGAGGACCAAAGCACCCAAGATTCAGCATCTTGTTACTCTACATGTCCTGC
AATACAAACACTGGTATTGCTCAGAAGAAACAGCATACTAAGAAAAATAAGAAAGAGCCA
CAAAATATGTTAAACTTTTGGCCAAGAGAATGAAGGAGACTAAAGAAAAACTCCAGGAGC
AGGTTACCAGAGACACAGGTTGTCCCCTCTGTAAGCTTCTACTTCTGAGTCTAGTCAAAA
ATAAGATTTTTTGACTTACTTAACAAATGAGTAAGATCATACCACCCCAGCAAAATAAT
CAATAAAGACTAAGGACATTGATGAAATGATGGAGAAGATGATGACTTCCATGAGTACT
TTAAAGGAGAAACTTAAAGCAACTTGTATAATTTTTAAGACTGCAGAGCTGACATGTGGT
AACTTATGCTGAATCTGCTCAGTAGCTTCCCACAGCCCCCAAATCTGAATCACATTCCTT
CAATGTGAAGAATGCCTCATAAGCTAAAGTTGAGGAACTAAATAAACTGATTAAGTCTCT
GTCTTATGACACCTCCCACCCCCTATCACAGTTCTATCCAGGGCAGCATTGACTAGCGTA
ATAGCAGGGTGTGATATGTGGTAGGACAGATAGGATGGGGAGGACAGGGAATGATGTTAG
GTGGAGATGGGGAATGACAAGGAGTCTGGTGTGAGGGAGCCCACTGAGGGAGGGCTAGG
TGGTAGAAGCTAATGCTGGCCAGGTAGCTAGGTGCTAGATTAGAGAGCACCTTGCTAGCC
ACACTGAAGACCTGAGTACTTTGGAAGCCAGTGGAAACTTCTGAGCAAGGAGTGACACAA
TCAGACTCATATGTGAGAAGGAGACTGTGGGTGAGGGAGATAAGTTAGGTGACTATTGTG
GGGTTCAACTGAAAGAGGAGGTAAAAGCATGGGTCAGGGTTACAATGGTGCAGACAGAGA
GAAATAGTTATAGTTTATCTGTAGTTTGAATATAAAACCAACCGGATTCCCTTTGAATTG
AATATGATACATCAGGGAAAAGAGGAATCAATCTTAGTGCATACTCTATGTCAGGCCTT
GTTCCTATGTTTTACATATATTCATAACAATAAAAATAATATCAAATGCCTTTCTAATAC
CTTCCCTATGCCAGATTCTATATGCTTTAATCTACTTTCACCCACATCACCCTTACTGCA
ATCCCATAGGGTAGGCACTATTATCATTTCCATTTCTGATGAGAAACTGAGGCACAGAC
AGGAAGGGCAATGCACACGGGAAATGCTGGAGCTGATTTAGACCCCAGACGTTCTGGCT
GCAGAGTTGAGATTCACAATCACTGCAAACACTGCATTCCATGGTCACAAGGTTTTGGTC
CGAGCAGTTGAGTGGGTGATGTTGCTATCGACCAAGACAGGAATACCTGAGGCAGAGCAG
```

```
GTAAGTGCTCACAAGATCTGGTTGTTTAAAAGTGAGTGGCATCTCTCTCCAAC
TCTCTTGGTCCTGATTTCCTCATGTGATATGCCTGCTTCCATTTTGCGTTCCGC
CATGATTCTAACTTTCCTGAAGCCTTCCCAGAAGCTATGCTTCCTGTATTTGCC
TTCTGCCATGATTGTAAGTTTCCTGAAGCTTTCCCAGAAGCTGATGCAGAAGC
TATGCTTTCTGTACAGCCTGCAGAAGCATGAGCCCATTAAACCTCTTTTCTTC
TTAATTACTCAGTCTCAATTATTTATATTAGCAATGCAAGAACAGACTAATAC
AGTCCTTAGCCCAGATCTTACACATAATAGGTATTCAATGTACACTGTGTGTT
GTTGATATTCACAAATTACTTCCTCTCTTTCTACAAAATGTTGAATAATACCTC
CATCAGAAAAACCTGGGTTAAAGTAAGGGTATTTTTGTCTATCTGCAAAAAG
ATAAACATATTCTAATTTTTCTATAATGATTGCGGGTAGAGATAATCTCTGCC
CTCAACAACACTCTTCCCTCATAGAGGGAAATGAAACTACAAATGTATTTGA
ATATAATAATAGTGAAGGAAATAATGTATGCTGTGGTCCGTTTCCAAGACAA
AGTGCCTTGAATCGGTTTAGGTCAGCAAACCACAGAAGAAATAGGATATACT
AGGCCCCTGCTTGGATAGCCAATGCCTGCTTGTCACCACTTCCCCTTAGTTGC
CCTCACCCAAACCAAAGAAGTTTAGTCTGAAATGAAAGCTTACTAGCCTGCA
AAATAGCTCGTTTTTTCTGTTCTTATTAGCCTACCCAGCTACTTAGGTCATAAG
TCAAATACTTGAGTTCCTAAGCTAACTAGGATTGCAATGTATTGTGGGCTGCA
ACAAAATGCAGCAGGACAACCCTAAAGAAAACACCTAAAGCCACTACCCAA
CAACCGATAGGCAATGTCCAGGAAGACTGTGACCCCATAGTACTCAGCCTGT
GAGGAACCGGGGGAAGGGACCTGTGCATTAGGGAATAAATTGCTTTTTGTAA
CTGTGCTGGGTGTGCCTGCCCACCGGACAGCCAATCTTGCAAGACCATCACG
AAAAATCTCACTTTTACTGTTCTCTGGGTCTCTGAGTCCATTCTTTGGGCTTGG
ATGGTGAGTTTGTTTCTCACAATAGCAACAAATGCAACAACAACAGAAGCTA
ATTTTTATTGGGCACTTACTATATGCCAGGATCTGCTTAAAGCACTTTACATG
TGTTAGCTTATTCAATCCTAAAAATAATTCTTCTAATCACATGCCTCCACATT
GTCTTAAGAAACTCATCCTGTGTTCAAAAGCTGGATAATTTTCCAATTTTACA
GAATCAGGTTGACATACTCTACAATCCTAGTCAGCATGATAAAGTGACACTC
ATACATTCATTTGAAAGACTTTAGGGAAATAGTTACTACATTGGCACAGAGA
TGTGGTGCCTCAACTCTGTCATGAAATTAGGACTTGTATGTGTTACAAGAAGA
GGTGTGGATGAACTAAAGAAATTGTTTCTATGAGTAGAGATTTTGAAACAGA
GAGTCCACTGGATCCCAAGTCACTGCTGTGTGAACTCACTCACCACACGGGA
ATTCTCCAAGTACCATCCTGCCTGACTCATTAATCTTATGAAGCACAGAGTGA
TCACACATGCCCCTGAAATGACTGTATGTAAAGTAAATTCAGGCTGTAACAC
ACAAAGTTTTCAAGGTTGGCCTCATAGCACTGTAGATTCCCCCAGCAGATGG
GCAGAGGAAGGAAACTTACTCTGTCTGAGATTCTCTCGTATTTCCAGGGCAA
CAAATCATGCGTAATGAAAACAAAGCAAAGTCAGTACCAGCCCAGGGCCAG
CCATCACCCCACCCAAACCAGAAGGGCAGGAGCCTAATTCATGAAATGTGCT
GTGCTTCTTCCTCCGGCCAGCCAGGCTCGGGGTTTCCTGATGTGTTCCTGGAA
CCAGAGCTAATGGAATCAGGAAAGCATGTTACTTTGCCACTGCCAGTCATTG
CAAGTACAACAAAATAAATATTGCTTTAAAGAAAACAATTATCATAAAGACA
ATTAGTAATGAAAACAGTTATGCCTTCCTTTGTTTTGAGACAGGGTCTCACT
CTGTCACCCAGGCTGGAGTACAGTGGCACAATCTCTGCTCACTGCAACCTCCG
CCTCCCCATTCAAGCAATTTTCGTGTCTCGACCTCCCGAGTAGTTGGGACTAC
AGGTATGCATCACCACATCTGGCTAATTTTTGTATTTTTTGGTAGAGACGGGG
TTTCAACCATGTTGGTCAGGGTGGTCTCGAACTGCTGATCTCAAGGGATCAGC
CCACTTCAGCTTTTCAAAGTGCTGGGATTACCAGCGTGAGCCACCGTGCCCGA
```

Figure 1 Cont

```
CCCAGTTCCGCCTTTCTAAATTGGCCTCTTAATATTTTAGAACATTTCATTCCT
CTGGCCTTGAGTGAAGAATAGAAACTACAGAGGGAAGGATTTGGAGTGGCTA
ATGTTGGCAGAAGTGAGAATCAGAATTATGGAACTGCAAAGTCCTATGACCT
TCCATTTACTGAAGAGGAAACAGAAGCACAGCAAGAGTGCTCAAGAGACTTA
CCTAATGCCACTCCACACAGTAAGTACTGGAATCCGGGACTTGGACTGCCAA
TTCCATGTGCTTTCATTTGTGACATTACTTTTTTTTTTAAAAAAAAAGAACA
ATGTAATGTTTCAATAAAATTTAAAATTTTGGTTAAAAATCACCTATAATCAT
AACCTTCTGATAACTATTATCATTCTTGTATGTTTCCTTCCAACATTATTTTCA
TACATTTAACATAATCATAGCCATTAACCATATGTGTTTCTGTTTTTTTTGTTT
GTTTGTTTGTTTGTTTTGAGACAGAGTCTCGCTCTGTTGCCCAGGCTGGAGT
GCGGTGGCGTGATTTTGGCTTACTGCAACCTCGGACTCTCAGGTTCAACGGGT
TCAAGCAATTCTCCTGTCTCAGCCTCCCGAGTAGTCGGGACTACAGGCGCCTA
CCACCATGCCTGGCTAATTTTGTATTTTTAGCAGAGACGAGATTTCACCATA
TTGCTCAGACCGGTCTCAAACTCCTGACCAAAACGAAGTGTTTTTTTAACCTA
CAATTTAAGTAAATGTTTAATGTTTATTTATAATTTATTTATTAAATGTTTACA
TTCACCAGGCACTATTCTAAATAAAACAATGTTGCTGTCCTCACATAATGAAG
ATTCTGGAGGGGTCAACATAGAATACGTACATAACCAAGTAATGTACAACAT
TCCACCATGATGAAGATAATTTGTTCCTAAATAAAGGTCCTCGTGGGTGAATT
CTCATAGGCTGAAAATGTACCTAACATTCATTTTGACAGAAAAGACACTCTTT
TCTCTTAAGCCCCCAAATTAACACCTATTTATGTTAAAATAACATCAATCCCA
TTAAAACAGGTACAATTATCTCAAAGGTAAATGGTTATCATAGGACTGATGT
CTGTGCTCATAAAGCATCAAAGCAACCATATGATTCTCTGCGTTTATGTAATT
AAATGTTTAATGAAAAAACAAAAACAAAAACATGAGCTCTTTTTGTGGCAC
CTTGGAGGCAATTAGCTGCTTCAGGATGAAGCTAAATATCTCCTCCCCAGCCA
CTGGCTGACAGACACTCATTGGATTGGACAACGAATGGCAATTTTGTACTTAT
GAGAAGCATATGGCACAGAGGTTGCTGCCGACGCTCTGGAAGAGTTATGTGG
TCCGAGTCAGTGGTGGGACCAACGAACAAGGTTTCCTCATGAAGCAGTGTGT
CCTGACCCATGGCTGGGTCTGCCTACTGCTACTGAGTAGGGGCATTCCTGTTA
TAGACCAAGGAGAACTGGAGAAAGAAAGTGCGAATCTGTTTGGGGTTTCATT
GTGCATGCCAATCTGAGCATTCTCCAGTTGGTTATCTTAAAAAAAAAAAAAA
AAAAGGAGGGAAGGATACTCCTGGACTGACTGATACTATGGTGTCATGTTGC
TGGGGGCCCAAAAGAGCTAACAGAAATGCAAACTTTTCAGTCTCTCTAAAGA
AGACAATGCCCCCACCCATATGTTGCCAGAAAGCCCTTAAACAAAGAGAGT
AAGATACTGAGGACCAAAGCACCCAAGATTCAGCATCTTGTTACTCTACATG
TCCTGCAATACAAACACTGGTATTGCTCAGAAGAAACAGCATACTAAGAAAA
ATAAGAAAGAGCCACAAAATATGTTAAACTTTTGGCCAAGAGAATGAAGGA
GACTAAAGAAAAACTCCAGGAGCAGGTACCAGAGACACAGGTTGTCCCCTC
TGTAAGCTTCTACTTCTGAGTCTAGTCAAAAATAAGATTTTTTGACTTACTTA
ACAAATGAGTAAGATCATACCACCCCCAGCAAAATAATCAATAAAGACTAAG
GACATTGATGAAAATGATGGAGAAGATGATGACTTCCATGAGTACTTTAAAG
GAGAAACTTAAAGCAACTTGTATAATTTTTAAGACTGCAGAGCTGACATGTG
GTAACTTATGCTGAATCTGCTCAGTAGCTTCCCACAGCCCCCAAATCTGAATC
ACATTCCTTCAATGTGAAGAATGCCTCATAAGCTAAAGTTGAGGAACTAAAT
AAACTGATTAAGTCTCTGTCTTATGACACCTCCCACCCCCTATCACAGTTCTA
TCCAGGGCAGCATTGACTAGCGTAATAGCAGGGTGTGATATGTGGTAGGACA
GATAGGATGGGGAGGACAGGGAATGATGTTAGGTGGAGATGGGGGAATGAC
```

Figure 1 Cont

```
AAGGAGTCTGGTGTGAGGGAGCCCACTGAGGGAGGGCTAGGTGGTAGAAGC
TAATGCTGGCCAGGTAGCTAGGTGCTAGATTAGAGAGCACCTTGCTAGCCAC
ACTGAAGACCTGAGTACTTTGGAAGCCAGTGGAAACTTCTGAGCAAGGAGTG
ACACAATCAGACTCATATGTGAGAAGGAGACTGTGGGTGAGGGAGATAAGTT
AGGTGACTATTGTGGGGTTCAACTGAAAGAGGAGGTAAAAGCATGGGTCAG
GGTTACAATGGTGCAGACAGAGAGAAATAGTTATAGTTTATCTGTAGTTTGA
ATATAAAACCAACCGGATTCCCTTTGAATTGAATATGATACATCAGGGAAAA
AGAGGAATCAATCTTAGTGCATACTCTATGTCAGGCCTTGTTCCTATGTTTTA
CATATATTCATAACAATAAAAATAATATCAAATGCCTTTCTAATACCTTCCCT
ATGCCAGATTCTATATGCTTTAATCTACTTTCACCCACATCACCCTTACTGCA
ATCCCATAGGGTAGGCACTATTATCATTTCCATTTTCTGATGAGAAACTGAGG
CACAGACAGGAAGGGCAATGCACACGGGAAATGCTGGAGCTGATTTTAGAC
CCCAGACGTTCTGGCTGCAGAGTTGAGATTCACAATCACTGCAAACACTGCA
TTCCATGGTCACAAGGTTTTGGTCCGAGCAGTTGAGTGGGTGATGTTGCTATC
GACCAAGACAGGAATACCTGAGGCAGAGCAGGTTTGGGGGAGTGGATAGCG
AAGGCCTGGGTTTTTGGCCATGCTAAGTTTGGGATGCCTGTTAGACCTCTAAG
TGGAAATGTTGTGTGGCCATAGGGTGTGAAGAATCTGGAGTTTAGGAAAGGA
GCCAGAACTGGAGATAGCTGAGCTATATGGAATGATCAGCTCATAAACAGAA
CTTAAAGCTGCGGGACAGGATGAAAGTACTGAGGAAGACTAAGTCCTGGTCA
CTCCAGCATTTACAGTCCAGAAATAGGAGGAGCTCCAGCAAAAGAGATTGGG
AAGGAGTGACCTGTAAGGCTGGAGGAAACCAGGAGAGTGTGCTGGAAGGTA
AAAAATTTCTAGGAGGGAATGATCCACTCTGTGAAATGCTGCTGAGAAGTCC
AGCAAAGGGAGGATGCTGCCAGATGTCATGATGCTCAGTTTAATTGTTGCAT
ACAACTTCTTCAAGTGGAAGAATTCTCTTTTTATCTACTCTTGCATTTTCAACC
CCTTCACATATAGCTCACAAAGTAGAGGAAGAGAGCTCATCTAACTTCAACG
TGAAGTTGTTAATTTGAATTCAGTTTAAATATTTATTGGGTGTCAGGTATGGT
ACTAGGCCACAGAGATTCAGGGGTAAGTGAATCACAGAGTTCTTGCTTTTTTT
TTTTTTTAGACAAGGTCTCGCTCTGTCACCCAGGCTGGAATACAGTGGCAAT
CACGGTTCACGGCAACTTCTATCTCCTGGGGCTCAAGCAATCTTCCCACCTAA
GCCTACCAAGTAGCTGGGATTATAGGTACATGCCACCACATGGGTATTTATTT
TATTTTTTGTAGAGATGGGGTCTTGCCATGTGGCCCAGGCTGGTCTCTAACTC
CTGGCCTCAAGTGATTTTCCCACCTTGGCCTCCCAATGTGCTGGGATTATAGG
CATGAGTCACTATGCTGGGAGGGTTCTTGCTCTAGACAATGGACTAAGCAAT
GAGAAGGAGGAGGGGAGGGAAAATAGGAGGAGGAGAATGATGAGGAGGGG
TGCTGGGGAGGAGGGGAAAGGAGAGGAGAGGGAGAAGGAAAGGAAAGGGA
GAAGGGAGGAGGAAGAAGTGGAGAAAGAAGAATACCATGATAATATTAATA
TTAACATTTGGAGGTTGCCTAATGAACTCAGCCAGAACACCCCATAGAAAAG
CCCAATGGTTGACACACCTCCGCTTAACAGGCCATAAAGTACTAGGGGGAGA
ATAAAGGCTTTTTCACATATGCTCATTCTCAAAATAATGATCTCCTGTGCATG
CTTTCTCAGGACGCTACTGGATGATATGCACGGCCAAGACAAGGGAGTATCC
AAAGAAGAAACATGAGATTCAGGCAATAAAGAATCAGTAGGATACAGGCCA
GAATAATTCCCACCATATTTTAAACTGAGATCCCAAGACAAACACTGTGCAC
CAGGTCTAGATAACAATCAGTCCACATTGATTGCCTGATTTTCAAAACATATT
AAGTGGAGGTTTACGCTCTTGGGGAAGAGTTTGGGAAGGAGATTATGGGGGA
AGGTTGCAGGGGGTGTTTCATTTTTGATTTTGTTTCTGAGTATGTAGACATTCC
CTTAGTTCCCCAGTGTTCAATACAGAGGCCGCCTCACAGTTACATCAGTGTTC
```

Figure 1 Cont.

```
CCTGTCCGGAGTCTCCTGTTAAGTTCTGTGAGTAAGACTTCAGTCTTCTGCTA
GGCTAGGGGAGGGACAGTTGCCCAGCTGCACAGGGTAGGCAAGGGGATAGG
TGAAATGTCCCTTCATACAGATTTGCAACCAACTCTGTTTTTAAGTCTCTATC
CCAACATAGGCCCTGCTTCAAGAGCTATCACAACATCCAATTCCTGCTCCTTT
TGGGGCTTCTGAGATACAAATAAGCCTGCTTCTAAGACCTTCTCATGCTGCTG
TCTTGAATTTCAGCTTTCTCTGCTTTTCTAAGTGAGTCTCTTCTTATTCACCTG
CTTTTTGGATCCCAGAATTATATGAGTGTTTTGTTTTTGTCTCTTACTCTCTTT
ATCCTTATGACTAGAGTCATTTTTGTGAAGTTTGGAAGGGAACAAAAGGTAA
AATATGTGCTCAATCTGCCACACTGTTTAAAAAGTGGTTTTCTTTTTAAATTA
CCAAATATATGCATACAGTTTAATATATATTATAAAGTGAATGATCATTAACC
AACACTCAAATCAAGAAATAAACATTGCTAGCTTCCCTAAAGCCCCCCATAT
GTCCCCACCTGATTACAACTAGTTCTCTCCCTTTAGATGTGACACCATCCTAC
CTTTTATGATTACTGCTTCCTTCTTTTCCTTTACAGTTTTACCACCTATGTATCC
ATTGTGAAACAACTGAGTTTAGCTTTGCCTGCTTTTGAATTTTATGTAAATAG
AGACATATGGTGCATATTCTTTTGTGTTTGGTTTCTTTTACTCAGCTCTGTAAA
ATTCAACCACATCATCATTACATATATCCACTTTGGTTATACACGGATACCAC
AGACTATCCATGTTACTGTGGATGTACTTCTGAGTTGTTTCTAGTTTGGAGTA
AATCTTAATGCTATGAATATTCTTGTACACACTCTTTGTGCACATATACACAC
GTTTCATTTGGTATGCCACAAGAAGTGGAAATTCTGTGGCACAGTGCATAAA
CATCTTCATCCTTCTAGATATTATCCGTTGTTTTCCACAGTGCTTGTACCAGCA
GTCTATGCAAGTTCCCAGTGCTCCACGTTTGTGCCAACATTGGTATTGTCTGA
CTTCAGTGGTGGCTGTACAACCTAACGTGTTCAGCTGGAAATACCTTGTTAAG
TTTTCCATGTACCTTCTATCGCTTCATCACTGCACTTTTGGAAAGAGCTTCTAA
AACTCCTTTCTTATAGAGGGCAGACCCATAAGGCAACCTACATGTTCCATTGT
TTTTTCTTAGAGAAGATTTCAGGTAGAGCTTCTGACAACCTGCTCCAATTGGG
ACTAGCTGCTCACTAATTCTGCCTCAATCATCCGTTTCCTGAATCTCATGTCTT
TTTTTTTTCTGCATTTTTCCCGTTTTCATAGAGCACATCTTCCAGAAGCTTCA
TGAGAAATGATGTGTAAGGAAATACTATTTTTGAGACCTTGCATATTTGAAA
ATATCTTTATTCTCCACTCATAGTAAATAGTTTGGGTAGAGAATTTTAGGTTG
GAAATAATTTTTCATAAAAAACTTTGAAGGCATTTTTATTTTCCTCTAGCTTTC
GATGTTGCTGTTGAGAAGTCTGATGCCATTCTGATTTCTGATCTTTGTATATG
ACCTATTTTTTTTTCCCTCTCTATGGAAGCTTTTAGGATTGTCTCTGTGTTTCTG
ACATTTCACAACAGAAGTGAATTGTTAAATTCACTACACACTTGGTGAGCACT
TTCAGTATGAAGAATATGTTCTTAAGATTTTGGAAATTTTCCTGAATTTTCCT
TTGATAATTGCCTTCCCTCCACTCTTTCTCTAGAATTCCTAGAGTCATGTTTTC
AACCTCCAGCATTAAACCTCTAATTTTCTTTTCTTTCCACTTTTATTTTTCATCT
CTGGGTATTTTGTTCCACTTTATAGAAGCTTTCCTCAATTTTATCTCCTAACC
CTTCCACTAATTCTGCTCCTATATTTTTAGTTCCAAGAGCTCCTTCTTATTCT
TTATATGTGACATTTTAATAGGAAACTCTTCACATTTAATGAAAGCAAAATTG
TCCTCCTTTTTAGAAAATGGTAACTAGTTTAAAATGTTTCTTTTGCCTCTG
CATTTACTGTTTTCTCAATGTTTCTTTACAGTTTATTTGGACTCTGTCTCCTA
TGTGAAAGGTTTTTCCAAGTGGCTAGTGATCCCTAACTGACCAGTTCATGTG
AAGGGGAGAGGCACCATGAGCTAATCAGAAACTTATGCGGAGGGGGACAT
ACAGATTAGAGGGTCTCACTTTAGGATAACCAGGTGGGAGCCCTGTCTTTTA
TAGCCTCTAAATGCCAGTTTTTGTTTTGTTTTGTTTTTGTCTATTCTTTGGGC
TGCTTGGTTTTTCTAGAAAGGAATTCTCTCCAATCCTGCCTAAAATAGTGTAA
```

Figure 1 Cont

```
GTCTGGTATTTAGCATTCTGGGAGCCTGGTAGGGGAAAGGGTGGATGGGTCA
GGGATGGTGGAGTGTTGTCTCACTCTTCATTAGGCGAACTTCTCTGATTTTTA
TTTTCCAGTAAAATGCCTTGCTCTAGCCCTTAGCTGTGACTAGTGCCCTTAAG
CCAGAGTTTTTTGGTTTTTGTTTAGTTTAACCTCTCCAGAAAGGGTATCTTTAG
TTTTCTGTCAAGAAGAAGGGAGGAGCAGTTACCTGGCTGCCCAGTCTAGGAG
AGGGGAAAGGATGTGGTCTCTAAGAACTCCGTATATGAGTCCTTGGGTTTTTC
ATTCTACCTCATATCTCTGCCTTTAGAGGTATACAGCATATCTGATTTTGGAT
ATTTCTTAGGGGATGTATTAGTCCGTTTTCACGCTGCTGATAAAGACATACCC
TAGACTGGGTAATTCATACAGAAAAAGAGACTTAATGGGCTCACAGTTCCAC
GTGGCTGGGGAGGCCTCACAATCATGGTGGAAGGTGAAAGGCAGGTCTTACA
TGGCCCCAGGGAGAATGAGAGAGAAAGAGAGAGAGAGAAAGAGAGAGA
GAGAATCAAGCAAAAGGGGTTTCCCCTTATAAAACCATCAGATTTCTTGAGA
CTTATTCACTAACATGAGAACAGTATGGGGGAACTGTCCCTATGATTCAATTA
TCTCTCACCAGGTCCCTCCCACAACATGTGGGAATTATCAGAGCTACAATTCA
AGATGAGATTTGGGTGGGGACTCAGCCAAACCATATCAGGGAGCACTATAGC
ACAGATTGTTTTGTTCTTGTTGCCTTTCATCTTTTATGGTATTTAACAAATGAA
GAAGGCTAAAATTGAAGTTAATTTCCACTTGTTTGTCTGCATTCATTCTTCCA
AAATTGTATTGAATACAGTCGATAAATTGTATTTATCTGCAGTCACCCCTTGT
CTCCTTCTCTTTGTCCCTATAAGCTAAACACCTTTTTTATTCCTTTAATGCCAT
TTTAGTGGAGTATATACAATCCATACATTTTCCTAGGTATTTTCTTTCTTCAT
TCATACTTTCTATATCCAAAAGAGGATTTGAGCTTGTTGCAATAAAATATACA
TATGCGAAAAAGTTGAAATTTGGGAAAAGTAAAAAATATCAAGTAGTAAAA
GAAAGGAAACACCTGTGGTGGAAATCTAGGCTAAGGATATAGGCCGTGACTG
TACAAAGGTTGGCCCTTACTAAACACCTTGGCAGTTCTGCTAAAAGGAGGAA
CAGGAGGAATTTCTCAGCCCTCATTATCTAACAGGAAGCACTCCAGGGCATC
AGATAAAACTTCTGCTAAGTTTACTGAGTGAGTTGATTCTGTAACTGAATAAA
AGTTCTTGGTGCTCCAACTTGGAATTGATTCTACTGAAGAGATTAGAGTGAGA
CCCAGATAAGAAAAATAAATAAATAAAGATAGATGTGAGGGGTAGGGATGC
TAAGTCTTGATTGATTGGCATCTTTCCCAACTCAAGCACTGTGATGACACCAT
CTGTTGTTACTCACTCTATATTCCCAATTTATTCAGGGTTTCTAGGTGGAAGG
ACATTAAGAAAGTACCCTGTAGAGGAATTCTTATAGTCTTCTCTTTCTTTTCC
ATTTCAACAGGATATTCTCAGAGCCCTCTAGCAACTGTGACTGTGATTTCAAG
GCAAGAAGTAAACAGACAGTAGGGAATTATGTTAGGAGTATATATTCCTTTA
CTTTTCCTCTCAAAGAGAGAGAAAATAGGCTTTTTTTTTTCCTGATAAGAAA
GTGTATGAGTAAGCCTAGATTCAGGGCCCAATAAGATCATGCTCAGATTTTC
AAATTACAGTTTTAGAAATTTTGGGGGAAATTCTTGATGCCAAAAGGCATTGT
GAAATAGTATCAATACAATTGCAGGTTTAGCATTTTCTTTATGCAATAAACAG
TACAGGGCTCTGGGGCTTTACAAAGATGAGCAAGCAACAGTCCCTTTTCCCA
AGGAGCTTACAGTGTCTCACAGGAGATAATAAAATGACACAAGTGATTAATA
GAGGAGAGAGCTTCAGAATGTCTAGCCAGCTACACATGTCTAGCCACCTGCC
TACATGGAGACCCAGTCCCCTTTTCCCACCCACAAGGTGAATCTGGGAAGCC
ACAAACAGGAACCCTGCCCTTCTAACTGCAGCTGATTAAATTAGAGGTCAAG
AGATACGTGACCTAAGGAAAACCAATTGGATTTCCTCTCCAAAGATTTAAAA
TTAGAATTCAAAGGTGCTAATCAGTCTCTGCTGTCCACTGATTTAAGGGCGTA
GAAGCACTGGCTTGGATATTTCTGACCAGGCACCAGTGGCAATGCAGAGAAA
ACACATCTGGAGAGAAAGAGGCATGCAGAGTGGCTTTCCAGTCCTGCTTTTG
```

Figure 1 Cont.

```
GCCTCATGGGATCCATGAGATACTCCCATATTAAAAGTTTTGATTCAAACAAC
TGTAATACAATACTACTGTGAAGACTATGAAATATATGCTAAGGGGGCTCAA
AGAGGGAGAGAAAGCACATATTATTGTGGAGCAGGTGGGATTAGAAATAGT
GAAATATTACATGAAAATTTTTACGACTGAGTTCACCTTAAATGATGGGTA
AGATTCTAACAGGAGGAGATAGGTTGAGAGCATTAATTAGTGAAAGAACCAT
ATGGGGGAGAGAGAAACCAGGTGTGTATGTTCCAAGGTGCCTGGGGGTGGTT
AGGTTTTATGATGAAAATTAAATAGCTCTTGGAGTAGATTCTATCTTTGCATC
AGCTATGACGCAAGTCAGCATATTCTAGGTCCTTTCTCCACTTGGAAAGAATT
ACTGCCAATTATCAGTCCATTTCCATTGGCTTCCCTCTAACTACTTTGCTTCAA
AAAAAATGAAAGTTCATTTATTCCTATAGTTCTATAAAAGAAATCTACTCAA
AAAGATGTGAAATGACTTATAATGCAATACTGTAATTTTTTATATAAACTTCA
TCTTTGTTTCCTTGTTACAGGATAAGTGGTAAGTAAATATTGCCTAGTAATGT
GACATGAGTAACAGAAAATACAAACTTATTTTCGCCCTAGGGAAGCCTGCTT
ACTTTTCTTGACCCTCTTCTCAATATCTATCTATAATCTTCAGATATAGCAAAG
GGCCAGCAACCACTTTTCTGGGAAAAAAGATATTTTGCCAAACTTTGAAAA
CACACCAAAATATGGGACTGAAAAATAGTGCATATATATCAATTGAGTGCAG
TGGTCTGATCATAGTTCACTGCAGCCTCGAACTCTTGGCCTTAAGGGATCCTC
CTGCCTCAGCCTCACAAAATGCTGGGATTACTGGTGCCTTGCCCTATTGTTTA
AACTAACATTTTTCATAAAATACTAAATGTGAATATCTTCCAAAACTTGAAAG
AACTATGCAGTTATAAAGCATTATAAAAATAGGCATATTAGATATTTTTATAT
GTTTTTAAGTTCATTGATTAGCGAGAGGAATAAAACTGAACTCAGTAGAAAA
GTTTTGGAGAGAAACAAAAAAGTGAGGATTTTACCTTATAGCTAACATTAT
CTACCTCATTTAGAGAAGGATCTTGTTTTTATACTATAATCCTTTTAGACAAC
AAGCCAATGAAATTTTAAATTCAAAGGCAACTCAAATGATTCTTGACAAGGG
TGACAAGACTTTTCAATGGAAAAGGGTAGTATTTTAAGCAAATAGTACTAGG
AAAACTGAATATCTACATGCAGAAGAATCAAGTTGGACCCTTACCTAACACT
GTATACAAAAATTAACTCAAAATGGACCAAAGACTTTTTAAGACCTAAAATG
ATACAATTCTTAGAAGAAAACATAGGTCAAGTCTTGAAGATATTAGAGTTGG
CAATGATTTCTTGGATATGACACCAAAGGAACAGGGCACAAAAGTCAATAAA
TTGGATTGCATAATGATTTAAAAATTTTGTGCATCAAAAGACACTATCAACAG
AGGAAAATGATAACCCACAAAATGGGAGAAAATATTCACCAACCATATACCT
GATAAGCGATTAATATCCAGAATATGTAGACAAATCTTACAATTCAACAAAA
AACAATTTAAAATGGGCAAAATACTTAATAAACACTTCTCCAAAGAAGATAT
GCAAATAGCAATAAGCACATGAAAAGGTGCCCAACATCACTAATTATTAGTG
AAATGCAAATCAAAACTACAAGATACCACCTCACACCCATAGGATGGCTACT
ATTTTTTTTAAAAAGAAAATAACAAGTGCTGACAAGGGTGTGGAGAAATTAG
AATGCTTGTGCACTGTTGGTGGGAATGTCAAATGTTACAGCCACTGTGGAAA
ACAGTATGGCAGTTCTTGAAAAAAAAATAGAATTAGTGTATGATCCAGCAA
TTCCACTTTTAGGTATATGCTCAAAAGAATAGAAAGTAAGGATTTATGAAAC
ATTTGTATATTCATGTTCTAGCAGCATTATTCTCAATAGCAAAAACATGGAAG
TAACCGAAGTGTCCACTGACAGATGAATGGATAAGCAAAATGTGGTATATCC
ATACAATGGAATATAACTCAGTCTTAAAAAGGAAGGAGATTCTGACCTATGC
TACAATGTGGATGAATCTTGAGAGTATTATGCTAAGTTAAATAAACTAGTCA
CAAGAAGACAAATGCTGTATGATTACACTTATATGAGGTATTTTGAGTATTCA
AAACCACAGAGACAAAGTAGAATGGTGGTTGTAGGGGGTTAGGGGATGGGT
CAATGGAGAGTTAGTGTTTAATGGATATAGAATTTAAGTTTTACAAGATGAA
```

```
TCTGATATAGCTTTTTTATCATACACTAGGCTAGACTAAATGCATTCTGTGGATTGTTTA
CCTAGGACCAGATGGTATATTATAAAGTTGTATACAAATGAACAAGGACTGCCTGAAATG
GATTGATAGCTGAGCACATTTGGCTGGAGCGTCTATTTTAGAAGGAAAACCTGAGAATCA
TATTATTTGAGTGTGATTCATGTGTTAATAGTATTTCAAGACAAGCCACTTAAAATATGT
CCTGAGTGGTGATGCTGGAAATGATCTTTTCTTCAGTGTTTTCAAGTGTCTTCATTTAAG
TGTACACATTTTGCCTACCTATAACACGTATCTACACATTGTGATTAAGAGAGCAAACTC
TGAAATCAGACCTAGATTAAAGATCTTAATCTCTGCCAGTTGATTGGGCAAGTGACTTAA
TCATTCGACAGTAATTTCTGCATTTGAAAATGCCTATCTCAAGGGTAATGAGAATTACAC
TGGTTCACCAAAAGAATTACACTGACTAATATAAAACGTGCCAAGCATGTATGTGTCACA
TGAAGGCTCATTAAAAGTGGATATTATTGTTAATCTTCCAATAACTACTATTTCCAACA
ACAGGCTGAAGGGGCTCAGAAACGTTGTTGAGTAAAAACACAAGGAAACAGTAGCACAG
ATTTCCTGCTCTCCTTTACGATCGATGACCGTCTAAGGACTGTGATCTCTGTTCGCTACA
GATTGTCACCTGCATTAATCTACTGTCACCCATTAACCTATCAAATAAGGCAGTCTAAAA
ACTCCAGGCGTCCCTTTCCGTAAGGACCCGGACTGTTGAACTGGAAAGCTAAAATTCAAG
GCGTGACAATTGCCCTTTGTCCCACATTCCTCCACCGGTCGCCTGCTTATTTAAATGGTG
CGTCCCCTCGGGTACCACTTGAACAAAACCTGCCCAGAGCGCTCCTGTGTAGATTCGCT
GGAAGCAGCTGGAGGCTCCAGTTCTCATCTGCTCAGGTGTCCCCGGCGCCTTGGCGAACT
CGGCCACTCCAGTTCCTCACGTGGTGAGCACTCAGGGCAGCGGGTCGATTTTCCGAGGTC
CCATACCTGGGTTTGAGGGGCGCGGCTCGCAGCGGCGGGTGCAGGGCGACTGCCAGCCC
TCACCCCGCCTCGGGGTGCGTTCGGAGGCCGACACCTGGAGGACGCCTCCAGTCCCCGCG
GGACGCCACGCCTGCGCGCCAGGGATCCGGGATAAGAAGTGCGCGCCGGGCTCCGGCTGC
GCGCCGCGGGGCCACCAGTTTGCGCGCAGGGCTCAGGCGACCGTGCGGCCATGGACACGC
CACGGGGCATCGGCACCTTCGTGGTGTGGGACTACGTGGTGTTCGCGGGCATGCTGGTCA
TCTCGGCCGCCATCGGCATCTACTACGCCTTCGCTGGGGGCGGCCAGCAGACCTCCAAGG
ACTTCCTGATGGGCGGCCGCAGAATGACCGCAGTGCCCGTGGCGCTGTCCCTCACCGCTA
GCTTCATGTCAGCCGTCACTGTCCTGGGCACCCCCTCCGAGGTCTACCGTTTGGGGCCA
TTTTTAGCATCTTTGCCTTCACCTACTTCTTTGTGGTGGTCATCAGCGCGGAGGTCTTCC
TCCCGGTGTTCTACAAACTGGGAATTACCAGCACCTACGAGGTAAGGGGCAGGGTGGGCT
GGGACCATGCAGGGCGCGGGGGAAGGGGACTCTGCAGACCTCTGGAGGCGTTTTCTTGGG
GGCAGACTGTCACTGCCACATCGAAATCTCTCCCCGTCCATCGTCATCATCACCCTCCCT
TCACTCCTCCCCGTCCCCGATCTTCACCTGGCATCTTTCCCTTCTACTGAGAGGCGTCC
TCTAAGGGTGAAAAATTCTTGGGATTTACTCTCCTGGGCTTAGTGAAAAAAGAGGCTT
CCAAAGTGAACGGATTGCAACAGTAGTGCTCGCTATGGTCCTTTCTACCTTTAGCATCTT
TGATTCCCAGGCAAGGGGAAGATTTTGGGGAAGGTAAGTTCTTCAGGTCTCAGGCCCT
GCTTCTTGAAAGGAATACTCTTGTTCCAGGTCCTCAGCCCCATTCACTCTTCCAAGATAG
TTGGTAAAGAATTTGTACTCCCCTTCCTTCCCCTTCCACACCCACCCCCTTTCCACTGAA
ACAGGCACCCAAGTGGCTAAGGTGTACCAGTACCTGTATTTCGGACCAGATTCTACCACT
TACTAGCTGGGTGACCTTGGGTGACTTACCCAACCTTTTGTGCCTATTCCTCAAAAATAA
AATAATATCACCTACCTCATCCAGTTGGGAGGATTAAATGAGATGATGCAAGGTGTAGCA
TTTAGAATAGAGTTTGACACAGAGTAAGTGCCAGATAGGTATTGGCCATAATTACTGTGG
TGGTGCTAGTTGTGATGGTGGTAGTTATCTTGGGATCAGTAGGAAAATTAGGCAGCAAGG
TTCTCAAACAGCTCTGCCTTCTCTATGGAAAGACAATTAAGGAAACTGTCTTTCCTCTA
TTGCACAGGTCCCCTGGCTATAGGTTTTCTCAAGTTGTCTGCAAGAAAGGGCTTTGAAAA
GATGATGCACGTTTAGTTTAAAGAGCTGTTGAATGGGAGGTGGGGCGGGATCAAAGCTC
```

```
CCACCACAAGAACTGTATGGGGGAAACCACCCCCTTGATTCAATTATCTCCTA
CTGGGTCCCTCCCATAACACATGGGAATTATGGGAGCTATAATTCAAAATGA
GATTTGGGAGAGGACACAGCCAAACCATATCATTCTACTCCTGGCCCCTCCC
AAATCTCATGTCCTCACATTTCAAAACCAGTCATGCCTTCCCGACAGTCCCTC
AAAGTCTTATTTCAGCATTAACTCAAAAGTCCACTGTCTAAAGTGTCATCTGA
GACAAGGCAAGTCCCTTCCACCTATGAGCCTGTAAAATCAAGAAGCAAGTCA
GTTACTTCCTAGATACAATGGGGGTACTGGCATTGGATAAATATACCCATTCC
AAATGGGAGAAATTGACCAAATAAAGGAGCTAAAGGCCCCATGCAAGTCCA
AAATCCAGTGGGGCTGTCAAATCTTAAAACTCCCAAATGATCTTTTTTGACTC
CATGTTTCACATGCAGGTCACACTGGTGCAAGAGGTGGGTTCCCATGGTCTA
AGGCAGCTCCACCTCTGTGGCTTTGCAGGGTACAGCCTCTCTCTTGGCTGCTT
TCACAGGCTGGCATTGTCTGTGGCTTTCTCAGGCACATGGCACAAGTTGTTGG
TGGATCTACAATTCTGGGGTCTGCAGGATGGTGGCCCTTTTCTCACAGTTCCA
CTGCGCAGTGCCCCGTGGGGACTCTGTGTGGTGGCGTCAACCCCACATTTCC
CTTCTGCACTGCCCTAGCAGGTGTTCTCCATGAGGGCCCTGCCCCTGCAGCAA
ACTTCTGCCTGGACATCCAGATGTTTTCATGCATCTCTGAAATCTAGGCAGAG
GTTCCCAAACCTCAATTCTTGACTTCTGTGCACAAGCAGGCACAACACCACAT
GGTAGCTGCCAAAGCTTGGGGCTTGCACCCTCTGAAGCCATAGCCCAAGCTG
TACCTTGGCCCCTTCTAGCCATGGCTGGAGCAGCTAGAACACAAGACACCAA
GTCCCTAGGCTAGACACAGCAGGGGGTCCTGGGCCTGACCCACAAACCATTT
TTCCTCCTAGGCCTCTGGGCCTGTGATGGGAAAGGCTGCTGCAAAGTTCTCTG
ACATGGCCTGGAGACATTTTCCCCATTGTCTTGGAGATTAACATTTGGTTCCT
CATTACTTATGCAAATTTCTGCAGCAGGCTTGAGTTTCTCCCCAGAAAATGGG
TTTTTCCTTTCTATTGCATCATCAGGCTGTAAATTTTCCAAACTTTCATGCTCT
GCTTCCTTTTAAAACTGAATGCTTTCAACGTCACCCAAGTCACCTCTTGAAT
GCTTTGCTGCTTAGATATTTCTTCTACCAGATACCCTAGATCATCTTCCTCAAG
TTCAAAGTTCCACAAATCTCCAGGGCAGGGCAAAATGCCATCAGTCTCTTT
GCTAAAACATAGGAAGAGTCACCTTCACTTCAGTTCCCAACAAGTTTCTCATC
TCCATCTGAGACCACCTCAGCCTGGATTTCATTGTCCATATCATTATCAGCAT
TTTTGTCAAAGCCGTTCAACAAGTCTTTAGGAAGTTCCAAATTTCCCCACATT
TTCCTGTCTTCCGAGTCCTCCAAACTGTTCCAACCTCTGTCTGTTGCCAAGTTC
CAAAGTCTCTTCCACATTTTCAGGTATTTTACAGCAGCACTACACTGTACCA
GTACAAACTTACTGTATTAGTCCATTTTCACACTGCTAATAAAGACAAACTCG
AGACTGGGTAATTTATAAAGAAAAGAGGTTTAATGGACTCACAGTTCCACA
CGGCTGGGGAGACCTCACAATCAGAAGGAGAACGGTATGGGGGAAACCACC
TCAATGATTCAATTATCTCCCACTAGGTACCTCCCACAACATGTGGGAATTAT
GGGAGCTACAATTCAAAATGAGATTTGGGTGGGGACAGAGCCCAACCATATC
AGTTGGGCAGCCAGCCATCTGTTGTTGGGTGATTTTACCAAAGTGCATCTTT
CTCTGTACAATCAGAGGCTTCCACCTCCAGAGAATGTGTTATCTTAATCCTCT
GGCTGGATGCTTATGAGGATAGAGTAAACTGGCAATGCGCAGTGAATCTTGG
GAGGGGTCATCCTTACAAATAAAGCACTACAGTTTGGTAGAGATGGAAGAAC
TTCAGATGCAGTGGATGCTGTAACCGATGGCTTTTATGATGGTATTTCATGGT
GATAGTGTGAGAACGCCAGACAGAGGGAACAGGTGACAATATTGTCTCTGTC
CAAAAGAGTCATAGTAAATGCAAATCTGCTTATCATGCTATTGAGTTAGGTA
CTAAACTTTGCTATGCCATCCAGTTGTAAAACCTAGAGCCCCAAAGAAGAGA
ATAATAAGATAGAAAACAACACAACTGATCTTTTGGCTAACACTAAGTCTGG
```

Figure 1 Cont.

```
AAATTACCCTTCCATTTGAGATGATTGCCAGAAAAATCATCAATATATATCCT
ATGAAAAACTCCTGAGGGGCAGAGGAATGGGATCAATGCTTCAAAGACTCA
GAGAAAGAAAATCACTATAAAAATTATTTGCTCCTAGAATGTAAAAAATATT
TTAAGAAAACTGCTTGGCATTCTAAAGGTGAAAAGACTTTAGAATGAGATAA
AAGGGAGAAGATTACTTTTAAAAATTCAGCGACATTAAAAATGTAATGACAG
AAGTAAAATCTACATCGGGAGTAGGAATGTAGACTCCTGTAGCATTACTATG
ACAGACACCAGAGTCAATGACATGAAAGACAAACTTAAGATCTTTTCAGGTA
TGTGGTAAAAGAAAAAGGATTCAAGTGAATGATATAGAGGACTGGGGCTG
GGCATGGTGGCTCACGTCTGTAATCCCAGCACTTCGGGAGGCCAAGATGGGC
GGATCACGAGGTCAGGAGATAGGGACCATCCTGGCCAACATGGTGAAACCCT
GTCTCTACTGAAAATACAAAAATCAGCCGGGCGTGGTGGTGTGCACCTGTAG
TCTCAGCTACTCAGGAGGCTGAGGCAGGAGGATCGCTTGAACCTGGGAGGTG
GAGGTTGTAGTGAGCCAAGCTTACACCGCTGCACTCCAGCCTGGGCAACAGA
GTGAGACTACATCTCAAAAAAAAAAAAAAAAAAAGAAGAAGAATATAGAGG
ACTGGATAGATTTATTTAAGAATTATACATTTCTGAGGAAGGTACTAGAAGA
ATTAGAACAACAATAATTAAAGATATCACTTTAAAAAACAAGACCTGACTAT
TCAAATTGAAAGGACTCACCATTCTAGATGATAGTAATGAAAGAGGGCTAT
TCTAGAAATACCCTGGCAAAGGTTTGGGAATGCAAGTATAAAGAAAAAAATC
ACATCTATTAGTATTCTGTCATAAAGCAAGTAATTTATGAGGAAACAAAAT
CTAGCTGTTCTCAGATAGCTCTCCAGTAAGAAATGCCAGAAGACAACAGAAA
AAATACTTAAAATTCTTTGAAGAAAAGACTATGACCTAAGAATTTTCTCAG
CTGAATTTTTTTTCTCATATGTGAAGACAACAAATGAACAATCCCATATATTC
AAAGGCTCAGGAAATAGAGCATTCATGTATTCTTCATGAAAATATTATTTGG
AGACATACATCAGACACCCGAAAGATGTGAAAGAAGAATAGGGTATGGATT
ACACATAGTTCATGGCATTATGTAAATGTTATAAAGCAAGATGACATAGCTT
GGGAAAACAAAAGCTGTGTCTAATAGCAGTACTTCCAAGCCATAACTTACAG
TAGCCCAATTCTCAATAAATTGGAAGGCAGCTAAACAATCATACAGTGCTAG
TATTTTATAGTGTCAGGGTCTATTCACATATAATCTCATTTAACCCATTTTAAT
TCCGTGAGATAAAAACCAATATCCCCATCTAAGATATGGGAAACTAAGACGT
AGAAGAAAGCACTTGGCTAAGATATCATGGCTCGTAGGTGGCAGTCAAGAGG
TCAGTTTGCAGTCTACAGATTTAACCTCAGACTATTCTGCTTCTAACATGACT
ATAGAAATGTATTGATCATTAGCTGCCTGAAGTTCTGTTCTTAACTCTAGGTG
TCCAAAAGAAGATGAATTTTGTTTAGATAGCATTTTCCCATATCTAGGGCTGT
TGGCTTTAAAGAAGTTCCCAGAAGTGAATCCAATTCCCAGAAGGATCAAGGT
GGATTCTTTTGTGTGTTACTCTAACAGGTTGCTTTATATATATATATAAGTTAT
ATAATATACACATATAATTTATGTATTATATATAAGTATGTATAACATCATAT
GTAATATATAAATATAGTACATTTCACACTGGTAGGACGTAATTCCAAACCA
CATATTTGTTTAACCAATTGAATTACTTGGATTTAGTTTCTATTTCCCTCTTTA
TTTCCTTCTGAAAATATTATACAAATAACATCAGTTTACAAAAAATAAAATCT
GATATAGCTTTTTTATCATACACTAGGCTAGACTAAATGCATTCTGTGGATTG
TTTACCTAGGACCAGATGGTATATTATAAAGTTGTATACAAATGAACAAGGA
CTGCCTGAAATGGATTGATAGCTGAGCACATTTGGCTGGAGCGTCTATTTTAG
AAGGAAAACCTGAGAATCATATTATTTGAGTGTGATTCATGTGTTAATAGTAT
TTCAAGACAAGCCACTTAAAATATGTCCTGAGTGGTGATGCTGGAAATGATC
TTTTCTTCAGTGTTTTCAAGTGTCTTCATTTAAGTGTACACATTTTGCCTACCT
ATAACACGTATCTACACATTGTGATTAAGAGAGCAAACTCTGAAATCAGACC
```

Figure 1 Cont.

```
TAGATTAAAGATCTTAATCTCTGCCAGTTGATTGGGCAAGTGACTTAATCATT
CGACAGTAATTTCTGCATTTGAAAATGCCTATCTCAAGGGTAATGAGAATTAC
ACTGGTTCACCAAAAGAATTACACTGACTAATATAAAACGTGCCAAGCATGT
ATGTGTCACATGAAGGCTCATTAAAAAGTGGATATTATTGTTAATCTTCCAAT
AACTACTATTTCCAACAACAGGCTGAAGGGGCTCAGAAACGTTTGTTGAGTA
AAAACACAAGGAAACAGTAGCACAGATTTCCTGCTCTCCTTTACGATCGATG
ACCTGTCTAAGGACTGTGATCTCTGTTCGCTACAGATTGTCACCTGCATTAAT
CTACTGTCACCCATTAACCTATCAAATAAGGCAGTCTAAAAACTCCAGGCGT
CCCTTTCCGTAAGGACCCGGACTGTTGAACTGGAAAGCTAAAATTCAAGGCG
TGACAATTGCCCTTTGTCCCACATTCCTCCACCGGTCGCCTGCTTATTTAAATG
GTGCGTCCCCTCGGGTACGACTTGAACAAAACCTGCCCAGAGCGCTCCCTGT
GTAGATTCGCTGGAAGCAGCTGGAGGCTCCAGTTCTCATCTGCTGAGGTGTCC
CCGGCGCCTTGGCGAACTCGGCCACTCCAGTTCCTCACGTGGTGAGCACTCA
GGGCAGCGGGTCGATTTTCCGAGGTGCCATACCTGGGTTTGAGGGGCGCGGC
TCGCAGCGGCGGGTGCAGGGCGACTGCCAGCCCTCACCCCGCCTCGGGGTG
CGTTCGGAGGCCGACACCTGGAGGACGCCTCCAGTCCCGCGGGACGCCACG
CCTGCGCGCCAGGGATGCGGGATAAGAAGTGCGCGCCGGGCTCCGGCTGCGC
GCCGCGGGGCCACCAGTTTGCGCGCAGGGCTCAGGCGACCGTGCGGCCATGG
ACACGCCACGGGGCATCGGCACCTTCGTGGTGTGGGACTACGTGGTGTTCGC
GGGCATGCTGGTCATCTCGGCCGGCCATCGGCATCTACTACGCCTTCGCTGGGG
GCGGCCAGCAGACCTCGAAGGACTTCCTGATGGGCGGCCGCAGAATGACCGC
AGTGCCCGTGGCGGCTGTCCCGTCACCGCTAGCTTCATGTCAGCCGTCACTGTCC
TGGGCAGCCCCTCCGAGGTCTACGGTTTTGGGGCCATTTTTAGGATCTTTGCC
TTCACCTACTTCTTTGTGGTGGTCATCAGCGCGGAGGTCTTCCTCCCGGTGTTC
TACAAACTGGGAATTACCAGCACCTACGAGGTAAGGGGCAGGGTGGGCTGG
GACCATGCAGGGCGCGGGGGAAGGGGACTCTGCAGACCTCTGGAGGCGTTTT
CTTGGGGGCAGACTGTCACTGCCACATCGAAATCTCTCCCCGTCCATCGTCAT
CATCACCCTCCCTTCACTCCTCCCCGTCCCCGATCTTCACCTGGCATCTTTCC
CTTCTACTGAGAGGCGTCCTCTAAGGGTGAAAAAATTCTTGGGATTTACTCTC
CTGGGCTTAGTGAAAAAAGAGGCTTCCAAAGTGAACGGATTGCAACAGTAG
TGCTCGCTATGGTCCTTTCTACCTTTAGCATCTTTGATTCCCAGGCAAGGGGA
AAGATTTTTGGGGAAGGTAAGTTCTTCAGGTCTCAGGCCCTGCTTCTTGAAAG
GAATACTCTTGTTCCAGGTCCTCAGCCCCATTCACTCTTCCAAGATAGTTGGT
AAAGAATTTGTACTCCCCTTCCTTCCCCTTCCACACCCACCCCCTTTCCACTGA
AACAGGCACCCAAGTGGCTAAGGTGTACCAGTACCTGTATTTCGGACCAGAT
TCTACCACTTACTAGCTGGGTGACCTTGGGTGACTTACCCAACCTTTTGTGCC
TATTCCTCAAAAATAAAATAATATCACCTACCTCATCCAGTTGGGAGGATTAA
ATGAGATGATGCAAGGTGTAGCATTTAGAATAGAGTTTGACACAGAGTAAGT
GCCAGATAGGTATTGGCCATAATTACTGTGGTGGTGCTAGTTGTGATGGTGGT
AGTTATCTTGGGATCAGTAGGAAAATTAGGCAGCAAGGTTCTCAAACAGCTC
TGCCTTCTCTATGGAAAGACAATTAAGGAAAACTGTCTTTCCTCTATTGCACA
GGTCCCCTGGCTATAGGTTTTCTCAAGTTGTCTGCAAGAAAGGGCTTTGAAAA
GATGATGCACGTTTAGTTTAAAGAGCTGTTAATGGGAGGTGGGGCGGGAT
CAAAGCTCAGGGGAGTGGCGGGGCCCAGTTCAGTGCCTTCAGTGGTCTCCCT
CACCCAGCACTGGTCCTTGAGCTACATGGGACAAGCCTGCAGAAGTTTCCTCT
CTATTAGGCCATTACCCAGAGGACTCCAATCCTGAGATTCTGGCAGGTGGTTT
```

Figure 1 Cont.

```
CCTAGTGAGGCTGGTTCAACTGGTGCTGGGGACAGGGCCTTAACGGCACAAC
AAACATTGGTGACACACTCTGCCTGGGCTCTAGTGACATCTTCCAGGGCGAG
GCACCCCTGGGCAGCATTGCCTTCCATTCACTCTGGGGCTGTGTTTGGGAGAG
CTCAATAATTATCCCAGAAGTGAGCAGGATGCAGTTTCTCAGGTTTGCTCAGA
AGCGACAAACTGGCGAAATTCCCCAGACCAAATTCACTTCTCAGTCATTTTTT
TTTTTACTTCTCCTTATAGTGAGAAGAAATAAAATATAATTTCAGACTATGA
CTTCTTTCGAGAACTCAAAAGGCTGGTAACACTGGGCCCATGCTCCCTGTGGC
CACAGGAACTCAAGTTTATAGCTATTGCTCTCACTCTCTATTAAACTTCTATA
TTGAAGTCTTATCTTTGTGTTTCATGGTTACTGTTTTTTGGTAGAGAAATTT
TTATCTGCATTTATGTCTTTATCAAAAAATGTGAAAGGCAAAATGGACAGGG
GTAAAGGGATCTCTTGTTTCCAGGGAGATGTAAGAAAACATATATCTTAGTG
GGTGGGAGGAATATTCCAACATGTTAATATGTGAACACCTGGCCACTGTCAC
TTATGTATGTTACCTGATGGAACCTGGAGGCATCTGAGTCTGTGAGCTGTGAT
CTATAGCTAACCAATTCCCAAACTTGGAAAGGGTTTGAAGAATCTGGCAGGA
GGACTTCAGTCCCCACACATGAATGCTGCTCTCATAACCACTGACCCATGCCT
CTTCGGGGCTACAACATTAACTCAAGCAGAAACAGATTTCCCTCATGCTTGCA
GTGGTAGAGGCTAAGTTAGCAGGGGTTCCAGCTAAAAATGTCAAAAAGCAA
AAGTTCATTGAATGCTGAACACATGCCAGGCACTGGGCTGCATTGCATGTTTT
ACATACATTATCTGACTCACATTCAGAACAATCCTTATGAGGCAAGTACTATC
AAGAGCCCCATTTTGTGGACAGAGACTCAGAGTAAGTTAAGCTACTAGGAAT
GTGAAGCAGCGTAGACATATGCCTAGCAGCATACTGGCTGCTTCTGAAGGCT
CTGATGAGTCTGTTATAACCCCAAGCAATGCTTACGCCAGTGCAGAGAGAAC
AAGGGAAGCAATATAGGACACGTGAAGTTGTGGGCACACTGCAGGCATCCA
CCTCCAGGGTGCCAGGCAGTTGGGAACGGGGAAGTTAGGCAACATGCTAAG
ACCCTCCCAATTGGTCATGGCAAAGACTTTCCTGTGGAGTATATTGTTTATTG
TTTTATGCTGAGAGGTACAGAATCTATACAGAATATGCTGTACAGTGTTGAGT
GATTGATACCCTGGCATTCTTGCTCAAGTATGAAATCTCTCCCTGTTGACATT
TCTTTAGTGAAAATTAGCTGTTCACAAGCATTTTTTTTCATCCATCACTGCCTT
CAAAATGTAGTCCTGATAGGTGTTTAGCAACTTCCAGACCCAAGTATAATGC
AGGAATCCAATTTAATCCACCAATTCTTCAAGATCCTTCTGGAGCCAACTAAA
TCTGTGTTTTAAATTGAGTTGCTTAGACCTTATGTTTCTTTGTTATTTATATATT
TATTCATATCAACAGAAGCAATTCAAAGTTCTGAGGACCACGAGAGATCTTG
ATTAATTTAGGCACCTATCATTACTCTGTAATTATGTCTAGAAGTCTTACAAG
TATTCCCTAAGGCTGCTGCACAGTGACTTGGGCATCTGGTCCAGTCTCCGGGT
ATTTCTTCAGCAGCCTAGTAATTGATGGCTGAGATCGTAATAGACTTCTTGGT
TCTGTCTTGAGTTGGTCCTTGGGCTTAAATCACAGGTTTCCCTGGATCAGTTG
ATTAACTTACTTGCTTCAGTTTGGTTCAATTTATTTGGGTCTCCAGCAATTTGG
ATTCATGTACCTAGAAAAACAAAGACTTCTCTTCTATTGATGTCCATTCACA
TGTTTAGTGATTCATAGAGATTTACAAAACAAACAAACCAAAAATAAACTTC
TAAAGAAATATAATAATACTGCCTTGTTCCCAGACTTAATAAACTTCTCCAGT
CTTCTAAAAAGGCTTCCAAAATATCCCTGAATGATTTTGACACTTGTAATTTA
TTGAGATTCAATTTTCTCCAGGCCCATTGATTTGGATACCAATAGGTTCTTAA
TATCTTACTTTTTGAGTTTACATTTCCCCATCCATTTATGTCACTGAATAGTCT
CCAAACCCTGCAAAATGAGAGGGAAACAAATTATTATTATGCCCCTCATTTT
AAAGAGAAAGAACCTGACATTTGGAGAATGATTGCCACAAGCTGATGGAGTC
AGGCGTGGGACTGGGTCAAGGGCTGGAACTCTTCCTCCAGTGTACTACAAGG
```

Figure 1 Cont.

```
CACTGTGTATTTTTGTCACCGATCAGTGATCTGGGAGTGAGGTCTTACTCTGT
GTTAGTTTCACCCATTCACTTATTGAGTCTTAAATATGTAGTCAGATTATTTAC
TTATATATGCAGAAAAATGTGCACAGATTTTGGCATCAAAGGTTTTAAATGTG
TACTGTGGCCCTGGCAAGTTTGCAAGGTTTTCAACTTGATGTTCTATCTGAGG
CCCAGTGTTCTTGTCTCTAACATGGGTTTATACACAGTACCTGGCTCATAGAG
TTGTTGGGAGGACCATGCACACAGCAAGTACTCTGTATGTGTTAGCCATGATC
ACGGGGCAAAAAAATCAGATGTCTTTTCCTCTGATTATTACCTAATGCCAGTT
TTTCCTTCCTCTTCTTTTCTACTCTATGAAGATTGTTGTCAGCCTTAAACTTCTT
AGTAATTATATTCAAGTTAAAGAAAATCTTAGCTCCCAGCTCTGAAATTCTAT
GATCCTAACTCTGTAATATGTATATTATAATACATTATATAACATAGTAGACA
AGCAGACTATGTTATAAGACATAGCAGATTTCAAGTAGAATAGGAAAAATTG
GCATGGTCATTGGCACTGAACAGAAACTGACTTGGGTGATTTAAGTTTAAAA
AAACAATTGTTAGAAGGACATGGGGGTAGCTCATAGAACAGAGGGACAGGC
TGAGTAAGCAAGCCTTGGAAAGGACAGAAACCGGGGCAGCCTTTTCAGGCCA
CTCTGTCAGGATCAGTCATTTTTTGTCTTTGTATCCTGCCTTTAAGATTCAAAT
ACCCAATGGAAGGAAAAGCTGATTGGCTGAGCTGGGATCATGTGATTTCCTC
TTGGTCAGAAGAGGCAGGGCAATTGGCTGACTATTCCATCACAATAGTCTGC
AGTCAGAAAGGGTTGATGCCCCAGGTGAGCCAAGAAAAATGTATGGAGTAG
ATACCAAGAGAAAGAGAACAACAGATTGCTCGCTCTAAAAATACAGAAAGT
AATTTCATTTATATGACATTCTGGAAAAGGCCAAACTAGAGAGGGAAAGCAG
ATCAGTGATTGCTAGGGTTTGGCGGGGGAGAAGAGGGCTTGATCATGAAGGG
GAAGCCCGAGGGAGTTTTCTGGGTGATGGAACTGTCTTGTGTCCTGATTGTGA
CAGGGGTTACATGAATCAGTGTGTGTTAAAACCCATTGAACTGTACTCTAAA
ACAAAAGAGTCAATTTTGCTGTGTATAAATAAAAATAACACTAAAATAAAAA
TACAGAATACAAATCAGTTATGAAGTTGCTTTACATTTCTAAATTTAAATTTT
CTTCTTGAGCTGCTGATTTTAAAAAAGGCATCCAGAGGATTCGCATAATTTTT
TTTTTTGCAACAGTATTTAGAACTTCGATTTAACAAATGTGTTCGTCTCTGTGG
AACAGTCCTCTTCATTGTTCAAACAGTAAGTAGCTCTCCATTTATTTTATCTTT
TGTCAGCTAAAATGTTTTTAACCATGGCATCTGGATTAAGCTTACCTGGGAAT
CACATAAAAGACAAAAAGAGATGTTGAAAAAATGAGGGAACAAAAAAGG
AAAAACACTTGTCACTGTACAGCATCAACCCTTAAGATCATCAAACAGTGTTT
CAGTAAATGCTTTACTTCCTGGGATTTAAGTGAATGTTAAATATTATACTGAT
AAAGCAACAGTCGGAAAATATGCTTCCCTTTATCTGACCTCCCTTCACCTCCA
CCAAGGTGACAGGAAGGGCATTACTACATGACAAAGATATTTGTTGCTGACA
GTGGGAATTCTAACAAAAGGAAAACAAGTAGCATGTTCACAGTATTTCTGTA
ACATATTAATAGGTATGAAAAAATTAACTTCCATAGGAAGACAGTAGGAAAT
AATTTTCTTTGAAATCGTACTTTAAAAGTCAGTGCTCTTTTAAAAATTAGACT
ACAAGAACCAACTAAAGCAGTCCTTAGAGTGTAAAACAACAGAATCATAAA
CTCTGGAGGACTCTTTAAAGCCAAATACTCAATCCAGTAATTCAAGAACATG
CGCTTATAGATCTACTGATTGACACAAAGGGAAAGCAAGGATTTGCCAAGTG
GTCAGTGACAGAGAATGCTTTCCACTGTTCACCGTGCTTCTGGAAGATTGTAA
TGATCATTGTCATGACTATTTATATACACATTTTCCTCTTGTCAGTTAAGCACT
TTAGGGCTGGGTTTGCTAATGGAGGTTGTGGAAGAGATTTGCATTCTTGTCTC
TAATTGCAATTCCACTTCTCCAATCAAAAGCTACCTAAGGGCCAGCCGCGGT
GGCTCATGCCTGTAATCCCAGCACTTTGGGAGGCCAAGGCAAGTGGATCACC
TGAGGTCAGGAGTTCAAGACCAGCCTGGCCAACATGGTGAAACCCCATCTCT
```

Figure 1 Cont.

```
ACAAAAATACAAAAATTAGCCAGGCATGAGGGCAGGTGCCTGTAATCCCAGC
TACTGGGGAGGCTAAGGTGGGAGAATCACTTGAACCCAGGAGGCAGAAGTT
GTAGTGAGCCGAGATCATGCCATTGCACCCCAGCCTGGGTGACAGGGCAAGA
CTCTGTTTCAAAAAAAAAAAGGAAAAAAAGCTGCCTTAGGATTTGCTGCAGT
GAGACAGAGTGCCTTTGTAAATTATGTAACTTGACTCCATTTTATATCTTTGC
AAATTATATAACTTAAATTTTATCAGTCCTTAACAACTGCAGTGTAAAAGGAA
GGAATCCTTTGGTGTCTCTTAGAGACTTGAGCCTGGTAGCTTGCATTCACCAA
CTGTTCAGAACCTCATTGGATCTTGTTAGAGATGCAACAGAAATCAGAAG
TAGGGATAAGTGTTAGGAAGGTGGCCTGTGGTCATGTTTTAAATCTTCAACT
TGGACAGAATAATGACTGTGGAAAGTTAGTTCATTTTGCAAAAAGAGGGGA
GCTTTACCACCTCCCATTTGAAGGACTTCATAGCTCTACTCATGTAATATAAT
CAAACATTCAAGGTACTGAATAGATTTTTATTTTCATAATATGCTTTTATAG
AATAATCATGGAATTTGCTTTTATGGGATATATTTGAAAGATCAAGTGCAATC
AAAATTACATTTTGAGAAAAGACCGTATTTATCTTACTCACTACTGTACCCC
AGATCAATAAATAGTTAAGTGTATGAATGAAAATAATGAATAATATTAAAAA
GATTGAATGTGGTTTTCATTGGCTTTCAGGATTTTTTAGTGCAAATTTATACT
TTTGTTTAATTTATGAACAGTAAAAGTTTAGAAATAGGCTTTCCAAATTTTTA
CTATTTTCTTGATTAATTATGCAGGGATTAACAGTTTGAAGACATAATTGAGG
GGTCATCCTCTTTTATATTATTATTATTTATTTTTTCTAATTATTTCAGATGTA
GGAAATTTTATTTCAAGCTTGAGTTGGTGGATCAGTGACCATTTGCACTAAGC
ACCATATAAAAGTCCGTATTTTTACATAAGCCGGTCACAAAAAAATATTTGTA
ACTTATGACCGGTCATACCGTAAACAGAAGAGTCAACTTTACTTAAATATTTT
GCAAGTTACAAACAAATTTTATTAGGTGTTTTGAAACTGTTGTTTTAAGTCAT
AATTGAAGTTATAGGAAAACAATCAATATTTTATAACTCAGACGTAATTCAT
GAATTTTATAATTCATATAATTCATTTGGCTTTCTTTCTCCCCCCTAGATTCTG
TATACTGGAATTGTTATTTATGCCCCTGCCCTGGCTTTGAATCAAGGTACATT
TTAGAGTTGCCAGTTAGGTAACTCACATTTTGGGGTTCACTTTCAACAAGCCT
TATTTCTCCTTGGGGAGATGGGGAGATGGAGGAATGCTTCTAGTAACCTGC
ATCAGCTTTACTTAGCGGGGCAGGATGGGTTCAGTGTCTACACTAGCTTCTTT
GGGTTTTTGGATGGACAGCTCCAAAGTGTCTGTAGACCACAGAGGTGGACTT
CTCCAGGTGGTACTTCTCTGGGATGTGCCCATCAGCCCATTCACTCCTTTAGA
ATTAAAGCTCCCTGTAGCCAAAGTCAGGATTGACGGCATCCCCTCTTGTGAAT
CTATAACCTGGAGCCCATCTCCAGGAAGCTTCCCTGTAATTCTGCTCAGGCCT
GTTGTAAAATCTGGCAGGGAGAAAAGCTTTTCTTCTCCACACTTCTAATAAGG
CCCAAAATGAAAGAGAAAGAGAGCCATGTGATTTGAATGATCAGACTGCTCC
TAGTGACAAAAGGACAGATGTCTGTAGTGCCCTTACAAATAAATTTAGGAAG
ATTGTGCTGCTCAACAAAGTATCTATACTCTCTAGATTTGGGAAGATAAATGC
AGTGAGGCTGGGATAGTTTATTGAAGCAAACGTTCATGCTAGTCATAGTTTCA
AAAGGCTTTGGGGAAACACCATGCCCTTTGAATTCTTATCTATTCGAAGTGAA
TTTCTCTAAAACGTCCTTGTAAAATGGACATGTGGACTCTGTGATGGGAAGA
ATGTGGTACAATTCCTGGGGTTAAAATGACATGAAGAAAACCTACTAATTCC
ACACTCTGTTTTCTTGATTTATGATAGACATGACAGTAGTTACCACCTGTTTC
TGAAGTGAACAATATTATTACCAAGAGGAACTTCATGTGTAAGGTGCTCTTG
AACTCTGAATTCTGGGCATGTTCCACATCGGTATTACCAACATCACAAGTGGA
TCATCTCATTTGTCGAGAACTGAGTTATAAACTTCATGAGTTACCTATTTAGG
ACTTAAGTGTAATTGAACATATTATGGTTTTAAAATGCAGTTCTGGGAATTAC
```

Figure 1 Cont.

```
CAGAGGACTGACTTTAATCTGTGAAGAAATCAAGCATTCTGTTCTTATCAGGC
TCAAACCACTCCCTGAGAGTAAATTAGAATGAAAGTGAAGGTGTTTTGATGA
CTAGAGTGTCAGTTGTGTGTTTTACTGTGACCAAAGCTGTAGGTACAGGCATA
GACACAGAACTTAGTGTGCAATAGATGCTCAAAAAAGCTTATTTAACTGAAT
TGAAAATTAACATTCTCTAGGTCTAACCTCTTTTTTTCTTTTAAAATTTTGGA
AATCCTCATACAAATACTAAGAGAGAATAGAGCCCCTTAATGTGCTCATTCA
TCACTCTATGTTAATATTTATCAACTAATGGTCCATTTTAATTCACTCCCCCTT
ACCTCTAATAGATTATTTTGCTGCAAATATGTTATGTCATTTCATCTGTATTTC
AGTATGTCCTTTAGAAATAAAGACTTTAAAAACCATAATCATACCATCATTGT
ACCTAAAATAGTAATATTAATTTCTTAATTTCATATCAAGTCAGTGTTTACAT
TTCCCTGATTTTTTTTCAGTGTTTATAAGAATCAGGATCCAAATAAGCTTATGT
GATTGCAATCAGTTGATGTCTCTTAAGTTTCCCTTTTCTGCTTTTTAAAATTGA
AAACCAGTTTTTCTTTCTTTCTTTTTCCTGACCGCCTGATGCCTGTTGAGAAA
ACTAGTTTTTATTGAGGTATAGTTAACATACAATAAAATGCACAGAGCATGG
GGAAGTGTACAGTTGGATGAGTTTTAGTAGTTGCCTAATAGCTTGTGTGACTA
CTACCCCGCTCAAGATATAGACTATTTCCGTCATCCACTCTCAGAAATTTTCC
TTGCATGTCTTTCTAACAAATCTCCTATGGGCCCAAGAAATCATTTCTGAGT
TATGCTACCATAAACTAGTTTTCCCTGTTGTTAGATTTTATATAAGTGGAATC
ATATAGAGCCTTTTCATGTCTGGTTTCTTTTGCTCAGCAAAATGTTTTGAGATT
CATTCATGCTGCTACATATATCAGTAGTTCATTCCCTTTTTTTTTTTTTTTTT
TTTTTTTTTTTTTTTTTTTTTTTTGCTGGTAGTACTTCATTTTATGCCTCTA
CCAACATTTTTTATCCATTCTCTTGTTATAGACTTGGGTTGTTTCCAGTTTTA
GGCTATAGTGAAGTAAGGGTGCCAAGAACATTCTTCTAAAGGTTTTGTGCATT
TTGTTTTTCTTTTTCACACCTGTTTTCACTTCCATTGGAAATGAAATACATGGA
TGTAGTATAAAATTAAAAATATAATTCTATTTGGACCCAGCTGAGGATAGAA
ATGTGTGCAAATTTACAAGAAATTGCCAAACAGTTTTTCCAAGTGGCTATATC
GTTTTCCATGTCCACTACGCAATATGTGAGAATTCTAGTCATTCCACATCCTT
GCCAGCATTTGATATTATTCTTTTTTATTTCAGTCATTCTAGTGGGTATTACCT
ATTATTTTATTGTTGTTTCAGTTTTCACTTTCTATATGACTATTATGGCTTAGCT
TATTATTAGACTATTATGGCTTAGCTTATTGGCTTCTGAAATAATAAAGTGAA
TAAAGACAAATAACCTAATAAAAAGTGAGCCAAAGACTTGAACACTTCACAA
AAGCAGATATTCTTCTAATACATTACATGATATATCTATTCATTTACCTAGGC
CTTTAAAAATTTCTCTTAGTGCTCACTTTGGCAGCATGTATACTAAAACTGGA
ACAATACAGAGAATATTAGCATGGCCCTTGCACAAAAATGATATGCAAATTT
GTGAAGCATTCCATATTTTTAAAAAAGGAAGAAAAGAAATAATAAAATAAA
AAGTCTCTTAGTAATGTTTTGTAGCTTTGGATGTTGAGGTCTTTTACTATTTCT
TAGATTTATTCCTAGATAATTGTTGTTTTTATGCTATTGCAAATGTCATTGTT
TTATTTTTCAATTATTCGTTGCAAGTGTATAAAAATACAACTGACTTTTATATG
TTGATATTCCATCCTGAGAACTTGCTGAATTTGCTTTTAAATCAAGCAGATT
TTTGGTGATCCCTTAGGATTTTCATGTTGTTTATGAATAGTGACAATTTTACTT
CTTTTCTAATCCTTATAGCTCTTAGTTCTCTTCCTGTCTTATTGTAATGTTAAT
GTGGAAAGTTACATTGACTGAATTTTGAATATTAAACCAATTTTTGCATTCTT
GGGATAAACCCTGCTTGCTCATAATGTATTATCCTTTTTATATATTACCGAATT
CGATTTGCTAACATTTGATAAGGCTTCATAAATGAATTGAAAGTGTTCCCT
CCTCCATTTTCTGAAATAGTTTATATAAAATTGTGTATTTATTTCTTACATGCT
TGGTAGAAATCACCCTGAAGGCATCTGGGCCTACTCTTTGTTTTTGTAGAAAG
```

Figure 1 Cont

```
ATTTTGGTTTATGGATTCAGTTTATTTCGTAAATATAGAGTTATTCATATTTTA
AAAGTCTTGTTGGGTCAGTTTTGGTAAATTGTATTTTTTAGGGAATGCTTCCA
TTTGGTCTAACTTATCAAATTCATTAGCATAAAACTGCATATAATACCCTCTT
GTTATGCTTTTAATGTTTATAGTATCTATAGTGACATCCCTTCTAATTATTCCT
AATATCGATAAGTTTCTATCTTCTTATTTGATATATCTTTCCAGTATTCTAT
TGATGTTTTAAATCTCTTCTAAGAATCAGTGTTTTGGCTCATTGATTTCTTTG
TTTCTATTTCATTAATTTGTGCTATTTATTGTTTCTTTCTTCTAATAACTTTG
GGTTTTCTAGCTTCTTAAGGTAGGCGCTTAGGTCATTGATTTTAAATATTTCTT
ATTTCATAAAGCAAACATTTAAAGTTATTAATTTTTTGAAACACTGCTTTAT
CTGCAGCCCATATATTTTGATACCTTGTGTTTTATTTAGTTCTCAAAATATTT
TCTAACTTCTCCTGTGATTTCTTTTGCCCATGGGTTATTTATAAGTGTATTGCT
TAATTTTCAATATTTGAGGATTTTCTATCATGTCTTTTTGTTATTTATTCCTAA
ATTAATACTGCTTTGGTCAGAGAACTAATATGATTTTAATCATTTGAAATTTA
TGGATTTGTTTTATGGCCCAGGATCAGGTCTGTCTTGAACATTCCATATGCTC
TCAAAAAGAATGTATATTGTGTGCTTTTGGATGTAATGTTCTATAAGGTCAA
AGGTTTAGTTGGCTAATAGTGTTATCACATCTTTGATATCTTTATGGAATTTT
TTTACTTGTTCTACCAATTGCTGAGAGAAGGATGCTAAAATCTCCAGATATAA
TTATCGATTTTCTATTGCTGCTATTTCTCTGTCAATTTTACTGAATGTATTGT
GAGGCTCTTTTAAAGTCTCTTTTTAAATTTACAATCTCCCTTCTATTCCTTTTC
ATTTAAATTGCAACATATTTGCAGAAGAAACTGGGTTATTTGTTCTGTCCAGT
TTTCCAGATTCTAGGTTTAACAATTACATCTGTATGGGGTCATTTAATGTTCA
CCATTCCTCTGTATTTCTTGTAAACTGGTAGTAGTTTACTAGTAGTAGTTAGAT
CTAGACTCTTTTTCAGACTCCACTTCAACTTTTTGGAAATCATATTTCATAGGC
AGTATCTATAAGTTTATTTCCTTCAGGAGTCCCAGAATGTCATTTGAAAAATT
ATCAGCAGCTATTGATGATCATTCTAGATTCATTATTTCATTGAGGCTTATAA
AATGGAGTATTCTAGTTCTGTGAATTCTTCTTCATTAGTTAGATGGAATACTG
CTATAAAGAGAAACTTCCTCTTATCAACTATTTGCTTTCTCTGAAAAATAGTT
TGTATAGGAAAGGGAGGATAAATGTCAGATTTTTCCCCTTATGAATTTTAAAA
ATAATAAATTGGTTTCCTACTATCCCCCAAGGGTGACTGAGATTTTTAAAAAA
TTCTTACGAACTCATGGATTTAAAGGTTTGCTGTTATTTCATAGCATTATCGTT
AGTATTATTATTGATGCTCAAATTGTCCCATTTTATCCAGCCGGAGCCCCCTT
AAGTTCCTCCTGATTTTAGCCTTGGCTGCATATTGGACTCACTTGCGGGGTGG
GGAGCTTTCAAAAATACCAATACCTCAGTCCCCATCACCAGAACTCTGAGT
TAATTAGGCTGTTGAGTGGCCCAGTTATCAGGATTCCATAAATTTCCTATGTT
GATTTTAAGGTGCAGTCACAATTGAGAGCCATGGATGTAATAGTTTTAGAAT
AGCAACTCTAAGCCATAATGAATAATATAATGGCCTAACACAGTTAAAAATA
TTATTCTTTGTTGTTCTTTTTTCTTGGGTGTATCTCAGTAGGAATGTATGTTAA
ATTACTGTGTTAAATATTTTGTGACATGTTTCCTCTGTGTGGTAATGTCACAA
ACTTGATATACAGTTAGGTTCCATTTATTTCATTTTGCAATTGATTTTGAGGAG
TTTTTTTTCTAATTTAACTTTATATTTATGTGGAATATTTATGTGTTCCAAAG
TGAAATCTATACATCAAAATATGTTTAAAGTAGCCTGACTTGTATCTCTGTCT
TCTCTACCCTGTTTTCTCCCTCTCCTAGGAGTAATTTTTGGCTTTGATTTATCC
TTTAATTTTAGTATATGTACTGCTGAAACAAGCACAATTCTTTTCTTTTAAAA
AAATGAAATAAAGTCCCCACTTCTTAGATAAATAGGAGCAAATTATAAAGAC
TTTTCTCCATCTAGATCCCATTTTGGTAGCACATATCTTAGTAACGCCTTCTTC
AAGGACTGGTGAAATTGCGTGTTTACATGGACACACAGAGGAGAACAACAC
```

Figure 1 Cont.

ACAGTGGGGCCTATTGGAGGGTGGAAGGTGGGAGGAGGGAGAGGATCAGGA
AAAACAACAAATGGGTTAATGGGTACTAGGCTTGATACCTGGGTGATGAAAT
AATCTGTACAAGGAACCCCATGACACAAGTTCACCTATGTAACAAACCTCC
ACATGTACATCTGAACTTAAAAGTTTTTTAAAAAGCATTACCGGCCAGGCGC
GGTGGCTCACGCTTGTAATCCCAGCACTTTGGGAGGCTAAGGCAGGTGGATC
ACGAAGTCAGGCGATTGAGACCATCCTGTCCAACATGGTGAAACCCGTCTCT
ACTAAAAGTACAAAAAATTAGCTGGGCATGGTGCTGCGTGCCTGTAGTCCCA
GCTACTCGAGAGGCTGAGTCAGGTGAATTGCTTGAACCCAGGAGGTGGAGAT
TGCAGTGAGCTGAGATCACACCACTGCACTCCAGCCTGGTAACAAAGCAAGA
CTTCGCCAAAAAAAAAAAAAAAAAAAAAGGAATTACCATTACCTTTATTAAA
TTTCTGAAATCAGATCCGCAATCTGCAATGTTATAAAGATTACATTTGAATCC
TTTCGTGTTGTCTTCATTTGAATCTATACATCATAGCAATTTGATATTGTCATT
ATATTGTCAGTATGATACATTATCCTCAAATTCAGGTATTTGCAACATTACAT
AAAAATAGAGTGTTTATTTGAACCGCGTCTAATCGGGAGAGAGATAAGAAAT
ACCCATCACAGTATCAAGGAGTTTCTTAGCTTAATTACAATATAAACGCCTTT
CCATGTATTGAATTAAGCCAGTGTCAGATCTGTGTGTCTGAGAGTAGAAAATT
ATCAAATACAATTTTAAACTCCATTTGTTTTGAGACATTTATGAGATTTGGA
GCTAGTTTTAGCTTTAGGCAAGTGGGTATAGAGGAAGGTGCCTGATAAATGA
TATAGCTTCCTTCTCTGATGATTTTGAGGATTATTTTATTGTGCATATTTCA
CAATTATATATGCATTCTATTTTTTCTACAGTCACAGGATTTGATCTGTGGGG
CGCGGTAGTGGCAACGGGGGTGGTCTGCACATTCTACTGCACACTGGTACGT
CCAGGACATATTTCCCTTTTCACTCTACCCACTTGCTTTGCAAAATTGAAAAT
TCCAGTTGTTGTATACCGCAATCTTGTTTGTCCACACTTACTCTCCTATTCCCA
ACCTCCTGCAGTGTAACTTTTTTTGTGTGAGAAATAATCTGTAGTATAATTTG
ATCCTTTGTAGAAAATGGAGCATAACTGAAATTTTTTCTTTTATCTGATCCATT
GCAATGGTTCCTAATCTTGTCTCTTGATTCATCTGTACTGTTGCCAAGTTATTA
TATTTGTGCTCATACTATTCCTCAGCTTAAAAACCTATCATAGGTCATAGGCA
CAGTGGCTCCCACCTGTAATACCAGCAATTTGGGAGGCCGAGGTGGAAGGAT
CACTGGAGCCCAGGAATTTGAGACCAGCCTGGGCAACAAAGTGAGACTCTGT
CTCTACAAAAAAACAAAAAAAATTTTTTAAAATTAGGAGGCATGGTGGCATA
CACCTGTAGTCCCAGCTACTCAGGAGGCTGAGGTGGGAGGATCGCCTGAGCC
CAGGAATTTGAGGCTGCAGTGAGCTGTGATTGCACCACCGCACTCCCGCTTG
GGCAGCAAAGAAACCCTGTCTCAAAACAAAAACAAATCTGTGATAACTTCC
CCTTGCTTATAGGTAGGGGTGACAAAATATGCAAAATCAGTATGGCATGGCA
CTGATATTATTATGTGTGCTGGTCCGAGGCAGTGAGAAAATCTTATGGAATCC
TTGACACTCTATGTCTTAACCCTTTAGGTGCTGGATCTTGTAGAAGATGGGGC
CCTCAGCCAGGTGCTGGTTCTGCTTAGGTCATAGAGAAACTTGGGAAATTTCT
TGTGGTGGCTAGTACAGATCACTTATAGTATATAACAGTGGAAATGACCATC
TGAGTGAAACCAATTAAATATCACCTCTGCCTGTAGGATAAAATTCATATTA
TTTACTAGTAATTTGACTCGGATTTTTCTTCCCAACAATCTCCCGACACCACTC
CACTTTATTCTGTGGAATGTATCTGGCCCCATTCAGCATGCCATGTAGTTTCA
CTCCTTTATGTTTTGCCCATGCTGTTTTCTGCTGGGCGGAACCTCCATCTT
TGCCTCTGCTTATGTTTGAAGACTTGATTTAAATATATCCTTCTGTATGAAGAT
TCTCCCAACCTGACTGTTTCCCTTGAGTGCACTTCTTAGCCAACATTCATGTTT
ATATCATTTTTCTCCAGTATAGTGTATAAGTGTGTAGATGCTTAATAATGTCT
AATAGAAGCATTAATCCTAATATACTTTCCCCTCAAAGGGTGGTCTTAAAGCA

Figure 1 Cont.

```
GTTATCTGGACAGATGTTTTTCAAATTGGGATCATGGTGGCTGGATTTGCATC
CGTGATTATACAGGCTGTGGTGATGCAAGGTGGAATCAGCACTATTTTAAAT
GATGCCTATGATGGTGGAAGATTAAATTTCTGGAAGTAAGTGTCTAGTACTTG
GGTAACTGAACACATCTTTTGTATTCTATAAAAATAATCTCTTTATTGAAATA
GTAGATTTACATTAAAAAACAAGCCAACAAATTGCTAAGGATGTGGTAGAGC
AAATTGAAGCAGAGAAGTAAATACGTAAGGAGCCTCCCTCTGTTCTTTAAGG
GATTAAACCTGTCAGATGGTACTTAGCTACATGGTGCTTAGAGCAATGTTTCC
TTCTGAGAAGGGACTTAAAGCAAAAAAGTATTTTCTTCCAGGTATTAAAGT
CCAGAATAGGTTGAAAAGTGGGACAGGGTGATAAGGAAAGAGACAGTGGAA
AGTTAAGAAAAGGCAGCTTCTGGCCAGGCACAGTGGCTCACACCTGTAATCC
CAGCACTTTGGGAGGCCAAGGTGGGTGGATCACCTGAGGCCAGGAGTTCGAG
ACCAGCCTGGCCAACATGGCGAAACCCCATCTCTACTAAAAATACAAAAAAT
TAGCCAGGTGTGGTGGCAGGCACCTGTAATCCCAGTTGCTTGGGAAGCTGAG
GCAGGATAATTGCTTGAACCCAGGAGGCAGAGGTTGCAGTGAGCCGAGATCA
CGCCACTGCACTTCAGCCTGTGCAACAGAGTGAGACTCTGTCTCAAAAAAAA
AAAAAAAAGAGAAAAGGTAGCCTCTTAAGAGACAAACACTAGCATATTGGA
TTAGCACCTGCCATAAAAAAAAAAAAGAGACAGAGACAGACACTGAAAGAC
AGTGATTTCATTTTGACAATTCTTTGTTTTAAGCAACTTTGAGAGTTTCTCTTT
TGATATTGCCCTGGCAATCTATAGTATATTAACATAGTAGCTTATGATTATGT
ATTATAATTCTATGTATGTGTATGTATTATATAATGAACATTATCTAATATGA
AGTATTATTTCTAGAGAATTGACTAGGAAAGTTACAGTCTATGCTTCAAATGA
CAGTACAGCACATGATGTAACATGTTTTAAGCAGTTATTCAGTTTTCCTAAAG
AAAGAACAATGAAGAGACTAGATATTTCATCCCAAGTATATCACACAATTCA
AAAGAATATTGAAAATGCCTTCCGTTTTGGATCAATAGTGTTGTCCTTTTGCA
ATATGGAAAGGGACAACCCATGTTGTCTTGAACTAGCCTATCTTCTCTTTGAG
ATCGCAGCCCCGCTTTAACATAGGCAGTTTGAAGAAAAAAAACCCATTTTGC
ACTTGGTGGCTCTTTTCTGGTCTTCTGAAAATAAGCACCAAAGTTTGAGAAAA
AGCTTTTTCAGAAATTGGACAGGGTCAATGTGTTAATTTACAGGGATAAATTT
TAGTGAATCAACTTTGACTATTTTCAATATTTCTTTCCTTCTTTTAGCTCAAGA
TTCAGATTCTAAGGAAAAGAGGCTCTAGTTGCCTAGCTTGGACCTTGGTTCCA
CCCCTTGGCCAGGGCAGAACAAGATATTTTGACTGATCGTCAATTGAGACTA
TTTAATGGAGAAATGGTAGTTTCCCCAAAGCAAACCTGGGTTGCTTTTACCAG
AACAGGGAGAGGGGAAGTCCAGGAAGTGGAAACAACCAATGACTACTCTTG
ATTGCTCCCAAATCTCTTCCTGGTAGGCCAGGCTGAGGAGAGAGGGTATGGA
ACCAATCATTTTCTGCAAGATAGCTGTCACTTTATATGAAGGATACATATAT
TGGAGCACAGAAGTGATAGCTTATACACATTAGTAAGAGATTTTTAAAAAAA
GATTAAACATTTTTATGACCTTAGTTTTGAAAGTCATTAAGTAACAATAAAAA
GCCTTATTTGTGTTTCATACTTTTCAAGAGTATCCCTTGTTATTCTGATATGTT
TTGAGAATATGATAGACAAAGTATTGCTCAAGTTAAGATAAATGAAGAGAAG
AAGGATATTGTATTGGTATTTTCTGTGTCGTCTGCCATTGGCCTATGTATTCTG
TATGGCCTAAACCACTAAAGTGAGTGTTTTAAATCTTGTCATACTTCCCTCAG
ATAGCTTACTGACTCCTTTTGGCTCTTCAGTTAGCTAATATAGTAGCTTCTCTC
TCTTGGGGAGAAAGGGTCAACAGTCTTGAAACTCTTACACTTTGATATGAAA
TGTTAGACATGAAATAGAGGCTCTCACATTTCCACAAGAATGCCAGAATACA
CATACAATTAGAGCACTTAACTGATCTCAAATATAAGATTTGAAATGAATTTG
CAAAATTTCATAATTTTAAGGAAGTCTCCATGAAAGCTAACTTTGCAGAAAG
```

Figure 1 Cont.

```
TTTTCTAGCTCATATTGTATATCAGAGATGAACAAAATCATTCCTTCCAGTAA
AAAAGATTAAAAGATCTTTCAAACATGGAAGTTGAGCTTTCCCTGTGACAAT
GTTTTGGACTTATGTACATGATGTCATAAAGTGGCTTTAAACTATTAGTATTT
AGCTTGCACGCACAGCATTTTAATAAAGCATGATTACAATGACATGCAGTTTT
TAGAAAATGCAAAACTTGAAACTGCATTAATTGACTGATTTGTTGAACGTGA
ATATAGATTAGAACTATGATTACATGTGCTGGGAGAGGAATTCTATACACAA
AATGTGTTGATTTCGTGTTCATTTTAGTGCCATCTCGTCTGCTGTGGTGCACTT
AGGAATGTTTTTCTCTTTCTCTTTCTCTATGTTTCATGTTCTTCTCTGATTATAT
CATGTCAGATTTGTTTAAATGACAGTTTCCTTAGATCACAGGAGAACAAGTTA
TATAAATGCTCAGAAGGATTGCAACATTCATTTCCCCCAGTCTCTTCTAGTAT
TTTCAGATCTCTGAAAATAGTATTTTTTATTTCATTGAACTTAAGTTGGAAAT
ATTTCTACCTTTTAAATTAATTAATAAATTTTACATATTTATGTATGTGTTGT
GTATATAAATGTGCATTGCTTGCTTCCAAATATAGTCTAAGAGAATTTTTTTT
AGTCTCTGCTAATAGTTCAGATTTGTTTTCTGTTTCTTGTCATTTAGTTTTAAT
CCTAACCCTTTGCAAAGACACACCTTCTGGACAATTATTATAGGAGGGACCTT
CACATGGACCAGCATCTACGGTGTCAACCAATCCCAGGTGCAGAGATATATT
TCTTGTAAAAGCAGATTCCAGGCAAAACTGTAAGTCACACACCATGGTATAT
GAATCATTAATAGCCATCAGTTGTCTTTATGGAAACTCTTTCATAAGTCACGT
TTAGCTCCTTTATGTCTTTTGTGTCATGAAATTCCAAGAGATAAATGATATAT
TTGGTTACAAAAGGACCAAGAACAAATTGTTACTGTATGTTTTAAATCAGCTA
TTTGAAAATATTTATAGGAATTATTAATGAAAACAAATCAGCATTTATTGTGC
ATCTGTTTGCATAAGAACCCATGGGGGATAAATATATATGGCTTTTGTCTGAA
GAAAATTAACCTCAAATTAGGAAAATACATGCAAGTATGTGAAAAAATAAA
ATAATACTGGAGATATGTAACAGTTTCATGAAATGATATAGCAATAGAGAAA
ATGTTCCAGAGTACATATAGTGCTTTATATTTCATTTCAGACACAGTCATGG
ATTTATAACCCTGCTCTAATATTTGCTATTTGAGTGATCCTGGGCACATTCTGC
AGTCTCTTTGAGCTGCAGTTTCTAAACTTGTAAAAGGAGCATAAGAAATACT
ATACACCTCATGGGAGGTGTCGTAAAATACTGTGTTTGGCATACGCATGGTA
AAGGCCTAGTATATGTAAGTTCCTTTTTCCACTTCAACTGATGTGATGTGAAG
GTGGAGGATGGATGAGAGATTCCTATTGAACTGGCAGAATGAATATGAAGAA
TGATCATAATTTGGGCAGGTGGAGAAGAGTAGGAAGGCATTCTAGGTAGGTG
GAGTGATTTGGATGAACGCACAGAGGTAGGAAGGACAGCATGGTCCAGAAC
TCTCAAGCCCATCTTGGCTTGAGCAAAGAGTGTGGAATGGTGGCTGGTTCCTT
CTCTGGAGGCCTCACATCACTGCAGTGCTCACCACTCCCTGTGCTGATAAATA
GGCTGACTCTGCTGACATGCTTTAGGGGCTTTAAAGCTCTAAGGAGATTGAA
TAAGAGTCCAGGGTGGATAGGGTGAGGGAAGGAGGACAATTCTATTTCTATT
TAAAGGAGAAAATGAAAATATTGTGATGTCATATGTCAGAACTCAATATATT
GAGAGTAAATTGGTTTAGAGATTACCTAAATCTTTGAAGAACTCACAGTGAA
AAATCTATATGAATATGGATATAATAACCAGATATGGGATCCCCCCAAAATG
AACTTAGGAATTCTGGTATTTTACGGAATATTGGAGGAATGTAATTTATAGAT
AGAGTAGTCTATTGTACTTTTAAATCTATACTAGAGCTGATACCTCTCCCAGA
GTAATTGTGGACAAGCTCTTCTTCTCTTCCCTTGGGAACATGAAACCCAAAAA
GCCCGACTTGATAACTTAAATAGCAGCATTAGAGCTTTCTTGATAAAAATCA
ATTCCCATAAGCATAGTGGATCTCCTGCATGAAGCAGACTCTCGAAACCCAG
GGGACTCATTTTCGTCTGCCTTCTCACACTTACGCTATGGTAAGAATGAATCC
CTGCTAAAAAACCAAGACCTACTGACATTGATTGACAAAAGACAGTATGAGA
```

Figure 1 Cont.

```
TGTTGATAAGTGGTCAATCTGAATAGCATCAAAGTGAAATAAAACAATATAT
TAAACTCATATATAAGAGACAGGAGGTGTTTGGACAAGAGAGTATCTGGGCA
TAATTTTCTGGTGATTTGGAGATGAGCTAGCAATAGCAAAACATACTGCAAT
GTTAGTCAATTCAAGGGAGAAGGATAAATCTGATAAACCCACCTTTGATTCTT
CCGGAAGCAGACTCTGAGGTTGAGGTTAGCATGGAAGAGTTTATCAGAGAAT
CGCTATATGTAGAAGGGAAGAAAAGGAAACAGGATTGACGAGAGGGAGACG
CTGGACTGTAATGCAGTCTGAACAGAGGCCTCAAAGGGAGCTCTAGAGCTAG
GGTGGCTCTTCAGACTAGTCCCATGTTAGGGTGAGGGGACTGGGCCTTTAAA
CCTCTGAATCCATTTGTCATTGGATGCAGACTTCCTGCGGGGTTGGGAAGAA
GGAGGCATGACTTCAGGGATGGTACCTCTTTTCCACCTCGGGCAGCTCATCAC
TGTCCACTACAGCACCAGTGGAAAAATATGTAGCCATCTTAGCAAGAGAAA
TGTTTACTATTCAACTGATTATTAAGACATAGGATTCAATAACACTAACACTA
ATATCAATAACTAGTATTTAACAGGGGTTTATTATGTGTAAGTACCATGCTAT
ATGATAATATACTGTTTCATTTAGTTTTATAACTTTGTGACATAGGCATTGCTA
TCCTACACTTCAGTGAAGAAACTGAAGATCAGAGAGGTTGAATTACTGGCCC
AGGGTCACTTATGGTACAGCCAGGATTTATGCTCAGGACTGGCTCCAGTGCT
GTGTGTAAACCTTTATTCTCTACTGGAGCACACAGTATATTACAGTGCTGA
ATATTGTTTGAGAAGATACCTGTCCAAGGAATACAGATTTGCATTCCTACTTA
ATGTGTGGTCTTATAAACAACATTTAAACAAGTTTCATGAGTTACTGTGTAAA
TGTTAACAATGTTTAGCAGTTACAATTGCATTACTTTTAAAAGGAAAATGAG
TAATAGTTAATGCTCGATTGACTATTAAAATCTTTATTTCATGACAAGAAGAC
CTGAAGTAGTATAACTAGGTACCTTTATAAAGCTAACAATGCCCCTGGAGCT
CCGACCACGAGCATACACTCTTTCATGGGGAAATCCCATCCATTCAAATATTT
CCAAATACACTGTCGATTGATTGGTATCATAAGCAGAATATTAGGCTAGAAT
AAAATAAGTAGAGTTTTCGATAATCAAAAGATAATGTACATTTATTGAGTCT
AATCATGAAGGTCTCTTTTGATCATGTAACAGGTTTCCTAATCTTTGGGACAG
AAATTACAGTTGTCTTGCTGGTTTGTTTTCACTTCTTTAGGTCTCTCTACATCA
ATCTTGTGGGACTCTGGGCAATCCTCACATGCTCAGTGTTTTGTGGGCTCGCC
CTATATTCCAGGTACCATGACTGTGATCCTTGGACAGCCAAGAAAGTGTCTGC
ACCAGACCAGGTTCAGTACCATGTCTTTCTTACAGGTGTATTAATAATATTCA
AAAAGCTTATTAGTTGAGAGGAAAGAGCATTCATATTCTTGTAGAGAAACGG
AAAGTGGACATGCCATCATCATCTTACATTTCTATAAAACTTTGTTAAGAATT
TATTTTAGCAGATATAGCAAGAATGAAGAGTACTGCATCTAAAATGAAAATA
TGGAAATACCAGGAAAAAATCAAGCAGAGTGTTAAATAGGAATAGCTCAAG
GTTGGGAGTAGGAATGTGAACACAGTTTTTTGTTGTTGTTGTTTGTTTGTT
TGTTTTTTAAACTACACAAACCATTGTACTATAGAACATTTTGTGGGTGTTTG
TTAGAGCATTCATTTATAAGCAATTTATCTTCCAATTTTTTAAATGATGGAGA
GATGGATCCAATAAGTGAATATTTACTGAGTACCAACTATGTGGTGAGATTCT
GTGCCAAGAGCTTAACATGCTTCATTTAATTCTCACAACCCTGCAATCCTGAT
TTTACAGATGAGGAAATGCTTCTCAGAGAGGTTATATAACTTACCCAAGGTC
ACATTGCTAATAAGTAAGAATAACTATGAGCAGTTATCAAATACCCACCATG
GGCCAGGCACTACCATAATGCTTCATATAAATTTCAACTTTTAATCTTCACAG
TCACCCTCTGATGTAGGTTCTATGATTATCTGCCTTTCAAAGATGAGAGAACT
CAGGCCTAGAGAAGTTAAGTGAATAACTAGCTAGTAACCTGGAGCCAGGATT
TAAAACCAAGCAAGCTGCCACCAGAGTCCTAACTTTGAACCTCTGTGCCATTT
ATTGTCTTTCAAAAAGGGGAACTAGAATTCAAACACAGGATTGCCCAACCCT
```

Figure 1 Cont.

AAAGCCTGAGTTCTTGCCAAAATTATTTTCTAAGACTCACTTGCAGAACAAGT
TCCTAGGGGATTCATTAGAATGAAAATAGATTGAATTTCTGTTGATGCAAATG
CATCTCATGCTCCCAGAAAAATACAACTTGGTGGGCCGAGAAAATAAAAACA
CCCTGGAGCTGTTTCTCAACCCTATCTTAACTTATGCCCTCCTTTTGATAAACA
CACCCTCTCTGTTCTCTCAGAGAAGGTAAGAATCACGTTTACTATGAAGATGG
AGGCACACTTCTGTTACATCCCTCTAATAAAGAATATTTTGTGACTGTTATC
AATCTGTATTGTCTGTAGTTTGTATCATGAAGACAATAACGACTTTAAAAAAA
AGTTTGTAATATACTTTGCCTTTACCCTGGGCCAAAAAAAAAAAAAAAAAAAA
ATCCCTACGGCTTCCTACCTTTGAGACATCTTGTAGAATACATTCAGGGTGTC
TTGCTTGCATACGCTTAGAGAGTCCGTGAAGATTTCTCCCAACTGATATATT
TCCAGGACTGTGTTAGTTAACAAGTTAATTCAATTAACACTTCACTGGGGATA
CCATGCAAATAAGACAGTGGAAGATCGTGTCAAAACCTTATCCTCGCTCAGT
CGCGGTGGCTCACGCCTGTAATCTTAACACTTGGGAAGGCTGAGGCAGGCAA
ATCACTTGAGGTCAGGAGTTCGAGACCAGCCTGGTCAACATGGTAAAATCCG
TCTCTATTAAAAATACAAAAATTAGCTGGGCGTGGTGGTGGGCTCCCATAAT
CCCAGCTACACAGGAGGCTGAGGCAGGAGAATTGCTTGAACCTGGGAGGTG
GAGATTGCAGTGAGCCGAGATCGAGCCACTGCACTCCAACCTGGGTGAGAGA
GGGAGACTGCCTTAAAACAAACAAACAAAAATACAAAAAAACCCCTTATC
CTCAAGAGAGCAAGGATATGTTTCTCTATGCTCTGCTGGCATTTGCCCAGAGG
AAGCAGGCCAGTTTCTAGATATAGTTTTACTATTTTCCTCTCCATCAATCCTAT
TTCATTGGTTCTACCTATACTTGAGGGGCCACTCAGATACGAAATAATTACA
CCACAGATTTTTGAGAAAGTTGAAGATAGGATAGAGGATTTTGGACCTTTTA
TAACACTATAGATGGAACCTACTTTTGCTATTTGTGGGACATTGTTTAAAGTT
AAACCTTTATGATATCTTGGAAAAATTGGGTCTTGATCTCATATAGGGATAAA
TGCTATTCCGTTTTTCTGAGAATAAAGATTGAGTAAGCTTTGGAAAAGTGGAG
AACACAGTCCTAAAAGAACTGAAACAATCCTAATGTTGAAACATTTCTTTTCA
ACAGTGGAGGAAGTTCTTCCATATCCCATGAGCACACTATTGTTAAATGAAA
TTGAAGAGGCTATGGAAGCCGATAAAATAGGACATGTCATCTACTCTGTACT
GTGGGAGAAGTAATCAATAAGGTTTTAGTGCAAATGAGAGGACACTCTTCGA
GAAAATTGTCCACTTAGGACTCTTTTGATTCGGAAACTGATTTTGTAGAAAAA
CTGCCATGCAACAGAGTCCTGAAGTCACACACTTGATTATCCTAATTTGATAT
TTATTTTTTAAAATATAAGTTATCAAAAGCAAGTTAGTATCAGGAAGTTTTT
TAACAGAAGCAAGTTTAAGGGATTTCCTGAAGTCATTCTCCACCCATCATTAT
GTCTCGTACCTGATGCACCTAAAATTACATCTTCTGTCCTGGGCAGTGACTGA
AGTTCACAAAATGGCCTTGAGTCATCAAGTAAAGTTAAGTGGATGCTGCTTA
CTTAAGCACAGAGGTGTGTCAAATATTTCCTTAAAGACAACTTATTATTCTCA
AGAATAGCAACTACTTTGTTTTGAGCATTTATTATATTCCATATACTATACTAT
GAGTTTTACATAAATTATCTAAATTAACTTTTACAGCAACTCTATGAGGTTAG
TATTATTACAACTATTTTATAGATGAGGAAACTGAGGCTCAGAACTTCAGTTA
CAAAAGCCGTATCTGTGTGAATCCAAAGCCTCTTTACTTAACTACTGTGCTAT
TCGTTTCTCTAAGTGTTAGTAGTTAAACAGTTTAATTTTAGGTATTTGAAAATT
TCATTTGTGTGGAATAACTCCTTTCAGTTCCCGAAGGAGACAAGACAAATGA
TAAACTAGGCATTCATTAATTTTATTCAGTAGCGAAAGTACTTGGAAATAAAT
TTTGGAATTTTTCAGCTCATGCCTTATTTGGTACTGGACATTCTGCAAGATTAT
CCAGGACTTCCTGGACTTTTGTGGCCTGTGCTTACAGTGGGACATTAAGGTA
TGAACTATGACTCTAATAACATATGATTTCCCTGTTGGGATCTTTCTTTTATTA

Figure 1 Cont.

```
TTAGATACTTTAGCGGGATAATGTGGAGTTCTGGGCACAGACACAGATGGCC
CAAAGTAGGCAATCTGCTGTATGTGTCCTCTCTGTGGTCTGACTTATCTCTGT
GGACTAGCGTCCTGTTGTCATCGGCTCCACTTTTAACTAGGTCCCTGCTCTCT
AATACACCACCATACATCCTATGATGTGATACCTATGGTCACAATAATGACG
ATCGGTTGATGGTAGCTTTCACTGGTGATCAAAAATGGGTGCCACAGTCTTGA
TTGAAAACACACATGGGGCTGAAGCGTGGTCAACTGGAAAATTAGAATGAA
ATCTTCCATTTACATGTTGAATAATATATACTGCCCAAAGAATCTTACATTTT
GTGATCTATCATTGCCCTTTCTCCTTGCGTTTGTTCCAGAGAATTGTTATTATC
AACATGTACAGTGTGTGTTAGTGGGGATTCAGGAAATTAATATTGTTGATATT
TACAGCACATGGTAGGGAGGACTTATGACAGTCCTTTCTATGCACAAAGAAA
AATACATTTTAAAGTTGTTATGCATAGGAATACGGAGTAATCTATGTAGACTC
TTTTAGACACTGAGGATTAACAGCAAGTGGAAGCAACATGAACATATCCTTT
CTCTTTTACTGTCAAGCCTGTAGATATTGCCTGAATATCATTTTGGATGATA
ACAGTTCAAGAAAGACAGTGCTGTGATTATTAAAAATAGCATAGTAGAGCC
TGGTGTAGTGGCTCACGCTTGTAATCCCAGCACTTTGGGAGGTCAAGGCGGG
TGGATCATGAGGTCAGGAGATCGAGACCATCCTGGCTAACACAGTGAAACCC
TGTCTCTACTAAAAATACAAAAAATTAGCCAGACTTGTTGGCGGGCGCCTGT
AGTCCCAGCTACTTGGGAGGCTGAGGCAGGAGAATGGCGTGAACCCGGGAG
GCAGAGCTTGCAGTGAGTCGAGATCATGCCATTGCACTCCAGCCTGGGCGAC
AGAGCGAGACTCCGTCTCAAAAAAAAAAAAAAAAAAAAAAAAAAAAAAAAG
CATAGTAGAAATCAGGTTATATTTAGAAGTGACAATTTGTTTCCCCCTTTCT
CATTCCCACTTAAAGTATTATTAAAGGTAAAATATTATAAATCAAAGTTTTA
TTTTCCCTTACAGCACAGTGTCCTCCAGTATTAATGCCTTAGCAGCAGTAACT
GTGGAAGATCTAATCAAACCTTACTTCAGATCGCTCTCAGAAAGGTCTCTGTC
TTGGATTTCCCAAGGAATGAGTAAGTTTCTGTTTTCATAATTCCATTTTAGCTC
AGAGAGATGATTTTTTGAGACACAAAAATTTCTTTTTCCACTGAAGCTACAGA
GGAAGGACCTCTGAATATGACTGGATATCCACATATGTATGCCTATGACAAT
GCAGATTTTTAAAAAATGTTTGTATCAATGTTTAATGTTACCATATCTGTAAT
CAAGATTTGGGAGACACTTCAAACAATTAATTGTCAGTGAACCACAAAGGAC
AATTTCCAGGGGACCGATTTAGCTGTCCTTTTTCCTGTGCCTTCATCCTATCC
TAAATTTGTGTTAAAATTCTTAGCCACACACACAAAAAATTCAACTATTTTCC
TTTTCAACTGTAGTCCACAGTTCTAAGAAATATCCCTAGTTTGTAACCAAGAG
CCACACTTTTTCTGTTACCTAAGAAGGCACTGTCAGTTTCAGTTATGTTGTCTT
CCCATAAACACTTCCCAAATGTTTACAGAGGATTAGATTAAATTAGATTAATA
GATTAGATGAATTGAAGATAAAGAAACAGAGTGTTATGAATTTTGACTCGTC
TTAGTTGTCTGTTCTGTCTGCTTATGTACACTGTCCTGGAGATGAACTATAAA
TTTGTGCAAGAAATTCTCAACTTCTGTTCTGTTCAATCGTAGAGCCTCATTAG
GGGTTAAATACCAGCTTGAATAGAGTGGTTTAAGCATCTTCAGTTCCCAGATG
TCTCAAATGTAATATCCAACTCAAAGAAATCTTGCCAATGTACTGCATTCTTC
ATTTGACACCTTGAAATGCATGACTAACAAATTCCTTTCGAGAAAGAATCT
TTAACCTCAACACAATAACATCAATAGACTGTCAAAGAAATAGTAAATTATA
CCCCATTAGTAGCCATAATTCTATGTAAAATTGCCACAACTGTAGCCTGGAAT
GAGTCCTTAATTTATATCCTTCAGTATTCCCTAAATTTAAATAGCAATGCATC
ATTTTATTATGTACCCAATTTTAATCCTGGAACATAATTTCAGAATGATGCAA
TGCTTCCTAAAGGGTTTTTAGACTGGTTCATTATGGGATTATTGAAGCTGTGT
GGTTTAGTAGAATGAATAGATGAATAGATGCTTTTGAAGCCAGACAAACCCA
```

Figure 1 Cont.

```
GTCTTGCTTTGTTAATTTACTAGCTGTTAACCTTGAGAAAATCCAGTTACCCA
TACAAGCCTCTATTTCTCTATATAGGAAATGGGCACACAAATACTTTGCAGAA
TTGGGTTTTGAGATAATGCATATAAAACGGGAGGCACTGGCTGGTGCTCATG
GAATGATGTTGATGAATGACAAATCAACTCTGCTAATATAGACGAGACTTTC
ATTCATTTTAAAGGGTACTATGAAATCACAATCTTGAAGTATATGCAGTAAG
GACATAGAGAAGAATGTGGCAGATGATTTGAATGTGTTTCCAATAACTTTGA
ATTCCCAAAATTATAATGGTGACTATTCATAACCTATCAAATGGAGAATCAA
ACCAAATATATTGAAATATTATTTACATTAAAATTGAGAGGCGTAAAAATC
ATAGCAATGAGAACTCTTCAAAAAAATCAATTTAAAATTTTTCATTCAGATGC
ATTATTTACTCAATACGTTTAACAAAGGTATGAATGCTAAAATAAAATAGAA
ATAACATAAGGAATACAAAAATTTTATGATGGACAAATTTCCCATTCATTTTT
TTTCTGTATATTGAGTTTTGCATTTGGGAAATTATATCAACTGATTTCAGGTG
ACTTTTGCTGAATGGAAGTATTAAAACAAAGGGGGTTTTTTTGCATGATATTT
CCTATAATTTAAAAGGTAATACATGTACCTGGAGAAAATTTAGAAAATACTG
AAAGTCAATAGAAAAAAATATTCCACAATCTGACCACCAGTGGTGGTTTGAA
AACTTTTATAAAGAAGTTTGGGCTGAGTGTGGTGGCTCACACCTGTAATCCTA
GCACTTTGGGAGGCCAAGGTGGGAGGATCACTTGAGCCCAGGAGTTTGAGGC
CAGCCTGGGCAACATAGCGACACCCGTCTCTATGAAAAAAAATTTTTTA
AAGAAGTCTGGGGAAAACAACTTAGCATTAGGGCAGATGTGCTACTTATCCA
GAAGTTGCCTTTCTTTGCTAGTTTAATAGGAAGGGCTTGAGGATACTGATGGA
GATTATGAGGGGGCTAAAAGTCGTCCAACACCCCATAGTGTCCATTGCCACT
TCCCAAGGGAAATGAATGCTTAAAGTCAGAAGAGTCTAATTTCTGTTTATTAC
TCCTTCTCTCACCTTGTACAGAGCAGAGCTGAATAGTATTCTATTTTTGGCAA
GCTGAAAACAGAGACCTGAGCCTTTCTTTATATACAAATGTTTATGGATGATT
AGATTAATAACACAATATAGTTCTTAGTTTTAAATACCTATAGTTTATTCCAG
GAACTCTTTACTTATATAACCTACTGTTGTAACTAATCCTGGGACACAATGTA
AGGGCTTCGTCCTCTTGAAACACTGCTGATCCTAGAGGAAAATAGCCATTTCC
TTTATTCACTGGCTCTGATGTGTGTGGCCATTCTTCACCACAGTCATATTATCC
ACTTTGAATCAAAGGTGTGGTGGATTATTCTATTGAGAATTCTAATTCTCTGG
GTGTGGATTTTACACTGGCTTTTATGTTGTCCATTTAGGTGTGGTGTATGGAG
CCCTGTGTATTGGAATGGCTGCGCTGGCGTCACTTATGGGAGCTTTGTTGCAG
GTGAGAGCTGGCCCCTGGAGGTTTAAGTCATAAATCACTAAATCTTTTTTCAA
TGTTGATGTGACCATCCTTCCAGACTTCTCTCGATATATATCGACACCTGGAC
ATATCAAGTGGCAGGGATGACTACACTTTTAATTTTTTTAATTAAACTTTGT
GTTTGAGATAATTGTGGATTTACATGCAATTGTGAGATATAATACAGAGAG
ATCTCATATACTCTTTACTCAGTTTCCCTCAGTGGTAACATCTTGCAGTGGTA
ACATCTTGATAGTACAATATCAAACTCATATATTGACATTGATATAGCCAAGA
TACAAAACATTTCTATCACTACAAGAATCCTTGCTGTTGCCCATTTGTAGCCA
CAACCACTTCCCTTCTGCCCCTACTCCCTCCTTAATCCCTGGCAACAACTAAT
CTGTTTTCCATTTCTATAATTTTACCAGGTCAAGAATGCTACATACATGGAAT
TACATAGAATGTAACCTTTTCACTTGGCATAATTCCCTGGAGATTCATCCAG
GTTGTTGCGTATGTCAATAATCTGTCCTGTTTTATTATCAGATAGTATTCTCTG
GTAGGGATGTATCACAGTTTGTTTACCTACTCAGCTGATGAAGGACATCTAAA
TTGTTTCCAGTTTTTGAGTATTACAAACAAATCTGTTACAAACATTACATAAA
GGTTTTTGTGTGAGCATAAGTCTTCATTTCCCTGGGATAACTACCCAGGAGTG
CAACTGTCAGGTGACTGCTAAATGTCTACTTTTAAAAGAAACTGCCAAACTAT
```

Figure 1 Cont.

```
TTTCCAGAGCATGTCATTTTTATATCACTAGCATAGACAAATGGCCCAGTTTA
AACCTCATTCTTTCCAGCATTTAGTGGTGTCTTTTTTTTATATTAGCCATTCT
GATAGGCATATAGTGATATCTCATTGTAGTGTTAATTTGCATTTCCCTAATGG
CTAATGATGTTGAAAATGTTTTTCAGCGACTTATTTTTCATCTATGTATCTTCT
TTCATACATTATCTCATAATGTCTTTTGCTCATGTTCTAATTCAATTGTTTGCT
TTTTTTACTGGTGAGTTTTGAGTGTTCTTTATGTATTCTGTATACTAGCTCTTG
GTCAGATGTGGTTTACAAATATTTCTTACACTGTAGTTTGTCTTTTATCCTC
ATAACAGGGTCTGTCAAAGTGCATTTTTTTTTTTAGTTTGGATAAAGTCTA
GTTTATCAATTTGTCCTTTCATGGATTGTGTTCTGGTGTAAAGTCTAAGAACT
TTACCTAGCCCCAGCTTTTGAAGATTTTCTTCTATGTTTCTTTTCAAAGAGTTT
TAGAGTTTTACATTTTATATTTAAGTCTACAATCCCTTTGGAGTTAATTTTGTA
TAAAATGTGAGACTTAGGTTGACATTCTCTTTTCCTCTATGGATGTGCAACCA
GCACCATTTGTTGAAAAGGCTTCTTCCATTGACCTGCCTTTACACCTTCGTA
AAACGTCCATTAGGCATATTTGTGTGAGTCTATTTCTGAATTCTCTGTTTTCTT
TCATTTATTTATGTGTCTGTACTTCTGCCAATACCACACAGCTTTATAATTTGA
TTATTTTGATTACTGCAGCTTTAAAATAAGTTTCAAGATCAGGTCGATCGATT
CCTCCCACTGTATTCTTATTTTCGAAATTGTTTTAGCTATTCTAGTTCTTTTGC
CTTTCCATATGAAGTCTAGGATAATCTTGTCTGTATCTACAAAAAAAATCTTG
CTTAAATATTGATAGCCTGAAAGCTTTTATCCATTTGAGAAGAAATGACATC
TTTACCATGTTGAATTTTCTAAAACATGAACATGGTATGTCTCTTCATTTATTT
AGCTTTTCTATGCAAATCGTATTTTTTATGTTGATGTCTGTGTGTTCAATGCTA
AAATGTAGAAATAAAATTGATGTGTTTATATTTATCTTCAATCTTGTGACCTT
GCTGAGCTCACTTATTAGTTCTGATAATTTTTTGCTTCTTTGTTTTATGGTTTA
GTTTGTTTTGTTATATTCCTTGAGATATTCTACATAAACAGTCATGTCATCTTC
GAATGGGGCAGTTTTATTTCTTTCCTTCTGATCTGTATGAATGCCTTTTATTTC
CTTATTGCACTGGCTTCAACTTCCATATCATGTTGAATAGAAGTAGTGAGAGT
GGAAATCCTTACCCAGTTCCCCAATGTGAACAGGAAACTCTCTATTCCTATTC
TCTATTCCTATTTTTTCTGAGAGTTTTCACCATAAATGGCAGTTGAATTTTTT
CAAATGCTTTTCTGTAATCAATTTATATGATCATGTGATCTTCTTCTTTAGCC
TGCTTACAGGATGGATTACATTGATTGGTTTTTAATGCAGAACCAGCCTTGC
ATACCGGGAATAAACCTTGTTTGGTCATGGTGTGTAGTTATTTTTATATATTG
CTGAATTATATGTGCTAATATTTTATTAAGAATTTTTACATCTATGTTCATGAA
GGATATTGATCTGTAGTGGTGTGTGTGTGCATGCATGCGTGTGTGTGTGTG
TGTGTGTGTGTGTGTGTATACTGCCTTTGGTTTTGATAGCAGGGTTATACT
AGCTTCATAAAATAAATTGGGAAGGATTCTGTTTTCTATTTCTAGGAGAGAT
TGTCTAAAATTAGTGCTAATTCTTCCTTAATTATTTGGTAGAATTCTCTAGGG
AAAGCATCTGGGCCTGGATTTTTTTTAGTTTCAAAATTATGAATTTAATTTCC
TTAATAGTTACAGAGCTATTCAAATTATCCATTTCATATTCGATGAATTGTGA
CAATTTATGTTTTGAGGAATTGTTCCATTTTATCTAAGTTTGCAAATTTATAC
ATGTATAGTTGTTCATAGTAGTTCTGTACTATCCTTTGGCATCTGCAGGACCT
GTAGTGATAGCCCCTGTTCCATTCCTAATATTGGTAATTTGTATCTTATTTTT
TCAGTCTTGCTACAGGTTTGTCAATTTCATTGATGTTTTCAAAGAACCAGCTT
CTTTTTTTCATTGATTTTCTGTGTTGTTTTCTGTTTTCACTCATTGATTTTTA
ACTTTTATCTTTATGATTTCTTTTCTCCTTGCTTTGAGTTTTAATTTGCTGTTTT
CGAGGTGGGATCTTAGATTACTGATTTGAATCTTCTCCTCTTTTCTAATGTGTG
CATTTATTGCTGAAAATTTCCTTCTTGGCACCAGTTTAGCTGTGTTCCACAACT
```

Figure 1 Cont.

```
TTTGACATCTTGTATGTTTGTTTACAGTCAGCTGAATGTATTTTTACGTTTTCT
TTGAGATATTCTTTTGATTTATGGATTATTTAGAAGTATGGTACTTAGTTTGCA
AGTATTCAAAGATTTTCCTGTTATCTTTCTGTTATTGATTACTAGTTTGATTCT
ATTGTGATCAGAGAACACACTCTTTATGATTTCAGTACTTTTAAACTTGTTGA
GGTCTGTTTTATAACCTAGGATATGGTATTTGGTATATGTTCCATGAGCACT
TGAAAAGAATGTGTATTCTTTTTTTATTAGGTAGAGTGTTCCATAAATATCAA
TTACATTCTGTTTGTTGATGGTTGCTGATTTTCTGTTTGGTTGTTTATCAATTG
TTGAGAGAGGGGTGGTGAATTCTTCAACTATAATTGTGTATTTGTCTATTTCC
CTTTTAGTTCTATCAGTTTTTGCTTTGCTTCATGCATTGGGTCTTAATGAAGGA
TTAACCTTTTTGTTATTATATAATGTGCCTATCTGTCTCTGAGAAATTTTTTG
CTGTGAGGTGTATTTATTTATATTAATATAGTTACTTCTACTTTCCATTGATT
AATGGTTGCATAGTATATTTTCCATTTTTTCACTTTGAACCACCTATGTTGCT
ATATTAGAAGTGAGTTTTTTGTAGACAGCACACAGTTGAGTCTTTTTAAAA
ATCCATCCTGTCAATCTCTGTCTTTTCATTGGTGTACTTAGACCATTCACATTT
AATATAATTATTGGTATGTTATGTTAGGGCTTAAGAATCAGTTTTTAGTTGTC
TGTTTGGTATTTCTGTTTTTTGTTTCTGCCTTCCTGTGAGTTGTTCTGTGGTTC
CTTCTTTCTACCATTTCCTTTCTGTTTAGAAAACTTCTTTTAGCCATTCTTTTAG
TGTTCCTTCACCTGAGAATGTCTTGAGTTTCCCCTTTATCCCCAAAGGATATTT
TTGTTGGGTATATGATTCTGAGTTGCTAGTATTTTTCCCCAGGAGTTAAAAA
AATATTTTCTACTTTCTTTTTGTCTCTATCATTTCTGATGATAAATCTGCTACT
ATTCTAATTGTTTTCCCTTACAGGTAAGGAGTCATTTCTTTCTGAATGCTCTCA
GGTTTTTTGTTTTGTTTTGTTTTGTTTTTCTTTAGTTTTCAGAAGTTTAATTA
TGATGTATCTTGGTGTGTATTTCCTTGTTTTGAGTTTTTGATGTGTCTTGGCAC
GTGTTTCTTTCTTTTCCTATGTTTTAGGGTTACTCAGCTTCTTGAATCTTGAAT
CAGCTTCTTTCATAAGTCTGAAAGAGATTTATGTCTCTTATCAAATTTGAGAA
GTTCAGACATTAATTCTTTGAGTACTTTTCCACCCCATCTTCTTTCTCTTTTCCT
CTGGGACTCTCATGACATGAATGTTAAATATTTTGTTATAGTTCTACAGATC
CCTGAAGTTTATTTTATATTTCTTCATTTCATTTCTCTCTATTGTTCAGTTTGGG
TTATTTCTGTTGTTCTGTCATTCAGTTCACCGATCTTTTCTCTGTTCCTTCTAT
ACTGCTATTGTGCCCATTCATTTAAAATTTTTTATTTCAGTTATTGTATTTGTT
CAGAGTAACAGTTTCATTTGGTTCTTCCTAATATCTTCTTTTTTCCCTGAGAT
TTTTCTCTCTATATATATTTTTCCCTCTATTTTTTCATTAGTTTCAAGTGAATT
CTAATTGTTAAAGCATTTTTAAATCATGGCTGTTTAAATTTTTTATCAAATA
ATTCTGTTTCTGTAATCTTTATATTTAGTTTGAGATCTTCCTGGTTCTTTCTATG
AAAAGTTAATTTCTGTTGAAACCTGGGCATTTCAATATTATGTGATGAAACTT
TGAATCTTACCTTCTGTTTTAGCCAGCTTTCTCTGACACTACGTCAGTAGCATA
AGGGAGGGTGCCGCCTCATTACTTCAGGTGGAGGTAGAAGTCCAGAGGGAG
GAGCTCCTTGTTATGCTGGATAGGGGTGTGTAGAATACTATGAGACATATTGT
GGCTATAAGATTAATGATAGTGCATGAGGCCCACTGAAATATCTTGCAGGGC
TGATACTACATGTCATGTAGGAATTTACAACCCTGGCTCAGGGATTTCCAGGA
AAAAAAGCCACCTCAGCACAGAAGCAGCTTTCATAAACCTTAGAACAAAGC
TTACTTTTACAATAATAGCTTAAATACCCTTTATGAAAGAAACAGCTGGTAAC
TAACCTGGACTAAATACAGGTATAAGAAAGGGAGAAGGACCCCCAAAGTCT
GACAATGGTCTCTGGATGAAGACTCTCTGGTCAGTTCATGATCTGACCCCCTG
ACTGTATCTGGCCCATGACACCAGCTTATTCTCACTATCCATCTTCTAAGAGT
GCTGCCAGAATAAACCGATTGAGCATTAGATGGTGCCTAAGACTCATCTTTG
```

Figure 1 Cont.

ATGTGAAGTGAACAGAAAAGGAGACATCGCCCCTGGGGAAGCTGGTTAACT
AGGTCCACCTACAACCTCTGAACACAACTGGCATTGAGGATAGGATAAGTAA
GTGAGCAAGTAAGTAATGGCACCCATTTCTAAGGAAGGACTGGGAAAGGGT
GACTGGGGACTGGTTCTGATCAAGAAGTCAAATGAAGCCCTCCGGAACACTC
CGTAGTGTGTCTGGTAGTTTTTATTTTACTTTGTGGCCTGTTGCTGCCTTCTAC
ATACTTTGTCTGTGCCTCTGTTGTGAAATTGCCACCATGAAAAACCTGCCAAA
ATTATTCTTAAGACCACTCTGGTCCCCAGTAACTGGGGACAGGCTCTAAGGA
GGAGGAAGCAGAGGTGGAGGATGCCCCGGCTTGAAGAGCTAACCACTGGCT
GGTGTGTCTCTGGCTCCTGCTGTGGGAGGGTTGCTCCTTGCCCCAAGGATCT
TGGCACTGTGATGCCACAGACCAAGAAGGCAAAGGTGAAGCTTACCTGCTGA
AGGGTTATGTGCTGTTGCCCACCAGCTAGGGACTTAGAAGCATATTTCCCAAT
AGATCCTTGGACTAACACCACCAGTGAAGTCCACAAGAATCATCAAAGGGCA
TGTCGCAGCTGTTCCCAGCCCACCATGCACTCCAGCTGAGACAGTGTGGCTTC
TCAAGGGGTGTGCCCCAGCCTGTGATGTCTGCTGAGTGTTGCTGGCAGCAGC
CCATAGGCAACATGCCCAAGTCACGCGGGCTCACCTCAGAGTCGTGTCATTC
TGCCTGGTCGATCCAGAGCCCTGTGAGCTGTGGAATGATGATCCTGGGTGTG
CTGGCTTACCGCTGGCCACACCACAGGTGTCACCAGTCATCACTTGGGCTGA
GAAAGCTGCTGCCACCTCCACAGCTGGCTGAGATGAGGAAGTGTGTCCTAGA
CACCATATGGTCCATGAAGAGGTTCACCCCTAATGTGGACAGAAATTCAAAG
CCTGCTCAAAGACCTGGTGCAGGAACCCAAAGAGAAAGGCACCACCTGGCTG
TGCTGTGTGTACCTGAGAGGAAGTGCTTTGCAACTCATAGGCCGAGAAATAC
AAATACAGCAGCCAGCGGCTATCTTTAAAGATAATAAGATCATTTCCTTATTT
CAAGACCCTGTTGAGCTTATCCAGGCACAGAGTAGAGTGGGTAGACATAACT
GTCCCTGCAGTCCGCTGCAGTGGCTATTCAGGCCTGGCGAATAGCACCCCA
GAATGAGCCTCTTTTCATCAAGGGCTGAAGGTGGCTGGTGCACACTGAGGAA
GAAGGGGAGCCACTGTGGCGCTTAGGCATGCTCCAGTGAGTTTGCACAGCCG
CCACTCCCATGGGACAGGGCACAACTGGGAGACCTTGGAACAGACCACCTT
GCACCCGGATGGTTTACAGATGTTTTTAAGGAGAGCCCATCGTAAGCCAAAC
CAACTCTCCTGGCCCTGATGGCCACAGTCCCTGAAGTTAATTGAGCTCTGTAG
GTCCTCATCACCCTGGAAAATGCTGAAGAATAGCTAAGAATCCCTAAGAAAA
CTTAGGGAACTCACCCTATACCACTCTTCAGGTCCAGGGTCCCTAGCGGGCTG
CCTTCTTTGCACCTTTCAGACAGAACCATCCAACAGTGTTCACAACAGCACCT
CGCTCCCTACCCACCACACAGGACCTTGCAGCCAGAGGTCTCACACTGGGCT
CTGCTCTCCCTGGCCTTCTCACACCCATCACCCACGGGATGAGGCCCAGTCCA
GCTGTTCACAAGGGCAGAGTGACCTCTACTGGCAGATACGCTGAAGGGTGCT
TCCAAATTGGCTCCTGTCTGGCAAGCCTCATGAATTCCTGCAAACTCTCCTTA
ATACCAATGTCGTCCAGTCATCCCACCCACTGACCCACCACCCATCTGGATGG
CTGAGCATCAACTTCCACCTTTGGGAAGATGTCTTCACTGCTAACATTCCTGC
CCTGTGTCCAGGATGACCCACCTGGACTGTCCCACCCACCCTACCTATATCCC
TCCCTGGCAAGACCTTTACTGGTATATTTGCCTAGGGGTCTCTTGGGCCACCA
CTGTTCCTGCAGCCAGTGCCTCCTAGAGACACTTGGTGCCCCAGCTGTGCCTG
ACAGCCATCTGGAATGGACAACACCTTGAACTTTGGCTTCATCGGGCCGTGTT
CAAGATACGATTTTGGATCTTTGACAGCACCTCAGCACACACAGTGTCCCCA
GACCTAATTGCTTAGTTCTGTGTCCTCCTTATCCTTCTGTTCCATTTTCACCTG
TCATTGCTCTGTAATCAAGCAACTCTAAGCCTGCTACCACTGAGTCCATTCAA
CTCCTTTCACCTGCTCATGTAATCGTGTTTCCAAGCCCCAGTGTGCCCGTGTTC

Figure 1 Cont.

```
TTTTGCTGCTACTCCGGGTGGCCTGACTTTCCACATCCAACTGTGGCTTCTCCA
GACCTATTCACCAATTACTTGGCACTGAGGTCACTGACAGCCTCCACCACATT
TTGGCCACCCACTGAGCAGCTAACCTTCCAGCCTGCTGGGCATGCCTTCATTG
GCCTGCCACACATCCATTGCTTCCCGTCCAGACTTGGTCGCTACCTGTCCTCC
ACTCTTCCCCCATCATTGGCGAGTCTGCCCCAAAGCCACAGCCGAACCCCATT
CTCATGATCTCCCGTAACTGCTCAGCTGGACACTAGATCTACTGTATCCTCTC
TGTGATGATACAGTTCATTTCCAGGTTTTTCCAAGGGCGCCACCAACTCCTAC
TCACCGTCCTACAGAAGATCCATTTCTCAAGATTTGACTGACCATGGAGCGCA
CTTTCAAACTTGGGCAGCCTCTCAATTATTGACCCCCTCAGGGTCAGGGGTGG
AGTGTGGTATACAATGAGATATATTATGGCTATAAGATTAATGATAGGCATA
AGGCCACTCAAGCAACTCAGAGGGTCAGTCCTATCTGTCAAACTTAGCAGTA
TGAAGCAACCTGGCCGGGGATTTCCAACCAGATTTCCAGGAGACCAGGTCAC
CTCAGCACGATGCAATTTTCACAAACCTTGGAACAAAGCTTACCCTTACAAG
CATAGCTTAATCTCTCTTTGTGAACAAAACACCTGGTAACTGACCTGGATTGA
ATACAAGTATAAGAAAGGAGGAAGGATCCCCTAAACTCTGAGAAAGGTCTCT
AGATGAAAACCCTCCTGGTCTGTCAGTCATCTAACCTGTGACTAAATCTGGCC
CACGACACCATCCTGCTCCTGCTATTCTTCTGGTAAGAGCACTGCCAGAATAA
AATGCATGAGCATCAGACGGTGTACAAGACTCAACAATGATGCAAAGCGAA
CTCAAAGGAAGAGGCTTCCCTGGGAAGCTGGTTAACTAGGACCACCCGAAAC
ACGCGAGCACCACAGGGTGGAATTCACTGACATCATGGAGGAGGTGGCTTTG
TCACTGCTGGGCCATGGTGAAAGTCCCGATTCTCCACTAGGCCTCCCATGTCA
TTGCCAGCAGGGAGGCAAAGGGTGCCTGGTGACAGTCTGGGGGGATGGAAT
CTAGGCTGGCATGGGTGTGGGTGGGGTGAACAGATTATTCTGTGGTGTTCGG
ATGGAATGGAGCGGTTGGGGTCTAAGAGTTTTCTATCTTCCTAGGCTGCTCCT
TTCCTGGCCCTGTGTCTAGAGAGAACAGGATTTTGTGAGGGCTTTTTATCT
TTTTAAAGTTTTTTGCCTGTGTCTGTTGCCATTTCCAGGCTGGCTGGCTTCTT
CAGTTCTCAGGCTGGGATACATGAAGCAAAAAGAAAACTTAGGGAACTCACC
CTGTACCATTCTTCAGGTCCAGGGTCCCTAGCAGGCTGCCTTCTTTGCACCTTT
CAGAGTCTTCTTATGTTTATTTTATATGGAATGTCAGGATTTTTAATTTTATTA
GTAGGAGGAATAGAGAAACATATGTTTATCTTCTCAGAAGTAGAAATACTTC
ATTAAAAAAAATTTGTTTATTTACCTGAAGGGTCTTTCACCTCCTGTGGCGTT
TGCTCTTCTGATTAGAGAGCATTTTTGTGTTGGAAAGCTCCCTCCTGTTCCTGT
GGAGCTGTGGGCCTGGAGAGGACAGACCAATCTTTACAACAGTGTCTTCTTC
CTGAACCCTGTGGGCACCTCACTGTCTTCAACACGCAGGCCTTGGCATAGACT
TCTCCCTCTGCCTGCAACACCTTCCTCTCTACCTCGTCCACTGCCTAAGCCTTA
GTTATTCTTCAGTTTTCATTTAACACATTACTTATTTAAAGAGACTTTTCCTA
TTACCTGGATACATTTGCATTCCCTTCTGCTAAATGTTTCTAGAAGCACCTTGT
ACTTTCTTTATCATCTCCATTATCAAACTGTATTACAGTTATTTATTTAGTGTC
TGTTTTACTGAATAGCCTGTAATTCATGAAGGTGGGGAAGATGACTTCGTTGC
TCAATCCTGTATCAAATATCTGGTTCCTACTGCAGTGCCCAGGACAAAGCAA
GACATTAACAACTTTAGCTTGAATATTAACTAATAATGTAGTTAGGCTCATAA
ATATCCTATTATCTGATGACCCCAAGTGCTCCCTGAAATTTCCTTGGCCACTT
GGGCTGCTCCTCTGGGATCCTGGACCTCCCCTTGACCTAGAAACTTAAAGGCT
AGTACTGGCACAGCAGGGTCCTCCAGGATCTTTCTTCAGTCCTAAGGCTTGG
GGCCATTCTGGTTGGTTGTTGTTTAGGACATAGCAGTTGTAAAATAGTTTGAC
CCCATCCCTGATTATATGAATGAATGAATTAGATCCAGAAGCTCCAAGCCTG
```

Figure 1 Cont.

```
CCCAGCACTCCTAAACCACAGCCAGTCATACAGAATTTGCTTTCTTCATAGTC
TGCATTAGTGCCTGGAGCTCTTATTGTGGTTGATTCCCCTTTTTCCATATATCA
GCTATGGCCTGATTATATACAATGACATGTTCTAGCAAAGTCATCATAACTCC
AAGCCAGTTCATCCTTGCTTCATCTCTAGCCAAGGTCTTATTTCCTCTTGTAAT
CTTTTTTGGGTGTCTTTGTTATGTCTCCAAAACTGCTCACAGATCACACAGTC
ATCACTTGCTTTGTGGGTCATATGACGTCTTGCAGTGAAGTCTATCTCCCTTCT
GACTGGACTGTGTGTAAACTGACTCAGGATCACATCCTTGAGTCCGCATCCTT
TTAAACACTAGTTCTCCTCTCTACTCAGTACCACATCCTTTTCTTCTTCCATGA
AGTAGGCCTATTTAAAACAACAACGACAACAAGAAGCACTATTTCCTCTAAT
ATTTCCCTGACTTGGTATTTTCTCTTTGATTCATTCATTCTGCTCTATTAAACC
CCTTTACTCTCTGGACAAACCAGTGATTCCCTGCTCTTCTTTTATGGTTGTGTC
CATTCTTAAGAACTGGGCATTAGATTATTGGGAACGTATATCTCTTGGAAGCT
TCATTTAGTTGCTTTGCCTCATGCGATGTTTGCACTGTAAATCTTTTTTACTAT
CATGGATTTGATATCTCTACATCAAAGCAAAGGTTGCAGTTATCTAATTAGAT
TTTAAATCTATTTCTACATGATTTGATCAGTCTTTTTAAAATCGTATTTCTCAT
TCTAGTTTCATCCTTAGGGAATCAAATCAGGAATGGCAAATGGGTTTCATCCT
CCTCTCTGGTCACATAGCAGTACTCGTCCACCGTTATGAGAGGATTTTGAGAT
TATCAAAGCACAAGGAGTGCTGTGATTTATAAACACCTGCAAGAGCAATGC
TAAGAGGAGAGGTATCATTCATGATTTATACATTCACATAGGCACTACCATTG
TCGCAGACCTCTCTATCTTCTTTGTGTTGTGTGGCCTTTTTGAGGCTACTTGC
AGAAACAGATGGATCCTTGAGACTGAGATGCAGAAACTTGTAAGTTCTAATG
ACTTCTTTTCCAGTGATAAGGCTATCATGACTGAAACTATGATTTTCAGAAGG
AGGCCGAATACTTTAAGTCATTATCCTGATGAAATGACTTTGAAATATTTGAG
TTTCGATTTGAGATTGCTAATTGCTGACGTTGTATTATTTTGTAGGCAGCACT
CAGCGTATTTGGTATGGTTGGTGGACCACTTATGGGCCTGTTCGCTTTGGGCA
TTTTGGTTCCCTTTGCCAACTCAATTGTAAGTACAAAGAATGAATATGCTTGA
GGATTACTTTTGAACTATACTAGCAGCTCTACACTTTTTCTCAGTTGGTTCC
TTTGAGATTTGTCATTAGCTACTTGTCTTGATGACTTAAATTATTTCTGTTGAC
TTTGGTGGAGTGTACAAGGAAGTACTATGTATGGGGACCCTAAATGTGTGAA
GCTCAATGGAAACTTCCAGAACCATATAGGGCAATTTTAAATATTCATAATAT
AACTAAAGGAGCAACATTTTATGCACGTACCTACTTGCCCTTCTCAAAAATT
AATAGCTAGGATTTAAAAGAGATCAATAGGCTCAGAGATGAGAGATTTAAGG
GCAGAAAACTTAGGATTTCTGTAATAGCCATAGCACAGCAAAGAGAAGGA
ACACAATCTTACCACCTTGGCCAGGAATTTTCTACTCCTGACATTTAAAGCTG
TAGCTCCCACAACATGATTTAGCCCCAAAGGGGTGATCATAATTGGGAATAT
TTTCCAGAAAGACGTAATATCTCTGTCCTTCTACCTAGACATATCTGTGCTTA
GAAGTGCTAACTTTTGTTTGGAATAAATGAGCTAGAAATTATTTCTCTGAAAC
CCAGAAGAAAGTCCACTGGTTCAGTCTGGCTATAAGATGTAGTTCAGGAAAA
ACTGATAATGTATGTGCAGTCGCTTCAGATATAGAATAGCCATAGAACTCTG
ACTTCACATTTGGAATTCTATTTTCCTTATAAGGCATTAGGAATTGGTAAGGC
AGATATTAATAAGGACTATTGTGGTTATTATTTATTATCCTCAATGAAATGTC
ATATGAAAAGCTGCTTTTGTAGGAATTAATCACAATGGAAGAGATTTGTTTGT
GTCCACCTCAGAATGTTGAAGCTTGGATTAGATTCTTTGCATGATGAAATGCA
TTAGTTTGTTAAGTATTAGAAAAATGTATTTAAAAATCAACTTTTGATATTTG
GCATTTGTTGCCAGCGTGTATTTCCTCCGGAAGAGCTGTAGCTGACTAAGCTA
ACATGTCCTTTTCTGGGGGCGGTAACGGAAGAATAACATACTATTCTTCCTGC
```

Figure 1 Cont.

```
CATAAACAGTATCTTTTTTTTTTTAAACCATGTCCAGGTTTTTCACCAGCAGA
TTATCTGCCTTCCTTAAAAGTGGCCTTTCTCACTCCTTTTTCTCTCCCTGCCTC
AATACCTTTCATTCATTTATTCACTTGTTCATTTATTCAATAGATTTTTATGGG
CTGAGCACTATCTTGGGAGGAGAGAGCGTTGAATGTTTCTGCCCTTGTGAGTT
TTATAATTTCGTGCCATGTTGAACTTGGCTTTCTAATATTAATTTTGACATCAA
AGCAAATTGTATTATTTTTCTTTTAAAGGCATTCTTGTTTACAGGGAGCACTT
GTTGGTCTGATGGCTGGATTTGCCATTTCTCTATGGGTTGGAATTGGAGCTCA
AATATATCCTCCACTTCCTGAGAACATTGCCATTGCACCTTGATATCCAAG
GCTGTAACAGCACCTACAATGAGACAAATTTGATTACAACCACAGAAATGCC
ATTACTACTAGTGTTTTCAAATATACAATGTTCAAAGGTATTGAATTAAGT
TTTATTACATTATACTTTAAAAAATTTACGCAACAAGTAGAGAACCCCACTTG
CTTTTTGTCTTGCTTACAACACTGTGATTTTGCCTAATTCTGAAATGAGTAAA
ACCCATGTGGTTAGCTATAGTATTTCTGCAGCGGTAACAAAAAATGTCATAT
TTTCATAATTTCTCTAGAAATTTCTGCCTTGTCTACAGATCTAAGAAGACTTA
AATATTAATGAGAAACTTCTGTTATGTGTAAACTCTCCTAAACACCAGCTCTT
AGCTGCATGAAGAATTATCTTTGTCTTGGAAAAACTTTTAAAATGGAAAGCA
CAATTATAGAATAAATATTGCTTATATAGTCTTAGAAAGATAGATTTTACTGA
CCAAAAGCTACAATTATTTAAACATGTTAAATAACTGCCATTGTTCAGTTGA
AGATTCCAAATCTTTAAAGCATTAGAAGTGATTGCAGCTGTGATCTTCATGCT
ACAGATTTCAGTCATGCAGTACACTTTGGAGCCTCTAAATGCTGAAGTTGTCT
GATTTAACGTACTGAAATAGTGGGTAGAGGCATGCTTTATTGTACAGTGAAT
GTGAGGTCAAGACTTTCTTTAGTGGATATATAAGTGTCCAGCTTTAAAGCACA
AACCCTGTGAATACGTTCAAGGAATGCAAAGATGATGCCATTGCCCCTAGAG
TATTGCCCCAGTGCCAGCTTATCTGGAATGACATCAATATAGTCATACCTTTG
GGGTCAAGACACGGCATACCCCTCTTAAAATGGACACACTCCTGAGAGAAGG
AACGTGATCATACATATAGCCATTATTAGCAATTTGTGTTCTGGAGAGAATTC
AGCTATGAGAAAGCTAGCCAGTGGGACTTCCAGGGGCGTTCCAGGCAGGTAA
GCTGTGTATGGTAGAGTGGAAAGGTAGTTCCAGAGCCTGAGGCGTATTTGAG
GGAAGTTTTACTAGGTGAGGTGCTGTGGAGAGAGGGGCAAGGACATGTGGA
GAGCAGTCTGGACAGGCATGAAAGCACTAATGGGAGGGGACTGGGAGAGTC
ATCAGAGTCAGAAAGGGAGAAAAGATTAATTGAAGGTTAAGTGAGAAGACA
CAGGATGTTCTTCTTGTTTATGATTTGCTTAGCGTTTCCTAATTATGTAAA
TATTTGCCCTTAAAAGTCTAAGGCAAAATGGTTATTTGGATTCCTGAAACAAA
TAAATTAGCTGAAGTTTATTCTATGCCTGGTACCATAATAGTTTTATATGTTA
GTTTACTTATCAAATATTTCAGCTAATAAACAAGAATTTTTGAGCATGGACTA
TGTACCCAGCACTGTGCTGGCCATTTATTTAGTATCCATGGAAGAAAATCTTC
CTCTCCCAGCCACTGTTTCCTGCCTTCCAGAAAATTCTAATCTAGCAGGAGGG
AATGTGCAAATATACGCAAAACAATAAACTCAGTAAGCATGCTAAGTATAAA
AACTAAGACATAGTAAATAAAAATACTTGATACATTTTGTTAAAAGAGTG
AGTACAAAGTTGGAGTGTAAGTTAGCATGAAGACTTCAGAGATATACTACTA
CTTCAAGAATGCATAGGTTTGGCTAGATGAAGGGGAAGATCTGGAAAGTCAT
TCTTGTCACAGAAAATGACCAGAAGGGAAATTGGACAAGAAAATAAATTAA
AACATGCATTGTGGTAAGTAATATTCACAGGATATCATGGGAGCCAGAAGGA
GGAAGTCTGCCTGACTGAAGTCAAGGAAACCTTCTTAGAGGAGAATTGCATG
GGCTGGAGTTAGTCAGGTAGCAGGATTGAGCACAGGGACACAATCTGTATCG
CAAGGAAGGAGGAGTGTGTGTCGCAGAATGAAGAAACGACCGGTGCAAAAG
```

Figure 1 Cont.

```
CATGAAGGACTGAAGAATCAGGGCATCTTAGGAAATCATCCTAGTTCCATAG
GGCTGGAGCACAAGGGTTGTGAGCCACCCAGCTGAAGGTTGAATGTGTGATG
CTTTGGTTGCCTAGATACAAATTGTTTCAATTGCCTAGATTCAGTTTTGATTTT
TTTAAGTTTACAATATTTGATGGTTACATTGGTAGCTTGCTGTGGTTTTAATTT
GTATTTCCCTTAAGATTAATGAAGTCAAATACATTTTCATTTGTTTGTTGGCCA
TTTGGATATTTACTTTTGCGACTTAGTTATTGAAGTCTTTAGTCCATCTGAAAT
GGATTCTCTGTCTTTTCTTACTTACATAGGAGTTCATGACATATTCTACATAT
GAGATATGTTTTGAAAATGTTTCTCTCCCATTCTATGGGTTACCTTTTACTCT
TTTAATGATACTTTTTTGTCAGTCAAAATTTCTTAATTTTAATTTATTTCTGTT
TCTCAGTTTTTCCTATATGGTTAGTCCTTTATGTGTCTTGTTTAAGAAATCCT
TGTCTACCCTGCAATCATAAAGATATTCCACTAATTTTTTATTTAAAAGCTTTA
TTGTTAACCATTTCCATTGAGGAAGTGTAATCCACTTTGGAATTGATTTCTGT
GGGTGGTGTGATCAAGATTATTTTTCCCCATGTGGATACTCAGTTAACTAAAA
ACCATTTATTGAAAGACTCCCCTTTTGCCCCATTGAATGCACTGGCGATGAA
AACGATGTTAACCAAGTAACTATTTTTCTGTGGGTCTATTTCTCAATTCTCTAC
TCTGTTCTATTTTGTCTGTCTTTGGCTCAATATCACACTCTCTTAATTTCATTA
GCTTAACTCAATGTGTTCCCCTCCTTTCTGGGTTCTTGTCACCTCAAGTTCTCA
TTGTTTTGTTTTTGTTTTGTTTGAGACGGAGTCTCAGTCTGTTGCCCAGGCTC
GAGTTCAATGCAACCTCCACCTCTGGGTTCAAGTGATTTTGTGCCTCAGCCT
CCCAAGTAGCTGGGATTACAGGCATGTGCCACCACACCTGGACAATTTTTGT
ATCTTTAGTAGAGATGGGGTTTCACCAGGTTGGCCAGACTGGTCTTGAACTCC
TGACCTCAGGTTATCCACCTGCCTTGGTCTCCCAAAGTGCTGGGATTATAGGT
GTGTGCCACCACCCCAGCCAAGTTCTCATTGTCTTGATCTCTCTGATAGCTTC
AAAAACCTGCCTCCCTCCCCATGCCCCAGGTTTTATATATTGTTCTCAGCAGA
ATGATTGTTCTAAATCAAGCAGCTATCAAAACTGAAAGTGGAATCCTAGAGC
AATCATTGTAGAAATGATCATAGAATGTTCATGTTACTCTTTCACTTAAAACA
TTGCAATGAGTGCCATTGCCTGTAGAGTAAAATTCCAACTCATGCCTGGTCCC
ACAAAAAGCCCCCTGCCTATCTTTCATCTTGTAATCACTGTCTTGCTCACTGT
GCCTCAGTCAGCTGGTGTTAGTCTCTGTTTTCCTCAAGAACATTTTGTTTCTC
AGATCTCAGTTCAAATGTCATTTATTCCCAAAGGTTTTCTCTGACCACTTGTA
GTGTAGTTCCTCCCTCTTCACCCTGTTAATAGCACATCATCTTGTTTTACTTTC
CTTACAGCACTTTCTACTAGTGGAAATTATTATATTTATTAATTTGTTTATTGT
ATTTATCTCTCCATTAGAGCATAAACTATATGTTAGCAGGAATCTTATCTACT
TTATTTTTAAAAAATAATTTCAACTTTTATTTTAGATACCTGTGCAGGTTTCTT
ACTTGGGTAAACTCTTGCCTGTCTCCCTTCACCCTCTGGTAGTCCCCAGTGTCT
ATTGTTCCCTTCTTTGTGTCCATAAGTAACCAACATTTAGCTCCTACTTATAAG
TGAGAACATGTGGTATTTGGTTTTCTGTGCCTGCATTAACTTGCTTGGATAAT
GGCCTCCAGCTGCATCCATGTTGCTGAAAAGGACATGATTTTGTTCTTTTTTC
ATGGCTGCATGGTATTCCATGGTGTATATGTACCACATTTTCTTTATCCAGTCC
ACCATTGATGGGCACCTAGGTTGATTGCATGTCTTTGCTGTTGGGAATAGTGC
TGCGATGAACATATAAGTGCACGTGTCTTTTGGTAGAACAATTTATTTTCCT
TTGGATGTATACCCAGTAGTGGGATTGCTGGGTCAAATGGTTTATCTACCTTA
TTTATGGCTGACTGTCCAATCACAAGAGCAGTGCCTGGGACATCATGCAGAA
TTGAATGAATAAACATGACCTTCAAGTATTTAGTATATAGTCAAGGTGAAGT
TTTGCTTTCAATTCCTGATCTGATAAGATAAAATTAGGACAGCAGGTTATGAC
ATTAAAAACATTATTAAGTGTTATATTTTGACCTTGCCATGGGAATCACTGGT
```

Figure 1 Cont.

```
ATATACTGGTAGTTGCTAGTGGCATTACATGAAATCTTACCGTTGTGTTTTG
CTCTCTTAGGACTCCACTGATGGATAACTGGTATTCTTTATCATATCTGTACTT
CAGCACTGTTGGAACTTTGGTAACATTATTAGTGGGGATACTTGTCAGTTTAT
CAACAGGTAACTATCTAAACATTAGTATTGTTGTATTTACCTCTATATCAGTT
TTTACTGTATCTGTTTTATAGCTATTTATGTTATTTTACTATGATCCTATTGCC
AACTAGTTTAATTATTTCTTCTGTTTTACTCATGGGAAATCTGAAGGCCTAGA
CTTGAAAGCAGAAGACTCATTTCTATTTGAATCTTGGTTCTGCCCTTTAGGGG
CTGCATGAACTTGGGCAAGTCACATAGCTACACTGAGCCTCAGCTTTCTTATG
TATAAAATGAGGACAATAATAATCGACCTGCCCATCTCACAAGTTGCTGTAA
GACAAAAATAAGATGCTTGAAAAGAACTTCATAACTGCTATGATGTTAGGGA
TTTTACACATATTTTTATAATAACCCAATATGCTGTGATCTTTACATGGTCCAG
TATTCATTCTTTGTGAACTGTAAAGAAGCATACACAGGTTATATCTAAACATA
GTGTGGAGGCTTTTTTTTCAGATATTTATCATTTTTTAAAAAGTGTGTTCATTT
TTAAAAAATCAAATTGATACACATAGTATATAAATTGCTCTCTGGGATTGCTA
TAGAACGGTTATCTTGGGACTCCATTTGTCCTCATTCTATGAATTCTCTTAGC
CCCTGTTCCTGTGTTGGGTTTTCTACTGCCTATATTCATTACTTCTCATTCTCAT
TTACTCCCTTAATTGAATGAAACACATCCTATAGCATATTCTCAAGAAAGAGT
AGACAAAAGAAGAGGTTTTGGAAACTTTGTGTGTCTGAAAAAAAAATTATTT
AATCTATCTTATGCTTGATTGATTGTTTGAGTAGAAATTGCTAGGGTTGAAAA
GAACTTTTCTTTTTTCTGAGAGGATGTCTGAATTTTTTTCTAGCTTGCTATGTT
GCTGTTGTGACAGCGCTCTGCTACCAGCTGACACTTTGTGTGTGTCCCATTTT
CACAATGACTGCCTTGGCCTAGGCCTTCAGTAGGGCCCATTCAATCTGAAGAT
CCATGCCCTTCAGTTCTGGACATTTTCTTTTTGTTTCTTTTCTTCCTTTTTAT
TTCTATTTTTAATAATTTTCTGTGTTCTCTCTGAGAACTCCTATTAGTCAAA
CATTTGAATCAGAATCATGGACAGTTCCTCTAATTTTCTCGTTTTTTTCTCTCT
TATTTTTCCTCTCCGTGTCTTTTAGGTCTACTATGTGAGATATTTTTCACTTAC
TTTTCCAATAATTCTCAAAGGAGTGCTCTGATCCAATTTTGAGAATAGTCTGT
AGGGGAACGAGGGCAGGGAAGAGGCTATTGCAGTAACCCAGGTGAGAGATC
ACAGTGCTGGGGCCGGGGTAGTGCGGAGTTGGTGAAACATGCTGGGCTCCCT
GACTCCCTACATCCCCTCACATGTATGCATCCATAGCAGCCACGCCAGGGGA
AGGGTGCAACTGCCTCCTTCAACATGTGTTACAACTAGTTGTGTTCAAGGATG
TCTGATGTCTTTGTTTGCTCCATGCTACAAAGCTGCCAGCACTGTGCCACTTT
ACAGAATCCTGCTATCATTTTCTGTTTTTTGGCACTGAGATAGCACTGTCTCTC
AAACTTCTGTGACACTTGTATTTATAATTATAAATTTGTTGCTATTCATTATT
TCTCAGTTGTTGGAAAATATTCTTTCTTTTCCAAAAGGACTGTGCTCTTTCTCA
AAAATAAAATTCCCAGTACAGTAGGTTTATTAATTTGTTTGGTCCAGTTTGAT
ATATTTTCAGACAGATTTTTGTTGTTGTTGTTGCTGTTGAGATGGAATCTC
GCTCTTTTGCCCAGGCTGGAGTACAGTGGTGCGATCTTGGCTCACTGTAACCT
CTGCCTCCTGCGTTCAAGGGATTCTTCTGCCTCAGCTTCCCGAGTAGCTGGGA
CTACAGGCACGCACCACCACGCCCGGCTAATTTTTGTAATTTTAATAGAGATG
GGGTTTCACCATATTGGCCAGGCTGGTCTCGAACTCCTGACCTCAGGTGATCT
GCCCACCTTGGTCTCCCAAATTGTAGGGATTACAGGCGTGAGCCACCACCAT
GCCCAGTCTTAAGACAGATTTTCATCTTTTCCCAGCAGTTATTCAGTTGTTCA
GATCTGGAATACACCTAACCAGTCTCCCTGTACTATTTGCCCTTTGGTCCTTAT
TTAGCTCATTTTTTAAAAGAAAGTGGAGTATCAGAGTAGCTCCTTTGAATACT
CCTTTTTTTCTTTTAAATGCTTTGATTCTGAAAAACCATATACAGCTATATCTT
```

Figure 1 Cont.

```
TTGTTTCAAGAAGTAACACTCTACCTCAGTGACTGGGATCCAGTAATAGAAA
ACACTTCAACTTCATTAACTTCACAAATAACTTATTCCTACTTCACAGAAGCA
GTGAGTACCTTGAAAACTATGAGAAGCACACAATTTTGATGCTCCCTGGGAA
ACAGATTTTAAAACCTATCGTAGTATACTAAAACTCCCATAAGAGTTCAGGC
CTTACAGACTTGGTTGGCGTTTCAGCACTCCCCTGATTTTTACTATGCAGAAG
GCTATGTTTTCATCAGGAAAATGGGGGCAAATAGTTTCCTAAGTAGATCACA
AACTGTGGGCACAGAGATTGTTTTGTTTCTTTGTTTCTCTAGCACCTAGCAGC
ATCTCCAGCACACAGTAGGTACTCAATAACATTGAACGAATTCATTTAAAATT
GATTCTATCTCCAGAACAGCAGAGGTTCCCATAATTAAAAGTCTAGTATTTGT
ACTAAAGTAGTGGTTCTTAAACTTTAGAGGGCATAAGGATCCTCTTGGAAATT
TTATAAAAATCAGGCTTCAGGGGTCCTACCTGCAGAGGTCCTAATTTGGTCAG
TCCAGGCTAGAGTCTGGGAATCTGCATTTTAAGTACATTCCTTGAATGATTTG
GGGAAGGGTAGTTTGAGGACCACTCTTTGAGATACACAATTTTTAAAAGCAT
CCTCTTTGATCCACAAAAAATACCAAAGCAAAATAGAATTTTTTTTTTTTTTT
TTGTAAAGAAAACCTTAGGGAAGAGGATTTGGATCAAACGTCAGTCAGCATA
CTAATTTTCACTTAAGTAATTTATTCAGCAGTTCCGAATTGCCTGCATTTCTTC
ATAGACATGTATATTTGTAGCCAACAAAGTGGGGAAAAGCAGCTCCACTGTC
TGAAGCGGGCAGATGGTTTGATATTTTACTGATGGCATGGAGGGTGCTTTTA
AACCAGTTTTCCTACCAGCATTGGGCCAGATGACTGTTTCTCTAGTTGAGTAC
CAGATGAAGCAGTTGGCTTGCGTTTAAGCTCTATCTCACACACATATATATGA
TACATATATATATATATATATATATATATATATAGAGAGAGAGAGAGA
GAGAGAGAGAGAGAGAGAGAGAGAGAGAGAGAGAGAGAGAGAGAGACT
CATATTTATTATAGTGAGAGGCTTTCAAGACCTGGGGCTAATTAAGGAAAGG
GGAATTGCGGGCTAAGTGATCAGTGCTTTTAAGTTTCCCTTTCTCTTTGTGTTT
TTTGAATGTATGGAGTTGAACGTGAACAAGTTAAATGCCTGTATAATGGAAT
GTCTCTGTGTAGTTACTGGTGTCCTTTTTAACAACGTAAGTCATGTACATTTT
TTTTCCAGGAGGAAGAAAACAGAACTTAGACCCCAGATATATACTAACCAAA
GAGGACTTTTTATCCAATTTTGATATTTTAAGAAAGTGAGTTGGCTTTCATTT
ACCTTGAGTTAGGAAACTGGGCTTTATTACCTGGATAGAACACTAATTAGTTC
TCAACCTCTTTCTTGAAAAGTGATGGACAAGGAAGGTATAGACCCTATATAA
TCTGATGATCTATATATGTTGGATAGCTCTCTATCCTATGATGATCTATATCTG
TTTTATAGCTCCATATCCTCTGATACGCTATACCTATTGCTTATCTGTGTATCC
TCTGATGAGCTATATCTGTTGCATATCCTCTTTCCTTTGATGATCTTTATCTGC
TGTATATCTCTATCCTCTGATAACCTATATCTGTTGTATATCCCTCTATTCT
CTGATGAGCTACACCTGTTGTATATCTATCTCTCTATCCTCTGATAACCTAT
ATCTGTTGTATATCCCTCTATTCTCTGATGAGCTATACCTGTTGTATATCTCTC
TATATCTGTCTATCCTCTGATAATCTATATCTATTGTATCTCTCTATATCTG
TCTATCCTCTGATAACCTGTATCTGTTGTATATCTCTATATCTGTCTATCCT
CTGATAACTTATATCTGTTATATCTCTATATATCTGTCTATCCTCTGATATT
ATAAATCTGTTGTATATCTATTGTCTGATGGACTATTTTGTATCTATCTTCTGA
TAACCTGTATCTGTTGAATATCTCGGTATCCTCTGAGGAAGTATACCTGTTAT
ATATTTCTCTCCCTCAGTAGATTAGAAAGCTGATGCAGAGAAATAAAAATAG
TAGAAACAATTATTTAGAATTACATGAATGAAGAGCTTCTTTTTCTCCCCCTA
ATCACCATGTTAACATTTTCTTTTAGAAGAAGCATGTTTTGAGCTATAAATCA
CATCCAGTGGAAGATGGTGGAACTGATAATCCTGCTTTCAACCACATTGAATT
GAACTCAGATCAGAGTGGCAAGAGCAATGGGACTCGTTTGTGAAGCTGCTCT
```

Figure 1 Cont.

```
GATACTAGATATCCTTAAATGATGTTTCAATTTTATATGTTTTCTAAGATAATT
GGATCAGGTTTTCTTTGTGTGTGTGTGTGTTGTATCATGAGTGTTTGGGGG
ATAAGTTTTTGTTAAAACAAAGTCTGGACTATCTTCATTTACTACATCATTAA
TTGATGTTACTCTGGAGTTTAGAATTCTGGCATTGACATTTCCCTCTCTTTCCT
TTATTTCGATGAAGCTATAATTGTGAAAATTGTAACTACATAGATGCTGAAAG
GCTAATACACATATGCACATGTATTTGATTGTCAAAGGTATATTCTTAAAT
TTGGGTATTATTGAAAATATTTTCCATGCCTTGGTGCTAGCATATAAGTTTGG
AAGTTTGCCAACATCACAATTCATCTTGAAAAGAGCTTTTTCCCTCCTACCA
CATACACCATTCTTAGGGAGCAATGAGGTAACAGGTCTGTGTTGTCTAGATCT
TTGCTTTTTATCCCCTATCAGTCCAGGGCATATACTAACCTGCAAACTGATT
CTGAATCAGGAAGGTGGTAATCAATAAGTATTCTGGCTGGGAAAGACCGTGG
GCCCAATGATCAAAGTCTTCTTGGTGCTGTTCATTAATTCTTGTGCCTTTTGGC
TTGTTTTCTAGAGTTTCTGGGCTTTGGCTGCTGATACTGCCTTTCTTAGACTGT
AATTTTTATCTGCATGCCCAGTTTCTGACCTATCAACTTGGGTTTTATTGTGCA
CTCTAACTGAGCTTGTCTTCATAATTTTCTGTTTATTGCCCTGGGCTTGGATAT
GTCTCAAGACACTCATGTGAATCATGCCACCCCAAATCCTGGCTTATCAAGTC
CCAGACTATAAATTATGAACTCCCATTAGCTTGGTACTAACATATACTTGATG
TAGGTATTTATGGACTTGATGATCCAAGAATATTATATTCTTCAAAATGGTTA
AGCTCCATGGAGTTAGATGACTACACTTAATGCTATTAAGTTGAACTTTTGAA
TGTCAACTAATTTGCAATCAATTAAAGATACATATGCCTAGAAATTTTGAAAT
TTCGGTATATTTATCCAGTTAAAGGGCTAAATTATATAAGCAAACACTACTTT
TTTTAAAACGTCTGGACTCAAAAAATGCTTTGTTCCATGTTTTAAAATTTTA
AGTAGCAGTCTCAAAGTTGCTTAGCTGTTTATTTGCTATGTTCCTAGCTAAG
AGTTTGGTTATAGGAGTTCATCAATAACTTATTTTTGTACAGTTCCCACATTA
GATACTGTTTAAAAGTTCTTTTTTAAACTCAATTTTTTTAGAAACATAAGAG
AAATATTTAGATACATACAAATGTTTTTATGATTAAATAATTTTATGCTTATTT
TCTGATACGTGTTATTTAGGTAATCATGCCCTGTACATTTAGAGGTTGCTAAC
TGACAATGTTAAGAAATTTTAAAAAAAAAAAAAAGCCTGGGCATGATGGCTC
ATGCTTGTAATCTGAACATTTGGGAGGCTGAGGCAGGAAGATCGCTTGAGGT
CCAGAGTTTAAGTCCAGCCTGGAAACATAGTTAGACCTCATCTCTACAAAAA
TAAAAAATAAAAATAAAAAAAACTTAGCTAGGCATGTTGCCACATACTTGTA
GTCCCAGTTATTAGGGAAGCTGAGGTGGGAGGATAGCTTAAGCCCAGGATTT
CAAGGCTGCATTGAGCTATGATTACACCACTGCACTCCAGCCTGGGTAACAG
AGTGAAATCTTGTCTCTGGGAAAAAAAAAAAAAAAAAAAAAAAGAGAGAGA
GAGAGAGGGAGATTTATATAACATTTAAATTAACTGCATAAACCTGGGCAAT
GTTCAAAACTCCATCTCTACAAAAAAACACAAGAATTAGCCAGGCACGGTGG
TGTGTGTCTGTAGTCTCAGCTACTTAGGAGGCTGAGGTGGGAAGATTGCTAG
AGCCAGGAGGTCGAGGCTGCACTGAGCTGTGATTGCGCTACTGTACTCCACC
CTGGGTGATGAAGCCCTAACTCAATAAATAAATAAATAAATAATACAA
ATAAATTAACTATATATTCATGTATTTCTTATGTGGATATATGTTATTTTTTT
TTCCTGCTTTTCTTTTTTTTATTTTTTATTATACTTTAAGTTTTAGGGTACAT
GCGCACATTGTGCAGGTTAGTTACATATGTATACATGTGACATGCTGGTGCGC
TGCACCCACTAACTCGTCATCTAGCATTAGGTATATCTCCCAATGCTATCCCT
ACCCCCTCCCCCCACCCTACCACAGTCCCCAGAGTGGATATTCCCCTTCCTGT
GTCCATGTGATCTCATTGTTCAATTCCCACCTATGAGTGAGAATATGCGGTGT
TTGGTTTTTTGTTCTTGCCATAGTTTACTGAGAATGATGATTTCCAATTTCATC
```

Figure 1 Cont.

CATGTCCCTACAAAGGACATGAACTCATCATTTTTATGGCTGCATAGTATTC
CATGGTGTATAAGTGCCACATTTTCTTAATCCAGTCTATCATTGTTGGACATTT
GGGTTGGTTCCAAGTCTTTGCTATTGTGAATAATGCTGCAATAAACATACGTG
TGCATGTGTCTTTATAGCAGCATGATTTATAGTGCTTTGGGTATATACCCAGT
AATGGGATGGCTGGGTCAAATGGTATTTCTAGTTCTAGATCCCTGAGGAATC
GCCACACTGACTTCCACAGTGGTTGAACTAGTTTACAGTCCCACCAACAGTGT
AAAAGTGTTCCTGTTTCTCCACATCCTCCCCAGCACCTGTTGTTTCCTGACTTT
TTAATCATTGCCATTCTAACTGGTGTGAGATGGTATCTCATTGTGGTTTTGATT
TGCATTTCTCTGATGGCCAGTGATGATGAGCATTTTTCATGTGTTTTTGGCT
GCATAAATGTCTTCTTTTGAGAAGTGTCTGTTCATGTCCTTCGCCCACTTTTTG
ATGGGGTTGTTTGTTTTTTTCTTGTAAATTTGTTTGAGTTCATTGTAGATTCTG
GATATTAGCCCTTTGTCAGATGAGTAGGTTGCAAAAATTTTCTCCCATTTTGC
AGGTTGCCTGTTCACTCTGATGGTAGTTTCTTTTGCTGTGCAGAAGCTCTTTAG
TTTAATTAGATCCCATTTGTCAATTTTGTCTTTTGTTGCCATTGCTTTTGGTGTT
TTGGACATGAAGTCCTTGCCCATGCCTATGTCCTGAATGGTAATGCCTAGGTT
TTCTTCTAGAGTTTTTATGGTTTTAGGTCTAACGTTTAAGTCTTTAATCCATCT
TGAATTGATTTTTGTATAAGGTGTAAGGAAGGGATCCAGTTTCAGCTTTCTAC
ATATGGCTAGCCAGTTTTCCCAGCACCATTTATTAAATAGGGAATCCTTTCCC
CATTGCTTGTTTTCTCAGGTTTGTCAAAGATCAGATAGTTGTAGATATGAGG
CGTTATTTCTGAGGGCTCTGTTCTGTTCCATTGATCTATATCTCTGTTTTGGTA
CCAGTACCATGCTGTTTTGGTTACTGTAGCCTTGTAGTATAGTTTGAAGTGAG
GTAGCGTGATGCCTCCAGCTTGTTCTTTTGGCTTAAGATTGCCTTGGCAATG
CGGGCTCTTTTTTGGTTCCATATGAACTTTAAAGTAGTTTTTTCCAATTCTGTG
AAGAAAGTCATTGGTAGCTTTATGGGGATAGCATTGAATCTGTAAATTACCTT
GGGCAGTATGGCCATTTTCACGATATTGATTCTTCTTACCCATGAGCATGGAA
TGTTCTTCCATTTGTTTGTATCCTCTTTTATTTCCTTGAGCAGTGGTTTGTAGTT
CTCCTTGAAGAGGTCCTTCACATCCCTTGTAAGTTGGATTCCTAGGTATTTTAT
TCTCTTTGAAGCAATTGTGAATGGGAGTTCACTCATGATTTGGCTCTCTGTTT
GTCTGTTGTTGGTGTATAAGAATGCTTGTGATTTTGGTACATTCATTTGTATC
CTGAGACTCTGCTGAAGTTGCTTATCAGCTTAAGGAGATTTTGGGCTGAGTCA
ATGGGGTTTTCTAGATATACAATCATGTCGTCTGCAAACAGGGACAATTTGAC
TTCCTCTTTTCCTAATTGAATACCCTTTATTTCCTTCTCCTGCCTGATTGCCCTG
GCCAGAACTTCCAACACTATGTTGAATAGGAGCGGTGAGAGAGGGCATCCCT
GTCTTGTGCCAGTTTTCAAAGGGAATGCTTCCAGTTTTTGCCTATTCAGTATG
ATATTGGCTGTAGGTCTGTCATAGATAGCTCTTATTATTTTGAAATACATCCC
ATCAATACCTAATTTATTGAGAGTTTTTAGCATGAAGGGTTGTTGAATTTTGT
CAAAGGCTTTTTCTGCATCTATTGAGATAATCATGTGGTTTTTGTCTTTGGCTC
TGTTTATATACTGGATTACATTTATTGATTTGCATATATTGAACCAGCCTTGCA
TCCCAGGGATGAAGCCCACTTGATCATGGTGGATAAGCTTTTGATGTGCTGC
TGGATTCGTTTTGCCAGTATTTTATTGAGGATTTTTGCATCAATGTTCATCAAG
GATATTGGTCTAAAATTCTCTCTTTTGGTTGTGTCTCTGCCCGGCTTTGTTATC
AGAATGATGCTGGCCTCATAAAATGAGTTAGGGAGGATTCCCTCTTTTTCTAT
TGATTGGAATAGTTTCAGAAGGAATGGTACCAGTTCCTCCTTGTACCTCTGGT
AGAATTCGGCTGTGAATCCATCTGGTCCTGGACTCTTTTGGTTGGTAAACTA
TTGATAATTGCCACAATTTCAGCTCCTGTTATTGGTCTATTCAGAGATTCAAC
TTCTTCCTGGTTTAGTCTTGGGAGAGTGTATGTGTCGAGGAATTTTTCCATTTC

Figure 1 Cont.

```
TTCTAGATTTTCTAGTTTATTTGCGTAGAGTTGTTTGTAGTATTCTCTGATGGT
AGTTTGTATTTCTGTGGGATCGGTGGTGATATCCCCTTTATCATTTTTTATTGT
GTCTATTTGATTCTTCTCTCTTTTTTTCTTTATTAGTCTTGCTAGCGGTCTATCA
ATTTTGTTGATCCTTTCAAAAAACCAGCTCCTGGATTCATTAATTTTTGGAAG
GGTTTTTTGTGTCTCTATTTCCTTCAGTTCTGCTCTGATTTAGTTATTTCTTGC
CTTCTGCTAGCTTTTGAATGTGTTTGCTCTTGCTTTTCTAGTTTTTTTTTTTTA
TTATTATACTCTAAGTTTTAGGGTACATGTGCACATTGTGCAGGTTAGTTACA
TATGTATACATGTGACATGCTGGTGCGCTGCACCCACCAACGTGTCATCTAGC
ATTAGGTATATCTCCCAATGCTATCCCTCCCCCCTCCCCCGACCCCACCACAG
TCCCCAGAGTGTGATATTCCCCTTCCTGTGTCCATGTGATCTCATTGTTCAATT
CCCACCTATGAGTGAGAATATGTGGTGTTTGGTTTTTGTTCTTGCGATAGTTT
ACTGAGAATGATGGTTTCCAATTTCATCCATGTCCCTACAAAGGACATGAACT
CATCATTTTTATGGCTGTATAGTATTCCATGGTGTATATGTGCCACATTTTCT
TAATCCAGTCTATCATTGTTGGACATTTGGGTTGGTTCCAAGTCTTTGCTATTG
TGAATAGTGCCGCAATAAACATACGTGTGCATGTGTCTTTATAGCAGCATGAT
TTATAGTCCTTTGGGTATATACCCAGTAATGGGATGGCTGGGTCAAATGGTAT
TTCTAGTTCTAGATCCCTGAGGAATCGCCACACTGACTTCCACAATGGTTGAA
CTAGTTTACAGTCCCACCAACAGTGTAAAAGTGTTCCTATTTCTCCACATCCT
CTCCAGCACCTGTTGTTTCCTGACTTTTTAATGATTGCCATTCTAACTGGTGTG
AGATGATATCTCATAGTGGTTTTGATTTGCATTTCTCTGATGGCCAGTGATGA
TGAGCATTTCTTCATGTGTTTTTGGCTGCATAAATGTCTTCTTTTGAGAAGTG
TCTGTTCATGTCCTTCGCCCACTTTTTGATGGGGTTGTTTGTTTTTTCTTGTAA
ATTTGTTTGAGTTCATTGTAGATTCTGGATATTAGCCCTTTGTCAGATGAGTA
GGTTGCGAAAATTTTCTCCCATGTTGTAGGTTGCCTGTTCACTCTGATGGTAG
TTTCTTTTGCTGTGCAGAAGCTCTTTAGTTTAATTAGATCCCATTTGTCAATTT
TGGCTTTTGTTGCCATTGCTTTTGGTGTTTTGGACATGAAGTCCTTGCCCACGC
CTATGTCCTGAATGGTAATGCCTAGGTTTTCTTCTAGGGTTTTTATGGTTTTAG
GTCTAACGTTTAAGTCTTTAATCCATCTTGAATTGATTTTGTATAAGGTGTAA
GGAAGGGATCCAGTTTCAGCTTTCTACATATGGCTAGCCAGTTTTCCCAGCAC
CATTTATTAAATAGGGAATCCTTTCCCCATTGCTTGTTTTTCTCAGGTTTGTCA
AAGATCAGATAGTTGTAGATATGCGGCATTATTTCTGAGGGCTCTGTTCTGTT
CCATTGATCTATATCTCTGTTTTGGTACCAGTACCATGCTGTTTTGGTTACTGT
AGCCTTGTAGTATAGTTTGAAGTCAGGTAGTGTGATGCCTCCAGCTTTGTTCT
TTTGGCTTAGGATTGACTTGGCGATGTGGGCTCTTTTTGGTTCCATATGAACT
TTAAAGTAGTTTTTTCTAATTCTGTGAAGAAAGTCATTGGTAGCTTGATGGGG
ATGGCATTGAATCTGTAAATTACCTTGGGCAGTATGGCCATTTTCACGATATT
GATTCTTCCTACCCATAAGCATGGAATGTTCTTCCATTTGTTTGTGTCCTCTTT
TATTTCCTTGAGCAGTGGTTTGTAGTTCTCCTTGAAGAGGTCCTTCACATCCCT
TGTAAGTTGGATTCCTAGGTATTTTATTCTCTTTGAAGCAATTGTGAATGGGA
GTTCACTCATGATTTGGCTCTCTGTTTGTCTGTTGTTGGTGTATAAGAATGCTT
GTGATTTTGGTACATTGATTTTGTATCCTGAGACTTTGCTGAAGTTGCTTATCA
GCTTAAGGAGATTTTGGGCTGAGTCAATGGGGTTTTCTAGATATACAATCATG
TCGTCTGCAAACAGGGACAATTTGACTTCCTCTTTTCCTAATTGAATACCCTTT
ATTTCCTTCTCCTGCCTGATTGCCCTGGCCAGAACTTCCAACACTATGTTGAA
TAGGAGCGGTGAGAGAGGGCATCCCTGTGTTGTGCCAGTTTTCAAAGGGAAT
GCTTCCAGTTTTTGCCCATTCAGTATGATATTGGCTGTGGGTTTGTCATAGAT
```

Figure 1 Cont.

```
AGCTCTTATTATTTTGAAATACGTCCCATCAATACCTAATTTATTGAGAGTTTT
TAGCATGAAGGGTTGTTGAATTTTGTCAAAGGCTTTTCTGCATCTATTGAGA
TAATCATGTGGTTTTTGTCTTTGGCTCTGTTTATATGCTGGATTACATTTATTG
ATTTGCGTATATTGAACCAGCCTTGCATCCCAGGGATGAAGCCCACTTGATCA
TGGTGGATAAGCTTTTGATGTGCTGCTGGATTCGGTTTGCCAGTATTTTATTG
AGGATTTTTGCATCAATGTTCATCAATGATATTGGTCTAAAATTCTCTTTTTTG
GTTGTGTCTCTGCCTGGCTTTGGTATCAGAATGATGCTGGCCTCATAAAATGA
GTTAGGGAGGATTCCCTCTTTTTCTATTGATTGGAATAGTTTCAGAAGGAATG
GTACCAGTTCCTCCTTGTACCTCTGGTAGAATTCGGCTGTGAATCCATCTGGT
CCTGGACTCTTTTGGTTGGTAAACTATTGATTATTGCCACAATTTCAGCTCCT
GTTATTGGTCTATTCAGAGATTCAACTTCTTCCTGGTTTAGTCTTGGGAGAGT
GTATGTGTCGAGGAATGTATCCAATTCTTCTAGATTTTCTAGTTTATTTGCGTA
GAGTTGTTTGTAGTATTCTCTGATGGTAGTTTGTATTTCTGTGGGATCGGTGGT
GATATCCCCTTTATCATTTTTATTGTGTCTATTTGATTCTTCTCTCTTTTTTC
TTTATTAGTCTTGCTAGCGGTCTATCAATTTGTTGATCCTTTCAAAAAACCAG
CTCCTGGATTCATTGATTTTGGAAGGGTTTTTTGTGTCTCTATTTCCTTCAGT
TCTGCTCTGATTTAGTTATTTCTTGCCTTCTGCTAGCTTTTGAATGTGTTTGCT
CTTGCTTTTCTAGTTTTTTTAATTGTGCTGTTAGGGTGTCAATTTGGATCTTTC
CTGCTTTCTCTTGTGGGCATTTAGTGCTGTAAATTTCCCTCTACACACTGCTTT
GAATGCGTCCCAGAGATTCTGGTATGTTGTGTCTTTGTTCTCGTTGGTTTCAA
AGAACATCTTTATTTCTGCCTTCATTTCGTTATGTATCCAGTAGTCATTCAGGA
GCAGGTTGTTCAGTTCCATGTAGTTGAGCGGTTTTGAGTGAGATTCTTAATC
CTGAGTTCTAGTTTGATTGCACTGTGGTCTGAGAGATAGTTTGTTATAATCTC
TGTTCTTTTACATTGCTGAGGAGAGCTTTACTTCCAAGTATGTGGTCAATTTT
GGAATAGGTGTGGTGTGATGCTGAAAAAAATGTATATTCTGTTGATTTGGGG
TGGAGAGTTCTGTAGATGTCTATTAGGTCCGCTTGGTGCAGAGTTGAGTTCAA
TTCCTGGGTATCCTTGTTCACTTCCTGTCTCGTTGATCTGTCTAATGTTGACAG
TGGGGTGTTAAAGTCTCCCATTATTAATGTGTGGGAGTCTAAGTCTTTTGTA
GGTCACTCAGGACTTGCTTTATGAATCTGGGTGCTCCTGTATTGGGTGTATAT
ATATTTAGGATAGTTAGCTCTTCTTGTTGAATTGATCCCTTTACCATTATGTAA
CGGCCTTCTTTGTCTCTTTTGATCTTTGTTGGTTTAAAGTCTGTTTTATCCGAG
ACTAGGATTGCAACCCCTGCCTTTTTTGTTTTCCATTTGCTTGGTAGATCTTC
CTTCATCCTTTTATTTTGAGCCTATGTGTGTCTCTGCACGTGAGATGGGTTTCC
TGAATACAGCACACTGATGGGTCTTGACTCTTTATCCAATTTGCCAGCCTGTG
TCTTTTAATTGGAGCATTTAATCCATTTACATTTAAAGTTAATATTGTTATGTG
TGAATTTGATCCTGTCATTATGATGTTAGCTGGTGATTTGCTCGTTAGTTAAT
GCAGTTTCTTCCTAGTCTCGATGGTCTTACATGTTGGCATGATTTGCAGCG
GCTGGTACCGGTTGTTCCTTTCCATGTTAGCGCTTCCTTCAGGAGCTCTTTTA
GGGCAGGCCTGGTGGTGACAAAATCTCTCAGCATTTGCTTGTCTGTAAAGTAT
TTTATTTCTTCTTCACTTATGAAGCTTAGTTTGGCTGGATATGAAATTCTGGGT
TGAAAATTCTTTTCTTTAAGAATGTTGAATATTGGCCCCACTCTCTTCTGGCT
TATAGGGTTTCTGCCGAGAGATCTGCTGTTAGTCTGATGGGCTTCCCTTTGAG
GGTAACCTGACCTTTCTCTCTGGCTGCCCTTAACATTTTTTCCTTCATTTCAAC
TTTGGTGAATCTGACAATTATGTGTCTTGGAGTTGCTCTTCTTGAGGAGTATC
TTTGTGGCGTTCTCTGTATTTCCTGAATCTGAACGTTGGCCTGCCTTGCTAGAT
TGGGGAAGTTCTCCTGGATAATATCCTGCAGAGTGTTTTCCAACTTGGTTCCA
```

Figure 1 Cont.

```
TTCTCCCCATCACTTTCCGGTACACCGATCAGACGTAGATTTGGTCTTTTCAC
ATAGTCCCATATTTCTTGGAGGCTTTGCTCATTTCTTTTTATTCTTTTTTCTCTA
AACTTCCCTTCTCGCTTCATTTCATTCATTTCATCTTCCATCGCTGATACCCTT
TCTTCCAGTTGATCGCATTGGCTCCTGAGGCTTCTGCATTCTTCACATAGTTCT
CGAGCCTTGGTTTTCAGCTCCATCAGCTCCTTTAAGCACTTCTCTGTATTGGTT
ATTCTAGTTATACATTCTTCTAAATTTTTTTCAAAGTTTTCAACTTCTTTGCCTT
TGGTTTGAATGTCCTCCCATAGCTCAGAGTAATTTGATCGTCTGAAGCCTTCT
TCTCTCAGCTCGTCAAAGTCATTCTCCATCCAGCTTTGTTCCGTTGCTGGTGAG
GAACTGCGTTCCTTTGGAGGAGGAGAGGCGCTCTGCGTTTTAAAGTTTCCAGT
TTTTCTGTTCTGTTTTTTCCCCATCTTTGTGGTTTTATCTACTTTTGGTCTTTGA
TGATGGTGATGTACAGATGGGTTTTTGGTGTGGATGTCCTTTCTGTTTGTTAGT
TTTCCTTCTAACAGACAGGACCCTCAGCTGCAGGTCTGTTGGAATACCCTGCC
CTGTGAGGTGTCAGTGTGCCCCTGCTGGGGGGTGCCTCCCAGTTAGGCTGCTC
AGGGGTCAGGGACCCACTTGAGGAGGCAGTCTGCCCGTTCTCAGATCTCCAG
CTGCGTGCTGGGAGAACCACTGCTCTCTACAAAGCTGTCAGACAGGGACATT
TAAGTCTGCAGAGGTTACTGCTGTCTTTTGTTTGTCTGTGCCCTGCCCCCAGA
GGTGGAGCCTACAGAGGCAGGCAGGCCTCCTTGAGCTGTGGTGGGCTCCACC
CAGTTCGAGCTTCCCGGCTGTTTTGTTTACCTAATCAAGCCTGGGCAATGGCG
GGCGCCCTCCCCCAGCCTCGCTGCCGCCTTGCAGTTTGATCTCAGACTGCTG
TGCTAGCAATCAGCGAGATTCCGTGGGCGTAGGACCCTCCGAGCCAGGTGCA
GGATATAATCTCGTGGTGCGCCGTTTTTTAAGCCGGTCCGAAAAGCGCAATAT
TCGGGTGGGAGTGACCTGATTATCCAGGTGCGTCTGTCACCCCTTTTTTTGAC
TCGGAAAGGGAACTCCCTGTCCCCTTGCGCTTCCCAAGTGAGACAATGCCTC
GCCCTGCTTCGGCTTGCGCATGGTGCACGCACCCACTGACCCGCGCCCACTGT
CTGGCACTCCCTAGTGAGATGAACCCTGTACCTCAGATGGAAATGCAGAAAT
CACCTGTCTTCTGCGTCGCTCACGCTGGGAGCTGTATACCGGAGCTGTTCCTA
TTTGGCCATCTTGGCTCCTCCCCCGGTATTCCTTCTTTTCTTCCACTGTGAGAG
TTACTTAAAGCTCGGCGTCCGTGATGGTCTAGGGGGCTTCTGAGGCGATCGG
GCAGTGTCCGTCTTCAGCCGCTAAGCCGAGAAGATCTGGGAAGGAGTCAGTC
AGAGAGCCTTGGGCCAGAGTTCCAGGGCCTCTGGGAGTGGCTGCCAGGTGAG
TTGAACAGTCCGATTTTCAGTGGGGTCCCACACAGATGGGACATGGCTTAGG
AGGAATCCCAGGCTGTGGGCATTCCTTGGCCCAGTGGCCAGATTCGATATAT
GTTATTTTTAAATCACTGTATTTGTAAGCAAATATCAAATTTAGGGAAGTCTT
TCTACAATGTTTTAATAAGTAGAAAGATATGTTTGTTTTACATGAATGTGTTT
TGAACTATGGTTATTTGTTTAATAATTCTAAATGCATATGTGTGTAAAATGCT
TCAATTTTGGAAATCAAAGTCAGGCCATTTTTTTGTCTTACCTGATTGCCAGG
GAGTTACGCCATGTATTCTTAATGAGAAACATGATGTTTCCATTCTTGTTCAC
TTTCCTTTAGACAGAATATATTTTTGTGACATTTAGAACTATCAATATTTTAGT
TTTATAAACACAGGAGAATGCCTGATAGAATTCTTAAGAAAGCAATGTAACA
GTATTAGCTCAAAATAATTTATCTTAATTTCTAAATTTTTAGATAAAACCAAA
TAAGGGTTAAATGTTAATCCATTGTCACTTAAATTACATAATCTGCTACTCTT
AGTTATTTGAATGACAAAAACACCAGTGGGGGAAAAACCATACAAGTTGTCA
ATGTCTGTTTTGCTGTTGACAAGTTGTATACCCTTAAATTGACCCCTAATCTCC
TCTAACAATGGTACATAGCACTAAGCTCCTACCTACCTCACAGAAATAATGTC
AGTAGAAAAGATCAGGTTGAGTTCTTTGGCAGAATAGCACTTTACTAACTCA
AATAGTGTTACTTAATATTTCAATATGATTGGGAATCAAAGTTTGAGACAAA
```

Figure 1 Cont.

```
AGTCATTTGCCAGTTTTAAAAAATAGAGCTGTTAATTTGCAATATCATGATGT
AGAGATAGTGCCTTCTCTTAAAAATGTGTGTCATGGAAATAGTAAAATATATT
TAGGAGTCAGCAGGATTATTCCAACAGAGGGAGTGTAAACTTTAAAGAAAAA
TATGATTCGGGAGGCTGAGGTGGGTGGATCATGAGGTCAGGAGTTCGAGACC
AGCCTGGCCAACATAGTGAAACCCCGTCTCTACTAAAAATACAAAAATTAGC
TGGGCATGGTGGCACACACCTGTAGTCCCAGCTACTCGGGAGGCTGAGGCAG
GAGAATCGCTTGAACCTGGGAGGTGGAGGTTGTGGTGAGCCGAGATCACACC
ACTGCACTCCAGCCTGGGCAACAGAGCGAGATTCCATCTCAAAAAATACATA
TATATTTTGACATATATAATATATATATGTCAGTAATATTCACCCCATAGAA
AATGAAAATTTTATAGGAAAGATGTAAAACAGCATAAATTCACATTCATCTT
ATTAGTTGCTTATGCAATCATTTCTCTCCAGATCATTGGTTCTCAAAGGGGA
CAATTTTGCCTCTCAGGGGATATTTGGAAATGTCTGGAGACATTTTTGGATGG
CACTAGTGGTATCTAGTAGGTAGAATTTAGGGAAACTGGTAAACATCTCCTG
AGGCCTGCAAGGGTGCTCTCCTCCTCCACAACAAAAAATTATCCAGCCTAAG
ATGTCCATAGTGTAGAGTTGGAGAAACCTTGCCCTGGAGAATAAGGTTGATT
TTCTTGAAGTCACACAGCCTGGTTGTGTTTCTATAGGGAAACAGCCTGAAAAT
TCTATCTGAATGTTCTCATCTACAGGTAAGGATGAAAATGCCACTGGCATATC
TAATATTATGATGCAGAACAATGACCATGTATTTTCACAGCATTATGAAATTA
TTAAGGACCATAGAATTGTGAATAATTATTTAAAGAAGTCTTAGGACAGTTT
AGATTCTCCACATGCCTTCTAATATTGACACACATTAGGATGAAGGAAATATT
AAATACATACATGTAAAGATTTTGAATTTTTTTCAACTGAGCGTCCAGGATA
TAAATACAAGGAACAGGGAGGGGGTTGAGATGGCGGAAGTAACTCTGTATT
GATTCTTATAGGAAATTCTGAGTTTTTCCATAAAGACAAAGAGTTTATTGAGT
ACATGAGCATTTAGTTACTGAAAATTCACTGTATGCTTTCTAAGTTTTGAGC
TTATTGTTTATGAAATCCTTGAGAAAGTTGAACATTTCAATGTAAAAACATGG
TTGTGAATCTGAATTTTCAACTTGCTGATTAAACTCCCTGCAAGTTTCTTTGCA
GTTGTCTGTTTTGGGGGGATAAATGTCAAATTGAATACAGTTAATTTTATCAG
CCTTTACAAAAGATACTTCCACCCTATTTACAACATAAAGGACTATTCCTAA
GTGCTGTCTGTAGATTACAAAAAGTATAAACATGTAGAATTTTTGTCACAGA
AGACTATTTTATTTTAATGAATTAACACCGTATTGAAAAATAAAAAGTACAA
AAAAGTACAAACTTTTCTGTCCCAATACATTATAAAACGTTTTATTTTAATAG
CTTTAGAGGTACAGTTTTTGGTTACATGGGTGAATCGTATAGTGGTGAAGTGT
GAAGGTTCAGTGCACTGGTCACCTGAGTAGTGTACATGGTGCCCAATAGATA
GTTTTTCATTCCTCTTCCTCAGCCTCCCCACCTTCTGAGTCTCTAATGTCCATT
ATACCACTCTGTATGCCTTTGTGTACTCATAGCTTAGCTCCCACTTACAAATG
AAAACATGTGGTATTTGCTTTTCCATTCCTGACTTATGTCACTTAGAATAATA
GCCTCCGGTTCCATCTAAGTTGCTGCAATAGACATTATTTCATTCTTTTTTATC
CCTGAGTAGTACTCCATGGTGTATGTGTATGTATACATATATATATATATA
TATCTCACATTTCATATATACTCACATTTTTTATCCACTCATCAGTTGATAG
GCACTTAGGTTGATTCCATATCCTTGCAATTGTGAATCGTGCTGCGATAAACA
TGTGCATACAGGTGTCTTTTTGACATAGTGACTTCTTTTCCTTTAGGCAGATAC
CCAATAGTTGTTCCAATCCAATTTTTAATTGGGGTAATTTAATCTTTTAAAAG
TTGGTCCAAGTTAATTGTTGATAATATCAGGACTTTAAAAGAGAAACAGAAG
TTCTTAACCTGAGTGTTTTTCTTTCTTTTGAAAAAATATCAGTTTGAAGTTTT
AAATTTCTATTTTATATCTCAAAGCTATAGTTTTGCTTGTGGGTATAAAATT
AAGTGGACAACTAAGACAGAGAACTTAGGTGCCAAAGATGACCATGTTTATA
```

Figure 1 Cont.

```
CTCAATCACCCAATTTGGAACCACATCATCAAAGAAGCAGTTGCCAGTGTTC
CCCCTAGTGTGAAGTTTCCACTTCTCTCAGTTAAAGCACCTGTCTGTCATCTC
ATTTAAAGCACCTACTTACTTCCTACCTATTCAAGTCTTGATTAAGCAAAATG
CAGATTTTCCATATACAGGAAATTTGGCATAACCTTTCACTTTAAAGGTCAAA
TCAGGTCTCCATCATTTAAATTCATCAAAGAAGAATATTTTGAAGTTGTTGA
CTTTGTTACTCATTCCCATTTTGCAATCATGTATTGTTATTCCCTTCCTCATTTA
AAAAGGCTTCTTTTACCCCTTACCCTTGTTAGGCTGCACCACCAAAGGTCAT
TGGATATCAATGGATGGGATTCACTCCTGGAGCTCCAGACTCACTCACACAT
GTGCATCAAGGATTCAGGATTCTCTCCATTTCTGCTTTCCTTAACTTTCCAAAG
CCAGACCTTTATTCTCTTCTGTATTAGGATCTGGTCTGTCACTGGGCTTTTCTC
ATTCTATTCTAGAGCTTCTTAAACTTCAGTGTTCATCAGAAGCACCTGGAGGA
GCTGGTTAAAACACAGATTGCTGGGCTTCACCCCAGAGTGTCTGATTTAACA
GCTCTCAGGTGGGTCCTGAGAATTTACCTTTCTCAAAATTTTCCTGAGGATGA
TGGTGCTTCTGGTCTGGGAGTCACACTTTGGAAACTACTGTTCCAGTCCACAG
TTGTCTCTTTGGAAACCGAATCTGATGATTCACTCCTCTGCTTGAAGATCTCT
ATGACTACAGAATAAAAGCCCCATCCCTTAGCCTGATGGGCTTCTCAGAAGT
ATTTATTGGTACCCTCCTTCACATGTTACATAGGCTTGTCACATTGAGCTTCTC
ATATGTGCTAAATATACCACCATTTTCTTGCCTTCTTGTTATTTTACATGCTAT
CCTCTTTGTCTAGGCTACCCATCCTCTGTCTACTTCTCAGATCTTTGAAAAACA
CCTGCTCAGTTGTTAGAACCCAGCTTACCTATCACTTCTCTAACTCTTGACAC
ATTCCATGGGTGATCGTGATCTTATACTTACCTCCGGCTCTAGTCATTTTGTTG
TACTGTACATGTATTAATGTACACAGCTATCTCTTAGGTGGCACATAGTCTCT
ATTCCTGATGTTTCCATCCAGGTGGATGAACTGTCCATTAGAGTAACTTTCTG
GATCTCTCTCTGCCCCTTTCCTGCTTATTCTCCCTATGTAAACAGGAAGTGACT
TTTGTGATCAGTAAGTCTGAGAGAGGAATCAGACATGTATATCTTAGTCCTTT
CCACTTCCATTTCTTTTGGCATCTGCCTGCTTAAAGAATATGCATGATCTATG
CCTTACAACTCCTTGCTCCCATGATCTCTTTGACCTCTATTACTCCATGCCAGG
TCTTGCCATTCCTTAAAAACATGTTCCCACCTCACGGTCATGTGCATTGCTTA
CAACACCCTACTCAATATCCATTTGGCTCACTCTTTCAGCTCCTACAGGTCTTT
ATTCAGATGTCATCTTCTAGGTGAGGTATTCTCTGATCTCTATTTAAAATTGC
AACTTTCCTCCGCCATGCACCCTATCCCCCTTGCTTGCTTTATTTCTCTCCCAT
CTCTATTATCATTGAACACACAATATTTTACTTGTTTGTTGTATGTCATTCCCC
AATAAAATAAAAACTCCAAGAGGTGAGGATTTTGCTGGTTCTGTTTAGTAAT
TTCTCTAGCAGATGTAGAACATGGAAGGCACTCAATACAAATTGGAATACAT
GCTTTTGGTCATGAGATAAGGGTTAGTGATAAAAATAGCCTGCTTCCATAGG
GATGCTTGGGGTCTTGACACCAGCCGGTGACTAGATATGTGTAATTCTCAGAT
TTAGTGTTAGGGAAACTTTGTTGACTTGTAGTTAGTCATGTCTTCCAATCATC
CATTACCAATAATATTAGTAATATTGTAATAAATAAGAGACTCATCTCTACCA
TCACTGAGTTTATTGTCTAATACAGAAAATGGGCAAAATACAAGTAGTTACA
GTAAAGTGTTGTAACCTGAACACAGATGTGCCTGCTCGCCACTTGAAAACTA
AAATAAAGAGAAGAGAGTTGGTGGGAGGAAACGCAGGTTTATTTGGAGA
ACCAGCAGACCAAGAAGATGATAAACTGTTGTCCTAAAGTACCATCTTAAGT
CAGTACAAATTGCAGATTATTTTTATGTTAAGAACAGGGGGAAGGAAAGGTG
GGTGGGATCAAGAGGTGACTGACAACTGCAGACATCTGGGCACCAACAAGG
GTCTGAGGAGGTTGAGAACTTCTATTTCCTTGGTCAGGTCACAATGCTCTTAT
AAATATTTAACAAAACATAGTTGTTTACATACTTTCCCTTTAATCACAGAGTT
```

Figure 1 Cont.

```
AGTTTCAAAAACTACATGATTGTTTCTTTGCATATGATATGGTTTGTATTTATG
TCCCCACTCAAATTTCATGTGGAATTGTAATCCCTACTGTTGGAGAAGAGGCC
TGCTGGAAGTTGATTGGATCATGAGGCCGACTTCCCCATTGCTGTTCTTGTGA
TAATGAATGAGTTCTCATGAGATCCGGTTGTTTAGAAGTGTGTAGCACCTCCC
CTTTTGCTCTTTTGCCTCCTGCTCCAGCCATGTAAGATGTGCCTCCTTCCTCTT
TGCCTTCTGCCATGATTGTAAGTTTCCTGAGGCCTCCTCAGCCATGCTTTCTGT
ACAGCCTGCAGAATCATGAGCCAATTAAACCTCTTTGCTTTATAAATTACCCA
GTCTCAGGTAGTTTCTTACATTTAATAGCAATGCGAGAACGGACTAATTCAGC
ATATTATCTCACTGCTCTAAAATGATCCTAACCTACATGCAGGAATGGGTAAA
GGCTCCTTAAACAAAAATGGAGTTATATATGTTAGTTCTTTTGCTGTTTCACT
GTTACAGTGTGGTAAGTATTGCAATTGGAGCATTGCATGTGCTATAATCCAAA
CACGTGCTAAGTGACATAAGTATCAACGAGGGAGTAACAGGGATGGACAAA
AAGGGACCAAATCCAGCTATAGAATACTTTCCTGACTAGATGAGGAATAAGC
TCAGATTTGAAAGATGTATAGTCATTAGCTAAGCAAAGGAAAGGAAAAGAA
GAAGTGGTTTAGGCAAAGGGAACCACATGTTCTAAAGCCTAGAGGACTGAGG
GATCATGGTGCATAAGAAGAGTATGTATATAGGGTAGAGTGAATGATAACAT
GGGCACCAGCCAGACTATGGGAAGTCATGCTTGAGGTTTTAGACTTTATCCTT
ATGGGGATAAGAAACCACTGAAGAGTTGTAGGAAGAGACGTACGATATGAT
CAAATTTGGATTTCTGAAAGTTCAGTTCACCATAGCTATAAAGTGAAGAATG
GATGGGTGGAAGGGAGTATGCCTGAGGATCAGGAGACTATTTAGGAGTCTGT
GTTGTAGTCTTTGTGAGAGAAAATGGTGGCCTAGATTATGATGGTGGTAATG
AGGATGAAGAAAGATAGATACATGTGAGAGGATTGAATTGACAGGACTTGG
TACATTATTGGAAAGAAAGATGTCAGAAATTACTTATGTTTTTCTGCTTAAGC
ATTTTGGGTGGACATGGAGCCATTCAAAAGGTAGTTACCATAAAAAACTTGG
TGTAGGATAGGATGCTCAGTTTCAGACCTATTGGGTTCCAGCAGCAATTCTCA
ACCTAGGAAAGTTCTTAAAAATAAAATAAATTAAATCTGTGAGTTATTAGTG
ATACTAAAATCATAATCAATTTGTAACCATTCCATTTATCCTTTTCTTCTCCTT
CTTCTGCTCCTTCTTCATCATTGTCCTCATCTCCTTCTCCTTCTACTATTGTTTT
ATTCATGTTGGGGTTCCATAGACTATTAGTAGCTGATTATTTGTGGGAAGGGA
AGGTATTTGAGTGTCTTACTAATTTTCTTTTATTAGGTTGGTACAAAAGTAATT
GCAGTTTTTGTTAATATTATTTTTCTGACATATTTTCCAGAAACTTCAAATTTT
CTGCTAAATTTTTCAGAACATTTGTTAATCTGAAAATATTAGATTAACTCTCA
TATGACAATTTATCTGGTTAACAAATTTTAGTTTGAGAGTTCACCCAACATTT
TTAAATATTCTTCCATTATCTTTTAGTATCTATTCCTGATGTTGAGATGTTTGC
TGTCTGCCTAGTTGTTATCCCTTGGAGATACAGTAGCCTTTGATATATGTGGA
TAATTGGTTCTAGGTCTCCCAACGTAACCAAAATTTGCATATACTCAAGTCCT
GTATTCAGCCCTGCAGAACTCGTGTATACAAAAGTTGACTCTCCATATATGC
AAGTTTCACCTCCTGCAAATACTTCATTTTTGGTATATTTTCGATCTGCATTCA
TTTGAAAAAAATCCATGTAAAAGTGGAACCTTCCAGTTCAAACCTGTGTTGT
TCCAAGGGGCAACTGTAATCTCTCTTTTCTTTGTGAAAGCATTTAAAATTTAC
TCCTTATTGTGCTTTTTCTCTAGTTTTGCCACAATGAGTCTAGGTATGAATTTG
TTTTTATTTCCTCCTTGGGACTTTTGTTTCTTCAATGTAGAATCATACCTTTAA
TATTGGAAATATTTTTGGTATTATGTCTGAATATTTCCCCTTTCCCATATTTTT
TCTATTCTGTACCTCTTTAATTCCTGTTAGTTGTATGTTGTACCTTTTAAATCCT
GTCCTTCGTATCTCCTAATTTGGTTCATCTTTTCCATCTTTTTGTATTTATGTGA
TGCATCCTGGACAATTTTCTCAGATATTTTCTTTCATTCCCCTTCCCAGCTGTT
```

Figure 1 Cont.

```
TCTAATCTGCTATTAATTTGTCCATACAGTTCTCCATTTCAGTGACTTAACTTT
TTTTCATTTCTAGAGTTGGATATGCTTCTTTTTCAAAATTTGCTATTCTTTAATT
CATAATATTGGATTTTTTCATTATTATTTTCAATCATTATTTTATTACTCCAAT
AATTTTAACCATATTTATGACCCCTTAATTTTGTTATATTATCTGAAGTTAGTG
GGGTGCTAGTTCTTTTATTTGTTCATTTGCACACTCTCTGTCTTGGTGGTTCCT
TTTCTTATGTAGTTGATCTTTTTTATCTGGGAGTTTATCTTCAGAAGAGGCTGC
ATTTTTTCTAGTGACAGTTCCTTGGGCTGTGGTTAATGAAAGAGTCCCTACAT
AGTTTCAAATTAGATTTTGCTGTGTCCTAGTTGTTTCAATGGCCTTCAAACAA
TTTTACATTATCATCTCAGGTTAGGGCTTTTCTCTTAGGTTCGTAATATAAATT
TGCATCCTAGACCCATGGCACAAAACTTAAGCACAGGGCTTAAATTTTGATG
CCTCAAGTAACTTTTGTTTGTTTTCCATCCAAAGAGTTGGCTAGAAGCAAACT
TTCTTAATATTTAATTAAGGCTTTTGGTATGCTTTTAAAAATCCCCTTTTAAGT
GATCAGGCAGTTCTTTAAGATATCAGGCTTTTGATGATACCTGGAATCAAGTT
CTAGCTTCTTTACATTCTGTAGGCAGAAACCTCATTTTTCCTCCCATGAAAAC
ATAAGAACTCAGCAGATCTACACCTGCACTTATTCCTCAACATCTCCTGGCTT
CATTTCTTTGCTTTGATTTCCTTTTCAATTCTGGGATTGGAGCTTTTCTTTTATT
CTTATAAATTTGACTATGCATTAAAATGTTTATTTTGTGACATTTTACCCAGA
ATTTCAATGGTTTTGTAGCAGCCAGGAAAGTCTAGCTCTCTGTTATGATTCTT
TTAACTTGTTCAGTCCTGGGTTGTGGAGGTATGAGGAGCTATCCATCACACAT
GGCAATTTCAAAGCAACATGCAAAATACAATAATATAAGCGGAACACATGA
AAGCTGGAGGACAGTGAGAGATTTTTGGTTTTGCATAATAGCTTTACTGAGA
CATAATTAACATGCCATACAACTCACTCATTTATGTGCAACTCAATGGTTTTT
GTATTTACAGAGTTGTACAATTATCACCACAATCTTAGAAAATTTTCATTACC
CCCAGAAGAAACCCCATATCCATTTGTATTCAGTCTCCATTTTGTCCCATTCA
CTCCCTTTAGCCCTAGGCAACCACTAATCTACTTTCTGTCTCTGTAGATTTGTC
TATTCTGAACACTTCATATACATAAAATTACATTCTATGTGGTCCTCTGTGATT
GGCTCCTTTCATGTAGCATAATGTTTTCAAGGTTTATCTATGTAGCATGTATC
AGTATTTCATTCATTTTTATGGCCTAATAAAATCATGCACCACATAATGACCT
TTTGGTCAATGACAGACCTCACACTTGACAGTGGTCCCATAAGATTATAATGC
AGTTGAAAAATTCCTATTGCCTAGTGACATCACAGCCGTTGTAATATCATACA
GTCATAAAGCAACTCATTACCTTTTCTGTGTTTAGGTACACACATATTTACCA
TTGTGTTATAGTTGCCTACAGTATTCAGTATAGTAACATGCTATACACGTTTG
TATCCTAGGGACAGCCGGCTATATAGCATATAGCCTAAGTGTGTAGTAGGCT
ATACCATCTAAGTTTGTGTAAGTACACTCTATGATGTTCACACAATGATAAAA
TTACTCAATGATTAAATTCTTAGAATGTATCCCAATTGTTAAGTGACATATGA
TTGTATTCCATTGTATGGCTATCCTATATTTTATTTATGCATGAATCAGTTGAT
GAACATTTGTGTTGTTTCCACTTATTGGTTATTAAGAAACATGTTGCTCTGAA
CATTTGTGTACAAGTTCTATGCGAGCATATGTTTTCAGTTCTTTGGGAGATA
TATTTAGCAGTGGAATGGCTGGGTCATATGGTAATTCTATGCTTAACCATTTT
GGGAACTGCCAGACTATTTTCCAAAGCAGCTGCACCATTTAACATTCCTATCA
ACAGTGTATGAGGGTTCCAATTTCTCCATATCCTGGACAACACTTATTATCTG
TATATTTTATTTTGGCCATTCTAATGCATGTGAAGTGGTATCTCATTGTGACTT
TGATTTGCATTTCCCTGATGGCTAATGATATTGACCATCTTGTCATGTTTATTG
GCCATTTGTATATCTTCTTTGGAGACATGTCTAATCAAATCCTTTGCCCATTTT
TAAATTGGCTTATTTGTTTTTGTTAATTATTGAGTTGTAAGAGTTCTCAGAAGT
CTTATGTTTAAGACTTGCAATTAATATATTTAAGATATAATCCCCTTAGATAC
```

Figure 1 Cont.

ATAATTTGCAAGCCTTTTTTCCCCATTCTTTGGGTTGGAGAGGTTTTTTTTT
AATTGAAGTTCTCTGAGTTACAGAGAAAAGTCACAGAAGTAAAATATAATGG
GACTTTTGAAGTACAGAAATATAAAGCCTCCTATTCATCCATTTAAGTCGCAG
TAGAAACATGACATTTTAGTAAATAAGACATACAAAATACAGTGCAATTTAT
AACAGGACCAGTTGTGGAAGTGGACAGAGAAAAAAGGAAACAGATGAGAG
AGGTGGAAAGTTAAGAGGAGAGATAAATGCATAGTTCTGCCTTTTTGCTCAA
ACCAAGGATGGCATCATTATATAACACTGGGTGGAAGCCAGGATACCCAGGA
AGAGCAAGACTGAAAATAAATGGTAGGAGAGATTCAAGGAATGCCTTGCTTT
ATATGCCTTTGGAGAGGCAAGGGTCTGGCCCAATGAGGTGGAAAGGGAGTCT
ACAAGGGAAGTGATCAACCAGAGAAGAGTGTGAGAGGGTTCAGAGGAAAGT
ATAGTGGTGGGATATTCGGAGCATTAACCAATGATCCAAAGTCTAGCCTCTT
ATGTTGACAATAATAAAACAGCTTGGGTGGTAGGAGCTAGGTTTCCCAACCC
CAAACTGGAAATGGATTTCCTGTGCTGGGAAAGTTGGAGGGAACAGGTGAGC
ACCAATGTATTATCAAGTCTCTGAGGCCTATATCCCCATTGGTTCTTTGTGTCC
TAACACCATATGCTGAGCTCTGGGATGGTGGCAGCAAACCACCATCGATTTG
TGGAATTTAAAAGCTGACAAAATCTGTTCCCCATCTTTTGGATAGAGCTTACA
GTCACAAGACCCCAGGAAAGACACAGCTGAGTGGTGTTTCTAAGCAAACATA
GGGCTTTGGAAAGTTAGAGAGACTTTACCATGTTTGGTGAGCATTAAAAGAA
GAAATTGCTGCCTGAAGTATCCAGGGGAATAGGTCTCTAAACAGCCTCACAA
TTTTCCACCACCCATGGTAGTGGAAAAACAGTATAATGACTTTCAAGCTCCCA
AGGGCAGCATGGAGGTAGGGAAGGAAACCTGCATGGCAGTAAAGCTCAATC
AGGCTGAGACATGCTTAGGAAATCAAGAATCTGTGGTTGCAGAATAGAACAT
GAATATTATAAACTGAGGCAATTTTAAAAAGGCGGATGGGGAGTGGTGATGA
GAGGAAGAGACACTATTCTTTTATTCTCTTTTTATATCAAATAGTCAATCAAT
ACTGTACCTAATGATTGATTTCAACCTTAATGCTCTTCCTAATTGTTTCCCTTC
AAGTTAGACACCTGTGTTCACTGCTGTATTCTTAGCATCCAGAACAGAACTGG
CTGGCTCAATAAATATTTAATGAATGAACGAATCCATAGGATTCCCACATCTT
AGAGTTTTTGTCCACTTTTTTAAAAAAATTAATGTTGCAGGCTTGATTCCCTG
GGAAGCAGACTCTAATAGGGAGGGTAGTGTGCTTAGCATTTATTTAGGATCA
ATATCTATGGAAGAAAGAAGAAGGAAGCAGGTTTGGGTAGAGGTGGAGGTT
GAGCTACAATGCAGGTTCAAGCAGAGTCTCCCCACAGAGAGCACTGAAGTGA
GGGAGCCCTTCACAGTTGTCCTAATATTGCCAGGCTTTCGTATTCATGCATCG
ATTAGTCATTGACATGGGCTGCCACAGAAAGGGGCAGGTCTTGGATCAGGTG
ACCCTCTGCAATGAAACAGTCTTGAGGAGCCTGACAGCTGGAGGGAGTCTAC
CAACAGCACTCCCAAAAGCTTGGGCAAGACATCTTTCATTGAAGAGGGACCT
TGGCAGCATACCATGGTGTCCACCCCATGAAGCAACTATATCTTAGAAAACT
TAAGTCCTTTGTCTTACACCTTGGATCCAAACTTAGTTTTGTCTGACTCCAGA
GCCCATAATCAGAATAGAGTTTCTCTATTGTACATGGTGATGTAAACTCAGTC
CTAAACTGGCGAGGGTGCTGGTTGGACTTGGGAAGAGTTATTCTCAGTGTTCT
GGGTTAATGCAAAATGCAGGCCAAGGTGAAGGACCTTTGTGTGGCACTGACC
CAATCCATCAAGATGAGTTCATGTCCTTTGTAGGGACACGGATGAAGCTGGA
AACCATCATTCTGAGCAAACTATCGCAAGGACAAAAACCAAACACCGCATA
TTCTCACTCATAGGTGGGAATTGAACAATGAGAACACATGGACACAGGAAGG
GGAACATCTCACACTGGGGCCTGTTGTGGGTGGGGGAAGGGGGGAGGGAT
AGCATTTGGAGATATACCTAATGTTAAATGATGAGTTACTGGGTGCAGCACA
CCAATATGGCACATGTATACATATGTAACTAACCTGCACGTTGTGCACCTGTA

Figure 1 Cont.

```
CCCTAAAACTTAAAGTATAATAAAACAAAACAAAACAAAAGAAACACCCTA
TGCTCCACTCAGCTGGGAGGCCTGCACAGCAGTGATCTGTATTGAATGATAT
GATTAACTGATAATTGCTACTGTAACTAAGATTACAGTTTGACATTGCTGCCC
ACCTGCCTTTCTACCAGGGTGGTAGTTCACTAAAATATTATACAATCAGATAA
AATGAATTAAACTCAGCTTGAATTGTAGAGTATATTAAAGTGATTCAAATTAT
GGCCATAAGATATTGATTAGATCAGTAGTTTGCAGAATGTGGCCCCACCCA
ATAGAAACAACATCATCTAGGTACTTTATCAAAATTGAAATTTCCTGGTCCAC
CATATACTTACTGAATCAGAAACGGTGGTGGTAGGGCCCAGGTGATTCT
AATGTATGGTAGAGTTTGAGGAATACTGGACTACATGAAAATTAGTAGGAAA
AAATAAAAATTGGGTTTATAATTAGCAAATAAATGTTAAATAAATGATTCTTT
TAAAAACTATTTGTAAAATGACTACTCAAGTCAAGAAATAGTACATTGCCAG
CACCTTGGATGCCTGTTTATCCCTTCTCACTCACACCCCAAAGCAAACACTTC
GTTTTATTTTATGCTTTTAATATCTAGGAATACATCCCTGAGTACAAGTTTTTG
AAGTTTGTGTTAATAAGCAAAATAGTAATAAATATTAAAAAATGATTGAGGC
CACACGCAGTGGCTCACACCTGCAATCCCAGCACTTTGGGAGGCAGAGACGG
GCATATCACCTGAGGTCAGGACTTCGAGACCAGCCTGGCCAACATGATGAAA
CCCCGTCTCTACTTAAAATACAAAAAAACTAGCCAGGCTTGGTGGCAGGTGC
CTGTACTCCCAGCTACTCGGGAGGCTGAGGCAAAAGAATCGCTTGAACCTGG
GAGGCGGAGGTTGCAGTGAGCCGAGATCAATCGCGCCACTGCACTCCAGCCT
GGCCAACAAGAGCAAAACTCCATCACACACACACACACACACACACACACA
CACACACACACACACACACACACGATTGGACTATTTCCTTTACTTTGTTCA
TAGAACTTGTTTTACATAACGGACCTCAGGCTATCCAAATGATCACAACTTCC
TAATTAGGAAGGTCTGAATTAATGAAGGTTCAAGATTGCCTCCTTGGGGGCT
AATGTGTATGCAAGCTGCGACCCACTGGTAACAGCTTTACTATTTACTCTTCC
CTGCCAGGGGATTAGTGGAATCTAAATTGAACAGTTAGGTATTTAAAACCAC
TCATGTGGTTTTAACCACTAAAAGGGTTGTTAAGCAAGTCTTCTTTAATTTTTT
TTTTGTTGAAAATATTATAAAATTGGTGTCTAAATGCTGACAGTCAATGGGC
AACTTGGGAAATTACTCAATGTCTGTTTTGGGAAAACAGTAACTGGCACTTAC
ATATCACATGTGATCTGAGTAGCGTTAACTCCTTCTCTAGAGTACAGGATTGT
ATGAAGTTGAGGTCCTACCCTTAATTCTTTCACGTTGAAATATATAGTTACAG
GAAAGTGAGTTTAAATTGATTGCATGTTACTGTCTCCCTTTTAGAGTCATTTA
TTTTAAGAAGCACTGAAAGGCCGGGCGCGGTGGCTCACGCCTGTAATCCCAG
CACTTTGGGAGGCCAAGACGGGTGGATCAGGAGGTCAGGAGATCGAGATCA
TCCTGGCTAACACGGTGAAACCTCGTCTCTACTAAAAATACAAAAAATTAGC
CGGGCGTGGTGGCAGGCGCCTGTAGTCCCAGCTACTCGGGAGGCTGAGGCAG
GAGAATGGTGTCAACCCGGGAGGCGGAGCTTGCAGTGAGCTGAGATCGCGCC
ACTGCACTCCAACCTGGGCGACAGAGCAAGACTCCGTCTCAAAAAAAAAAA
AAAAAAAAAGCACTGAAAAACTTGCGTAAAGGCATCACACTCTGTTGGGCA
ATGGGGAAGGGGAAGGTGGGTTTCTCGCCCTCTGTCACTGATATGGTTTGGTT
GTGTCCCCACCCAAATCTCACCCTGAATTGTGATAATCCCCACGTGTCAAGGG
CACGGCCAGGTGGAGATAACTGAATCATGGGGCGGTTTCCCCCGTATTGTT
CTCATGGTAGTGAATTAGTCTCACGAAATCTAATGGTTTTATAAAGGGCAGTT
CCCCTGCACAAGCTCTCTTGCCTGTCATCATGTAAGATGTGACTTTGCTCCTC
ATTTGCCTTCTGCCATGATCATGAGGCCTCCCCAGCCATGTGGACCTGTGAGT
CAATTAAACCTCTTTCCTTTATAAATTACCCAGTTTCGGGTATGTCTTTATTAG
CAGCATGAGAACAGACTAATACAGTCATTTACAAGCTATCTGGGGCTATAAG
```

Figure 1 Cont.

```
AAGGATATGCATGTCCTAGGTGAGGAATACTGCACAGGGGAAAGAGTCTGA
GTGAGTAGGGCAGATTGTGCAATGTGAGGCTTTAGGGGATCCCAGGGGACAA
GACTTGGGAGACACATTTGTAGAAAGGTTGGAGTTTTACAGTGATGCCACTG
AATTATCAATGGAAGGATATGATTTCCTTCGTACAAGAAATCTGGAAAGTAT
ATGGCATTTATAGACAGGTTCCACTTCAAAAAATCAAGCAGCATATTATTT
GCCAGTTTAAAAGTTAACCCTGCTTGCTTTTGTTTTGTCTTGTTTTGTTTTGA
GACAGTCTCACTCTGTCACCCATGCAGGAGTACAATGGCGCGATCTCGGCTC
ACTGCAACCTCCAACTCCTGGGTTCAAGTGATTCTCCTGCCTCAGCCTCCCAA
GTAGCTGAGACTACAGGTACCTGCCACCACACCTGGCTAATTTTTGTATTTTT
AGTAGAGGCAGGGTTTCACCATGTTGGGCAGGCCAGTCTCGAACTCCTGACC
TCAAATCACCCACCTTGGCCTCCCAAAGTGCTGGGATTACAGGCATGAGCCA
CCAAGCCCAGCCTGGTTGCTAACTATTTGGATAACTGTTTGGAATCACTACAT
TCCTGAGTGAGTGATTCAGACAACAGAGGTTTTTAAAAAAACTTTAAAAAA
ATTTTTATCTTAATAGTTTTTTGGGTACAGGTGGTTTTTGGTTACATAGGTAA
GTTCATTAATGGTGATTTCTGAGATTCTGGTGCACCTGTTACCCACACAGTGT
ATACTGTGCCCAATATGCAGTCTTTTTTCACTCACCCTCCTTCCACCGTTTCCC
CTGGAGTCCGCAAAGTCCATTATATTATTCTTATACCTTTGCATCCTCATAGCT
TAGCTCCCACTTATAAGTGAGACCATATGATATTTGGTTTTCCATTCCTGAGT
TACTTCACTTACTTACAATAATGGCCTCCAGCTCCAACCAAATTGCTGCAAAA
GACATTACTTTGTTCCTGTTTATGGCTAAGTAGTATTCCATGGTATATATACTA
TTTTCTTTCTTTTTCTTTTTTTTTTTTTGAGACAGAGTCTCGCTCTGTTGCC
CAGGCTGGAGTGCAGCAGCGCGATCTCCGCTCACTGCAAGCTCCACCACCCG
GGTTCATGCCATTCTCCTGACTCAGCCTCCCTAGTAGCTGGGACTACAGGCAC
CCACCACCACGCCCAGCTAATTTTTTTGTATTTTTAGTAGAGACAGGGTTTCA
CCGTGTTAGCCAGGATCGTCTCAATCTCCTGACTTCGTGATCCACCCGCCTCG
GCCTCCCAAAGTGCTGGAATTATAGGCGTGAGCCACCGTGCCCGGCTATATA
CTACATTTTCTTTATCCACTCCTTGGTTGATGGGCACTTAGGTTGGTTCTGTAT
TTTTGCAATTGTTAATTGCAGACAACTGAGGTTTTAATGAAGATTATAGTGTT
GAAGTAGGATATTTCTAATATTCTAGTCTTATGAGGACTTATAAAATTGGGTA
GATTATCAAATCCTCAAATTACGGCATATTCATTTTGGCTTATATTTAAAATA
TTCCACCATCAAGACTGGGGAAAAAGTTCATCAGAAACATACGCTGATATT
TGGCTATATTGTTTGTTTTTGCATGCATTTATGCAATAAACAAACATCTGATTT
CTTGCACAGTCCCTCAGATATTCTCCTCACATTAAAGATTCCACTTACTTATTC
TGTGATTTCTCTTATTCTATGAGACAAAAATACAACAGAATGTCAGAAGAGC
CAGCTGAAAATATTCCATGTGCAGAAATTTATTTTAAATTTTATTGCATCACA
TTATACAAGCATTAATCATGGCTTCATATTGATGACTATTTAAATGTGAAAAT
TCACTCATGTCAGTACTTTTTGGCTATTTACAAGTAAGGAATTTCTATGTACTT
TATATATCTCTGTATTTGTATGTACATATGCAGGAATACATGACTATACATAT
GTACACACAGAAATACATCTATGGCCATACACATAGCTATAGATATGTCATA
TATAATAATCTTCTCAGAAAGGTCTAAAATTAAAAAAAAGGAAAGAAAAAGT
TGTAAACAGGGTCTTGTCTGTGTTGTTGGTGACATGGAATTAGGACCATATGA
TGACATTCTAGGAATGTGTGTCCATGTGTCTGAATACCCTTTTAGCCCAGTG
TCTGTAAAATTCACATGGGATAGAATGCAAAAAGGTAGCAAACAGGCTGA
AAAACAGGCCCAGTATACAAGTTCCCCTTGATTTTAAAAACTTGAGAATGTA
ACTGCCCATAATGTGCATGCTTGCTTGGTCAAGAATGGTCTATGGATAGATAG
CAATTGTGCGCTGGACTGCAACGTGATTTCACAGCAGTGTGACTCCAACGCC
```

Figure 1 Cont.

```
AGTCCTCTACTGGATGCTGCCCCTCCTGCGGCCGCCGGTATCTGCAACATGCA
CTGTGGTTGCATTTTTAGTCATTCACTTGAGTGTGCTTTTGCACAGCCAGAAG
AAGTAAACAGAATTCAGGTCCTTGGCCTGGAAAGGGACTATTTTCTGGAAAG
AGAAAAGAAGGCATAAAGATCTTATGCATACACAATTGCTTTAAAACATGAG
GTGCAATAGTTTGTACTTACCATGCACCAAAGGCATTCAAAGAATTTGTAACC
CCAAATGGAGTCAGGGATGGTATAAACATTTTTATGCTTGCTTTATGGGTGAA
CAGACTGAGTCAGAAGGGCAGTCTAAAGCAACATCACATCCTGCCAACTATC
GGGGAAATAGAAACAGGCAGGCAGATACTATGCTTTCAAGCAAAAATTAGA
AATGGCCTTTTTGGGAAGAAAGCAGCCAGTAGTGGTGGGGCCAGAAGAAATT
CTTCATCAGTTACTGGTCCTGCAGCCCAGGACAGCCCTGTTGCACCTTGGTCT
CTGGCCGCTGAGGCTTTCAGGAAGAATTCTCTTTGCTAATGTCTGCCTCCCAC
CCACCTAGAAAGAAGGGGCATGTTTCCCTGGGGATATTAAAGAAAACAGCCC
GGCTGGAGGAAAAGAGAGAGGACGCTTTGTTTCAGGGAACTCCTAGGCCAAT
TCATGAAGACCTTGACTGATAGGCCAGAGTCTGGCAAGAAGGCAGAGAAGT
GTTGCAGAAGGTATGTGGGAGGGGAAGATCAAGCAAAATTTGCAACGATTA
AAGTAAAAAACAAGCTTCTTTTGGATTGGGAAGCTTCTAAGGAGTTTATTTTG
ATCCCTGTTACTGCAACAATGGTAAGCTTTGCTTCAGGGAGTTTAAAGCACCC
ATTCAACCTCGGAATGGCCTCAGACGCTGAGCACACCTCTCACCTACATGGTC
ACGGCCACTCGTTGTGGTGTGCTTTTCCATTCTTCTTCCTCTCCTTTCGTTCCTT
CTGGAGACGTTCCAGTTCTGCTTCATACATCATCTCCTGAATCAAGTACTTCT
CTCTTCTCATTCGATCCCTTAGGTCTTTTGGGAGGTCTGGGATCAGATATGAA
ATGAGGTGCTTTATACAAAACACGAGGTGCTAAAACAGAGGAGAATGTAAC
AGCGTCAGGTCTACTGTGCATCCTGAATGAGGTTAGAGAGTTGGCTGAAGAA
GGATGTGGACCCTCTGGGGTATGTGGAGAGTGCAAAGTGACCAGGGGAGGC
GTGTGTAATGCAAGATGATAGGACAGGTGAGGCCTGAACTGGTCTGATGGCA
CCACCTAAGGAATAGAAAGAGGAGTCTGGAAGGAAGGTGGGAAAAGAATGG
TCAGATAATTAATTCAAAGGAGAGCCAGAAGAATGTATTCTGTGGAGTCAGA
AAACCCAGGTTGAAGCTGGTAGCTTTCACTGCTTAAGGGCTGTCTGTCTACCT
GAGGATGAATTATTTAATTTATCTGAGCCTCATTCCCCTCATCTATAAAGTGA
GTATTGTGAGAATTATGAGAAAATGTTTAAAAATGCCTTGTAGACTGTCAAG
TGCTTTACAAATCTTGGTTATAAGAATTATCAGTGGGCCTAGGGAAATGATCA
TTTCAGGAAGAAGCTTTTTCTTTTGGTAAACAGTCACAAATTCTTTACTTGA
AATACTAATAGCTGGAATTCTAGAGTCACTGTCACTTCTGCTCATCTATATAA
TGGTGACCAAGGAAGTACTAGATGACAATTTAAGGGCTATTACAATTCTAAA
GTATTAAATAGAGACTAAATCATGTTCAAATGATACTGCTAAGTATTCTTCGT
TTTATTTAAAACTTGATAAATTTGGTGATGCATGGATGGCACAAAATTAAGA
AGCTTTTCTGCATAGTTCTCATATTTTCAAATAGTTAATAACAAAATATTAAA
AGAAAATGGAAATTCTATTTGAAAAGCCAAATAAGGCAGCCTTTTAAAAAG
TTTTGTCTGACAGATTTACAGCAGAATTCTACCAGAGGTACAATGAAGAGCT
GATACCATTTCTATGGAAACTATTCCAAAAAATTAAAAAGGAGGGACTCCTC
CTTAACTCATTTATGAGGCCAGTGTCATCCTGATACCAAAACCTGGCAGAGA
GACAACAAAAAACTTCAGGCCAATATCCCCGATGAACATTGATGCAAAAAG
CCTCAATACAATACTGGCAAACCAAATCCAGCAGCACATCAAAAAGCTTATC
TACCATGATCAAGTTGGCTTCATCCCTGGGATAAAAAGTTGGTTCAACATATG
CAAATCAGTAAACATCACATAAGCATAAGTAATTCATCACATAAGCAGAACT
AAAGACAAAAACCACATGATTATCTCAATAGCTGCAGAAAAGGTCTTTGATA
```

Figure 1 Cont.

```
ACAATCCAACATCCCTTCATGTTAAAAATTCTCAATAAGCATTCCCCTTAAAA
ACCGGCACAAGACAAGGATGCCCTCTCTTACCACTCCTTTTCAACGCAGTATT
GGAAGTTCTGGCCCAGGCAGTCAGGCAAGAGAAATAAATAAAGGGTATTCA
AATAGGAAGAGAGGAAGTCAAATTATCTTTTTTTTGCAGATGACCTGATCCC
GTGTCTAGAAAATCCCATCATCTTGGCCCAAAAGCTTCTTAAGCTGATAAGCA
ACTTCAGCAGAGTCTCAGGATACAAAATCAATGTGCAAAATCATTAGTATT
CCTAACCACTAACAACAGGCAAGCAGAAAGCCAAATCATGGATGAACTCCCA
TTCACAACTGCTGCAAAAGAATAAAATACCTAGGAATACAGCTAACAAGAAA
AGTGAATGACTTCTTCAAGAACTACAGACCACTGCTCAAGGAAATCAGAAAG
GACACAAGCAGATGGAAAAATGTTCCATGCTCATGGATAGAAAGAATCAATA
TTGTGAAAACGGCCATCTGCCCAAAGTAATTTATAGATTCAATGCTATTCCCA
TTAAACTACCATTGACACTCTTCACAGAATTAGAAGAAACTCTTTTAAAATTC
ATGTGGAACCAAAAAGAGTCCAAATAGCCAAGACAAGACTAAGCAAAAAG
AACAAAGCTGGAAGCATCACACTACCCAACTTCAAATTATACTAAAAGGCTA
CAGTAACCAAAACAGCATGGTACTAGTACAAAAACAGACACATAGACCAAT
GGAACAGATTAGAGATCTCAGATATAAGACCACACATCTACAACCATCTGAT
CTTTGAAAAACCTGACAAAAACAAGCAATGGGGGAAAGGATTCCCTACTTAA
TAAATGGTTTTGGGAGAACTGGCTAGCCATATGCAGAAAATCGAAACTGAAC
CCCTTCCTTACACCTTATATAAAAATTAACTCAAGATGGATTAAAGACTTAAA
TGTAAAGCCCCAAACTATAAAAATCCTAGAAGAAAATCTAGGCAATGCCATT
CAGGATGTAGGCATGGGCAAAAATTTCATGATGAAAACACCAAAAGCAATTG
CAACAAAAGAAAAAATTGACAAATGGGATCTAATTAAATGAAAGTACTTCTG
CACAGCACAAAAAAACTATCATCAGAGCAAACAGTAACCTATAGAATGGGA
GAACATTTTTGTAATCTATCCATCTAACAAAGGTCTGATATCCAGAGTCTACA
AGGAACTTAAACACATCTACAAAAAAAATACCAAGCAACCCCATTAAAAAGT
GGGCAAAAGACATAAACAGACATTCTTCAAAAGAAGACATTCATGCAGCCA
ACAAACATATGAAAAAAGCTCAACATTATTGATAATTAAAGAACTGCAAAT
AAAAATCACAATGAGATACCATCTTACACCAGTCAGAATGTTGATTATTTAA
AAGTCCAGAAACAACAGATGCTGGCAAGGTTTCAGAGAAAAAGGAACACTT
TTACACTGTTGGTGGGAGTATAAATTAGTTCAACCATTGTGGAAGACAGTGT
GGCAATTCCTCAGTGATTTACAAGCAGAAATACCATTTTACCCAGCAATTCTA
TAACTTGTATGGCAAAGGACACAAACAGATACCTCTCAAAAGAAGATATACA
AGCAGCCAAAAATAATATGAAAAGATGCTCAGAATCTCTAAGGAGATTAGA
GAAATGCAAATCAAAACCACAATGAAATATTATCTCATACCAGTCAGTATGG
CGCTTATTAGAAAGGAATATAAATCATTCTATTATAAACATACATGCATGCAT
ATGTTCATTGCAGCACTATTCACAATAGCAAAGGCATAGAATCAACCCAAAT
GCCCATCAATGATAGGCTGGATAAAAAAATGTGGTACATATACACCATGAAA
TACTATGCAACCATAAAAAGGGATGAGATAATGTCCTTTGCAGGGACATGGA
CAGAACTGGAAGCTGTTATCCTCAGCAAACTGACAAAGGAACAGAAAACCA
AATACCACATGTTCTCACTTATAAGTGGGAGCTGAATGATGAGAACACATGG
ACACATGGTGGGAAACAACACACAAGGGGCCTGTTGGGGGTGGGGGTGGG
GGAAGGGAGAGCATCAGAAAGAATAGCTAAGGGATGCTGAGCTTAATACCT
GGGTGACGGGTTGATCTGTGCAGCAGATGACCGTGGCACACATTTACCTGTG
TAACAAACCTGTATGTCCTGCACATGTACCCTGGAACTTAAAATAAAAAAT
CCCAAACAAACAACAAGAAGTTTTGTCTGAAAAATTTTAAGACAGTGATGGG
TTAAAAATATCTTCTTTAAAGAGAGAGTGTGCCATTGGTAAGATAATTTCCAG
```

Figure 1 Cont.

GGAAGAGCAGCTTAATATTTTCTTCTTTTGGTTCCCTGGACTGAAGGAAAAAG
CAGTGATAGAATAGTCTTGAAGAGGTCTAGGAAACTTTAGATCCAAGCCGAG
AGGCAACCTTGGCTTTTATTAATCTGGCTTTAATATATGTGACAAGAGATGAA
ATTTCCACTTATGACTAGAGTCATAGAAATGCAAACTATTTTTACAGCAATTT
TCTTAAACCCTGAAAGAAAATAGATAATATATTTTTATTGACATATAATATAG
ACAATTGCTAGACAGATTTTACTTTATAATTCCATTTTGAGTCTTAGCTAATA
AATACTTACTTGGATGCTTGAATATAAATAATTCCGTGATGATACACAACCAG
AAATACCACTTGTAATACCCAGTCCTATTGGAAAATGCTTATGATCATGTTGG
GAAATCCTGATAACTATTTGAAAATCATAAATTAACTATATGAATCAGTATAT
TTCAATATGTGTGGTAATGATGATGGCAATAATTGGAGACATTTAGAAAGAG
TGAATCTCCAACTTGACAAAAACAAGCAGTGGGGGAAGGATTCCTTGTTCAA
TAAATGGTGCTGAGATAACTGGCTATCCATATGCAGAAGAATGAAACTGGAC
TTCTACCTATCATCATAAACAAAATTTAACTCAAGATGAATTAAAGACTTACA
TGTAAGACCTCAACTATAAAAATGCTAGAAGAAAACCTAGGAAATACCCTTC
TCAATACTGGCCTGGGCAAAGAATTTATGGTGAAGTCCTGAAAAGCAATTGC
AACAAAAACAAAAATTGCTAAGTCAAATCTAATTAAAGAGCTTCTGCACAGC
AAGAGAAACTGTCAAAGAAGTAAACAGACACCGTACAGAATGGGAGAAAAT
ATTTGCAAACTATGCACCCAATAAAGGTCTAATACCCAGAATCTGTAAGGAA
CTTAAACAAATCAACATGTAAAAAACAAATAACCCCATTAAAAAGTGGTCAA
AGGACACAAACAGATACTTCTCAAAAGAAGATATAGAAGCAGACAACAATA
ATATGAAAAAATGCTCAGAATCTCTAAGGAAATTAGAGAAATGCAAATCAAA
ACCACAATGAGACACCATCTCACACCAGTCAGTACGGCTTTTATTAGAAAGT
CAGGCCAAGTGCAGTGGCTCACGCCTGTAATCCCAGCACTTTGGGAGGCCAA
GGCGGATGGATCATGAGGTCAGGTTAAGACCAGCCTGGCCAAGACAGTGAA
ACCCCGTCTCCACTAAAAATACAAAAATTAGCCAGGTGTGGTAGCGGGTGCC
TGTAATCCCACCTACTCAGGAGGCTGAGGCAGAGAATTACTTGAACCTGGGA
GGCAGAGGTTGCAGTGAGCCGAGATTGTGCCATTGCACTCCAGCCTGGGCGA
CAGAGAGAGAATCAGTCTTAAAAAAAAAAAAAAAAGTAAACAAATTAACAG
ATGCTGGCGAGGCTTCAGAGAAAAGGGGACACCTGCACACTGTTGGTGGAAA
GGTAAATTAGTCCAACTACTGTGTAGTCTGGAGATTTCTCAAAGAACAAAGG
GCTTAACTACCATTCAACCCAGCAATCCCATTTCTGGGTATATACTCAAAAGA
AAATAAAGCATTCTACCAAAAAGACACATGTACTCATATGTCAATCACAGGA
CTATTCACAATAGCAAAGACATGGAATCAACCTGGGTGCCCATCAATGGTGG
ACCAGATAGAGAAATGTGGTATGTATACACCATGGAATACTATGTGGCCAT
AAAAAAGAATGAAACCATGTCCTTTGCAGCAACATGGATGTAGCTGGAGGCC
ATTATCTTAAGTGAAATAATGTAGAAACTGAAAACTAAACACTGCAAGTTCT
TATTGTACGTACTTAGAGTGGAAGCTAAACACTGGGTACACATGGACATAAA
GATGAGAACAACAGACACTGGGGACTACTATAGAGGGGAGAGGGGGAGGGG
ACAAGGGCTGAATAACTACCTATTGAATACTATGCTCGCTACCTGGGTGGTG
GGTTCAGTCGCACCCCAAACCTCAACATCATGCAATGTAACTTTGTAACAAA
CTTGCACATGTACCCACTGTATCTAAAATAAAGTTGAAAAAGAAAAAGAAA
AAAAGAATGAATCTTACTGGGCTGATGTTTTCCAAATGTTTCCAAATTATGGT
CCCAGAATGCCTATAGTCAGAATCATTACAACGAGCTCATGAAAAACAAGCC
ACAGACATGGTATGTCAGAATATCTGGGAGTGAGGATGGAAAAACTGCATTT
TTGCTAAAGTTTAAGAACTATGGCCCCAGAAAATTACATTTAGGAGCAACGA
GTTCAGATTTGTCCATTAAAAACCAACTATGGACTTTCAAATATGTCTTGGAA

Figure 1 Cont.

```
AAATCAAATGCTTCAATTAAGAAAAAAGATCAAAAGAGGTTACATAATATG
ACACTACTACTTCTGGAAATATAGATAATCACATTCAAAATCCCCATCACTTA
TTTTTATTCATTACTCCTACTGACTTCATTATGTCAAAGGAAATAAAGAATTT
GGCTGAGGAAACTTACCTCAAAGACAATGATAAAAGCTAATCGAGCAGCTAG
GACATGCCAAAACTGCAGTGTGTAGCCATAGGGCACCAGTGAATGAGGCGG
GTCACGGTAGTCCCGGTATCTATAAAGACACAGAAAAATGTTGCATTCAAAC
TATGATTTTTCTGATTCTCAAATCTCTTCCATTCTCATTATATAGTCCTCATTC
AATAGGAGGGAAATTTGAAGTTTCTCTATACTAGATATCTGTTGTTTTGCTTG
TCCAGCATTTTTCTTCTGATAAAATAATATCTCTTCTCTGGGGAATCATCTGTG
TGGGTTGACTAGGACTTCCCCCTCCACCTGCCTGATCTCAGCTCAAAAGATGA
GCCAGACCTGATCAGTGACATCATCAAGATGTCTGCCAGAACTATCACTTAG
TGAATGATCACTAAGCCCACAGAAGGCAAAAGCCTGGGACTCCTGGTGGCCT
TGTATGGAGAGAGAGAGCCTGCTTGAGAAGGAAGTCAAGAAAACAAAGCAG
AGACAGCAGAGAGGCAGCATCCTGCTGACACTGCTTGAGGCCTGGGATCCGG
CCATTACTGAAGCTCATATCACCCCTTGACTCTCCCAGCTAACTGAACAATTT
TTTGTTGTTTAAGTCAGTTTACCCTGGATTTCTGCCACTTGCCACTAGAAGAG
TCCTTCCTAATGTATCCTCCAGCTATCACTTTTGAGTCGGCATAAAATTCCAC
AAATGTTTGCCGAATACCTGTTGGGGACCAGGCACTATTCAGAGAACTTTAA
TCCATGTGACTCCATTAAAGTAATACTTTAATAATACAACAAGCTCTCATAAA
TCCACTATGAAGCCCAAGAACTAAAACATTACCAGGAACTTACATCAATTGC
TTCCCTTACCCTGAATTTCATTTTTATTTTTAACTTATATGTATATGCATTTGTC
TGAATATTGTACTATTTAGTTTGTTTTTGAACTTTATAGAAAGGGTACTATACT
ATATGTAGTTTGCTGGGGCTTGCTTTTTTTACTATTATGTCACTAAGATTCATT
CACATTATTGCATGTGGTTTATTTTTATTGCTGTATAATAGACTCTAGTGTGAC
TATATTATGGTTGTTTATATAGCATATAAGTATACACTTACAGGCTGGTCAT
TCCTATATTTTCTTTTCTTTTATGTTGAGACAGAATCTCGCTCTGTCACCCAGG
CTGGAGTGCAGTGGTGCGATCTTGGCTCACTGCAATCTCTGCCTCCCAGACTC
AAGTGATACTCCTACCTCCCAAGTAGCTGGGACTACAGGTGTGCACAAAAAT
GCCTGGCTAATTTTTTTGTATTTTTGGTAGAGACAGGGTTTTACCATGTTGCCC
AGGCTGGTCTCAAACTCTTGACCTTAAGCTATCTACTCACCTCAGCCTCCCAA
AGTGCTGGGATTACAGGGTGAGCCACTGCACCTGGCCTCTATATTTTCTTTCA
CTTTCCCTAACCATGGAAAGCTTTGAAAAAGAAAGCTCCATCAATGATAGAC
TGGATTAAGAAAATGTGGCACAGATACACCATGGAATACTATGCAGCCATAA
AAAAGGATGAGTTCATGTCCTTTGTAGGGACATGGATGAAGCTGGAAACCAT
CATTCTCAGCAAACTATCTCAAGGACAAAAAACCAAACACCGCATGTTCTCA
TTCATAGGTGGGAACTGAACAATGAGAACACTTGGACACAGGAAGGGGAAC
ATCACACACCGGGGCCTGTCGTGGGGTGGGGGGAGGGGGGAGGGATAGCAT
TAGGAGATATACCTAATGTAAATGATGAGTTAATGGGTGCAGCACACCAACA
TGGCACATGTATACATATGTAACAAACCTGCATGCTGTGCACATGTACTCTAG
AACTTAAAGTATAAAAGATAAATAAATAAATAAAAAGAAAGCTCCAGTCC
ACTCACTTCAGCAAATTCCCTTTGGGTAAAAGTTGGCTGCAATGCTCTGTGTA
CCACTTCTTTCTGCCTTAGAATACCAAATATTCTTCCCAGGTCATTAATGTATT
TGAGAAGGTGTTTTAAATTTTTCTCTACATGTTTAGATATTTTCAGCCCGCAA
GCTGATCTGGGTGCCTCACCTGCTATATGACTGAAAACAAACCTGAAAATAT
TATTTTACATGATTTTAATTAGAAATTTTAAAATGTTTTCTTTGGGGACTTTT
AAGAAAAATGCTAAACAAAACAATCATAATTTAACTTAATGGTGCCAGCATT
```

Figure 1 Cont.

```
AATACCTCCATTCACATTAATAATTTCTGGAATATACTTTTATGATACTATGT
GAGACAGGCAGGAAGAATTATGAGCCAGGAAGCAGAAGAGGAGAAAGACTC
TGTATTTTATCTTATTTTCAAATGATTACAAAGTTTTTAACTCCAAATAATAG
TTGGCATTTTATTTTGAAGCATTTCATACTTAGGATCCTGTATATGTCTAACAA
TGCTTGCTAAATAATTTCATGTACGAAATGGTCTGGACAAGCAAGTGGGAAA
TCTACTGAAGAAAGTATCAATTGTTGCTTAATTGCTTGCTTCTCCACTAGACC
CCAACAGAGAGCGGCACTAGATTATATTCCAGCCAGTCTTTCTCCCCATCTTA
CTTGTTACTCCATGTGGGAAAGGAAATAAGCCATCTGATGAGATGTGACAGC
CAATGAGACCTGGGAACTTGGCATGAGTGTTTAAAGGGGTGGAGGGTATGCT
GTCACTGCACAGAAATGGGGAGCCCCTGGCTTCTCTCACCTTCACCTTCTGTA
AGATGAGGGACTGAAGTGGATCATTACAAAAGTCCCTATGTCAAAGCATCTA
GGACTCCATGGCTGTTCTTCCTTGTGGCTTTGATTACAGGGAGAACATAGAAT
GTCATGATAGGGAATCTCCAAAATTCTTTGTTTTGTTTTTGAGACAAGGTCTT
GCTCCATAGTTTGAATGCAGTGGTGCTATCATAGCTCACTGCAGCCTTGACTG
CCTGGACTTAAGTGATCCTCCCAACTTGGCCTCCTCAAGTGCTGGGATTACAG
GTGTGAGCCCACAAAATTCTTATAACGTCAAAGTATTAAGAGAAAAAGGTGC
CATCTGGACTCTTCAAGAACTGTGCACAAGTAATCTCATTGAGCTTTTAGTGA
ATGGTTTTATCATTTGTCAGATGAGATAATATTGCCTAACTTAGAAGGCTGAT
GTGACGATTAAATGGAGTAACAGTTTCTGGCACAGAGTAGGTGCTCAACAAA
TTCTCCTTCATGTACGTTTGTATAGATACACATCAAGAGGCACAGTTTAATTC
ATTTCCTTTTAGAGGGAGAGAAAGAAAGAGAGAATGAGCACATGTTGCAGA
GGCTACTGTGGTGGAACCTGAAATGAACTGGGCCTCTTTCCACAGGCTTCTGA
GTTGTTTAACATTTAGAAATGTGATGTGATATACTCTGGGCAAGAGAGAGAA
GCAGAACAAAGACAAGTGCCCTCAACAGCTGTCGCTCAACCCGCCTGGGGAT
TGTCTGTCCCTGAGTCCCTGGAGCAGCGGTATAACCTTCACTACTATATTTTT
AGTTTTTCCCTTTAAGCTAGCAGTTCTCAATTCTGACTGCACCTGGTTTCTGAG
TTCCACTCCCTGACATTCTGTTTTAATTGGTTTGGGTTGTATCCCGGGCAAGA
GAAGGCTTGAAAATTCTTCATGTGCTTTTAATGCATTGTTGAGATTGACAGTC
ACTGCTTTAAACACACTCAGCCAGAAGGGGCCTTCAGAGTAAAACCTCCCCA
CGGTGGAGCCAGCCCAGCTCAGGCAGAGCCACGCTGGGTGCCACACTCACCT
GCAGTACTTAAGAGGAGTCCCCGAGAACTCACTGCCATCAGATTCAGGCTCA
GATCGGTTCTCAAAGTCAGAAATTCGAAATACAGACAAGCTGGCATTCACAT
AGCCAACCATGCACCTATAAGAGGAGGCACATTCTACCATTAGAACACTCAT
CACCTTCTCTGTATCCAGTTCCCTGAAGACCCTGCTTCCAGACGTCCCTGCA
ATTGTAAATGCCTTTAACTGGCCCTTCCTTGTCAACCAGGACTCAGGTTGGGA
TACGCTGGAAAGCCCTGGGCATGTTGAATCAGGAACAAGTTGCTTGTTTTGGT
TCTCATCCTTTTCTGCAGAATCATCATATAGAACATCTCTACCCCAATTAAT
GTTCAGTGAAATAGGTAAAAGCAGCATTACATGATGGGCATAAATTGTAT
GTAAGCCACAGCTTCTTTTGTTGATGATACACATAAACACAGTTCCTCATTAA
TGGTTTCATATATATTTATAGATATTCTCAAAATGTTCCAAATATGATTGGTG
TGCATATGATCCCCCAACTCATATCCCATGCTACAGTCCTGTTAGACTATAT
TCCCTGAAAGCTTCTGATGTTTTCATGCCTCTGCTTGTTATCTTTTCTGTTAGA
ATTCCCTACCTCTTCCTTTACAAGTGGAAATAGTATTTATCCTTCAGCGGCCA
ACTGAAACACCACTCCTACTAGGAAGACAACCTAATCACTCCAGTCACAACA
TCTCACTCCTTTCCCTCTCTGTAGTGCCACCATACTTACTTAGTTCACCATT
ACCAGATCGCTTGTACTAGAGTTGGCAGCATATATGTATGCCCTCTCCTTTGG
```

Figure 1 Cont.

```
ACTGCAATTTTTTGGGAGCAGAGCAGGTATCTTAGGTATTTGTGTATCCTATG
ACTTAGGACAGTCTTGTGCAGTGTAGGAATCCCATAAATATTGAATCGATCTG
ATTGGAGGAAACTAAAGTATGAGATTCTATTGATCATTCTAGATTGAATGGG
TAGATAAAATCAAGATTTAATCATTCTGTCAATAATTCCATTCAAGAAAAAG
CCCATTTTAAAAGTATCATAGCAAGTAGCACTCTTAGAAACATCTTTTCTCCA
AGTCTCTAAACAGTTTTACATATTGAACATTGTGGTTAACACATGCACTTACT
GAAATAACAATGTTTGAAACTTTGGGTGAAATTAGCACTTAGATACATCCTGT
ATACATTTTTCTTTAAATAGTGTTTTACATACAAAAGCTTGGGTTTTGGGGTC
AAATCTTAGTTCTGCTGGTTTCTAGTCATGTAATATTGGCACGTTATATAACTT
CTTACTTCTTCTTTTTTTTTCTGAGACAGGGCCTTGCTCTGTTGCTCATTGCTG
GAGTGCAGTGGTATGATCATGGCTCACTGCAGCTTTGACCTCCCAGGCTCAA
ACGATCCTCCCACCTCAGACTCCTGAATAGCTGGGACTACAGGCATGTGTCA
CCACACCCGATTTACGTAACTTCTTAAAGTGACAGAAGTTCCCACCTCATAGG
GTCCTTGAGGGGATTATATTAAACAATGAATGTATAGCATGTGATAAGATCTT
AGCCTATAAGTAAGATAAACATGAGTGGTGATTATTCATTTTATTTATTTCTT
GCATCTAGCAGGGGGTCAATAAGTAATTACTGATTGAATGAATAAATCATGA
TCTTCAGATTCTCTTCATTAACAAGTCTGGCATGATTATTCCAAGCTGCTGAA
CACTAAACCAAAATGATGACATGAACACAGTTCTGAGAACACATGGGTTCTG
CATGTTATCGTGCTCAAGACAAATCACTGGCTTTATCATGGCCTTAAAAAAAA
TGAACCAAGCTGAAGGACCCATTTGTCAAGTCACTCGTGGGTGAAAACAAAT
GGTCAGGGAGTGTGTAACATGCCTTAATCCAACTGGCAGCAGGACTCCCCTA
CTGAAAGGGTAATTTGGAATGATGTCTCCCTTACCTAGGAACTGTCTAGACCT
GGACATGAAAATAAATTAGTGCCTTGAGGATGATTAGCTGTCACAGAGAGGG
AGTAAGTTTTAGCAGAGTCTTTCTAGAGATCTGAGCTGTGGGAAGGGAAAGG
TGTTCTGGGAACTGGTGAAAAAAAAAGGCCCAGCACTGAAATGGAATATTCA
TAACCCCTCCTGCACTCTTATCTCACAGACCAGCCCCGAGGCTTTATCAAGAC
TAACGCTACTGTCCATTGGTTGTTCTGCTCAAAAACTCCATTAAGAAAATTTA
AATTTAAATAAAACACCTGTTTCATGGACCTAATGCATGAATGACAGTCATA
AATCCAAGTTGAAAATGTGTCTTTAGAGGGTGGTTACTCCTGAGTGCAAAGC
ATTAAATGTGTACCTAGTACAGGAACACACAGTTATCAGCTGTGTACATCTTC
CTTCCATATCATTTCCATAATGGGGGAAAAGATGCACGGACAGCTAGACGTT
TCACTAATTCCTTTCACCTTTTGTAGACTGTTAGCTATTGTCAATATCAAATAG
TGAAAGTTGTCATCAATTCAGGCAAGTGAGATTTATCACATTTTGCTGTATAA
AATTCAGCTAGTGGCATGCAAGTGTCAACTCACTGACCCATTGTTATAGCAG
GAAGGTCACAGGTAGTAGAGAGCCCATGTCTATCACTGGGTTTACTGGCAGG
AATGCTATATACCCTCACTGTGACCCACCACCAGCTCTCAATGAGACAGAGG
GAGATGAGGCTACACTGATGATCAGGGAGAATTGAGAAGTACCAAGAAAAA
AGTAACAGACGAAGGGTTTCCTGTGAATATAAAGTCAGTTTTCTTAAAGGAA
TGGTAGATGGCCTCTGTAGGCACTTCCAAGAAAGATCTAGAAAATGTCTTCT
ACAGGGTAGTGCCATTTGGATTAGGATGCATATCTCTTCCATGTAACTTCTGA
GAAGACCACACACTCATTTAAATGTGAGAATTCTACCGTGAAAGCCACTCAC
CACTTATAATTTTCAATCCTTTAATACATAAGAAAGGGATGAGCCAGCAATC
ACTGTACTACCCTAAAGGCTTATGACTTTCTATACCTTGACAATTCTGCTACT
CTTATGAGTTCAATAATTTCTAAAGCATTTCTAAATTGGAAAAATAAAAAAA
ATCTGAAAAGTAATAGAGTGGCCAGTGAGGCAGAAAATAAGATTCATGAAG
AAACATACATAAATTTAACTACTTGAAAACATGAAAAATGACTAATGGATTA
```

Figure 1 Cont.

```
GAAAACAAAAGGCAGATCCATAAATTGAAAGTGGCAGAAGGCTCCTAAGTC
AAAGAGAAAGGTTAAAAAGAAAGAAAGAAAAGAAAAGCTCCAAAGAGCC
CAGTAAAATTGATACAAGGAGGCTATGAGATACACTTTAATCACTGTGGACA
TTGTCTTAAATCTACCAGGTTGTTAAAATTCTAAATCTTTGATTCACTATCAAT
TGTGCATAAAGGTTCCCATTTTGTTTTGGTTCCCCCTAAAACAAGATAGATT
TCACCATATTTGAATTTGGGAAGAACTGAAACACCATTACGACGGAAAATC
CAGGGGGTTTACTGTTAAGGGACAGCCTCAAGGGCTGTGAGGTGCGGGATGG
AGAGTGAGTCGAGGCTCCACCTTCACATGGGCTCCCAGAGTTACTATGCCTTG
TGATTCTGGACTTAACCTCTTTTAATCTCTTCCTGCTCCTCAAAGTGAAGATTA
TAATGCACATCCCACTCCCAGGGCTGTTTGAGAATCAACTAAAAACACATG
TGAAAGTGGTTTGAGTGAAAGTAAGCTTTTCAGGCTAAGCCAAGCAGAGAA
TGTCAACGATAGTTGCAATTAGAAAGAAATGCCTGGGCAAAATAACATGTCT
TTACATTTCTCTTAAAATGGGATGGTATGCTCACTAAAAGTTGCTAGATAATT
AGTGTGTCATGGCCACATGCTTATAGTAGTCAAGAACTTTACAGAAGCCTTTT
CAAATAACTGGATTGTGAGCTTTATGACATTCCTCAATCATCCACACCTTAGC
CCATTTATGTAGGATTCATAATGAATTGGACCCAGGCCAGGTTTGCATGAGTT
CAGTTGATTTGCTTTGGTGGCACTTAACTCCTTGGGGTCGATCAGCTACAATG
GCTGTAGAGGATGAATCAATCTGGCTCAGGCTAGTAAACCAGGGCTGCTTGT
ATAAGTAGACAGCAGCCCATGTAGGGTGATTTCTGGGTTATTAAGAAGACCC
TGTGATCCCCAAACACACCTCACTCTGACCTATAGACATCAAAATCCCATAAT
AAGAGTTTAACTATTTTGGCTTTAACCAAACAGGGATTTTTAAAGCATGTTAA
GACTTCTTGCCCTTTCTCCAAGGTACAGGAATGAAACTAGGGGATGTTATAAT
TTTGACTTATCTTTATCTGACCATATATAGCGTGCCCTGGCTTTGCAAACCATT
GAGGCAATGCCATAGAATTGATCCTCCCAAGGAGTTTAGTCCACTCAGCTTG
CTTGGGGTAATATAGGCATTGGTCAGGTCAATACCCATGAAAAGTCATTCA
CTTACTTATTCCACGAATACTTATTGAGGACCTACTGGGTACTCAGTACCTAG
TTCCGTATTTCCTATGTAAGATCTGCAGAGTTTACACATAATGACACAATGTA
AATCAGATTGTAACTGTCCTTTGCAAACTCATAAAATGATATAACTATATAT
ACATCATATGCTACTGTTTTGGTATACACATTAGCATATCACACATTTCTAAA
TTCATAGTGGGCAGAGGTCAGGGGTGGGGAAAATGATTAATTGCCACTCTTA
CATTGGATTCCATCTAAAACCTGTCTGACTTGTATGTCCTCCAACTCTTTGGTA
GATGAGGACATGTTTCTTTGGCTGACAGTGTTATTATTATTTATAATAA
ATCATAATTCCACCTCCCCTATCACAGGCCTCTCCTTCTGGGCATGTATTCCA
TATTCTCCAGTGCAGTCTTCTGTCTGAGTGTCCAACCTCAAAAAATGGCTAGG
AAATAGAAACTGTATAGTGGTTTATAGCAAACTTACTTTTGCCCAGCTTCTC
CTTGGCCTGCACAAGGTCCATACTTATAAGCATACACCAAGCGAGGGATAAA
GTCAGATGTTATCGCTATGACAAATGCATTTGTGATAACAGAGAGAATTCCA
ATGCCTTCAAGAATTC
```

```
GTGTAGATTCGCTGGAAGCAGCTGGAGGCTCCAGTTCTCATCTGCTCAGGTGT
CCCCGGCGCCTTGGCGAACTCGGCCACTCCAGTTCCTCACGTGGTGAGCACTC
AGGGCAGCGGGTCGATTTTCCGAGGTCCCATACCTGGGTTTGAGGGGCGCGG
CTCGCAGCGGCGGGTGCAGGGGCGACTGCCAGCCCTCACCCCGCCTCGGGGT
GCGTTCGGAGGCCGACACCTGGAGGACGCCTCCAGTCCCGCGGGACGCCAC
GCCTGCGCGCCAGGGATCCGGGATAAGAAGTGCGCGCCGGGCTCCGGCTGCG
CGCCGCGGGGCCACCAGTTTGCGCGCAGGGCTCAGGCGACCGTGCGGCCATG
GACACGCCACGGGGCATCGGCACCTTCGTGGTGTGGGACTACGTGGTGTTCG
CGGGCATGCTGGTCATCTCGGCCGCCATCGGCATCTACTACGCCTTCGCTGGG
GGCGGCCAGCAGACCTCCAAGGACTTCCTGATGGGCGGCCGCAGAATGACCG
CAGTGCCCGTGGCGCTGTCCCTCACCGCTAGCTTCATGTCAGCCGTCACTGTC
CTGGGCACCCCCTCCGAGGTCTACCGTTTGGGGCCATTTTAGCATCTTTGC
CTTCACCTACTTCTTTGTGGTGGTCATCAGCGCGGAGGTCTTCCTCCCGGTGTT
CTACAAACTGGGAATTACCAGCACCTACGAGTATTTAGAACTTCGATTTAAC
AAATGTGTTCGTCTCTGTGGAACAGTCCTCTTCATTGTTCAAACAATTCTGTA
TACTGGAATTGTTATTTATGCCCCTGCCCTGGCTTTGAATCAAGTCACAGGAT
TTGATCTGTGGGGCGCGGTAGTGGCAACGGGGGTGGTCTGCACATTCTACTG
CACACTGGGTGGTCTTAAAGCAGTTATCTGGACAGATGTTTTCAAATTGGGA
TCATGGTGGCTGGATTTGCATCCGTGATTATACAGGCTGTGGTGATGCAAGGT
GGAATCAGCACTATTTTAAATGATGCCTATGATGGTGGAAGATTAAATTTCTG
GAATTTTAATCCTAACCCTTTGCAAAGACACACCTTCTGGACAATTATTATAG
GAGGGACCTTCACATGGACCAGCATCTACGGTGTCAACCAATCCCAGGTGCA
GAGATATATTTCTTGTAAAAGCAGATTCCAGGCAAAACTGTCTCTCTACATCA
ATCTTGTGGGACTCTGGGCAATCCTCACATGCTCAGTGTTTTGTGGGCTCGCC
CTATATTCCAGGTACCATGACTGTGATCCTTGGACAGCCAAGAAAGTGTCTGC
ACCAGACCAGCTCATGCCTTATTGGTACTGGACATTCTGCAAGATTATCCAG
GACTTCCTGGACTTTTTGTGGCCTGTGCTTACAGTGGGACATTAAGCACAGTG
TCCTCCAGTATTAATGCCTTAGCAGCAGTAACTGTGGAAGATCTAATCAAACC
TTACTTCAGATCGCTCTCAGAAAGGTCTCTGTCTTGGATTTCCCAAGGAATGA
GTGTGGTGTATGGAGCCCTGTGTATTGGAATGGCTGCGCTGGCGTCACTTATG
GGAGCTTTGTTGCAGGCAGCACTCAGCGTATTTGGTATGGTTGGTGGACCACT
TATGGGCCTGTTCGCTTTGGGCATTTTGGTTCCCTTTGCCAACTCAATTGGAG
CACTTGTTGGTCTGATGGCTGGATTTGCCATTTCTATGGGTTGGAATTGGA
GCTCAAATATATCCTCCACTTCCTGAGAGAACATTGCCATTGCACCTTGATAT
CCAAGGCTGTAACAGCACCTACAATGAGACAAATTTGATTACAACCACAGAA
ATGCCATTTACTACTAGTGTTTTTCAAATATACAATGTTCAAAGGACTCCACT
GATGGATAACTGGTATTCTTTATCATATCTGTACTTCAGCACTGTTGGAACTT
TGGTAACATTATTAGTGGGGATACTTGTCAGTTTATCAACAGGAGGAAGAAA
ACAGAACTTAGACCCCAGATATATACTAACCAAAGAGGACTTTTTATCCAAT
TTTGATATTTTTAAGAAAAGAAGCATGTTTTGAGCTATAAATCACATCCAGT
GGAAGATGGTGGANCTGATAATCCTGCTTTCAACCACATTGAATTGAACTCA
GATCAGAGTGGCAAGAGCAATGGGACTCGTTTGTGAAGCTGCTCTGATACTA
GATATCCTTAAATGATGTTTCAATTTTATATGTTTTCTAAGATAATTGGATCA
```

Fig. 2-1

Testing 4-Hpa2 and 6-Hpa2 Site Methylation Assays in Colon Cancer Cell Lines

| Cell lines | 4-Hpa2 | 6Hpa2 |
|---|---|---|
| True positive* | 22 | 15 |
| False positive* | 3 | 0 |
| False negative | 0 | 7 |
| True negative* | 5 | 8 |

Sensitivity 100% 68%
Specificity 63% 100%

Note: * True positive: DNA is methylated and no transcription.
False positive: DNA is methylated, but has transcription.
False negative: DNA is not methylated, but no transcription.
True negative: DNA is not methylated and has transcription.

Figure 5

Testing 4-Hpa2 and 6-Hpa2 Site Methylation Assay in Normal and Colon Cancer Tissue

| Tumor/Normal status | 4-Hpa2 | 6Hpa2 |
|---|---|---|
| Tumor-methylated<br>Normal-unmethylated | 21 | 14 |
| Tumor-methylated<br>Normal-methylated | 5 | 3 |
| Tumor-unmethylated<br>Normal-methylated | 0 | 0 |
| Tumor-unmethylated<br>Normal-unmethylated | 8 | 17 |
| % of tumors detected | 76% | 50% |

Figure 6

Antisense strand wild-type sequence showing MS and UMS PCR1 primers and CpGs

Antisense strand wild-type sequence. Arrows show positions of PCR primers specific for amplifying bisulfite converted DNA from methylated (MS-PCR1) and Unmethylated (UMS-PCR1) templates.

AC063951 82200-83267 as-methyl

TTGATGATTATTATAAAGAAGTAGGTGAAGGTAAAGATGTTAAAAATGGTTTTAAAAACGGTAGATTTCGAGGAGGGGTGTTTTAGGATAGTGACGGTTGATATGAAGTTAGCGGTGAGG
                    20                    40                    60                    80                   100

GATAGCGGTTACGGGTATTGCGGTTATTTTGCGGTCGTTTATTAGGAAGTTTTGGAGTTTGTTGGTCGTTTTTAGCGAAGGCGTAGTAGATGTCGATGCCGGTCGAGATGATTAGT
                   120                   140                   160                   180                   200                   220

ATG
ATGTTCGCCGAATATTACGTAGTTTTATATTACGAAGGTGTCGATGTTTCGTGGCCGTGTTTATTGGTCGTACCGTCGTTTGAGTTTTCGCCGGTAAATTGGTTGTTTCGCCGGCGTAGT
    240                   260                   280                   300                   320                   340

AS-meth-442-459s
                                                              →
CGGAGTTCGGCCGCGTATTTTTTATTTCGGATTTTTGGCGCCGTAGGCGTGGCGTTTCCGGGGATTGGAGGCGTTTTTAGGTGTCGGTTTCGAACGTATTTCGAGGCGGGGTGAGG
   360                   380                   400                   420                   440                   460

GTTGGTAGTCGTTTTTGTATTCGTCGTTGCGAGTCGCCGTTTTTAAATTTAGTATGGGATTTCGGAAAAATCGATTCGTTGTTTTGAGTGTTTATTACGTGAGGAATTGGAGTGGTC
   480                   500                   520                   540                   560                   580
              As-meth-550bs
              ←

GAGTTCGTTAAGGCGTCGGGGGATATTTGAGTAGATGAGAATTTAGCGAATTTATATAGGGAGGCGTTTTGTTTTTTAAGTGGTAGGTTTGTTTAAGTGGTATTCGAGGG
   600                   620                   640                   660                   680                   700

GACGTATTATTTAAATAAGTAGGCGATCCGTGGAGGAATGTGGGATAAAAGGGTAATTGTTACGTTTTGAATTTTAGTTTTTAGTTTAATAGTTCGGGTTTTTTACGGAAAGGGACGT
   720                   740                   760                   780                   800

TTGGAGTTTTTTAGATTGTTTATTTGATAGGTTAATGGGTGATAGTAAATGGTGATAATTGTAGCGAATAGAGATTATAGTTTTTAGATAGGTTATCGATCGTAAAGGA
   820                   840                   860                   880                   900                   920

GAGTAGGAAATTTGTGTTATTGTTTTTTTGTTTTTATTTAATAAACGTTTTTGTTGTTGGAAATAGTAGTTATTGGAAGATTAATAATAATATTTATTTT
   940                   960                   980                  1000                  1020                  1040

TTAATCAGTTTTAT
   1060

Bisulfite-converted, methyl-antisense strand, MS-PCR1

Figure 10

AC063951 82200-83267 as-umethyl

TTGATGATTATTATAAAGAAGTAGGTGAAGGTAAAGATGTTAAAAATGGTTTTTAAAAATGGTAGATTTTGGAGGGGGTGTTTAGGATAGTGATGGTTGATATGAAGTTAGTGGTGAGG
                                                                                                              100

GATAGTGTTATGGGTATTGGTTGTTATTTGTGGTTGTTATTAGGAAGTTTTTGTGGTTGTGTTTTAGTGAAGGTGTAGTAGATGTTGATGGTGGTTGAGATGATTAGT
                                              200

ATGTTTGTGAATATTATGTAGTTTTTATATTATGAAGGTGTTGATGTTTTATGGTGTATGGTTTTATGGTGTATGGTTTTTGAGTTTTGTGTGTAAATTGGTGGTTTTGTGGTGTGTAGT
                                                                        ATG      300

AS-unmeth-442s=3D-unmeth-207as →
TGGAGTTTGGTGTGTATTTTTATTTTGGATTTTTTGGTGTGTAGGTGTGGTGTGTTTTGTGGGATTGAAGGTGTTTTTAGGTGTGTTGGTTTTTGAATGTATTTTGAGGTGGGGTGAGG
                                              400

GTTGGTAGTTGTGTTTTTGTATTTGTTGTTGTGAGTTGTGTTGTGTTTTGAGTGTTTATTATGTGAAGGAATTGGAGTGGTT
                                500
                                                ← AS-unmeth-542as=3D-unmeth-107s GAGTTTGTTAAGGTGTTGGGGATATTTGAGTAGATGAGAATTGGAGTGTTTTAGTGAATTTATATAGGAGTGTTTGTTTGTTGGGTAGGTGTTTTGTTTAAGTGGTATTTGAGGG
                      600                                                                                     700

GATGTATTATTTAAATAAGTAGGTGATTGGTGGAGGAATGTGGGATAAAGGGTAATTGTTTATGTTTTTAGTTTTTAATAGTTTGGGTTTTTATGGAAAGGGATGT
                                                                                   800

TTGGAGTTTTTAGATTGTTTTATTTGATAGGTTAATGGGTGATAGTAAATTGTGAGTGAATAGGTGAATAATTGTAGTGAATAGATTATAGTTTTTAGATAGTTTTAGATAGGTTATTGATTGTAAAGGA
                                                                      900

GAGTAGGAAATTGTGTTATTGTTTTTGTGTTTTATTTAATAAATGTTTTTGAGTTTTTAGTTGTTGTTGGAAATAGTAGTTATTGGAAAGATTAATAATATTTATTTT
                                              1000

TTAATGAGTTTTTAT

Bisulfite-converted, unmethyl-antisense strand-UMS-PCR1

Figure 11 ac063951 82200-83267 s-unmethyl

ATGAAGGTTATTATTAAAAAGTGGATATTATTGTTAATTTTTAATAATTTATTTTTAATAATAGGTTGAAGGGTTTAGAAATGTTGTTGAGTAAAAATATAAGGA

AATAGTAGTATAGATTTTTTGTTTTTTTTTATGATTGATATTTGTTGTTTAAGGATTGTGATTTTTGTTATAGATTGTTATTTGTATTAATTTATTGTTATTTATT

AATTTATTAAATAAGGTAGTTTAAAAAATTTAGGTGTTTTTTTTGTAAGGATTGTTGAATTGGAAAGTTAAAATTTAAGGTGTGATAATTGTTTTTTGTTT

TATATATTTTTATTGTTGTTTGTTTATTTAAATGGTGTGTTTTTTGGGTATTATTGTTGAATAAAATTTGTTTAGAGTGTTTTTTGTAGAGATTTGTTGGAAGTAGTT

GGAGGTTTAGTTTTATTGTTTAGGTGTTTTGGTGTTTTTATTTGGTGAATTTGGTTATTTAGTTTTTATGTGGTGAGTATTTAGGGAGTGGGTTGATTTTTTGAGG

TTTTATATTTGGGTTTGAGGGGTGTGTTAGTGGTGGGTGTAGTGGTGGGTGTGTTTTGGGGTTTGTGTTGTTTGGGGTTGATATTTGAGGATGT

TTTTAGTTTTTGTGGGATGTTATGTTATTGTTAGGGATTTGGGATAAGAAGTGTGTTGTGTGGGATTATGTGGTGTTTGTGTTATTTGTGTAGGGTTT

AGGGATTGTGTAGGTTATGGGGTATTGGTATTTTTGTGTGGTGTGGGATTATGTGGTGTTTGTGGGTATGTTGGTTATTTTTGGTTATTGGTTATTGGTATTTA

TTATGTTTTGTGGGGGTGGTTAGTAGATTTTTAAGGATTTTTTGATGGGTGGTGTAGAATGATTGTTGTGATGTTGTGTTTTTATTGTTAGTTTTATGTT

AGTTGTTATTGTTTGGGTATTTTTTGAGGTTTATTGTTTGGGGTTATTTTAGTATTTTTGTTTTATTATTTTTTGTGGTGGTTATTAG

Bisulfite converted sequence of unmethylated sense strand

Figure 12 ac063951 82200-83267 s-methyl

ATGAAGGTTTATTAAAAAGTGGATATTATTATTGTTAATTTTTAATAATTATTTTTAATAGGTTGAAGGGGTTTAGAAACGTTTGTTGAGTAAAAATATAAGGA
         20              40              60              80             100

AATAGTAGTTATAGATTTTTTGTTTTTTTTTTACGATCGATGATTTGTTTATTGTTTCGTTATAGATTGTTATTTGTATTAATTTATTGTTATTATT
        120             140             160             180             200

AATTTATTAAATAAGGTAGTTTAAAAATTTTAGGGGTTTTTTTCGTAAGGATTCGGATTGTTGAATTGAAAGTTAAAATTTAAGGCGTGATAATTGTTTTTGTTT
        220             240             260             280             320

TATATTTTTTATCGGTCGTTGTTTATTTAAATGGTGCGTTTTTTCGGGTATTATTGAATAAAATTTGTTTAGAGGCGTTTTTTGTGTAGATTCGTTGGAAGTAGTT
        340             360             380             400             420

GGAGGTTTTAGTTTTTTATTTGTTTAGGTGTTTTCGGCGTTTGGCGAATTCGGTTTATTTTAGTTTTTACGTGGTGAGTATTTAGGTAGCGGGTCGATTTTTCGAGG
        440             460             480             500             540

TTTTATATTTGGGTTTGAGGGGCGGCGGTTACGTTCGGCGTTAGGGATTCGGATTCGGATTGTAGGGGCGGATTGTTAGTTTTATTTCGTTTCGGGTGCGTTCGGAGAGTCGATATTTGGAGGACGT
        560             580             600             620             640

TTTTAGTTTTCGCGGGACGTTACGTTTGGCGCGTTAGGGATTCGGGATAAGAAGTGCGCGTCGGGTTTCGGTTGCGCGTCGCGGGGTTATTAGTTTGCGCGTAGGGTTT
        660             680             700             720             740

AGGCGATCGTGCGGTTATGGATACGTTACGGGGTATCGGGTATTTCGTGGTGTGGGATTACGTGGTGTTCGCGGGTATGTTGGTTATTTCGGTCGTTATCGGTATTTA
        760             780             800             820             850

TTACGTTTTCGTTGGGGCGGTTAGTAGATTTTTAAGGATTTTTTGATGGGCGGTCGTAGAATGATCGTAGTGTTCGTGGCGTTGTTTTTATCGTTAGTTTTATGTT
        860             880             900             920             960

AGTCGTTATTGTTTTGGGTATTTTTTCGAGGTTTATCGTTTTGGGGTTATTTTAGTATTTTGTTTTATTATTTTTTGTGGTGGTTATTAG
        980            1000            1020            1040            1060

Bisulfite converted sequence of methylated sense strand

Figure 13

Testing MS-PCR1 Methylation Assay in Colon Cancer Cell Lines

| Cell lines | MS-PCR1 |
|---|---|
| True positive* | 16 |
| False positive* | 0 |
| False negative | 7 |
| True negative* | 8 |

Sensitivity 70%
Specificity 100%

Note: * True positive: DNA is methylated and no transcription.
False positive: DNA is methylated, but has transcription.
False negative: DNA is not methylated, but no transcription.
True negative: DNA is not methylated and has transcription.

Figure 14

Testing MS-PCR1 Methylation Assay in Normal and Colon Cancer Tissue

| Tumor/Normal status | |
|---|---|
| Tumor-methylated<br>Normal-unmethylated | 34 |
| Tumor-methylated<br>Normal-methylated | 3 |
| Tumor-unmethylated<br>Normal-methylated | 0 |
| Tumor-unmethylated<br>Normal-unmethylated | 26 |

% of tumors detected    59%

Figure 15

Testing MS-PCR1 Methylation Assay in Normal Colon Tissues in Non-Cancer Patients

| Normal status | |
|---|---|
| Normal-unmethylated | 12 |
| Normal-methylated | 0 |

Figure 16

MDTPRGIGTFVVWDYVVFAGMLVISAAIGIYYAFAGGGQQTSKDFLMGGRRMTAV
PVALSLTASFMSAVTVLGTPSEVYRFGAIFSIFAFTYFFVVVISAEVFLPVFYKL
GITSTYEYLELRFNKCVRLCGTVLFIVQTILYTGIVIYAPALALNQVTGFDLWGA
VVATGVVCTFYCTLGGLKAVIWTDVFQVGIMVAGFASVIIQAVVMQGGISTILND
AYDGGRLNFWNFNPNPLQRHTFWTIIIGGTFTWTSIYGVNQSQVQRYISCKSRFQ
AKLSLYINLVGLWAILTCSVFCGLALYSRYHDCDPWTAKKVSAPDQLMPYLVLDI
LQDYPGLPGLFVACAYSGTLSTVSSSINALAAVTVEDLIKPYFRSLSERSLSWIS
QGMSVVYGALCIGMAALASLMGALLQAALSVFGMVGGPLMGLFALGILVPFANSI
GALVGLMAGFAISLWVGIGAQIYPPLPERTLPLHLDIQGCNSTYNETNLMTTTEM
PFTTSVFQIYNVQRTPLMDNWYSLSYLYFSTVGTLVTLLVGILVSLSTGGRKQNL
DPRYILTKEDFLSNFDIFKKKHVLSYKSHPVEDGGXDNPAFNHIELNSDQSGKS
NGTRL

SEQUENCE LISTING

<160> NUMBER OF SEQ ID NOS: 61

<210> SEQ ID NO 1
<211> LENGTH: 610

-continued

```
<212> TYPE: PRT
<213> ORGANISM: Homo sapiens

<400> SEQUENCE: 1

Met Asp Thr Pro Arg Gly Ile Gly Thr Phe Val Val Trp Asp Tyr Val
1               5                   10                  15

Val Phe Ala Gly Met Leu Val Ile Ser Ala Ala Ile Gly Ile Tyr Tyr
            20                  25                  30

Ala Phe Ala Gly Gly Gln Gln Thr Ser Lys Asp Phe Leu Met Gly
        35                  40                  45

Gly Arg Arg Met Thr Ala Val Pro Val Ala Leu Ser Leu Thr Ala Ser
50                  55                  60

Phe Met Ser Ala Val Thr Val Leu Gly Thr Pro Ser Glu Val Tyr Arg
65                  70                  75                  80

Phe Gly Ala Ile Phe Ser Ile Phe Ala Phe Thr Tyr Phe Phe Val Val
                85                  90                  95

Val Ile Ser Ala Glu Val Phe Leu Pro Val Phe Tyr Lys Leu Gly Ile
            100                 105                 110

Thr Ser Thr Tyr Glu Tyr Leu Glu Leu Arg Phe Asn Lys Cys Val Arg
        115                 120                 125

Leu Cys Gly Thr Val Leu Phe Ile Val Gln Thr Ile Leu Tyr Thr Gly
130                 135                 140

Ile Val Ile Tyr Ala Pro Ala Leu Ala Leu Asn Gln Val Thr Gly Phe
145                 150                 155                 160

Asp Leu Trp Gly Ala Val Val Ala Thr Gly Val Val Cys Thr Phe Tyr
                165                 170                 175

Cys Thr Leu Gly Gly Leu Lys Ala Val Ile Trp Thr Asp Val Phe Gln
            180                 185                 190

Ile Gly Ile Met Val Ala Gly Phe Ala Ser Val Ile Gln Ala Val
        195                 200                 205

Val Met Gln Gly Gly Ile Ser Thr Ile Leu Asn Asp Ala Tyr Asp Gly
210                 215                 220

Gly Arg Leu Asn Phe Trp Asn Phe Asn Pro Asn Pro Leu Gln Arg His
225                 230                 235                 240

Thr Phe Trp Thr Ile Ile Gly Gly Thr Phe Thr Trp Thr Ser Ile
                245                 250                 255

Tyr Gly Val Asn Gln Ser Gln Val Gln Arg Tyr Ile Ser Cys Lys Ser
            260                 265                 270

Arg Phe Gln Ala Lys Leu Ser Leu Tyr Ile Asn Leu Val Gly Leu Trp
        275                 280                 285

Ala Ile Leu Thr Cys Ser Val Phe Cys Gly Leu Ala Leu Tyr Ser Arg
290                 295                 300

Tyr His Asp Cys Asp Pro Trp Thr Ala Lys Lys Val Ser Ala Pro Asp
305                 310                 315                 320

Gln Leu Met Pro Tyr Leu Val Leu Asp Ile Leu Gln Asp Tyr Pro Gly
                325                 330                 335

Leu Pro Gly Leu Phe Val Ala Cys Ala Tyr Ser Gly Thr Leu Ser Thr
            340                 345                 350

Val Ser Ser Ser Ile Asn Ala Leu Ala Ala Val Thr Val Glu Asp Leu
        355                 360                 365

Ile Lys Pro Tyr Phe Arg Ser Leu Ser Glu Arg Ser Leu Ser Trp Ile
370                 375                 380

Ser Gln Gly Met Ser Val Val Tyr Gly Ala Leu Cys Ile Gly Met Ala
385                 390                 395                 400
```

```
Ala Leu Ala Ser Leu Met Gly Ala Leu Leu Gln Ala Ala Leu Ser Val
                405                 410                 415
Phe Gly Met Val Gly Gly Pro Leu Met Gly Leu Phe Ala Leu Gly Ile
            420                 425                 430
Leu Val Pro Phe Ala Asn Ser Ile Gly Ala Leu Val Gly Leu Met Ala
        435                 440                 445
Gly Phe Ala Ile Ser Leu Trp Val Gly Ile Gly Ala Gln Ile Tyr Pro
    450                 455                 460
Pro Leu Pro Glu Arg Thr Leu Pro Leu His Leu Asp Ile Gln Gly Cys
465                 470                 475                 480
Asn Ser Thr Tyr Asn Glu Thr Asn Leu Ile Thr Thr Glu Met Pro
                485                 490                 495
Phe Thr Thr Ser Val Phe Gln Ile Tyr Asn Val Gln Arg Thr Pro Leu
                500                 505                 510
Met Asp Asn Trp Tyr Ser Leu Ser Tyr Leu Tyr Phe Ser Thr Val Gly
            515                 520                 525
Thr Leu Val Thr Leu Leu Val Gly Ile Leu Val Ser Leu Ser Thr Gly
        530                 535                 540
Gly Arg Lys Gln Asn Leu Asp Pro Arg Tyr Ile Leu Thr Lys Glu Asp
545                 550                 555                 560
Phe Leu Ser Asn Phe Asp Ile Phe Lys Lys Lys His Val Leu Ser
                565                 570                 575
Tyr Lys Ser His Pro Val Glu Asp Gly Gly Thr Asp Asn Pro Ala Phe
            580                 585                 590
Asn His Ile Glu Leu Asn Ser Asp Gln Ser Gly Lys Ser Asn Gly Thr
        595                 600                 605
Arg Leu
    610

<210> SEQ ID NO 2
<211> LENGTH: 181259
<212> TYPE: DNA
<213> ORGANISM: Homo sapiens

<400> SEQUENCE: 2
gaattctttc agggtcctcc actaatgcag gataaaaccc aacctaactt ttcaaagcca     60
agccagagct ttgctgatat catgtcatat catgtgtcca tgcgctcaga ctgcaaacat    120
ttatgaacac acgtcttttc tgttccctct cttagtattt ttaaccccgc ttctgactgg    180
cagactgctt ttcaaccttc aaggactatc ccaaatacaa gtcctttgaa aagctttctc    240
tgttcctcaa ccccaggcag aattaatagt tataattcaa tatatctcca acagacaaat    300
tcgctagact ataactactc ggttccaggc tccatttctc caacaactat caaaacctgc    360
aggcatcact gtttaccctg gaatagccag ctcatcccca gcacacagta agctctactg    420
cttactgcaa tatgtgctta catatattgc agaatatgta tagatttagc ttttgccaca    480 ctttatttg cttatttgct atataaatta agcttttatc acactttatt ttgtttattt    540
acattactgc atgcaattcc catttcctta acaagattat aaattccttg agggcagagc    600
ctttgtcaca cttcacttgt attcctcaga aggttactca atgctaaaca tattattaac    660
tgctcaatta atatttgttg aagtaaatta cttttttctat ggtttctttg atgagggtct    720
ccggcaagga acattttca cccaggatca aagcagaaat tacatccaag agggtctccc    780
agcaagatgt ggagagactg gctacttgca gtgtttgaga taacacctgc aaaagaaaa    840
```

```
aacaatgcat actcagcaat cagcttttaa aaaccagact ctcgagcata ttaagttggg      900
aactcacctt acagacatca gcaggcgtgg gtatctttgt cccacttcca tgttttacaa      960
gtataaggta tgtttccaac aaccttttaa tctgttcaga actttcacaa cagttagttt     1020
ttgttacttt tgtgtgtaga tccaagagcg attcctgcaa acaaagaatt taacagagag     1080
aatataaagt atcaaactca actgttaatc caacaataaa aactgtggga cagttcaact     1140
tttcccattc tcttgctttg gaagaaaaag atacatttac caggactcac taacgataac     1200
agctaacatt ggctgagtgc attgttctaa gtcttttttt tttttttttt ttttgagat     1260
ggagtttcac tcttattgcc caggctggag tgcaatggcg caatctttgc tcaccgcaac     1320
ctctgcctcc caggttcaag cgattctcct gcctcaccct cccaagtagc tgggattgca     1380
ggcatgcgcc attttgtatt tttagtagag acagcgtttc tccatgttgt tcaggctggt     1440
ctcgaactcc caacctcagg tgatccaccc acctcggcct cccaaagtgc tgggattaca     1500
ggtgtgagcc actgtgcccg gcccattcta agttttttac aagtattcac tcatcatcct     1560
cacagcaacc ctgagggaga gaatattact accccccattt attatctgaa gagactgggg    1620
aatcgagatt tcaaataatt ttcccaggtt acactagcag taagtggaag ggtcaagatt     1680
caaacaggca gtctggctcc agagccttct actgcatctc aagataacat atcaaataaa     1740
aaatagcaca ggggggcaga gggaaggaaa attttaatat gtgtacagaa gtataaataa     1800
aacaattata aaatataact tctaggagtg atttgcaaaa ctgagagcag aaacagtaaa     1860
ttcttagact ccttatcaaa aacccatcct taaagattag aactcacttg caaacattca     1920
aaaaatgtac caaaatgttc cttggagatg taggatacag tggatttgac catgttttg     1980
agtgtttctc caattaacat ccatggtagt tgagtttctg tttcagtgac tggtcctagc     2040
tttcgcaaaa ttagcttcac tgcctgtggg aatacaagtc attaacatta atatataaac     2100
tcttattttc aagtattgct ctgggagtca ccactctgat tacattagct accttaaaaa     2160
tcaggtctgg aatagtcaag gatatggcaa ctttgatggt taataacgtg tcccaaaagg     2220
aacttctaaa ctaggatggg aattttatca ttacaactgt tccctcccca cctgcccttg     2280
cccattaatc aatttatctt accccctagc atccaaaata aagaagacat caatggctct     2340
gtaagtaaca tctcactgtc caaggcctac attgggtaag cattgttact gaacacccaa     2400
cactcctcat ctagtgctat gtactctagg ctgtcttccc tccacatcat ttgcctcatt     2460
cttttctact ttctgtttca tccatccaca tagactctaa gcaccctcc ccattatgta     2520
cctggcctgt acaggagtga aacatatttc taactccttt gcacatttca aagagcaact    2580
gtccaacacc ttcaactttt tctggatgtt tatcaagatc aagaaacatt aaattgaaaa    2640
gtgcgttttt atcagagacc taaaatataa agtagaaatg gaaaattata ttcacaaaca    2700
taaacatatc caaatgaaga actctcattt gctattctat atattgttat ttaaatatac    2760
ttaggaaaaa attgtgaaaa gaacagacat ttgtaatgat ttcaaactac tctaatagtg    2820
tgttctcact tggaatgtca cacaaaagag tgaattcatt ggtattacag gaagatatgt    2880
actacaaaaa aaactacaga agtcaacatt ctatctttta aagtaaatac atttgtattt    2940
tgtattgtat acagtaaaat atttgtattt tatgaaataa aaaatttaat attaatgttt    3000
ttgttttatt acaaaaaccc tctaaaattt actatgaata ttttatacaa acacaaatga    3060
caccatgcta ccagttactt ccaggaaact attagaaaag ttcttgttaa tgtcacagtt    3120
catgtattta ctgacttgaa ttagagagca ttttgatat atacacactg aaagctatca    3180
caaacctaaa taacaataca atagtgaccc aaattagatc acatcaattt gtgagcaaca    3240
```

```
aataagtctt actgtgagat aaattcaaaa tagtaacaga tttctgttaa gtatatatat    3300
agatacatag aaaaaattag cccataataa ccacatttt aaaagatatc tacttctatt    3360
catcagatta ttattattat tattattact agtgtgtgtg tgtatgtgtg tgtgtgtgtg    3420
atatggagtc ttgctctgtc gcctaggctg gagtgcagtg gtgtgatctc agctcactgc    3480
aacttccacc tcctgggctc aagcaattct catgtctcag cctcccaagt agctgaggat    3540
acaggtgcgc gccaccacgc ccagctaatt tttgcatttt tagtagagac ggggttttgc    3600
catgttggtc aggctggtct ccaattcctg acctcaggtg atccacctgc ctcggcctcc    3660
caaggtgttg ggattacagg catgagccac cacgcctggc ctattcatca gattcttgat    3720
gattagcaac aaacagataa aataccagac taacctttct catcaaaaaa gtaaaacttt    3780
cagcagcaaa atttcttata tgtagttttt tatgagccag gagtgtgctg tacatgctat    3840
acatgaaaaa aataagatac atttcattaa tcatataatt gtaataaata catactacat    3900
gtcaacaata tgggcaacaa tgtgctgggt atgcaaggaa tacacagcag gtatcaaaca    3960
aatttaaaat ctcattcatt tatggagaca cccacatgtt gaaaggaaga cttgaccaca    4020
gacatgaaga gtcctaggac tggtggtact ggttttacaa acaagactcc aggaaaagtt    4080
gaaatttgta atgagctctg aatgaaagaa gaattaggtg gggactgcag tccatattat    4140
tggtataaaa gcaagagcaa agatgaggca ggtggaaatg atcatggtca tgacaaggag    4200
gctggtccat ctaaaagagg aaagatgata cagtagagga gagcagctat ggataaagtt    4260
ggtcaggtag acaggtctag cttacatctg tataagcact tactctgtgt tacgccattt    4320
aatcagcaca ataactctat gggatgggta ctattataat cctcccattc tacagataat    4380
gaaagtgagg cagaaagcat aagcaacttg ctcaaggtca agcagccatg catctataac    4440
taaataatta cttatatata atcacattgt taaatttggt ctccctaatg atagaagggt    4500
atggaatata tctctccaat tttctcataa ccccagtacc taatagttcc ttgctgacag    4560
caggtactaa taaatgttgg ctgaatgaga aatgaccatt ttcagaaaga ctaatttggc    4620
agcaatatac aggataaaat aaaggaggaa agaagagtct gctaattcag tcagaaaggt    4680
gctcaagtca tacaagcttg ggctaacagg catgaaagag actggaagga gaggcaaaat    4740
ggcaagggat gaacccagta gacatttcag gagtgcccac aatgaagctg aagaccttac    4800
agcggtccac agggccctgg atgatctggc gccttactac tgcttctctg acatcactta    4860
gctagtctca cccttataca ggctgctcgg ccacctaaaa cttctcccgg gcatgtgccc    4920
aagacattct cccccctgcta aaatgtaaac tttgtgagaa gagcattttt tatctgtttt    4980
atctgtgact gtatctcaag tgcctgacat acagacagtg tccaataaat attgactgag    5040
caaatgcatg aatgacagaa tcaagaggat gtggacacct ctgaagacaa ctgggttagt    5100
gatgcctctg atattccaaa actcagagac aggaagaacg ttagtattaa tgacagaaaa    5160
tgggcaacca acagggcct ggcatacggc agacactcaa tacctattta ctgaacactt    5220
gaatgaatgt acagataaga ggagttgatt taacaggaaa gtgttgagtt cagtttcagt    5280
aatacaagtg aaaatagcca ggctactgaa gttgtcacac cgaaagcaaa taaatttaga    5340
actgaagagc ctgacttagg agacataaaa gtggcagctt ttatgacagc tgaagtcata    5400
aaactaaatc aattattccc caaagacctt gttggttgtt taatgaaata atattggttt    5460
ctaacatatt tgaccaaaag cttcataggg aactagtaaa ggctggaaaa agatttcttt    5520 ctcttctte attcaaagtt cctaaaagag aacggtgggc tgagtgaaac gggtggcata    5580
```

```
aaacaaagtc tattgtccca taccatgcat acaccattta ctgtggggta agggctgat    5640 gactgatatt aaacactcct gtggcaatta tagaacatga aaacaaccgg aagaccaagt    5700
ggaaaatccc accaaacccc agacttaaac agataataag acaatttatg cttactttaa    5760 acaaaggtt actacaaaat tcattctctt tccttgtcca catttactca caaatactga    5820
gtgtctcttt caccttagta agtattagtg gctggggaaa tgtcagtgtt taaaacaggg    5880
ctcttaacct gtcttaaacc tcccttatac caggtgtaga gaggacagca atacattata    5940
accaaacaat tctggtaaaa gttgtgtgac ataggtggtt aaaaaatgcc aagaggatag    6000
agagtacaaa attttattaa tacttctggc aaagtgcct gtttgtggag ctgtaggga     6060 ccgagtcagg ccttcttggg tgggtatact tccagtagct ggagaggaga gatggtcatg    6120
gcaactcaga ctggcagact agattgtgga ccactttggc tggagaatca actttgtaca    6180
tggaaacaat taggcactga gctggcaaag tggtttggag tcataaagaa gccagggaaa    6240
aagaagcagg caattaaaaa acatactaga gagagaaagg ggttacctgt atatactgga    6300
catgtccttc accatcagtc tccacaggta cttataaaga tatgataacg aggtgaaagc    6360
ccattctaac aactctgtgt cctgagtctc caggatcgag gtgatagtca aaaaaaactc    6420
tggaaagtgt gggtagaaat ccatctgcag atctcgtgcc aactgtacaa ccaaactgga    6480
ttaaaaaaag aagcaactga tcatgtggat ttttttaaaa ggctacaaat ctacttaacg    6540
atagtaggtg gcctatgatc ataggattaa ttaaataaaa atacttctaa atcaagtctg    6600
aaaaattata aaattcttta aatcttaaga tctcagcaaa gaaatcaggc aagaagttac    6660
attccatcat aagttgtagc caactgttcc tatagtgtca agaaaaatg agattatctt     6720 agtatataac aaatgcgaaa ttataccccca agattccact ttatggtaat gcacttattc    6780
ctaacagaaa aggaaaatcc tccttgtttc taaattatga gcacctgatc tgcggtatat    6840
gtagctttga aacacaatct ttcttaaaat tcaggcaaat atagttgtga gctttctctc    6900
aagatgctac ttactccaaa aggggttgat aggcaaaact gttcttaact tgcaggtgag    6960
tcttcaaact ctgaactatc tcgttttggt gatacaccaa ctgattgaat gattggcatt    7020
tgtcaataac ttcttttgtaa aattttcctg agtgggggaa aaaaaaatat gttcttttct    7080
atcacaccac tattcagctg tatggaacat ataaagtgca aactatgggt gaataaaata    7140
gaaacgaaat agaaaatacc gaagtgttct gtgaggttta attctctcca tttcagcaga    7200
ccctcaaaaa agtaggtttc aacctcctgt caagattaaa gcagtccatt aatcaaataa    7260
ctctaagaaa gcaatgatca aggtaaatag aataatgata tattaatatc ttaagacaat    7320
gatactgaag agtttaagaa ctccttttag ttttttaaaa caggccatta agtaacacac    7380
taaaaagcaa tcagaagtta tcaataggcc acttataaaa tgctgttttg ttgatttggt    7440
ttcagcaaat aattttctgg ggcctatata tattgtccac taagggaaaa ttattttctg    7500 tgtttttta taatttaggt caagaataa ggtgttggtt ctttacagtt ccttcattct     7560
gcttttagaa atatgaatta ctacaacctt ataagaagt aatatggcat tcctgttaaa     7620
attcaaaata gttacgctct ttgacccagg tagttcttat aaagtttgca agcctttaag    7680
taaaagatgt ttattcagct taactacagt gtggggaaac attaaacagg ctaaatatc     7740 cgacaatagg aaaatggttg gaatagccca tggtctatat atactaaggt atattatgtg    7800
gctactaaaa agagctatat ctctattgaa ctagaactac actgaagata tgcccccaaa    7860
atgataaaag ttatgcagtg agagggtatg gcaggattca attttcctta aaaacaaaa    7920 ataaaaaacc ctctataaat gtttgtacat acgaacatga gaggacagta tggaagaata    7980
```

```
caactatact gaactgtcag tgttggcttc cttgggaatt aggggtggga ggagtgagat    8040
aatgggcttt tcgtaagttt accactatgt tacttaactt gttaacatgg tatcaattac    8100
tttgtacttt gaaaggtaaa gccaataaat tatcatacat gtatgacatg tatgtataca    8160
tgtacgtatg tgtgtatata gatgtataaa taaatgcata ccccccaaa acaatcattc     8220 taccaaaaag atacatgcct tcgtatgttt atctctacac tatccacaat agcaaagaca    8280
ttgaattgtc ccaggtgtcc atcaacagta gattggataa agaaaatata gtacatatac    8340
accatggaat attatatgcc ttaaaaaaga atgaaatcgt gtcctttgca gcaacatgga    8400
tacagctgga gtccataata ctaagcaaat taacatagga acagaaaacc aaaaactgca    8460
tgttctgact tataagtggg agctaaatat tgagtacaca tagacataaa tataagaaca    8520
atgaacactg tggattacta gagggtggag gaagtgggga tgggttaaaa aaaactacct    8580
gtggggtact atgctcacta cctgggtgac aggatcccata ctccaaacct cagcatcaca    8640
caatattccc atgtaacaaa cctgcacagg tacccctgt atctaaaatc aaagttgaaa     8700
taaaaataaa aataaataca aatatgtgtt tatagagaga gagaaaaaag agagaataaa    8760
cacataagca cacatgcaaa cagcatgcca aatctacaat atcaaaaaaa aaaatcctta    8820
aactgttctt tggaaatctt taaaatcaat agttaggcag aatagatact atgtaaccac    8880
aaatattaaa aactaaaaat taaaaaaaaa ggcagaaaag aaagagaatc ccattaaatt    8940
ttgttttagg ctggggacaa tggctcatgc ctgtaatccc aacagtggga ggctgaggca    9000
ggaagagcat ttgagcccag gagtttgaga ctagcctagg caacaacacg agatcctatc    9060 tctattttc aaaagtaaaa atattaaaat tttttgttg ttgttttcat gtcctttaag      9120
gcattttcat gtcctttaag gcagaaagaa aatatgcaac acagtttaaa acttaaatgc    9180
agaacgcatt tctagcctag cacagacctg gcgtatgtca gctatgtgtg agagaccatg    9240
tcacgtcctt ttgcaaggta actctggagc tcctttcacc aagagacgga gtctgttcc     9300 tcacccttg aatctggcct ggcctcctga cttgctttga ctaataacat gcgatgaaag     9360
tgactctcat gaccaaagca aaactttatg aggtcttgac agcttctgcc ttcactctat    9420
tgaaaagatt ctgccaccat gaaaagaagc ctagtctagc ttattgggga ataagaggcc    9480
atgaaaagaa ccaagatcaa caagccacag ccaactgcca gacacgtgac agaggccatt    9540
ctggaccatc cagtccagga ttctaatttc aggctgtctt ctctgccttc ttaacactgc    9600
ctcttgatac cttcaacctc tcctgtggct taaattatta atcatattct aaatgccaaa    9660
tctgtaattt cacctctgaa gtcacctata ctccagatcc atatatacaa acatcttttg    9720
gacactatca tttggatggc caaaggtatt tcaaattcaa gccccaaatg gaactaatta    9780
tcttatcttt acaaccttgt gctcctttac ctataaatat atcttgatga gtaacatcct    9840
caaccattca gccttaacct cattatcttc cttgctgcaa acccagtagg tcacaagtcc    9900
tatccattca ttctacttcc tcaacatctc tggaatcttt ctcttctctc tatcttgatt    9960
gctgctacca taatcatttc ttacttagat aacagtcaaa tcctcacaac tggacaactg    10020
agattggatc tccaagttaa aggcatgtta cacaggacct taaaaggcta gcagaggaat    10080
catgacatga tgaagaactg cagtcctgct ctttttctcca cactaaagcc agagagattg    10140
aaaatttaaa cctgatcatg tcattcattc ccctgcttac agtcctagaa ctctaagtcc    10200
ctacagcttc aggataaaac cccaacttag cttcacatat gaagtccttt atgatccttg    10260
cctatttctc cagctttatc tcaccagttg cccccttgcc ccatcccagt caccatgaat    10320
```

```
acaaaaaaaa aacaccctat acacacctat aaccacactg gactgctttg cagtttcttg   10380
aatgtgacat gcattctcta gcttctgttc ctttatatag gcttctccct cagcctggaa   10440
caggctttcc tgtcctcttt accatgctaa aacctatata aacaaaattc aggtgtcacc   10500
tcgtctagat caccgttttt ttgacacccc taaagaatgt aggttaggtt ccctttacta   10560
tgagttctca aagcacaatg tgctcaccta gacgacatca tttaacacat tgaatttaca   10620
cagtggagat aatgcattca aagacccagc gagtggagtc tgattatagt aaagaagaat   10680
attacgaact gagattggat cgccaaggta taggcatgtt acgtacgacc ttaaaatgct   10740
aggaggaata acgacatgat gcagaaaaag acttctgcat aaaaggatga caaggccggg   10800
cgtggtggct cacacctgta atcccagcac tttcggaggc caaggcgagc agatcacgag   10860
gtcaggagat tgagaccatc ctggccaaca tgtcaaaacc ccgtctctac taaaaatgca   10920
aaaattagct gggtgtggtg gcacgtacct gtaatcccag ctactcggga ggctgaggca   10980
ggagaatcgc ttaaacctgg gaggtggaga ttgcagtgag ccaagatcac gccactgcac   11040
tccaacctgg agacggagcg agactccatc tcaaaaaaat gaataaataa ataaaagtaa   11100
aataaaggga tgacagagtc agagtatggt taaaactgga aaatattatg tagtctagcc   11160
cctttatttt tataaaggag aaaattaagc cccgggaaaa gggcttcctc aaaatcactt   11220
taaagttata gcttcaggaa tatggatctg cagcagtgct tggaatgcat aagggaaagg   11280
gagaggctag aatcacaaag acagctgaaa gtcaagtcaa ttgtctaata gagcttcacc   11340
caacagaact ttctgcaaag atgaaaatgt tccaattcta tatttattca atatgttagc   11400
aactagccac atttgggcac ccaaattttt aatttacttt aaatccaatt tgtcatatgt   11460
ggctactgta tgaaacagca caggtctaaa gcatttcatg tccaaaaagg aataccttga   11520
aaaacaattc acttctacta acagaagaaa ctaaacacc atgaacactt gaagattgac    11580
tagtatcaca ttctcttacc tcctcatagc ttgcagttct atcaatccgg tgaataaat    11640 caatattaac attccccagt cgttcagcaa atgtaagaaa ctggaaggga aagtatattt   11700
aagatacata attaattaaa atttatcaga tctttaatat ctatttgaat gctgcatgta   11760
ggcatctcta atcacaaagg ataagtggaa aaataaactg aaaaacatac ggccgtaaac   11820
aaatttactg catcactgtt caaagataat gaatacttct atgtttgcat aatttctctc   11880
agctatgtca tttcaaataa aatttccatt gccagactgg tgagcctagg tggatgctgg   11940
caattagtct cgctagatct attaggtttc ataccctccc ataagcatgg ggacctagca   12000
aagtcgctgc aataaaagtg tttttaaaca tatacagacc tatgattgta tcctaaggaa   12060
gacctggaaa caatctatca aggggcaaac agagaaagcg ctgtatattt gcccttagct   12120
gggaatcact caccgccagc cgactcgccc aattcggtct ttaaagataa aagagcaggg   12180
gagaattggt cctaagcaat ctcctggaat agtgaattta attctggact acaggaaatt   12240
cccaggactg gccagacccc ataaaacatg ggtgaaactt gctgtccaca cttctttcct   12300
cctccaaccc atgtttacta catccagtgt ctccctcttt cgccggagcc tccaggaaag   12360
tgacacactc ggcccagaag tctgaggccc ctggagtctc gctcagagcc tgtctcacga   12420
ctgaggcagc ggagacccgc ggctccctgc ctaagctccc gcgctcaccc ggtaggtgtt   12480
ctcggtcttg tgggaaacgg gctttgtctt catggctgca gagggccagt ggcccgcgac   12540
ggcctcggga gtgtcgaagg gatgcaaccg acagtaagga ggggaaagcg gctcacaggc   12600
tatactctcc gattcccaga tgcccagact ttctcacgtg cggcttgagc ccctgggcgc   12660
cgccatgttg gagacaagga ggagcctgag tgggtcacgt ggacggaaaa aagaacggcg   12720
```

```
caggcgcacc ctttggtggg gtggggccta caggaggcgg ggctgcgcac ataagggcgg    12780
gcgtttgggt gaggtgttct tttcactccc ttcggtaaag gtttagaaga caaatgtatt    12840
ttcattataa aataaaacat acctgtaatc gttatcaact aacattactg tccctcacta    12900
cgtacctgca tcgtgcaaag atcctttcat ccataatttc acagtaaagc ttattaggga    12960
tgttaataca aaggaggtac tgcgtctatc tatatatcta tatatagata tatacttttt    13020
tttttttttt tttgagacgg agtctcactc tgtctcccag gctggagggc agtggcgcga    13080
tctcggctca ctacaatctc cgcctcccgg gttcaagcag ttctcctgcc tcagcgtcca    13140
aagtagctgg gactacaggc acccgccgcc acgcccggct aattcttttg tattttagta    13200
gagacggggt ttcaccttgt tgcccaggct ggtcgcgaac tcctgagctc aggcaatccg    13260
cccgcctcgg ttttccaaag tgctgggatt acaggtgtga gccaccgcgc ctggccggta    13320
ctgtgtatat tttaagcca atttgacaca agaggaaacc aaggttgtgc agctggtaac    13380
tggcagtctt cactcagact ctaaattttg gtattcttaa ccactacgct gtaaataaaa    13440
ttgaaaaata gagaaggagt tttaagaaaa atcttttaat ttcatgcaca accgctgtta    13500
atgtttggtg tttttcccat cactttaatg tctacacata gcatgttgtt aaattgtaca    13560
gttatatata catatatgta caatttttaaa aaataattta aaaatataat tatttaccccc    13620 attttacatt cattcattca ttcagcaact atttcttgag agtcctctgt ggaccaggta    13680
ctgttctggg agccaaacga gaaaggcaat aatagtatta attaattatt tgaaaatatt    13740
cacagccttc aattcctggg ctaaagtgag cctcccacct cagcctccca agtagctagg    13800
gctacaggca tgcaccacca cacccagctc ttttattatt attattatta ttattattat    13860
tattattatt atttgtagag atgggatctt gctatattgc ccaggctggt atcaaacttc    13920
tggactcaag cagtcctctt ggcttggcct cccaaagtgc tgggattaca ggggtgagcc    13980
accatgccca gactggaaat acttggtctg agatgcttac attttagtca aggagtgatg    14040
ttaagtagac aattggatat attgttgtac agagctcact gtagcagtct gggctgcaga    14100
cgtgacttaa atacacctaa atacctcaag tgtgaggcat ttgcgactgg gaaagagagc    14160
cagtaaggta gaaacagact agttatggca tggaagcaga gctggtggcc aactatactg    14220
caaattcgag gatagagaag tggttgctgg atctgacaag gtgaaggtca ctggtgacct    14280
tgctaagtac agtctagttg gaagaaagga agtgaaatat gcatggattg aggaggtaat    14340
cagagttgag aaagtgaaca taacactttc aaattgttat tggcattatc acatcaacat    14400
tttctgtgtc accacagggt tgttctaaat attttaatgc ctccatagca tttatagatt    14460
tttttataat aaaatattga cgtgcctaat gttccattgg ctttcagtag gctaataatt    14520 ggtcttttt ttttaaaagc cttttatggg tcacagggaa atctaagaaa gctgtagaac    14580
ttctcccaga aagatgcaaa gaagctcatc cacactaaaa tgtgcacgtt tcagagagtt    14640
agaagcctgc agttaactga gggtagaagc ccccactcaa agcaatattt tcccaacctg    14700
ttgccaaaat cacccccaca tcattgtgcc attttccttc tctgcaattt attttttggta    14760 atggagttaa ctgacaata aggagtgaag agaaaaatca aagaaactga agaactgac    14820 acaagttata ttgaccattt attgtttgca ttgttcttca ttacatgacc ctcacacact    14880
gacttgactc tgactggctt aacaatatgt caatagaaca tggtggttga gagcatagat    14940
gctggaacca ggttgtctgg aggtaatcct ggttctgcca tttattagta gggtcagtta    15000 cccttttcaga atgacatttc cgtatatgta aatgaagcta acaaaagtag ctacctcacg    15060
```

```
ggtggtgatt atgcagagta aataagctaa tggataaaag atgcttagaa tgtgccagac      15120
accataattg cgcaagctca gaaattactt aacctttctg agacccaatt tcctcatcta      15180
taaaatagag atgacaataa taccagtctt tcaagatact gtgttggtgc atagagcatg      15240
aaataaatgt ttgctaagtg gataaataaa tgaccattta ttctctacta cctggctacc      15300
tgacaagttc cttaagggct gacaccttat actttttcaa ctttgtgtca tcagttccct      15360
tgaacataag agttgtttaa tgaatgtctg ttgaattaac aaagcttata atacttacat      15420
tgacccggac aaatttaaga gtaatatagt tccagcattg gatgtgaatt gcaccacatg      15480 attttttggta tctctcaaaa ctaagtttct aagctttaat ggaataccga agcatccgt      15540 gaagagcacg agtgtttctt ataaacattt ccttgcttcc agcgtttgtc ctctgtcaag      15600
gtataggatg aaatatcctat accatccttt atatcctttt tccattaggg ctctgcctgt      15660
cctaactact ccagccagta aataacatac attatttttt cattcttttta ttcttaagct      15720 ttataggcg ctcctggaag ttttgctttt taatttttgt ttccttattg cttagcgtgc      15780
tgcaatttca agccaagaaa ctttaagagc atgtaagagc taggcccagt ggctcatgcc      15840
tgtaatccca gagctttggg aggtcaaggt gagaggatt cttgaaccca gaaatttgag      15900
accagtcttg ggcaacaagg cgaaatccca tctctacaaa aaatacaaaa attagccaga      15960
catggggatg tgcacctgta gtcccagcta ctcaggaggc tgaggtggga ggaacacttg      16020
atccaggagg tcaaggctcc agtgctgtga tcctgcgact gcactccagc ttgggtaaca      16080
gagtgagacc ctgtcttgaa agaaaaaaaa ggaaggaagg agagggagaa agaagggaaa      16140
gtaaaggaaa ggaagggagg ggagaggagg gaaaggaagg gaagaaagca catgaggagt      16200
ttacccagcc tagacaagaa agtggaatcc agagaaggct tcttgggga agtgacatct      16260 aagctgagac ctggaaaatg aataggaatt agccaggcaa ggaatggaca tgaatggtgt      16320
tatctaggta gagggaggag tataggcatt tgtctcaaaa tggttgagac aaatttggtt      16380
acttttagtt tccaaggcaa agccacaccc tgtcaaatta gcattggcca tgggtatcat      16440
ctttagcatc cttggactaa taataggaaa gaatagggac aagatgaagc tcagaggtaa      16500
gaagagcctt ggttttctca tctgtaaagt gagatagaca tatgagaaag tcaacagtca      16560
tatgagacag ttgaaagatt aacacattgt atcacttctc acagtcatat gagaccgttg      16620
aaagattaat taatacattg tatcgcttct cagccttttg gctaagatca agtctagtaa      16680
ttaacacatt gtatgtggtg atctggaagg gggcaagtcg acctagtggc atggtcttgt      16740
ttagaaagca gttcaaggag tgctgtgtat cagggcagag aggatttgac tcagaacaag      16800
ggaccaagga agtgaatgta aaaaaaagaa agagaagaga agttttagt aattctttgt      16860 tggttttttc ttaaatagag acaggggtct cactacattg cccaggctgg tcttgaactc      16920
ctgggctcaa gcgatcctcc tgcccagccg agtagttctt gactgtggta gtaaggaaag      16980
ctgatccacg tatctcttct tgagaaaact gtgtattgtt gacagtgtgt gtaaatcagg      17040
aagcagtgag agcatggagt ttggatttgg acaactggg tcccagttct agcatttttc      17100
atgtattagc cagtaactgg gcaactgact taacctttca gcctcagttt cctcatcttt      17160
aaaacaggca taataactag ttctgccttt tcccttaacg gttgctaaga agaccattcg      17220
atataaagca ggcaaagtcc cctgtaacca atacagagga gttacagaaa cactaagtat      17280
tgtttccctt tgcattgtgt gatcatgttc agccctgata ccacagagct tctattctcc      17340
tttccttatt ttgaagctca ggcattagaa acattagacc agaaattgcg gatttgtggg      17400
gcctataagc tcaggtagcc cacagataag ttttgtttac caaacatatt cttcttcttc      17460
```

```
tttttttttt taagagagtg tctcgctccg ttgtccaggc tggagtacag tggcacgatc   17520
gtcacttact gccaacctca agctccttgg ctcaagcgat cctcccaccc cagcctccct   17580
ggtagctaca gatactacag gtgtgcatca ccatgtccag ctaattttaa aaacatttt    17640 agaggtgagt cttgctgtgt tgcccaggct gatctcgaac tactgggctc aagtgatctt   17700
cctattccag cttcccaaag tgctggcatt acagacatga gctgccatgc ccagcatacc   17760
agatgatatt cttgaaattt attttattt tttataatca gatactctct cagcagaatc     17820
acaaatgttt taatttgtta aaatctgaa aattttaggt aaaactctag attttcaact    17880
tctcttgaaa agtaaaaaaa aagaaaactg caatactggg cccatatttt gagaagcaac   17940
aaccagctgg agttgagtag tagtggctct ttgatgccac cactttgtct ctgtgcacac   18000
cactccttcc ttttttgtcct accccaggcc catgtcatga cttaaggtgg atacctggcc  18060
cctgtggaaa gctcagtgtg tagcctctgc ctcagaatat tcctcaggca gaaggctgtt  18120
ctcgtctttg gttttaaaca tgcctcatag gcagcagatt attttctgt tgcttctgca    18180 gctgcttta ttgtttaatg cagtgagtga ctcaacttgt tgttgctgtt gttgtttctg    18240
ttgtttgaga cagactctca ctctgtcttc caggctggag tgcactggcg tgatctcggc   18300
tcactgcaac ctccacctct caggttcaag tgattctcct gcctcagcct cccacatagc   18360
tgggattaca ggcacccgcc accatacctg gctaattttt gtattttag tagagacgga    18420 atttcgccat gttgtccagg ctggtctcga actcctgacc tcaagtgatc cacctgcctc  18480
ggcctcccaa agtgctggga ttacaggcat gagccacccc gcccagttga gtgactcaac   18540
tttttataag ggagtcagtg cagttttttca gttggtattc aaatatttgt aacaccttcc  18600
ctatccctga acacacacac acacacacac acacacacac acacacacac cactgtggtc  18660
tgtattcatc ttgttttcct tcctcacttt cgctcaccat ttgcatttct gtcatggact   18720
ttaatttcct tattctttaa agtaagctat ctcagaggat aatctaaatt aacctgcttt   18780
tagaacaatt taaacatcca catacttta cctacccctg tttatgattt ttatcctttc    18840
ttttgatcat tagctaaact gttggcatca tgtttaggaa ggatgagtag tctcaccact   18900
gggttgtatc tcccctttat tttctcacct ttctcttggt ttggttttgg tttccattgt   18960
tacagtgtga ttgcttcttt gaacacaagg cgctacatca cagtacaaag gagcttggac   19020
tctgcaccca gccctcccag gctcacacac ttgggctgcc actgctctag gagcttccat   19080
ttactcatca atacggggga tactagtgcc cctcatgggg tggttatgag gaggcaatga   19140
cctcatacat tgcttctcaa gtgtggtccc tgaccagcag tatcagcacc tcatgagaac   19200
ttggttagca ctgtaaattc tcagaccctg ctccaaccct cctgaatcaa gaactctggg   19260
gatggggccc agcaaactgc tttcataagc cttccaggtg attctgaggc aggctctagt   19320
atgggaatca ctgacttaac atacactaca gcacctagaa cattgtccaa cacataccat   19380
gtgctacaga aagtgtttat tcttattact gtctagtctt tacataaatg tttgcatcat   19440
cattatttaa ttcttctatt catctctctg atatagtagt atgatactgt tagccttttt   19500
attttttatt tttatggata cataacaatt atatatattt atgggctaca tgtgatattt   19560
tgatacaagt atacaatgtg taatggtcaa attagggtaa ttgggatatt catcacctca   19620
agcttttatt atttttttgt tagaaacaat ccagctcccg tcttctagtt attttgagat   19680
gtgcaataaa ttattgttaa ctacagttgc tctattatgc taccaaacac tggatcttat   19740
tccttcaatc tcattgtatt tttgtatcca ataaccaccc cctttttatg cttcctccac   19800
```

```
tacccttccc agcttctggt agccatcatt ctacattcta tctccatgag atcaattttt   19860
ttagctccca catatgagtg agaacactca tattatttgt ttttctgtgc ctggcttact   19920
tcattttaca taacatcctc cagttccatc catgctgttg caaatgatag gatttcatat   19980
tttttatggc tgaataatat tccattgtgt atatttacta cattttcttt acccatgcat   20040
ccattaatga acacttagat tgagtctatg ttgattatta tgaatagtac tgcaataaat   20100
attggaatgc agatatctct ttgatatgct gatttccttt tcttttgata tatcccagc    20160 agtgagattg ctggatcata tcataggtct aatttttagtt ttttgaggac cctctatact   20220
gttctccata gccattgtac taatttacat ttccaccaac aacatatgag agttcccttt   20280
ctccacatta tcaccagcac ccattattgc ctgtcttttt tataaaagtc attttaactg   20340
gagtgagatg atacctcatt gtagttgttt gtggggcttt ttaaaatttt gttttgtttg   20400
tcagacttga gcatttccca ggctggagtg cagtggcatg atcataactc actgcagcct   20460
tgaactccta ggctcaggca tcctcctgcc tcagcatcca aagtagctgg gactacttgt   20520
agttttgatt tgcatttctc tgatgataag tgatgttgag cacctttta catgcctatt    20580 tgccatttgt atgtcttctt ttcagaaatg tctatccaaa tattttgccc attttttaaa   20640
tcacatttat ttttactatt gagcttcttc tatattctgg ttattaatcc cttgccagat   20700
gggctttgaa aatattttct ccccatggat tgtttcttca ctttgttggt tgtttccttt   20760
gctgtgcaga agctttttta gtttgatgta atctcatttg tccattttttg cccttggctg   20820 cctatgcttt tgaggtctta ctcaggaaat ctttgtccag actaatgtcc ttgagcattt   20880
cctcaatgtt ttcttctagt atttcatagt ttggggtctc agatttaagt atttaagtca   20940
ttttgatttg atttgatttt tgtatatgat gagagaaagg agtctagttt cattcttctg   21000
catgtggata tccagttttc ccagcatcat ttattgaaga cactgtcctt tccccaatgt   21060
atgtttttga tgcttttgtt aaaaaagaat tgactggctg ggcacagtgg ctcttgcctg   21120
taacccagca ctttgggagg ccgaggtggg aggatcattt gaggtcagga gtttgagacc   21180
agcctggcca acatagtgaa acccatctc tactaaaaat acaaaaaatt agccagatgt   21240
ggtggcacac gcttgtaatc ccagctattc agaggccga ggtgagagaa tcactggaat   21300
ccaggaggcg gaggttgcag tgagccaaaa tcatgccact gcactccagc ttgggcaaca   21360
aagtgagact catctcaaaa aaaaaaaaaa aaaggagggg ggagttgact gtaaacatgt   21420
ggatttattt ctaggttctc catcttgttc cattgtttta tgtgtctatt tttatgccag   21480
tatattatgt ttttggttac tatagttttg caatataatt cgaagtcagg taatgtgatg   21540
cctctagctt tgttctttat aagtagcctc attttaaatg agggatctga ggctcagaga   21600
actgctaaat ggtagaaaga gttgaagctg ggtcttctaa cttcatgttc agtgctctgt   21660
ttcatgtccc cacactatcc cacatcttaa gagtgtaaac taataggggc aaatttagat   21720
aaattggcca ggcatggtgg ctcacgcctg taatcccagc actttgggag gctgaggtgg   21780
gtggatcact tgaggtcaga gtttgagacc agcctggcca acatgatgaa accctgtctc   21840
tactaaaaat acaaaattag ccaggtgtgg tggctcatgc ctgtagtccc acttactcag   21900
gaggctgagt caggagaatt gctagaaccc aggaagcaga gattgctgtg agctgagacc   21960
atgccactgc actccagcct gggagacaga gcgagactcc gtctcaaaaa aaggaaaaaa   22020
agataaataa atgcttggct gttgtagata tttgtagatt tccttgtcct ctcttttcag   22080
cagcagtccc caaccttgtt ggcaccaggg gctggtttcg tggaagacaa ttttttccaca   22140 gactgggggc tgcgagtgag ggggtggttt caggatgaaa ctgttctgcc tcagatcatc   22200
```

```
aagcattagt tagattctca taagaagcac tgcaagctgg atccctgtat gcgcagttca   22260
caatggggtt ccactcctat gagaatctaa tgccgccgct gatctgacag gaggcgaagc   22320
tcagattgta atgctctttt gcctatctct cacctcctgt tgcgcagccc agttcctaac   22380
aggccatgaa ccggtaccgg tccgcggctc aggggttggg gaccccttt caggaaacag   22440 catcctgatt ttcctttgaa gaatcaatct gccttcactc ttagtgtctg aggttcgagc   22500
tagggtccag ggaaggtctg tgtcctaggc tgcatttctt tgacaacatc attggcttag   22560
agatgggcag gtaccccaag ctgggccaag cccctgagct gaacttttac tagagctaag   22620
ccataggtaa gaaggtgctt cttttctta gatttgccag gatgctagga gcctgaagtt   22680
tttggtggtc ctcgttgtca cttcatggag aggtcggcct gagaatgaag cctatgcaaa   22740
ggaaaacaga ggggacaggg agagagaaat tgataataag tattgattag cttattggat   22800
ccatccagtc cttggacttt cagtaacctt agttcactaa ttccctcttt tgtgtttaag   22860
ccaatttgag ttgggttctg tcatttgcaa ccaaaacaat atagaattta tgccgataat   22920
ttaagatttg tatgttgctc ataagattgg aaacctaagc cttcctccga acacaaatat   22980
gtgagtaaga ataaaaaaag tcaaatacaa agtcttgatg ataacagtca atgggatgga   23040 tttgaaagt gtctcagact aggagtcaga aaacctgggt gctgatccta ggaggttcac   23100
ttagccatgt gactttgtaa aatgtgtgaa actaacgctg taaaatatga aaaattaacc   23160
ctgcaacaaa aaagtaatgt acacatacat attttgaatg ttgcatgata taaagtcaag   23220
taagtaattt attagagttg ctcccagaac ttttctgta tatccaataa ttagttttca   23280
ataatagtga aggaaagacc taggagtgga catttctcag tctctcatac accatatgca   23340
ctgatctggg tgacagaata cctttaaaga tacacttaaa aatgcatctt aagagaataa   23400
gacaagccac agactgggaa aaatatctgc aaaacactta tctaataaag ttttgtattc   23460
aaaatatgca aacaccctta aaactccaca ataaaaaaca aatagcccaa ttaaaaaatg   23520
aatgagagat ctgaacagac acctcactgc agaatatata cagtatgaaa agatgctcaa   23580
catcatatgt cattagagaa ttgaaattta aaataacaag ataccactac acacctatta   23640
cagtggctcc actccaaaat actgacaaca ctaaatgctg gaaaggacgt ggagcagcag   23700
aaattctcat tcattgctgg tgagaataca aaatggcaca gccactttag gagacaccta   23760
tttcttagaa agtgaaacat aggcttacca tatggtccag cgattgtgct cttaagtact   23820
catccaaatg aactgaaaac ttatagccac acaaaaacca gcacacaaat atttatagca   23880
gctttattca taattgccaa aaattggaag tgaccaagat gttcttcaat ggataaacaa   23940
accatggaac atttagacaa tggaatatta ttccaggata aaagaaacc aactatcagg   24000 ctattgcaaa gtgaaagaaa ccaatctgaa aaggctacat aggcttcatc tttaagactc   24060
caaatatgac attctagaaa agttaaaact gtagagacaa taaaaatatc agtggtacta   24120
gagtgagtgg gggaaagaag ggagggatca ttaggtggaa cacagggcat tcttaggtca   24180
gtgacactac ttttatgaca ctgtaattat agatacatga ctaatgcaac atattactaa   24240
tgaagaaaat tgtgcgggga gggaaagtag gcatatggaa actctctgta ctttctgttc   24300
aatttttcta taaacctaaa accactataa aaataaagtc tattaatttt ttttaaaaaa   24360
tgtgtctctc tgtaattcct tctgcctctc atcctgaagt cctctatgaa atggaatcag   24420
gaaagacaac accttactct tgaatcctgg gagcccaag aagaagtagg actggaatct   24480
caggagtact agaaaccagg aaaatttgga tccactgaca tccaaagtgg atcagaaaga   24540
```

```
aaagtgagtg cctcagacac caattggaaa agaaaaattt atttactttc tcaatgaata   24600
tttattgagt gcctcctgtg taaggcactg gtctaagagc tgaagataca acagtaaaca   24660
aagtttctcc cgtcacgagg ctcaggttct agtttggagg gacaaaaaga aaaaaacatg   24720
tgaatttata gactgtcaga tgcaataagt gccatggaga taatatagct ggtgagtagt   24780
gtgtggcaga agctgttaat tgttccgtag aattaattgt tccattcatc ttttagaaaa   24840
agaagcctca tctcaaagtt tacttggtta tgcatctgta cattacaatc ttcatttccc   24900
cagatccatt ctactctcct gcccccttgc acctagatac agccttgtga ccaaggtcag   24960
ccccatggga agtgctctgc gtaacttcca ggtcatttgc taaagataaa agctacttgc   25020
cttggattct ttcttttctct ctcctattga ctgggaaata atgattgaag aatccttgga   25080
agccaaaagt ggaagacagc agagccccca gttgtagtct gttcgattct tagctgttac   25140
atgagaggaa attttttttt ttgagacttc cccaatgcct ggacttttca gtaacataag   25200
gcaatatatc cccttgtgtg tataggcaag gctgagtcag cttctgtca cttgtaacct   25260
agattaattt tttctgatta attaattgtt ccaattagta caagaataat ttatatacta   25320
gactttctgc ctcaccttga aacctggaag ctcactgtat cagttctctc ttgccacaat   25380
gaagttgctt gtaaaacaac cacagtggca agcaacaagt ctacagttgg ctgagtggct   25440
ctgctattct gtattggtct tggctgatct tggctgggct cattcatgtg tctgtggtca   25500
gctggcagac tggctggggg ctggctaatc tagcacagtt ttggcttaaa tgacccaact   25560
acctggctct gcttcacagc atctctcatc atccattagg ctatcctgag ctttttttcat  25620
ggtaaagcag ggttctgaga cagacaggca gaatgcaagg tctaagctca taatggtcac   25680
agtaccactc ccacagcatt tgttgggta cagtaagtca caaggaaggt ccatatttaa   25740
ggatggagga aatagtctct actccgaaga gctgcaaatt cctattgcaa agggcatggc   25800
tactacaggg aggggtggag aattggagac atttttgcaa tcagtctacc acatttatca   25860
taattattcc cataattaaa cagtggtggt agagagaaaa ggagcaactg gatactggag   25920
cttaaccagg tgcctactaa gcacaaattc ctcagtacat gcaggggatg aagctatcct   25980
attctgattc cacccattta gcatatgtga ttttttttt aagttggaaa taggcagaga   26040
gaccctgttt tgaaagagaa cttaagggtc atccggccca atctccatat tgtttcagaa   26100
aaaagaacca ggcaccaaag ttaggggact tgcccagggc cacacagtga gtgagggaca   26160
cacgtgggtc tagatgtttg cctgctgact ccccgcacag cagaccttcc acggtcctgt   26220
gctgttctct tctcacgcca aggcagaaca cagcagtggc cacgtgcttg cactttggag   26280
gcagttagcc tgggttgtct ttcttccttc ctttctttt ttttgagacg gagttttgct   26340
cttgttgctc aggctggagt gcaatggtgt gatctccgct cactgcaacc tccacctccc   26400
agattcaagc tattctcctg cctcagcctc ccgagtagct gggattacag gcatgcacca   26460
ccacgcccag ctaattttgt atttttagta gagacagggt ttctccatgt tggtcaggct   26520
gctctcgaac tcctgacctg agatgatcca cccacctcgg cctcccaaag tgctgggatt   26580
acaggcgtga gccaccatgc ccagccagcc tgggttttca acctggcctc ttgcttatta   26640
cttatgagac tttggacaaa ttatttaacc cctctatcaa tgattgtaat agtactgggc   26700
ctcataggt tgttgggcag attaaatgaa agaaaggaaa taaagcacat agcaagtgct   26760
caataaattt tagctattat atttttctcta aaaatacagc attttcctat ttggtttgtt   26820
cttgtgtgca tttagtctgg gtttaggcat tcaagagagc tgaaaatatc ataatactaa   26880
atatttagat ggcaaagaat gaattcaact tataaaagta cctggagtat aaattcacat   26940
```

```
tttcttgtaa gaagagatat ttataatctg gtttatttgt ttacttacta acaaacattt   27000
actgagagtc tactgcgagt caggcattgt agtagtttgc tcttgctgca acatattacc   27060
acaaacttag tgccttaaaa caacatatgt tctggaagtc agaagtctga aatggatcat   27120
ctgggctgtt ccttatggaa gccccagggg acaatctgtt tctttggttt ttccagcttc   27180
tggaggctgc cagaattcct tggatcatgg cctgtttcac tccaatctct gcttccacca   27240
tcacctcttc tctcccttga ctccattgtc tcattgcctt ctctgacact cttgcctgtc   27300
cattatcagc ctctccatat ggattgtgct ttcttacagc atggtggcct cagggtagtc   27360
agacatggtg gctcaaggct ccaaaaatga gtattttcag caagcaaaac aaaagctcca   27420
tgctctttca tgaattcaca ttagaagtca catagctttg tattccatgt gggagttgaa   27480
gaatgagaag tcatggacac agggagggga acaacacact ctgggtcctg ttgtgggatg   27540
agggatgagg ggagggacaa atacctaatg catgcagggc ttaaaaccta gatgacgagg   27600
ctaggaagaa actgcatcaa ctaacgagca aaataaccag ctaacatcat aatgacagga   27660
ccaaattcac atataacaat attaacttta aatgtaaatg ggctaaatgc tccaattaaa   27720
agacacagac tggcaaattg gataaagagt caagacccat cagtgtgctg tatttaggaa   27780
acccatctca cgtgcagaga cacacatagg ctcaaaataa agggatggag gaagatctac   27840
caagcaaatg gaaaacaaaa aaaggcaggg gttgcaatcc tagtctcgga taaaacagac   27900
tttaaatcaa caaagatcaa aagagacaaa gaaggccact acataatggt aaagggatca   27960
attcaacaag aagagctaac tatcctaaat atatatgcac ccaatacagg agcacccaga   28020
ttcataaagc aagtccttag tgacctacaa agagacttag actcccacac aataataatg   28080
ggagacttta acatcccact gtcaacatta gacagatcaa tgatacagaa agttaaaaag   28140
gatacccagg aattgaactc agctctgcac caagtggacc taaaagacat ctacagaact   28200
ctccaccccaa atcaacaga atatacattt tttttcagca ccacaccaca cctattccaa   28260
aattgaccac atagttggaa ggaaagcact cctcagcaaa tgtgaaagaa cagaaatgat   28320
aacaaactgt ctctcagacc acagtgcaat caaactagaa ctcaggatta agaaactcac   28380
tcaaaactgc tcaactacat ggaaactgaa caacctgctc ctgaatgact actgggtaca   28440
taacgaaatg aaggcagata taagatgtt ctttgaaacc aacgagaaca agacacaac   28500
ataccagaat ctctgggaca cattcaaagc agtgtgtaga gggaaattta tagcactaaa   28560
tggccacaaa agaaagcagg aaagatccaa aattgacacc ctaacatcac aattaaaaga   28620
actagaaaag caagagcaaa cacattcaaa agctagcaga aggcaagaaa taactaaaat   28680
cagagcagaa ctgaaggaaa tagagacaca aaaaaccctt caaaaaatta atgaatccag   28740
gagctggttt tttgaaagga tcaacaaaat tgatagagcg ctagcaagac taataaagaa   28800
gaaaagagag aagaatcaaa tagatgcaat aaaaaatgat aaaggggata tcaccaccga   28860
tcccacagaa atacaaacta ccattggaga atactacaaa catctctatg caaataaact   28920
agaaaatcta gaagaaatgg aaaaattcct tgacacatac actctcccaa gactaaacca   28980
ggaagaagtt gaatctctga atagaccaat aacaggagct gaaattgtgg caataatcaa   29040
tagcttacca accaaaaaaa gtccaggacc agatggattc acagccgaat tctaccagag   29100
gtacaaggag gagatggtac cattcttcct gaaactattc caattaatag aaaaagaggg   29160
aatcctcccc aactcatttt atgaggccag catcatcctg ataccaaagc ctggcagaga   29220
cacaaccaaa aaagagaatt ttagaccaat atccttgatg aacattgatg caaaaatcct   29280
```

```
caataaaata ctggcaaacc gaatccagca gcacatcaaa aagcttatcc accatgatca   29340
agttggcttc atccctggga tgcaaggctg gttcaacata cacaaatcaa taaacgcaat   29400
ccatcacata aacagaacca atgacaaaaa ccacatgatt atctcaatag atgcagaaaa   29460
ggcctttgac aaaattcaac aacccttcat gctaaaaact ctcaataaat taggtattga   29520
tgggacatat ctcaaaataa taagagctgt ctatgacaaa cccacagcca atatcatact   29580
gaatgggcaa aaactggaag cattcccttg aaaactggca caagacaggg atgccctctc   29640
tcaccactcc tattcaacat agtgttggaa gttctggcca gggcaattag gcaggagaag   29700
gaaataaagg gtattcaatt aggaaaagag gaagtcaaat tgtccctgtt tgcagatgac   29760
atgattgtat atctagaaaa ccccattgtc tcagctcaaa atctccttaa gctgataagc   29820
aacttcagcg aagtctcagg atacaaaatc aatgtaccaa atcacaagc attcttatac   29880 accaataaca gacaaacaga gagccaaatc atgagtgaac tcccattcac aattgcttca   29940
aagagaataa ataccctagg aatccaactt acaaggacg tgaagtacct cttcaaggag   30000
aactacaaac cactgctcag tgaaataaaa gaggatataa acaaatggaa gaacattcca   30060
tgctcatggg taggaagaat caatatcgtg aaaatggcca tactgcctaa agtaatttat   30120
agattcaatg ccatccccat caagctacca atgactttct tcacagaatt ggaaaaaact   30180
actttaaagt tcatatggaa ccaaaaaaga gcccgcatcg ccaaggcaat cctaagccaa   30240
aagaacaaag ctggaggcat cacgctacct gacttcaaac tatactacaa ggctacagta   30300
accaaaacag catggtactg gtaccaaaac agagatatag atcaatggaa cagaacagag   30360
ccctcagaaa taacgcctca tatctacaac tatctgatct ttgacaaacc tgagaaaaac   30420
aagcaatggg gaaaggattc cctatttaat aaatggtgct gggaaaactg gctagccatt   30480
tgtagaaagc tgaaaccgga tcccttcctt acaccttata caaaaattaa ttcaagatgg   30540
attaaagact taacatgtta gacctaaaac cataaaaatc ctagaagaaa acctaggcaa   30600
tactatccag gacataggca tgggcaagga cttcatgtct aaaacaccaa aagcaatggc   30660
aacaaaagac aaaattgaca aatgggatct aattaaacta aagagcttct gcacagcaaa   30720
agaaactacc atcagagtga acaggcaacc tgcaaaatgg gagaaaattt tcgcaaccta   30780
ctcatctgac aaagggctaa tatccagaat ctacaatgaa ctcaaacaat tcacaagaaa   30840
aaaacaaaca accccatcaa aaagtgggca aaggatatga acagacactt ctcaaaagaa   30900
gacatttatg cagccaaaaa atacatgaaa aaatgctcat catcactggc catcagagaa   30960
atacaaatca aaaccacaat gagataccat ctcacaccag ttagaatggc catcattaaa   31020
aagtcaggaa acaacaggtg ctggagagga tgtggagaaa taggaacact tttacactgt   31080
tggtgggact gtaaactagt ttaaccattg tggaagtcag tgtggcgatt cctcaggat   31140 ctagaactag aaataccatt tgacccagcc atcccattac tgggtatata cccaaaggat   31200
tataaatcat gctactataa agacacatgc acacgtatgt ttattgcagc actattcaca   31260
atagcaaaga ctattgtctt ttgctatttg gaaccaaccc aaatgtctaa caatgataga   31320
ctggattaag aaaatgtggc acatatacac catggaatac tatgcagcca taaaaaatga   31380
tgagttcatg tcctttgtag ggacatggat gaagctggaa atcatcattc tcagtaaact   31440
atcacaagga caaaaaacca aacgccgcat attctcactc ataagtggga attgaacaat   31500
gagaacacat ggacacagga agggaacat cacactccgg ggactcttgt ggggtggggg   31560 aagggggag agagagcatt aggagatata cctaatgcta aatgacgagt taatgggtgc   31620
agcacaccaa catggcacat gtatgcgtat gtaacaaacc tgcacattgt gcgcatgtac   31680
```

```
cctaaaactt aaagtataat aaaaaaaaaa aacctagatg acgggttgag aggtgcagca  31740
aaccaccatg gcacatgtat agctatgtaa gaaacctgca tgttcttcac atgtatccca  31800
gatcttaaaa taaataaaaa ataaaaataa ataaataaaa ataaaaatta tattaaaaaa  31860
gaagtcacat agctttattt ccatacccca tgggttgaag cagtcacagc ccattcagat  31920
tccagggaaa gggacacagg ccacatctct tgatgaaaag aacatgaaag aatgtgcagt  31980
tatgttttaa aaacatccca gtagagttca cgaacatgag ttttacagc agacactaca  32040
tttccctgcc agtttacctg ccttgggatg gtggaggtct ctgaagttgg cagtcgtttc  32100
ctgcaggatt ctaagttgga tggcagcagc tctccagctc tgaggcaacg aaactgaaag  32160
ctagtggaga gttgcctgaa ttttgccttc tcaggtcttt ccataagttc tgtgaacact  32220
caatttcctg tatcaaattc cttcttcttg aaaatgctta gagtgatacc tgttttttct  32280
actggagtct gactgattca agctccaaag tctgccctcc taactgcctc tcgcgttgtt  32340
ctaaaccttt ctggtgctcc tggcctgctc ctttgcaacc cacacacact cacacatcca  32400
gcatacccta agaagatgac actgcctctt agtgctcaca aaaggagtgc aagttatatg  32460
aacctcaact atcctttcta tccaactgga actgtatctg tctgtttttc cccttctgc  32520
tccgtcttag aagaaaagtt catcaatact tttgggaaaa aggtaaactt ttaaacacga  32580
tgcatggcac ccttcattta tcttttcaac ctgattttct gccatctttt tatatgtgcc  32640
catgttaatt atggtagact aactgcttta ccaaatagac tcataaaatt ggtggaatta  32700
ttgctgcaac agaaagaccc aaaggtctac aatggcctaa accctgtaaa agtttatttc  32760
ttgctcaaat aacaattata ggcaagcaaa taatcagtgg catatgccct tctctatgta  32820
gggacttaaa ctaatagaga gacaaccatt tccttccctc cctccctccc tctctctctc  32880
tctttctttc tttctttttt tttttttttt tttttttgat ggagtcttgc tctgtcaccc  32940
aggctggagt gcagtggcgc gatctaggct cactgcaacc tccgcctccc gggttcaagc  33000
gattctcctg cctcagcctc ctgagcacct gggattatag gcgcccacca ccacgctcga  33060
ctaattttg tatttttagt agagacaggg tttcgccacg ttggccaggc tggtctcaaa  33120
gtcctaacct caggtgatca gcccgccttg gcttcccaaa gtgctgggat tacaggcgtg  33180
agccactgcg cctagcctga gacaaccatt ttcaacattt gctttccaag gtcacccttt  33240
ccagacatcc agaagagaat gtaaactaaa aataaaatcc taagcccccc aaccaactga  33300
acagacccc tcttggccaa gaagacctca agaaaaactt aaaaactgaa ttcctggcca  33360
tcacaagaag ggaaggtcca atatgctttg ttatcctccc tccctttggg agtttaggca  33420
caactgaaca gcattagtgt taaaatagag atcgtaaagc taacaaaatg gacttattgt  33480
cacaataaga tgccaaatta caaataggac ctaacacgac acaagaaggg ttgagtcaca  33540
cattcttata attcactgta acccagtgta ctggaaaaca atatcttaat atgaaatatt  33600
cctttttgc tgcctccgaa tttttagaca aagctttatt tctttaacca attgtaaatt  33660
aaacagtctc tgaatttact tatacccctgt aagcacctgc ttcaagatat cccacctttt  33720
caggctgaat cagtgtaaat accttccatg tgactgattt atatctttgc ctgtaacgcc  33780
tgcctcccta aaatgtgtaa aactgtactg taatcctact accaagggtg cactttctca  33840
ggacctcttg aaactgtgtt ccccaggcca tggtcactca tattgactca gaataacatc  33900
tttaaaatat tttagccagg tgtggtggct aacactcata atcccagcac tttgggagac  33960
catggctaga ggttagcttg aggccaggag tttaatgccc agcctgaaga acatagcaag  34020
```

```
atcctatctc tacaaaaaaa aaaaaaaaat tagctgggta tggtagcaca tacctgcagt    34080
cctagctgct caggaggctg aagtgggagg atcgcttgag cctggagttt gaggctgcag    34140
tgagctatga ttatgatcat tccactgcac tccagcctgg gtaacggagc aagaccttgt    34200
ttaaggaaaa gaagaaaaga aaaagaaaga aagaaaagaa agaaagaga gagagaaaga    34260 aagaaagaga gagagaaaa ggtagaaaga aagaaagaaa gagaaagaaa gaaagaaaaa    34320
aagaaagaaa aagaaaagaa aaagaaggaa agaaagaaaa gaaagaaaga aagaaaaaat    34380
tttttatgga gtttagtttc tccattaacg ggggaagcat acagagggta tatgtgagag    34440
gcttttatgg gttagccctg gacatggtac acatcacttc tgctcccatt ccactagcta    34500
gaattcagtc acaaggctac atctagctgc aagggaggct gggaaacgtc acctaactgt    34560
gtgcccagga agaagagaaa atgagttttg gtgaatgacc agctagcagt gtgtgccatt    34620
gtgccttaaa ccttggcatg cttatttaat tttcctatag ttcagctttg tcatttcaaa    34680
gttgaggatc atcgtggcac ctccttcaca gggctattgt aaggattaat tacattagta    34740
ctgtgaagac cttagaacat tgcctggctt tttgtaagca tcccataaaa gttatctact    34800
attgttatta ttcttgtaat ccttagggac tctgctttga tactacttcc ttacatgaaa    34860
tctttcttct ccctttcccc tctggcccat tctctctagc accatcatat tgtattatag    34920
ctgtctgttt tctggttggt ccctccccta aatgcttctt gaggataagg attatgttta    34980
gctacatttt aagtaactaa catagtctct ggcatatgat aggtactcac taaatatttg    35040
ttgagggagt aaaggagaaa gtgataaagg tgagaaggaa agccacaaag tggatcagta    35100
tcttgtcatg gggagatctg tgaaaggacg gtttgataaa ttgtcccttc atggattgta    35160
gtcaccatct tccaggtccc agagggtcac ttggtactga agtcttatca gcctagggac    35220
caaggctgcc tgcccttcat gccctgtgtg agacaccgct tctgaactgc tcacgtcct    35280 ctcaacctac cttttctcca gtccctgctg cagcacccag cacccagaga agtgaatcta    35340 cttttccctca ccttgtaact gagtctttca actttgaatg catttttaaaa cttttttcct    35400 ctctttctag tcttaagatg taacctcgaa actgagtgta gaaactctct tttccttagt    35460
cttaaaatat accttgaaat gtactttgaa actctgcttc cctctctttc ccaccagact    35520
ctcccttgca ccatggacac gtatctaact gtatacttgt taataaattc caggggctga    35580
ttttacacaa cagccaggca aggagaccca gctgcagaat tctcccctac ttggagatta    35640
cctcatgaca gacatctata acctgactgc aactgagatg gcaccagcca gcactccaag    35700
tggacaacaa ctcaaaataa cccttggaag aagacatgca ggcctgtatc ttgtgttact    35760
ctggcatggt tctcatacta agtatccccct tttatttttt tatttatttt taacatattt    35820
tttgaaacag agtctctctc tgttgctcag gctggagtgc agtggtgtga acgtggctca    35880
ctgcagcctc aactcccagg ctcaagcagt cctcccaact cttagcctcc agagtagctg    35940
ggactacagg tgtgcaccac cacatctggc taatttttt tgtatctttt gtagagatgg    36000
gttttcacta tgttgcccag gctagtttca aactcctcgg ttcaagcaat cggacagcct    36060
cggcctcaca aagtgctggg attacaggca tgagccactg cgcctggcca gtctcccccc    36120
tttaaaatcc cttccttcag tctaacactt gaaatggtct tttggaggca caagcctggc    36180
catttcccaa ttgctagcat ttgaataaag ttgctttcct tttactcgct tctcatattt    36240
tggctctcaa gtcatgagca gccagacttg cattcagtca caacgtggct gccctgcatc    36300
tcattctgcc ctggggttgc tcttgctcaa cttccttgga cattgttaga aatgtatttt    36360
gactgtcaca tatgcaagta tgcaagtgca agggagttgg catctcatgg ggcaatgtaa    36420
```

```
ccactgcagg acatgaacta gttgataaat attcgtctct tctgactctt gagcagatga    36480
ttctgaaagg gtgatgaact catcctggct ttccacggat ctgagttttc tctgagttag    36540
cactggaaat cccatgttgc tgttggttac cttaattctg aaatgcatta tgcaggactc    36600
cttagggggt cccagtgaga tcaagttcca gtttcccaca gcttaataac acagattgtt    36660
ttgccttttc ctgcatttct gggattactt cccaatatat actgccttca cacaagcttg    36720
tgtcttcggc tctgttttct atggggaatc tagctggtct ttgaattggg caatgcttag    36780
cttatctgtg cagtgatgag tgtttccaac tttaggaaac ttaaaaagac agaggcaagt    36840
gaaataagtc agggccccaa acagccaaat tatcactttc ctgacgttgt tacaaaatta    36900
gtctggaagg tatggcactg ttcaaagaca gtgtaatgaa atatttatta taaggtttaa    36960
ttgcttgaac agccagatat agaaaggact gcagacagat agtcaggaga cttaacttct    37020
ggtcccactt ttagtattta aaatcctatg tgacctttga cacgcttctc cttgggcctc    37080
agtttcttca tctccaaatt cttggctgct actctgctaa gatcaagtgt acaaaattag    37140
gaggttaggc tagattttgc ttttaccagt tgttctattg cagcaggtgc agttatacat    37200
gatgggcaaa ggcttgtggg gtgtcagggg ccttgtccct tcctagcgcc actagggtta    37260
ataggcctgg tggcctgttt catgtccatt tcactagttg agcacatatt gaagaaagat    37320
tttatatatg ggtcatagtg gaccatgaag aactcccaac ttatttccct gacaacattc    37380
ttttttttcc tttgagacag ccttgctttg ttgcccaggc tgtagtgcag tggcatgatt    37440
tcggctcact gcaacctccg cctccctggt tcaaacagtt ctcctgcttc agcctcccaa    37500
gtagctggga ctacaggcat gtgccaccat gcctggctat tttttttttt gtattttagt    37560
agagatgggg tttcaccatg ttgaccaggc tggtctcgaa ctcctgacct caagcgatcc    37620
acccacctcc gcctcccaga gtgctgagat tacaggcatg aaccactgca cccagacccc    37680
tgacaagatt ctcgagattt aacaatctca aatcttcttt ccgcagtgcc aactagacaa    37740
gatatcaggg ccaaaaatat ttggctctga gatgtaagaa aggtctttct aattactgta    37800
gaacttgagg tcatgatcat cacagccagt ggtgtgctgc tcctacctgc ttgtaaaagc    37860
cagttgctaa atattcagga atgtttcaag ccaaacaacc actggtagct tgaaatcagt    37920
catggggaga gtattgacac cacagaagtt gacagatgct acaaatccat gttctctcca    37980
catccacccc tccctgagcc agtttaccag caattccccg catccagctc ttaacactgg    38040 aagttttat ccaggactat ggctaaatta aatatgtgtg tcttaaaaag aattttttc    38100 cctgcttttt ggtttgtgga tacaaagagc tgaatcatta aaacttgttt ttctctccac    38160
ctcaacagtg gctttcttta tagattctat gaatctgaaa gatacaagtt ccaccagagg    38220
tcttggtagg gttccacagc cccaagctct gcaggttctg acaaaggata ggctgggccc    38280
tgccaggaaa actcacagaa ccacatcaag gtgtttgtgc tgctgcttta agagtttgtc    38340
ctcaagacaa ataagagttt gcctatttgg gggctttgga aattttttt taggattttg    38400 gaagcctgtt ctgttacttg ctagttgtgt tactggacaa gttagttaac cttgctgatc    38460
ctgggaagta atctcaggaa agcagggaaa ggcaaaacag cgtgtgttat taagctgtgg    38520
gaaactggga cttgatgccc ctgggactct ctaagcagtc ctgcaaattg catttcggaa    38580
ttaggataac caacagcaac acgggatttc catgctaaac cagggaaaac tcaggtccct    38640
ggaaagccag gatgagttcg tcacccattc agaatcatct gcctaagagt cagaagaggg    38700
gaacatttat ccactagttc atgccctgta gtggttaagt tgccccatga gatgccaact    38760
```

```
cccttgcact tgcatacttg tatatgttca agtatggtgc acatgcttga gacaggatct    38820
cgctctgttg cccaggctgg agtgctctgg cttatcacgg ctcactgcag cctcaaccac    38880
ccgggctcaa gtgatccttc cacctcagcc tcctgagtag ctgggaccac aggcatgcat    38940
caccatgcct ggctaactta aaaaatttt  ttgtagagat ggagtctcac tatgttgccc    39000
agcctggcct caaactcctg aactcaaatg attctcctac gttggcctcc caaagtgctg    39060
ggattgcagg aataagccac tgtgcccagc caaccttgct gagcttcact tatatgtgga    39120
atggatgaga ccacttcaga gggtttatgg gtttgtcatg aagctcaggg agcttaaggc    39180
tcaagacacc tcacttgtac aagcttctca caggagggct ttaggtacac tgtatttgta    39240
attttctagt ctaaagaccc ctgccctctt cccaaaatgt gtcatcttca gagctgcaca    39300
aaccttggat ctgatcctgc ttgtgaggat gaatcacgtg taaaacactt attcttgagt    39360
ctggcccatt gtaaaagcct cagaaatagt ccttgctgtt gtcagtggaa gtactttccc    39420
tccattatca catatccaca tattctttct cccactgcct aaatgtcaat gcccatccac    39480
gtctgctcag agtttgcttc ttttcctata atgtcagttt cttgccaatc actccccact    39540
tgccattttg ccagtcttat tccataaggt gcatctgcac ttcctcactg cgtccttttt    39600
cataatggga aaacaatgtc cagcgattat attcttcaca gaagtgatgt gacagcaaag    39660
agagatcata aatgaatcgc ctgaagcttg ttggtgtgag ggggaaacca aagtcatatt    39720
aatacttaac aaaacaagca acaggacagg aaaacaaaag gtaattaagg caaagctgtg    39780
atgttttgcc agttgttaac ataagaggcc aattgtcagc tgactgtgat gtaaagacgc    39840
ttcctttaag agcatgtgta atatgtatct cagaatcatc aaagggctct aagtcaccct    39900
aataatgggt ctgtaccaca aacagagaga atgcaaacca cattttgtct taaaagacac    39960
agcaaattgc actgcagctg taacaagaat ctcagagtca tttgcattaa ctggggatga    40020
gtgaaggggc taagtggagt gtctgtgtgc aacatggcac ttcttccttg acctgtgaga    40080
aaggaacttg acagccaggc tcagtggctc atgcctgtaa tcccagcact ctgggaggct    40140
gaggcaggtg gatcacgagg tcaagagttc aagatcagcc tggccaacac agtgaaaccc    40200
cgtttctact aaaagtaaaa gaaaaaaaaa ttagccgggc atggtggcgg acgcctgtag    40260
ttccagctac ttgggaggct gaggcaggag aatggcatga acccgggagg cagaggttgc    40320
agcgagctga gatcgtgcca ctgcactcca gcctgggaga cacagcgaaa ctctgtctca    40380
aaaaacaaaa aaggaaagaa aagaaaggaa cttgacttat atacacttag gtgcagccat    40440
cattgagggc ttgttgtgca aggtgctatg gatggtgatg agtaaaacca ggtgtccttt    40500
ctattatgct gtgctggaag cttctttggc aagtgaaggg agtgtggcct ttgggatcag    40560
atgaatctgg tggaatcctg gctctgtgct cagcatatga tttagacatt tatgtaacct    40620
tcttgagcct caagtttcct catctgtaaa atggtaacaa tactacccat cttacagaat    40680
cacagagagg attaaatggg aaaaaaaaga caaagtgtct gaaatatagc aagttcttaa    40740
taaatattaa ctttcttacc cccttctgga ggcatagaat cttagtgcaa tcttggtact    40800
ctcagaaact gtttatgtag ctcatctgaa tcttattttt ttagtagttg aaacattttg    40860
tcttaataca gaagcaatac atatttgtag cacaagaatt agaatattta tttatatata    40920
tatttattta tttttgagac caagtctcac tctgttgcac aggctggagt tcagtggtgc    40980
aatctcagct cactgcaacc tccacctcct gggttcaagg gattctcctg cctcagcctc    41040
ctgaatagct gagattacag gcgtgcacca ccatgcccgg ctaattttgt atattttaa     41100
tagagccagg gtttcaccat gttggccagg ctggtcttga actcctgacc tcaagtgatc    41160
```

-continued

```
cacccgcctc agcctcccaa agtgctggga ttacaggggt gagccaccgc gcccggcaag    41220
aattagaata tttagataag aaaaaaattc aaaattacaa ataattctaa tacgttaaca    41280
cccttgggtg tatccttcca ggacactttt atgcctgtta atacatacgt attattaaaa    41340
atataattat acaatacata ttattttata acctgctttg ttttcatacg ttacgtcatt    41400
atgggaaatc tttgaaaaaa tctctcccat gaaaaggcca gctaacaatt atgggaagta    41460
tgggaagtgg tttcgattaa catactgtga caactatcta ttattaagaa agtcacgaca    41520
aaattttggt gcccctttcc cagatgaagg ccacatagct gctataaggg acaaggacca    41580
gtaatatctt caaatcctct ttttgaagtg ccttcattta aaaatcatgc attttctttt    41640
aagagtttta taaatctag gaggaaactt atccctttgt gtttagaaca aggcaaaaga    41700
aatttctgat tggatattgt tatgggccca tgacttctgt tgcagagaag gtaatagaaa    41760
aaggtaaaat acttctacgc tctataattc accttgctgg aaaaaaaaca actggattgg    41820
cttgacaggg gcttagacgg gtgaccaggt tactgtttgg ttggttgaga gacggaagca    41880
gtacagaatg acaaaagtgt gtggtgggcc accggccact ggttcatcat agcaggacct    41940
caaaccaatg tctagtccat gaatgtttat atatggggttg gtatatgaag gtggatattt    42000
gcaaacaaat gcttagtttt agtgtcagga ttttcttcct aattaatgaa aagagactgt    42060
atgttttcaa gttctgtagg cctaactaga agaaaagag ttcaggattt cagattgtgc    42120
tactttcaca agatgtaggt atatctttac caaaacacac atggctatgc acatgttcaa    42180
gtatcttgtt ataagaaggg tgtggtgtaa gtggaaaaat tgcttctgtt attcttgtga    42240
ggcagtgtaa cttagtggtt agaagcactg attgaagagc aagactacct agtcttgaat    42300
tcagcttcac caactgttag ctgggcaatc ttgggcaagt tagttactct ttctgagtct    42360 ctattttct tgacctgtaa gaaaggaaat tgatggccag gagtggtggc tcatgcctgt    42420
aatcccagca ctttgggagg tttaggcagg cggatcacaa gttcaagatc agcctggcca    42480
acacagtgaa accccatctc tactgaaagt aaaagtaaaa aacaaaaaaa aacaaaaaaa    42540
gaaaaaacaa attagctggg catgatggtg ggtgctggga ggctgaggca ggagaatggc    42600
gtgaacccgg gaggcagagg ttgcagtgag ccgagatcgt gccactgtct tctagctttg    42660
agacagcgaa actctgtctc aaaaaaaaaa aaaagaaaa agaaaagaaa ggaacatgac    42720
ttatgtatat ttaggtgcag ccatgattga gggcttgttg tgcaagctgc tatggatggt    42780
catgagtaaa actaggtctc cttactatta tgctgtgctg gaagcttcct tatgggtata    42840
ataatagttg ctcctattaa tgagtatatc caccctcatag ggttgttgaa ggatttgaaa    42900
aatattttag aaagtaacaa ctttcagcat ttagaacagt gcctagtata taataggaag    42960
tatgtgttag ctattgccat tttattagag ttttaacagg tcagtccaac agaactggca    43020
atttcctgag tgatactttt ttttttttcct gggacagagt gttgctctgt tgcccaggct    43080
ggagtgtagt ggtgtgatct tggctaactg caacttcttc ctcctgggtt caagccattc    43140
tcctgcctca gcctcagggt agctggaat tatgagaacg caccaacacg cccagctaat    43200
tattgtattt tagtagagac ggggggtttca ctgtgttgtc caggctggtc tccaactcct    43260
gacctcaagt gatctgccca cctcagcctc ccacagtgct gggattacag gcgtgagcta    43320
cttttaattc attcattact caaacaacac ggtatcctgg atgtctatat atggttaggc    43380
actatgctag gctctgggca actgaaaaaa aaatgccaat attctatatc tttgaaaagt    43440
aaaaactgac tactcgtgtc ttctcaagaa gctttgtgac tgaggttatg caggtctttt    43500
```

```
tatctagagt aggcttcctg gaaggaggac aagactagct cacctgcaaa gaactcagtc  43560
acttatcagg aatgaatgaa gtgcagagcg tattgggatt ccctaacacc aactcttcct  43620
gaacatgcac ctttgtcaaa cctgccactg tcagagctgc cgacacaggc aatggatggg  43680
gacatcagga cagggcttgg ggtgggagcc tgcagttcct ggaatttgcc ctgctgacct  43740
cacactaggt gattttatcc tacttcccag aaactttccc ccagttagtc taaagttggg  43800
atgaagctac aaattatttg ctctgaaaat tctgagtcta ttctagagtt aatttcctgt  43860
acatgttaca tggtttgcat tattagaagg gccaaggggc cccggcagtg cattcctttt  43920
cattttctgt aaaagggatc tgtgggactc tttcatcttc cattaatgat gagaatgtgg  43980
aaagggagg gtggggtaag agaactaaca attattgagc acttactctg tgccaggtac  44040
tttgtacatg ttcctggcac agagtcagtg ctcaataatt atcggttttt gggggaactg  44100
aaacgaaaat ctgagaggcc aggggccatg ttttttgtcaa tacgtctatt ttggcaatga  44160
gcacattacc atgtatattg tcagtggtcc atgttgttga atgatatgat tatacacatg  44220
ttatgtgtgc atatccacca cctatctatg tatcatcact tgtctatcac ttattgaatc  44280
ttagctaaag ctcatgctat ttaaaattac aattgccttg gtctcagttg aataccatcc  44340
cataatttct atgtgaaaca attgattttg tgatttctat ttcataattg cagaattaac  44400
taatttatta ttcaagtcct ttgaacttaa agatgttttc agtagtgtgg attgaatata  44460
tctatgggtt tgatgaaatt aactttttt tttttttatga gacggagttt cactcttgtt  44520
tcccaggctg gagtgcagtg gcgcaatctt ggctcactgc aacctctgcc tcctgggttc  44580
gagcaattct cctgcctcag cctcctaagt agctgggatt acaggcgccc gccaccatgc  44640
tcggctaatt ttttgtattt ttagtagaga cgggatttca tcatgttggc caggctggtc  44700
tcgaagtccc gacctcaggt gatcccccta cctcggcctc ccaaagtgca gggattacag  44760
gcataagcca ctgtgctcgg ccgaaagtaa cttttaattg tgataattac attgcccttta 44820
tttccattac gcatgaaaca gaactcctct gtcttcttat ggtaaaattt tggcactgaa  44880
gaccagttga agatgaagga tgcatcttgg taagttgaaa gaggagagag agtggggcca  44940
gggaagccac agtgggcaac agattggcat cccagctttc acccctctct atcattctta  45000
ggtatttcag gtcagaatta agaggaacta attggagata tcatcttctt ggaattgttt  45060
gtgcctcata acactttaaa aatgcattga cgcagtgatt tctgaagttc agtcatttgt  45120
gtattgcctt cacgaatttt gctataccct tgaatcacct gtactcatac tgacttgagt  45180
ttttaatcat ctcactttct taaaattaaa tactttttctt ttttgggaag aggatctcat  45240
attattactt tttaaaaaat ctcttttttcc acacgttcta gttatatcat tactataaaa  45300
ttgaagacag gcttcacttg ttaaaaactg aatgtaacta taaaattcaa tccaagaaaa  45360
acaaagaaaa tgttagacaa aatttttagct aagccttatt tttcttggac ttgaagccta  45420
agttttgctc cctgtcagag ggttgctaaa agaccagcag caaactgaga gtttaccttg  45480
gaggtaatca gaaagaaaaa ataatttttaa ggggaataac tttctccccc atataattcg  45540
gtgtattttta atgcctggtt gagccactgt aatactatgg aagattatgt catcttccgt  45600
aatacacatt atctcacaca tggcaaaaca cttcatgaga agagaaactg acatctcatg  45660
attttgacct tcaccacata tacaagtttt tttgttagaa atatcactca cgaaaaatgg  45720
atgaagtagt cttccatgca gaagtttgga catttcaatt taatgtctct ggtaaagatt  45780
ttccagttaa aagcacattg accacaatgt ttcgtcttct cttttaacact gaaaagggga  45840
ggaacggcct tattagcagt caatactatc aaagtcaatg gaggcaaggg accaatggcc  45900
```

```
catcatagtc ctaatatcac ttactgtttt cgaaggagga catctttcat agtggtatct    45960
accatctctt ggggagaaga gcaggaatgg atagattaac ctcttccaga catctgctca    46020
cagtcccgat gcggtttctg acttagaggg ttttcttag  agatcttctc tgctgtcctc    46080
tgcagctgtc agggcattct ccagatgggg cctggtagga gtccttgaat tgactcaggt    46140
cccacatctc cctgcagttc atttatgctt caggtcaagg gtcacaaata ttcacttgat    46200
aagggatgac agattagtca cagctagctg ctgaaagtgg agttgcatga agtgcacatt    46260
tagcttgcat gagggagagc acaaattgga aacttatcaa aattgccttg gtgggtctct    46320
ttcaaggctt ctttggaggc tgctctcaga tctattacct ctggaaattc ttgaggactt    46380
ttaaaaatac aatgacatct catctcttct taaattctgt ctagtggaca atttgtgagg    46440
ggtgtatgtg ggaatctgca attgaattct tcctcaggta cggtgagttg ggcctcattc    46500
cagctccacc gccatcatca tcagaatcct agtgggaatt tcccttcctc agaagactga    46560
aactccacct gtgctggtaa tgccaggccc cctacatagc tccagtctat tacctcaagg    46620
gaacacaaag gcacactctt acaatatata tttacacctg agcttgtaaa tatgacagct    46680
aagaatcaga aatgttgttt tacttaaatg ggcttgtcag tagattggga gtatattgta    46740
ttccaaggaa atgcttttta gatgtaattt taggtacaaa ctctggattt tccttcacgt    46800
acaaaaatta aactttgat  tacacactag cagaaatgac agcagtaaga gttttttat     46860
tttaattgta tttattaaac aattaggaaa cactgtatac tttctaattg ttctaagttg    46920
ctttataatt cttaattcat ttcaactcta ttacaacctt atgatcacct actatgtgac    46980
tgtaaagcac tgtactttat tacattagct ctaattctta caatcatcct tgaaggtagt    47040
tagtactccc attgttatga atgaccactc ttcagaagca ggagggaccc tcatccaaat    47100
ttgatttgga tgtcaaaact gatgatgcca cacatccacc tcacataggt atgaaaacta    47160
ttattcacat aatgaggctt tctggggata gcagtgtggt ttccaagcag ataaaaaaaa    47220
atggcttgag agagagcaca gaaaggagac tggcttaggg tttgttttgt tggtggttga    47280
ggtggggcca gggtgagggt tcccacacat ggtttgaagt tgccatgcag cttcctagta    47340
gcaaaggagg gaatatcctg gtttctttat cagttctcct ggatatgggc agatgaggaa    47400
gagggagggg taaggcttaa aagctggcag tagtcaaaag tcaaaaaatg gagtcagatt    47460
ccttattata cccattttac caatgaagaa actgcgattc taggatatca tgcattgtgt    47520
caggcatgac tttagtgcag taattctctg tgaaacttag ccccacactg cactgtactg    47580
tggtcttgga gaagtagaag caataggaaa tacacacaca cacacacaca cacacacaca    47640
cacacacaca cacacacaca gtgatttact ataaggaatt agctcacatg attaaggagc    47700
ctgagaagtc caagatctgc attcagcaag acagagaccc aggggagtta atggtataag    47760
ttccagtcag agtctaaagg caggagaaaa ttgatgatgt ctcagcttga agacagtcag    47820
gcaaagagaa ataattcttt cttactcaat ctttaatct  attcgggcct tcaatgaatt    47880
ggatgaggcc cacccacatt ggggatggcc atctgcttta ctcagtctac ctattcaagt    47940
gttaatctca tccagaaaca ccctcacaga cacactcagc agtaatattc agccaaatat    48000
ctggctattt catgacccat acaagttgat atatgcagat aaccatcaca gtatcccact    48060
tgaaaatgca catcccttat tattgaaggg gagtgggagg cagaggaaat cctaaacacc    48120
attgcaaatc tatatattct agagagacta tgaaagcaat gtagcttggc atggtggaag    48180
gagcatggtc tttgggatca gaagatttgg ttataatttg gctttgccat ttattggctg    48240
```

```
tgttatcttg aaaattgctt agccttactg agttttagtg atacagaaca tctccagtga   48300
catgcaaatt tataaaacat cccattctat tttgggggtc tccattggaa agctctttct   48360
taaataatgg catttcccta tattaggttt ggggtgcata catagtctct actggtatat   48420
caaggcaagt taccaggaat tccaatgtat aaggacacag ctggccatct ggaacaaata   48480
ttggaaggga ttttggagaa cagaggttag atccaggggc aataaggtcc agactcttca   48540
caagagatga gatgaaggcc atgctctgcc tatttaggaa tccacaggac actgagagtt   48600
accccaagac aagagaaagt tcaaataccc aagacattga ttgactactg gcaatagttt   48660
ttggcacaac cctgggattt gctgcccaaa tgttgtttca gtcttgtccc aggagagctc   48720
agttctcagg ctggctccac agcctaccat gttagcaagc ccaaaagtga atatgtcttt   48780
tgtaattttt ccagcaaaaa ttccagggct gactctcatt gatccaaatt tggtcacagg   48840
cccatccatg aatcaattgc tgtgaccaat ttactaggcc tgagtcactg gtctgtccac   48900
cccaggtgtc ttgtggtcag ctcacctgaa cagcacggac tgagacccaa gaaaaactga   48960
tgcactgtta ctaaaaaagt gaggaagtga ggctgagtag gcaaaacagc agatgtccat   49020
tacaggaaag atctccaaaa tgtaacctca ctcatttttt ctgtatgtgt aactctgtgt   49080
gaacttagcg cctgccccaa gggtggcatt tacttagact gtgatgaaaa tagagaccct   49140
ggatttgtgc agtgctctgt cttcccccct ctctttctgc taccacgatt tctccaactt   49200
ctggttgtat caggtttcag ctaagggagg gaagacatga cttaacgcat aggcttccat   49260
agagattcca tactgggact tcaaataggt cacactactg gtgagtccca gcacacagat   49320
cctagtgcca agatactcat gctgttgatt cagaacttcc agacatacat gtgcttcctc   49380
tgacagggaa ggctgctact acctatatct tctgaattgg ttcatattaa tcataggtca   49440
tgtgtaccac tggtaacaat agtcatcgtt tagtgaatgt ttacaagtga gaacactgcc   49500
tattcataag cttgaaatta tctgtgaatt tgggaatgtg tgccagccgt aagctgacca   49560
gacatactta ctggtcatta atcaacaggg ttttgtttcc ttatccctat gtttgactga   49620
gacaaattcc tctccctaca tcactcaaat gtggatacag aagtcttctc cccttcctat   49680
ttataacctc aaaaggttgc aatttggact ggaggtaagg aggagataaa gtacttacaa   49740
actacttgtg gaattccccc agtcccctcc accccctgct ttttccctgt gtcttgacca   49800
aaaatcacag agtaccttga tcacactatg acacaaccag cagcaggctt ttcccagcag   49860
gcttgacacc agggctttga acattccag gccctcatac aggtatcaag gtttacgagg   49920
aagaaactgg tcctagcctt agcccaaatc cttaaacctt tatataaact ccatgccctg   49980
acctcctcac agcagacata actagataga acaccgttgt ctcttgctgt ttgttgcaaa   50040
gattgctaca gccttctctg tgcctaagtt tttctaatca atgctttgga tggatcaaaa   50100
agaaaaaaaa gaatttataa ctaaaaggaa aatattgtgt actatatatt atatatagca   50160
tatataatat ataatctgta taaaatacat gtaacatata atccattgta tgttatatgt   50220
aatttttatg gaaatacaac aaattataag tataataatt atgtatgtta catatatata   50280
tattttttca cgttttttaac ttgaggttta agtacctgtg atctttttt ttttttttt   50340
tttttgagac agaatctagc tctgtcatcc aggctgcagg gcagtggctt gatctcggct   50400
cactgcaagc tccaccccct gggttcacgc cattctcctg cctcagcctc cagaatagct   50460
gggactctag gcgcccgcca ccacgcccgg ctaattttt gtgtttttag tagagatggg   50520
gtttcaccat gttagccagg atggtctcga tctcctgacc ttgtgatccg cctgcctcgg   50580
cctcccatag tgctgggatt acaggcatga gccaccgcgc ccagcctatc tgtgatctta   50640
```

```
accaatttat cttgccttt  ctgatgcatg actaagaact tatggggaat tcaaatagat   50700
cactaatata aagacaattt aaagtgcttg acttgccagt gttcttatag caaaactttc   50760
ataaagttta tgacacttct ttgatttcta aggttttagg ggtacaggca tatcttatta   50820
tagagtattt ttcctctttc atttaaagat ttaatttact acgcatcatt tccaagctcc   50880
ttgacctttt ctggatcccc accaccacct gccctaatgg atactgacac cagctgtgaa   50940
tatgtataat ataaactggc caaaacacat ggcctgggca ggttaataac ttgctgcccc   51000
ttcaaactga tattatttaa atttgtattt aacacttgaa cactgtcata ggctgatcct   51060
aaaatgaacc ccaataatcc atgcctcttg gtagttatgc cctgtgtaat ctcctcccca   51120
tgagtgtggg ctgacctagc aacttgcttt taactactat aaaatagcaa cagtgatggg   51180
ctgtcatttc tgtgatggtg ttacataaga gttttacttc tgttttatta acagaccctc   51240
tcaatgcctt ctcagcttgc atactttgat gaaacaagca gctgggttaa gagatgtcca   51300
tgtcgcaagg aaatgagggc agcctccatc aacagccagc aaacaactga ggctctcagt   51360
ctgacagccc atgagtaact gaatcctgcc aacaagcatg caagcttgga agcagatcct   51420
tccccagtca agcttttgaa tgcaacctca gcccctgctg cacttaatg gtgccttgtg   51480
agggccctgt aggcagtgga gcaagctaag ctgtacctgg attcatgacc cacacaaact   51540
gggaggcaac aaatgtgtgt tgtttttacac cacaaaattt gtggtaattt gttacacagt   51600
gacagattaa tacaagtact gagtggggaa ggttgcatat accattcagc caaagctctc   51660
ttgttaactg gaaccaccct aattacaaga taatttaatg aatgactgtg ttacctgaac   51720
acacccttca gagaccccat cacttgcatg agtcagagct ctatgggctt caagtgacag   51780
aaatccattc taattagctt aagtaaaaaa gggatttgtt gatttacata cctgagaggc   51840
caagggtgta ccaagcaccc tcaatttcag atctactaaa aaggactctg actggccctt   51900
tttagataca tgccaatcat taaagattta atgtatctat aataagatac tatataataa   51960
gatattagga ccaatcattg tgtctagttg gatagagttc tctgagtggt tggcttgggt   52020
ttcatgccta cccttgcggt ggagaagggg agaagaacat tacatttgaa agccttatca   52080
tgtaatatac agatagttac ccaaagaaat ttttttttt ttttgctcta aaaaggcgag   52140
aatgtacaca gggcaggcag gcaaaacaac agctgtctac tatactgcct actcccagc   52200
tgggaggcaa agtgactcca tcttggatgc taacctgcca tgttgacttc tgattagcca   52260
caatcctgtg aatatctcct gattcctact ttatttactg tttgtgtata agaacatgtc   52320
aaccttgatg ttatcacaca cattttttgcc tgtttgggag ggtcgccttt aattgtcttg   52380
ctggagcatg tataccattt tcctgtcata ttcatatata agccttgggt cagcagagta   52440
acagtgcaaa gatttacctg tcttgtggct gcctaagacc acacttctat ctgtaagttc   52500
ccccaataaa acactctttg ccaacaaact ggatttgtct gtcttgttct ttggtttctc   52560
agctcctttg gcacttgagg gccaatttgt atatatggcc ctttcacaga acatcagcat   52620
ctcatgaaaa tattgcttcc catcacatac aaacttctct tccaaagaca ttctggtaaa   52680
tgtggaatat tgggtctctt tagaattcca gtgatttttag acatttttta ttgaattata   52740
taatattcac atatcctaag agtacaaata gatgaatttt cacgaactga gttcatctta   52800
aaccaccatc cagatgaagg cacattaccg ttatgggatc tttgggatgt cgcttttctg   52860
gctggaaacc tctgtggccg ttggtgcctt tgcctgagtt cttgtcctgc atccaggaag   52920
aatgaagtat gcagacaagt ggagggtgaa caagataaag aggagcttta ttgagtgtga   52980
```

```
gaatagctca gaggagacct gcagtgggta gcacctctct gtaggcaggc tgtcccaccg    53040
agtaatcggc tctcagcaga aaggaggccc tggagagggt ggcctctctc tgccagctgg    53100
tcatcctgtc acctctgcag ctcttagcag agagggtagc tcctcggtgc atctggtcac    53160
ctcatatccc gctatcagca gagacagtag ctcatctcta cagaatggtc atgccatcat    53220
ctctctattc tctgccctgc tctggctgag cctggggttt ttatggacct cagaggggag    53280
gaagtgcaca gcaactggtc catgggcaac catggatggg ccagaaaagg caccacaggt    53340
ccccactctg gtacgtgggt ctggaagccc tgccctcagc ctttgggacc tccctggtct    53400
gaaggtggag ccttatggag gacccatctc cttctgccca ggaatctgtc tgcctcctgc    53460
tgctgttcat ggctgcctag actcagcccc aacgttgttc caagattgga gccagcacca    53520
acagcaggga aaaactaggc agcaggacag gttctttgga gcctgcaagg gcaggggggcc   53580 ttcctaggcc cacaatagtg cagggatgcc tgaggctgca gcctggccca ggagggtggg    53640
gctcccacct gctccgtgga gttggaggct gggtctgca gcgtggtttt gggtggctgc     53700
agcggtactc caggagctcc tgccctaatt tgcaaggggt ggggctcttg cttgtccccg    53760
gctcctgccg actccatgga acatgcagcc ccaggctgcc tgccatctgc agccagtgtg    53820
atgacagcag taagccatct ggagtggcca ctgccatcat tactgacacc acagaagccc    53880
tgctttatgc ttcttttctg ttcttatcca catccctctc ccccattcca ggacaaccac    53940
tgtcctgact tctaccaaca ttgattagtg tttcctactt ttatatttta tgtgaaggga    54000
acaataccac attctctgtt ttgtatttgg cttttttgct taacattatg tttctaagtt    54060
tcatccatat tgttgtagtt ctagatttgt tcacatttct gcatagaatt ccatcgtgtg    54120
aatatatgac aatttattta tccattctac cgtctatggg cacttgggaa atttccactt    54180
ggggactatt atttaaagtg ctgctacaaa catgttagtg cttgtctttc tgtgaacaca    54240
tgtatgcatt ggcatacaca tatgagaatt tctgggtctt agggatggca tatgttcagc    54300
tttagtagat gctgccaaac tgtttttccca agaggttgta ttaacttaca atgctaccga    54360
tagcatatgt ggattctggt tgctgcacat ctttgtcaag acgtggcatt ttacatcttt    54420 tttatttttaa ccattctggt gggtaagtac taatatcatc ccattatggt tttaatttgc    54480
aattccctga tgactgatga agaggaacac tttttaataa acattttagc tatttgaata    54540
tcctcttgtt tttttgtaaa tcttttggta attgttctgt tgagtgtctt ttttcttatc    54600
gatttgtaga aattctttat aaattctggt taggagtgac tcatctaata taattattgc    54660
aaatattgtc tgcaactttta tggtcgcttt ttcatcttga tggcttttga tgaacagagt    54720
tctcaatttt aacataatct atactttttt ctaccttta tatttagtgt tttattgcgt     54780
cctgtctaag aaaatgtggc cacctccgaa tttaattcca gtgatgtctt atcatatcta    54840
agtgatattt taaggaccac acgttcaggc gacatcaatc atagacagta agacaggttg    54900
atagttcagt tacctttgaa agaggcttaa ttttaaatt tccatataga acccaatagc     54960
caacaaatat gtcttgggat gtcacatttc agtaaaatat tgcttccacc ttacttattt    55020
ttttgagtca cagcttaacc gtcaagttta gaggaaaact caaaatgttc tttactcaac    55080
ttttcctttt ctttcagaga cagcttcgcc taaagaaaaa agcacccatt tagtacaatg    55140
ggcttgtgtc tgatgctatt taatagcaaa tcactttctg tctcctaacc atagtaacca    55200
cgtctgcaaa agttgaagaa taattcctgc tatgtcaata ttgcagtgtt gttatgaaaa    55260
taacaacaat aacaatagga tgaaaaagtg cctgcaatgc agtgatactt tatgaagtag    55320
cgcactgcca agaatgttgg tgaataagag tgactgtaac acagagtctg aggcttatag    55380
```

-continued

```
cctatcgtgg tgacaggaag gtaccataac caaaattttc aaggagaaag ttaatctacc    55440
agagattaac tcttttgatt atctctggag aagtgttcct tcttgtacca ttcttccaaa    55500
gcacagccaa aggctttata agtttatatg caaataataa aatcacacaa ccaaatctgt    55560
aaaagattca gcaggtgaat gtcaatcttt aatatgatac taacatttat actgtacaca    55620
aacctatggc tctgttttgt tagttcctgc tcagaatctg actacctttt tcactgaata    55680
ttttggaaag ctaactactc tttcaaatcc tgccttttga ccaggtacag tggctcatgc    55740
ctgttatctc acctactctg gaggctgagg tgggaggatc acttgagccc aggagactgc    55800
agtgagctag gattgcacta ctgccctcca gcctgggcaa cagagtgaga gtctgtctca    55860
aaataaaaat aaaaataata aaattctgcc actgattaaa cccatttttca aaaattcttt    55920
aagcatttct gtgagagaca gtttacaaga cccatgagaa aacctgtctg tttactttat    55980
agtgttattt ttaaccaaaa gtggcattat ccttcttgac atcagacttc actttgaaag    56040
actttagact gtgtctaaaa tcacagccac catccaagca aggttggcat cagtcaagtt    56100
gtttacatac aagtgcacag acatagggtt tctggagtta aaaaaaaaaa ccaaccaacc    56160
aaccaaatca tcccctctt ccaccaaatt ccaggacacc cagttaaatt tgaatttcag    56220
ataaacagtg aataattttt cattataatt tatgtcccat gcttataaca aattcaaatt    56280
aactgggcac ttgtattttg tctggcagcc cgacccaggg ctgaaaataa ttctagaaga    56340
agagtttctg aaactgcttt gttaatggca gcattatgag actagaatat agtctctcaa    56400
ggcaacagcc ctcatttaca catctaaatt atgagatcct tttttaagaa aggggatcac    56460
ctgatctttc tgtaagactt cattacattg tagtcaagaa aaggacacat tagcaggtag    56520
caagcaaaaa agtatgtgaa tttcattagt gttcattgtt tgttacacct tgaccaggct    56580
cttaaattag caaataagca gttccttata acctttccaa aatctaccta tgtttattta    56640
agttgagtca gatcaactgg ttttactcaa atattgtaag gaataatgaa taaaacaaat    56700
agaaaagtta tgctaccaca acaacaaaca aaaagggaaa ttccccattg aagattggtc    56760
tgtgaggacc acttcctggt cttaactttg cttcctctga ctccattggt agagaggtac    56820
gcaaatttct aagggagcac cctagtgcct cataactctt tggtttaacc atcatctagt    56880
aatagccacc tgtcattaaa aaacccaagc agtgaaacac tgccaacaca tggaaggcgt    56940
atagaactga gagggctgag gctgtcaggc atgggaacag gtattttgt atccttttcaa    57000
atatttcagt agtgcttatt atatagtcag tgtcttcctg acacagtatg ccttctattc    57060
tcaacatgaa tttccttaga gtcacttttc tttgtgcttt cgatagtttc cagttttatt    57120
tttatttatt tatttatata tatatattta tttattttct atttatttta ttattattat    57180
actttaagtt ttagggtaca tgtgcacaat gtgcaggtta gttacatatg tatacatgtg    57240
ccatgctggt gtgctgcacc cattaactcg tcatttagca ttaggtatat ctcctaatgt    57300
tatccctccc ccttcccccc acccacaac agtccccaga gtgtgctgtt ccccttcctg    57360
ttttattttt aaaagggaga actcaccttt ctgtaaaaga acatcaatag aagaattttg    57420
ccagaaagaa agaaaggcaa tacagagtct tttctaattc tgtcaatgga aatgtctttt    57480
ttaaaaaata cacaggcttt ctttgattag tcaattttt tccccaagag ttgtatctca    57540
ctgagtacag tttttttatt caagagttgt atctcacagt gagaaagaaa gaagaaaga    57600
aagaagaaa gaaagaaaga aagaagaaa gaaaaaaaaa aacttgaaat aaagaaactt    57660
gaaagaaggt tgagaattgt tacttatttg caaatcttga gttttggcct gagagtggag    57720
```

```
agtaattgga acattgaaga tgaaaaaatt tctaagagat taaaaaaaaa aacaagaaaa   57780
gaaaaaagaa aagaaagaga aacaactatt aattctaaga aaagcacaag gttacataaa   57840
aaagccaatt tcttcttagc acattgtgtg acttagctgt gaataatatt tatataatca   57900
aaaataaaat atgtgttgac catttctcta acaaaaaatt atgacatatc tctcttgggg   57960
aattatggaa caggaagtgt gtgtatatgt gtgtgaaggt agggaaagga gggggctagg   58020
taagagagct aaatttccct agcaggaaat taacagaaaa tacctaagct ttaaaacatc   58080
aggaaatagc tatcatacat agctacgtag acatatagtg gtcaatatta aaaagaaaca   58140
actaaaataa tataatgtac tttttttttt tttttttttt tttgctggtg agtggaaatc   58200
agaggtaggg acactattgc tgttttggtt aaaagcctta tagccttatt tggctgtttt   58260
gctgatatac acgtattagc ctaatacaat taaaatttta ataaaatcag agacccttcc   58320
aagaaactaa tattcaaaaa aacaaatatc aaagtaaaa aaaataataa aacaagagga   58380
aacaattgtc tggggccagg gtagggtact actcctagtt ccaagccagt ttttaaataa   58440
atggacttta ggaacataac ctgttcataa ggatggactt tccacatttc aaacccagta   58500
atggtagaat aactgcctta ggagattcta gatacagcct ttctttccgc caacttgccc   58560
cactgttcga ctgtttctca tcatgctggg ggtgaacagc atcctctcgg atgcttgtaa   58620
agcaatggcc tgaacagagc taatgttttt aggtccatgt aactccattt tcctagacat   58680
aaagttgaga gttaagtttt gaggcctaat ggtccctttc ctaatctgag aatgagttgg   58740
aaagctcagc tctccttcct ttctctgggc tgctcctttc caggtgaagg ggtttgtgat   58800
gttgtaagcg aggagatttg tcagattaag cacacagggt gccatggaag gtaaattaaa   58860
ttgacgatag attcagctta ataagacttt gcaaactttc caaattcttc agtcaagctt   58920
caaatttcca gggaaaagtg aaagctctta atttactggg tttaggttgg tctgcccaag   58980
ttttccactt gagtagtaaa atccctccaa cttctagaat tcgaagagca gccagggctg   59040
agctgggagc atttctccca tctgtgatag gccaagcttc tcaggaatca attatccttc   59100
ttttggcatc aaactcccat tagccaatga cagttccaac ataaccacct ggtccaggtg   59160
gctacactta ggagaagaaa gtagggggta gggggaaaga cccccacagt gcctttgagc   59220
agagctcttg caatgtgaag agatacttct tgcaccttta gaggaaagga aattccgaac   59280
atttgctttc tgctgttgtt ccttcttctc atcttagggg ttctgagccc atttgcttca   59340
gtataaagat agttctatgc tagttcagtc acagagaggg ctggaccaga cccttgccag   59400
aatctccaga gacaagtgcc catgccatac agagcccaag agttaagaat acccttgcta   59460
ctctggtgcc acattggtat gacatctccc ttaggcattc cttagtcctt gcagtagaag   59520
aagcccacct tatcttaaac ctgacatgca aaaactgagt gataaagtaa attaaagaat   59580
gagtatctgt tttgaagtat gatctttaca aagggttca ccaaagactg cttagattat   59640
tagattgatc aaaaaatcaa tttatgatac atcttttttca gatgcgtatt atataaaaca   59700
aaagtgctaa gactgggtat aactgctagc aacaacaata caagtagcta gaaccaaaag   59760
catgcaccac catgcccagc tgattttta attttatttt agagatgggg tctcactatg   59820
ttgcccaggc tggtctcaaa cttctggact caagtgatcc tcctacctca agcatcccaa   59880
agtgctggga ttcagctat tttatatata tatatatata tatatatata tatatatata   59940
tatatatata cacacatata tacacacata tatatataca catacacata tatatgtata   60000
tatatacata tatatatata cacacacata atttactttt ctcatgagcc ttgtctgcgt   60060
gattagaata taagatccat gaagtcaaga ctggtgtgac acatttctttt ttatcttagt   60120
```

```
ccctgatata gtttggatgt tatcccaccc aaatctcata ttgaaatgta atccccaatg    60180
ttgaaggtgg ggcctgttgg gaggtgattg gatgaatgat gggggccgat ctctcaggaa    60240
tgatttagta cttccccctt tgtactgttc tcgtgatagt gagtaagtgc tcacaagatc    60300
tggttgttta aaagtgagtg gcatctctct ccaactctct tggtcctgat ttcctcatgt    60360
gatatgcctg cttccatttt gcgttccgcc atgattctaa ctttcctgaa gccttcccag    60420
aagctatgct tcctgtattt gccttctgcc atgattgtaa gtttcctgaa gctttcccag    60480
aagctgatgc agaagctatg ctttctgtac agcctgcaga agcatgagcc cattaaacct    60540
cttttcttct taattactca gtctcaatta tttatattag caatgcaaga acagactaat    60600
acagtcctta gcccagatct tacacataat aggtattcaa tgtacactgt gtgttgttga    60660
tattcacaaa ttacttcctc tctttctaca aaatgttgaa taatacctcc atcagaaaaa    60720
cctgggttaa agtaagggta ttttttgtcta tctgcaaaaa gataaacata ttctaatttt    60780
tctataatga ttgcgggtag agataatctc tgccctcaac aacactcttc cctcatagag    60840
ggaaatgaaa ctacaaatgt atttgaatat aataatagtg aaggaaataa tgtatgctgt    60900
ggtccgtttc caagacaaag tgccttgaat cggtttaggt cagcaaacca cagaagaaat    60960
aggatatact aggcccctgc ttggatagcc aatgcctgct tgtcaccact tccccttagt    61020
tgccctcacc caaccaaag aagtttagtc tgaaatgaaa gcttactagc ctgcaaaata    61080
gctcgttttt tctgttctta ttagcctacc cagctactta ggtcataagt caaatacttg    61140
agttcctaag ctaactagga ttgcaatgta ttgtgggctg caacaaaatg cagcaggaca    61200
accctaaaga aaacacctaa agccactacc caacaaccga taggcaatgt ccaggaagac    61260
tgtgacccca tagtactcag cctgtgagga accgggggaa gggacctgtg cattaggaa     61320 taaattgctt tttgtaactg tgctgggtgt gcctgcccac cggacagcca atcttgcaag    61380
accatcacga aaaatctcac ttttactgtt ctctgggtct ctgagtccat tctttgggct    61440
tggatggtga gtttgtttct cacaatagca acaaatgcaa caacaacaga agctaatttt    61500
tattgggcac ttactatatg ccaggatctg cttaaagcac tttacatgtg ttagcttatt    61560
caatcctaaa aataattctt ctaatcacat gcctccacat tgtcttaaga aactcatcct    61620
gtgttcaaaa gctggataat tttccaattt tacagaatca ggttgacata ctctacaatc    61680
ctagtcagca tgataaagtg acactcatac attcatttga aagactttag ggaaatagtt    61740
actacattgg cacagagatg tggtgcctca actctgtcat gaaattagga cttgtatgtg    61800
ttacaagaag aggtgtggat gaactaaaga aattgtttct atgagtagag attttgaaac    61860
agagagtcca ctggatccca agtcactgct gtgtgaactc actcaccaca cgggaattct    61920
ccaagtacca tcctgcctga ctcattaatc ttatgaagca cagagtgatc acacatgccc    61980
ctgaaatgac tgtatgtaaa gtaaattcag gctgtaacac acaaagtttt caaggttggc    62040
ctcatagcac tgtagattcc cccagcagat gggcagagga aggaaactta ctctgtctga    62100
gattctctcg tatttccagg gcaacaaatc atgcgtaatg aaaacaaagc aaagtcagta    62160
ccagcccagg gccagccatc accccaccca aaccagaagg gcaggagcct aattcatgaa    62220
atgtgctgtg cttcttcctc cggccagcca ggctcgggggt ttcctgatgt gttcctggaa    62280
ccagagctaa tggaatcagg aaagcatgtt actttgccac tgccagtcat tgcaagtaca    62340
acaaaataaa tattgcttta agaaaacaa ttatcataaa gacaattagt aatgaaaaca    62400
gttatgcctt cctttgtttt tgagacaggg tctcactctg tcacccaggc tggagtacag    62460
```

```
tggcacaatc tctgctcact gcaacctccg cctccccatt caagcaattt tcgtgtctcg    62520
acctcccgag tagttgggac tacaggtatg catcaccaca tctggctaat ttttgtattt    62580
tttggtagag acggggtttc aaccatgttg gtcagggtgg tctcgaactg ctgatctcaa    62640
gggatcagcc cacttcagct tttcaaagtg ctgggattac cagcgtgagc caccgtgccc    62700
gacccagttc cgcctttcta aattggcctc ttaatatttt agaacatttc attcctctgg    62760
ccttgagtga agaatagaaa ctacagaggg aaggatttgg agtggctaat gttggcagaa    62820
gtgagaatca gaattatgga actgcaaagt cctatgacct tccatttact gaagaggaaa    62880
cagaagcaca gcaagagtgc tcaagagact tacctaatgc cactccacac agtaagtact    62940
ggaatccggg acttggactg ccaattccat gtgctttcat ttgtgacatt acttttttt     63000
ttttaaaaaa aaagaacaat gtaatgtttc aataaaattt aaaatttggg ttaaaaatca    63060
cctataatca taaccttctg ataactatta tcattcttgt atgtttcctt ccaacattat    63120
tttcatacat ttaacataat catagccatt aaccatatgt gtttctgttt ttttttgtttg   63180
tttgtttgtt tgttttttgag acagagtctc gctctgttgc ccaggctgga gtgcggtggc    63240
gtgattttgg cttactgcaa cctcggactc tcaggttcaa cggggttcaag caattctcct   63300
gtctcagcct cccgagtagt cgggactaca ggcgcctacc accatgcctg gctaattttt    63360
gtatttttag cagagacgag atttcaccat attgctcaga ccggtctcaa actcctgacc    63420
aaaacgaagt gtttttttaa cctacaattt aagtaaatgt ttaatgttta tttataattt    63480
atttattaaa tgtttacatt caccaggcac tattctaaat aaaacaatgt tgctgtcctc    63540
acataatgaa gattctggag gggtcaacat agaatacgta cataaccaag taatgtacaa    63600
cattccacca tgatgaagat aatttgttcc taaataaagg tcctcgtggg tgaattctca    63660
taggctgaaa atgtacctaa cattcatttt gacagaaaag acactctttt ctcttaagcc    63720
cccaaattaa cacctatttta tgttaaaata acatcaatcc cattaaaaca ggtacaatta    63780
tctcaaaggt aaatggttat cataggactg atgtctgtgc tcataaagca tcaaagcaac    63840
catatgattc tctgcgttta tgtaattaaa tgtttaatga aaaacaaaa acaaaaacat     63900
gagctctttt ttgtggcacc ttggaggcaa ttagctgctt caggatgaag ctaaatatct    63960
cctcccccagc cactggctga cagacactca ttggattgga caacgaatgg caattttgta    64020
cttatgagaa gcatatggca cagaggttgc tgccgacgct ctggaagagt tatgtggtcc    64080
gagtcagtgg tgggaccaac gaacaaggtt tcctcatgaa gcagtgtgtc ctgacccatg    64140
gctgggtctg cctactgcta ctgagtaggg gcattcctgt tatagaccaa ggagaactgg    64200
agaaagaaag tgcgaatctg tttggggttt cattgtgcat gccaatctga gcattctcca    64260
gttggttatc ttaaaaaaaa aaaaaaaaa ggagggaagg atactcctgg actgactgat    64320
actatggtgt catgttgctg ggggcccaaa agagctaaca gaaatgcaaa cttttcagtc    64380
tctctaaaga agacaatgcc ccccacccat atgttgccag aaagccctta aacaaagaga    64440
gtaagatact gaggaccaaa gcacccaaga ttcagcatct tgttactcta catgtcctgc    64500
aatacaaaca ctggtattgc tcagaagaaa cagcatacta agaaaaataa gaaagagcca    64560
caaaatatgt taaactttttg gccaagagaa tgaaggagac taaagaaaaa ctccaggagc    64620
aggttaccag agacacaggt tgtcccctct gtaagcttct acttctgagt ctagtcaaaa    64680
ataagatttt ttgacttact taacaaatga gtaagatcat accaccccca gcaaaataat    64740
caataaagac taaggacatt gatgaaaatg atggagaaga tgatgacttc catgagtact    64800
ttaaaggaga aacttaaagc aacttgtata attttttaaga ctgcagagct gacatgtggt    64860
```

```
aacttatgct gaatctgctc agtagcttcc cacagccccc aaatctgaat cacattcctt    64920
caatgtgaag aatgcctcat aagctaaagt tgaggaacta aataaactga ttaagtctct    64980
gtcttatgac acctcccacc ccctatcaca gttctatcca gggcagcatt gactagcgta    65040
atagcagggt gtgatatgtg gtaggacaga taggatgggg aggacaggga atgatgttag    65100
gtggagatgg gggaatgaca aggagtctgg tgtgagggag cccactgagg gagggctagg    65160
tggtagaagc taatgctggc caggtagcta ggtgctagat tagagagcac cttgctagcc    65220
acactgaaga cctgagtact ttggaagcca gtggaaactt ctgagcaagg agtgacacaa    65280
tcagactcat atgtgagaag gagactgtgg gtgagggaga taagttaggt gactattgtg    65340
gggttcaact gaaagaggag gtaaaagcat gggtcaggt tacaatggtg cagacagaga    65400
gaaatagtta tagtttatct gtagtttgaa tataaaacca accggattcc ctttgaattg    65460
aatatgatac atcagggaaa aagaggaatc aatcttagtg catactctat gtcaggcctt    65520
gttcctatgt tttacatata ttcataacaa taaaaataat atcaaatgcc tttctaatac    65580
cttccctatg ccagattcta tatgctttaa tctactttca cccacatcac ccttactgca    65640
atcccatagg gtaggcacta ttatcatttc cattttctga tgagaaactg aggcacagac    65700
aggaagggca atgcacacgg gaaatgctgg agctgatttt agaccccaga cgttctggct    65760
gcagagttga gattcacaat cactgcaaac actgcattcc atggtcacaa ggttttggtc    65820
cgagcagttg agtgggtgat gttgctatcg accaagacag gaatacctga ggcagagcag    65880
gtttggggga gtggatagcg aaggcctggg ttttggcca tgctaagttt gggatgcctg    65940
ttagacctct aagtggaaat gttgtgtggc cataggggt gaagaatctg gagtttagga    66000
aaggagccag aactggagat agctgagcta tatggaatga tcagctcata aacagaactt    66060
aaagctgcgg gacaggatga aagtactgag gaagactaag tcctggtcac tccagcattt    66120
acagtccaga aataggagga gctccagcaa aagagattgg gaaggagtga cctgtaaggc    66180
tggaggaaac caggagagtg tgctggaagg taaaaaattt ctaggaggga atgatccact    66240
ctgtgaaatg ctgctgagaa gtccagcaaa gggaggatgc tgccagatgt catgatgctc    66300
agtttaattg ttgcatacaa cttcttcaag tggaagaatt ctcttttat ctactcttgc    66360 attttcaacc ccttcacata tagctcacaa agtagaggaa gagagctcat ctaacttcaa    66420
cgtgaagttg ttaatttgaa ttcagtttaa atatttattg ggtgtcaggt atggtactag    66480
gccacagaga ttcaggggta agtgaatcac agagttcttg cttttttttt tttttagac    66540 aaggtctcgc tctgtcaccc aggctggaat acagtggcaa tcacggttca cggcaacttc    66600
tatctcctgg ggctcaagca atcttccac ctaagcctac caagtagctg ggattatagg    66660
tacatgccac cacatgggta tttatttat ttttgtaga gatggggtct tgccatgtgg    66720
cccaggctgt tctctaactc ctggcctcaa gtgattttcc cccttggcc tcccaatgtg    66780 ctgggattat aggcatgagt cactatgctg ggagggttct tgctctagac aatggactaa    66840
gcaatgagaa ggaggagggg agggaaaata ggaggaggag aatgatgagg aggggtgctg    66900
gggaggaggg gaaaggagag gagagggaga aggaaaggaa agggagaagg gaggaggaag    66960
aagtggagaa agaagaatac catgataata ttaatattaa catttggagg ttgcctaatg    67020
aactcagcca gaacaccca tagaaaagcc caatggttga cacacctccg cttaacaggc    67080
cataaagtac taggggagaa ataaaggctt tttcacatat gctcattctc aaaataatga    67140
tctcctgtgc atgctttctc aggacgctac tggatgatat gcacgccaa gacaagggag    67200
```

```
tatccaaaga agaaacatga gattcaggca ataaagaatc agtaggatac aggccagaat    67260
aattcccacc atattttaaa ctgagatccc aagacaaaca ctgtgcacca ggtctagata    67320
acaatcagtc cacattgatt gcctgatttt caaaacatat taagtggagg tttacgctct    67380
tggggaagag tttgggaagg agattatggg ggaaggttgc aggggggtgtt tcattttttga    67440 ttttgtttct gagtatgtag acattccctt agttccccag tgttcaatac agaggccgcc    67500
tcacagttac atcagtgttc cctgtccgga gtctcctgtt aagttctgtg agtaagactt    67560
cagtcttctg ctaggctagg ggagggacag ttgcccagct gcacagggta ggcaagggga    67620
taggtgaaat gtcccttcat acagatttgc aaccaactct gttttttaag tctctatccc    67680
aacataggcc ctgcttcaag agctatcaca acatccaatt cctgctcctt tggggcttc    67740 tgagatacaa ataagcctgc ttctaagacc ttctcatgct gctgtcttga atttcagctt    67800
tctctgcttt tctaagtgag tctcttctta ttcacctgct ttttggatcc cagaattata    67860
tgagtgtttt gttttttgtc tcttactctc tttatcctta tgactagagt cattttttgtg    67920 aagtttggaa gggaacaaaa ggtaaaatat gtgctcaatc tgccacactg tttaaaaagt    67980
ggttttcttt ttaaattacc aaatatatgc atacagttta atatatatta taaagtgaat    68040
gatcattaac caacactcaa atcaagaaat aaacattgct agcttcccta agccccccca    68100 tatgtccccca cctgattaca actagttctc tcccttttaga tgtgacacca tcctacctttt    68160 tatgattact gcttccttct tttcctttac agttttacca cctatgtatc cattgtgaaa    68220
caactgagtt tagcttttgcc tgcttttgaa ttttatgtaa atagagacat atggtgcata    68280
ttcttttgtg tttggtttct tttactcagc tctgtaaaat tcaaccacat catcattaca    68340
tatatccact ttggttatac acggatacca cagactatcc atgttactgt ggatgtactt    68400
ctgagttgtt tctagtttgg agtaaatctt aatgctatga atattcttgt acacactctt    68460
tgtgcacata tacacacgtt tcatttggta tgccacaaga agtggaaatt ctgtggcaca    68520
gtgcataaac atcttcatcc ttctagatat tatccgttgt tttccacagt gcttgtacca    68580
gcagtctatg caagttccca gtgctccacg tttgtgccaa cattggtatt gtctgacttc    68640
agtggtggct gtacaaccta acgtgttcag ctggaaatac cttgttaagt tttccatgta    68700
ccttctatcg cttcatcact gcacttttgg aaagagcttc taaaactcct ttcttataga    68760
gggcagaccc ataaggcaac ctacatgttc cattgttttt tcttagagaa gatttcaggt    68820
agagcttctg acaacctgct ccaattggga ctagctgctc actaattctg cctcaatcat    68880
ccgtttcctg aatctcatgt ctttttttttt ttctgcattt ttcccgtttt catagagcac    68940
atcttccaga agcttcatga gaaatgatgt gtaaggaaat actattttttg agaccttgca    69000 tatttgaaaa tatctttatt ctccactcat agtaaatagt ttgggtagag aattttaggt    69060
tggaaataat ttttcataaa aaactttgaa ggcatttttta ttttcctcta gctttcgatg    69120
ttgctgttga gaagtctgat gccattctga tttctgatct ttgtatatga cctatttttt    69180
tttccctctc tatggaagct tttaggattg tctctgtgtt tctgacattt cacaacagaa    69240
gtgaattgtt aaattcacta cacacttggt gagcactttc agtatgaaga atatgttctt    69300 aagattttttg gaaattttccc tgaattttcc tttgataatt gccttccctc cactctttct    69360
ctagaattcc tagagtcatg ttttcaacct ccagcattaa acctctaatt ttcttttcctt    69420 tccactttta tttttcatct ctgggtattt ttgttccact ttatagaagc tttcctcaat    69480
tttatctcct aaccccttcca ctaattctgc tcctatattt tttagttttcc aagagctcct    69540 tcttattctt tatatgtgac atttttaatag gaaactcttc acatttaatg aaagcaaaat    69600
```

```
tgtcctcctt ttttagaaaa tggtaactag ttttaaaatg ttttcttttg cctctgcatt    69660
tactgttttc tcaatgtttc ttttacagtt tattttggac tctgtctcct atgtgaaagg    69720
ttttttccaa gtggctagtg atccctaact gaccagttca tgtgaagggg agaggcacca    69780
tgagctaatc agaaacttat gcggaggggg gacatacaga ttagagggtc tcactttagg    69840
ataaccaggt gggagccctg tcttttata gcctctaaat gccagttttt gttttgtttt     69900
gttttttgtc tattcttttg ggctgcttgg ttttttctaga aaggaattct ctccaatcct   69960
gcctaaaata gtgtaagtct ggtatttagc attctgggag cctggtaggg gaaagggtgg    70020
atgggtcagg gatggtggag tgttgtctca ctcttcatta ggcgaacttc tctgattttt    70080
attttccagt aaaatgcctt gctctagccc ttagctgtga ctagtgccct taagccagag    70140 tttttttggtt tttgtttagt ttaacctctc cagaaagggt atctttagtt ttctgtcaag   70200 aagagggag gagcagttac ctggctgccc agtctaggag aggggaaagg atgtggtctc     70260
taagaactcc gtatatgagt ccttgggttt ttcattctac ctcatatctc tgcctttaga    70320
ggtatacagc atatctgatt ttggatattt cttaggggat gtattagtcc gttttcacgc    70380
tgctgataaa gacatacccct agactgggta attcatacag aaaagagac ttaatgggct    70440 cacagttcca cgtggctggg gaggcctcac aatcatggtg gaaggtgaaa ggcaggtctt    70500
acatggcccc agggagaatg agagagaaag agagagagag agaaagagag agagagaatc    70560
aagcaaaagg ggtttcccct tataaaacca tcagatttct tgagacttat tcactaacat    70620
gagaacagta tgggggaact gtccctatga ttcaattatc tctcaccagg tccctcccac    70680
aacatgtggg aattatcaga gctacaattc aagatgagat ttgggtgggg actcagccaa    70740
accatatcag ggagcactat agcacagatt gttttgttct tgttgccttt catcttttat    70800
ggtatttaac aaatgaagaa ggctaaaatt gaagttaatt tccacttgtt tgtctgcatt    70860
cattcttcca aaattgtatt gaatacagtc gataaattgt atttatctgc agtcaccccc    70920
tgtctccttc tctttgtccc tataagctaa acacctttt tattcctta atgccatttt      70980 agtggagtat atacaatcca tacattttcc taggtatttt tctttcttca ttcatacttt    71040
ctatatccaa aagaggattt gagcttgttg caataaaata tacatatgcg aaaaagttga    71100
aatttgggaa aagtaaaaaa tatcaagtag taaaagaaag gaaacacctg tggtggaaat    71160
ctaggctaag gatataggcc gtgactgtac aaaggttggc ccttactaaa caccttggca    71220
gttctgctaa aaggaggaac aggaggaatt tctcagccct cattatctaa caggaagcac    71280
tccagggcat cagataaaac ttctgctaag tttactgagt gagttgattc tgtaactgaa    71340
taaaagttct tggtgctcca acttggaatt gattctactg aagagattag agtgagaccc    71400
agataagaaa aataaataaa taaagataga tgtgagggggt agggatgcta agtcttgatt   71460
gattggcatc tttcccaact caagcactgt gatgacacca tctgttgtta ctcactctat    71520
attcccaatt tattcagggt ttctaggtgg aaggacatta agaaagtacc ctgtagagga    71580
attcttatag tcttctcttt cttttccatt tcaacaggat attctcagag ccctctagca    71640
actgtgactg tgatttcaag gcaagaagta aacagacagt agggaattat gttaggagta    71700
tatattcctt tacttttcct ctcaaagaga gagaaaatag gctttttttt tttcctgata    71760
agaaagtgta tgagtaagcc tagattcagg gcccaataag atcatgctca gattttcaaa    71820
ttacagtttt agaaattttg ggggaaattc ttgatgccaa aaggcattgt gaaatagtat    71880
caatacaatt gcaggtttag catttctctt atgcaataaa cagtacaggg ctctgggggct  71940
```

```
ttacaaagat gagcaagcaa cagtcccttt tcccaaggag cttacagtgt ctcacaggag    72000
ataataaaat gacacaagtg attaatagag gagagagctt cagaatgtct agccagctac    72060
acatgtctag ccacctgcct acatggagac ccagtcccct tttcccaccc acaaggtgaa    72120
tctgggaagc cacaaacagg aaccctgccc ttctaactgc agctgattaa attagaggtc    72180
aagagatacg tgacctaagg aaaaccaatt ggatttcctc tccaaagatt taaaattaga    72240
attcaaaggt gctaatcagt ctctgctgtc cactgattta agggcgtaga agcactggct    72300
tggatatttc tgaccaggca ccagtggcaa tgcagagaaa acacatctgg agagaaagag    72360
gcatgcagag tggctttcca gtcctgcttt tggcctcatg ggatccatga gatactccca    72420
tattaaaagt tttgattcaa acaactgtaa tacaatacta ctgtgaagac tatgaaatat    72480
atgctaaggg ggctcaaaga gggagagaaa gcacatatta ttgtggagca ggtgggatta    72540
gaaatagtga atattacat gaaaatttt tacgactgag ttcaccttaa atgatgggta     72600
agattctaac aggaggagat aggttgagag cattaattag tgaaagaacc atatggggga    72660
gagagaaacc aggtgtgtat gttccaaggt gcctgggggt ggttaggttt tatgatgaaa    72720
attaaatagc tcttggagta gattctatct ttgcatcagc tatgacgcaa gtcagcatat    72780
tctaggtcct ttctccactt ggaaagaatt actgccaatt atcagtccat ttccattggc    72840
ttccctctaa ctactttgct tcaaaaaaaa tgaaaagttc atttattcct atagttctat    72900
aaaagaaatc tactcaaaaa gatgtgaaat gacttataat gcaatactgt aattttttat    72960
ataaacttca tctttgtttc cttgttacag gataagtggt aagtaaatat tgcctagtaa    73020
tgtgacatga gtaacagaaa atacaaactt attttcgccc tagggaagcc tgcttacttt    73080
tcttgaccct cttctcaata tctatctata atcttcagat atagcaaagg gccagcaacc    73140
acttttctgg gaaaaaaga tattttgcca aactttgaaa acacaccaaa atatgggact    73200
gaaaaatagt gcatatatat caattgagtg cagtggtctg atcatagttc actgcagcct    73260
cgaactcttg gccttaaggg atcctcctgc ctcagcctca caaaatgctg ggattactgg    73320
tgccttgccc tattgtttaa actaacattt ttcataaaat actaaatgtg aatatcttcc    73380
aaaacttgaa agaactatgc agttataaag cattataaaa ataggcatat tagatatttt    73440
tatatgtttt taagttcatt gattagcgag aggaataaaa ctgaactcag tagaaaagtt    73500
ttggagagaa acaaaaaagt gaggattttt accttatagc taacattatc tacctcattt    73560
agagaaggat cttgtttta tactataatc cttttagaca acaagccaat gaaattttaa    73620
attcaaaggc aactcaaatg attcttgaca agggtgacaa gacttttcaa tggaaaaggg    73680
tagtatttta agcaaatagt actaggaaaa ctgaatatct acatgcagaa gaatcaagtt    73740
ggacccttac ctaacactgt atacaaaaat taactcaaaa tggaccaaag acttttttaag   73800 acctaaaatg atacaattct tagaagaaaa cataggtcaa gtcttgaaga tattagagtt    73860
ggcaatgatt tcttggatat gacaccaaag gaacagggca caaagtcaa taaattggat     73920 tgcataatga tttaaaaatt ttgtgcatca aaagacacta tcaacagagg aaaatgataa    73980
cccacaaaat gggagaaaat attcaccaac catatacctg ataagcgatt aatatccaga    74040
atatgtagac aaatcttaca attcaacaaa aaacaattta aaatgggcaa aatacttaat    74100
aaacacttct ccaaagaaga tatgcaaata gcaataagca catgaaaagg tgcccaacat    74160
cactaattat tagtgaaatg caaatcaaaa ctacaagata ccacctcaca cccataggat    74220
ggctactatt ttttttaaaa agaaaataac aagtgctgac aagggtgtgg agaaattaga    74280
atgcttgtgc actgttggtg ggaatgtcaa atgttacagc cactgtggaa aacagtatgg    74340
```

```
cagttcttga aaaaaaaaat agaattagtg tatgatccag caattccact tttaggtata    74400
tgctcaaaag aatagaaagt aaggatttat gaaacatttg tatattcatg ttctagcagc    74460
attattctca atagcaaaaa catggaagta accgaagtgt ccactgacag atgaatggat    74520
aagcaaaatg tggtatatcc atacaatgga atataactca gtcttaaaaa ggaaggagat    74580
tctgacctat gctacaatgt ggatgaatct tgagagtatt atgctaagtt aaataaaacta   74640 gtcacaagaa gacaaatgct gtatgattac acttatatga ggtattttga gtattcaaaa    74700
ccacagagac aaagtagaat ggtggttgta gggggttagg ggatgggtca atggagagtt    74760 agtgttttaat ggatatagaa tttaagtttt acaagatgaa gagttatgga gttggacgtt   74820
ggtgatggtt gcatgacatt atgaatgtgt ttaatgctac tgaattgtac actttaaaat    74880
ggttaagata gtagatttca tcttatgtgt atttaccaca atgaaaaata ttgggaaggc    74940
caggtgcggt ggctcacgcc tataatccca gcactttggg aggctgaggt gtgtggatca    75000
cctgaggtca ggagttcgag accagcctgg ccaaaatggt gaaacccccat ctctactaaa   75060 aatacaaaaa ttagccaggc atggtggcag gcacctgtag tcccagctat ttgggagcct    75120
gaggcaggag aatggcttga acccgagagg cgaaggctgt agtgacccag gatcgcacca    75180
ttgcactcca gcctgggtga cagagagata ctccatctca aaaaaaaagg ggggggggaa    75240
agtaagtcat atttcaaaat atactcaaga aatattttct tcaaaggatc tgagcagcca    75300
agtaaggggc agtccactgt gtcaagatgc ataccgttc tggtgcactg tgtgtctctc     75360
cattctgggt ctgcctctgc cttccacttc accgtgcttc tgcctcagtg gtcctggtgc    75420
cagtggtctt ctaagtagct ccctagaaga gaacagctgt ttgccacaac aagggaaaaa    75480
ctggagacta tcaacttgaa gtagagaagg taacagtagg aactggttat tgtcatagtg    75540
tttttaaatc tgagaacttt taactttgcc aactaaggat gattgatggg gaaagagtaa    75600
aatatctggg aaactggtct ctgagaaaga aatttgttcg gtggaggttg tgggtgagat    75660
ggatgcggca gagactgcta ctatccccta ggttccattc tctccttctt ctttagaaat    75720
aggaccttca gtttttagtt cagcatgtgg tcctctggta caaaggctac atttcccagt    75780
ctcccttgca actacatgtg gtcatgtgac taagttttgt ccaatgggat gtaagtggaa    75840
ctgccttgta aaattgatgg taaaagtcct taaagggcat agctatgccc catcagccct    75900 ttccttttc atactacagt ggaagtccaa tgtgaggata gcagaactgt taagagagga     75960
gttttaatcc caaacaactt tctatggcct catcccctga cctactccaa tcctgggcta    76020
cctatttctg tactttaaat tgaaagagaa tacatttgca tcttgtttaa gctattgtta    76080
ttttggtttc tgtcactcag ccaaactcaa tactacttga taaaattggt aaaaaaaaaa    76140
tgataaatta gaaaactgct ttatgtctaa tgaagcttta aaataaaaag tacttcctca    76200
tatgggttct ctgttttttcc tccaaaatgt ctatgaagac acagaaaaag aggaaattta   76260
caacattaga aattaggacc agtgcaactt agttgagaga attttctaat aattccttct    76320
tttgtctatt catttgttca gcatgtttat taaaaagtac ccctcatgtg ctaggctgtt    76380
ctaggcccag ggaatatagt ggtgaacaaa acagataaag ttcttgtctt catggacctt    76440
ctattctagt gggagaacag agaccaccat caagataaaa aaaataaaata taatgtcagt   76500 ttgtatatgt agatgaagaa aaacaaagca aaggaaagga gtagaaaatg atagacacaa    76560
attgtgaatt gagtggtcag agagggcctc ttggaggagg gtgacatctg agcagatccc    76620
tgaatgaaat gacagtggga gttctggtga tatctggaag aagagcattc aaagcagcga    76680
```

```
gaacaacatg tgcaaaggcc ctgagacaga aacaggcttg gcagattcca gaaatggtaa    76740
ggaagacgat gtgcttagag aagagtaagt ggatgaaaag aagtggtaag aagagatgtc    76800
agagcttgtc aggggacaga cagtgtagga taaattgaca ggagataagt tgattaaaaa    76860
tcatactttg tgtccactct gaaaagaaaa tgttgtgaaa tgatgggaag acctcttgtc    76920
cctccattac aatctacaat gggttcagaa tcataacacc tactctcatg agagagatgg    76980
agtattagtc cattttcatg ctgctgataa agacatactt gagactggt  aatttataaa    77040
gaaaaagagg tttaatggac tcacagttcc atgtggctag ggaggcctct caatcatggt    77100
ggaaggtaaa aggcatgtct tacatggtgg cagacaagag agaatgagag ccaagtgaaa    77160
ggggtttccc cttataaaac catcagatct catgagactt tttcaccacc acaagaactg    77220
tatgggggaa accaccccct tgattcaatt atctcctact gggtccctcc cataacacat    77280
gggaattatg ggagctataa ttcaaaatga gatttgggag aggacacagc caaaccatat    77340
cattctactc ctggcccctc ccaaatctca tgtcctcaca tttcaaaacc agtcatgcct    77400
tcccgacagt ccctcaaagt cttatttcag cattaactca aaagtccact gtctaaagtg    77460
tcatctgaga caaggcaagt cccttccacc tatgagcctg taaaatcaag aagcaagtca    77520
gttacttcct agatacaatg ggggtactgg cattggataa atatacccat tccaaatggg    77580
agaaattgac caaataaagg agctaaaggc cccatgcaag tccaaaatcc agtgggctg    77640
tcaaatctta aaactcccaa atgatctttt ttgactccat gtttcacatg caggtcacac    77700
tggtgcaaga ggtgggttcc catggtctaa ggcagctcca cctctgtggc tttgcagggt    77760
acagcctctc tcttggctgc tttcacaggc tggcattgtc tgtggctttc tcaggcacat    77820
ggcacaagtt gttggtggat ctacaattct ggggtctgca ggatggtggc ccttttctca    77880
cagttccact gcgcagtgcc cccgtgggga ctctgtgtgg tggcgtcaac cccacatttc    77940
ccttctgcac tgccctagca ggtgttctcc atgagggccc tgcccctgca gcaaacttct    78000
gcctggacat ccagatgttt tcatgcatct ctgaaatcta ggcagaggtt cccaaacctc    78060
aattcttgac ttctgtgcac aagcaggcac aacaccacat ggtagctgcc aaagcttggg    78120
gcttgcaccc tctgaagcca tagcccaagc tgtaccttgg cccttctag ccatggctgg    78180
agcagctaga acacaagaca ccaagtccct aggctagaca cagcagggg  tcctgggcct    78240
gacccacaaa ccatttttcc tcctaggcct ctgggcctgt gatgggaaag gctgctgcaa    78300
agttctctga catggcctgg agacattttc cccattgtct tggagattaa catttggttc    78360
ctcattactt atgcaaattt ctgcagcagg cttgagtttc tccccagaaa atgggttttt    78420
cctttctatt gcatcatcag gctgtaaatt ttccaaactt tcatgctctg cttccttttt    78480
aaaactgaat gctttcaacg tcacccaagt cacctcttga atgctttgct gcttagatat    78540
ttcttctacc agataccta  gatcatcttc ctcaagttca agttccaca  aatctccagg    78600
gcaggggcaa aatgccatca gtctctttgc taaaacatag gaagagtcac cttcacttca    78660
gttcccaaca gtttctcat  ctccatctga gaccacctca gcctggattt cattgtccat    78720
atcattatca gcattttgt  caaagccgtt caacaagtct ttaggaagtt ccaaattccc    78780
ccacattttc ctgtcttccg agtcctccaa actgttccaa cctctgtctg ttgccaagtt    78840
ccaagtctc  ttccacattt tcaggtattt ttacagcagc actacactgt accagtacaa    78900
acttactgta ttagtccatt ttcacactgc taataaagac aaactcgaga ctgggtaatt    78960
tataaagaaa aagaggttta atggactcac agttccacac ggctggggag acctcacaat    79020
cagaaggaga acggtatggg ggaaaccacc tcaatgattc aattatctcc cactaggtac    79080
```

```
ctcccacaac atgtgggaat tatgggagct acaattcaaa atgagatttg ggtggggaca    79140
gagcccaacc atatcagttg ggcagccagc catctgttgt tgggtgattt ttaccaaagt    79200
gcatctttct ctgtacaatc agaggcttcc acctccagag aatgtgttat cttaatcctc    79260
tggctggatg cttatgagga tagagtaaac tggcaatgcg cagtgaatct tgggaggggt    79320
catccttaca aataaagcac tacagtttgg tagagatgaa agaacttcag atgcagtgga    79380
tgctgtaacc gatggctttt atgatggtat ttcatggtga tagtgtgaga acgccagaca    79440
gagggaacag gtgacaatat tgtctctgtc caaaagagtc atagtaaatg caaatctgct    79500
tatcatgcta ttgagttagg tactaaactt tgctatgcca tccagttgta aaacctagag    79560
ccccaaagaa gagaataata agatagaaaa caacacaact gatcttttgg ctaacactaa    79620
gtctggaaat taccccttcca tttgagatga ttgccagaaa aatcatcaat atatatccta    79680
tgaaaaactc ctgaggggca gaggaatggg atcaatgctt caaagactca gagaaagaaa    79740
atcactataa aaattatttg ctcctagaat gtaaaaaata ttttaagaaa actgcttggc    79800
attctaaagg tgaaaagact ttagaatgag ataaaaggga gaagattact tttaaaaatt    79860
cagcgacatt aaaaatgtaa tgacagaagt aaaatctaca tcgggagtag gaatgtagac    79920
tcctgtagca ttactatgac agacaccaga gtcaatgaca tgaaagacaa acttaagatc    79980
ttttcaggta tgtggtaaaa gaaaaaagga ttcaagtgaa tgatatagag gactgggct    80040 gggcatggtg gctcacgtct gtaatcccag cacttcggga ggccaagatg gcggatcac    80100 gaggtcagga gatagggacc atcctggcca acatggtgaa accctgtctc tactgaaaat    80160
acaaaaatca gccgggcgtg gtggtgtgca cctgtagtct cagctactca ggaggctgag    80220
gcaggaggat cgcttgaacc tgggaggtgg aggttgtagt gagccaagct tacaccgctg    80280
cactccagcc tgggcaacag agtgagacta catctcaaaa aaaaaaaaaa aaaaagaaga    80340
agaatataga ggactggata gatttattta agaattatac atttctgagg aaggtactag    80400
aagaattaga acaacaataa ttaaagatat cactttaaaa aacaagacct gactattcaa    80460
attgaaagga ctcaccattc tagatgatag taatgaaaag agggctattc tagaaatacc    80520
ctggcaaagg tttgggaatg caagtataaa gaaaaaaatc acatctatta gtattctgtc    80580
ataaagcaag taatttatga ggaaacaaaa atctagctgt tctcagatag ctctccagta    80640
agaaatgcca gaagacaaca gaaaaaatac ttaaaattct ttgaagaaaa agactatgac    80700
ctaagaattt tctcagctga attttttttc tcatatgtga agacaacaaa tgaacaatcc    80760
catatattca aaggctcagg aaatagagca ttcatgtatt cttcatgaaa atattatttg    80820
gagacataca tcagacaccc gaaagatgtg aaagaagaat agggtatgga ttacacatag    80880
ttcatggcat tatgtaaatg ttataaagca agatgacata gcttgggaaa acaaaagctg    80940
tgtctaatag cagtacttcc aagccataac ttacagtagc ccaattctca ataaattgga    81000
aggcagctaa acaatcatac agtgctagta ttttatagtg tcagggtcta ttcacatata    81060 atctcatttta acccattttta attccgtgag ataaaaacca atatccccat ctaagatatg    81120
ggaaactaag acgtagaaga aagcacttgg ctaagatatc atggctcgta ggtggcagtc    81180
aagaggtcag tttgcagtct acagatttaa cctcagacta ttctgcttct aacatgacta    81240
tagaaatgta ttgatcatta gctgcctgaa gttctgttct taactctagg tgtccaaaag    81300
aagatgaatt tgtttagat agcatttttcc catatctagg gctgttggct ttaaagaagt    81360
tcccagaagt gaatccaatt cccagaagga tcaaggtgga ttcttttgtg tgttactcta    81420
```

```
acaggttgct ttatatatat atataagtta taaatatac acatataatt tatgtattat   81480
atataagtat gtaacatc atatgtaata taaaatata gtacatttca cactggtagg    81540
acgtaattcc aaaccacata tttgtttaac caattgaatt acttggattt agtttctatt  81600
tccctcttta tttccttctg aaaatattat acaaataaca tcagtttaca aaaaataaaa  81660
tctgatatag ctttttatc atacactagg ctagactaaa tgcattctgt ggattgttta   81720
cctaggacca gatggtatat tataaagttg tatacaaatg aacaaggact gcctgaaatg  81780
gattgatagc tgagcacatt tggctggagc gtctatttta gaaggaaaac ctgagaatca  81840
tattatttga gtgtgattca tgtgttaata gtatttcaag acaagccact taaaatatgt  81900
cctgagtggt gatgctggaa atgatctttt cttcagtgtt ttcaagtgtc ttcatttaag  81960
tgtacacatt ttgcctacct ataacacgta tctacacatt gtgattaaga gagcaaactc  82020
tgaaatcaga cctagattaa agatcttaat ctctgccagt tgattgggca agtgacttaa  82080
tcattcgaca gtaatttctg catttgaaaa tgcctatctc aagggtaatg agaattacac  82140
tggttcacca aaagaattac actgactaat ataaaacgtg ccaagcatgt atgtgtcaca  82200
tgaaggctca ttaaaaagtg gatattattg ttaatcttcc aataactact atttccaaca  82260
acaggctgaa ggggctcaga acgtttgtt gagtaaaaac acaaggaaac agtagcacag   82320
atttcctgct ctcctttacg atcgatgacc tgtctaagga ctgtgatctc tgttcgctac  82380
agattgtcac ctgcattaat ctactgtcac ccattaacct atcaaataag gcagtctaaa  82440
aactccaggc gtcccttttcc gtaaggaccc ggactgttga actggaaagc taaaattcaa  82500
ggcgtgacaa ttgccctttg tcccacattc ctccaccggt cgcctgctta tttaaatggt  82560
gcgtcccctc gggtaccact tgaacaaaac ctgcccagag cgctccctgt gtagattcgc  82620
tggaagcagc tggaggctcc agttctcatc tgctcaggtg tccccggcgc cttggcgaac  82680
tcggccactc cagttcctca cgtggtgagc actcagggca gcgggtcgat tttccgaggt  82740
cccatacctg ggtttgaggg gcgcggctcg cagcggcggg tgcaggggcg actgccagcc  82800
ctcaccccgc ctcggggtgc gttcggaggc cgacacctgg aggacgcctc cagtcccgc   82860 gggacgccac gcctgcgcgc cagggatccg ggataagaag tgcgcgccgg gctccggctg  82920
cgcgccgcgg ggccaccagt ttgcgcgcag ggctcaggcg accgtgcggc catggacacg  82980
ccacggggca tcggcaccct cgtggtgtgg gactacgtgg tgttcgcggg catgctggtc  83040
atctcggccg ccatcggcat ctactacgcc ttcgctgggg gcggccagca gacctccaag  83100
gacttcctga tgggcggccg cagaatgacc gcagtgcccg tggcgctgtc cctcaccgct  83160
agcttcatgt cagccgtcac tgtcctgggc acccctccg aggtctaccg ttttggggcc    83220 attttagca tctttgcctt cacctacttc tttgtggtgg tcatcagcgc ggaggtcttc  83280
ctcccggtgt tctacaaact gggaattacc agcacctacg aggtaagggg cagggtgggc  83340
tgggaccatg cagggcgcgg gggaagggga ctctgcagac ctctggaggc gttttcttgg  83400
gggcagactg tcactgccac atcgaaatct ctccccgtcc atcgtcatca tcaccctccc  83460
ttcactcctc cccgtcccc gatcttcacc tggcatcttt cccttctact gagaggcgtc    83520
ctctaagggt gaaaaaattc ttgggattta ctctcctggg cttagtgaaa aaagaggct   83580 tccaaagtga acggattgca acagtagtgc tcgctatggt cctttctacc tttagcatct   83640
ttgattccca ggcaagggga aagatttttg gggaaggtaa gttcttcagg tctcaggccc  83700
tgcttcttga aaggaatact cttgttccag gtcctcagcc ccattcactc ttccaagata   83760
gttggtaaag aatttgtact cccctccctt ccccttccac acccacccc tttccactga   83820
```

```
aacaggcacc caagtggcta aggtgtacca gtacctgtat ttcggaccag attctaccac    83880
ttactagctg ggtgaccttg ggtgacttac ccaaccttt gtgcctattc ctcaaaaata    83940
aaataatatc acctacctca tccagttggg aggattaaat gagatgatgc aaggtgtagc    84000
atttagaata gagtttgaca cagagtaagt gccagatagg tattggccat aattactgtg    84060
gtggtgctag ttgtgatggt ggtagttatc ttgggatcag taggaaaatt aggcagcaag    84120
gttctcaaac agctctgcct tctctatgga aagacaatta aggaaaactg tctttcctct    84180
attgcacagg tcccctggct ataggttttc tcaagttgtc tgcaagaaag ggctttgaaa    84240
agatgatgca cgtttagttt aaagagctgt tgaatgggag gtgggggcgg gatcaaagct    84300
caggggagtg gcggggccca gttcagtgcc ttcagtggtc tccctcaccc agcactggtc    84360
cttgagctac atgggacaag cctgcagaag tttcctctct attaggccat tacccagagg    84420
actccaatcc tgagattctg gcaggtggtt cctagtgag gctggttcaa ctggtgctgg    84480
ggacagggcc ttaacggcac aacaaacatt ggtgacacac tctgcctggg ctctagtgac    84540
atcttccagg gcgaggcacc cctgggcagc attgccttcc attcactctg gggctgtgtt    84600
tgggagagct caataattat cccagaagtg agcaggatgc agtttctcag gtttgctcag    84660
aagcgacaaa ctggcgaaat tccccagacc aaattcactt tcagtcatt tttttttttt    84720 acttctcctt atagtgagaa gaaataaaat ataatttcag actatgactt ctttcgagaa    84780
ctcaaaaggc tggtaacact gggcccatgc tccctgtggc cacaggaact caagttata    84840 gctattgctc tcactctcta ttaaacttct atattgaagt cttatcttg tgttttcatg    84900 gttactgttt ttttggtaga gaaattttta tctgcattta tgtctttatc aaaaaatgtg    84960
aaaggcaaaa tggacagggg taagggatc tcttgtttcc agggagatgt aagaaaacat    85020
atatcttagt gggtgggagg aatattccaa catgttaata tgtgaacacc tggccactgt    85080
cacttatgta tgttacctga tggaacctgg aggcatctga gtctgtgagc tgtgatctat    85140
agctaaccaa ttcccaaact tggaaagggt ttgaagaatc tggcaggagg acttcagtcc    85200
ccacacatga atgctgctct cataaccact gaccccatgcc tcttcgggggc tacaacatta    85260 actcaagcag aaacagattt ccctcatgct tgcagtggta gaggctaagt tagcaggggt    85320
tccagctaaa aatgtcaaaa agcaaaagtt cattgaatgc tgaacacatg ccaggcactg    85380
ggctgcattg catgttttac atacattatc tgactcacat tcagaacaat ccttatgagg    85440
caagtactat caagagcccc attttgtgga cagagactca gagtaagtta agctactagg    85500
aatgtgaagc agcgtagaca tatgcctagc agcatactgg ctgcttctga aggctctgat    85560
gagtctgtta taaccccaag caatgcttac gccagtgcag agagaacaag ggaagcaata    85620
taggacacgt gaagttgtgg gcacactgca ggcatccacc tccagggtgc caggcagttg    85680
ggaacgggga agttaggcaa catgctaaga cccctcccaat tggtcatggc aaagactttc    85740
ctgtggagta tattgtttat tgtttatgc tgagaggtac agaatctata cagaatatgc    85800
tgtacagtgt tgagtgattg ataccctggc attcttgctc aagtatgaaa tctctccctg    85860
ttgacatttc tttagtgaaa attagctgtt cacaagcatt ttttttcatc catcactgcc    85920
ttcaaaatgt agtcctgata ggtgtttagc aacttccaga cccaagtata atgcaggaat    85980
ccaatttaat ccaccaattc ttcaagatcc ttctggagcc aactaaatct gtgttttaaa    86040
ttgagttgct tagaccttat gtttctttgt tatttatata tttattcata tcaacagaag    86100
caattcaaag ttctgaggac cacgagagat cttgattaat ttaggcacct atcattactc    86160
```

```
tgtaattatg tctagaagtc ttacaagtat tccctaaggc tgctgcacag tgacttgggc    86220
atctggtcca gtctccgggt atttcttcag cagcctagta attgatggct gagatcgtaa    86280
tagacttctt ggttctgtct tgagttggtc cttgggctta aatcacaggt ttccctggat    86340
cagttgatta acttacttgc ttcagttttgg ttcaatttat ttgggtctcc agcaatttgg    86400
attcatgtac ctagaaaaaa caaagacttc tcttctattg atgtccattc acatgtttag    86460
tgattcatag agatttacaa aacaaacaaa ccaaaaataa acttctaaag aaatataata    86520
atactgcctt gttcccagac ttaataaact tctccagtct tctaaaaagg cttccaaaat    86580
atccctgaat gattttgaca cttgtaattt attgagattc aattttctcc aggcccattg    86640
atttggatac caataggttc ttaatatctt acttttttgag tttacatttc cccatccatt    86700
tatgtcactg aatagtctcc aaaccctgca aaatgagagg gaaacaaatt attattatgc    86760
ccctcatttt aaagagaaag aacctgacat ttggagaatg attgccacaa gctgatggag    86820
tcaggcgtgg gactgggtca agggctggaa ctcttcctcc agtgtactac aaggcactgt    86880 gtattttttgt caccgatcag tgatctggga gtgaggtctt actctgtgtt agtttcaccc    86940
attcacttat tgagtcttaa atatgtagtc agattattta cttatatatg cagaaaaatg    87000
tgcacagatt ttggcatcaa aggttttaaa tgtgtactgt ggccctggca agtttgcaag    87060
gttttcaact tgatgttcta tctgaggccc agtgttcttg tctctaacat gggtttatac    87120
acagtacctg gctcatagag ttgttgggag gaccatgcac acagcaagta ctctgtatgt    87180
gttagccatg atcacggggc aaaaaaatca gatgtctttt cctctgatta ttacctaatg    87240 ccagttttttc cttcctcttc ttttctactc tatgaagatt gttgtcagcc ttaaacttct    87300
tagtaattat attcaagtta agaaaaatct tagctcccag ctctgaaatt ctatgatcct    87360
aactctgtaa tatgtatatt ataatacatt atataacata gtagacaagc agactatgtt    87420
ataagacata gcagatttca gtagaatag gaaaaattgg catggtcatt ggcactgaac    87480
agaaactgac ttgggtgatt taagtttaaa aaaacaattg ttagaaggac atggggtag    87540 ctcatagaac agagggacag gctgagtaag caagccttgg aaaggacaga accggggca    87600 gccttttcag gccactctgt caggatcagt catttttttgt ctttgtatcc tgcctttaag    87660
attcaaatac ccaatggaag gaaaagctga ttggctgagc tgggatcatg tgatttcctc    87720
ttggtcagaa gaggcagggc aattggctga ctattccatc acaatagtct gcagtcagaa    87780
agggttgatg ccccaggtga gccaagaaaa atgtatggag tagataccaa gagaaagaga    87840
acaacagatt gctcgctcta aaaatacaga aagtaatttc atttatatga cattctggaa    87900
aaggccaaac tagagaggga aagcagatca gtgattgcta gggtttggcg ggggagaaga    87960
gggcttgatc atgaagggga agcccgaggg agttttctgg gtgatggaac tgtcttgtgt    88020
cctgattgtg acaggggtta catgaatcag tgtgtgttaa aacccattga actgtactct    88080
aaaacaaaag agtcaatttt gctgtgtata aataaaaata acactaaaat aaaaatacag    88140
aatacaaatc agttatgaag ttgctttaca tttctaaatt taaattttct tcttgagctg    88200
ctgattttaa aaaggcatc cagaggattc gcataatttt ttttttttgca acagtattta    88260 gaacttcgat ttaacaaatg tgttcgtctc tgtggaacag tcctcttcat tgttcaaaca    88320
gtaagtagct ctccatttat tttatctttt gtcagctaaa atgttttaa ccatggcatc    88380 tggattaagc ttacctggga atcacataaa agacaaaaaa gagatgttga aaaaatgagg    88440
gaacaaaaaa ggaaaaacac ttgtcactgt acagcatcaa cccttaagat catcaaacag    88500
tgtttcagta aatgctttac ttcctgggat ttaagtgaat gttaaatatt atactgataa    88560
```

```
agcaacagtc ggaaaatatg cttcccttta tctgacctcc cttcacctcc accaaggtga    88620
caggaagggc attactacat gacaaagata tttgttgctg acagtgggaa ttctaacaaa    88680
aggaaaacaa gtagcatgtt cacagtattt ctgtaacata ttaataggta tgaaaaaatt    88740
aacttccata ggaagacagt aggaaataat tttctttgaa atcgtacttt aaaagtcagt    88800
gctcttttaa aaattagact acaagaacca actaaagcag tccttagagt gtaaaacaac    88860
agaatcataa actctggagg actctttaaa gccaaatact caatccagta attcaagaac    88920
atgcgcttat agatctactg attgacacaa agggaaagca aggatttgcc aagtggtcag    88980
tgacagagaa tgcttttccac tgttcaccgt gcttctggaa gattgtaatg atcattgtca    89040
tgactattta tatacacatt ttcctcttgt cagttaagca cttttagggct gggtttgcta    89100
atggaggttg tggaagagat ttgcattctt gtctctaatt gcaattccac ttctccaatc    89160
aaaagctacc taagggccag ccgcggtggc tcatgcctgt aatcccagca ctttgggagg    89220
ccaaggcaag tggatcacct gaggtcagga gttcaagacc agcctggcca acatggtgaa    89280
accccatctc tacaaaaata caaaaattag ccaggcatga gggcaggtgc ctgtaatccc    89340
agctactggg gaggctaagg tgggagaatc acttgaaccc aggaggcaga agttgtagtg    89400
agccgagatc atgccattgc accccagcct gggtgacagg gcaagactct gtttcaaaaa    89460
aaaaaaggaa aaaaagctgc cttaggattt gctgcagtga gacagagtgc ctttgtaaat    89520
tatgtaactt gactccattt tatatctttg caaattatat aacttaaatt ttatcagtcc    89580
ttaacaactg cagtgtaaaa ggaaggaatc ctttggtgtc tcttagagac ttgagcctgg    89640
tagcttgcat tcaccaactg ttcagaacct cattggatct tgttagaga tgccaacaga    89700
aatcagaagt agggataagt gttaggaagg tggcctgtgg tcatgttttt aaatcttcaa    89760
cttggacaga ataatgactg tggaaagtta gttcattttt gcaaaaagag gggagcttta    89820
ccacctccca tttgaaggac ttcatagctc tactcatgta atataatcaa acattcaaag    89880
gtactgaata gatttttatt ttcataatat gcttttatag aataatcatg gaatttgctt    89940
ttatgggata tatttgaaag atcaagtgca atcaaaatta catttgaga aaaagaccgt    90000
atttatctta ctcactactg taccccagat caataaatag ttaagtgtat gaatgaaaat    90060
aatgaataat attaaaaaga ttgaatgtgg ttttcattgg ctttcaggat ttttttagtg    90120
caaatttata cttttgttta atttatgaac agtaaaagtt tagaaatagg ctttccaaat    90180
ttttactatt ttcttgatta attatgcagg gattaacagt ttgaagacat aattgagggg    90240
tcatcctctt ttatattatt attatttatt tttttctaat tatttcagat gtaggaaatt    90300
ttatttcaag cttgagttgg tggatcagtg accatttgca ctaagcacca tataaaagtc    90360
cgtatttta cataagccgg tcacaaaaaa atatttgtaa cttatgaccg tcataccgt    90420
aaacagaaga gtcaacttta cttaaatatt ttgcaagtta caaacaaatt ttattaggtg    90480
ttttgaaact gttgttttaa gtcataattg aagttatagg aaaacaatca atattttata    90540
actcagacgt aattcatgaa ttttataatt catataattc atttggcttt ctttctcccc    90600
cctagattct gtatactgga attgttattt atgcccctgc cctggctttg aatcaaggta    90660
cattttagag ttgccagtta ggtaactcac attttggggt tcactttcaa caagccttat    90720
tttctccttg gggagatggg gagatggagg aatgcttcta gtaacctgca tcagctttac    90780
ttagcgggc aggatgggtt cagtgtctac actagcttct ttgggttttt ggatggacag    90840
ctccaaagtg tctgtagacc acagaggtgg acttctccag gtggtacttc tctgggatgt    90900
```

```
gcccatcagc ccattcactc ctttagaatt aaagctccct gtagccaaag tcaggattga   90960
cggcatcccc tcttgtgaat ctataacctg gagcccatct ccaggaagct tccctgtaat   91020
tctgctcagg cctgttgtaa aatctggcag ggagaaaagc ttttcttctc cacacttcta   91080
ataaggccca aaatgaaaga gaaagagagc catgtgattt gaatgatcag actgctccta   91140
gtgacaaaag gacagatgtc tgtagtgccc ttacaaataa atttaggaag attgtgctgc   91200
tcaacaaagt atctatactc tctagatttg ggaagataaa tgcagtgagg ctgggatagt   91260
ttattgaagc aaacgttcat gctagtcata gtttcaaaag ctttgggga aacaccatgc    91320
cctttgaatt cttatctatt cgaagtgaat ttctctaaaa cgtccttgta aaatggacat   91380
gtggactctg tgatgggaag aatgtggtac aattcctggg gttaaaatga catgaagaaa   91440
acctactaat tccacactct gttttcttga ttttatgata gacatgacag tagttaccac   91500
ctgtttctga agtgaacaat attattacca agaggaactt catgtgtaag gtgctcttga   91560
actctgaatt ctgggcatgt tccacatcgg tattaccaac atcacaagtg gatcatctca   91620
tttgtcgaga actgagttat aaacttcatg agttacctat ttaggactta agtgtaattg   91680
aacatattat ggttttaaaa tgcagttctg ggaattacca gaggactgac tttaatctgt   91740
gaagaaatca agcattctgt tcttatcagg ctcaaaccac tccctgagag taaattagaa   91800
tgaaagtgaa ggtgttttga tgactagagt gtcagttgtg tgttttactg tgaccaaagc   91860
tgtaggtaca ggcatagaca cagaacttag tgtgcaatag atgctcaaaa aagcttattt   91920
aactgaattg aaaattaaca ttctctaggt ctaacctctt ttttctttt taaaattttg    91980
gaaatcctca tacaaatact aagagagaat agagcccctt aatgtgctca ttcatcactc   92040
tatgttaata tttatcaact aatggtccat tttaattcac tcccccttac ctctaataga   92100
ttattttgct gcaaatatgt tatgtcattt catctgtatt tcagtatgtc ctttagaaat   92160
aaagacttta aaaccataa tcataccatc attgtaccta aaatagtaat attaatttct    92220
taatttcata tcaagtcagt gtttacattt ccctgatttt ttttcagtgt ttataagaat   92280
caggatccaa ataagcttat gtgattgcaa tcagttgatg tctcttaagt ttcccttttc   92340
tgcttttaa aattgaaaac cagttttct ttctttcttt tttcctgacc gcctgatgcc    92400
tgttgagaaa actagttttt attgaggtat agttaacata caataaaatg cacagagcat   92460
ggggaagtgt acagttggat gagttttagt agttgcctaa tagcttgtgt gactactacc   92520
ccgctcaaga tatagactat ttccgtcatc cactctcaga aattttcctt gcatgtcttt   92580
ctaacaaatc tcctatgggc ccaagaaatc attttctgag ttatgctacc ataaactagt   92640
tttccctgtt gttagatttt atataagtgg aatcatatag agccttttca tgtctggttt   92700
cttttgctca gcaaaatgtt ttgagattca ttcatgctgc tacatatata tcagtagttc   92760
attcccttt tttttttttt tttttttttt ttttttttt tgctggtagt              92820
acttcatttt atgcctctac caacattttt ttatccattc tcttgttata gacttgggtt   92880
gtttccagtt ttaggctata gtgaagtaag ggtgccaaga acattcttct aaaggttttg   92940
tgcattttgt ttttctttt cacacctgtt ttcacttcca ttggaaatga aatacatgga    93000
tgtagtataa aattaaaaat ataattctat ttggacccag ctgaggatag aaatgtgtgc   93060
aaatttacaa gaaattgcca aacagttttt ccaagtggct atatcgtttt ccatgtccac   93120
tacgcaatat gtgagaattc tagtcattcc acatccttgc cagcatttga tattattctt   93180
ttttatttca gtcattctag tgggtattac ctattatttt attgttgttt cagttttcac   93240
tttctatatg actattatgg cttagcttat tattagacta ttatggctta gcttattggc   93300
```

```
ttctgaaata ataaagtgaa taaagacaaa taacctaata aaaagtgagc caaagacttg   93360
aacacttcac aaaagcagat attcttctaa tacattacat gatatatcta ttcatttacc   93420
taggccttta aaaatttctc ttagtgctca ctttggcagc atgtatacta aaactggaac   93480
aatacagaga atattagcat ggcccttgca caaaaatgat atgcaaattt gtgaagcatt   93540 ccatatttt taaaaaagga agaaaagaaa taataaaata aaaagtctct tagtaatgtt    93600
ttgtagcttt ggatgttgag gtcttttact atttcttaga tttattccta gataattgtt   93660
gttttttatg ctattgcaaa tgtcattgtt ttattttca attattcgtt gcaagtgtat    93720
aaaaatacaa ctgacttta tatgttgata ttccatcctg agaacttgct gaatttgctt    93780
tttaaatcaa gcagattttt ggtgatccct taggattttc atgttgttta tgaatagtga   93840
caattttact tcttttctaa tccttatagc tcttagttct ctttcctgtc ttattgtaat   93900
gttaatgtgg aaagttacat tgactgaatt ttgaatatta aaccaatttt tgcattcttg   93960
ggataaaccc tgcttgctca taatgtatta tccttttat atattaccga attcgatttg    94020
ctaacatttt gataaggctt cataaatgaa ttgaaaagtg ttccctcctc catttttctga  94080 aatagtttat ataaaattgt gtatttattt cttacatgct tggtagaaat caccctgaag   94140
gcatctgggc ctactctttg tttttgtaga aagattttgg tttatggatt cagtttattt   94200
cgtaaatata gagttattca tattttaaaa gtcttgttgg gtcagttttg gtaaattgta   94260 tttttaggg aatgcttcca tttggtctaa cttatcaaat tcattagcat aaaactgcat    94320 ataatacct cttgttatgc ttttaatgtt tatagtatct atagtgacat cccttctaat    94380
tattcctaat atcgataagt tttctatctt cttattttga tatatctttc cagtattcta   94440
ttgatgtttt aaatctcttc taagaatcag tgttttggct cattgatttt ctttgttttc   94500
tatttcatta atttgtgcta tttattgttt cttttcttct aataactttg ggttttctag   94560
cttcttaagg taggcgctta ggtcattgat tttaaatatt tcttatttca taaagcaaac   94620
atttaaagtt attaattttt ttgaaacact gctttatctg cagcccatat attttgatac   94680
cttgtgtttt tatttagttc tcaaaatatt ttctaacttc tcctgtgatt tcttttgccc   94740
atgggttatt tataagtgta ttgcttaatt ttcaatattt gaggattttc tatcatgtct   94800
ttttgttatt tattcctaaa ttaatactgc tttggtcaga gaactaatat gattttaatc   94860
atttgaaatt tatggatttg ttttatggcc caggatcagg tctgtcttga acattccata   94920
tgctctcaaa aagaatgtat attgtgtgct ttttggatgt aatgttctat aaggtcaaag   94980
gtttagttgg ctaatagtgt tatcacatct ttgatatctt tatggaattt ttttacttg    95040 ttctaccaat tgctgagaga aggatgctaa aatctccaga tataattatc gattttcta    95100 ttgctgctat ttctctgtca attttactg aatgtattgt gaggctcttt taaagtctct    95160
ttttaaattt acaatctccc ttctattcct tttcatttaa attgcaacat atttgcagaa   95220
gaaactgggt tatttgttct gtccagtttt ccagattcta ggtttaacaa ttacatctgt   95280
atggggtcat ttaatgttca ccattcctct gtatttcttg taaactggta gtagtttact   95340
agtagtagtt agatctagac tcttttcag actccacttc aacttttgg aaatcatatt     95400 tcataggcag tatctataag tttatttcct tcaggagtcc cagaatgtca tttgaaaaat   95460
tatcagcagc tattgatgat cattctagat tcattatttc attgaggctt ataaaatgga   95520
gtattctagt tctgtgaatt cttcttcatt agttagatgg aatactgcta taagagaaa    95580 cttcctctta tcaactattt gctttctctg aaaaatagtt tgtataggaa agggaggata   95640
```

-continued

```
aatgtcagat ttttcccctt atgaatttta aaaataataa attggtttcc tactatcccc   95700
caagggtgac tgagattttt aaaaaattct tacgaactca tggatttaaa ggtttgctgt   95760
tatttcatag cattatcgtt agtattatta ttgatgctca aattgtccca tttttatcca   95820
gccggagccc ccttaagttc ctcctgattt tagccttggc tgcatattgg actcacttgc   95880
ggggtggggg agctttcaaa ataccaata cctcagtccc catcaccaga actctgagtt    95940
aattaggctg ttgagtggcc cagttatcag gattccataa atttcctatg ttgattttaa   96000
ggtgcagtca caattgagag ccatggatgt aatagtttta gaatagcaac tctaagccat   96060
aatgaataat ataatggcct aacacagtta aaaatattat tctttgttgt tcttttttct   96120
tgggtgtatc tcagtaggaa tgtatgttaa attactgtgt taaatatttt gtgacatgtt   96180
tcctctgtgt ggtaatgtca caaacttgat atacagttag gttccattta tttcattttg   96240
caattgattt tgaggagttt ttttttctaa tttaacttta tatttatgtg gaatatttat   96300
gtgttccaaa gtgaaatcta tacatcaaaa tatgtttaaa gtagcctgac ttgtatctct   96360
gtcttctcta ccctgttttc tccctctcct aggagtaatt ttttggcttt gatttatcct   96420
ttaattttag tatatgtact gctgaaacaa gcacaattct tttcttttaa aaaaatgaaa   96480
taaagtcccc acttcttaga taaataggag caaattataa agacttttct ccatctagat   96540
cccattttgg tagcacatat cttagtaacg ccttcttcaa ggactggtga aattgcgtgt   96600
ttacatggac acacagagga gaacaacaca cagtgggggcc tattggaggg tggaaggtgg   96660
gaggagggag aggatcagga aaaacaacaa atgggttaat gggtactagg cttgatacct   96720
gggtgatgaa ataatctgta caaggaaccc ccatgacaca agttcaccta tgtaacaaac   96780
ctccacatgt acatctgaac ttaaaagttt tttaaaaagc attaccggcc aggcgcggtg   96840
gctcacgctt gtaatcccag cactttggga ggctaaggca ggtggatcac gaagtcaggc   96900
gattgagacc atcctgtcca acatggtgaa acccgtctct actaaaagta caaaaaatta   96960
gctgggcatg gtgctgcgtg cctgtagtcc cagctactcg agaggctgag tcaggtgaat   97020
tgcttgaacc caggaggtgg agattgcagt gagctgagat cacaccactg cactccagcc   97080
tggtaacaaa gcaagacttc gccaaaaaaa aaaaaaaaa aaaggaatt accattacct     97140 ttattaaatt tctgaaatca gatccgcaat ctgcaatgtt ataaagatta catttgaatc   97200
ctttcgtgtt gtcttcattt gaatctatac atcatagcaa tttgatattg tcattatatt   97260
gtcagtatga tacattatcc tcaaattcag gtatttgcaa cattacataa aaatagagtg   97320
tttatttgaa ccgcgtctaa tcgggagaga gataagaaat acccatcaca gtatcaagga   97380
gtttcttagc ttaattacaa tataaacgcc tttccatgta ttgaattaag ccagtgtcag   97440
atctgtgtgt ctgagagtag aaaattatca aatacaattt taaactccat ttgtttttga   97500
gacatttatg agatttggag ctagttttag ctttaggcaa gtgggtatag aggaaggtgc   97560
ctgataaatg atatagcttc cttctctgat gattttgag gattattttt attgtgcata    97620
tttcacaatt atatatgcat tctatttttt tctacagtca caggatttga tctgtggggc   97680
gcggtagtgg caacggggt ggtctgcaca ttctactgca cactggtacg tccaggacat    97740
atttcccttt tcactctacc cacttgcttt gcaaaattga aaattccagt tgttgtatac   97800
cgcaatcttg tttgtccaca cttactctcc tattcccaac ctcctgcagt gtaacttttt   97860
ttgtgtgaga ataatctgt agtataattt gatcctttgt agaaaatgga gcataactga   97920 aatttttct tttatctgat ccattgcaat ggttcctaat cttgtctctt gattcatctg    97980
tactgttgcc aagttattat atttgtgctc atactattcc tcagcttaaa aacctatcat   98040
```

```
aggtcatagg cacagtggct cccacctgta ataccagcaa tttgggaggc cgaggtggaa   98100
ggatcactgg agcccaggaa tttgagacca gcctgggcaa caaagtgaga ctctgtctct   98160
acaaaaaaac aaaaaaaatt ttttaaaatt aggaggcatg gtggcataca cctgtagtcc   98220
cagctactca ggaggctgag gtgggaggat cgcctgagcc caggaatttg aggctgcagt   98280
gagctgtgat tgcaccaccg cactcccgct gggcagcaa agaaaccct gtctcaaaac    98340 aaaaacaaat ctgtgataac ttccccttgc ttataggtag gggtgacaaa atatgcaaaa   98400
tcagtatggc atggcactga tattattatg tgtgctggtc cgaggcagtg agaaaatctt   98460
atggaatcct tgacactcta tgtcttaacc ctttaggtgc tggatcttgt agaagatggg   98520
gccctcagcc aggtgctggt tctgcttagg tcatagagaa acttgggaaa tttcttgtgg   98580
tggctagtac agatcactta tagtatataa cagtggaaat gaccatctga gtgaaaacca   98640
attaaatatc acctctgcct gtaggataaa attcatatta tttactagta atttgactcg   98700
gatttttctt cccaacaatc tcccgacacc actccacttt attctgtgga atgtatctgg   98760
ccccattcag catgccatgt agtttcactc ctttatgttt tgcccatgc tgttttctct    98820 gctgggcgga acctccatct ttgcctctgc ttatgtttga agacttgatt taaatatatc   98880
cttctgtatg aagattctcc caacctgact gtttcccttg agtgcacttc ttagccaaca   98940
ttcatgttta tcattttt ctccagtata gtgtataagt gtgtagatgc ttaataatgt     99000
ctaatagaag cattaatcct aatatacttt cccctcaaag ggtggtctta aagcagttat   99060
ctggacagat gtttttcaaa ttgggatcat ggtggctgga tttgcatccg tgattataca   99120
ggctgtggtg atgcaaggtg gaatcagcac tatttttaaat gatgcctatg atggtggaag  99180
attaaatttc tggaagtaag tgtctagtac ttgggtaact gaacacatct tttgtattct   99240
ataaaaataa tctctttatt gaaatagtag atttacatta aaaacaagc caacaaattg   99300 ctaaggatgt ggtagagcaa attgaagcag agaagtaaat acgtaaggag cctccctctg   99360
ttctttaagg gattaaacct gtcagatggt acttagctac atggtgctta gagcaatgtt   99420
tccttctgag aagggactta aagcaaaaaa agtattttct tccaggtatt aaagtccaga   99480
ataggttgaa aagtgggaca gggtgataag gaaagagaca gtggaaagtt aagaaaaggc   99540
agcttctggc caggcacagt ggctcacacc tgtaatccca gcactttggg aggccaaggt   99600
gggtggatca cctgaggcca ggagttcgag accagcctgg ccaacatggc gaaaccccat   99660
ctctactaaa aatacaaaaa attagccagg tgtggtggca ggcacctgta atcccagttg   99720
cttgggaagc tgaggcagga taattgcttg aacccaggag gcagaggttg cagtgagccg   99780
agatcacgcc actgcacttc agcctgtgca acagagtgag actctgtctc aaaaaaaaaa   99840 aaaaagaga aaaggtagcc tcttaagaga caaacactag catattggat tagcacctgc   99900
cataaaaaaa aaaagagac agagacagac actgaaagac agtgatttca ttttgacaat   99960
tctttgtttt aagcaacttt gagagtttct cttttgatat tgccctggca atctatagta  100020
tattaacata gtagcttatg attatgtatt ataattctat gtatgtgtat gtattatata  100080
atgaacatta tctaatatga agtattattt ctagagaatt gactaggaaa gttacagtct  100140
atgcttcaaa tgcacagtaca gcacatgatg taacatgttt taagcagtta ttcagttttc  100200
ctaaagaaag aacaatgaag agactagata tttcatccca agtatatcac acaattcaaa  100260
agaatattga aaatgccttc cgttttggat caatagtgtt gtccttttgc aatatggaaa  100320
gggacaaccc atgttgtctt gaactagcct atcttctctt tgagatcgca gccccgcttt  100380
```

```
aacataggca gtttgaagaa aaaaaaccca ttttgcactt ggtggctctt ttctggtctt   100440
ctgaaaataa gcaccaaagt ttgagaaaaa gcttttcag aaattggaca gggtcaatgt    100500
gttaatttac agggataaat tttagtgaat caactttgac tattttcaat atttcttcc    100560 ttcttttagc tcaagattca gattctaagg aaaagaggct ctagttgcct agcttggacc   100620
ttggttccac cccttggcca gggcagaaca agatattttg actgatcgtc aattgagact   100680
atttaatgga gaaatggtag tttcccaaa gcaaacctgg gttgcttta ccagaacagg     100740 gagaggggaa gtccaggaag tggaaacaac caatgactac tcttgattgc tcccaaatct   100800
cttcctggta ggccaggctg aggagagagg gtatggaacc aatcatttt ctgcaagata    100860 gctgtcactt tatatgaagg atacatatat tggagcacag aagtgatagc ttatacacat   100920
tagtaagaga ttttaaaaa aagattaaac atttttatga ccttagtttt gaaagtcatt    100980
aagtaacaat aaaaagcctt atttgtgttt catactttc aagagtatcc cttgttattc    101040
tgatatgttt tgagaatatg atagacaaag tattgctcaa gttaagataa atgaagaaa    101100 gaaggatatt gtattggtat tttctgtgtc gtctgccatt ggcctatgta ttctgtatgg   101160
cctaaaccac taaagtgagt gttttaaatc ttgtcatact tccctcagat agcttactga   101220
ctccttttgg ctcttcagtt agctaatata gtagcttctc tctcttgggg agaaagggtc   101280
aacagtcttg aaactcttac actttgatat gaaatgttag acatgaaata gaggctctca   101340
catttccaca agaatgccag aatacacata caattagagc acttaactga tctcaaatat   101400
aagatttgaa atgaatttgc aaaatttcat aattttaagg aagtctccat gaaagctaac   101460
tttgcagaaa gttttctagc tcatattgta tatcagagat gaacaaaatc attccttcca   101520
gtaaaaaaga ttaaagatc tttcaaacat ggaagttgag ctttccctgt gacaatgttt    101580
tggacttatg tacatgatgt cataaagtgg ctttaaacta ttagtattta gcttgcacgc   101640
acagcatttt aataaagcat gattacaatg acatgcagtt tttagaaaat gcaaaacttg   101700
aaactgcatt aattgactga tttgttgaac gtgaatatag attagaacta tgattacatg   101760
tgctgggaga ggaattctat acacaaatg tgttgatttc gtgttcattt tagtgccatc    101820
tcgtctgctg tggtgcactt aggaatgttt ttctctttct cttctctat gtttcatgtt    101880 cttctctgat tatatcatgt cagatttgtt taaatgacag tttccttaga tcacaggaga   101940
acaagttata taaatgctca gaaggattgc aacattcatt tccccagtc tcttctagta    102000 ttttcagatc tctgaaaata gtattttta tttcattgaa cttaagttgg aaatatttct    102060 acctttaaa ttaattaata aattttaca tatttatgta tgtgttgtgt atataaatgt     102120
gcattgcttg cttccaaata tagtctaaga gaatttttt tagtctctgc taatagttca   102180
gatttgtttt ctgtttcttg tcatttagtt ttaatcctaa cccttgcaa agacacacct    102240 tctggacaat tattatagga gggaccttca catggaccag catctacggt gtcaaccaat   102300
cccaggtgca gagatatatt tcttgtaaaa gcagattcca ggcaaactg taagtcacac    102360 accatggtat atgaatcatt aatagccatc agttgtcttt atggaaactc tttcataagt   102420
cacgtttagc tcctttatgt cttttgtgtc atgaaattcc aagagataaa tgatatattt   102480
ggttacaaaa ggaccaagaa caaattgtta ctgtatgttt taaatcagct atttgaaaat   102540
atttatagga attattaatg aaaacaaatc agcatttatt gtgcatctgt ttgcataaga   102600
acccatgggg gataaatata tatggctttt gtctgaagaa aattaacctc aaattaggaa   102660
aatacatgca agtatgtgaa aaaataaaat aatactggag atatgtaaca gtttcatgaa   102720
atgatatagc aatagagaaa atgttccaga gtacatatag tgctttatat ttcatttca   102780
```

```
gacacagtca tggatttata accctgctct aatatttgct atttgagtga tcctgggcac  102840
attctgcagt ctctttgagc tgcagtttct aaacttgtaa aaggagcata agaaatacta  102900
tacacctcat gggaggtgtc gtaaaatact gtgtttggca tacgcatggt aaaggcctag  102960
tatatgtaag ttccttttc cacttcaact gatgtgatgt gaaggtggag gatggatgag   103020
agattcctat tgaactggca gaatgaatat gaagaatgat cataatttgg gcaggtggag  103080
aagagtagga aggcattcta ggtaggtgga gtgatttgga tgaacgcaca gaggtaggaa  103140
ggacagcatg gtccagaact ctcaagccca tcttggcttg agcaaagagt gtggaatggt  103200
ggctggttcc ttctctggag gcctcacatc actgcagtgc tcaccactcc ctgtgctgat  103260
aaataggctg actctgctga catgctttta ggggctttaa agctctaagg agattgaata  103320
agagtccagg gtggataggg tgagggaagg aggacaattc tatttctatt taaggagaa   103380 aatgaaaata ttgtgatgtc atatgtcaga actcaatata ttgagagtaa attggtttag  103440
agattaccta aatctttgaa gaactcacag tgaaaaatct atatgaatat ggatataata  103500
accagatatg ggatccccc aaaatgaact taggaattct ggtatttac ggaatattgg    103560 aggaatgtaa tttatagata gagtagtcta ttgtactttt aaatctatac tagagctgat  103620
acctctccca gagtaattgt ggacaagctc ttcttctctt cccttgggaa catgaaaccc  103680
aaaaagcccg acttgataac ttaaatagca gcattagagc tttcttgata aaaatcaatt  103740
cccataagca tagtggatct cctgcatgaa gcagactctc gaaacccagg ggactcattt  103800
tcgtctgcct tctcacactt acgctatggt aagaatgaat ccctgctaaa aaaccaagac  103860
ctactgacat tgattgacaa aagacagtat gagatgttga taagtggtca atctgaatag  103920
catcaaagtg aaataaaaca atatattaaa ctcatatata agagacagga ggtgtttgga  103980
caagagagta tctgggcata attttctggt gatttggaga tgagctagca atagcaaaac  104040
atactgcaat gttagtcaat tcaagggaga aggataaatc tgataaaccc acctttgatt  104100
cttccggaag cagactctga ggttgaggtt agcatggaag agtttatcag agaatcgcta  104160
tatgtagaag ggaagaaaag gaaacaggat tgacgagagg gagacgctgg actgtaatgc  104220
agtctgaaca gaggcctcaa agggagctct agagctaggg tggctcttca gactagtccc  104280
atgttagggt gaggggactg ggcctttaaa cctctgaatc catttgtcat tggatgcaga  104340
cttcctgcgg gggttgggaa gaaggaggca tgacttcagg gatggtacct cttttccacc  104400
tcgggcagct catcactgtc cactacagca ccagtggaaa aaatatgtag ccatcttagc  104460
aagagaaatg tttactattc aactgattat taagacatag gattcaataa cactaacact  104520
aatatcaata actagtattt aacaggggtt tattatgtgt aagtaccatg ctatatgata  104580
atatactgtt tcatttagtt ttataacttt gtgacatagg cattgctatc ctacacttca  104640
gtgaagaaac tgaagatcag agaggttgaa ttactggccc agggtcactt atggtacagc  104700
caggatttat gctcaggact ggctccagtg ctgtgtgtaa acctttattc tctactggag  104760
cacacacagt atattacagt gctgaatatt gtttgagaag atacctgtcc aaggaataca  104820
gatttgcatt cctacttaat gtgtggtctt ataaacaaca tttaaacaag tttcatgagt  104880
tactgtgtaa atgttaacaa tgtttagcag tttacaattg cattacttt aaaggaaaa    104940 tgagtaatag ttaatgctcg attgactatt aaaatctta tttcatgaca agaagacctg    105000
aagtagtata actaggtacc tttataaagc taacaatgcc cctggagctc cgaccacgag  105060
catacactct ttcatgggga aatcccatcc attcaaatat ttccaaatac actgtcgatt  105120
```

```
gattggtatc ataagcagaa tattaggcta gaataaaata agtagagttt cgataatca    105180 aaagataatg tacatttatt gagtctaatc atgaaggtct cttttgatca tgtaacaggt    105240
ttcctaatct tgggacagaa aattacagtt gtcttgctgg tttgttttca cttctttagg    105300
tctctctaca tcaatcttgt gggactctgg gcaatcctca catgctcagt gttttgtggg    105360
ctcgccctat attccaggta ccatgactgt gatccttgga cagccaagaa agtgtctgca    105420
ccagaccagg ttcagtacca tgtctttctt acaggtgtat taataatatt caaaaagctt    105480
attagttgag aggaaagagc attcatattc ttgtagagaa acggaaagtg gacatgccat    105540
catcatctta catttctata aactttgtt aagaatttat tttagcagat atagcaagaa     105600
tgaagagtac tgcatctaaa atgaaaatat ggaaatacca ggaaaaaatc aagcagagtg    105660
ttaaatagga atagctcaag gttgggagta ggaatgtgaa cacagttttt tgttgttgtt    105720
gttgtttgtt tgtttgtttt ttaaactaca caaaccattg tactatagaa cattttgtgg    105780
gtgtttgtta gagcattcat ttataagcaa tttatcttcc aattttttaa atgatggaga    105840
gatggatcca ataagtgaat atttactgag taccaactat gtggtgagat tctgtgccaa    105900
gagcttaaca tgcttcattt aattctcaca accctgcaat cctgattta cagatgagga     105960 aatgcttctc agagaggtta tataacttac ccaaggtcac attgctaata agtaagaata    106020
actatgagca gttatcaaat acccaccatg ggccaggcac taccataatg cttcatataa    106080
atttcaactt ttaatcttca cagtcaccct ctgatgtagg ttctatgatt atctgccttt    106140
caaagatgag agaactcagg cctagagaag ttaagtgaat aactagctag taacctggag    106200
ccaggattta aaccaagca agctgccacc agagtcctaa ctttgaacct ctgtgccatt      106260
tattgtcttt caaaagggg aactagaatt caaacacagg attgcccaac cctaaagcct      106320
gagttcttgc caaaattatt ttctaagact cacttgcaga acaagttcct aggggattca    106380
ttagaatgaa aatagattga atttctgttg atgcaaatgc atctcatgct cccagaaaaa    106440
tacaacttgg tgggccgaga aaataaaaac accctggagc tgtttctcaa ccctatctta    106500
acttatgccc tccttttgat aaacacaccc tctctgttct ctcagagaag gtaagaatca    106560
cgtttactat gaagatggag gcacacttct gttacatccc ctctaataaa gaatattttg    106620
tgactgttat caatctgtat tgtctgtagt ttgtatcatg aagacaataa cgactttaaa    106680
aaaaagtttg taatatactt tgcctttacc ctgggccaaa aaaaaaaaa aaaaaatcc      106740 ctacggcttc ctacctttga gacatcttgt agaatacatt cagggtgtct tgcttgcata    106800
cgcttagaga gtccgtgaag atttctcccc aactgatata tttccaggac tgtgttagtt    106860
aacaagttaa ttcaattaac acttcactgg ggataccatg caaataagac agtggaagat    106920
cgtgtcaaaa ccttatcctc gctcagtcgc ggtggctcac gcctgtaatc ttaacacttg    106980
ggaaggctga ggcaggcaaa tcacttgagg tcaggagttc gagaccagcc tggtcaacat    107040
ggtaaaatcc gtctctatta aaaatacaaa aattagctgg gcgtggtggt gggctcccat    107100
aatcccagct acacaggagg ctgaggcagg agaattgctt gaacctggga ggtggagatt    107160
gcagtgagcc gagatcgagc cactgcactc caacctgggt gagagaggga gactgcctta    107220
aaacaaacaa acaaaaaata caaaaaaacc ccttatcctc aagagagcaa ggatatgttt    107280
ctctatgctc tgctggcatt tgcccagagg aagcaggcca gtttctagat atagttttac    107340
tattttcctc tccatcaatc ctatttcatt ggttctacct atacttgagg gggccactca    107400
gatacgaaat aattacacca cagattttg agaaagttga agataggata gaggattttg      107460 gacctttta taacactata gatggaacct acttttgcta tttgtgggac attgtttaaa     107520
```

```
gttaaacctt tatgatatct tggaaaaatt gggtcttgat ctcatatagg gataaatgct 107580
attccgtttt tctgagaata aagattgagt aagctttgga aaagtggaga acacagtcct 107640
aaaagaactg aaacaatcct aatgttgaaa catttctttt caacagtgga ggaagttctt 107700
ccatatccca tgagcacact attgttaaat gaaattgaag aggctatgga agccgataaa 107760
ataggacatg tcatctactc tgtactgtgg gagaagtaat caataaggtt ttagtgcaaa 107820
tgagaggaca ctcttcgaga aaattgtcca cttaggactc ttttgattcg gaaactgatt 107880
ttgtagaaaa actgccatgc aacagagtcc tgaagtcaca cacttgatta tcctaatttg 107940
atatttattt tttaaaatat aagttatcaa aaagcaagtt agtatcagga agtttttaa 108000 cagaagcaag tttaagggat ttcctgaagt cattctccac ccatcattat gtctcgtacc 108060
tgatgcacct aaaattacat cttctgtcct gggcagtgac tgaagttcac aaaatggcct 108120
tgagtcatca agtaaagtta agtggatgct gcttacttaa gcacagaggt gtgtcaaata 108180
tttccttaaa gacaacttat tattctcaag aatagcaact actttgtttt gagcatttat 108240
tatattccat atactatact atgagttta cataaaatta ctaaattaac ttttacagca 108300
actctatgag gttagtatta ttacaactat tttatagatg aggaaactga ggctcagaac 108360
ttcagttaca aaagccgtat ctgtgtgaat ccaaagcctc tttacttaac tactgtgcta 108420
ttcgtttctc taagtgttag tagttaaaca gtttaatttt aggtatttga aaatttcatt 108480
tgtgtggaat aactcctttc agttcccgaa ggagacaaga caaatgataa actaggcatt 108540
cattaatttt attcagtagc gaaagtactt ggaaataaat tttggaattt ttcagctcat 108600
gccttatttg gtactggaca ttctgcaaga ttatccagga cttcctggac tttttgtggc 108660
ctgtgcttac agtgggacat taaggtatga actatgactc taataacata tgatttccct 108720
gttgggatct ttcttttatt attagatact ttagcgggat aatgtggagt tctgggcaca 108780
gacacagatg gcccaaagta ggcaatctgc tgtatgtgtc ctctctgtgg tctgacttat 108840
ctctgtggac tagcgtcctg ttgtcatcgg ctccactttt aactaggtcc ctgctctcta 108900
atacaccacc atacatccta tgatgtgata cctatggtca caataatgac gatcggttga 108960
tggtagcttt cactggtgat caaaaatggg tgccacagtc ttgattgaaa acacacatgg 109020
ggctgaagcg tggtcaactg gaaaattaga atgaaatctt ccatttacat gttgaataat 109080
atatactgcc caaagaatct tacattttgt gatctatcat tgcccttct ccttgcgttt 109140 gttccagaga attgttatta tcaacatgta cagtgtgtgt tagtggggat tcaggaaatt 109200
aatattgttg atatttacag cacatggtag ggaggactta tgacagtcct ttctatgcac 109260
aaagaaaaat acattttaaa gttgttatgc ataggaatac ggagtaatct atgtagactc 109320
ttttagacac tgaggattaa cagcaagtgg aagcaacatg aacatatcct ttctctttta 109380
ctgtcaagcc tgtagatatt gcctgaatat cattttggga tgataacagt ttcaagaaag 109440
acagtgctgt gattattaaa aatagcatag tagagcctgg tgtagtggct cacgcttgta 109500
atcccagcac tttgggaggt caaggcgggt ggatcatgag gtcaggagat cgagaccatc 109560
ctggctaaca cagtgaaacc ctgtctctac taaaaataca aaaattagc cagacttgtt 109620 ggcgggcgcc tgtagtccca gctacttggg aggctgaggc aggagaatgg cgtgaacccg 109680
ggaggcagag cttgcagtga gtcgagatca tgccattgca ctccagcctg ggcgacagag 109740
cgagactccg tctcaaaaaa aaaaaaaaaa aaaaaaaaa aaaaagcata gtagaaatca 109800
ggttatattt tagaagtgac aatttgtttc cccctttctc attcccactt aaagtattat 109860
```

-continued

```
taaaggtaaa atattataaa tcaaaagttt tattttccct tacagcacag tgtcctccag 109920
tattaatgcc ttagcagcag taactgtgga agatctaatc aaaccttact tcagatcgct 109980
ctcagaaagg tctctgtctt ggatttccca aggaatgagt aagtttctgt tttcataatt 110040
ccattttagc tcagagagat gattttttga gacacaaaaa tttcttttcc actgaagcta 110100
cagaggaagg acctctgaat atgactggat atccacatat gtatgcctat gacaatgcag 110160 attttaaaa aatgtttgta tcaatgttta atgttaccat atctgtaatc aagatttggg 110220
agacacttca aacaattaat tgtcagtgaa ccacaaagga caatttccag gggaccgatt 110280
tagctgtcct ttttcctgt gccttcatcc tatcctaaat ttgtgttaaa attcttagcc 110340
acacacacaa aaaattcaac tattttcctt ttcaactgta gtccacagtt ctaagaaata 110400
tccctagttt gtaaccaaga gccacacttt ttctgttacc taagaaggca ctgtcagttt 110460
cagttatgtt gtcttcccat aaacacttcc caaatgttta cagaggatta gattaaatta 110520
gattaataga ttagatgaat tgaagataaa gaaacagagt gttatgaatt ttgactcgtc 110580
ttagttgtct gttctgtctg cttatgtaca ctgtcctgga gatgaactat aaatttgtgc 110640
aagaaattct caacttctgt tctgttcaat cgtagagcct cattaggggt taaataccag 110700
cttgaataga gtggtttaag catcttcagt tcccagatgt ctcaaatgta atatccaact 110760
caaagaaatc ttgccaatgt actgcattct tcattttgac accttgaaat gcatgactaa 110820
caaattcctt ttcgagaaag aatctttaac ctcaacacaa taacatcaat agactgtcaa 110880
agaaatagta aattatacccc cattagtagc cataattcta tgtaaaattg ccacaactgt 110940
agcctggaat gagtccttaa tttatatcct tcagtattcc ctaaatttaa atagcaatgc 111000
atcattttat tatgtaccca attttaatcc tggaacataa tttcagaatg atgcaatgct 111060
tcctaaaggg tttttagact ggttcattat gggattattg aagctgtgtg gtttagtaga 111120
atgaatagat gaatagatgc ttttgaagcc agacaaaccc agtcttgctt tgttaattta 111180
ctagctgtta accttgagaa aatccagtta cccatacaag cctctatttc tctatatagg 111240
aaatgggcac acaaatactt tgcagaattg ggttttgaga taatgcatat aaaacgggag 111300
gcactggctg gtgctcatgg aatgatgttg atgaatgaca aatcaactct gctaatatag 111360
acgagacttt cattcatttt aaagggtact atgaaatcac aatcttgaag tatatgcagt 111420
aaggacatag agaagaatgt ggcagatgat ttgaatgtgt ttccaataac tttgaattcc 111480
caaaattata atggtgacta ttcataacct atcaaatgga gaatcaaacc aaatatattg 111540
aaaatattat ttacattaaa attgagaggc gtaaaaatca tagcaatgag aactcttcaa 111600
aaaaatcaat ttaaaatttt tcattcagat gcattattta ctcaatacgt ttaacaaagg 111660
tatgaatgct aaaataaaat agaaataaca taaggaatac aaaaattta tgatggacaa 111720 atttcccatt cattttttt ctgtatattg agttttgcat ttgggaaatt atatcaactg 111780
atttcaggtg acttttgctg aatggaagta ttaaaacaaa gggggttttt ttgcatgata 111840
tttcctataa tttaaaaggt aatacatgta cctggagaaa atttagaaaa tactgaaagt 111900
caatagaaaa aaatattcca caatctgacc accagtggtg gtttgaaaac ttttataaag 111960
aagtttgggc tgagtgtggt ggctcacacc tgtaatccta gcactttggg aggccaaggt 112020
gggaggatca cttgagccca ggagtttgag gccagcctgg gcaacatagc gacacccccgt 112080 ctctatgaaa aaaaaatttt tttaaagaag tctggggaaa acaacttagc attagggcag 112140
atgtgctact tatccagaag ttgccttttct ttgctagttt aataggaagg gcttgaggat 112200
actgatggag attatgaggg ggctaaaagt cgtccaacac cccatagtgt ccattgccac 112260
```

```
ttcccaaggg aaatgaatgc ttaaagtcag aagagtctaa tttctgttta ttactccttc  112320
tctcaccttg tacagagcag agctgaatag tattctattt ttggcaagct gaaaacagag  112380
acctgagcct ttctttatat acaaatgttt atggatgatt agattaataa cacaatatag  112440
ttcttagttt taaataccta tagtttattc caggaactct ttacttatat aacctactgt  112500
tgtaactaat cctgggacac aatgtaaggg cttcgtcctc ttgaaacact gctgatccta  112560
gaggaaaata gccatttcct ttattcactg gctctgatgt gtgtggccat tcttcaccac  112620
agtcatatta tccactttga atcaaaggtg tggtggatta ttctattgag aattctaatt  112680
ctctgggtgt ggattttaca ctggctttta tgttgtccat ttaggtgtgg tgtatggagc  112740
cctgtgtatt ggaatggctg cgctggcgtc acttatggga gctttgttgc aggtgagagc  112800
tggcccctgg aggtttaagt cataaatcac taaatctttt ttcaatgttg atgtgaccat  112860
ccttccagac ttctctcgat atatatcgac acctggacat atcaagtggc agggatgact  112920 acactttta  attttttta  attaaacttt gtgttttgag ataattgtgg atttacatgc  112980
aattgtgaga tataatacag agagatctca tatactcttt actcagtttc cctcagtggt  113040
aacatcttgc agtggtaaca tcttgatagt acaatatcaa actcatatat tgacattgat  113100
atagccaaga tacaaaacat ttctatcact acaagaatcc ttgctgttgc ccatttgtag  113160
ccacaaccac ttcccttctg cccctactcc ctccttaatc cctggcaaca actaatctgt  113220
tttccatttc tataatttta ccaggtcaag aatgctacat acatggaatt acatagaatg  113280
taaccttttt cacttggcat aattccctgg agattcatcc aggttgttgc gtatgtcaat  113340
aatctgtcct gttttattat cagatagtat tctctggtag ggatgtatca cagtttgttt  113400
acctactcag ctgatgaagg acatctaaat tgtttccagt ttttgagtat tacaaacaaa  113460
tctgttacaa acattacata aaggtttttg tgtgagcata agtcttcatt tccctgggat  113520
aactacccag gagtgcaact gtcaggtgac tgctaaatgt ctactttttaa aagaaactgc  113580 caaactattt tccagagcat gtcatttttta tatcactagc atagacaaat ggcccagttt  113640
aaacctcatt ctttccagca tttagtggtg tcttttttttt tatattagcc attctgatag  113700
gcatatagtg atatctcatt gtagtgttaa tttgcatttc cctaatggct aatgatgttg  113760
aaaatgtttt tcagcgactt atttttcatc tatgtatctt ctttcataca ttatctcata  113820
atgtcttttg ctcatgttct aattcaattg tttgctttt ttactggtga gttttgagtg  113880
ttctttatgt attctgtata ctagctcttg gtcagatgtg gttacaaat attttcttac  113940 actgtagttt gtctttttat cctcataaca gggtctgtca aagtgcattt tttttttttt  114000
agtttggata aagtctagtt tatcaatttg tcctttcatg gattgtgttt ctggtgtaaa  114060
gtctaagaac tttacctagc cccagctttt gaagattttc ttctatgttt cttttcaaag  114120
agttttagag tttacatttt tatatttaag tctacaatcc ctttggagtt aattttgtat  114180
aaaatgtgag acttaggttg acattctctt ttcctctatg gatgtgcaac cagcaccatt  114240
tgttgaaaag gctttcttcc attgacctgc ctttacacct tcgtaaaacg tccattaggc  114300
atatttgtgt gagtctattt ctgaattctc tgttttcttt catttattta tgtgtctgta  114360
cttctgccaa taccacacag ctttataatt tgattatttt gattactgca gctttaaaat  114420
aagtttcaag atcaggtcga tcgattcctc ccactgtatt cttatttttc gaaattgttt  114480
tagctattct agttcttttg cctttccata tgaagtctag gataatcttg tctgtatcta  114540
caaaaaaaat cttgcttaaa tattgatagc ctgaaagctt tttatccatt tgagaagaaa  114600
```

```
tgacatcttt accatgttga attttctaaa acatgaacat ggtatgtctc ttcatttatt  114660
tagcttttct atgcaaatcg tatttttat gttgatgtct gtgtgttcaa tgctaaaatg  114720
tagaaataaa attgatgtgt ttatatttat cttcaatctt gtgaccttgc tgagctcact  114780
tattagttct gataatttt tgcttctttg ttttatggtt tagtttgttt tgttatattc  114840
cttgagatat tctacataaa cagtcatgtc atcttcgaat ggggcagttt tatttctttc  114900
cttctgatct gtatgaatgc cttttatttc cttattgcac tggcttcaac ttccatatca  114960
tgttgaatag aagtagtgag agtggaaatc cttacccagt tccccaatgt gaacaggaaa  115020
ctctctattc ctattctcta ttcctatttt tttctgagag ttttcaccat aaatggcagt  115080
tgaatttttt caaatgcttt ttctgtaatc aatttatatg atcatgtgat cttcttcttt  115140
agcctgctta caggatggat tacattgatt ggtttttaa tgcagaacca gccttgcata  115200
ccgggaataa accttgtttg gtcatggtgt gtagttattt ttatatattg ctgaattata  115260
tgtgctaata ttttattaag aattttaca tctatgttca tgaaggatat tgatctgtag  115320
tggtgtgtgt gtgtgcatgc atgcgtgtgt gtgtgtgtgt gtgtgtgtgt gtgtgtatac  115380
tgcctttggt tttgatagca gggttatact agcttcataa aataaattgg gaaggattct  115440
gttttctatt ttctaggaga gattgtctaa aattagtgct aattcttcct taattatttg  115500
gtagaattct ctagggaaag catctgggcc tggattttt tttagtttca aaattatgaa  115560
tttaatttcc ttaatagtta cagagctatt caaattatcc atttcatatt cgatgaattg  115620
tgacaattta tgttttgag gaattgttcc attttatcta agtttgcaaa tttatacatg  115680
tatagttgtt catagtagtt ctgtactatc ctttggcatc tgcaggacct gtagtgatag  115740
cccctgttcc attcctaata ttggtaattt gtatcttatt ttttcagtc ttgctacagg  115800 tttgtcaatt tcattgatgt tttcaaagaa ccagcttctt tttttcattg attttctgt  115860 gttgttttc tgttttcact cattgatttt taacttttat ctttatgatt tcttttctcc  115920
ttgctttgag ttttaatttg ctgttttcga ggtgggatct tagattactg atttgaatct  115980
tctcctcttt tctaatgtgt gcatttattg ctgaaaattt ccttcttggc accagtttag  116040
ctgtgttcca caacttttga catcttgtat gttttgttac agtcagctga atgtattttt  116100 acgtttctt tgagatattc ttttgattta tggattattt agaagtatgg tacttagttt  116160
gcaagtattc aaagattttc ctgttatctt tctgttattg attactagtt tgattctatt  116220
gtgatcagag aacacactct ttatgatttc agtacttta aacttgttga ggtctgtttt  116280
ataacctagg atatggtatt ttggtatatg ttccatgagc acttgaaaag aatgtgtatt  116340 cttttttat taggtagagt gttccataaa tatcaattac attctgtttg ttgatggttg  116400 ctgatttct gtttggttgt tttatcaatt gttgagagag gggtggtgaa ttcttcaact  116460
ataattgtgt atttgtctat ttcccttta gttctatcag ttttgctttt gcttcatgca  116520
ttgggtctta atgaaggatt aaccttttg ttattatata atgtgcctat ctgtctctga  116580
gaaatttttt tgctgtgagg tgtatttatt ttatattaat atagttactt ctactttcca  116640
ttgattaatg gttgcatagt atattttcc attttttcac tttgaaccac ctatgttgct  116700
atattagaag tgagttttt tgtagacagc acacagttga gtcttttta aaaatccatc  116760 ctgtcaatct ctgtctttc attggtgtac ttagaccatt cacatttaat ataattattg  116820
gtatgttatg ttagggctta agaatcagtt tttagttgtc tgtttggtat ttctgtttt  116880 tgttttctgc cttcctgtga gttgttctgt ggttccttct ttctaccatt tcctttctgt  116940
ttagaaaact tcttttagcc attcttttag tgttccttca cctgagaatg tcttgagttt  117000
```

```
cccctttatc cccaaaggat attttttgttg ggtatatgat tctgagttgc tagtattttt  117060
tccccaggag ttaaaaaaat attttttctac tttcttttttg tctctatcat ttctgatgat  117120
aaatctgcta ctattctaat tgttttccct tacaggtaag gagtcatttc tttctgaatg  117180
ctctcaggtt tttttgtttt gttttgtttt gttttttctt tagttttcag aagtttaatt  117240
atgatgtatc ttggtgtgta tttccttgtt ttgagttttt gatgtgtctt ggcacgtgtt  117300 tctttcttttt cctatgtttt tagggttact cagcttcttg aatcttgaat cagcttcttt  117360
cataagtctg aaagagattt atgtctctta tcaaatttga aagttcaga cattaattct  117420 ttgagtactt ttccacccca tcttctttct cttttcctct gggactctca tgacatgaat  117480
gttaaatatt tttgttatag ttctacagat ccctgaagtt tatttatat ttcttcattt  117540 catttctctc tattgttcag tttgggttat ttctgttgtt ctgtcattca gttcaccgat  117600 cttttctct gttccttcta tactgctatt gtgcccattc atttaaaatt ttttatttca  117660
gttattgtat ttgttcagag taacagtttc atttggttct tcctaatatc ttcttttttt  117720
ccctgagatt tttctctcta tatatatttt ttccctctat tttttcatta gtttcaagtg  117780
aattctaatt gttaaagcat tttttaaatc atggctgttt taaatttttt atcaaataat  117840
tctgtttctg taatctttat atttagtttg agatcttcct ggttcttttct atgaaaagtt  117900 aatttctgtt gaaacctggg catttcaata ttatgtgatg aaactttgaa tcttaccttc  117960
tgttttagcc agcttttctct gacactacgt cagtagcata agggagggtg ccgcctcatt  118020
acttcaggtg gaggtagaag tccagaggga ggagctcctt gttatgctgg atagggtgt  118080 gtagaatact atgagacata ttgtggctat aagattaatg atagtgcatg aggcccactg  118140
aaatatcttg cagggctgat actacatgtc atgtaggaat ttacaaccct ggctcaggga  118200
tttccaggaa aaaaagcca cctcagcaca gaagcagctt tcataaacct tagaacaaag  118260
cttactttta caataatagc ttaaataccc tttatgaaag aaacagctgg taactaacct  118320
ggactaaata caggtataag aaagggagaa ggaccccccaa agtctgacaa tggtctctgg  118380
atgaagactc tctggtcagt tcatgatctg acccccctgac tgtatctggc ccatgacacc  118440
agcttattct cactatccat cttctaagag tgctgccaga ataaaccgat tgagcattag  118500
atggtgccta agactcatct ttgatgtgaa gtgaacagaa aaggagacat cgcccctggg  118560
gaagctggtt aactaggtcc acctacaacc tctgaacaca actggcattg aggataggat  118620
aagtaagtga gcaagtaagt aatggcaccc atttctaagg aaggactggg aaagggtgac  118680
tggggactgg ttctgatcaa gaagtcaaat gaagccctcc ggaacactcc gtagtgtgtc  118740
tggtagtttt tatttttactt tgtggcctgt tgctgccttc tacatactttt gtctgtgcct  118800 ctgttgtgaa attgccacca tgaaaaacct gccaaaatta ttcttaagac cactctggtc  118860
cccagtaact ggggacaggc tctaaggagg aggaagcaga ggtggaggat gccccggctt  118920
gaagagctaa ccactggctg tgtgtctct ggctcctgct gtgggagggt tgctccttgc  118980
ccccaaggat cttggcactg tgatgccaca gaccaagaag gcaaaggtga agcttacctg  119040
ctgaagggtt atgtgctgtt gcccaccagc tagggactta gaagcatatt tcccaataga  119100
tccttggact aacaccacca gtgaagtcca caagaatcat caaagggcat gtcgcagctg  119160 tttcccagccc accatgcact ccagctgaga cagtgtggct tctcaagggg tgtgcccag  119220 cctgtgatgt ctgctgagtg ttgctggcag cagcccatag gcaacatgcc caagtcacg  119280 gggctcacct cagagtcgtg tcattctgcc tggtcgatcc agagccctgt gagctgtgga  119340
```

```
atgatgatcc tgggtgtgct ggcttaccgc tggccacacc acaggtgtca ccagtcatca  119400
cttgggctga gaaagctgct gccacctcca cagctggctg agatgaggaa gtgtgtccta  119460
gacaccatat ggtccatgaa gaggttcacc cctaatgtgg acagaaattc aaagcctgct  119520
caaagacctg gtgcaggaac ccaaagagaa aggcaccacc tggctgtgct gtgtgtacct  119580
gagaggaagt gctttgcaac tcataggccg agaaatacaa atacagcagc cagcggctat  119640 cttaaagat aataagatca tttccttatt tcaagaccct gttgagctta tccaggcaca  119700
gagtagagtg ggtagacata actgtccctg cagtccgctg cagtggctat tcaggcctgg  119760
cgaatagcac ccccagaatg agcctctttt catcaagggc tgaaggtggc tggtgcacac  119820
tgaggaagaa ggggagccac tgtggcgctt aggcatgctc cagtgagttt gcacagccgc  119880
cactcccatg ggacaggggc acaactggga gaccttggaa cagaccacct tgcacccgga  119940
tggtttacag atgtttttaa ggagagccca tcgtaagcca aaccaactct cctggccctg  120000
atggccacag tccctgaagt taattgagct ctgtaggtcc tcatcaccct ggaaaatgct  120060
gaagaatagc taagaatccc taagaaaact tagggaactc accctatacc actcttcagg  120120
tccagggtcc ctagcgggct gccttctttg cacctttcag acagaaccat ccaacagtgt  120180
tcacaacagc acctcgctcc ctacccacca cacaggacct tgcagccaga ggtctcacac  120240
tgggctctgc tctccctggc cttctcacac ccatcaccca cgggatgagg cccagtccag  120300
ctgttcacaa gggcagagtg acctctactg gcagatacgc tgaagggtgc ttccaaattg  120360
gctcctgtct ggcaagcctc atgaattcct gcaaactctc cttaatacca atgtcgtcca  120420
gtcatcccac ccactgaccc accacccatc tggatggctg agcatcaact tccacctttg  120480
ggaagatgtc ttcactgcta acattcctgc cctgtgtcca ggatgaccca cctggactgt  120540
cccacccacc ctacctatat ccctccctgg caagaccttt actggtatat ttgcctaggg  120600
gtctcttggg ccaccactgt tcctgcagcc agtgcctcct agagacactt ggtgcccag  120660 ctgtgcctga cagccatctg gaatggacaa caccttgaac tttggcttca tcgggccgtg  120720
ttcaagatca cgattttgga tctttgacag cacctcagca cacacagtgt ccccagacct  120780
aattgcttag ttctgtgtcc tccttatcct tctgttccat tttcacctgt cattgctctg  120840
taatcaagca actctaagcc tgctaccact gagtccattc aactccttc acctgctcat  120900 gtaatcgtgt ttccaagccc cagtgtgccc gtgttctttt gctgctactc cgggtggcct  120960
gactttccac atccaactgt ggcttctcca gacctattca ccaattactt ggcactgagg  121020
tcactgacag cctccaccac attttggcca cccactgagc agctaacctt ccagcctgct  121080
gggcatgcct tcattggcct gccacacatc cattgcttcc cgtccagact tggtcgctac  121140
ctgtcctcca ctcttccccc atcattggcg agtctgcccc aaagccacag ccgaacccca  121200
ttctcatgat ctcccgtaac tgctcagctg gacactagat ctactgtatc ctctctgtga  121260
tgatacagtt catttccagg ttttttccaag ggcgccacca actcctactc accgtcctac  121320
agaagatcca tttctcaaga tttgactgac catggagcgc actttcaaac ttgggcagcc  121380
tctcaattat tgaccccctc agggtcaggg gtggagtgtg gtatacaatg agatatatta  121440
tggctataag attaatgata ggcataaggc cactcaagca actcagaggg tcagtcctat  121500
ctgtcaaact tagcagtatg aagcaacctg gccggggatt ccaaccagaa tttccaggag  121560
accaggtcac ctcagcacga tgcaatttc acaaaccttg gaacaaagct taccccttaca  121620 agcatagctt aatctctctt tgtgaacaaa acacctggta actgacctgg attgaataca  121680
agtataagaa aggaggaagg atcccctaaa ctctgagaaa ggtctctaga tgaaaaccct  121740
```

```
cctggtctgt cagtcatcta acctgtgact aaatctggcc cacgacacca tcctgctcct 121800
gctattcttc tggtaagagc actgccagaa taaaatgcat gagcatcaga cggtgtacaa 121860
gactcaacaa tgatgcaaag cgaactcaaa ggaagaggct ccctgggaa gctggttaac 121920
taggaccacc cgaaacacgc gagcaccaca gggtggaatt cactgacatc atggaggagg 121980
tggctttgtc actgctgggc catggtgaaa gtcccgattc tccactaggc ctcccatgtc 122040
attgccagca gggaggcaaa gggtgcctgg tgacagtctg gggggatgga atctaggctg 122100
gcatgggtgt gggtggggtg aacagattat tctgtggtgt tcggatggaa tggagcggtt 122160
ggggtctaag agttttctat cttcctaggc tgctcctttc ctggccctgt gtctagagag 122220
agaacaggat tttgtgaggg cttttttatct ttttaaagtt tttttgcctg tgtctgttgc 122280
catttccagg ctggctggct tcttcagttc tcaggctggg atacatgaag caaaagaaa 122340
acttagggaa ctcaccctgt accattcttc aggtccaggg tccctagcag gctgccttct 122400
ttgcaccttt cagagtcttc ttatgtttat tttatatgga atgtcaggat ttttaatttt 122460
attagtagga ggaatagaga aacatatgtt tatcttctca gaagtagaaa tacttcatta 122520
aaaaaatttt gtttatttac ctgaagggtc tttcacctcc tgtggcgttt gctcttctga 122580
ttagagagca ttttttgtgtt ggaaagctcc ctcctgttcc tgtggagctg tgggcctgga 122640
gaggacagac caatctttac aacagtgtct tcttcctgaa ccctgtgggc acctcactgt 122700
cttcaacacg caggccttgg catagacttc tccctctgcc tgcaacacct tcctctctac 122760
ctcgtccact gcctaagcct tagttattct tcagttttca ttttaacaca ttacttattt 122820
aaagagactt ttcctattac ctggatacat ttgcattccc ttctgctaaa tgtttctaga 122880
agcaccttgt actttcttta tcatctccat tatcaaactg tattacagtt atttatttag 122940
tgtctgtttt actgaatagc ctgtaattca tgaaggtggg gaagatgact tcgttgctca 123000
atcctgtatc aaatatctgg ttcctactgc agtgcccagg acaaagcaag acattaacaa 123060
ctttagcttg aatattaact aataatgtag ttaggctcat aaatatccta ttatctgatg 123120
accccaagtc ctccctgaaa tttccttggc cacttgggct gctcctctgg gatcctggac 123180
ctcccctttga cctagaaact taaaggctag tactggcaca gcaggggtcc tccaggatct 123240
ttcttcagtc ctaaggcttg gggccattct ggttggttgt tgtttaggac atagcagttg 123300
taaaatagtt tgaccccatc cctgattata tgaatgaatg aattagatcc agaagctcca 123360
agcctgccca gcactcctaa accacagcca gtcatacaga atttgctttc ttcatagtct 123420
gcattagtgc ctggagctct tattgtggtt gattcccctt tttccatata tcagctatgg 123480
cctgattata tacaatgaca tgttctagca aagtcatcat aactccaagc cagttcatcc 123540
ttgcttcatc tctagccaag gtcttatttc ctcttgtaat cttttttggg tgtctttgtt 123600
atgtctccaa aactgctcac agatcacaca gtcatcactt gctttgtggg tcatatgacg 123660
tcttgcagtg aagtctatct cccttctgac tggactgtgt gtaaactgac tcaggatcac 123720
atccttgagt ccgcatcctt ttaaacacta gttctcctct ctactcagta ccacatcctt 123780
ttcttcttcc atgaagtagg cctatttaaa acaacaacga caacaagaag cactatttcc 123840
tctaatatttt ccctgacttg gtattttctc tttgattcat tcattctgct ctattaaacc 123900
cctttactct ctggacaaac cagtgattcc ctgctcttct tttatggttg tgtccattct 123960
taagaactgg gcattagatt attgggaacg tatatctctt ggaagcttca tttagttgct 124020
ttgcctcatg cgatgtttgc actgtaaatc tttttttacta tcatggattt gatatctcta 124080
```

```
catcaaagca aaggttgcag ttatctaatt agattttaaa tctatttcta catgatttga  124140
tcagtctttt taaaatcgta tttctcattc tagtttcatc cttagggaat caaatcagga  124200
atggcaaatg ggtttcatcc tcctctctgg tcacatagca gtactcgtcc accgttatga  124260
gaggattttg agattatcaa agcacaaagg agtgctgtga tttataaaca cctgcaagag  124320
caatgctaag aggagaggta tcattcatga tttatacatt cacataggca ctaccattgt  124380
cgcagacctc tctatcttct ttgtgttgtg tggccttttt tgaggctact tgcagaaaca  124440
gatggatcct tgagactgag atgcagaaac ttgtaagttc taatgacttc ttttccagtg  124500
ataaggctat catgactgaa actatgattt tcagaaggag gccgaatact ttaagtcatt  124560
atcctgatga aatgactttg aaatatttga gtttcgattt gagattgcta attgctgacg  124620
ttgtattatt tttgtaggca gcactcagcg tatttggtat ggttggtgga ccacttatgg  124680
gcctgttcgc tttgggcatt ttggttccct ttgccaactc aattgtaagt acaaagaatg  124740
aatatgcttg aggattactt tttgaactat actagcagct ctacactttt ttctcagttg  124800
gttcctttga gatttgtcat tagctacttg tcttgatgac ttaaattatt tctgttgact  124860
ttggtggagt gtacaaggaa gtactatgta tggggaccct aaatgtgtga agctcaatgg  124920
aaacttccag aaccatatag ggcaatttta aatattcata atataactaa aggagcaaca  124980
tttttatgca cgtacctact tgcccttctc aaaaattaat agctaggatt taaaagagat  125040
caataggctc agagatgaga gatttaaggg cagaaaactt aggatttctg tgaatagcca  125100
tagcacagca aagagaagga acacaatctt accaccttgg ccaggaattt tctactcctg  125160
acatttaaag ctgtagctcc cacaacatga tttagcccca aagggggtgat cataattggg  125220
aatatttttcc agaaagacgt aatatctctg tccttctacc tagacatatc tgtgcttaga  125280
agtgctaact tttgtttgga ataaatgagc tagaaattat ttctctgaaa cccagaagaa  125340
agtccactgg ttcagtctgg ctataagatg tagttcagga aaaactgata atgtatgtgc  125400
agtcgcttca gatatagaat agccatagaa ctctgacttc acatttggaa ttctattttc  125460
cttataaggc attaggaatt ggtaaggcag atattaataa ggactattgt ggttattatt  125520
tattatcctc aatgaaatgt catatgaaaa gctgcttttg taggaattaa tcacaatgga  125580
agagatttgt ttgtgtccac ctcagaatgt tgaagcttgg attagattct ttgcatgatg  125640
aaatgcatta gtttgttaag tattagaaaa atgtatttaa aaatcaactt ttgatatttg  125700
gcatttgttg ccagcgtgta tttcctccgg aagagctgta gctgactaag ctaacatgtc  125760
cttttctggg ggcggtaacg gaagaataac atactattct tcctgccata aacagtatct  125820
ttttttttttt taaaccatgt ccaggttttt caccagcaga ttatctgcct tccttaaaag  125880
tggcctttct cactcctttt tctctccctg cctcaatacc tttcattcat ttattcactt  125940
gttcatttat tcaatagatt tttatgggct gagcactatc ttgggaggag agagcgttga  126000
atgtttctgc ccttgtgagt tttataattt cgtgccatgt tgaacttggc tttctaatat  126060
taattttgac atcaaagcaa attgtattat ttttcttttta aaggcattct tgttttacag  126120
ggagcacttg ttggtctgat ggctggattt gccattctc tatgggttgg aattggagct  126180
caaatatatc ctccacttcc tgagagaaca ttgccattgc accttgatat ccaaggctgt  126240
aacagcacct acaatgagac aaatttgatt acaaccacag aaatgccatt tactactagt  126300
gttttttcaaa tatacaatgt tcaaaggtat tgaattaagt tttattacat tatactttaa  126360
aaaatttacg caacaagtag agaacccac ttgcttttg tcttgcttac aacactgtga  126420
ttttgcctaa ttctgaaatg agtaaaaccc atgtggttag ctatagtatt ttctgcagcg  126480
```

```
gtaacaaaaa atgtcatatt ttcataattt ctctagaaat ttctgccttg tctacagatc  126540
taagaagact taaatattaa tgagaaactt ctgttatgtg taaactctcc taaacaccag  126600
ctcttagctg catgaagaat tatctttgtc ttggaaaaac ttttaaaatg aaagcacaa   126660 ttatagaata aatattgctt atatagtctt agaaagatag attttactga ccaaaagcta  126720
caattattta aacatgttaa ataactgcca tttgttcagt tgaagattcc aaatctttaa  126780
agcattagaa gtgattgcag ctgtgatctt catgctacag atttcagtca tgcagtacac  126840
tttggagcct ctaaatgctg aagttgtctg atttaacgta ctgaaatagt gggtagaggc  126900
atgctttatt gtacagtgaa tgtgaggtca agactttctt tagtggatat ataagtgtcc  126960
agctttaaag cacaaaccct gtgaatacgt tcaaggaatg caaagatgat gccattgccc  127020
ctagagtatt gccccagtgc cagcttatct ggaatgacat caatatagtc atacctttgg  127080
ggtcaagaca cggcataccc ctcttaaaat ggacacactc ctgagagaag gaacgtgatc  127140
atacatatag ccattattag caatttgtgt tctggagaga attcagctat gagaaagcta  127200
gccagtggga cttccagggg cgttccaggc aggtaagctg tgtatggtag agtggaaagg  127260
tagttccaga gcctgaggcg tatttgaggg aagtttttact aggtgaggtg ctgtggagag  127320
aggggcaagg acatgtggag agcagtctgg acaggcatga aagcactaat gggaggggac  127380
tgggagagtc atcagagtca gaaagggaga aaagattaat tgaaggttaa gtgagaagac  127440
acaggatgtt cttcttgttt tatgattttg cttagcgttt tcctaattat gtaaatattt  127500
gcccttaaaa gtctaaggca aaatggttat ttggattcct gaaacaaata aattagctga  127560
agtttattct atgcctggta ccataatagt tttatatgtt agtttactta tcaaatattt  127620
cagctaataa acaagaattt tgagcatgg  actatgtacc cagcactgtg ctggccattt  127680
atttagtatc catggaagaa aatcttcctc tcccagccac tgtttcctgc cttccagaaa  127740
attctaatct agcaggaggg aatgtgcaaa tatacgcaaa acaataaact cagtaagcat  127800
gctaagtata aaaactaaga catagtaaat aaaaaatact tgatacattt ttgttaaaag  127860
agtgagtaca aagttggagt gtaagttagc atgaagactt cagagatata ctactacttc  127920
aagaatgcat aggtttggct agatgaaggg gaagatctgg aaagtcattc ttgtcacaga  127980
aaatgaccag aagggaaatt ggacaagaaa ataaattaaa acatgcattg tggtaagtaa  128040
tattcacagg atatcatggg agccagaagg aggaagtctg cctgactgaa gtcaaggaaa  128100
ccttcttaga ggagaattgc atgggctgga gttagtcagg tagcaggatt gagcacaggg  128160
acacaatctg tatcgcaagg aaggaggagt gtgtgtcgca gaatgaagaa acgaccggtg  128220
caaaagcatg aaggactgaa gaatcagggc atcttaggaa atcatcctag ttccataggg  128280
ctggagcaca agggttgtga gccacccagc tgaaggttga atgtgtgatg ctttggttgc  128340
ctagatacaa attgtttcaa ttgcctagat tcagttttga ttttttttaag tttacaatat  128400 ttgatggtta cattggtagc ttgctgtggt tttaatttgt atttccctta agattaatga  128460
agtcaaatac attttcattt gtttgttggc catttggata tttacttttg cgacttagtt  128520
attgaagtct ttagtccatc tgaaatggat tctctgtctt tttcttactt acataggagt  128580
tcatgacata ttctacatat gagatatgtt ttgaaaatgt ttctctccca ttctatgggt  128640 tacctttta ctcttttaat gatactttt ttgtcagtca aaatttctta attttaattt  128700
atttctgttt ctcagttttt tcctatatgg ttagtccttt atgtgtcttg tttaagaaat  128760
ccttgtctac cctgcaatca taaagatatt ccactaattt tttatttaaa agctttattg  128820
```

```
ttaaccattt ccattgagga agtgtaatcc actttggaat tgatttctgt gggtggtgtg 128880
atcaagatta ttttccccca tgtggatact cagttaacta aaaaccattt attgaaaaga 128940 ctccccttt gccccattga atgcactggc gatgaaaacg atgttaacca agtaactatt 129000
tttctgtggg tctatttctc aattctctac tctgttctat tttgtctgtc tttggctcaa 129060
tatcacactc tcttaatttc attagcttaa ctcaatgtgt tcccctcctt tctgggttct 129120
tgtcacctca agttctcatt gttttgtttt tgttttttgtt tgagacggag tctcagtctg 129180
ttgcccaggc tcgagttcaa tgcaacctcc acctctgggt tcaagtgatt tttgtgcctc 129240
agcctcccaa gtagctggga ttacaggcat gtgccaccac acctggacaa ttttttgtatc 129300 tttagtagag atgggtttc accaggttgg ccagactggt cttgaactcc tgacctcagg 129360
ttatccacct gccttggtct cccaaagtgc tgggattata ggtgtgtgcc accacccag 129420 ccaagttctc attgtcttga tctctctgat agcttcaaaa acctgcctcc ctccccatgc 129480
cccaggtttt atatattgtt ctcagcagaa tgattgttct aaatcaagca gctatcaaaa 129540
ctgaaagtgg aatcctagag caatcattgt agaaatgatc atagaatgtt catgttactc 129600
tttcacttaa acattgcaa tgagtgccat tgcctgtaga gtaaaattcc aactcatgcc 129660
tggtcccaca aaaagccccc tgcctatctt tcatcttgta atcactgtct tgctcactgt 129720
gcctcagtca gctggtgttt agtctctgtt ttcctcaaga acattttgtt tctcagatct 129780
cagttcaaat gtcatttatt cccaaaggtt ttctctgacc acttgtagtg tagttcctcc 129840
ctcttcaccc tgttaatagc acatcatctt gttttacttt ccttacagca ctttctacta 129900
gtggaaatta ttatatttat taatttgttt attgtattta tctctccatt agagcataaa 129960
ctatatgtta gcaggaatct tatctacttt atttttaaaa ataatttca actttttatttt 130020 tagatacctg tgcaggtttc ttacttgggt aaactcttgc ctgtctccct tcaccctctg 130080
gtagtcccca gtgtctattg ttcccttctt tgtgtccata agtaaccaac atttagctcc 130140
tacttataag tgagaacatg tggtatttgg ttttctgtgc ctgcattaac ttgcttggat 130200
aatggcctcc agctgcatcc atgttgctga aaaggacatg atttgttct ttttcatgg 130260 ctgcatggta ttccatggtg tatatgtacc acatttcctt tatccagtcc accattgatg 130320
ggcacctagg ttgattgcat gtcttgctg ttgggaatag tgctgcgatg aacatataag 130380
tgcacgtgtc ttttttggtag aacaatttat ttccttttgg atgtatacc agtagtggga 130440 ttgctgggtc aaatggttta tctaccttat ttatggctga ctgtccaatc acaagagcag 130500
tgcctgggac atcatgcaga attgaatgaa taaacatgac cttcaagtat tttagtatat 130560
agtcaaggtg aagttttgct ttcaattcct gatctgataa gataaaatta ggacagcagg 130620
ttatgacatt aaaaacatta ttaagtgtta tattttgacc ttgccatggg aatcactggt 130680
atatactggt agttgctagt ggcattacat gaaatcttac cgttgtgttt ttgctctctt 130740
aggactccac tgatggataa ctggtattct ttatcatatc tgtacttcag cactgttgga 130800
actttggtaa cattattagt ggggatactt gtcagtttat caacaggtaa ctatctaaac 130860
attagtattg ttgtatttac ctctatatca gttttttactg tatctgttt atagctattt 130920 atgttatttt actatgatcc tattgccaac tagtttaatt attctcttctg ttttactcat 130980 gggaaatctg aaggcctaga cttgaaagca gaagactcat ttctatttga atcttggttc 131040
tgccctttag gggctgcatg aacttgggca agtcacatag ctacactgag cctcagcttt 131100
cttatgtata aaatgaggac aataataatc gacctgccca tctcacaagt tgctgtaaga 131160
caaaaataag atgcttgaaa agaacttcat aactgctatg atgttaggga ttttacacat 131220
```

```
atttttataa taacccaata tgctgtgatc tttacatggt ccagtattca ttctttgtga  131280
actgtaaaga agcatacaca ggttatatct aaacatagtg tggaggcttt tttttcagat  131340
atttatcatt ttttaaaaag tgtgttcatt tttaaaaaat caaattgata cacatagtat  131400
ataaattgct ctctgggatt gctatagaac ggttatcttg ggactccatt ttgtcctcat  131460
tctatgaatt ctcttagccc ctgttcctgt gttgggtttt ctactgccta tattcattac  131520
ttctcattct catttactcc cttaattgaa tgaaacacat cctatagcat attctcaaga  131580
aagagtagac aaaagaagag gttttggaaa ctttgtgtgt ctgaaaaaaa aattatttaa  131640
tctatcttat gcttgattga ttgtttgagt agaaattgct agggttgaaa agaacttttc  131700
ttttttctga gaggatgtct gaattttttt ctagcttgct atgttgctgt tgtgacagcg  131760
ctctgctacc agctgacact tgtgtgtgt cccattttca caatgactgc cttggcctag  131820
gccttcagta gggcccattc aatctgaaga tccatgccct tcagttctgg acattttctt  131880
ttttgttttc ttttcttcct ttttatttct atttttaata attttctgtg ttctctctct  131940
gagaactcct attagtcaaa catttgaatc agaatcatgg acagttcctc taattttctc  132000
gtttttttct ctcttatttt tcctctccgt gtcttttagg tctactatgt gagatatttt  132060
ttcacttact tttccaataa ttctcaaagg agtgctctga tccaattttg agaatagtct  132120
gtagggaac gagggcaggg aagaggctat tgcagtaacc caggtgagag atcacagtgc  132180
tggggccggg gtagtgcgga gttggtgaaa catgctgggc tccctgactc cctacatccc  132240
ctcacatgta tgcatccata gcagccacgc caggggaagg gtgcaactgc ctccttcaac  132300
atgtgttaca actagttgtg ttcaaggatg tctgatgtct ttgtttgctc catgctacaa  132360
agctgccagc actgtgccac tttacagaat cctgctatca ttttctgttt tttggcactg  132420
agatagcact gtctctcaaa cttctgtgac acttgtattt ataattataa aatttgttgc  132480
tattcattat ttctcagttg ttggaaaata ttctttcttt tccaaaagga ctgtgctctt  132540
tctcaaaaat aaaattccca gtacagtagg tttattaatt tgtttggtcc agtttgatat  132600
attttcagac agattttgt tgttgttgtt ttgctgttg agatggaatc tcgctctttt  132660
gcccaggctg gagtacagtg gtgcgatctt ggctcactgt aacctctgcc tcctgcgttc  132720
aagggattct tctgcctcag cttcccgagt agctgggact acaggcacgc accaccacgc  132780
ccggctaatt tttgtaattt taatagagat ggggtttcac catattggcc aggctggtct  132840
cgaactcctg acctcaggtg atctgcccac cttggtctcc caaattgtag ggattacagg  132900
cgtgagccac caccatgccc agtcttaaga cagattttca tcttttccca gcagttattc  132960
agttgttcag atctggaata cacctaacca gtctccctgt actatttgcc ctttggtcct  133020
tatttagctc atttttttaaa agaaagtgga gtatcagagt agctcctttg aatactcctt  133080
ttttctttt aaatgctttg attctgaaaa accatataca gctatatctt ttgtttcaag  133140
aagtaacact ctacctcagt gactgggatc cagtaataga aaacacttca acttcattaa  133200
cttcacaaat aacttattcc tacttcacag aagcagtgag taccttgaaa actatgagaa  133260
gcacacaatt ttgatgctcc ctgggaaaca gattttaaaa cctatcgtag tatactaaaa  133320
ctcccataag agttcaggcc ttacagactt ggttggcgtt tcagcactcc cctgattttt  133380
actatgcaga aggctatgtt ttcatcagga aaatgggggc aaatagtttc ctaagtagat  133440
cacaaactgt gggcacagag attgttttgt tctttgtttt ctctagcacc tagcagcatc  133500
tccagcacac agtaggtact caataacatt gaacgaattc atttaaaatt gattctatct  133560
```

```
ccagaacagc agaggttccc ataattaaaa gtctagtatt tgtactaaag tagtggttct   133620
taaactttag agggcataag gatcctcttg gaaattttat aaaaatcagg cttcaggggt   133680
cctacctgca gaggtcctaa tttggtcagt ccaggctaga gtctgggaat ctgcatttta   133740
agtacattcc ttgaatgatt tggggaaggg tagtttgagg accactcttt gagatacaca   133800
attttttaaaa gcatcctctt tgatccacaa aaaataccaa agcaaaatag aattttttttt   133860
tttttttttt gtaaagaaaa ccttagggaa gaggatttgg atcaaacgtc agtcagcata   133920
ctaattttca cttaagtaat ttattcagca gttccgaatt gcctgcattt cttcatagac   133980
atgtatattt gtagccaaca aagtggggaa aagcagctcc actgtctgaa gcggggcaga   134040
tggtttgata ttttactgat ggcatggagg gtgcttttaa accagttttc ctaccagcat   134100
tgggccagat gactgtttct ctagttgagt accagatgaa gcagttggct tgcgtttaag   134160
ctctatctca cacacatata tatgatacat atatatatat atatatatat atatatatat   134220
atagagagag agagagagag agagagagag agagagagag agagagagag agagagagag   134280
agagactcat atttattata gtgagaggct ttcaagacct ggggctaatt aaggaaaggg   134340
gaattgcggg ctaagtgatc agtgctttta agtttcccctt tctcttttgtg ttttttgaat   134400
gtatggagtt gaacgtgaac aagttaaatg cctgtataat ggaatgtctc tgtgtagtta   134460
ctggtgtcct ttaacaac gtaagtcatg tacattttttt tttccaggag gaagaaaaca   134520
gaacttagac cccagatata tactaaccaa agaggacttt ttatccaatt ttgatatttt   134580
taagaaagtg agttggcttt catttacctt gagttaggaa actgggcttt attacctgga   134640
tagaacacta attagttctc aacctctttc ttgaaaagtg atggacaagg aaggtataga   134700
ccctatataa tctgatgatc tatatatgtt ggatagctct ctatcctatg atgatctata   134760
tctgttttat agctccatat cctctgatac gctatacta ttgcttatct gtgtatcctc   134820
tgatgagcta tatctgttgc atatcctctt tcctttgatg atctttatct gctgtatatc   134880
tctctatcct ctgataacct atatctgttg tatatccctc tattctctga tgagctacac   134940
ctgttgtata tctatctctc tctatcctct gataacctat atctgttgta tatccctcta   135000
ttctctgatg agctatacct gttgtatatc tctctatatc tgtctatcct ctgataatct   135060
atatctattg tatctctctc tatatctgtc tatcctctga taacctgtat ctgttgtata   135120
tctctctata tctgtctatc ctctgataac ttatatctgt tatatctctc tatatatctg   135180
tctatcctct gatattataa atctgttgta tatctattgt ctgatggact attttgtatc   135240
tatcttctga taacctgtat ctgttgaata tctcggtatc ctctgaggaa gtatacctgt   135300
tatatatttc tctccctcag tagattagaa agctgatgca gagaaataaa aatagtagaa   135360
acaattattt agaattacat gaatgaagag cttcttttttc tccccctaat caccatgtta   135420
acatttttctt ttagaagaag catgttttga gctataaatc acatccagtg gaagatggtg   135480
gaactgataa tcctgctttc aaccacattg aattgaactc agatcagagt ggcaagagca   135540
atgggactcg tttgtgaagc tgctctgata ctagatatcc ttaaatgatg tttcaatttt   135600
atatgttttc taagataatt ggatcaggtt ttcttttgtgt gtgtgtgtgt gttgtatcat   135660
gagtgtttgg gggataagtt tttgttaaaa caaagtctgg actatcttca tttactacat   135720
cattaattga tgttactctg gagtttagaa ttctggcatt gacatttccc tctctttcct   135780
ttatttcgat gaagctataa ttgtgaaaat tgtaactaca tagatgctga aaggctaata   135840
cacacatatg cacatgtatt tgattgtcaa aggtatattc ttaaatttgg gtattattga   135900
aaatattttc catgccttgg tgctagcata taagtttgga agtttgccaa catcacaatt   135960
```

```
catcttgaaa agagctttt tccctcctac cacatacacc attcttaggg agcaatgagg    136020
taacaggtct gtgttgtcta gatctttgct ttttatcccc ctatcagtcc agggcatata    136080
ctaacctgca aactgattct gaatcaggaa ggtggtaatc aataagtatt ctggctggga    136140
aagaccgtgg gcccaatgat caaagtcttc ttggtgctgt tcattaattc ttgtgccttt    136200
tggcttgttt tctagagttt ctgggctttg gctgctgata ctgcctttct tagactgtaa    136260
ttttttatctg catgcccagt ttctgaccta tcaacttggg ttttattgtg cactctaact    136320
gagcttgtct tcataatttt ctgtttattg ccctgggctt ggatatgtct caagacactc    136380
atgtgaatca tgccaccca atcctggct tatcaagtcc cagactataa attatgaact    136440
cccattagct tggtactaac atatacttga tgtaggtatt tatggacttg atgatccaag    136500
aatattatat tcttcaaaat ggttaagctc catggagtta gatgactaca cttaatgcta    136560
ttaagttgaa cttttgaatg tcaactaatt tgcaatcaat taaagataca tatgcctaga    136620
aattttgaaa tttcggtata tttatccagt taaagggcta aattatataa gcaaacacta    136680
ctttttttaa aacgtctgga ctcaaaaaat gctttgttcc atgttttaaa attttttaagt    136740
agcagtctca aagttgctta gctgtttatt ttgctatgtt cctagctaag agtttggtta    136800
taggagttca tcaataactt atttttttgta cagttcccac attagatact gtttaaaagt    136860
tctttttaa actcaatttt ttttagaaac ataagagaaa tatttagata catacaaatg    136920
tttttatgat taaataattt tatgcttatt ttctgatacg tgttattag gtaatcatgc    136980
cctgtacatt tagaggttgc taactgacaa tgttaagaaa tttaaaaaa aaaaaaagc    137040
ctgggcatga tggctcatgc ttgtaatctg aacatttggg aggctgaggc aggaagatcg    137100
cttgaggtcc agagtttaag tccagcctgg aaacatagtt agacctcatc tctacaaaaa    137160
taaaaaataa aaataaaaaa aacttagcta ggcatgttgc cacatacttg tagtcccagt    137220
tattagggaa gctgaggtgg gaggatagct taagcccagg atttcaaggc tgcattgagc    137280
tatgattaca ccactgcact ccagcctggg taacagagtg aaatcttgtc tctgggaaaa    137340
aaaaaaaaa aaaaaaaag agagagagag agagggagat ttatataaca tttaaattaa    137400
ctgcataaac ctgggcaatg ttcaaaactc catctctaca aaaaaacaca agaattagcc    137460
aggcacggtg gtgtgtgtct gtagtctcag ctacttagga ggctgaggtg ggaagattgc    137520
tagagccagg aggtcgaggc tgcactgagc tgtgattgcg ctactgtact ccaccctggg    137580
tgatgaagcc ctaactcaat aaataaataa ataaatatat aatacaaata aattaactat    137640
atattcatgt atttcttatg tggatatatg ttatttttt tttcctgctt ttctttttt    137700
ttatttttt attatacttt aagttttagg gtacatgcgc acattgtgca ggttagttac    137760
atatgtatac atgtgacatg ctggtgcgct gcacccacta actcgtcatc tagcattagg    137820
tatatctccc aatgctatcc ctacccctc ccccacccct accacagtcc ccagagtgga    137880
tattcccctt cctgtgtcca tgtgatctca ttgttcaatt cccacctatg agtgagaata    137940
tgcggtgttt ggttttttgt tcttgccata gtttactgag aatgatgatt tccaatttca    138000
tccatgtccc tacaaaggac atgaactcat catttttat ggctgcatag tattccatgg    138060
tgtataagtg ccacattttc ttaatccagt ctatcattgt tggacatttg gttggttcc    138120
aagtcttgc tattgtgaat aatgctgcaa taaacatacg tgtgcatgtg tctttatagc    138180
agcatgattt atagtgcttt gggtatatac ccagtaatgg gatggctggg tcaaatggta    138240
tttctagttc tagatccctg aggaatcgcc acactgactt ccacagtggt tgaactagtt    138300
```

```
tacagtccca ccaacagtgt aaaagtgttc ctgtttctcc acatcctccc cagcacctgt   138360
tgtttcctga cttttaatc attgccattc taactggtgt gagatggtat ctcattgtgg   138420
ttttgatttg catttctctg atggccagtg atgatgagca ttttttcatg tgttttttgg   138480
ctgcataaat gtcttctttt gagaagtgtc tgttcatgtc cttcgcccac ttttgatgg    138540 ggttgtttgt ttttttcttg taaatttgtt tgagttcatt gtagattctg gatattagcc   138600
ctttgtcaga tgagtaggtt gcaaaaattt tctcccattt tgcaggttgc ctgttcactc   138660
tgatggtagt ttcttttgct gtgcagaagc tctttagttt aattagatcc catttgtcaa   138720
ttttgtcttt tgttgccatt gcttttggtg ttttggacat gaagtcctg cccatgccta    138780 tgtcctgaat ggtaatgcct aggttttctt ctagagtttt tatggttta ggtctaacgt    138840 ttaagtcttt aatccatctt gaattgattt ttgtataagg tgtaaggaag ggatccagtt   138900
tcagctttct acatatggct agccagtttt cccagcacca tttattaaat agggaatcct   138960
ttccccattg cttgttttc tcaggtttgt caaagatcag atagttgtag atatgaggcg    139020
ttatttctga gggctctgtt ctgttccatt gatctatatc tctgttttgg taccagtacc   139080
atgctgtttt ggttactgta gccttgtagt atagtttgaa gtgaggtagc gtgatgcctc   139140
cagctttgtt cttttggctt aagattgcct tggcaatgcg ggctcttttt tggttccata   139200
tgaactttaa agtagttttt tccaattctg tgaagaaagt cattggtagc tttatgggga   139260
tagcattgaa tctgtaaatt accttgggca gtatggccat tttcacgata ttgattcttc   139320
ttacccatga gcatggaatg ttcttccatt tgtttgtatc ctcttttatt tccttgagca   139380
gtggtttgta gttctccttg aagaggtcct tcacatccct tgtaagttgg attcctaggt   139440
attttattct ctttgaagca attgtgaatg ggagttcact catgatttgg ctctctgttt   139500
gtctgttgtt ggtgtataag aatgcttgtg attttggtac attcattttg tatcctgaga   139560
ctctgctgaa gttgcttatc agcttaagga gattttgggc tgagtcaatg gggttttcta   139620
gatatacaat catgtcgtct gcaaacaggg acaatttgac ttcctctttt cctaattgaa   139680
taccctttat ttccttctcc tgcctgattg ccctggccag aacttccaac actatgttga   139740
ataggagcgg tgagagaggg catccctgtc ttgtgccagt tttcaaaggg aatgcttcca   139800
gtttttgcct attcagtatg atattggctg taggtctgtc atagatagct cttattattt   139860
tgaaatacat cccatcaata cctaatttat tgagagtttt tagcatgaag ggttgttgaa   139920
ttttgtcaaa gcttttttct gcatctattg agataatcat gtggttttgt tctttggctc   139980
tgtttatata ctggattaca tttattgatt tgcatatatt gaaccagcct tgcatcccag   140040
ggatgaagcc cacttgatca tggtggataa gcttttgat gtgctgctgg attcgttttg    140100
ccagtatttt attgaggatt tttgcatcaa tgttcatcaa ggatattggt ctaaaattct   140160
ctcttttggt tgtgtctctg cccggctttg ttatcagaat gatgctggcc tcataaaatg   140220
agttagggag gattccctct ttttctattg attggaatag tttcagaagg aatggtacca   140280
gttcctcctt gtacctctgg tagaattcgg ctgtgaatcc atctggtcct ggactctttt   140340
tggttggtaa actattgata attgccacaa tttcagctcc tgttattggt ctattcagag   140400
attcaacttc ttcctggttt agtcttggga gagtgtatgt gtcgaggaat tttccatttt  140460
cttctagatt ttctagttta tttgcgtaga gttgttgta gtattctctg atggtagttt   140520
gtatttctgt gggatcggtg gtgatatccc ctttatcatt tttattgtg tctatttgat   140580 tcttctctct tttttctttt attagtcttg ctagcggtct atcaatttg ttgatccttt    140640 caaaaaacca gctcctggat tcattaattt ttggaagggt tttttgtgtc tctatttcct   140700
```

```
tcagttctgc tctgatttta gttatttctt gccttctgct agcttttgaa tgtgtttgct 140760
cttgcttttc tagttttttt tttttttatta ttatactcta agttttaggg tacatgtgca 140820
cattgtgcag gttagttaca tatgtataca tgtgacatgc tggtgcgctg cacccaccaa 140880
cgtgtcatct agcattaggt atatctccca atgctatccc tcccccctcc cccgacccca 140940
ccacagtccc cagagtgtga tattcccctt cctgtgtcca tgtgatctca ttgttcaatt 141000
cccacctatg agtgagaata tgtggtgttt ggttttttgt tcttgcgata gtttactgag 141060
aatgatggtt tccaatttca tccatgtccc tacaaaggac atgaactcat cattttttat 141120
ggctgtatag tattccatgg tgtatatgtg ccacattttc ttaatccagt ctatcattgt 141180
tggacatttg ggttggttcc aagtctttgc tattgtgaat agtgccgcaa taaacatacg 141240
tgtgcatgtg tctttatagc agcatgattt atagtccttt gggtatatac ccagtaatgg 141300
gatggctggg tcaaatggta tttctagttc tagatccctg aggaatcgcc acactgactt 141360
ccacaatggt tgaactagtt tacagtccca ccaacagtgt aaaagtgttc ctatttctcc 141420
acatcctctc cagcacctgt tgtttcctga ctttttaatg attgccattc taactggtgt 141480
gagatgatat ctcatagtgg ttttgatttg catttctctg atggccagtg atgatgagca 141540
tttcttcatg tgtttttggg ctgcataaat gtcttctttt gagaagtgtc tgttcatgtc 141600
cttcgcccac tttttgatgg ggtgtttgt tttttcttg taaatttgtt tgagttcatt 141660
gtagattctg gatattagcc ctttgtcaga tgagtaggtt gcgaaaattt tctcccatgt 141720
tgtaggttgc ctgttcactc tgatggtagt ttcttttgct gtgcagaagc tctttagttt 141780
aattagatcc catttgtcaa ttttggcttt tgttgccatt gcttttggtg ttttggacat 141840
gaagtccttg cccacgccta tgtcctgaat ggtaatgcct aggttttctt ctagggtttt 141900 tatggttttta ggtctaacgt ttaagtcttt aatccatctt gaattgattt ttgtataagg 141960
tgtaaggaag ggatccagtt tcagctttct acatatggct agccagtttt cccagcacca 142020
tttattaaat agggaatcct ttccccattg cttgttttc tcaggtttgt caaagatcag 142080
atagttgtag atatgcggca ttatttctga gggctctgtt ctgttccatt gatctatatc 142140
tctgttttgg taccagtacc atgctgtttt ggttactgta gccttgtagt atagtttgaa 142200
gtcaggtagt gtgatgcctc cagctttgtt cttttggctt aggattgact tggcgatgtg 142260
ggctcttttt tggttccata tgaactttaa agtagttttt tctaattctg tgaagaaagt 142320
cattggtagc ttgatgggga tggcattgaa tctgtaaatt accttgggca gtatggccat 142380
tttcacgata ttgattcttc ctacccataa gcatggaatg ttcttccatt tgtttgtgtc 142440 ctctttttatt tccttgagca gtggtttgta gttctccttg aagaggtcct tcacatccct 142500
tgtaagttgg attcctaggt attttattct ctttgaagca attgtgaatg ggagttcact 142560
catgatttgg ctctctgttt gtctgttgtt ggtgtataag aatgcttgtg attttggtac 142620
attgattttg tatcctgaga ctttgctgaa gttgcttatc agcttaagga gattttgggc 142680
tgagtcaatg gggttttcta gatatacaat catgtcgtct gcaaacaggg acaatttgac 142740
ttcctctttt cctaattgaa tacccttat ttccttctcc tgcctgattg ccctggccag 142800
aacttccaac actatgttga ataggagcgg tgagagaggg catccctgtg ttgtgccagt 142860
tttcaaaggg aatgcttcca gttttgccc attcagtatg atattggctg tgggtttgtc 142920
atagatagct cttattattt tgaaatacgt cccatcaata cctaatttat tgagagtttt 142980
tagcatgaag ggttgttgaa ttttgtcaaa ggcttttct gcatctattg agataatcat 143040
```

```
gtggttttg  tctttggctc  tgtttatatg  ctggattaca  tttattgatt  tgcgtatatt  143100
gaaccagcct  tgcatcccag  ggatgaagcc  cacttgatca  tggtggataa  gcttttgat   143160
gtgctgctgg  attcggtttg  ccagtatttt  attgaggatt  tttgcatcaa  tgttcatcaa  143220
tgatattggt  ctaaaattct  ctttttggt   tgtgtctctg  cctggctttg  gtatcagaat  143280
gatgctggcc  tcataaaatg  agttagggag  gattccctct  ttttctattg  attggaatag  143340
tttcagaagg  aatggtacca  gttcctcctt  gtacctctgg  tagaattcgg  ctgtgaatcc  143400
atctggtcct  ggactctttt  tggttggtaa  actattgatt  attgccacaa  tttcagctcc  143460
tgttattggt  ctattcagag  attcaacttc  ttcctggttt  agtcttggga  gagtgtatgt  143520
gtcgaggaat  gtatccaatt  cttctagatt  ttctagttta  tttgcgtaga  gttgtttgta  143580
gtattctctg  atggtagttt  gtattctgt   gggatcggtg  gtgatatccc  ctttatcatt  143640
ttttattgtg  tctatttgat  tcttctctct  ttttttcttt  attagtcttg  ctagcggtct  143700
atcaattttg  ttgatccttt  caaaaaacca  gctcctggat  tcattgattt  ttggaagggt  143760
tttttgtgtc  tctatttcct  tcagttctgc  tctgatttta  gttatttctt  gccttctgct  143820
agcttttgaa  tgtgtttgct  cttgcttttc  tagtttttt   aattgtgctg  ttagggtgtc  143880
aatttggatc  tttcctgctt  tctcttgtgg  gcatttagtg  ctgtaaattt  ccctctacac  143940
actgctttga  atgcgtccca  gagattctgg  tatgttgtgt  ctttgttctc  gttggtttca  144000
aagaacatct  ttatttctgc  cttcatttcg  ttatgtatcc  agtagtcatt  caggagcagg  144060
ttgttcagtt  tccatgtagt  tgagcggttt  tgagtgagat  tcttaatcct  gagttctagt  144120
ttgattgcac  tgtggtctga  gagatagttt  gttataatct  ctgttctttt  acatttgctg  144180
aggagagctt  tacttccaag  tatgtggtca  attttggaat  aggtgtggtg  tgatgctgaa  144240
aaaaatgtat  attctgttga  tttggggtgg  agagttctgt  agatgtctat  taggtccgct  144300
tggtgcagag  ttgagttcaa  ttcctgggta  tccttgttca  cttcctgtct  cgttgatctg  144360
tctaatgttg  acagtggggt  gttaaagtct  cccattatta  atgtgtggga  gtctaagtct  144420
ttttgtaggt  cactcaggac  ttgctttatg  aatctgggtg  ctcctgtatt  gggtgtatat  144480
atatttagga  tagttagctc  ttcttgttga  attgatccct  ttaccattat  gtaacggcct  144540
tctttgtctc  ttttgatctt  tgttggttta  aagtctgttt  tatccgagac  taggattgca  144600
accctgcct   ttttttgttt  tccatttgct  tggtagatct  tccttcatcc  ttttattttg  144660
agcctatgtg  tgtctctgca  cgtgagatgg  gtttcctgaa  tacagcacac  tgatgggtct  144720
tgactcttta  tccaatttgc  cagcctgtgt  cttttaattg  gagcatttaa  tccatttaca  144780
tttaaagtta  atattgttat  gtgtgaattt  gatcctgtca  ttatgatgtt  agctggtgat  144840
tttgctcgtt  agttaatgca  gtttcttcct  agtctcgatg  gtctttacat  gttggcatga  144900
ttttgcagcg  gctggtaccg  gttgttcctt  tccatgttta  gcgcttcctt  caggagctct  144960
tttagggcag  gcctggtggt  gacaaaatct  ctcagcattt  gcttgtctgt  aaagtatttt  145020
atttcttctt  cacttatgaa  gcttagtttg  gctggatatg  aaattctggg  ttgaaaattc  145080
ttttctttaa  gaatgttgaa  tattggcccc  cactctcttc  tggcttatag  ggtttctgcc  145140
gagagatctg  ctgttagtct  gatgggcttc  cctttgaggg  taacctgacc  tttctctctg  145200
gctgccctta  acattttttc  cttcatttca  actttggtga  atctgacaat  tatgtgtctt  145260
ggagttgctc  ttcttgagga  gtatctttgt  ggcgttctct  gtatttcctg  aatctgaacg  145320
ttggcctgcc  ttgctagatt  ggggaagttc  tcctggataa  tatcctgcag  agtgttttcc  145380
aacttggttc  cattctcccc  atcactttcc  ggtacaccga  tcagacgtag  atttggtctt  145440
```

```
ttcacatagt cccatatttc ttggaggctt tgctcatttc tttttattct tttttctcta 145500
aacttccctt ctcgcttcat ttcattcatt tcatcttcca tcgctgatac cctttcttcc 145560
agttgatcgc attggctcct gaggcttctg cattcttcac atagttctcg agccttggtt 145620
ttcagctcca tcagctcctt taagcacttc tctgtattgg ttattctagt tatacattct 145680
tctaaatttt tttcaaagtt ttcaacttct ttgcctttgg tttgaatgtc ctcccatagc 145740
tcagagtaat ttgatcgtct gaagccttct tctctcagct cgtcaaagtc attctccatc 145800
cagctttgtt ccgttgctgg tgaggaactg cgttcctttg gaggaggaga ggcgctctgc 145860
gttttaaagt ttccagtttt tctgttctgt tttttcccca tctttgtggt tttatctact 145920
tttggtcttt gatgatggtg atgtacagat gggttttgg tgtggatgtc ctttctgttt 145980
gttagttttc cttctaacag acaggaccct cagctgcagg tctgttggaa taccctgccc 146040
tgtgaggtgt cagtgtgccc ctgctggggg gtgcctccca gttaggctgc tcagggtca 146100 gggacccact tgaggaggca gtctgcccgt tctcagatct ccagctgcgt gctgggagaa 146160
ccactgctct ctacaaagct gtcagacagg gacatttaag tctgcagagg ttactgctgt 146220 cttttttgttt gtctgtgccc tgcccccaga ggtggagcct acagaggcag gcaggcctcc 146280
ttgagctgtg gtgggctcca cccagttcga gcttccggc tgttttgttt acctaatcaa 146340
gcctgggcaa tggcgggcgc ccctccccca gcctcgctgc cgccttgcag tttgatctca 146400
gactgctgtg ctagcaatca gcgagattcc gtgggcgtag gaccctccga gccaggtgca 146460
ggatataatc tcgtggtgcg ccgttttta agccggtccg aaaagcgcaa tattcgggtg 146520
ggagtgacct gattatccag gtgcgtctgt caccccttt tttgactcgg aaagggaact 146580
ccctgtcccc ttgcgcttcc caagtgagac aatgcctcgc cctgcttcgg cttgcgcatg 146640
gtgcacgcac ccactgaccc gcgcccactg tctggcactc cctagtgaga tgaaccctgt 146700
acctcagatg gaaatgcaga atcacctgt cttctgcgtc gctcacgctg ggagctgtat 146760
accggagctg ttcctatttg gccatcttgg ctcctccccc ggtattcctt cttttcttcc 146820
actgtgagag ttacttaaag ctcggcgtcc gtgatggtct aggggcttc tgaggcgatc 146880 gggcagtgtc cgtcttcagc cgctaagccg agaagatctg ggaaggagtc agtcagagag 146940
ccttgggcca gagttccagg gcctctggga gtggctgcca ggtgagttga acagtccgat 147000
tttcagtggg gtcccacaca gatgggacat ggcttaggag gaatcccagg ctgtgggcat 147060
tccttggccc agtggccaga ttcgatatat gttatttta aatcactgta tttgtaagca 147120
aatatcaaat ttagggaagt ctttctacaa tgttttaata agtagaaaga tatgtttgtt 147180
ttacatgaat gtgttttgaa ctatggttat ttgtttaata attctaaatg catatgtgtg 147240
taaaatgctt caattttgga aatcaaagtc aggccatttt tttgtcttac ctgattgcca 147300
gggagttacg ccatgtattc ttaatgagaa acatgatgtt tccattcttg ttcactttcc 147360
tttagacaga atatattttt gtgacattta gaactatcaa tattttagtt ttataaacac 147420
aggagaatgc ctgatagaat tcttaagaaa gcaatgtaac agtattagct caaataatt 147480 tatcttaatt tctaaatttt tagataaaac caaataaggg ttaaatgtta atccattgtc 147540
acttaaatta cataatctgc tactcttagt tatttgaatg acaaaaacac cagtggggga 147600
aaaaccatac aagttgtcaa tgtctgtttt gctgttgaca agttgtatac ccttaaattg 147660 accccctaatc tcctctaaca atggtacata gcactaagct cctacctacc tcacagaaat 147720
aatgtcagta gaaaagatca ggttgagttc tttggcagaa tagcacttta ctaactcaaa 147780
```

```
tagtgttact taatatttca atatgattgg gaatcaaagt ttgagacaaa agtcatttgc 147840
cagttttaaa aaatagagct gttaatttgc aatatcatga tgtagagata gtgccttctc 147900
ttaaaaatgt gtgtcatgga aatagtaaaa tatatttagg agtcagcagg attattccaa 147960
cagagggagt gtaaacttta aagaaaaata tgattcggga ggctgaggtg ggtggatcat 148020
gaggtcagga gttcgagacc agcctggcca acatagtgaa accccgtctc tactaaaaat 148080
acaaaaatta gctgggcatg gtggcacaca cctgtagtcc cagctactcg ggaggctgag 148140
gcaggagaat cgcttgaacc tgggaggtgg aggttgtggt gagccgagat cacaccactg 148200
cactccagcc tgggcaacag agcgagattc catctcaaaa aatacatata tattttgac 148260 atatataata tatatatgtc agtaatattc accccataga aaatgaaaat tttataggaa 148320
agatgtaaaa cagcataaat tcacattcat cttattagtt gcttatgcaa tcattttctc 148380
tccagatcat tggttctcaa aggggacaat tttgcctctc aggggatatt tggaaatgtc 148440
tggagacatt tttggatggc actagtggta tctagtaggt agaatttagg gaaactggta 148500
aacatctcct gaggcctgca agggtgctct cctcctccac aacaaaaaat tatccagcct 148560
aagatgtcca tagtgtagag ttggagaaac cttgccctgg agaataaggt tgattttctt 148620
gaagtcacac agcctggttg tgtttctata gggaaacagc ctgaaaattc tatctgaatg 148680
ttctcatcta caggtaagga tgaaaatgcc actggcatat ctaatattat gatgcagaac 148740
aatgaccatg tattttcaca gcattatgaa attattaagg accatagaat tgtgaataat 148800
tatttaaaga agtcttagga cagtttagat tctccacatg ccttctaata ttgacacaca 148860
ttaggatgaa ggaaatatta aatacataca tgtaaagatt ttgaattttt tttcaactga 148920
gcgtccagga tataaataca aggaacaggg aggggttga gatggcggaa gtaactctgt 148980
attgattctt ataggaaatt ctgagttttt ccataaagac aaagagttta ttgagtacat 149040
gagcatttag ttactgaaaa ttcactgtat gcttttctaa gttttgagct tattgttat 149100 gaaatccttg agaaagttga acatttcaat gtaaaaacat ggttgtgaat ctgaattttc 149160
aacttgctga ttaaactccc tgcaagtttc tttgcagttg tctgttttgg ggggataaat 149220
gtcaaattga atacagttaa ttttatcagc ctttacaaaa agatacttcc accctattta 149280
caacataaag gactattcct aagtgctgtc tgtagattac aaaaagtata aacatgtaga 149340
atttttgtca cagaagacta ttttattttt aatgaattaa caccgtattg aaaaataaaa 149400
agtacaaaaa agtacaaact tttctgtccc aatacattat aaaacgtttt attttaatag 149460
ctttagaggt acagttttg gttacatggg tgaatcgtat agtggtgaag tgtgaaggtt 149520
cagtgcactg gtcacctgag tagtgtacat ggtgcccaat agatagtttt tcattcctct 149580
tcctcagcct ccccaccttc tgagtctcta atgtccatta taccactctg tatgcctttg 149640
tgtactcata gcttagctcc cacttacaaa tgaaaacatg tggtatttgc ttttccattc 149700
ctgacttatg tcacttagaa taatagcctc cggttccatc taagttgctg caatagacat 149760
tatttcattc ttttttatcc ctgagtagta ctccatggtg tatgtgtatg tatatacata 149820
tatatatata tatatctcac atttcatata tatactcaca ttttttatcc actcatcagt 149880
tgataggcac ttaggttgat tccatatcct tgcaattgtg aatcgtgctg cgataaacat 149940
gtgcatacag gtgtcttttt gacatagtga cttcttttcc tttaggcaga tacccaatag 150000
ttgttccaat ccaattttta attggggtaa tttaatcttt taaaagttgg tccaagttaa 150060
ttgttgataa tatcaggact ttaaaagaga aacagaagtt cttaacctga gtgttttttc 150120
tttcttttga aaaaatatca gtttgaagtt ttaaatttct attttatatc tcaaagctat 150180
```

-continued

```
agttttgctt gtggggtata aaattaagtg dacaactaag acagagaact taggtgccaa 150240
agatgaccat gtttatactc aatcacccaa tttggaacca catcatcaaa gaagcagttg 150300
ccagtgttcc ccctagtgtg aagtttccac ttctctcagt taaagcacct gtctgtcatc 150360
tcatttaaag cacctactta cttcctacct attcaagtct tgattaagca aaatgcagat 150420
tttccatata caggaaattt ggcataacct ttcactttaa aggtcaaatc aggtctccat 150480
catttaaatt catcaaagaa agaatatttt gaagttgttg actttgttac tcattcccat 150540
tttgcaatca tgtattgtta ttcccttcct catttaaaaa ggcttctttt accccttacc 150600
cttgtttagg ctgcaccacc aaaggtcatt ggatatcaat ggatgggatt cactcctgga 150660
gctccagact cactcacaca tgtgcatcaa ggattcagga ttctctccat ttctgctttc 150720
cttaactttc caaagccaga cctttattct cttctgtatt aggatctggt ctgtcactgg 150780
gcttttctca ttctattcta gagcttctta aacttcagtg ttcatcagaa gcacctggag 150840
gagctggtta aaacacagat tgctgggctt caccccagag tgtctgattt aacagctctc 150900
aggtgggtcc tgagaattta cctttctcaa aattttcctg aggatgatgg tgcttctggt 150960
ctgggagtca cactttggaa actactgttc cagtccacag ttgtctcttt ggaaaccgaa 151020
tctgatgatt cactcctctg cttgaagatc tctatgacta cagaataaaa gccccatccc 151080
ttagcctgat gggcttctca gaagtattta ttggtaccct ccttcacatg ttacataggc 151140
ttgtcacatt gagcttctca tatgtgctaa ataccacc attttcttgc cttcttgtta 151200
ttttacatgc tatcctcttt gtctaggcta cccatcctct gtctacttct cagatctttg 151260
aaaaacacct gctcagttgt tagaacccag cttacctatc acttctctaa ctcttgacac 151320
attccatggg tgatcgtgat cttatactta cctccggctc tagtcatttt gttgtactgt 151380
acatgtatta atgtacacag ctatctctta ggtggcacat agtctctatt cctgatgttt 151440
ccatccaggt ggatgaactg tccattagag taactttctg gatctctctc tgccccttc 151500
ctgcttattc tccctatgta aacaggaagt gacttttgtg atcagtaagt ctgagagagg 151560
aatcagacat gtatatctta gtcctttcca cttccatttc tttttggcat ctgcctgctt 151620
aaagaatatg catgatctat gccttacaac tccttgctcc catgatctct ttgacctcta 151680
ttactccatg ccaggtcttg ccattcctta aaaacatgtt cccacctcac ggtcatgtgc 151740
attgcttaca acaccctact caatatccat ttggctcact ctttcagctc ctacaggtct 151800
ttattcagat gtcatcttct aggtgaggta ttctctgatc tctatttaaa attgcaactt 151860
tcctccgcca tgcaccctat cccccttgct tgctttattt ctctcccatc tctattatca 151920
ttgaacacac aatattttac ttgtttgttg tatgtcattc cccaataaaa taaaaactcc 151980
aagaggtgag gattttgct ggttctgtt agtaatttct ctagcagatg tagaacatgg 152040
aaggcactca atacaaattg gaatacatgc ttttggtcat gagataaggg ttagtgataa 152100
aaatagcctg cttccatagg gatgcttggg gtcttgacac cagccggtga ctagatatgt 152160
gtaattctca gatttagtgt tagggaaact ttgttgactt gtagttagtc atgtcttcca 152220
atcatccatt accaataata ttagtaatat tgtaataaat aagagactca tctctaccat 152280
cactgagttt attgtctaat acagaaaatg ggcaaaatac aagtagttac agtaaagtgt 152340
tgtaacctga acacagatgt gcctgctcgc cacttgaaaa ctaaaataaa gagagaagag 152400
agttggtggg aggaaacgca ggtttatttg gagaaccagc agaccaagaa gatgataaac 152460
tgttgtccta aagtaccatc ttaagtcagt acaaattgca gattattttt atgttaagaa 152520
```

```
caggggaag gaaaggtggg tgggatcaag aggtgactga caactgcaga catctgggca    152580
ccaacaaggg tctgaggagg ttgagaactt ctatttcctt ggtcaggtca caatgctctt    152640
ataaatattt aacaaaacat agttgtttac atactttccc tttaatcaca gagttagttt    152700
caaaaactac atgattgttt ctttgcatat gatatggttt gtatttatgt ccccactcaa    152760
atttcatgtg gaattgtaat ccctactgtt ggagaagagg cctgctggaa gttgattgga    152820
tcatgaggcc gacttcccca ttgctgttct tgtgataatg aatgagttct catgagatcc    152880
ggttgtttag aagtgtgtag caccteccct tttgctcttt tgcctcctgc tccagccatg    152940
taagatgtgc ctccttcctc tttgccttct gccatgattg taagtttcct gaggcctcct    153000
cagccatgct ttctgtacag cctgcagaat catgagccaa ttaaacctct ttgctttata    153060
aattacccag tctcaggtag tttcttacat ttaatagcaa tgcgagaacg gactaattca    153120
gcatattatc tcactgctct aaaatgatcc taacctacat gcaggaatgg gtaaaggctc    153180
cttaaacaaa aatggagtta tatatgttag ttcttttgct gtttcactgt tacagtgtgg    153240
taagtattgc aattggagca ttgcatgtgc tataatccaa acacgtgcta agtgacataa    153300
gtatcaacga gggagtaaca gggatggaca aaaagggacc aaatccagct atagaatact    153360
ttcctgacta gatgaggaat aagctcagat ttgaaagatg tatagtcatt agctaagcaa    153420
aggaaaggaa aagaagaagt ggtttaggca aagggaacca catgttctaa agcctagagg    153480
actgagggat catggtgcat aagaagagta tgtatatagg gtagagtgaa tgataacatg    153540
ggcaccagcc agactatggg aagtcatgct tgaggtttta gactttatcc ttatggggat    153600
aagaaaccac tgaagagttg taggaagaga cgtacgatat gatcaaattt ggatttctga    153660
aagttcagtt caccatagct ataaagtgaa gaatggatgg gtggaaggga gtatgcctga    153720
ggatcaggag actatttagg agtctgtgtt gtagtctttg tgagagaaaa tggtggccta    153780
gattatgatg gtggtaatga ggatgaagaa agatagatac atgtgagagg attgaattga    153840
caggacttgg tacattattg gaaagaaaga tgtcagaaat tacttatgtt tttctgctta    153900
agcattttgg gtggacatgg agccattcaa aaggtagtta ccataaaaaa cttggtgtag    153960
gataggatgc tcagtttcag acctattggg ttccagcagc aattctcaac ctaggaaagt    154020
tcttaaaaat aaaataaatt aaatctgtga gttattagtg atactaaaat cataatcaat    154080
ttgtaaccat tccatttatc cttttcttct ccttcttctg ctccttcttc atcattgtcc    154140
tcatctcctt ctccttctac tattgtttta ttcatgttgg ggttccatag actattagta    154200
gctgattatt tgtgggaagg gaaggtattt gagtgtctta ctaattttct tttattaggt    154260
tggtacaaaa gtaattgcag ttttttgttaa tattattttt ctgacatatt ttccagaaac    154320
ttcaaatttt ctgctaaatt tttcagaaca tttgttaatc tgaaaatatt agattaactc    154380
tcatatgaca atttatctgg ttaacaaatt ttagtttgag agttcaccca acattttta    154440 atattcttcc attatctttt agtatctatt cctgatgttg agatgtttgc tgtctgccta    154500
gttgttatcc cttggagata cagtagccct tgatatatgt ggataattgg ttctaggtct    154560
cccaacgtaa ccaaaatttg catatactca agtcctgtat tcagccctgc agaactcgtg    154620
tatacaaaaa gttgactctc catatatgca agtttcacct cctgcaaata cttcattttt    154680
ggtatatttt cgatctgcat tcatttgaaa aaaaatccat gtaaagtgg aaccttccag    154740 ttcaaacctg tgttgttcca agggcaact gtaatctctc ttttctttgt gaaagcattt    154800
aaaatttact cctattgtg cttttctctc agttttgcca caatgagtct aggtatgaat    154860 ttgttttttat ttcctccttg ggactttgt ttcttcaatg tagaatcata cctttaatat    154920
```

```
tggaaatatt tttggtatta tgtctgaata tttccccttt cccatatttt ttctattctg   154980
tacctcttta attcctgtta gttgtatgtt gtacctttta aatcctgtcc ttcgtatctc   155040
ctaatttggt tcatcttttc catcttttg tatttatgtg atgcatcctg gacaattttc    155100
tcagatattt tctttcattc cccttcccag ctgtttctaa tctgctatta atttgtccat   155160
acagttctcc atttcagtga cttaactttt tttcatttct agagttggat atgcttcttt   155220
ttcaaaattt gctattcttt aattcataat attggatttt ttcattatta ttttcaatca   155280 ttatttatt actccaataa ttttaaccat atttatgacc ccttaatttt gttatattat    155340
ctgaagttag tggggtgcta gttctttat ttgttcattt gcacactctc tgtcttggtg    155400
gttccttttc ttatgtagtt gatcttttt atctgggagt ttatcttcag aagaggctgc    155460 atttttcta gtgacagttc cttgggctgt ggttaatgaa agagtcccta catagtttca    155520
aattagattt tgctgtgtcc tagttgtttc aatggccttc aaacaatttt acattatcat   155580
ctcaggttag ggcttttctc ttaggttcgt aatataaatt tgcatcctag acccatggca   155640
caaaacttaa gcacagggct taaattttga tgcctcaagt aacttttgtt tgttttccat   155700
ccaaagagtt ggctagaagc aaactttctt aatatttaat taaggctttt ggtatgcttt   155760
taaaaatccc cttttaagtg atcaggcagt tctttaagat atcaggcttt tgatgatacc   155820
tggaatcaag ttctagcttc tttacattct gtaggcagaa acctcatttt tcctcccatg   155880
aaaacataag aactcagcag atctacacct gcacttattc ctcaacatct cctggcttca   155940
tttctttgct ttgatttcct tttcaattct gggattggag cttttcttt attcttataa    156000 atttgactat gcattaaaat gtttattttg tgacatttta cccagaattt caatggtttt   156060
gtagcagcca ggaaagtcta gctctctgtt atgattcttt taacttgttc agtcctgggt   156120
tgtggaggta tgaggagcta tccatcacac atggcaattt caaagcaaca tgcaaaatac   156180
aataatataa gcggaacaca tgaaagctgg aggacagtga gagattttg gttttgcata    156240 atagctttac tgagacataa ttaacatgcc atacaactca ctcatttatg tgcaactcaa   156300 tggttttgt atttacagag ttgtacaatt atcaccacaa tcttagaaaa ttttcattac    156360
ccccagaaga aaccccatat ccatttgtat tcagtctcca ttttgtccca ttcactccct   156420
ttagccctag gcaaccacta atctactttc tgtctctgta gatttgtcta ttctgaacac   156480
ttcatataca taaaattaca ttctatgtgg tcctctgtga ttggctcctt tcatgtagca   156540
taatgttttc aaggtttatc tatgtagcat gtatcagtat ttcattcatt tttatggcct   156600
aataaaatca tgcaccacat aatgacctt tggtcaatga cagacctcac acttgacagt    156660
ggtcccataa gattataatg cagttgaaaa attcctattg cctagtgaca tcacagccgt   156720
tgtaatatca tacagtcata aagcaactca ttaccttttc tgtgtttagg tacacacata   156780
tttaccattg tgttatagtt gcctacagta ttcagtatag taacatgcta tacacgtttg   156840
tatcctaggg acagccggct atatagcata tagcctaagt gtgtagtagg ctataccatc   156900
taagtttgtg taagtacact ctatgatgtt cacacaatga taaaattact caatgattaa   156960
attcttagaa tgtatcccaa ttgttaagtg acatatgatt gtattccatt gtatggctat   157020
cctatatttt atttatgcat gaatcagttg atgaacattt gtgttgtttc cacttattgg   157080
ttattaagaa acatgttgct ctgaacattt gtgtacaagt ttctatgcga gcatatgttt   157140
tcagttcttt gggagatata tttagcagtg gaatggctgg gtcatatggt aattctatgc   157200
ttaaccattt tgggaactgc cagactattt tccaaagcag ctgcaccatt taacattcct   157260
```

```
atcaacagtg tatgagggtt ccaatttctc catatcctgg acaacactta ttatctgtat   157320
attttatttt ggccattcta atgcatgtga agtggtatct cattgtgact ttgatttgca   157380
tttccctgat ggctaatgat attgaccatc ttgtcatgtt tattggccat ttgtatatct   157440
tctttggaga catgtctaat caaatccttt gcccatttt aaattggctt atttgttttt    157500
gttaattatt gagttgtaag agttctcaga agtcttatgt ttaagacttg caattaatat   157560
atttaagata taatccccctt agatacataa tttgcaagcc ttttttttccc cattctttgg 157620 gttggagagg ttttttttt aattgaagtt ctctgagtta cagagaaaag tcacagaagt    157680
aaaatataat gggactttg aagtacagaa atataaagcc tcctattcat ccatttaagt    157740
cgcagtagaa acatgacatt ttagtaaata agacatacaa aatacagtgc aatttataac   157800
aggaccagtt gtgaagtgg acagagaaaa aaggaaaca gatgagagag gtggaaagtt     157860
aagaggagag ataaatgcat agttctgcct ttttgctcaa accaaggatg gcatcattat   157920
ataacactgg gtgaagcca ggatacccag gaagagcaag actgaaaata aatggtagga    157980
gagattcaag gaatgccttg ctttatatgc ctttggagag gcaagggtct ggcccaatga   158040
ggtggaaagg gagtctacaa gggaagtgat caaccagaga agagtgtgag agggttcaga   158100
ggaaagtata gtggtgggat attcggagca ttaaccaatg atccaaagtc tagcctctta   158160
tgttgacaat aataaaacag cttgggtggt aggagctagg tttcccaacc ccaaactgga   158220
aatggatttc ctgtgctggg aaagttggag ggaacaggtg agcaccaatg tattatcaag   158280
tctctgaggc ctatatcccc attggttctt tgtgtcctaa caccatatgc tgagctctgg   158340
gatggtggca gcaaaccacc atcgatttgt ggaatttaaa agctgacaaa atctgttccc   158400
catcttttgg atagagctta cagtcacaag accccaggaa agacacagct gagtggtgtt   158460
tctaagcaaa catagggctt tggaaagtta gagagacttt accatgtttg gtgagcatta   158520
aaagaagaaa ttgctgcctg aagtatccag gggaataggt ctctaaacag cctcacaatt   158580
ttccaccacc catggtagtg gaaaaacagt ataatgactt tcaagctccc aagggcagca   158640
tggaggtagg gaaggaaacc tgcatggcag taaagctcaa tcaggctgag acatgcttag   158700
gaaatcaaga atctgtggtt gcagaataga acatgaatat tataaactga ggcaatttta   158760
aaaaggcgga tggggagtgg tgatgagagg aagagacact attctttat tctcttttta    158820 tatcaaatag tcaatcaata ctgtacctaa tgattgattt caaccttaat gctcttccta   158880
attgtttccc ttcaagttag acacctgtgt tcactgctgt attcttagca tccagaacag   158940
aactggctgg ctcaataaat atttaatgaa tgaacgaatc cataggattc ccacatctta   159000 gagttttgt ccacttttt aaaaaaatta atgttgcagg cttgattccc tgggaagcag     159060
actctaatag ggagggtagt gtgcttagca tttatttagg atcaatatct atggaagaaa   159120
gaagaaggaa gcaggtttgg gtagaggtgg aggttgagct acaatgcagg ttcaagcaga   159180
gtctccccac agagagcact gaagtgaggg agcccttcac agttgtccta atattgccag   159240
gctttcgtat tcatgcatcg attagtcatt gacatgggct gccacagaaa ggggcaggtc   159300
ttggatcagg tgaccctctg caatgaaaca gtcttgagga gcctgacagc tggagggagt   159360
ctaccaacag cactcccaaa agcttgggca agacatcttt cattgaagag ggaccttggc   159420
agcataccat ggtgtccacc ccatgaagca actatatctt agaaaactta agtcctttgt   159480
cttacacctt ggatccaaac ttagttttgt ctgactccag agcccataat cagaatagag   159540
tttctctatt gtacatggtg atgtaaactc agtcctaaac tggcgagggt gctggttgga   159600
cttgggaaga gttattctca gtgttctggg ttaatgcaaa atgcaggcca aggtgaagga   159660
```

```
cctttgtgtg gcactgaccc aatccatcaa gatgagttca tgtcctttgt agggacacgg    159720
atgaagctgg aaaccatcat tctgagcaaa ctatcgcaag acaaaaaac caaacaccgc     159780
atattctcac tcataggtgg gaattgaaca atgagaacac atggacacag aaggggaac     159840
atctcacact ggggcctgtt gtggggtggg ggaagggggg agggatagca tttggagata    159900
tacctaatgt taaatgatga gttactgggt gcagcacacc aatatggcac atgtatacat    159960
atgtaactaa cctgcacgtt gtgcacctgt accctaaaac ttaaagtata ataaaacaaa    160020
acaaaacaaa agaaacaccc tatgctccac tcagctggga ggcctgcaca gcagtgatct    160080
gtattgaatg atatgattaa ctgataattg ctactgtaac taagattaca gtttgacatt    160140
gctgcccacc tgccttttcta ccagggtggt agttcactaa aatattatac aatcagataa   160200
aatgaattaa actcagcttg aattgtagag tatattaaag tgattcaaat tatggccata    160260
agatattgat tagatcagta gtttgcagaa tgtggccccc acccaataga aacaacatca    160320
tctaggtact ttatcaaaat tgaaatttcc tggtccacca tatacttact gaatcagaaa    160380
cggtggtggt ggtagggccc aggtgattct aatgtatggt agagtttgag gaatactgga   160440
ctacatgaaa attagtagga aaaataaaa attgggttta taattagcaa ataaatgtta    160500
aataaatgat tcttttaaaa actatttgta aaatgactac tcaagtcaag aaatagtaca   160560
ttgccagcac cttggatgcc tgtttatccc ttctcactca caccccaaag caaacacttc    160620
gttttatttt atgcttttaa tatctaggaa tacatccctg agtacaagtt tttgaagttt    160680
gtgttaataa gcaaaatagt aataaatatt aaaaaatgat tgaggccaca cgcagtggct   160740
cacacctgca atcccagcac tttgggaggc agagacgggc atatcacctg aggtcaggac    160800
ttcgagacca gcctggccaa catgatgaaa ccccgtctct acttaaaata caaaaaaact    160860
agccaggctt ggtggcaggt gcctgtactc ccagctactc gggaggctga ggcaaaagaa    160920
tcgcttgaac ctgggaggcg gaggttcag tgagccgaga tcaatcgcgc cactgcactc    160980
cagcctggcc aacaagagca aaactccatc acacacacac acacacacac acacacacac    161040
acacacacac acacacacac acgattggac tatttccttt actttgttca tagaacttgt    161100
tttacataac ggacctcagg ctatccaaat gatcacaact tcctaattag gaaggtctga    161160
attaatgaag gttcaagatt gcctccttgg gggctaatgt gtatgcaagc tgcgaccac    161220
tggtaacagc tttactattt actcttccct gccaggggat tagtggaatc taaattgaac    161280
agttaggtat ttaaaccac tcatgtggtt ttaaccacta aaagggttgt taagcaagtc    161340
ttctttaatt tttttttttg ttgaaaatat tataaaattg gtgtctaaat gctgacagtc    161400
aatgggcaac ttgggaaatt actcaatgtc tgttttggga aaacagtaac tggcacttac    161460
atatcacatg tgatctgagt agcgttaact ccttctctag agtacaggat tgtatgaagt    161520
tgaggtccta ccccttaattc tttcacgttg aaatatatag ttacaggaaa gtgagtttaa    161580
attgattgca tgttactgtc tccctttag agtcatttat tttaagaagc actgaaaggc    161640
cgggcgcggt ggctcacgcc tgtaatccca gcactttggg aggccaagac gggtggatca    161700
ggaggtcagg agatcgagat catcctggct aacacggtga aacctcgtct ctactaaaaa    161760
tacaaaaaat agccgggcg tggtggcagg cgcctgtagt cccagctact cgggaggctg    161820
aggcaggaga atggtgtcaa cccgggaggc ggagcttgca gtgagctgag atcgcgccac    161880
tgcactccaa cctgggcgac agagcaagac tccgtctcaa aaaaaaaaa aaaaaaagc     161940
actgaaaaaa cttgcgtaaa ggcatcacac tctgttgggc aatggggaag gggaaggtgg    162000
```

```
gtttctcgcc ctctgtcact gatatggttt ggttgtgtcc ccacccaaat ctcaccctga  162060
attgtgataa tccccacgtg tcaagggcac ggccaggtgg agataactga atcatggggg  162120
cggtttcccc cgtattgttc tcatggtagt gaattagtct cacgaaatct aatggtttta  162180
taaagggcag ttcccctgca caagctctct tgcctgtcat catgtaagat gtgactttgc  162240
tcctcatttg ccttctgcca tgatcatgag gcctccccag ccatgtggac ctgtgagtca  162300
attaaacctc tttcctttat aaattaccca gtttcgggta tgtctttatt agcagcatga  162360
gaacagacta atacagtcat ttacaagcta tctggggcta taagaaggat atgcatgtcc  162420
taggtgagga atactgcaca ggggaaagag tctgagtgag tagggcagat tgtgcaatgt  162480
gaggctttag gggatcccag gggacaagac ttgggagaca catttgtaga aaggttggag  162540
ttttacagtg atgccactga attatcaatg aaggatatg  atttccttcg tacaagaaat  162600
ctggaaagta tatggcattt atagacaggt ttccacttca aaaaatcaag cagcatatta  162660
ttttgccagt ttaaaagtta accctgcttg cttttttgttt tgtcttgttt tgttttgaga  162720
cagtctcact ctgtcaccca tgcaggagta caatggcgcg atctcggctc actgcaacct  162780
ccaactcctg ggttcaagtg attctcctgc ctcagcctcc caagtagctg agactacagg  162840
tacctgccac cacacctggc taatttttgt attttagta gaggcagggt ttcaccatgt  162900
tgggcaggcc agtctcgaac tcctgacctc aaatcaccca ccttggcctc ccaaagtgct  162960
gggattacag gcatgagcca ccaagcccag cctggttgct aactatttgg ataactgttt  163020
ggaatcacta cattcctgag tgagtgattc agacaacaga ggttttttaa aaaaacttta  163080
aaaaaatttt tatcttaata gttttttggg gtacaggtgg ttttggtta  cataggtaag  163140
ttcattaatg gtgatttctg agattctggt gcacctgtta cccacacagt gtatactgtg  163200
cccaatatgc agtctttttt cactcaccct ccttccaccg tttcccctgg agtccgcaaa  163260
gtccattata ttattcttat acctttgcat cctcatagct tagctcccac ttataagtga  163320
gaccatatga tatttggttt tccattcctg agttacttca cttacttaca ataatggcct  163380
ccagctccaa ccaaattgct gcaaaagaca ttactttgtt cctgtttatg gctaagtagt  163440
attccatggt atatatacta ttttctttct ttttcttttt ttttttttt  tgagacagag  163500
tctcgctctg ttgcccaggc tggagtgcag cagcgcgatc tccgctcact gcaagctcca  163560
ccacccgggt tcatgccatt ctcctgactc agcctcccta gtagctggga ctacaggcac  163620
ccaccaccac gcccagctaa ttttttttgta ttttagtag agacagggtt tcaccgtgtt  163680
agccaggatc gtctcaatct cctgacttcg tgatccaccc gcctcggcct cccaaagtgc  163740
tggaattata ggcgtgagcc accgtgcccg gctatatact acatttttctt tatccactcc  163800
ttggttgatg ggcacttagg ttggttctgt attttttgcaa ttgttaattg cagacaactg  163860
aggttttaat gaagattata gtgttgaagt aggatatttc taatattcta gtcttatgag  163920
gacttataaa attgggtaga ttatcaaatc ctcaaattac ggcatattca ttttggctta  163980
tatttaaaat attccaccat caagactggg gaaaaagtt  catcagaaac atacgctgat  164040
atttggctat attgtttgtt tttgcatgca tttatgcaat aaacaaacat ctgatttctt  164100
gcacagtccc tcagatattc tcctcacatt aaagattcca cttacttatt ctgtgatttc  164160
tcttattcta tgagacaaaa atacaacaga atgtcagaag agccagctga aaatattcca  164220
tgtgcagaaa tttatttaa atttattgc atcacattat acaagcatta atcatggctt  164280
catattgatg actatttaaa tgtgaaaatt cactcatgtc agtactttt  ggctatttac  164340
aagtaaggaa tttctatgta ctttatatat ctctgtattt gtatgtacat atgcaggaat  164400
```

```
acatgactat acatatgtac acacagaaat acatctatgg ccatacacat agctatagat   164460
atgtcatata taataatctt ctcagaaagg tctaaaatta aaaaaaagga aagaaaaagt   164520
tgtaaacagg gtcttgtctg tgttgttggt gacatggaat taggaccata tgatgacatt   164580
ctaggaatgt gtgtccatgt gtctgaatac ccttttagc ccagtgtctg taaaattcac    164640
atgggataga atgcaaaaaa ggtagcaaac aggctgaaaa acaggcccag tatacaagtt   164700
ccccttgatt ttaaaaactt gagaatgtaa ctgcccataa tgtgcatgct tgcttggtca   164760
agaatggtct atggatagat agcaattgtg cgctggactg caacgtgatt tcacagcagt   164820
gtgactccaa cgccagtcct ctactggatg ctgcccctcc tgcggccgcc ggtatctgca   164880
acatgcactg tggttgcatt tttagtcatt cacttgagtg tgcttttgca cagccagaag   164940
aagtaaacag aattcaggtc cttggcctgg aaagggacta ttttctggaa agagaaaaga   165000
aggcataaag atcttatgca tacacaattg ctttaaaaca tgaggtgcaa tagtttgtac   165060
ttaccatgca ccaaaggcat tcaaagaatt tgtaaccca aatggagtca gggatggtat    165120
aaacattttt atgcttgctt tatgggtgaa cagactgagt cagaagggca gtctaaagca   165180
acatcacatc ctgccaacta tcggggaaat agaaacaggc aggcagatac tatgctttca   165240
agcaaaaatt agaaatggcc ttttggggaa gaaagcagcc agtagtggtg gggccagaag   165300
aaattcttca tcagttactg gtcctgcagc ccaggacagc cctgttgcac cttggtctct   165360
ggccgctgag gctttcagga agaattctct ttgctaatgt ctgcctccca cccacctaga   165420
aagaaggggc atgtttccct ggggatatta agaaaacag cccggctgga ggaaaagaga    165480
gaggacgctt tgtttcaggg aactcctagg ccaattcatg aagaccttga ctgataggcc   165540
agagtctggc aagaaggcag agaagtgttg cagaaggtat gtgggagggg aagatcaagc   165600
aaaatttgca acgattaaag taaaaaacaa gcttcttttg gattgggaag cttctaagga   165660
gtttattttg atccctgtta ctgcaacaat ggtaagcttt gcttcaggga gtttaaagca   165720
cccattcaac ctcggaatgg cctcagacgc tgagcacacc tctcacctac atggtcacgg   165780
ccactcgttg tggtgtgctt ttccattctt cttcctctcc tttcgttcct tctggagacg   165840
ttccagttct gcttcataca tcatctcctg aatcaagtac ttctctcttc tcattcgatc   165900
ccttaggtct tttgggaggt ctgggatcag atatgaaatg aggtgcttta tacaaaacac   165960
gaggtgctaa aacagaggag aatgtaacag cgtcaggtct actgtgcatc ctgaatgagg   166020
ttagagagtt ggctgaagaa ggatgtggac cctctgggt atgtggagag tgcaaagtga    166080
ccaggggagg cgtgtgtaat gcaagatgat aggacaggtg aggcctgaac tggtctgatg   166140
gcaccaccta aggaatagaa agaggagtct ggaaggaagg tgggaaaaga atggtcagat   166200
aattaattca aggagagcc agaagaatgt attctgtgga gtcagaaaac ccaggttgaa    166260
gctggtagct ttcactgctt aagggctgtc tgtctacctg aggatgaatt atttaattta   166320
tctgagcctc attcccctca tctataaagt gagtattgtg agaattatga gaaaatgttt   166380
aaaaatgcct tgtagactgt caagtgcttt acaaatcttg gttataagaa ttatcagtgg   166440
gcctagggaa atgatcattt caggaagaag cttttttctt tttggtaaac agtcacaaat   166500
tctttacttg aaatactaat agctggaatt ctagagtcac tgtcacttct gctcatctat   166560
ataatggtga ccaaggaagt actagatgac aatttaaggg ctattacaat tctaaagtat   166620
taaatagaga ctaaatcatg ttcaaatgat actgctaagt attcttcgtt ttatttaaaa   166680
cttgataaat ttggtgatgc atggatggca caaaattaag aagcttttct gcatagttct   166740
```

```
catattttca aatagttaat aacaaaatat taaaagaaaa tggaaaattc tatttgaaaa  166800
gccaaataag gcagccttt  aaaaagtttt gtctgacaga tttacagcag aattctacca  166860
gaggtacaat gaagagctga taccatttct atggaaacta ttccaaaaaa ttaaaaagga  166920
gggactcctc cttaactcat ttatgaggcc agtgtcatcc tgataccaaa acctggcaga  166980
gagacaacaa aaaaacttca ggccaatatc cccgatgaac attgatgcaa aaagcctcaa  167040
tacaatactg gcaaaccaaa tccagcagca catcaaaaag cttatctacc atgatcaagt  167100
tggcttcatc cctgggataa aaagttggtt caacatatgc aaatcagtaa acatcacata  167160
agcataagta attcatcaca taagcagaac taaagacaaa aaccacatga ttatctcaat  167220
agctgcagaa aaggtctttg ataacaatcc aacatccctt catgttaaaa attctcaata  167280
agcattcccc ttaaaaaccg gcacaagaca aggatgccct ctcttaccac tccttttcaa  167340
cgcagtattg gaagttctgg cccaggcagt caggcaagag aaataaataa agggtattca  167400
aataggaaga gaggaagtca aattatcttt tttttgcaga tgacctgatc ccgtgtctag  167460
aaaatcccat catcttggcc caaaagcttc ttaagctgat aagcaacttc agcagagtct  167520
caggatacaa aatcaatgtg caaaaatcat tagtattcct aaccactaac aacaggcaag  167580
cagaaagcca aatcatggat gaactcccat tcacaactgc tgcaaaagaa taaaatacct  167640
aggaatacag ctaacaagaa aagtgaatga cttcttcaag aactacagac cactgctcaa  167700
ggaaatcaga aaggacacaa gcagatggaa aaatgttcca tgctcatgga tagaaagaat  167760
caatattgtg aaaacggcca tctgcccaaa gtaatttata gattcaatgc tattcccatt  167820
aaactaccat tgacactctt cacagaatta gaagaaactc ttttaaaatt catgtggaac  167880
caaaaaagag tccaaatagc caagacaaga ctaagcaaaa agaacaaagc tggaagcatc  167940
acactaccca acttcaaatt atactaaaag gctacagtaa ccaaacagc atggtactag  168000 tacaaaaaca gacacataga ccaatggaac agattagaga tctcagatat aagaccacac  168060
atctacaacc atctgatctt tgaaaaacct gacaaaaaca agcaatgggg gaaaggattc  168120
cctacttaat aaatggtttt gggagaactg gctagccata tgcagaaaat cgaaactgaa  168180
ccccttcctt acaccttata taaaaattaa ctcaagatgg attaaagact taaatgtaaa  168240
gccccaaact ataaaaatcc tagaagaaaa tctaggcaat gccattcagg atgtaggcat  168300
gggcaaaaat ttcatgatga aaacaccaaa agcaattgca acaaaagaaa aaattgacaa  168360
atgggatcta attaaatgaa agtacttctg cacagcacaa aaaaactatc atcagagcaa  168420
acagtaacct atagaatggg agaacatttt tgtaatctat ccatctaaca aaggtctgat  168480
atccagagtc tacaaggaac ttaaacacat ctacaaaaaa aataccaagc aaccccatta  168540
aaaagtgggc aaaagacata aacagacatt cttcaaaaga agacattcat gcagccaaca  168600
aacatatgaa aaaaagctca acattattga taattaaaga actgcaaata aaaatcacaa  168660
tgagatacca tcttcacacca gtcagaatgt tgattattta aagtccagaa acaacagat  168720 gctggcaagg tttcagagaa aaaggaacac ttttacactg ttggtgggag tataaattag  168780
ttcaaccatt gtggaagaca gtgtggcaat tcctcagtga tttacaagca gaataccat  168840 tttacccagc aattctataa cttgtatggc aaaggacaca aacagatacc tctcaaagaa  168900
agatatacaa gcagccaaaa ataatatgaa aagatgctca gaatctctaa ggagattaga  168960
gaaatgcaaa tcaaaaccac aatgaaatat tatctcatac cagtcagtat ggcgcttatt  169020
agaaaggaat ataaatcatt ctattataaa catacatgca tgcatatgtt cattgcagca  169080
ctattcacaa tagcaaaggc atagaatcaa cccaaatgcc catcaatgat aggctggata  169140
```

```
aaaaaatgtg gtacatatac accatgaaat actatgcaac cataaaaagg gatgagataa 169200
tgtcctttgc agggacatgg acagaactgg aagctgttat cctcagcaaa ctgacaaagg 169260
aacagaaaac caaataccac atgttctcac ttataagtgg gagctgaatg atgagaacac 169320
atggacacat ggtgggaaac aacacacaaa ggggcctgtt gggggtgggg gtggggaag 169380 ggagagcatc agaaagaata gctaagggat gctgagctta atacctgggt gacgggttga 169440
tctgtgcagc agatgaccgt ggcacacatt tacctgtgta acaaacctgt atgtcctgca 169500 catgtacccct ggaacttaaa ataaaaaaat cccaaacaaa caacaagaag ttttgtctga 169560
aaaattttaa gacagtgatg ggttaaaaat atcttcttta aagagagagt gtgccattgg 169620
taagataatt tccagggaag agcagcttaa tattttcttc ttttggttcc ctggactgaa 169680
ggaaaaagca gtgatagaat agtcttgaag aggtctagga aactttagat ccaagccgag 169740
aggcaacctt ggcttttatt aatctggctt taatatatgt gacaagagat gaaatttcca 169800
cttatgacta gagtcataga aatgcaaact attttacag caattttctt aaaccctgaa 169860
agaaaataga taatatattt ttattgacat ataatataga caattgctag acagatttta 169920
ctttataatt ccattttgag tcttagctaa taaatactta cttggatgct tgaatataaa 169980
taattccgtg atgatacaca accagaaata ccacttgtaa tacccagtcc tattggaaaa 170040
tgcttatgat catgttggga aatcctgata actatttgaa aatcataaat taactatatg 170100
aatcagtata tttcaatatg tgtggtaatg atgatggcaa taattggaga catttagaaa 170160
gagtgaatct ccaacttgac aaaaacaagc agtgggggaa ggattccttg ttcaataaat 170220
ggtgctgaga taactggcta tccatatgca gaagaatgaa actggacttc tacctatcat 170280
cataaacaaa atttaactca agatgaatta aagacttaca tgtaagacct caactataaa 170340
aatgctagaa gaaaacctag gaaatacccct tctcaatact ggcctgggca aagaatttat 170400
ggtgaagtcc tgaaaagcaa ttgcaacaaa aacaaaaatt gctaagtcaa atctaattaa 170460
agagcttctg cacagcaaga gaaactgtca aagaagtaaa cagacaccgt acagaatggg 170520
agaaaatatt tgcaaactat gcacccaata aaggtctaat acccagaatc tgtaaggaac 170580
ttaaacaaat caacatgtaa aaaacaaata accccattaa aaagtggtca aaggacacaa 170640
acagatactt ctcaaaagaa gatatagaag cagacaacaa taatatgaaa aaatgctcag 170700
aatctctaag gaaattagag aaatgcaaat caaaaccaca atgagacacc atctcacacc 170760
agtcagtacg gcttttatta gaaagtcagg ccaagtgcag tggctcacgc ctgtaatccc 170820
agcactttgg gaggccaagg cggatggatc atgaggtcag gttaagacca gcctggccaa 170880
gacagtgaaa ccccgtctcc actaaaaata caaaaattag ccaggtgtgg tagcgggtgc 170940
ctgtaatccc acctactcag gaggctgagg cagagaatta cttgaacctg ggaggcagag 171000
gttgcagtga gccgagattg tgccattgca ctccagcctg ggcgacagag agagaatcag 171060
tcttaaaaaa aaaaaaaaa gtaaacaaat taacagatgc tggcgaggct tcagagaaaa 171120
ggggacacct gcacactgtt ggtggaaagg taaattagtc caactactgt gtagtctgga 171180
gatttctcaa agaacaaagg gcttaactac cattcaaccc agcaatccca tttctgggta 171240
tatactcaaa agaaaataaa gcattctacc aaaaagacac atgtactcat atgtcaatca 171300
caggactatt cacaatagca aagacatgga atcaacctgg gtgcccatca atggtggacc 171360
agatagagaa aatgtggtat gtatacacca tggaatacta tgtggccata aaaaagaatg 171420
aaaccatgtc ctttgcagca acatggatgt agctggaggc cattatctta agtgaaataa 171480
```

```
tgtagaaact gaaaactaaa cactgcaagt tcttattgta cgtacttaga gtggaagcta   171540
aacactgggt acacatggac ataaagatga gaacaacaga cactgggggac tactatagag  171600 gggagagggg gaggggacaa gggctgaata actacctatt gaatactatg ctcgctacct   171660
gggtggtggg ttcagtcgca ccccaaacct caacatcatg caatgtaact ttgtaacaaa   171720
cttgcacatg tacccactgt atctaaaata aaagttgaaa aagaaaaaga aaaaagaat    171780 gaatcttact gggctgatgt tttccaaatg tttccaaatt atggtcccag aatgcctata   171840
gtcagaatca ttacaacgag ctcatgaaaa acaagccaca gacatggtat gtcagaatat   171900
ctgggagtga ggatggaaaa actgcatttt tgctaaagtt taagaactat ggccccagaa   171960
aattacattt aggagcaacg agttcagatt tgtccattaa aaaccaacta tggactttca   172020
aatatgtctt ggaaaaatca aatgcttcaa ttaagaaaaa agatcaaaaa gaggttacat   172080
aatatgacac tactacttct ggaaatatag ataatcacat tcaaaatccc catcacttat   172140
ttttattcat tactccctact gacttcatta tgtcaaagga aataaagaat ttggctgagg  172200
aaacttacct caaagacaat gataaaagct aatcgagcag ctaggacatg ccaaaactgc   172260
agtgtgtagc catagggcac cagtgaatga ggcgggtcac ggtagtcccg gtatctataa   172320
agacacagaa aaatgttgca ttcaaactat gatttttctg attctcaaat ctcttccatt   172380
ctcattatat agtcctcatt caataggagg gaaatttgaa gtttctctat actagatatc   172440
tgttgttttg cttgtccagc atttttcttc tgataaaata atatctcttc tctggggaat   172500
catctgtgtg ggttgactag gacttccccc tccacctgcc tgatctcagc tcaaaagatg   172560
agccagacct gatcagtgac atcatcaaga tgtctgccag aactatcact tagtgaatga   172620
tcactaagcc cacagaaggc aaaagcctgg gactcctggt ggccttgtat ggagagagag   172680
agcctgcttg agaaggaagt caagaaaaca aagcagagac agcagagagg cagcatcctg   172740
ctgacactgc ttgaggcctg ggatccggcc attactgaag ctcatatcac ccccttgactc  172800 tcccagctaa ctgaacaatt ttttgttgtt taagtcagtt taccctggat ttctgccact   172860
tgccactaga agagtccttc ctaatgtatc ctccagctat cacttttgag tcggcataaa   172920
attccacaaa tgtttgccga atacctgttg gggaccaggc actattcaga gaactttaat   172980
ccatgtgact ccattaaagt aatactttaa taatacaaca agctctcata aatccactat   173040
gaagcccaag aactaaaaca ttaccaggaa cttacatcaa ttgcttccct taccctgaat   173100 ttcatttttat ttttttaactt atatgtatat gcatttgtct gaatattgta ctatttagtt  173160 tgttttgaa ctttatagaa agggtactat actatatgta gtttgctggg gcttgctttt    173220
tttactatta tgtcactaag attcattcac attattgcat gtggtttatt tttattgctg   173280
tataatagac tctagtgtga ctatattatg gttgttttat atagcatata agtatacact   173340
tacaggctgg tcattcctat atttctttt ctttttatgtt gagacagaat ctcgctctgt   173400
cacccaggct ggagtgcagt ggtgcgatct tggctcactg caatctctgc ctcccagact   173460
caagtgatac tcctacctcc caagtagctg ggactacagg tgtgcacaaa atgcctggc    173520 taatttttt gtatttttgg tagagacagg gttttaccat gttgcccagg ctggtctcaa   173580
actcttgacc ttaagctatc tactcacctc agcctcccaa agtgctggga ttacagggtg   173640
agccactgca cctggcctct atattttctt tcactttccc taaccatgga aagctttgaa   173700
aaagaaagct ccatcaatga tagactggat taagaaaatg tggcacagat acaccatgga   173760
atactatgca gccataaaaa aggatgagtt catgtccttt gtagggacat ggatgaagct   173820
ggaaaccatc attctcagca aactatctca aggacaaaaa accaaacacc gcatgttctc   173880
```

```
attcataggt gggaactgaa caatgagaac acttggacac aggaagggga acatcacaca  173940
ccggggcctg tcgtggggtg ggggaggggg ggagggatag cattaggaga tatacctaat  174000
gtaaatgatg agttaatggg tgcagcacac caacatggca catgtataca tatgtaacaa  174060
acctgcatgc tgtgcacatg tactctagaa cttaaagtat aaaaagataa ataaataaat  174120
aaaaagaaag ctccagtcca ctcacttcag caaattccct ttgggtaaaa gttggctgca  174180
atgctctgtg taccacttct ttctgcctta gaataccaaa tattcttccc aggtcattaa  174240
tgtatttgag aaggtgtttt taaattttc tctacatgtt tagatatttt cagcccgcaa  174300
gctgatctgg gtgcctcacc tgctatatga ctgaaaacaa acctgaaaat attattttac  174360
atgattttaa ttagaaattt taaaatgttt tctttggggg acttttaaga aaatgctaa  174420 acaaaacaat cataatttaa cttaatggtg ccagcattaa tacctccatt cacattaata  174480
atttctggaa tatacttta tgatactatg tgagacaggc aggaagaatt atgagccagg  174540
aagcagaaga ggagaaagac tctgtatttt tatcttattt tcaaatgatt acaaagtttt  174600
taactccaaa taatagttgg cattttattt tgaagcattt catacttagg atcctgtata  174660
tgtctaacaa tgcttgctaa ataatttcat gtacgaaatg gtctggacaa gcaagtggga  174720
aatctactga agaaagtatc aattgttgct taattgcttg cttctccact agaccccaac  174780
agagagcggc actagattat attccagcca gtctttctcc ccatcttact tgttactcca  174840
tgtgggaaag gaaataagcc atctgatgag atgtgacagc caatgagacc tgggaacttg  174900
gcatgagtgt ttaaagggt ggagggtatg ctgtcactgc acagaaatgg ggagccctg  174960 gcttctctca ccttcaccctt ctgtaagatg agggactgaa gtggatcatt acaaaagtcc  175020
ctatgtcaaa gcatctagga ctccatggct gttcttcctt gtggctttga ttacagggag  175080
aacatagaat gtcatgatag ggaatctcca aaattctttg ttttgttttt gagacaaggt  175140
cttgctccat agtttgaatg cagtggtgct atcatagctc actgcagcct tgactgcctg  175200
gacttaagtg atcctcccaa cttggcctcc tcaagtgctg ggattacagg tgtgagccca  175260
caaaattctt ataacgtcaa agtattaaga gaaaaaggtg ccatctggac tcttcaagaa  175320
ctgtgcacaa gtaatctcat tgagctttta gtgaatggtt ttatcatttg tcagatgaga  175380
taatattgcc taacttagaa ggctgatgtg acgattaaat ggagtaacag tttctggcac  175440
agagtaggtg ctcaacaaat tctccttcat gtacgtttgt atagatacac atcaagaggc  175500
acagtttaat tcatttcctt ttagagggag agaaagaaag agagaatgag cacatgttgc  175560
agaggctact gtggtggaac ctgaaatgaa ctgggcctct ttccacaggc ttctgagttg  175620
tttaacattt agaaatgtga tgtgatatac tctgggcaag agagagaagc agaacaaaga  175680
caagtgccct caacagctgt cgctcaaccc gcctgggat tgtctgtccc tgagtccctg  175740
gagcagcggt ataaccttca ctactatatt tttagttttt ccctttaagc tagcagttct  175800
caattctgac tgcacctggt ttctgagttc cactccctga cattctgttt taattggttt  175860
gggttgtatc ccgggcaaga gaaggcttga aaattcttca tgtgcttta atgcattgtt  175920 gagattgaca gtcactgctt taaacacact cagccagaag gggccttcag agtaaaacct  175980
ccccacggtg gagccagccc agctcaggca gagccacgct gggtgccaca ctcacctgca  176040
gtacttaaga ggagtccccg agaactcact gccatcagat tcaggctcag atcggttctc  176100
aaagtcagaa attcgaaata cagacaagct ggcattcaca tagccaacca tgcacctata  176160
agaggaggca cattctacca ttagaacact catcaccttc tctgtatcca gttccctgaa  176220
```

```
gaccctgctt cccagacgtc cctgcaattg taaatgcctt taactggccc ttccttgtca 176280
accaggactc aggttgggat acgctggaaa gccctgggca tgttgaatca ggaacaagtt 176340
gcttgttttg gttctcatcc ttttctgca gaatcatcat atagaacatc tctaccccaa 176400
ttaatgtttc agtgaaatag gtaaaaagca gcattacatg atgggcataa attgtatgta 176460
agccacagct tcttttgttg atgatacaca taaacacagt tcctcattaa tggtttcata 176520
tatatttata gatattctca aaatgttcca aatatgattg gtgtgcatat gatcccccca 176580
actcatatcc catgctacag tcctgttaga ctatattccc tgaaagcttc tgatgttttc 176640
atgcctctgc ttgttatctt ttctgttaga attccctacc tcttccttta caagtggaaa 176700
tagtatttat ccttcagcgg ccaactgaaa caccactcct actaggaaga caacctaatc 176760
actccagtca caacatctca ctcctttccc tctctctgta gtgccaccat acttacttag 176820
ttcaccatta ccagatcgct tgtactagag ttggcagcat atatgtatgc cctctccttt 176880
ggactgcaat ttttgggag cagagcaggt atcttaggta tttgtgtatc ctatgactta 176940
ggacagtctt gtgcagtgta ggaatcccat aaatattgaa tcgatctgat tggaggaaac 177000
taaagtatga gattctattg atcattctag attgaatggg tagataaaat caagatttaa 177060
tcattctgtc aataattcca ttcaagaaaa agcccatttt aaaagtatca tagcaagtag 177120
cactcttaga aacatctttt ctccaagtct ctaaacagtt ttacatattg aacattgtgg 177180
ttaacacatg cacttactga aataacaatg tttgaaactt tgggtgaaat tagcacttag 177240
atacatcctg tatacatttt tctttaaata gtgttttaca tacaaaagct tgggttttgg 177300
ggtcaaatct tagttctgct ggtttctagt catgtaatat tggcacgtta tataacttct 177360
tacttcttct ttttttttct gagacagggc cttgctctgt tgctcattgc tggagtgcag 177420
tggtatgatc atggctcact gcagctttga cctcccaggc tcaaacgatc ctcccacctc 177480
agactcctga atagctggga ctacaggcat gtgtcaccac acccgattta cgtaacttct 177540
taaagtgaca gaagttccca cctcataggg tccttgaggg gattatatta acaatgaat 177600
gtatagcatg tgataagatc ttagcctata agtaagataa acatgagtgg tgattattca 177660
ttttatttat ttcttgcatc tagcaggggg tcaataagta attactgatt gaatgaataa 177720
atcatgatct tcagattctc ttcattaaca agtctggcat gattattcca agctgctgaa 177780
cactaaacca aaatgatgac atgaacacag ttctgagaac acatgggttc tgcatgttat 177840
cgtgctcaag acaaatcact ggctttatca tggccttaaa aaaaatgaac caagctgaag 177900
gacccatttg tcaagtcact cgtgggtgaa acaaatggt cagggagtgt gtaacatgcc 177960
ttaatccaac tggcagcagg actccctac tgaaagggta atttggaatg atgtctccct 178020
tacctaggaa ctgtctagac ctggacatga aaataaatta gtgccttgag gatgattagc 178080
tgtcacagag agggagtaag ttttagcaga gtctttctag agatctgagc tgtgggaagg 178140
gaaaggtgtt ctgggaactg gtgaaaaaaa aaggcccagc actgaaatgg aatattcata 178200
accctcctg cactcttatc tcacagacca gccccgaggc tttatcaaga ctaacgctac 178260
tgtccattgg ttgttctgct caaaaactcc attaagaaaa tttaaattta aataaaacac 178320
ctgtttcatg gacctaatgc atgaatgaca gtcataaatc caagttgaaa atgtgtcttt 178380
agagggtggt tactcctgag tgcaaagcat taaatgtgta cctagtacag gaacacacag 178440
ttatcagctg tgtacatctt ccttccatat catttccata atgggggaaa agatgcacgg 178500
acagctagac gtttcactaa ttcctttcac cttttgtaga ctgttagcta ttgtcaatat 178560
caaatagtga aagttgtcat caattcaggc aagtgagatt tatcacattt tgctgtataa 178620
```

```
aattcagcta gtggcatgca agtgtcaact cactgaccca ttgttatagc aggaaggtca   178680
caggtagtag agagcccatg tctatcactg ggtttactgg caggaatgct atataccctc   178740
actgtgaccc accaccagct ctcaatgaga cagagggaga tgaggctaca ctgatgatca   178800
gggagaattg agaagtacca agaaaaaagt aacagacgaa gggtttcctg tgaatataaa   178860
gtcagttttc ttaaaggaat ggtagatggc ctctgtaggc acttccaaga aagatctaga   178920
aaatgtcttc tacagggtag tgccatttgg attaggatgc atatctcttc catgtaactt   178980
ctgagaagac cacacactca tttaaatgtg agaattctac cgtgaaagcc actcaccact   179040
tataattttc aatcctttaa tacataagaa agggatgagc cagcaatcac tgtactaccc   179100
taaaggctta tgactttcta taccttgaca attctgctac tcttatgagt tcaataattt   179160
ctaaagcatt tctaaattgg aaaaataaaa aaatctgaa aagtaataga gtggccagtg   179220
aggcagaaaa taagattcat gaagaaacat acataaattt aactacttga aaacatgaaa   179280
aatgactaat ggattagaaa acaaaaggca gatccataaa ttgaaagtgg cagaaggctc   179340
ctaagtcaaa gagaaaggtt aaaaaagaaa gaaagaaaag aaaagctcca aagagcccag   179400
taaaattgat acaaggaggc tatgagatac actttaatca ctgtggacat tgtcttaaat   179460
ctaccaggtt gttaaaattc taaatctttg attcactatc aattgtgcat aaaggttccc   179520
attttgtttt tggttccccc taaaacaaga tagatttcac catatttgaa tttgggaaag   179580
aactgaaaca ccattacgac ggaaaatcca gggggtttac tgttaaggga cagcctcaag   179640
ggctgtgagg tgcgggatgg agagtgagtc gaggctccac cttcacatgg gctcccagag   179700
ttactatgcc ttgtgattct ggacttaacc tcttttaatc tcttcctgct cctcaaagtg   179760
aagattataa tgcacatccc actcccaggg ctgttttgag aatcaactaa aaacacatgt   179820
gaaagtggtt tgagtgaaag taagcttttt caggctaagc caagcagaga atgtcaacga   179880
tagttgcaat tagaaagaaa tgcctgggca aaataacatg tctttacatt tctcttaaaa   179940
tgggatggta tgctcactaa aagttgctag ataattagtg tgtcatggcc acatgcttat   180000
agtagtcaag aactttacag aagccttttc aaataactgg attgtgagct ttatgacatt   180060
cctcaatcat ccacacctta gcccatttat gtaggattca taatgaattg gacccaggcc   180120
aggtttgcat gagttcagtt gatttgcttt ggtggcactt aactccttgg ggtcgatcag   180180
ctacaatggc tgtagaggat gaatcaatct ggctcaggct agtaaaccag ggctgcttgt   180240
ataagtagac agcagcccat gtagggtgat ttctgggtta ttaagaagac cctgtgatcc   180300
ccaaacacac ctcactctga cctatagaca tcaaaatccc ataataagag tttaactatt   180360
ttggctttaa ccaaacaggg attttttaaag catgttaaga cttcttgccc tttctccaag   180420
gtacaggaat gaaactaggg gatgttataa ttttgactta tctttatctg accatatata   180480
gcgtgccctg gctttgcaaa ccattgaggc aatgccatag aattgatcct cccaaggagt   180540
ttagtccact cagcttgctt ggggtaatat aggcattggt caggtcaata cccatgaaaa   180600
agtcattcac ttacttattc cacgaatact tattgaggac ctactgggta ctcagtacct   180660
agttccgtat ttcctatgta agatctgcag agtttacaca taatgacaca atgtaaatca   180720
gattgtaact gtccttttgc aaactcataa aatgatataa ctatatatac atcatatgct   180780
actgttttgg tatacacatt agcatatcac acatttctaa attcatagtg ggcagaggtc   180840
aggggtgggg aaaatgatta attgccactc ttacattgga ttccatctaa aacctgtctg   180900
acttgtatgt cctccaactc tttggtagat gaggacatgt tttctttggc tgacagtgtt   180960
```

| | |
|---|---|
| attattatta tttataataa atcataattc cacctcccct atcacaggcc tctccttctg | 181020 |
| ggcatgtatt ccatattctc cagtgcagtc ttctgtctga gtgtccaacc tcaaaaaatg | 181080 |
| gctaggaaat agaaactgta tagtggtttt atagcaaact tacttttgcc cagcttctcc | 181140 |
| ttggcctgca caaggtccat acttataagc atacaccaag cgagggataa agtcagatgt | 181200 |
| tatcgctatg acaaatgcat ttgtgataac agagagaatt ccaatgcctt caagaattc | 181259 |

<210> SEQ ID NO 3
<211> LENGTH: 3810
<212> TYPE: DNA
<213> ORGANISM: Homo sapiens

<400> SEQUENCE: 3

| | |
|---|---|
| gtgtagattc gctggaagca gctggaggct ccagttctca tctgctcagg tgtccccggc | 60 |
| gccttggcga actcggccac tccagttcct cacgtggtga gcactcaggg cagcgggtcg | 120 |
| attttccgag gtcccatacc tgggtttgag gggcgcggct cgcagcggcg ggtgcagggg | 180 |
| cgactgccag ccctcacccc gcctcggggt gcgttcggag gccgacacct ggaggacgcc | 240 |
| tccagtcccc gcgggacgcc acgcctgcgc gccaggatc cgggataaga agtgcgcgcc | 300 |
| gggctccggc tgcgcgccgc ggggccacca gtttgcgcgc agggctcagg cgaccgtgcg | 360 |
| gccatggaca cgccacgggg catcggcacc ttcgtggtgt gggactacgt ggtgttcgcg | 420 |
| ggcatgctgg tcatctcggc cgccatcggc atctactacg ccttcgctgg gggcggccag | 480 |
| cagacctcca aggacttcct gatgggcggc cgcagaatga ccgcagtgcc cgtggcgctg | 540 |
| tccctcaccg ctagcttcat gtcagccgtc actgtcctgg caccccctc cgaggtctac | 600 |
| cgttttgggg ccattttag catctttgcc ttcacctact ctttgtggt ggtcatcagc | 660 |
| gcggaggtct tcctcccggt gttctacaaa ctgggaatta ccagcaccta cgagtattta | 720 |
| gaacttcgat ttaacaaatg tgttcgtctc tgtggaacag tcctcttcat tgttcaaaca | 780 |
| attctgtata ctggaattgt tatttatgcc cctgccctgg ctttgaatca agtcacagga | 840 |
| tttgatctgt ggggcgcggt agtggcaacg ggggtggtct gcacattcta ctgcacactg | 900 |
| ggtggtctta aagcagttat ctggacagat gttttttcaaa ttgggatcat ggtggctgga | 960 |
| tttgcatccg tgattataca ggctgtggtg atgcaaggtg gaatcagcac tatttttaaat | 1020 |
| gatgcctatg atggtggaag attaaatttc tggaatttta tcctaacccc tttgcaaaga | 1080 |
| cacaccttct ggacaattat tataggaggg accttcacat ggaccagcat ctacggtgtc | 1140 |
| aaccaatccc aggtgcagag atatatttct tgtaaaagca gattccaggc aaaactgtct | 1200 |
| ctctacatca atcttgtggg actctgggca atcctcacat gctcagtgtt ttgtgggctc | 1260 |
| gccctatatt ccaggtacca tgactgtgat ccttggacag ccaagaaagt gtctgcacca | 1320 |
| gaccagctca tgcccttatt tggtactgga cattctgcaag attatccagg acttcctgga | 1380 |
| cttttttgtgg cctgtgctta cagtgggaca ttaagcacag tgtcctccag tattaatgcc | 1440 |
| ttagcagcag taactgtgga agatctaatc aaaccttact tcagatcgct ctcagaaagg | 1500 |
| tctctgtctt ggatttccca aggaatgagt gtggtgtatg agccctgtg tattggaatg | 1560 |
| gctgcgctgg cgtcacttat gggagctttg ttgcaggcag cactcagcgt atttggtatg | 1620 |
| gttggtggac cacttatggg cctgttcgct ttgggcattt tggttccctt gccaactca | 1680 |
| attggagcac ttgttggtct gatggctgga tttgccattt ctctatgggt tggaattgga | 1740 |
| gctcaaatat atcctccact tcctgagaga acattgccat tgcacttga tatccaaggc | 1800 |
| tgtaacagca cctacaatga gacaaatttg attacaacca cagaaatgcc atttactact | 1860 |

```
agtgttttc aaatatacaa tgttcaaagg actccactga tggataactg gtattcttta    1920
tcatatctgt acttcagcac tgttggaact ttggtaacat tattagtggg gatacttgtc    1980
agtttatcaa caggaggaag aaaacagaac ttagacccca gatatatact aaccaaagag    2040
gactttttat ccaatttga tatttttaag aaaaagaagc atgttttgag ctataaatca     2100
catccagtgg aagatggtgg aactgataat cctgctttca accacattga attgaactca    2160
gatcagagtg gcaagagcaa tgggactcgt tgtgaagct gctctgatac tagatatcct     2220
taaatgatgt ttcaatttta tatgttttct aagataattg gatcaggttt ctttgtgtg     2280
tgtgtgtgtg tgttgtatca tgagtgtttg ggggataagt ttttgttaaa acaaagtctg    2340
gactatcttc atttactaca tcattaattg atgttactct ggagtttaga attctggcat    2400
tgacatttcc ctctctttcc tttatttcga tgaagctata attgtgaaaa ttgtaactac    2460
atagatgctg aaaggctaat acacacatat gcacatgtat ttgattgtca aggtatatt    2520
cttaaatttg ggtattattg aaaatatttt ccatgccttg gtgctagcat ataagtttgg    2580
aagtttgcca acatcacaat tcatcttgaa aagagctttt ttccctccta ccacatacac    2640
cattcttagg gagcaatgag gtaacaggtc tgtgttgtct agatctttgc ttttatccc     2700
cctatcagtc cagggcatat actaacctgc aaactgattc tgaatcagga aggtggtaat    2760
caataagtat tctggctggg aaagaccgtg ggcccaatga tcaaagtctt cttggtgctg    2820
ttcattaatt cttgtgcctt ttggcttgtt ttctagagtt tctgggcttt ggctgctgat    2880
actgcctttc ttagactgta attttatct gcatgcccag tttctgacct atcaacttgg     2940
gtttattgt gcactctaac tgagcttgtc ttcataattt tctgtttatt gccctgggct     3000
tggatatgtc tcaagacact catgtgaatc atgccacccc aaatcctggc ttatcaagtc    3060
ccagactata aattatgaac tcccattagc ttggtactaa catatacttg atgtaggtat    3120
ttatggactt gatgatccaa gaatattata ttcttcaaaa tggttaagct ccatggagtt    3180
agatgactac acttaatgct attaagttga acttttgaat gtcaactaat ttgcaatcaa    3240
ttaaagatac atatgcctag aaattttgaa atttcggtat atttatccag ttaaagggct    3300
aaattatata agcaaacact actttttttta aaacgtctgg actcaaaaaa tgctttgttc    3360
catgttttaa aattttaag tagcagtctc aaagttgctt agctgtttat tttgctatgt     3420
tcctagctaa gagtttggtt ataggagttc atcaataact tattttttgt acagttccca    3480
cattagatac tgtttaaaag ttcttttta aactcaattt tttttagaaa cataagagaa     3540
atatttagat acatacaaat gttttatga ttaaataatt ttatgcttat tttctgatac     3600
gtgttattta ggtaatcatg ccctgtacat ttagaggttg ctaactgaca atgttaagaa    3660
atttaaaaaa aaaaaaagcc tgggcatgat ggctcatgct tgtaatctga acatttggga    3720
ggctgaggca ggaagatcgc ttgaggtcca gagtttaagt ccagcctgga aacatagtta    3780
gacctcatct ctacaaaaat cctcgtgccg                                     3810

<210> SEQ ID NO 4
<211> LENGTH: 1833
<212> TYPE: DNA
<213> ORGANISM: Homo sapiens

<400> SEQUENCE: 4
atggacacgc cacggggcat cggcaccttc gtgtgtgggg actacgtggt gttcgcgggc      60
atgctggtca tctcggccgc catcggcatc tactacgcct cgctgggggg cggccagcag     120
```

```
acctccaagg acttcctgat gggcggccgc agaatgaccg cagtgcccgt ggcgctgtcc      180
ctcaccgcta gcttcatgtc agccgtcact gtcctgggca ccccctccga ggtctaccgt      240
tttggggcca ttttagcat ctttgccttc acctacttct tgtggtggt catcagcgcg        300 gaggtcttcc tcccggtgtt ctacaaactg ggaattacca gcacctacga gtatttagaa      360
cttcgattta acaaatgtgt tcgtctctgt ggaacagtcc tcttcattgt tcaaacaatt      420
ctgtatactg gaattgttat ttatgcccct gccctggctt tgaatcaagt cacaggattt      480
gatctgtggg gcgcggtagt ggcaacgggg gtggtctgca cattctactg cacactgggt      540
ggtcttaaag cagttatctg gacagatgtt tttcaaattg ggatcatggt ggctggattt      600
gcatccgtga ttatacaggc tgtggtgatg caaggtggaa tcagcactat tttaaatgat      660
gcctatgatg gtgaagatt aaatttctgg aattttaatc ctaacccttt gcaaagacac       720
accttctgga caattattat aggagggacc ttcacatgga ccagcatcta cggtgtcaac      780
caatcccagg tgcagagata tatttcttgt aaaagcagat tccaggcaaa actgtctctc      840
tacatcaatc ttgtgggact ctgggcaatc ctcacatgct cagtgttttg tgggctcgcc      900
ctatattcca ggtaccatga ctgtgatcct tggacagcca agaaagtgtc tgcaccagac      960
cagctcatgc cttatttggt actggacatt ctgcaagatt atccaggact tcctggactt     1020
tttgtggcct gtgcttacag tgggacatta agcacagtgt cctccagtat taatgcctta     1080
gcagcagtaa ctgtggaaga tctaatcaaa ccttacttca gatcgctctc agaaaggtct     1140
ctgtcttgga tttcccaagg aatgagtgtg gtgtatggag ccctgtgtat tggaatggct     1200
gcgctggcgt cacttatggg agctttgttg caggcagcac tcagcgtatt tggtatggtt     1260
ggtggaccac ttatgggcct gttcgctttg gcattttgg ttcccttgc caactcaatt       1320 ggagcacttg ttggtctgat ggctggattt gccatttctc tatgggttgg aattggagct     1380
caaatatatc ctccacttcc tgagagaaca ttgccattgc accttgatat ccaaggctgt     1440
aacagcacct acaatgagac aaatttgatt acaaccacag aaatgccatt tactactagt     1500
gtttttcaaa tatacaatgt tcaaggact ccactgatgg ataactggta ttcttttatca      1560 tatctgtact tcagcactgt tggaactttg gtaacattat tagtggggat acttgtcagt     1620
ttatcaacag gaggaagaaa acagaactta gaccccagat atatactaac caaagaggac     1680
tttttatcca attttgatat ttttaagaaa aagaagcatg ttttgagcta taaatcacat     1740
ccagtggaag atggtggaac tgataatcct gctttcaacc acattgaatt gaactcagat     1800
cagagtggca agagcaatgg gactcgtttg tga                                   1833
```

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
ccagcgaagg cgtagtagat                                                   20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6

```
ggctccagtt ctcatctgct                                               20

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
ggcagtctaa aaactccagg c                                             21

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
ttgaatgtat tttgaggtg                                                19

<210> SEQ ID NO 9
<211> LENGTH: 18
<212> TYPE: DNA
<213> ORGANISM: Artificial Sequence
<220> FEATURE:
<223> OTHER INFORMATION: primer

<400> SEQUENCE: 9
tcaattttcc aaaatccc                                                 18

<210> SEQ ID NO 10
<211> LENGTH: 18
<212> TYPE: DNA
<213> ORGANISM: Artificial Sequence
<220> FEATURE:
<223> OTHER INFORMATION: primer

<400> SEQUENCE: 10
tcgaacgtat ttcgaggc                                                 18

<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
acaacgaatc gattttccg                                                19

<210> SEQ ID NO 12
<211> LENGTH: 1068
<212> TYPE: DNA
<213> ORGANISM: Homo sapiens

<400> SEQUENCE: 12
atgaaggctc attaaaaagt ggatattatt gttaatcttc caataactac tatttccaac    60
aacaggctga aggggctcag aaacgtttgt tgagtaaaaa cacaaggaaa cagtagcaca   120
gatttcctgc tctccttttac gatcgatgac ctgtctaagg actgtgatct ctgttcgcta   180
cagattgtca cctgcattaa tctactgtca cccattaacc tatcaaataa ggcagtctaa   240
```

```
aaactccagg cgtcccttc cgtaaggacc cggactgttg aactggaaag ctaaaattca    300
aggcgtgaca attgcccttt gtcccacatt cctccaccgg tcgcctgctt atttaaatgg    360
tgcgtcccct cgggtaccac ttgaacaaaa cctgcccaga gcgctccctg tgtagattcg    420
ctggaagcag ctggaggctc cagttctcat ctgctcaggt gtccccggcg ccttggcgaa    480
ctcggccact ccagttcctc acgtggtgag cactcagggc agcgggtcga ttttccgagg    540
tcccatacct gggtttgagg ggcgcggctc gcagcggcgg gtgcagggggc gactgccagc    600 cctcaccccg cctcggggtg cgttcggagg ccgacacctg aggacgcct ccagtccccg    660 cgggacgcca cgcctgcgcg ccagggatcc gggataagaa gtgcgcgccg ggctccggct    720
gcgcgccgcg gggccaccag tttgcgcgca gggctcaggc gaccgtgcgg ccatggacac    780
gccacggggc atcggcacct tcgtggtgtg ggactacgtg gtgttcgcgg gcatgctggt    840
catctcggcc gccatcggca tctactacgc cttcgctggg ggcggccagc agacctccaa    900
ggacttcctg atgggcggcc gcagaatgac cgcagtgccc gtggcgctgt ccctcaccgc    960
tagcttcatg tcagccgtca ctgtcctggg caccccctcc gaggtctacc gttttgggc   1020 catttttagc atctttgcct tcacctactt ctttgtggtg gtcatcag                1068

<210> SEQ ID NO 13
<211> LENGTH: 1068
<212> TYPE: DNA
<213> ORGANISM: Homo sapiens

<400> SEQUENCE: 13
ctgatgacca ccacaaagaa gtaggtgaag gcaaagatgc taaaaatggc cccaaaacgg     60
tagacctcgg aggggggtgcc caggacagtg acggctgaca tgaagctagc ggtgagggac    120
agcgccacgg gcactgcggt cattctgcgg ccgcccatca ggaagtcctt ggaggtctgc    180
tggccgcccc cagcgaaggc gtagtagatg ccgatggcgg ccgagatgac cagcatgccc    240
gcgaacacca cgtagtccca caccacgaag gtgccgatgc cccgtggcgt gtccatggcc    300
gcacggtcgc ctgagccctg cgcgcaaact ggtggcccg cggcgcgcag ccggagcccg    360
gcgcgcactt cttatcccgg atccctggcg cgcaggcgtg gcgtcccgcg gggactggag    420
gcgtcctcca ggtgtcggcc tccgaacgca ccccgaggcg gggtgagggc tggcagtcgc    480
ccctgcaccc gccgctgcga gccgcgcccc tcaaacccag gtatgggacc tcggaaaatc    540
gacccgctgc cctgagtgct caccacgtga ggaactggag tggccgagtt cgccaaggcg    600
ccggggacac ctgagcagat gagaactgga gcctccagct gcttccagcg aatctacaca    660
gggagcgctc tggcaggtt ttgttcaagt ggtacccgag gggacgcacc atttaaataa    720
gcaggcgacc ggtggaggaa tgtgggacaa agggcaattg tcacgccttg aattttagct    780
ttccagttca acagtccggg tccttacgga aagggacgcc tggagttttt agactgcctt    840
atttgatagg ttaatgggtg acagtagatt aatgcaggtc acaatctgta gcgaacagag    900
atcacagtcc ttagacaggt catcgatcgt aaaggagagc aggaaatctg tgctactgtt    960
tccttgtgtt tttactcaac aaacgtttct gagccccttc agcctgttgt tggaaatagt   1020
agttattgga agattaacaa taatatccac tttttaatga gccttcat                1068

<210> SEQ ID NO 14
<211> LENGTH: 301
<212> TYPE: DNA
<213> ORGANISM: Homo sapiens

<400> SEQUENCE: 14
```

```
gctggcagtc gccccgcac ccgccgctgc gagccgcgcc cctcaaaccc aggtatggga      60
cctcggaaaa tcgacccgct gccctgagtg ctcaccacgt gaggaactgg agtggccgag     120
ttcgccaagg cgccggggac acctgagcag atgagaactg agcctccag ctgcttccag      180 cgaatctaca cagggagcgc tctgggcagg ttttgttcaa gtggtacccg aggggacgca    240
ccatttaaat aagcaggcga ccggtggagg aatgtgggac aaagggcaat tgtcacgcct    300
t                                                                     301

<210> SEQ ID NO 15
<211> LENGTH: 1068
<212> TYPE: DNA
<213> ORGANISM: Homo sapiens

<400> SEQUENCE: 15
ttgatgatta ttataaagaa gtaggtgaag gtaaagatgt taaaaatggt tttaaaacgg      60
tagatttcgg agggggtgtt taggatagtg acggttgata tgaagttagc ggtgagggat    120
agcgttacgg gtattgcggt tattttgcgg tcgtttatta ggaagttttt ggaggtttgt    180
tggtcgtttt tagcgaaggc gtagtagatg tcgatggcgg tcgagatgat tagtatgttc    240
gcgaatatta cgtagtttta tattacgaag gtgtcgatgt ttcgtggcgt gtttatggtc    300
gtacggtcgt ttgagttttg cgcgtaaatt ggtggtttcg cggcgcgtag tcggagttcg    360
gcgcgtattt tttatttcgg attttttggcg cgtaggcgtg gcgtttcgcg gggattggag    420
gcgtttttta ggtgtcggtt ttcgaacgta tttcgaggcg gggtgagggt tggtagtcgt    480
ttttgtattc gtcgttgcga gtcgcgtttt ttaaatttag gtatgggatt tcggaaatc     540 gattcgttgt tttgagtgtt tattacgtga ggaattggag tggtcgagtt cgttaaggcg    600
tcggggatat tgagtagat gagaattgga gttttagtt gttttagcg aatttatata       660 gggagcgttt tgggtaggtt ttgtttaagt ggtattcgag gggacgtatt atttaaataa    720
gtaggcgatc ggtggaggaa tgtgggataa agggtaattg ttacgttttg aattttagtt    780
ttttagttta atagttcggg ttttacgga aaggacgtt tggagttttt agattgtttt      840
atttgatagg ttaatgggtg atagtagatt aatgtaggtg ataatttgta gcgaatagag    900
attatagttt ttagataggt tatcgatcgt aaaggagagt aggaaatttg tgttattgtt    960
tttttgtgtt tttatttaat aaacgttttt gagtttttt agtttgttgt tggaaatagt    1020
agttattgga agattaataa taatatttat tttttaatga gttttttat                1068

<210> SEQ ID NO 16
<211> LENGTH: 1068
<212> TYPE: DNA
<213> ORGANISM: Homo sapiens

<400> SEQUENCE: 16
ttgatgatta ttataaagaa gtaggtgaag gtaaagatgt taaaaatggt tttaaaatgg      60
tagattttgg agggggtgtt taggatagtg atggttgata tgaagttagt ggtgagggat    120
agtgttatgg gtattgtggt tattttgtgg ttgtttatta ggaagttttt ggaggtttgt    180
tggttgtttt tagtgaaggt gtagtagatg ttgatggtgg ttgagatgat tagtatgttt    240
gtgaatatta tgtagtttta tattatgaag gtgttgatgt tttgtggtgt gtttatggtt    300
gtatggttgt ttgagttttg tgtgtaaatt ggtggttttg tggtgtgtag ttggagtttg    360
gtgtgtattt tttattttgg attttttggtg tgtaggtgtg tgtttttgtg gggattggag    420
```

| | |
|---|---:|
| gtgttttta ggtgttggtt tttgaatgta ttttgaggtg gggtgagggt tggtagttgt | 480 |
| ttttgtattt gttgttgtga gttgtgtttt ttaaatttag gtatgggatt ttggaaaatt | 540 |
| gatttgttgt tttgagtgtt tattatgtga ggaattggag tggttgagtt tgttaaggtg | 600 |
| ttggggatat ttgagtagat gagaattgga gtttttagtt gttttagtg aatttatata | 660 |
| gggagtgttt tgggtaggtt ttgtttaagt ggtatttgag gggatgtatt atttaaataa | 720 |
| gtaggtgatt ggtggaggaa tgtgggataa agggtaattg ttatgttttg aattttagtt | 780 |
| ttttagttta atagtttggg tttttatgga aagggatgtt tggagttttt agattgtttt | 840 |
| atttgatagg ttaatgggtg atagtagatt aatgtaggta ataatttgta gtgaatagag | 900 |
| attatagttt ttagataggt tattgattgt aaaggagagt aggaaatttg tgttattgtt | 960 |
| tttttgtgtt tttattaat aaatgttttt gagtttttt agtttgttgt tggaaatagt | 1020 |
| agttattgga agattaataa taatatttat tttttaatga gttttat | 1068 |

<210> SEQ ID NO 17
<211> LENGTH: 1068
<212> TYPE: DNA
<213> ORGANISM: Homo sapiens

<400> SEQUENCE: 17

| | |
|---|---:|
| atgaaggttt attaaaaagt ggatattatt gttaatttt taataattat tatttttaat | 60 |
| aataggttga aggggtttag aaatgtttgt tgagtaaaaa tataaggaaa tagtagtata | 120 |
| gatttttgt tttttttat gattgatgat ttgtttaagg attgtgattt ttgtttgtta | 180 |
| tagattgtta tttgtattaa tttattgtta tttattaatt tattaaataa ggtagtttaa | 240 |
| aaattttagg tgttttttt tgtaaggatt tggattgttg aattggaaag ttaaaattta | 300 |
| aggtgtgata attgttttt gttttatatt ttttattgg ttgtttgttt atttaaatgg | 360 |
| tgtgttttt tgggtattat ttgaataaaa tttgttaga gtgtttttg tgtagatttg | 420 |
| ttggaagtag ttggaggttt tagttttat ttgtttaggt gtttttggtg ttttggtgaa | 480 |
| tttggttatt ttagtttttt atgtggtgag tatttagggt agtgggttga ttttttgagg | 540 |
| ttttatattt gggtttgagg ggtgtggttt gtagtggtgg gtgtaggggt gattgttagt | 600 |
| ttttattttg ttttggggtg tgtttggagg ttgatatttg gaggatgttt ttagtttttg | 660 |
| tgggatgtta tgtttgtgtg ttagggattt gggataagaa gtgtgtgttg ggttttggtt | 720 |
| gtgtgttgtg gggttattag tttgtgtgta gggtttaggt gattgtgtgg ttatggatat | 780 |
| gttatggggt attggtattt ttgtggtgtg ggattatgtg gtgtttgtgg gtatgttggt | 840 |
| tattttggtt gttattggta tttattatgt ttttgttggg ggtggttagt agatttttaa | 900 |
| ggattttga tgggtggttg tagaatgatt gtagtgtttg tggtgttgtt tttttattgt | 960 |
| tagttttatg ttagttgtta ttgttttggg tattttttt gaggtttatt gttttggggt | 1020 |
| tattttagt atttttgttt ttatttattt ttttgtggtg gttattag | 1068 |

<210> SEQ ID NO 18
<211> LENGTH: 1068
<212> TYPE: DNA
<213> ORGANISM: Homo sapiens

<400> SEQUENCE: 18

| | |
|---|---:|
| atgaaggttt attaaaaagt ggatattatt gttaatttt taataattat tatttttaat | 60 |
| aataggttga aggggtttag aaacgtttgt tgagtaaaaa tataaggaaa tagtagtata | 120 |
| gatttttgt tttttttac gatcgatgat ttgtttaagg attgtgattt ttgttcgtta | 180 |

-continued

```
tagattgtta tttgtattaa tttattgtta tttattaatt tattaaataa ggtagtttaa    240
aaattttagg cgttttttt cgtaaggatt cggattgttg aattggaaag ttaaaattta     300
aggcgtgata attgtttttt gttttatatt tttttatcgg tcgtttgttt atttaaatgg    360
tgcgtttttt cgggtattat ttgaataaaa tttgtttaga gcgttttttg tgtagattcg    420
ttggaagtag ttggaggttt tagtttttat ttgtttaggt gttttcggcg ttttggcgaa    480
ttcggttatt ttagtttttt acgtggtgag tatttagggt agcgggtcga ttttcgagg    540 ttttatattt gggtttgagg ggcgcggttc gtagcggcgg gtgtaggggc gattgttagt   600
ttttatttcg tttcggggtg cgttcggagg tcgatatttg gaggacgttt ttagttttcg    660
cgggacgtta cgtttgcgcg ttagggattc gggataagaa gtgcgcgtcg ggtttcggtt   720
gcgcgtcgcg gggttattag tttgcgcgta gggtttaggc gatcgtgcgg ttatggatac   780
gttacggggt atcggtattt tcgtggtgtg ggattacgtg gtgttcgcgg gtatgttggt    840
tatttcggtc gttatcggta tttattacgt tttcgttggg ggcggttagt agattttaa    900 ggatttttg atgggcggtc gtagaatgat cgtagtgttc gtggcgttgt tttttatcgt    960
tagttttatg ttagtcgtta ttgttttggg tattttttc gaggtttatc gttttggggt   1020 tattttagt attttgttt ttatttattt ttttgtggtg gttattag                  1068
```

<210> SEQ ID NO 19
<211> LENGTH: 23
<212> TYPE: PRT
<213> ORGANISM: Homo sapiens

<400> SEQUENCE: 19

Phe Val Val Trp Asp Tyr Val Val Phe Ala Gly Met Leu Val Ile Ser
1               5                   10                  15

Ala Ala Ile Gly Ile Tyr Tyr
            20

<210> SEQ ID NO 20
<211> LENGTH: 23
<212> TYPE: PRT
<213> ORGANISM: Homo sapiens

<400> SEQUENCE: 20

Met Thr Ala Val Pro Val Ala Leu Ser Leu Thr Ala Ser Phe Met Ser
1               5                   10                  15

Ala Val Thr Val Leu Gly Thr
            20

<210> SEQ ID NO 21
<211> LENGTH: 23
<212> TYPE: PRT
<213> ORGANISM: Homo sapiens

<400> SEQUENCE: 21

Ile Phe Ser Ile Phe Ala Phe Thr Tyr Phe Phe Val Val Val Ile Ser
1               5                   10                  15

Ala Glu Val Phe Leu Pro Val
            20

<210> SEQ ID NO 22
<211> LENGTH: 23
<212> TYPE: PRT
<213> ORGANISM: Homo sapiens -continued

```
<400> SEQUENCE: 22

Val Arg Leu Cys Gly Thr Val Leu Phe Ile Val Gln Thr Ile Leu Tyr
1               5                   10                  15

Thr Gly Ile Val Ile Tyr Ala
            20

<210> SEQ ID NO 23
<211> LENGTH: 23
<212> TYPE: PRT
<213> ORGANISM: Homo sapiens

<400> SEQUENCE: 23

Gly Ala Val Val Ala Thr Gly Val Val Cys Thr Phe Tyr Cys Thr Leu
1               5                   10                  15

Gly Gly Leu Lys Ala Val Ile
            20

<210> SEQ ID NO 24
<211> LENGTH: 23
<212> TYPE: PRT
<213> ORGANISM: Homo sapiens

<400> SEQUENCE: 24

Ile Gly Ile Met Val Ala Gly Phe Ala Ser Val Ile Ile Gln Ala Val
1               5                   10                  15

Val Met Gln Gly Gly Ile Ser
            20

<210> SEQ ID NO 25
<211> LENGTH: 20
<212> TYPE: PRT
<213> ORGANISM: Homo sapiens

<400> SEQUENCE: 25

His Thr Phe Trp Thr Ile Ile Gly Gly Thr Phe Thr Trp Thr Ser
1               5                   10                  15

Ile Tyr Gly Val
            20

<210> SEQ ID NO 26
<211> LENGTH: 23
<212> TYPE: PRT
<213> ORGANISM: Homo sapiens

<400> SEQUENCE: 26

Leu Tyr Ile Asn Leu Val Gly Leu Trp Ala Ile Leu Thr Cys Ser Val
1               5                   10                  15

Phe Cys Gly Leu Ala Leu Tyr
            20

<210> SEQ ID NO 27
<211> LENGTH: 23
<212> TYPE: PRT
<213> ORGANISM: Homo sapiens

<400> SEQUENCE: 27

Leu Pro Gly Leu Phe Val Ala Cys Ala Tyr Ser Gly Thr Leu Ser Thr
1               5                   10                  15

Val Ser Ser Ser Ile Asn Ala
            20
```

```
<210> SEQ ID NO 28
<211> LENGTH: 23
<212> TYPE: PRT
<213> ORGANISM: Homo sapiens

<400> SEQUENCE: 28

Ser Leu Ser Trp Ile Ser Gln Gly Met Ser Val Val Tyr Gly Ala Leu
1               5                   10                  15

Cys Ile Gly Met Ala Ala Leu
            20

<210> SEQ ID NO 29
<211> LENGTH: 23
<212> TYPE: PRT
<213> ORGANISM: Homo sapiens

<400> SEQUENCE: 29

Ala Ala Leu Ser Val Phe Gly Met Val Gly Gly Pro Leu Met Gly Leu
1               5                   10                  15

Phe Ala Leu Gly Ile Leu Val
            20

<210> SEQ ID NO 30
<211> LENGTH: 23
<212> TYPE: PRT
<213> ORGANISM: Homo sapiens

<400> SEQUENCE: 30

Gly Ala Leu Val Gly Leu Met Ala Gly Phe Ala Ile Ser Leu Trp Val
1               5                   10                  15

Gly Ile Gly Ala Gln Ile Tyr
            20

<210> SEQ ID NO 31
<211> LENGTH: 23
<212> TYPE: PRT
<213> ORGANISM: Homo sapiens

<400> SEQUENCE: 31

Leu Ser Tyr Leu Tyr Phe Ser Thr Val Gly Thr Leu Val Thr Leu Leu
1               5                   10                  15

Val Gly Ile Leu Val Ser Leu
            20

<210> SEQ ID NO 32
<211> LENGTH: 24
<212> TYPE: DNA
<213> ORGANISM: Artificial Sequence
<220> FEATURE:
<223> OTHER INFORMATION: primer

<400> SEQUENCE: 32
tggggtttcg tggtttttc gcgc                                          24

<210> SEQ ID NO 33
<211> LENGTH: 25
<212> TYPE: DNA
<213> ORGANISM: Artificial Sequence
<220> FEATURE:
<223> OTHER INFORMATION: primer

<400> SEQUENCE: 33
ccgcgaatcc aatcaaacgt cgacg                                        25
```

```
<210> SEQ ID NO 34
<211> LENGTH: 29
<212> TYPE: DNA
<213> ORGANISM: Artificial Sequence
<220> FEATURE:
<223> OTHER INFORMATION: primer

<400> SEQUENCE: 34
atttttgggg ttttgtggtt tttttgtgt                                    29

<210> SEQ ID NO 35
<211> LENGTH: 29
<212> TYPE: DNA
<213> ORGANISM: Artificial Sequence
<220> FEATURE:
<223> OTHER INFORMATION: primer

<400> SEQUENCE: 35
atcaccacaa atccaatcaa acatcaaca                                    29

<210> SEQ ID NO 36
<211> LENGTH: 26
<212> TYPE: DNA
<213> ORGANISM: Artificial Sequence
<220> FEATURE:
<223> OTHER INFORMATION: primer

<400> SEQUENCE: 36
gcacgactaa aaataaatc gccgcg                                        26

<210> SEQ ID NO 37
<211> LENGTH: 30
<212> TYPE: DNA
<213> ORGANISM: Artificial Sequence
<220> FEATURE:
<223> OTHER INFORMATION: primer

<400> SEQUENCE: 37
aaacacacaa ctaaaaaata aatcaccaca                                   30

<210> SEQ ID NO 38
<211> LENGTH: 25
<212> TYPE: DNA
<213> ORGANISM: Artificial Sequence
<220> FEATURE:
<223> OTHER INFORMATION: primer

<400> SEQUENCE: 38
taaaacctcg taactttccc gcgcg                                        25

<210> SEQ ID NO 39
<211> LENGTH: 25
<212> TYPE: DNA
<213> ORGANISM: Artificial Sequence
<220> FEATURE:
<223> OTHER INFORMATION: primer

<400> SEQUENCE: 39
gtcgcgagtt tagttagacg tcgac                                        25

<210> SEQ ID NO 40
<211> LENGTH: 28
<212> TYPE: DNA
<213> ORGANISM: Artificial Sequence
<220> FEATURE:
<223> OTHER INFORMATION: primer
```

<400> SEQUENCE: 40
tcctaaaacc tcataacttt cccacaca 28

<210> SEQ ID NO 41
<211> LENGTH: 29
<212> TYPE: DNA
<213> ORGANISM: Artificial Sequence
<220> FEATURE:
<223> OTHER INFORMATION: primer

<400> SEQUENCE: 41
agttgttgtg agtttagtta gatgttgat 29

<210> SEQ ID NO 42
<211> LENGTH: 28
<212> TYPE: DNA
<213> ORGANISM: Artificial Sequence
<220> FEATURE:
<223> OTHER INFORMATION: primer

<400> SEQUENCE: 42
aacgaattaa taggaagagc ggatagcg 28

<210> SEQ ID NO 43
<211> LENGTH: 27
<212> TYPE: DNA
<213> ORGANISM: Artificial Sequence
<220> FEATURE:
<223> OTHER INFORMATION: primer

<400> SEQUENCE: 43
cgtccctccc taaaacgact actaccc 27

<210> SEQ ID NO 44
<211> LENGTH: 29
<212> TYPE: DNA
<213> ORGANISM: Artificial Sequence
<220> FEATURE:
<223> OTHER INFORMATION: primer

<400> SEQUENCE: 44 cgttttttt tgaagcggtt attgtttgt 29

<210> SEQ ID NO 45
<211> LENGTH: 28
<212> TYPE: DNA
<213> ORGANISM: Artificial Sequence
<220> FEATURE:
<223> OTHER INFORMATION: primer

<400> SEQUENCE: 45
aacgaaccaa taaaaaaaac aaacaacg 28

<210> SEQ ID NO 46
<211> LENGTH: 19
<212> TYPE: DNA
<213> ORGANISM: Artificial Sequence
<220> FEATURE:
<223> OTHER INFORMATION: primer

<400> SEQUENCE: 46
tccgaggtct accgttttg 19

<210> SEQ ID NO 47

```
<211> LENGTH: 19
<212> TYPE: DNA
<213> ORGANISM: Artificial Sequence
<220> FEATURE:
<223> OTHER INFORMATION: primer

<400> SEQUENCE: 47
gggcaggggc ataaataac                                                 19

<210> SEQ ID NO 48
<211> LENGTH: 18
<212> TYPE: DNA
<213> ORGANISM: Artificial Sequence
<220> FEATURE:
<223> OTHER INFORMATION: primer

<400> SEQUENCE: 48
tccgggataa gaagtgcg                                                  18

<210> SEQ ID NO 49
<211> LENGTH: 24
<212> TYPE: DNA
<213> ORGANISM: Artificial Sequence
<220> FEATURE:
<223> OTHER INFORMATION: primer

<400> SEQUENCE: 49
tagtatcaga gcagcttcac aaac                                           24

<210> SEQ ID NO 50
<211> LENGTH: 19
<212> TYPE: DNA
<213> ORGANISM: Artificial Sequence
<220> FEATURE:
<223> OTHER INFORMATION: primer

<400> SEQUENCE: 50
tttgtggtgg tcatcagcg                                                 19

<210> SEQ ID NO 51
<211> LENGTH: 19
<212> TYPE: DNA
<213> ORGANISM: Artificial Sequence
<220> FEATURE:
<223> OTHER INFORMATION: primer

<400> SEQUENCE: 51
gggcaggggc ataaataac                                                 19

<210> SEQ ID NO 52
<211> LENGTH: 20
<212> TYPE: DNA
<213> ORGANISM: Artificial Sequence
<220> FEATURE:
<223> OTHER INFORMATION: primer

<400> SEQUENCE: 52
aggctgtggt gatgcaaggt                                                20

<210> SEQ ID NO 53
<211> LENGTH: 18
<212> TYPE: DNA
<213> ORGANISM: Artificial Sequence
<220> FEATURE:
<223> OTHER INFORMATION: primer

<400> SEQUENCE: 53
```

```
ttaatgcctt agcagcag                                            18
```

<210> SEQ ID NO 54
<211> LENGTH: 20
<212> TYPE: DNA
<213> ORGANISM: Artificial Sequence
<220> FEATURE:
<223> OTHER INFORMATION: primer

<400> SEQUENCE: 54

```
cctccacttc ctgagagaac                                          20
```

<210> SEQ ID NO 55
<211> LENGTH: 24
<212> TYPE: DNA
<213> ORGANISM: Artificial Sequence
<220> FEATURE:
<223> OTHER INFORMATION: primer

<400> SEQUENCE: 55

```
tctagtatca gagcagctac acaa                                     24
```

<210> SEQ ID NO 56
<211> LENGTH: 25
<212> TYPE: DNA
<213> ORGANISM: Artificial Sequence
<220> FEATURE:
<223> OTHER INFORMATION: primer

<400> SEQUENCE: 56

```
cgtgaaggta aagatgttaa aaatg                                    25
```

<210> SEQ ID NO 57
<211> LENGTH: 25
<212> TYPE: DNA
<213> ORGANISM: Artificial Sequence
<220> FEATURE:
<223> OTHER INFORMATION: primer

<400> SEQUENCE: 57

```
acaactaaaa actccaattc tcatc                                    25
```

<210> SEQ ID NO 58
<211> LENGTH: 29
<212> TYPE: DNA
<213> ORGANISM: Artificial Sequence
<220> FEATURE:
<223> OTHER INFORMATION: primer

<400> SEQUENCE: 58

```
caacgacgaa tacaaaaacg actaccaac                                29
```

<210> SEQ ID NO 59
<211> LENGTH: 23
<212> TYPE: DNA
<213> ORGANISM: Artificial Sequence
<220> FEATURE:
<223> OTHER INFORMATION: primer

<400> SEQUENCE: 59

```
ccaactccaa atcccctctc tat                                      23
```

<210> SEQ ID NO 60
<211> LENGTH: 30
<212> TYPE: DNA

-continued

```
<213> ORGANISM: Artificial Sequence
<220> FEATURE:
<223> OTHER INFORMATION: primer

<400> SEQUENCE: 60
tgattaattt agattgggtt tagagaagga                                    30

<210> SEQ ID NO 61
<211> LENGTH: 36
<212> TYPE: DNA
<213> ORGANISM: Artificial Sequence
<220> FEATURE:
<223> OTHER INFORMATION: primer

<400> SEQUENCE: 61
tcccttccta ttcctaaatc caacctaaat acctcc                             36
```

METHODS AND COMPOSITIONS FOR DETECTING CANCERS

CROSS-REFERENCE TO RELATED APPLICATIONS

This application is a continuation of U.S. application Ser. No. 10/456,930, filed on Jun. 5, 2003 now abandoned, which claims the benefit of priority of U.S. Provisional Application No. 60/386,653 filed Jun. 5, 2002. The entire teachings of the referenced applications are incorporated by reference herein in its entirety.

FUNDING

Work described herein was supported by National Institutes of Health Grant R01CA 67409. The United States Government has certain rights in the invention.

BACKGROUND

In 2001, over 1.2 million new cases of human cancer will be diagnosed and over 0.5 million people will die from cancer (American Cancer Society estimate). Despite this, more people than ever are living with and surviving cancer. In 1997, for example, approximately 8.9 million living Americans had a history of cancer (National Cancer Institute estimate). People are more likely to survive cancer if the disease is diagnosed at an early stage of development, since treatment at that time is more likely to be successful. Early detection depends upon availability of high-quality methods. Such methods are also useful for determining patient prognosis, selecting therapy, monitoring response to therapy and selecting patients for additional therapy. Consequently, there is a need for cancer diagnostic methods that are specific, accurate, minimally invasive, technically simple and inexpensive.

Colorectal cancer (cancer of the colon or rectum) is one particularly important type of human cancer. Colorectal cancer is the second most common cause of cancer mortality in adult Americans (Landis, et al., 1999, CA Cancer J Clin, 49:8-31). Approximately 40% of individuals with colorectal cancer die. In 2001, it is estimated that there will be 135,400 new cases of colorectal cancer (98,200 cases of colon and 37,200 cases of rectal cancer) and 56,700 deaths (48,000 colon cancer and 8,800 rectal cancer deaths) from the disease (American Cancer Society). As with other cancers, these rates can be decreased by improved methods for diagnosis. Although methods for detecting colon cancer exist, the methods are not ideal. Digital rectal exams (i.e., manual probing of rectum by a physician), for example, although relatively inexpensive, are unpleasant and can be inaccurate. Fecal occult blood testing (i.e., detection of blood in stool) is nonspecific because blood in the stool has multiple causes. Colonoscopy and sigmoidoscopy (i.e., direct examination of the colon with a flexible viewing instrument) are both uncomfortable for the patient and expensive. Double-contrast barium enema (i.e., taking X-rays of barium-filled colon) is also an expensive procedure, usually performed by a radiologist.

Other cancers such as breast cancer, thyroid cancer and stomach cancer, cause significant public health problem as well. For example, thyroid cancer is the most common endocrine malignancy. In the United States, there are approximately 14,000 new patients and 1,100 deaths per year (Shah et al., 1995, CA Cancer J Clin 45:352-68). Because of the disadvantages of existing methods for detecting and treating cancer, new methods and tools in cancer diagnosis and cancer therapy are needed.

SUMMARY OF THE INVENTION

In accordance with the present invention, new diagnostic tools and methods for detecting cancer (e.g., colon cancer, breast cancer, thyroid cancer, or stomach cancer) are provided. In certain aspects, the invention is based in part on the discovery of a novel polynucleotide sequence encoding a novel sodium/solute symporter-like protein (SLC5A8). Applicants previously referred to the SLC5A8 gene as the "Hui1" gene.

In one embodiment, the invention provides an isolated polypeptide comprising an amino acid sequence selected from the group consisting of: a) an amino acid sequence at least 95% identical to SEQ ID NO: 1; and b) an amino acid sequence encoded by a nucleic acid that hybridizes under high stringency conditions to a nucleic acid of any one of SEQ ID NOs: 3 or 4, wherein said polypeptide is a cell surface protein. The subject polypeptide comprises a transmembrane domain as set forth in any one of SEQ ID NOs: 19-31. The present invention contemplates the subject polypeptide as a sodium symporter.

In another embodiment, the invention provides an isolated antibody or fragment thereof, which is specifically immunoreactive with an epitope of a SCL5A8 protein sequence as set forth in SEQ ID NO: 1. The antibody of the invention can be selected from the group consisting of: a polyclonal antibody, a monoclonal antibody, an Fab fragment and a single chain antibody. Optionally, the antibody is labeled with a detectable label.

In another embodiment, the invention provides an isolated SCL5A8 nucleic acid selected from the group consisting of: a) a nucleic acid comprising the nucleotide sequence of SEQ ID NO: 2, or a complement thereof; b) a nucleic acid molecule that encodes a polypeptide comprising the amino acid sequence at least 95% identical to the amino acid sequence of SEQ ID NO: 7; and c) a nucleic acid molecule that hybridizes under stringent conditions to SEQ ID NO: 2. Optionally, the nucleic acid of the invention further comprises a vector nucleic acid sequence. In certain embodiments, the invention provides a kit comprising the SLC5A8 nucleic acid probes or primers and instructions for use.

In another embodiment, the invention provides a host cell which contains the subject SCL5A8 nucleic acid of the invention. In another embodiment, the invention provides a method for producing the subject polypeptide, comprising culturing the host cell under conditions in which the subject nucleic acid molecule is expressed.

In another embodiment, the invention provides a method for detecting the presence of the subject SCL5A8 polypeptide in a sample, comprising: a) contacting the sample with an antibody which selectively binds to the polypeptide of claim 1; and b) determining whether the antibody binds to the polypeptide in the sample.

In another embodiment, the invention provides a kit for detecting a human SCL5A8 polypeptide comprising: (i) an antibody of claim 2; and (ii) a detectable label for detecting said antibody.

In another embodiment, the invention provides a method for detecting the presence of the SCL5A8 nucleic acid in a sample, comprising: a) contacting the sample with an SCL5A8 probe or primer; and b) determining whether the probe or primer binds to a SCL5A8 nucleic acid in the sample.

In another embodiment, the invention provides a method for identifying a compound which binds to the SCL5A8 polypeptide, comprising: a) contacting the polypeptide, or a cell expressing the SCL5A8 polypeptide, with a test compound; and b) determining whether the polypeptide binds to the test compound.

In another embodiment, the invention provides a method for modulating the activity of the SCL5A8 polypeptide, comprising contacting the polypeptide or a cell expressing the polypeptide with a compound which binds to the polypeptide in a sufficient concentration to modulate the activity of the polypeptide.

In another embodiment, the invention provides a method of inhibiting aberrant activity of a SLC5A8-expressing cell, comprising contacting the cell with a compound that modulates the activity or expression of the polypeptide, in an amount which is effective to reduce or inhibit the aberrant activity of the cell.

In certain embodiments, compounds used in the methods of the invention are selected from the group consisting of a peptide, a phosphopeptide, a small organic molecule, an antibody, and a peptidomimetic. Cells in the methods of the invention can be found in the colon, kidney, lung, esophagus, small bowel, stomach, thyroid, uterus, and breast.

In another embodiment, the invention provides a method of treating or preventing a disorder characterized by aberrant activity of a SLC5A8-expressing cell, in a subject, comprising administering to the subject an effective amount of a compound that modulates the activity or expression of the SLC5A8 polypeptide, such that the aberrant activity of the SLC5A8-expressing cell is reduced or inhibited.

In another embodiment, the invention provides a transgenic mouse having germline and somatic cells comprising a chromosomally incorporated transgene that disrupts the genomic SLC5A8 gene and inhibits expression of said gene, wherein said disruption comprises insertion of a selectable marker sequence resulting in said transgenic mouse exhibiting increased susceptibility to the formation of tumors as compared to the wildtype mouse. The transgenic mouse can be homozygous r heterozygous for the disruption.

In another embodiment, the invention provides a transgenic mouse having germline and somatic cells in which at least one allele of a genomic SLC5A8 gene is disrupted by a chromosomally incorporated transgene, which transgene inhibits the expression of the genomic SLC5A8 gene, wherein (i) the genomic SLC5A8 gene encodes a SLC5A8 protein; and (ii) the disruption comprises insertion of a selectable marker sequence, which replaces all or a portion of the genomic SLC5A8 gene or is inserted into the coding sequence of the genomic SLC5A8 gene; and (iii) the transgenic mouse has increased susceptibility to the development of neoplasms.

In another embodiment, the invention provides isolated mammalian cells comprising a diploid genome including a chromosomally incorporated transgene, which transgene disrupts the genomic SLC5A8 gene and inhibits expression of said gene. Optionally, the cells are mouse cells.

In another embodiment, the invention provides a method for generating a mouse and mouse embryonic stem cells having a functionally disrupted endogenous SLC5A8 gene, comprising the steps of: (i) constructing a transgene construct including (a) a recombination region having all or a portion of the endogenous SLC5A8 gene, which recombination region directs recombination of the transgene with the endogenous SLC5A8 gene; and (b) a marker sequence which provides a detectable signal for identifying the presence of the transgene in a cell; (ii) transferring the transgene into embryonic stem cells of a mouse; (iii) selecting embryonic stem cells having a correctly targeted homologous recombination between the transgene and the SLC5A8 gene; (iv) transferring said cells identified in step (iii) into a mouse blastocyst and implanting the resulting chimeric blastocyst into a female mouse; and (v) selecting offspring harboring an endogenous SLC5A8 gene allele comprising the correctly targeted recombination.

In another embodiment, the invention provides a method of evaluating the carcinogenic potential of an agent comprising: (i) contacting the transgenic mouse of claim 16A with a test agent; and (ii) comparing the number of transformed cells in a sample from the treated mouse with the number of transformed cells in a sample from an untreated transgenic mouse or transgenic mouse treated with a control agent, wherein the difference in the number of transformed cells in the treated mouse, relative to the number of transformed cells in the absence of treatment or treatment with a control agent, indicates the carcinogenic potential of the test compound.

In another embodiment, the invention provides a method of evaluating an anti-proliferative activity of a test compound, comprising: (i) providing a transgenic mouse of claim 16A having germline and somatic cells in which the expression of the SLC5A8 gene is inhibited by said chromosomally incorporated transgene, or a sample of cells derived therefrom; (ii) contacting the transgenic mouse or the sample of cells with a test agent; and (iii) determining the number of transformed cells in a specimen from the transgenic mouse or in the sample of cells, wherein a statistically significant decrease in the number of transformed cells, relative to the number of transformed cells in the absence of the test agent, indicates the test compound is a potential anti-proliferative agent.

In certain aspects, the present invention is based, at least in part, on Applicants' discovery of a particular human genomic DNA region in which the cytosines within CpG dinucleotides are methylated in tissues from human cancers and unmethylated in normal human tissues. The region is referred to hereinafter as the "SLC5A8-methylation target region" is encompassed by base pairs 82200 to 83267 of GenBank entry AC063951, and is located in the promoter and/or exon 1 of the SLC5A8 gene. The present methods are also based, at least in part, on Applicants' discovery that the levels of SLC5A8 transcript in tissues from human cancers are lower than the levels of SLC5A8 transcript in normal tissues.

In one embodiment, the method comprises assaying for the presence of differentially methylated SLC5A8 nucleotide sequences (e.g., in the SLC5A8 methylation target region) in a tissue sample or a bodily fluid sample from a subject. Preferred bodily fluids include blood, serum, plasma, a blood-derived fraction, stool, colonic effluent or urine. In one embodiment, the method involves restriction enzyme/methylation-sensitive PCR. In another embodiment, the method comprises reacting DNA from the sample with a chemical compound that converts non-methylated cytosine bases (also called "conversion-sensitive" cytosines), but not methylated cytosine bases, to a different nucleotide base. In a preferred embodiment, the chemical compound is sodium bisulfite, which converts unmethylated cytosine bases to uracil. The compound-converted DNA is then amplified using a methylation-sensitive polymerase chain reaction (MSP) employing primers that amplify the compound-converted DNA template if cytosine bases within CpG dinucleotides of the DNA from the sample are methylated. Production of a PCR product indicates that the subject has cancer or precancerous adenomas. Other methods for assaying for the presence of methylated DNA are known in the art.

In another embodiment, the method comprises assaying for decreased levels of an SLC5A8 transcript in the sample. A sequence of the SLC5A8 transcript (SEQ ID NO: 3) is shown in FIG. 2. The SLC5A8 transcript is encoded by 15 exons within the present genomic contig. In another aspect the method comprises assaying for decreased levels of a protein encoded by the SLC5A8 transcript in the sample.

In another embodiment, the present invention provides a detection method for prognosis of a cancer (e.g., colon cancer, breast cancer, thyroid cancer, or stomach cancer) in a subject known to have or suspected of having cancer. Such method comprises assaying for the presence of methylated SLC5A8 DNA (e.g., in the SLC5A8 methylation target region) in a tissue sample or bodily fluid from the subject. In certain cases, it is expected that detection of methylated SLC5A8 DNA in a blood fraction is indicative of an advanced state of cancer (e.g., colon cancer). In other cased, detection of methylated SLC5A8 DNA in a tissue or stool derived sample or sample from other bodily fluids may be indicative of a cancer that will respond to therapeutic agents that demethylate DNA or reactivate expression of the SLC5A8 gene.

In another embodiment, the present invention provides a method for monitoring over time the status of cancer (e.g., colon cancer, breast cancer, thyroid cancer, or stomach cancer) in a subject. The method comprises assaying for the presence of methylated SLC5A8 DNA (e.g., in the SLC5A8 methylation target region) in a tissue sample or bodily fluid taken from the subject at a first time and in a corresponding tissue sample or bodily fluid taken from the subject at a second time. Absence of methylated SLC5A8 DNA from the tissue sample or bodily fluid taken at the first time and presence of methylated SLC5A8 DNA in the tissue sample or bodily fluid taken at the second time indicates that the cancer is progressing. Presence of methylated SLC5A8 DNA in the tissue sample or bodily fluid taken at the first time and absence of methylated SLC5A8 DNA from the tissue sample or bodily fluid taken at the second time indicates that the cancer is regressing.

In another embodiment, the present invention provides a method for evaluating therapy in a subject having cancer or suspected of having cancer (e.g., colon cancer, breast cancer, thyroid cancer, or stomach cancer). The method comprises assaying for the presence of methylated SLC5A8 DNA (e.g., in the SLC5A8 methylation target region) in a tissue sample or bodily fluid taken from the subject prior to therapy and a corresponding bodily fluid taken from the subject during or following therapy. Loss of or a decrease in the levels of methylated SLC5A8 DNA in the sample taken after or during therapy as compared to the levels of methylated SLC5A8 DNA in the sample taken before therapy is indicative of a positive effect of the therapy on cancer regression in the treated subject.

The present invention also relates to oligonucleotide primer sequences for use in assays (e.g., methylation-sensitive PCR assays or HpaII assays) designed to detect the methylation status of the SLC5A8 gene. The present invention also relates to antibodies and to oligonucleotides or oligomers for detecting the presence the SLC5A8 protein or the SLC5A8 transcript, respectively, in samples obtained from a subject.

The present invention also provides a method of inhibiting or reducing growth of cancer cells (e.g., colon cancer, breast cancer, thyroid cancer, or stomach cancer). The method comprises increasing the levels of the protein encoded by SLC5A8 in cancer cells. In one embodiment, the cells are contacted with the SLC5A8 protein or a biologically active equivalent or fragment thereof under conditions permitting uptake of the protein or fragment. In another embodiment, the cells are contacted with a nucleic acid encoding the SLC5A8 protein and comprising a promoter active in the cancer cell, wherein the promoter is operably linked to the region encoding the SLC5A8 protein, under conditions permitting the uptake of the nucleic acid by the cancer cell. In another embodiment, the method comprises demethylating the methylated SLC5A8 DNA, or otherwise reactivating the silenced SLC5A8 promoter.

In one embodiment, the application provides isolated or recombinant SLC5A8 nucleotide sequences that are at least 80%, 85%, 90%, 95%, 98%, 99% or identical to the nucleotide sequence of any one of SEQ ID NOs: 24 and 21, fragments of said sequences that are 10, 15, 20, 25, 50, 100, or 150 base pairs in length wherein the SLC5A8 nucleotide sequences are differentially methylated in an SLC5A8-associated disease cell.

In another embodiment, the application provides a method for detecting colon cancer, comprising: a) obtaining a sample from a patient; and b) assaying said sample for the presence of methylation of nucleotide sequences within at least two genes selected from the group consisting of: SLC5A8, HLTF, p16, and hMLH1; wherein methylation of nucleotide sequences within the two genes is indicative of colon cancer. In such methods, the sample is a bodily fluid selected from the group consisting of blood, serum, plasma, a blood-derived fraction, stool, urine, and a colonic effluent. For example, the bodily fluid is obtained from a subject suspected of having or is known to have colon cancer.

In another embodiment, the application provides a kit for detecting colon cancer in a subject, comprising primers for detecting methylation of nucleotide sequence within at least two genes selected from the group consisting of: SLC5A8, HLTF, p16, and hMLH1, wherein the primers for detecting methylation of SLC5A8 nucleotide sequence are selected from SEQ ID NOs: 5-11; wherein the primers for detecting methylation of HLTF nucleotide sequence are selected from 5'-TGGGGTTTCGTGGTTTTTTCGCGC-3',5'-CCGC-GAATCCAATCAAACGTCGACG-3',5'-ATTTTTGGGGTTTTGTGGTTTTTTTGTGT-3',5'-AT-CACCACAAATCCAATCAAACATCAACA-3',5'-GCACGACTAAAAAATAAATCGCCGCG-3',5'-AAACACACAACTAAAAAATAAATCACCACA-3',5'-TAAAACCTCGTAACTTTCCCGCGCG-3',5'-GTCGCGAGTTTAGTTAGACGTCGAC-3', 5'-TCCTAAAACCTCATAACTTTCCCACACA-3', and 5'-AGTTGTTGTGAGTTTAGTTAGATGTTGAT-3', wherein the primers for detecting methylation of hMLH1 nucleotide sequence are selected from 5'AACGAATTAAT-AGGAAGAGCGGATAGCG-3',5'-CGTCCCTC-CCTAAAACGACTACTACCC-3',5'-CGTTTTTTTTTGAAGCGGTTATTGTTTGT-3', and 5'-AACGAACCAATAAAAAAAACAAACAACG-3'. Tthe kit may further comprise a compound to convert a template DNA. Optioanally the compound is bisulfite.

BRIEF DESCRIPTION OF THE DRAWINGS

FIG. 1 shows the complete sequence of the Genomic clone AC063951 (SEQ ID NO: 2), with nucleotides 82200-83267 underlined on pages 35 of FIG. 1. This region (nucleotides 82200-83267 of AC063951, SEQ ID NO: 12, see FIG. 4) encompasses the promoter and/or exon 1 of the SLC5A8 gene, and is herein referred to as the "SLC5A8 methylation target region."

FIG. 2 shows the nucleotide sequence of the SLC5A8 mRNA transcript (SEQ ID NO: 3). The SLC5A8 transcript is encoded by 15 exons within the present genomic contig.

FIG. 5 shows the correlation between HpaII assays (over 4 HpaII sites and 6 HpaII sites) and silencing of expression of the SLC5A8 transcript.

FIG. 6 shows the results of the HpaII assays (over 4 HpaII sites and 6 HpaII sites) in actual colon cancer tumors and normal control colon tissues.

FIG. 10 shows the bisulfite converted sequence of a uniformly methylated SLC5A8 antisense strand (SEQ ID NO: 15), but not the wild-type sequence of the SLC5A8 antisense strand (corresponding to FIG. 8). Indicated again are the position of the methylation specific PCR primers for the MS-PCR1 assay.

FIG. 11 shows the bisulfite converted sequence of a uniformly unmethylated SLC5A8 antisense strand (SEQ ID NO: 16), but not the wild-type sequence of the SLC5A8 antisense strand shown in FIG. 8. Indicated are the position of the unmethylation specific PCR primers for the UMS-PCR1 assay.

FIG. 12 provides the bisulfite converted sequence of the unmethylated SLC5A8 sense strand of nucleotides 82200-83267 of AC063951, renumbered such that basepair 82200 is designated as nucleotide 1 (SEQ ID NO: 17).

FIG. 13 provides the bisulfite converted sequence of a uniformly methylated SLC5A8 sense strand of nucleotides 82200-83267 (SEQ ID NO: 18).

FIG. 14 shows the tabular results of MS-PCR1 assay performed on 31 colon cancer cell lines that do or do not express the SLC5A8 transcript.

FIG. 15 shows the tabular results of MS-PCR1 assay performed on 63 matched sets of primary colon cancer tumor tissue and accompanying normal colon tissue.

FIG. 16 shows the results of testing 12 normal colon tissues from individuals without colon cancer.

FIG. 18 shows the amino acid sequence (SEQ ID NO: 1) of the SLC5A8 protein.

FIG. 29 shows the protein alignments of SLC5A8, the closest murine homologue of SLC5A8, the human sodium iodide symporter SLC5A5, and the human sodium dependent multivitamin transporter SLC5A6.

DETAILED DESCRIPTION OF THE INVENTION

I. Definitions

Figure 3:
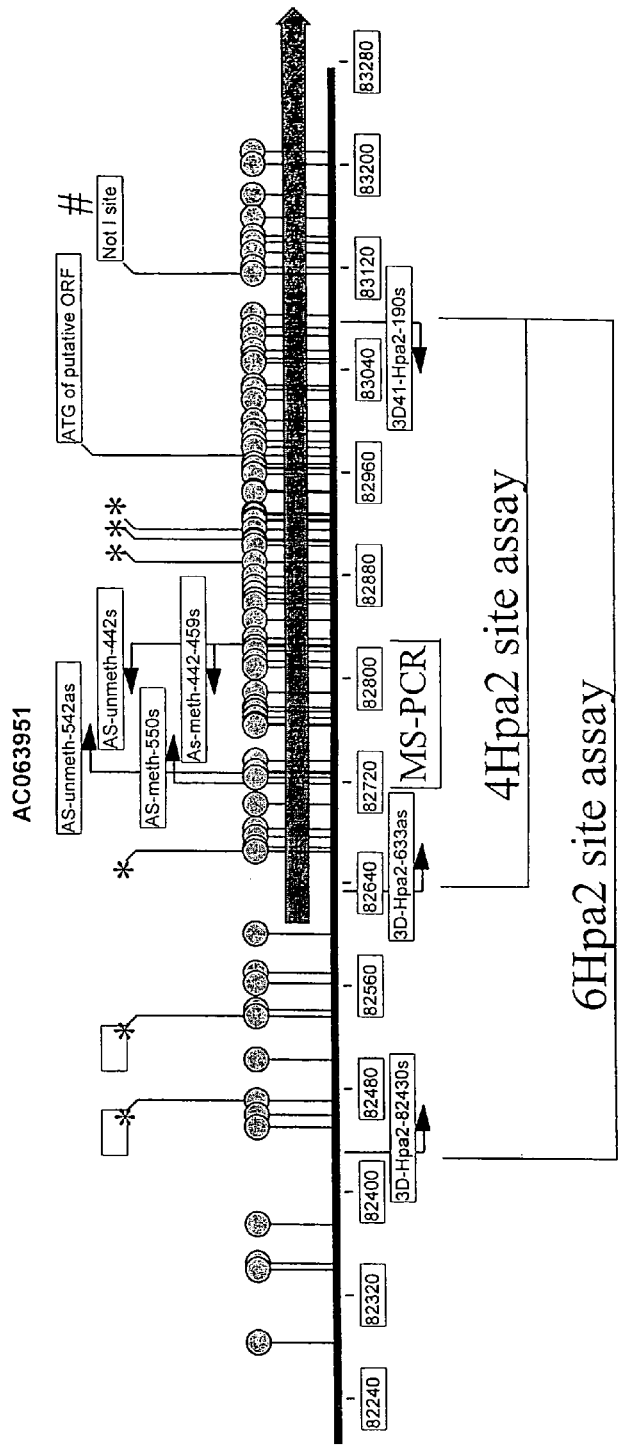
FIG. 3 shows a diagram of the SLC5A8 methylation target region. CpG sites are shown with circles and stems. The numerical coordinates are those of genomic clone AC063951. Lollipops designate CpG sites that are potential acceptors of aberrant methylation. Asterisks designate sites recognized by the HpaII restriction enzyme. Shown are the positions of PCR primers that amplify regions crossing 6 HpaII sites, or regions crossing 4 HpaII sites. Also shown is the position of PCR primers designed for a methyl-specific PCR (MS-PCR) assays. Also shown in the gray bar is the 5' end of exon 1 of the SLC5A8 transcript which overlaps with the methylation sites detected in both MS-PCR and HpaII based assays. Lastly indicated is a NotI site corresponding to methylation site 2D41 detected in Restriction Landmark Genome Scanning assay as methylated in colon cancer cell lines, though not in primary tumors.

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article, unless the context clearly indicates otherwise. By way of example, "an element" means one element or more than one element.

The terms "adenoma", "colon adenoma," and "polyp" are used herein to describe any precancerous neoplasia of the colon.

The term "blood-derived fraction" herein refers to a component or components of whole blood. Whole blood comprises a liquid portion (i.e., plasma) and a solid portion (i.e., blood cells). The liquid and solid portions of blood are each comprised of multiple components; e.g., different proteins in plasma or different cell types in the solid portion. One of these components or a mixture of any of these components is a blood-derived fraction as long as such fraction is missing one or more components found in whole blood.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric polypeptide" or "fusion polypeptide" is a fusion of a first amino acid sequence with a second amino acid sequence where the first and second amino acid sequences are not naturally present in a single polypeptide chain.

The term "colon" as used herein is intended to encompass the right colon (including the cecum), the transverse colon, the left colon, and the rectum.

The terms "colorectal cancer" and "colon cancer" are used interchangeably herein to refer to any cancerous neoplasia of the colon (including the rectum, as defined above).

The terms "compound", "test compound," and "agent" are used herein interchangeably and are meant to include, but are not limited to, peptides, nucleic acids, carbohydrates, small organic molecules, natural product extract libraries, and any other molecules (including, but not limited to, chemicals, metals, and organometallic compounds).

The term "compound-converted DNA" herein refers to DNA that has been treated or reacted with a chemical compound that converts unmethylated C bases in DNA to a different nucleotide base. For example, one such compound is sodium bisulfite, which converts unmethylated C to U. If DNA that contains conversion-sensitive cytosine is treated with sodium bisulfite, the compound-converted DNA will contain U in place of C. If the DNA which is treated with sodium bisulfite contains only methylcytosine, the compound-converted DNA will not contain uracil in place of the methylcytosine.

The term "de-methylating agent" as used herein refers agents that restore activity and/or gene expression of target genes silenced by methylation upon treatment with the agent. Examples of such agents include without limitation 5-azacytidine and 5-aza-2'-deoxycytidine.

The term "detection" is used herein to refer to any process of observing a marker, in a biological sample, whether or not the marker is actually detected. In other words, the act of probing a sample for a marker is a "detection" even if the marker is determined to be not present or below the level of sensitivity. Detection may be a quantitative, semi-quantitative or non-quantitative observation.

The term "differentially methylated SLC5A8 nucleotide sequence" refers to a region of the SLC5A8 nucleotide sequence that is found to be methylated in a SLC5A8-associated cancer such as a region of the SLC5A8 nucleotide sequence that is found to be methylated in cancer tissues or cell lines, but not methylated in the normal tissues or cell lines. For example, FIG. 3 delineates certain SLC5A8 regions that are differentially methylated, such as SEQ ID NOs: 11-13.

"Expression vector" refers to a replicable DNA construct used to express DNA which encodes the desired protein and which includes a transcriptional unit comprising an assembly of (1) genetic element(s) having a regulatory role in gene expression, for example, promoters, operators, or enhancers, operatively linked to (2) a DNA sequence encoding a desired protein (in this case, a SLC5A8 protein) which is transcribed into mRNA and translated into protein, and (3) appropriate transcription and translation initiation and termination sequences. The choice of promoter and other regulatory elements generally varies according to the intended host cell. In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

In the expression vectors, regulatory elements controlling transcription or translation can be generally derived from mammalian, microbial, viral or insect genes. The ability to replicate in a host, usually conferred by an origin of replication, and a selection gene to facilitate recognition of transformants may additionally be incorporated. Vectors derived from viruses, such as retroviruses, adenoviruses, and the like, may be employed.

As used herein, the phrase "gene expression" or "protein expression" includes any information pertaining to the amount of gene transcript or protein present in a sample, as well as information about the rate at which genes or proteins are produced or are accumulating or being degraded (e.g., reporter gene data, data from nuclear runoff experiments, pulse-chase data etc.). Certain kinds of data might be viewed as relating to both gene and protein expression. For example, protein levels in a cell are reflective of the level of protein as well as the level of transcription, and such data is intended to be included by the phrase "gene or protein expression information." Such information may be given in the form of amounts per cell, amounts relative to a control gene or protein, in unitless measures, etc.; the term "information" is not to be limited to any particular means of representation and is intended to mean any representation that provides relevant information. The term "expression levels" refers to a quantity reflected in or derivable from the gene or protein expression data, whether the data is directed to gene transcript accumulation or protein accumulation or protein synthesis rates, etc.

The terms "healthy", "normal," and "non-neoplastic" are used interchangeably herein to refer to a subject or particular cell or tissue that is devoid (at least to the limit of detection) of a disease condition, such as a neoplasia (e.g., cancer), that is associated with SLC5A8 such as for example neoplasia associated with silencing of SLC5A8 gene expression due to methylation. These terms are often used herein in reference to tissues and cells of the colon. Thus, for the purposes of this application, a patient with severe heart disease but lacking a SLC5A8 silencing-associated disease would be termed "healthy."

"Homology" or "identity" or "similarity" refers to sequence similarity between two peptides or between two nucleic acid molecules. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated" or "non-homologous" shares less than 40% identity, preferably less than 25% identity with a sequence of the present invention. In comparing two sequences, the absence of residues (amino acids or nucleic acids) or presence of extra residues also decreases the identity and homology/similarity.

The term "homology" describes a mathematically based comparison of sequence similarities which is used to identify genes or proteins with similar functions or motifs. The nucleic acid and protein sequences of the present invention may be used as a "query sequence" to perform a search against public databases to, for example, identify other family members, related sequences or homologs. Such searches can be performed using the NBLAST and XBLAST programs (version 2.0) of Altschul, et al. (1990) *J Mol. Biol.* 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and BLAST) can be used.

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in (*Computational Molecular Biology*, Lesk, A. M., ed., Oxford University Press, New York, 1988; *Biocomputing*: Informatics and Genome Projects, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM J. Applied Math., 48: 1073, 1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Altschul, S. F. et al., *J. Molec. Biol.* 215: 403-410 (1990) and Altschul et al. *Nuc. Acids Res.* 25: 3389-3402 (1997)). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403-410 (1990)). The well known Smith Waterman algorithm may also be used to determine identity.

"SLC5A8-associated cancer" refers to cancer associated with reduced expression or no expression of the SLC5A8 gene (previously referred to as the Hui1 gene), and cancer associated with differential methylation of SLC5A8 DNA. Examples of SLC5A8-associated cancer include, but are not limited to, colon cancer, breast cancer, thyroid cancer, and stomach cancer. As used herein, the SLC5A8-associated cancers includes both cancers and pre-cancer adenomas.

"SLC5A8-associated proliferative disorder" refers to a disease that is associated with either reduced expression or over-expression of the SLC5A8 gene.

A "SLC5A8-associated protein" refers to a protein capable of interacting with and/or binding to a SLC5A8 polypeptide. Generally, the SLC5A8-associated protein may interact directly or indirectly with the SLC5A8 polypeptide.

"SLC5A8-methylation target regions" as used herein refer to those regions of SLC5A8 that are found to be methylated. These regions include nucleotide regions that may be either constitutively or differentially methylated regions. For example, FIG. 3 discloses a SLC5A8 region wherein certain sequences of this region are differentially methylated regions.

"SLC5A8-nucleotide sequence" or "SLC5A8-nucleic acid sequence" as used herein refers to the SLC5A8 nucleotide sequences as set forth in SEQ ID NOs: 2-7 and fragments thereof.

"SLC5A8-silencing associated diseases" as used herein includes SLC5A8-associated cancer.

The term "including" is used herein to mean, and is used interchangeably with, the phrase "including but not limited to."

The term "isolated" as used in reference to nucleic acids or polypeptides indicates a nucleic acid or polypeptide, such as a SLC5A8 nucleic acid or polypeptide, that is isolated from, or otherwise substantially free of other proteins that are normally associated with the nucleic acid or polypeptide.

The term "methylation-sensitive PCR" (i.e., MSP) herein refers to a polymerase chain reaction in which amplification of the compound-converted template sequence is performed. Two sets of primers are designed for use in MSP. Each set of primers comprises a forward primer and a reverse primer. One set of primers, called methylation-specific primers, will amplify the compound-converted template sequence if C bases in CpG dinucleotides within the template DNA (e.g., a SLC5A8 nucleic acid) are methylated. Another set of primers, called unmethylation-specific primers, will amplify the compound-converted template sequences if C bases in CpG dinucleotides within the template DNA (e.g., a SLC5A8 nucleic acid) are not methylated.

The term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

"Operably linked" when describing the relationship between two DNA regions simply means that they are functionally related to each other. For example, a promoter or other transcriptional regulatory sequence is operably linked to a coding sequence if it controls the transcription of the coding sequence.

The term "or" is used herein to mean, and is used interchangeably with, the term "and/or", unless context clearly indicates otherwise.

The terms "polypeptide" and "protein" are used interchangeably herein.

The term "recombinant" as used in reference to a nucleic acid indicates any nucleic acid that is positioned adjacent to one or more nucleic acid sequences that it is not found adjacent to in nature. A recombinant nucleic acid may be generated in vitro, for example by using the methods of molecular biology, or in vivo, for example by insertion of a nucleic acid at a novel chromosomal location by homologous or non-homologous recombination. The term "recombinant" as used in reference to a polypeptide indicates any polypeptide that is produced by expression and translation of a recombinant nucleic acid.

A "sample" includes any material that is obtained or prepared for detection of a molecular marker or a change in a molecular marker such as the methylation state, or any material that is contacted with a detection reagent or detection device for the purpose of detecting a molecular marker or a change in the molecular marker.

A "subject" is any organism of interest, generally a mammalian subject, such as a mouse, and preferably a human subject.

The term "transgene" is used herein to describe genetic material which has been or is about to be artificially inserted into the genome of a mammal, particularly a mammalian cell of a living animal. By "transgenic animal" is meant a non-human animal, usually a mammal (e.g., mouse, rat, rabbit, hamster, etc.), having a non-endogenous nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

II. Overview

In certain aspects, the invention relates, in part, to methods for determining whether a patient is likely or unlikely to have a cancer, for example, colon neoplasia. A colon neoplasia is any cancerous or precancerous growth located in, or derived from, the colon. The colon is a portion of the intestinal tract that is roughly three feet in length, stretching from the end of the small intestine to the rectum. Viewed in cross section, the colon consists of four distinguishable layers arranged in concentric rings surrounding an interior space, termed the lumen, through which digested materials pass. In order, moving outward from the lumen, the layers are termed the mucosa, the submucosa, the muscularis propria and the subserosa. The mucosa includes the epithelial layer (cells adjacent to the lumen), the basement membrane, the lamina propria and the muscularis mucosae. In general, the "wall" of the colon is intended to refer to the submucosa and the layers outside of the submucosa. The "lining" is the mucosa.

Precancerous colon neoplasias are referred to as adenomas or adenomatous polyps. Adenomas are typically small mushroom-like or wart-like growths on the lining of the colon and do not invade into the wall of the colon. Adenomas may be visualized through a device such as a colonoscope or flexible sigmoidoscope. Several studies have shown that patients who undergo screening for and removal of adenomas have a decreased rate of mortality from colon cancer. For this and other reasons, it is generally accepted that adenomas are an obligate precursor for the vast majority of colon cancers. When a colon neoplasia invades into the basement membrane of the colon, it is considered a colon cancer, as the term "colon cancer" is used herein. In describing colon cancers, this specification will generally follow the so-called "Dukes" colon cancer staging system. The characteristics that describe a cancer are generally of greater significance than the particular term used to describe a recognizable stage. The most widely used staging systems generally use at least one of the following characteristics for staging: the extent of tumor penetration into the colon wall, with greater penetration generally correlating with a more dangerous tumor; the extent of invasion of the tumor through the colon wall and into other neighboring tissues, with greater invasion generally correlating with a more dangerous tumor; the extent of invasion of the tumor into the regional lymph nodes, with greater invasion generally correlating with a more dangerous tumor; and the extent of metastatic invasion into more distant tissues, such as the liver, with greater metastatic invasion generally correlating with a more dangerous disease state.

"Dukes A" and "Dukes B" colon cancers are neoplasias that have invaded into the wall of the colon but have not spread into other tissues. Dukes A colon cancers are cancers that have not invaded beyond the submucosa. Dukes B colon cancers are subdivided into two groups: Dukes B1 and Dukes B2. "Dukes B1" colon cancers are neoplasias that have invaded up to but not through the muscularis propria. Dukes B2 colon cancers are cancers that have breached completely through the muscularis propria. Over a five year period, patients with Dukes A cancer who receive surgical treatment (i.e., removal of the affected tissue) have a greater than 90% survival rate. Over the same period, patients with Dukes B1 and Dukes B2 cancer receiving surgical treatment have a survival rate of about 85% and 75%, respectively. Dukes A, B1 and B2 cancers are also referred to as T1, T2 and T3-T4 cancers, respectively. "Dukes C" colon cancers are cancers that have spread to the regional lymph nodes, such as the lymph nodes of the gut. Patients with Dukes C cancer who receive surgical treatment alone have a 35% survival rate over a five year period, but this survival rate is increased to 60% in patients that receive chemotherapy. "Dukes D" colon cancers are cancers that have metastasized to other organs. The liver is the most common organ in which metastatic colon cancer is found. Patients with Dukes D colon cancer have a survival rate of less than 5% over a five year period, regardless of the treatment regimen. In general, colon neoplasia develops through one of at least three different pathways, termed chromosomal instability, microsatellite instability, and the CpG island methylator phenotype (CIMP). Although there is some overlap, these pathways tend to present somewhat different biological behavior. By understanding the pathway of tumor development, the target genes involved, and the mechanisms underlying the genetic instability, it is possible to implement strategies to detect and treat the different types of colon neoplasias.

In one aspect, this application is based at least in part, on the recognition that certain target genes may be silenced or inactivated by the differential methylation of CpG islands in the 5' flanking or promoter regions of the target gene. CpG islands are clusters of cytosine-guanosine residues in a DNA sequence, that are prominently represented in the 5-flanking region or promoter region of about half the genes in our genome. In particular, this application is based at least in part on the recognition that differential methylation of the SLC5A8 nucleotide sequence may be indicative of a cancer (e.g., colon cancer, breast cancer, thyroid cancer, or stomach cancer).

As noted above, early detection of colon neoplasia, coupled with appropriate intervention, is important for increasing patient survival rates. Present systems for screening for colon neoplasia are deficient for a variety of reasons, including a lack of specificity and/or sensitivity (e.g., Fecal Occult Blood Test, flexible sigmoidoscopy) or a high cost and intensive use of medical resources (e.g., colonoscopy). Alternative systems for detection of colon neoplasia would be useful in a wide range of other clinical circumstances as well. For example, patients who receive surgical and/or pharmaceutical therapy for colon cancer may experience a relapse. It would be advantageous to have an alternative system for determining whether such patients have a recurrent or relapsed colon neoplasia. As a further example, an alternative diagnostic system would facilitate monitoring an increase, decrease or persistence of colon neoplasia in a patient known to have a colon neoplasia. A patient undergoing chemotherapy may be monitored to assess the effectiveness of the therapy.

In another aspect, the invention is also based, in part, on the discovery of a novel polynucleotide sequence encoding a novel sodium/solute symporter-like protein (SLC5A8). In particular, SLC5A8 is closely related to the human sodium iodide symporter (SLC5A5) and the human sodium-dependent multivitamin transporter (SLC5A6).

Cell surface receptors and transmembrane transporter systems facilitate communication between cells and their environment by direct exchange of chemicals between the intracellular and extracellular milieu. Distinct transporter systems (also called permeases, porters, transporters, carriers, and channel proteins) are specific for ions, small and medium size solutes and macromolecules. A major class of transporter proteins couple solute transport to the movement of other species (often cations, such as protons and sodium ions) either in the same direction (cotransporter or symporter) or in the opposite direction (counter transporter or antiporter). Sodium/solute symport is a widespread mechanism of solute transport across cytoplasmic membranes of prokaryotic and eukaryotic cells. Proteins that catalyze sodium/solute symport have been grouped into eleven families based on their degree of sequence similarities, their solute and cation specificities, size, topographical features, and evolutionary relationships (see, e.g., Reizer et al., (1994) Bichemica et Biphysica Acta, 1197:133-166). There are mixed families of transporters whose members differ in the choice of the coupling ion or catalyze symport or antiport processes.

Human sodium iodide transporter (NIS, or SLC5A5) is a best characterized member among the sodium/solute symporter superfamily. NIS localizes at the basolateral membrane and catalyses the active transport of iodide from blood into the cells using the inwardly directed sodium gradient with a 2 sodium 1 iodide stoichiometry. The tissue distribution of NIS includes the thyroid, salivary glands, stomach, thymus, and breast. Lower levels of expression of NIS are detected in the prostate, ovary, adrenal gland, lung, and heart. By contrast, the NIS gene has not been detected in the colon, orbital fibroblasts, or nasopharyngeal mucosa (see, e.g., Filetti et al., 1999, Eur J Endocrinol. 141:443-457). Abnormal NIS expression and/or iodide transport activity have been linked to many thyroid diseases including autoimmune thyroid diseases, thyroid nodular hyperplasia, thyroid adenoma, thyroid carcinoma, and congenital hypothyroidism, as well as non-thyroid diseases such as breast cancer and stomach cancer (Chung, 2002, J Nucl Med 43:1188-200).

Besides sequence homology to the human sodium iodide transporter, SLC5A8 transcript was found by Applicants to be expressed in the normal colon mucosa, kidney, lung, esophagus, small bowel, stomach, thyroid, and uterus. In addition, Applicants found that SLC5A8 may function as a sodium iodide transporter, and that differential methylation of SLC5A8 and/or reduced expression of SLC5A8 are linked to diseases such as colon cancer, breast cancer, and stomach cancer. Accordingly, the present invention relates to methods and compositions for detecting and treating such SLC5A8 associated cancers.

III. SLC5A8 Polypeptides

In certain aspects, the invention provides a full-length SLC5A8 polypeptide (SEQ ID NO: 1) and functional variants thereof. Preferred functional variants of SLC5A8 polypeptides are those that have tumor suppressor activity or sodium transporter activity. In certain aspects, the present invention includes biologically-active fragments of the SLC5A8 protein and fusion proteins including at least a portion of the SLC5A8 protein. These include proteins with SLC5A8 activity that have amino acid substitutions or have sugars or other molecules attached to amino acid functional groups.

In certain embodiments, the present disclosure makes available isolated and/or purified forms of the SLC5A8 polypeptides, which are isolated from, or otherwise substantially free of, other proteins which might normally be associated with the protein or a particular complex including the protein. In certain embodiments, variant polypeptides have an amino acid sequence that is at least 75% identical to an amino acid sequence as set forth in SEQ ID NO: 1. In other embodiments, the variant polypeptide has an amino acid sequence at least 80%, 85%, 90%, 95%, 97%, 98%, 99% or 100% identical to an amino acid sequence as set forth in SEQ ID NO: 1.

In certain aspects, variant SLC5A8 polypeptides are agonists or antagonists of the SLC5A8 polypeptide as set forth in SEQ ID NO: 1. Variants of these polypeptides may have a hyperactive or constitutive activity, or, act to prevent the tumor suppressor activity or sodium transporter activity of SLC5A8. For example, a truncated form lacking one or more domain may have a dominant negative effect.

In certain aspects, isolated peptidyl portions of the SLC5A8 polypeptide can be obtained by screening polypeptides recombinantly produced from the corresponding fragment of the nucleic acid encoding the polypeptide as set forth in SEQ ID NO: 1. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments which can function as either agonists or antagonists of the SLC5A8 activity (e.g., tumor suppressor or sodium solute symporter).

The SLC5A8 protein is a transmembrane protein, with portions of the protein that are positioned outside the cell (the extracellular portions) and portions of the protein that are positioned inside the cell (the intracellular portions). Sequences and positions of the predicated thirteen transmembrane domains (TM1-TM13) are listed below.

```
TM1 (residues 10-32):
FVVWDYVVFAGMLVISAAIGIYY       (SEQ ID NO: 19)

TM2 (residues 52-74):
MTAVPVALSLTASFMSAVTVLGT       (SEQ ID NO: 20)

TM3 (residues 84-106):
IFSIFAFTYFFVVVISAEVFLPV       (SEQ ID NO: 21)

TM4 (residues 127-149):
VRLCGTVLFIVQTILYTGIVIYA       (SEQ ID NO: 22)

TM5 (residues 164-186):
GAVVATGVVCTFYCTLGGLKAVI       (SEQ ID NO: 23)

TM6 (residues 193-215):
IGIMVAGFASVIIQAVVMQGGIS       (SEQ ID NO: 24)

TM7 (residues 240-259):
HTFWTIIIGGTFTWTSIYGV          (SEQ ID NO: 25)

TM8 (residues 280-302):
LYINLVGLWAILTCSVFCGLALY       (SEQ ID NO: 26)

TM9 (residues 337-359):
LPGLFVACAYSGTLSTVSSSINA       (SEQ ID NO: 27)

TM10 (residues 380-402):
SLSWISQGMSVVYGALCIGMAAL       (SEQ ID NO: 28)

TM11 (residues 412-434):
AALSVFGMVGGPLMGLFALGILV       (SEQ ID NO: 29)

TM12 (residues 441-463):
GALVGLMAGFAISLWVGIGAQIY       (SEQ ID NO: 30)

TM13 (residues 519-541):
LSYLYFSTVGTLVTLLVGILVSL       (SEQ ID NO: 31)
```

Thus, certain embodiments of the invention include SLC5A8 fragments comprising a transmembrane domain as set forth in any of SEQ ID NOs: 19-21. In other embodiments, the present invention includes SLC5A8 fragments comprising an intracellular domain or an extracellular portion of the SLC5A8 protein.

In certain aspects, variant SLC5A8 polypeptides containing one or more fusion domains. Well known examples of such fusion domains include, for example, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion polypeptide by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS$_6$) fusion partners. Another fusion domain well known in the art is green fluorescent protein (GFP). This fusion partner serves as a fluorescent "tag" which allows the fusion polypeptide of the invention to be identified by fluorescence microscopy or by flow cytometry. The GFP tag is useful when assessing subcellular localization of the fusion SLC5A8 polypeptide. The GFP tag is also useful for isolating cells which express the fusion SLC5A8 polypeptide by flow cytometric methods such as a fluorescence activated cell sorting (FACS). Fusion domains also include "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allow the relevant protease to partially digest the fusion SLC5A8 polypeptide and thereby liberate the recombinant polypeptide therefrom. The liberated polypeptide can then be isolated from the fusion partner by subsequent chromatographic separation.

Different elements of fusion proteins may be arranged in any manner that is consistent with the desired functionality. For example, a SLC5A8 polypeptide may be placed C-terminal to a heterologous domain, or, alternatively, a heterologous domain may be placed C-terminal to a SLC5A8 polypeptide. The SLC5A8 and the heterologous domain need not be adjacent in a fusion protein, and additional domains or amino acid sequences may be included C- or N-terminal to either domain or between the domains.

It is also possible to modify the structure of the subject SLC5A8 polypeptides for such purposes as enhancing therapeutic or prophylactic efficacy, or stability (e.g., ex vivo shelf life and resistance to proteolytic degradation in vivo). Such modified polypeptides, when designed to retain at least one activity of the naturally occurring form of the protein, are considered functional equivalents of the SLC5A8 polypeptides described in more detail herein. Such modified polypeptides can be produced, for instance, by amino acid substitution, deletion or addition.

For instance, it is reasonable to expect, for example, that an isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Conservative replacements are those that take place within a family of amino acids that are related in their side chains (see, for example, Biochemistry, 2nd ed., Ed. by L. Stryer, W.H. Freeman and Co., 1981). Whether a change in the amino acid sequence of a polypeptide results in a functional homolog can be readily determined by assessing the ability of the variant polypeptide to produce a response in cells in a fashion similar to the wild-type protein. For instance, such variant forms of a SLC5A8 polypeptide can be assessed, e.g., for their ability to transport sodium solute or their ability to suppress tumor formation. Polypeptides in which more than one replacement has taken place can readily be tested in the same manner.

This invention further contemplates a method of generating sets of combinatorial mutants of the SLC5A8 polypeptides, as well as truncation mutants, and is especially useful for identifying potential variant sequences (e.g., homologs) that are functional in binding to a SLC5A8 polypeptide. The purpose of screening such combinatorial libraries may be to generate, for example, SLC5A8 homologs which can act as either agonists or antagonist, or alternatively, which possess novel activities all together. Combinatorially-derived homologs can be generated which have a selective potency relative to a naturally occurring SLC5A8 polypeptide. Such proteins, when expressed from recombinant DNA constructs, can be used in gene therapy protocols. Likewise, mutagenesis can give rise to variants which have intracellular half-lives dramatically different than the corresponding wild-type protein. For example, the altered protein can be rendered either more stable or less stable to proteolytic degradation or other cellular process which result in destruction of, or otherwise inactivation of the SLC5A8 polypeptide of interest. Such variants, and the genes which encode them, can be utilized to alter SLC5A8 levels by modulating the half-life of the protein. For instance, a short half-life can give rise to more transient biological effects and, when part of an inducible expression system, can allow tighter control of recombinant SLC5A8 levels within the cell. As above, such proteins, and particularly their recombinant nucleic acid constructs, can be used in gene therapy protocols. In similar fashion, SLC5A8 homologs can be generated by the present combinatorial approach to act as antagonists, in that they are able to interfere with the ability of the corresponding wild-type protein to function.

In a representative embodiment of this method, the amino acid sequences for a population of SLC5A8 homologs are aligned, preferably to promote the highest homology possible. Such a population of variants can include, for example, homologs from one or more species, or homologs from the same species but which differ due to mutation. Amino acids which appear at each position of the aligned sequences may be selected to create a degenerate set of combinatorial sequences. In a preferred embodiment, the combinatorial library is produced by way of a degenerate library of genes encoding a library of polypeptides which each include at least a portion of potential SLC5A8 sequences. For instance, a mixture of synthetic oligonucleotides can be enzymatically ligated into gene sequences such that the degenerate set of potential SLC5A8 nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential SLC5A8 sequences. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. A G Walton, Amsterdam: Elsevier pp273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, SLC5A8 variants (both agonist and antagonist forms) can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193: 653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:

11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of SLC5A8 polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of SLC5A8 variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In an illustrative embodiment of a screening assay, candidate combinatorial gene products of one of the subject proteins are displayed on the surface of a cell or virus, and the ability of particular cells or viral particles to bind a SLC5A8 polypeptide is detected in a "panning assay." For instance, a library of SLC5A8 variants can be cloned into the gene for a surface membrane protein of a bacterial cell (Ladner et al., WO 88/06630; Fuchs et al., (1991) Bio/Technology 9:1370-1371; and Goward et al., (1992) TIBS 18:136-140), and the resulting fusion protein detected by panning, e.g., using a fluorescently labeled molecule which binds the SLC5A8 polypeptide, to score for potentially functional homologs. Cells can be visually inspected and separated under a fluorescence microscope, or, where the morphology of the cell permits, separated by a fluorescence-activated cell sorter.

In similar fashion, the gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd, and f1 are most often used in phage display libraries, as either of the phage gIII or gVIII coat proteins can be used to generate fusion proteins without disrupting the ultimate packaging of the viral particle (Ladner et al., PCT publication WO 90/02909; Garrard et al., PCT publication WO 92/09690; Marks et al., (1992) J. Biol. Chem. 267:16007-16010; Griffiths et al., (1993) EMBO J. 12:725-734; Clackson et al., (1991) Nature 352:624-628; and Barbas et al., (1992) PNAS USA 89:4457-4461).

In certain embodiments, the invention also provides for reduction of the subject SLC5A8 polypeptides to generate mimetics, e.g., peptide or non-peptide agents, which are able to mimic binding of the authentic protein to another cellular partner. Such mutagenic techniques as described above, as well as the thioredoxin system, are also particularly useful for mapping the determinants of a SLC5A8 polypeptide which participate in protein-protein interactions involved in, for example, binding of proteins involved in angiogenesis to each other. To illustrate, the critical residues of a SLC5A8 polypeptide which are involved in molecular recognition of a substrate protein can be determined and used to generate SLC5A8 polypeptide-derived peptidomimetics which bind to the substrate protein, and by inhibiting SLC5A8 binding, act to inhibit its biological activity. By employing, for example, scanning mutagenesis to map the amino acid residues of a SLC5A8 polypeptide which are involved in binding to another polypeptide, peptidomimetic compounds can be generated which mimic those residues involved in binding. For instance, non-hydrolyzable peptide analogs of such residues can be generated using benzodiazepine (e.g., see Freidinger et al., in Peptides: Chemistry and Biology, G. R. Marshall ed., ESCOM Publisher: Leiden, Netherlands, 1988), azepine (e.g., see Huffman et al., in Peptides: Chemistry and Biology, G. R. Marshall ed., ESCOM Publisher: Leiden, Netherlands, 1988), substituted gamma lactam rings (Garvey et al., in Peptides: Chemistry and Biology, G. R. Marshall ed., ESCOM Publisher: Leiden, Netherlands, 1988), keto-methylene pseudopeptides (Ewenson et al., (1986) J. Med. Chem. 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., (1985) Tetrahedron Lett 26:647; and Sato et al., (1986) J Chem Soc Perkin Trans 1:1231), and b-aminoalcohols (Gordon et al., (1985) Biochem Biophys Res Commun 126:419; and Dann et al., (1986) Biochem Biophys Res Commun 134:71).

In certain embodiments, the SLC5A8 polypeptides may further comprise post-translational or non-amino acid elements, such as hydrophobic modifications (e.g., polyethylene glycols or lipids), poly- or mono-saccharide modifications, phosphates, acetylations, etc. Effects of such elements on the functionality of a SLC5A8 polypeptide may be tested as described herein for other SLC5A8 variants.

In certain aspects, the present invention contemplates directly delivery of SLC5A8 polypeptides into a cell. Methods of directly introducing a polypeptide into a cell include, but are not limited to, protein transduction and protein therapy. For example, a protein transduction domain (PTD) can be fused to a nucleic acid encoding a SLC5A8 protein, and the fusion protein is expressed and purified. Fusion proteins containing the PTD are permeable to the cell membrane, and thus cells can be directly contacted with a fusion protein (Derossi et al. (1994) *Journal of Biological Chemistry* 269: 10444-10450; Han et al. (2000) *Molecules and Cells* 6: 728-732; Hall et al. (1996) *Current Biology* 6: 580-587; Theodore et al. (1995) *Journal of Neuroscience* 15: 7158-7167).

Although some protein transduction based methods rely on fusion of a polypeptide of interest to a sequence which mediates introduction of the protein into a cell, other protein transduction methods do not require covalent linkage of a protein of interest to a transduction domain. At least two commercially available reagents exist that mediate protein transduction without covalent modification of the protein (Chariot™, produced by Active Motif, and Bioporter® Protein Delivery Reagent, produced by Gene Therapy Systems,). Briefly, these protein transduction reagents can be used to deliver proteins, peptides and antibodies directly to cells including mammalian cells. Delivery of proteins directly to cells has a number of advantages. Firstly, many current techniques of gene delivery are based on delivery of a nucleic acid sequence which must be transcribed and/or translated by a cell before expression of the protein is achieved. This results in a time lag between delivery of the nucleic acid and expression of the protein. Direct delivery of a protein decreases this delay.

Secondly, delivery of a protein often results in transient expression of the protein in a cell.

As outlined herein, protein transduction mediated by covalent attachment of a PTD to a protein can be used to deliver a protein to a cell. These methods require that individual proteins be covalently appended with PTD moieties. In contrast, methods such as Chariot™ and Bioporter® facilitate transduction by forming a noncovalent interaction between the reagent and the protein. Without being bound by theory, these reagents are thought to facilitate transit of the cell membrane, and following internalization into a cell the reagent and protein complex disassociates so that the protein is free to function in the cell.

IV. SLC5A8 Nucleic Acids

In certain aspects, the invention provides isolated and/or recombinant SLC5A8 nucleic acids encoding SLC5A8 polypeptides, for example, SEQ ID NOs: 3 and 4. The SLC5A8 polynucleotides may be single-stranded or double stranded. Such nucleic acids may be DNA or RNA molecules. The SLC5A8 nucleic acids are useful as diagnostic or therapeutic agents, such as for example, these nucleic acid molecules encode the SLC5A8 protein, and are useful in assaying for the presence of SLC5A8 transcripts in cancer cells (e.g., colon cancer cells, breast cancer cells, thyroid cancer cells, or stomach cancer cells).

SLC5A8 nucleic acids of the invention are further understood to include nucleic acids that comprise variants of SEQ ID NOs: 3 and 4. Variant nucleotide sequences include sequences that differ by one or more nucleotide substitutions, additions or deletions, such as allelic variants; and will, therefore, include coding sequences that differ from the nucleotide sequence of the coding sequence designated in SEQ ID NOs: 3 and 4. Optionally, a SLC5A8 nucleic acid of the invention will genetically complement a partial or complete SLC5A8 loss of function phenotype. For example, a SLC5A8 nucleic acid of the invention may be expressed in a cell in which the endogenous SLC5A8 gene has been deleted, and the introduced SLC5A8 nucleic acid will mitigate a phenotype resulting from the gene deletion.

The present invention is based, at least in part, on the observation that SLC5A8 nucleotide sequences can be differentially methylated in certain SLC5A8-associated cancer, such as colon cancer, breast cancer, thyroid cancer or stomach cancer. Accordingly, certain aspects of the present invention provide SLC5A8 nucleic acids having certain regions that are differentially methylated in SLC5A8-associated cancer, for example, SEQ ID NOs: 12, 13, and 14, and fragments thereof. Detection of methylation in any one of such differentially methylated nucleic acid sequences would be indicative of a SLC5A8-associated cancer.

In certain embodiments, the application provides isolated or recombinant SLC5A8 nucleic acid sequences that are at least 80%, 85%, 90%, 95%, 97%, 98%, 99% or 100% identical to the SLC5A8 nucleic acid sequences (e.g., SEQ ID NOs: 3-4 and 12-14). One of ordinary skill in the art will appreciate that SLC5A8 nucleic acid sequences complementary to SEQ ID NOs: 3-4 and 12-14, and variants of SEQ ID NOs: 3-4 and 12-14 are also within the scope of this invention. In further embodiments, the SLC5A8 nucleic acid sequences of the invention can be isolated, recombinant, and/or fused with a heterologous nucleotide sequence, or in a DNA library.

In other embodiments, SLC5A8 nucleic acid sequences also include nucleotide sequences that hybridize under highly stringent conditions to the nucleotide sequences designated in SEQ ID NOs: 3-4 and 12-14, or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2× SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated SLC5A8 nucleic acids which differ from the nucleic acids (e.g., SEQ ID NOs: 3-4 and 12-14) due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant SLC5A8 nucleic acid may be operably linked to one or more regulatory nucleotide sequences in an expression construct. Regulatory nucleotide sequences will generally be appropriate for a host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects, the application provides methylated forms of SLC5A8 nucleic acid sequences of SEQ ID NOs: 12-14 or fragments thereof, wherein the cytosine bases of the CpG islands present in said sequences are methylated. In other words, the SLC5A8 nucleic acid sequences of the present invention may be either in the methylated status (e.g., as seen in SLC5A8-associated cancer tissues) or in the unmethylated status (e.g., as seen in normal tissues).

In certain embodiments, the present invention provides bisulfite-converted SLC5A8 template DNA sequences, for example, SEQ ID NOs: 15-18, and fragments thereof. Such bisulfite-converted SLC5A8 template DNA can be used for detecting the methylation status, for example, by an MSP reaction or by direct sequencing. These bisulfite-converted SLC5A8 sequences are also of use for designing primers for MS-PCR reactions that specifically detect methylated or unmethylated SLC5A8 templates following bisulfite conversion. In yet other embodiments, the bisulfite-converted SLC5A8 nucleotide sequences of the invention also include nucleotide sequences that will hybridize under highly stringent conditions to any nucleotide sequence selected from SEQ ID NOs: 15-18. In further aspects, the application provides methods for producing such bisulfite-converted nucleic acid sequences, for example, the application provides methods for treating a nucleotide sequence with a bisulfite agent such that the unmethylated cytosine bases are converted to a different nucleotide base such as a uracil.

The present invention also provides primers which can be used in PCR to obtain the SLC5A8 nucleic acids from cDNA The present invention also encompasses oligonucleotides that are useful as hybridization probes for detecting transcripts of the genes which encode the SLC5A8 protein Preferably, such oligonucleotides comprise at least 200 nucleotides. Such hybridization probes have a sequence which is at least 90% complementary with a contiguous sequence contained within the sense strand or antisense strand of a double stranded DNA molecule which encodes the SLC5A8 protein. Such hybridization probes bind to the sense strand or antisense under stringent conditions, preferably under highly stringent conditions. The probes are used in Northern assays to detect transcripts of SLC5A8 homologous genes and in Southern assays to detect SLC5A8 homologous genes. The identity of probes which are 200 nucleotides in length and have full complementarity with a portion of the sense or antisense strand of a double-stranded DNA molecule which encodes the SLC5A8 protein as set forth in SEQ ID NO: 1.

The various Sequence Identification Numbers that have been used in this application are summarized below in Table 1.

TABLE 1

Sequence Identification Numbers that have been used in this application.

| SEQ ID NO | Description/Name | Corresponding Figure |
| --- | --- | --- |
| 1 | amino acid sequence of human SLC5A8 protein. | FIG. 18. |
| 2 | genomic clone AC063951. Nucleotides 82200-83267 encompasses the promoter and/or exon 1 of the SLC5A8 gene, and referred to as the "SLC5A8 methylation target region." | FIG. 1. |
| 3 | nucleotide sequence of the SLC5A8 mRNA transcript. | FIG. 2. |
| 4 | nucleotide sequence of the SLC5A8 coding region. | FIG. 23B. |
| 5 | 3D41-Hpa2-190R | N/A. |
| 6 | 3D41-Hpa2-633F | N/A. |
| 7 | 3D41-Hpa2-82430F | N/A. |
| 8 | AS-unmeth-442s | N/A. |
| 9 | AS-unmeth-542as | N/A. |
| 10 | AS-meth-442-459s | N/A. |
| 11 | AS-meth-550as | N/A. |
| 12 | nucleotides 82200-83267 of AC063951, wild-type, sense strand. | FIG. 4. |
| 13 | nucleotides 82200-83267 of AC063951, wild-type, antisense strand. | FIG. 8. |

TABLE 1-continued

Sequence Identification Numbers that have been used in this application.

Figure 9:
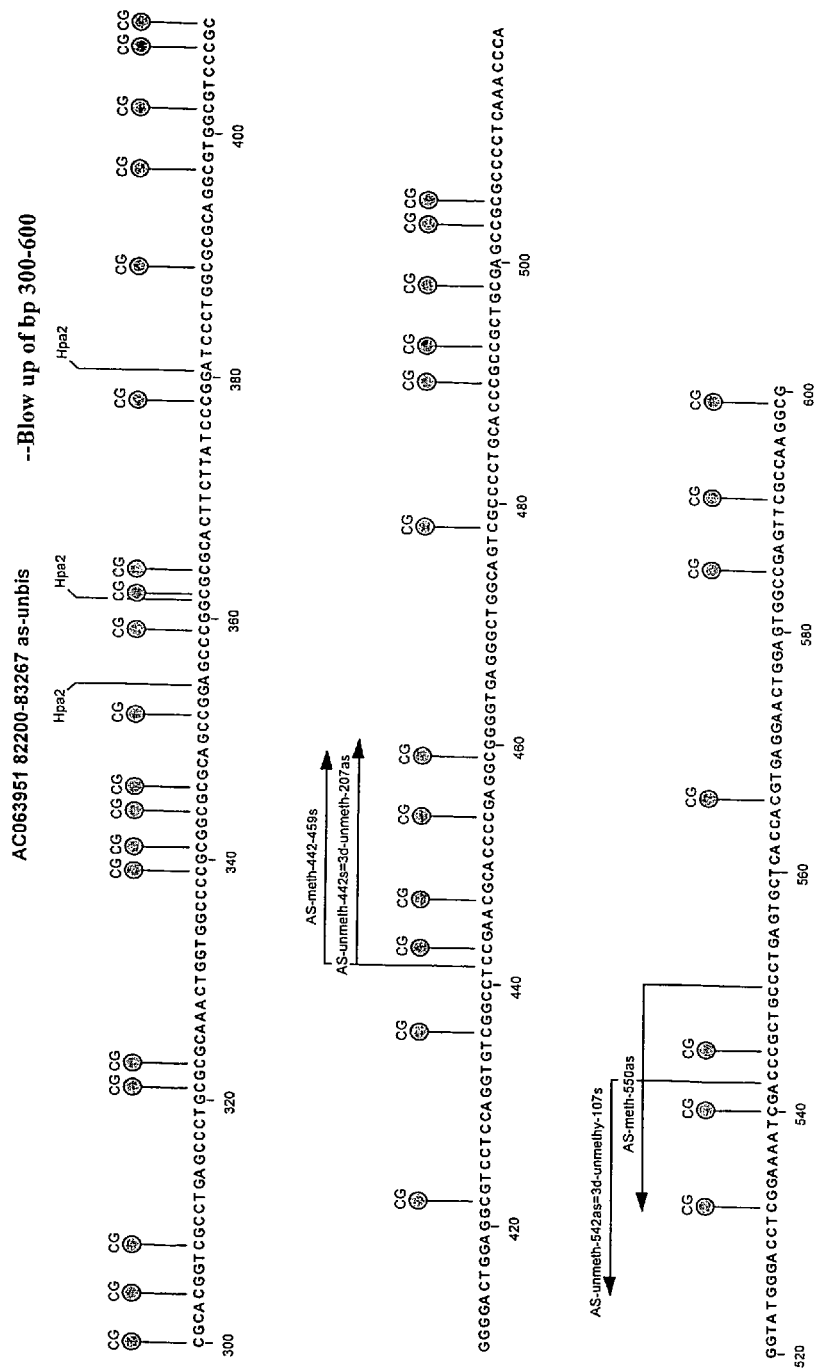
FIG. 9 shows a region within SEQ ID NO: 13 shown in FIG. 8 (nucleotides 300-600, SEQ ID NO: 14), and the sequences of the antisense strand that are amplified by the methyl-specific and unmethyl-specific PCR primers.

| SEQ ID NO | Description/Name | Corresponding Figure |
| --- | --- | --- |
| 14 | nucleotides 300-600 of SEQ ID NO: 12, wild-type, antisense strand. | FIG. 9. |
| 15 | nucleotides 82200-83267 of AC063951, antisense strand, bisulfite-converted/methylated. | FIG. 10. |
| 16 | nucleotides 82200-83267 of AC063951, antisense strand, bisulfite-converted/unmethylated. | FIG. 11. |
| 17 | nucleotides 82200-83267 of AC063951, sense strand, bisulfite-converted/methylated. | FIG. 12. |
| 18 | nucleotides 82200-83267 of AC063951, sense strand, bisulfite-converted/unmethylated. | FIG. 13. |

V. SLC5A8 Expression Vectors

In certain aspects, nucleic acids encoding SLC5A8 polypeptides and variants thereof may be used to increase SLC5A8 expression in an organism or cell by direct delivery of the nucleic acid. A nucleic acid therapy construct of the present invention can be delivered, for example, as an expression plasmid which, when transcribed in the cell, produces RNA which encodes a SLC5A8 polypeptide.

In another aspect of the invention, the subject nucleic acid is provided in an expression vector comprising a nucleotide sequence encoding a subject SLC5A8 polypeptide and operably linked to at least one regulatory sequence. Regulatory sequences are art-recognized and are selected to direct expression of the SLC5A8 polypeptide. Accordingly, the term regulatory sequence includes promoters, enhancers, and other expression control elements. Exemplary regulatory sequences are described in Goeddel; Gene Expression Technology: Methods in Enzymology, Academic Press, San Diego, Calif. (1990). For instance, any of a wide variety of expression control sequences that control the expression of a DNA sequence when operatively linked to it may be used in these vectors to express DNA sequences encoding a SLC5A8 polypeptide. Such useful expression control sequences, include, for example, the early and late promoters of SV40, tet promoter, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

As will be apparent, the subject gene constructs can be used to cause expression of the subject SLC5A8 polypeptides in cells propagated in culture, e.g., to produce proteins or polypeptides, including fusion proteins or polypeptides, for purification.

This invention also pertains to a host cell transfected with a recombinant gene including a coding sequence for one or more of the subject SLC5A8 polypeptides. The host cell may be any prokaryotic or eukaryotic cell. For example, a polypeptide of the present invention may be expressed in bacterial cells such as *E. coli*, insect cells (e.g., using a baculovirus expression system), yeast, or mammalian cells. Other suitable host cells are known to those skilled in the art.

Accordingly, the present invention further pertains to methods of producing the subject SLC5A8 polypeptides. For example, a host cell transfected with an expression vector encoding a SLC5A8 polypeptide can be cultured under appropriate conditions to allow expression of the polypeptide to occur. The polypeptide may be secreted and isolated from a mixture of cells and medium containing the polypeptide. Alternatively, the polypeptide may be retained cytoplasmically or in a membrane fraction and the cells harvested, lysed and the protein isolated. A cell culture includes host cells, media and other byproducts. Suitable media for cell culture are well known in the art. The polypeptide can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the polypeptide. In a preferred embodiment, the SLC5A8 polypeptide is a fusion protein containing a domain which facilitates its purification, such as a SLC5A8-GST fusion protein, SLC5A8-intein fusion protein, SLC5A8-cellulose binding domain fusion protein, SLC5A8-polyhistidine fusion protein, etc.

A recombinant SLC5A8 nucleic acid can be produced by ligating the cloned gene, or a portion thereof, into a vector suitable for expression in either prokaryotic cells, eukaryotic cells (yeast, avian, insect or mammalian), or both. Expression vehicles for production of a recombinant SLC5A8 polypeptides include plasmids and other vectors. For instance, suitable vectors for the expression of a SLC5A8 polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant SLC5A8 polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In another embodiment, a fusion gene coding for a purification leader sequence, such as a poly-(His)/enterokinase cleavage site sequence at the N-terminus of the desired portion of the recombinant SLC5A8 protein, can allow purification of the expressed fusion protein by affinity chromatography using a $Ni^{2+}$ metal resin. The purification leader sequence can then be subsequently removed by treatment with enterokinase to provide the purified SLC5A8 polypeptide (e.g., see Hochuli et al., (1987) *J. Chromatography* 411: 177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

VI. Antibodies

Another aspect of the invention pertains to an antibody reactive with a SLC5A8 polypeptide, preferably antibodies that are specifically reactive with SLC5A8 polypeptide. For example, by using immunogens derived from a SLC5A8 polypeptide, anti-protein/anti-peptide antisera or monoclonal antibodies can be made by standard protocols (see, for example, Antibodies: A Laboratory Manual ed. by Harlow and Lane (Cold Spring Harbor Press: 1988)). A mammal, such as a mouse, a hamster or rabbit can be immunized with an immunogenic form of the peptide (e.g., a SLC5A8 polypeptide or an antigenic fragment which is capable of eliciting an antibody response, or a fusion protein). Techniques for conferring immunogenicity on a protein or peptide include conjugation to carriers or other techniques well known in the art. An immunogenic portion of a SLC5A8 polypeptide can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a SLC5A8 polypeptide as set forth in SEQ ID NO: 1.

In one embodiment, antibodies are specific for the SLC5A8 protein as encoded by nucleic acid sequences as set forth in SEQ ID NOs: 3 and 4. In other embodiments, an antibody is immunoreactive with one or more proteins having an amino acid sequence that is at least 85%, 90%, 95%, 98%, 99%, 99.3%, 99.5%, 99.7% or 100% identical to an amino acid sequence as set forth in SEQ ID NO: 1.

In another embodiment, antibodies of the invention are specific for the extracellular portion of the SLC5A8 protein. In a set of exemplary embodiments, an antibody binds to an extracellular portion of SEQ ID NO: 1. In another embodiment, antibodies of the invention are specific for the intracellular portion or the transmembrane portion of the SLC5A8 protein. In a further embodiment, antibodies of the invention are specific for the soluble SLC5A8 protein and variants thereof.

Following immunization of an animal with an antigenic preparation of a SLC5A8 polypeptide, anti-SLC5A8 antisera can be obtained and, if desired, polyclonal anti-SLC5A8 antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with a SLC5A8 polypeptide of the present invention and monoclonal antibodies isolated from a culture comprising such hybridoma cells. In one embodiment, anti-SLC5A8 antibodies specifically react with the protein encoded by a nucleic acid having the sequence of SEQ ID NO: 3 or 4.

The term "antibody" as used herein is intended to include fragments thereof which are also specifically reactive with a subject SLC5A8 polypeptide. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific, single-chain, and chimeric and humanized molecules having affinity for a SLC5A8 polypeptide conferred by at least one CDR region of the antibody. In preferred embodiments, the antibody further comprises a label attached thereto and able to be detected (e.g., the label can be a radioisotope, fluorescent compound, enzyme or enzyme co-factor).

In certain preferred embodiments, an antibody of the invention is a monoclonal antibody, and in certain embodiments, the invention makes available methods for generating novel antibodies. For example, a method for generating a monoclonal antibody that binds specifically to a SLC5A8 polypeptide may comprise administering to a mouse an amount of an immunogenic composition comprising the SLC5A8 polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monocolonal antibody that binds specifically to the SLC5A8 polypeptide. Once obtained, a hybridoma can be propagated in a cell culture, optionally in culture conditions where the hybridoma-derived cells produce the monoclonal antibody that binds specifically to the SLC5A8 polypeptide. The monoclonal antibody may be purified from the cell culture.

Anti-SLC5A8 antibodies can be used, e.g., to detect SLC5A8 polypeptides in biological samples and/or to monitor SLC5A8 polypeptide levels in an individual. The level of SLC5A8 polypeptide maybe measured in a variety of sample types such as, for example, in cells, stools, and/or in bodily fluid, such as in whole blood samples, blood serum, blood plasma and urine. The adjective "specifically reactive with" as used in reference to an antibody is intended to mean, as is generally understood in the art, that the antibody is sufficiently selective between the antigen of interest (e.g., a SLC5A8 polypeptide) and other antigens that are not of interest that the antibody is useful for, at minimum, detecting the presence of the antigen of interest in a particular type of biological sample. In certain methods employing the antibody, a higher degree of specificity in binding may be desirable. For example, an antibody for use in detecting a low abundance protein of interest in the presence of one or more very high abundance protein that are not of interest may perform better if it has a higher degree of selectivity between the antigen of interest and other cross-reactants. Monoclonal antibodies generally have a greater tendency (as compared to polyclonal antibodies) to discriminate effectively between the desired antigens and cross-reacting polypeptides. In addition, an antibody that is effective at selectively identifying an antigen of interest in one type of biological sample (e.g., a stool sample) may not be as effective for selectively identifying the same antigen in a different type of biological sample (e.g., a blood sample). Likewise, an antibody that is effective at identifying an antigen of interest in a purified protein preparation that is devoid of other biological contaminants may not be as effective at identifying an antigen of interest in a crude biological sample, such as a blood or urine sample. Accordingly, in preferred embodiments, the application provides antibodies that have demonstrated specificity for a SLC5A8 protein in a sample type that is likely to be the sample type of choice for use of the antibody. In a particularly preferred embodiment, the application provides antibodies that bind specifically to a SLC5A8 polypeptide in a protein preparation from blood (optionally serum or plasma) from a patient that has a SLC5A8 associated cancer or that bind specifically in a crude blood sample (optionally a crude serum or plasma sample).

One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less.

In addition, the techniques used to screen antibodies in order to identify a desirable antibody may influence the properties of the antibody obtained. For example, an antibody to be used for certain therapeutic purposes will preferably be able to target a particular cell type. Accordingly, to obtain antibodies of this type, it may be desirable to screen for antibodies that bind to cells that express the antigen of interest (e.g., by fluorescence activated cell sorting). Likewise, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore binding assay, Biacore AB, Uppsala, Sweden), sandwich assays (e.g., the paramagnetic bead system of IGEN International, Inc., Gaithersburg, Md.), western blots, immunoprecipitation assays, and immunohistochemistry.

In certain embodiment, antibodies of the invention may be useful as diagnostic or therapeutic agents for detecting or treating SLC5A8-associated diseases (e.g., cancers). The diagnostic method comprises the steps of contacting a sample of test cells or a protein extract thereof with immunospecific anti-SLC5A8 antibodies and assaying for the formation of a complex between the antibodies and a protein in the sample. Formation of low levels of complex in the test cell as compared to the normal cells indicates that the test cell is cancerous.

VII. Transgenic Animals

Another aspect of the invention features transgenic non-human animals which express a heterologous SLC5A8 gene, e.g., having a sequence of SEQ ID NO: 3 or 4, or fragments thereof. In another aspect, the invention features transgenic non-human animals which have had one or both copies of the endogenous SLC5A8 genes disrupted in at least one of the tissue or cell-types of the animal. In one embodiment, the transgenic non-human animals is a mammal such as a mouse, rat, rabbit, goat, sheep, dog, cat, cow or non-human primate. Without being bound to theory, it is proposed that such an animal may display a phenomenon associated with reduced or increased chance of cancer development (e.g., colon cancer, breast cancer, thyroid cancer, or stomach cancer). Accordingly, such a transgenic animal may serve as a useful animal model to study the progression of cancer diseases.

The term "transgene" is used herein to describe genetic material that has been or is about to be artificially inserted into the genome of a mammalian cell, particularly a mammalian cell of a living animal. The transgene is used to transform a cell, meaning that a permanent or transient genetic change, preferably a permanent genetic change, is induced in a cell following incorporation of exogenous DNA. A permanent genetic change is generally achieved by introduction of the DNA into the genome of the cell. Vectors for stable integration include plasmids, retroviruses and other animal viruses, YACs, and the like. Of interest are transgenic mammals, e.g., cows, pigs, goats, horses, etc., and particularly rodents, e.g., rats, mice, etc. Preferably, the transgenic-animals are mice.

Transgenic animals comprise an exogenous nucleic acid sequence present as an extrachromosomal element or stably integrated in all or a portion of its cells, especially in germ cells. Unless otherwise indicated, it will be assumed that a transgenic animal comprises stable changes to the germline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

The exogenous gene is usually either from a different species than the animal host, or is otherwise altered in its coding or non-coding sequence. The introduced gene may be a wild-type gene, naturally occurring polymorphism, or a genetically manipulated sequence, for example having deletions, substitutions or insertions in the coding or non-coding regions. Where the introduced gene is a coding sequence, it is usually operably linked to a promoter, which may be constitutive or inducible, and other regulatory sequences required for expression in the host animal.

In one aspect of the invention, a SLC5A8 transgene can encode the wild-type form of the protein, homologs thereof, as well as antisense constructs. A SLC5A8 transgene can also encode a soluble form of SLC5A8 that has tumor suppressor activity or sodium solute transporter activity.

It may be desirable to express the heterologous SLC5A8 transgene conditionally such that either the timing or the level of SLC5A8 gene expression can be regulated. Such conditional expression can be provided using prokaryotic promoter sequences which require prokaryotic proteins to be simultaneous expressed in order to facilitate expression of the SLC5A8 transgene. Exemplary promoters and the corresponding trans-activating prokaryotic proteins are given in U.S. Pat. No. 4,833,080.

Moreover, transgenic animals exhibiting tissue specific expression can be generated, for example, by inserting a tissue specific regulatory element, such as an enhancer, into the transgene. For example, the endogenous SLC5A8 gene promoter or a portion thereof can be replaced with another promoter and/or enhancer, e.g., a CMV or a Moloney murine leukemia virus (MLV) promoter and/or enhancer.

Transgenic animals containing an inducible SLC5A8 transgene can be generated using inducible regulatory elements (e.g., metallothionein promoter), which are well-known in the art. SLC5A8 transgene expression can then be initiated in these animals by administering to the animal a compound which induces gene expression (e.g., heavy metals). Another preferred inducible system comprises a tetracycline-inducible transcriptional activator (U.S. Pat. Nos. 5,654,168 and 5,650,298).

The present invention provides transgenic animals that carry the transgene in all their cells, as well as animals that carry the transgene in some, but not all cells, i.e., mosaic animals. The transgene can be integrated as a single transgene or in tandem, e.g., head to head tandems, or head to tail or tail to tail or as multiple copies.

The successful expression of the transgene can be detected by any of several means well known to those skilled in the art. Non-limiting examples include Northern blot, in situ hybridization of mRNA analysis, Western blot analysis, immunohistochemistry, and FACS analysis of protein expression.

In a further aspect, the invention features non-human animal cells containing a SLC5A8 transgene, preferentially a human SLC5A8 transgene. For example, the animal cell (e.g., somatic cell or germ cell (i.e., egg or sperm)) can be obtained from the transgenic animal. Transgenic somatic cells or cell lines can be used, for example, in drug screening assays. Transgenic germ cells, on the other hand, can be used in generating transgenic progeny.

Although not necessary to the operability of the invention, the transgenic animals described herein may comprise alterations to endogenous genes in addition to, or alternatively, to the genetic alterations described above. For example, the host animals may be either "knockouts" or "knockins" for the SLC5A8 gene. Knockouts have a partial or complete loss of function in one or both alleles of an endogenous gene of interest. Knockins have an introduced transgene with altered genetic sequence and/or function from the endogenous gene. The two may be combined, for example, such that the naturally occurring gene is disabled, and an altered form introduced. For example, it may be desirable to knockout the host animal's endogenous SLC5A8 gene, while introducing an exogenous SLC5A8 gene (e.g., a human SLC5A8 gene).

In a knockout, preferably the target gene expression is undetectable or insignificant. For example, a knock-out of a SLC5A8 gene means that function of the SLC5A8 has been substantially decreased so that expression is not detectable or only present at insignificant levels. This may be achieved by a variety of mechanisms, including introduction of a disruption of the coding sequence, e.g., insertion of one or more stop codons, insertion of a DNA fragment, deletion of coding sequence, substitution of stop codons for coding sequence, etc. In some cases, the exogenous transgene sequences are ultimately deleted from the genome, leaving a net change to the native sequence. Different approaches may be used to achieve the "knock-out." A chromosomal deletion of all or part of the native gene may be induced, including deletions of the non-coding regions, particularly the promoter region, 3' regulatory sequences, enhancers, or deletions of gene that activate expression of APP genes. A functional knock-out may also be achieved by the introduction of an anti-sense construct that blocks expression of the native genes (for example, see Li and Cohen (1996) Cell 85:319-329). "Knock-outs" also include conditional knock-outs, for example, where alteration of the target gene occurs upon exposure of the animal to a substance that promotes target gene alteration, introduction of an enzyme that promotes recombination at the target gene site (e.g., Cre in the Cre-lox system), or other method for directing the target gene alteration postnatally.

A "knockin" of a target gene means an alteration in a host cell genome that results in altered expression or function of a native target gene. Increased (including ectopic) or decreased expression may be achieved by introduction of an additional copy of the target gene, or by operatively inserting a regulatory sequence that provides for enhanced expression of an endogenous copy of the target gene. These changes may be constitutive or conditional, i.e., dependent on the presence of an activator or repressor. The use of knockin technology may be combined with production of exogenous sequences to produce the transgenic animals of the invention.

DNA constructs for random integration need not include regions of homology to mediate recombination. Where homologous recombination is desired, the DNA constructs will comprise at least a portion of the target gene with the desired genetic modification, and will include regions of homology to the target locus. Conveniently, markers for positive and negative selection are included. Methods for generating cells having targeted gene modifications through homologous recombination are known in the art. For various techniques for transfecting mammalian cells, see Keown et al. (1990) Methods in Enzymology 185:527-537.

For embryonic stem (ES) cells, an ES cell line may be employed, or embryonic cells may be obtained freshly from a host, e.g., mouse, rat, or guinea pig. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture.

The transgenic animals of the present invention may be an animal model for a SLC5A8-associated disease (e.g., cancer), and display cancer-related phenotypes (e.g., colon cancer, breast cancer, thyroid cancer, or stomach cancer), depending on different alleles generated. Accordingly, such transgenic animals can be used in in vivo assays to identify cancer therapeutics. In an exemplary embodiment, the assay comprises administering a test compound to a transgenic animal of the invention, and comparing a phenotypic change in cancer development in the animal relative to a transgenic animal which has not received the test compound.

To illustrate, the transgenic animals and cell lines are particularly useful in screening compounds that have potential as prophylactic or therapeutic treatments of diseases such as may involve aberrant expression, or loss, of the SLC5A8 gene. Screening for a useful drug would involve administering the candidate drug over a range of doses to the transgenic animal, and assaying at various time points for the effect(s) of the drug on the disease or disorder being evaluated. Alternatively, or additionally, the drug could be administered prior to or simultaneously with exposure to induction of the disease, if applicable.

In one embodiment, candidate compounds are screened by being administered to the transgenic animal, over a range of doses, and evaluating the animal's physiological response to the compound(s) over time. Administration may be oral, or by suitable injection, depending on the chemical nature of the compound being evaluated. In some cases, it may be appropriate to administer the compound in conjunction with co-factors that would enhance the efficacy of the compound.

In screening cell lines derived from the subject transgenic animals for compounds useful in treating various disorders, the test compound is added to the cell culture medium at the appropriate time, and the cellular response to the compound is evaluated over time using the appropriate biochemical and/or histological assays. In some cases, it may be appropriate to apply the compound of interest to the culture medium in conjunction with co-factors that would enhance the efficacy of the compound.

In another aspect, the animals of this invention can be used as a source of cells, differentiated or precursor, which can be immortalized in cell culture. Cells in which the normal function of the SLC5A8 protein is altered by a transgene may be isolated from potentially any tissue of the animal, as well as form animals at any developmental stage, e.g. embryonic to adult. The subject transgenic animals can, accordingly, be used as a source of material for the growth, identification, purification and detailed analysis of, inter alia, precursor cells, including stem cells and pluripotent progenitor cells for a variety of tissues.

Vectors used for transforming animal embryos are constructed using methods well known in the art, including, without limitation, the standard techniques of restriction endonuclease digestion, ligation, plasmid and DNA and RNA purification, DNA sequencing, and the like as described, for example in Sambrook, Fritsch, and Maniatis, eds., Molecular Cloning: A Laboratory Manual., (Cold Spring Harbor Laboratory Press, Cold Spring Harbor, N.Y. >1989!). Most practitioners are familiar with the standard resource materials as well as specific conditions and procedures.

VIII. Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to SLC5A8 proteins, have a stimulatory or inhibitory effect on, for example, SLC5A8 expression or SLC5A8 activity, or have a stimulatory or inhibitory effect on, for example, the expression or activity of a SLC5A8 substrate.

Compounds thus identified can be used to modulate the activity of target gene products (e.g., the SLC5A8 gene) in a therapeutic protocol, to elaborate the biological function of the target gene product, or to identify compounds that disrupt normal target gene interactions. Given that the SLC5A8 polypeptide is a transmembrane protein, agents that bind to a SLC5A8 polypeptide may include its natural ligands, downstream signaling molecules, and other endogenous polypeptides as well as artificial compounds. In one embodiment, an assay detects agents which inhibit interaction of the subject SLC5A8 polypeptides with a SLC5A8-associated protein. A wide variety of assays may be used for this purpose, including labeled in vitro protein-protein binding assays, interaction trap assay, immunoassays for protein binding, and the like.

Given the role of SLC5A8 in transporting sodium solute and in cancer development, the agents that bind to SLC5A8 as well as the agents that interfere with SLC5A8 binding to SLC5A8-associated proteins may be able to modulate transporting sodium solute or cancer development. Accordingly, one aspect of the invention provides a method for assessing the ability of an agent to modulate transporting sodium solute or cancer development, comprising: 1) combining: a first polypeptide including at least a portion of a SLC5A8 polypeptide, a second polypeptide including at least a portion of a SLC5A8-associated protein that interacts with the first polypeptide, and an agent, under conditions wherein the first polypeptide interacts with the second polypeptide in the absence of said agent, 2) determining if said agent interferes with the interaction, and 3) for an agent that interferes with the interaction, further assessing its ability to interfere with SLC5A8's ability to transport sodium solute or suppress tumor development.

In one embodiment, an activity (e.g., the sodium solute transporting activity) of a SLC5A8 protein can be assayed as follows. *Xenopus laevis* oocytes are injected with mRNA encoding the SLC5A8 protein or a eukaryotic expression vector able to express such an mRNA, using a Drummond Nanoject (Drummond Scientific, Broomall, Pa. into the animal pole of defolliculated oocytes as described by Swick et al. ((1992) Proc. Natl. Acad. Sci. USA. 89:1812-1816). The injected oocytes are then transferred to microtiter wells about 12 to 24 hours prior to being assayed. The transporter function of oocyte-expressed SLC5A8 polypeptide is assessed by sodium uptakes as described (see e.g., Romera et al. (2000) J. Biol. Chem. 275:24552-24559; Sciortino et al. (1999) Am. J. Physiol. 277:F611-623).

A variety of assay formats will suffice and, in light of the present disclosure, those not expressly described herein will nevertheless be comprehended by one of ordinary skill in the art. Assay formats which approximate such conditions as formation of protein complexes, enzymatic activity, may be generated in many different forms, and include assays based on cell-free systems, e.g., purified proteins or cell lysates, as well as cell-based assays which utilize intact cells. Simple binding assays can also be used to detect agents which bind to SLC5A8. Such binding assays may also identify agents that act by disrupting the interaction between a SLC5A8 polypeptide and a SLC5A8 interacting protein. Agents to be tested can be produced, for example, by bacteria, yeast or other organisms (e.g., natural products), produced chemically (e.g., small molecules, including peptidomimetics), or produced recombinantly. In a preferred embodiment, the test agent is a small organic molecule, e.g., other than a peptide or oligonucleotide, having a molecular weight of less than about 2,000 daltons.

In many drug screening programs which test libraries of compounds and natural extracts, high throughput assays are desirable in order to maximize the number of compounds surveyed in a given period of time. Assays of the present invention which are performed in cell-free systems, such as may be developed with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target.

In preferred in vitro embodiments of the present assay, a reconstituted SLC5A8 complex comprises a reconstituted mixture of at least semi-purified proteins. By semi-purified, it is meant that the proteins utilized in the reconstituted mixture have been previously separated from other cellular or viral proteins. For instance, in contrast to cell lysates, the proteins involved in SLC5A8 complex formation are present in the mixture to at least 50% purity relative to all other proteins in the mixture, and more preferably are present at 90-95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure SLC5A8 complex assembly and/or disassembly.

Assaying SLC5A8 complexes, in the presence and absence of a candidate agent, can be accomplished in any vessel suitable for containing the reactants. Examples include microtitre plates, test tubes, and micro-centrifuge tubes. In a screening assay, the effect of a test agent may be assessed by, for example, assessing the effect of the test agent on kinetics, steady-state and/or endpoint of the reaction.

In one embodiment of the present invention, drug screening assays can be generated which detect inhibitory agents on the basis of their ability to interfere with assembly or stability of the SLC5A8 complex. In an exemplary binding assay, the compound of interest is contacted with a mixture comprising a SLC5A8 polypeptide and at least one interacting polypeptide. Detection and quantification of SLC5A8 complexes provides a means for determining the compound's efficacy at inhibiting (or potentiating) interaction between the two polypeptides. The efficacy of the compound can be assessed by generating dose response curves from data obtained using various concentrations of the test compound. Moreover, a control assay can also be performed to provide a baseline for comparison. In the control assay, the formation of complexes is quantitated in the absence of the test compound.

Complex formation between the SLC5A8 polypeptides and a substrate polypeptide may be detected by a variety of techniques. For instance, modulation in the formation of complexes can be quantitated using, for example, detectably labeled proteins (e.g., radiolabeled, fluorescently labeled, or enzymatically labeled), by immunoassay, or by chromatographic detection. Surface plasmon resonance systems, such as those available from Biacore International AB (Uppsala, Sweden), may also be used to detect protein-protein interaction.

Often, it will be desirable to immobilize one of the polypeptides to facilitate separation of complexes from uncomplexed forms of one of the proteins, as well as to accommodate automation of the assay. In an illustrative embodiment, a fusion protein can be provided which adds a domain that permits the protein to be bound to an insoluble matrix. For example, GST-SLC5A8 fusion proteins can be adsorbed onto glutathione sepharose beads (Sigma Chemical, St. Louis, Mo.) or glutathione derivatized microtitre plates, which are then combined with a potential interacting protein, e.g., an $^{35}$S-labeled polypeptide, and the test compound and incubated under conditions conducive to complex formation. Following incubation, the beads are washed to remove any unbound interacting protein, and the matrix bead-bound radiolabel determined directly (e.g., beads placed in scintillant), or in the supernatant after the complexes are dissociated, e.g., when microtitre plate is used. Alternatively, after washing away unbound protein, the complexes can be dissociated from the matrix, separated by SDS-PAGE gel, and the level of interacting polypeptide found in the matrix-bound fraction quantitated from the gel using standard electrophoretic techniques.

In a further embodiment, agents that bind to a SLC5A8 may be identified by using an immobilized SLC5A8. In an illustrative embodiment, a fusion protein can be provided which adds a domain that permits the protein to be bound to an insoluble matrix. For example, GST-SLC5A8 fusion proteins can be adsorbed onto glutathione sepharose beads (Sigma Chemical, St. Louis, Mo.) or glutathione derivatized microtitre plates, which are then combined with a potential labeled binding agent and incubated under conditions conducive to binding. Following incubation, the beads are washed to remove any unbound agent, and the matrix bead-bound label determined directly, or in the supernatant after the bound agent is dissociated.

In yet another embodiment, the SLC5A8 polypeptide and potential interacting polypeptide can be used to generate an interaction trap assay (see also, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696), for subsequently detecting agents which disrupt binding of the proteins to one and other.

One aspect of the present invention provides reconstituted protein preparations including a SLC5A8 polypeptide and one or more interacting polypeptides.

In still further embodiments of the present assay, the SLC5A8 complex is generated in whole cells, taking advantage of cell culture techniques to support the subject assay. For example, as described below, the SLC5A8 complex can be constituted in a eukaryotic cell culture system, including mammalian and yeast cells. Advantages to generating the subject assay in an intact cell include the ability to detect inhibitors which are functional in an environment more closely approximating that which therapeutic use of the inhibitor would require, including the ability of the agent to gain entry into the cell. Furthermore, certain of the in vivo embodiments of the assay, such as examples given below, are amenable to high through-put analysis of candidate agents.

The components of the SLC5A8 complex can be endogenous to the cell selected to support the assay. Alternatively, some or all of the components can be derived from exogenous sources. For instance, fusion proteins can be introduced into the cell by recombinant techniques (such as through the use of an expression vector), as well as by microinjecting the fusion protein itself or mRNA encoding the fusion protein.

In many embodiments, a cell is manipulated after incubation with a candidate agent and assayed for a SLC5A8 activity. In certain embodiments a SLC5A8 activity is represented by sodium transporting activity or tumor suppressing activity. In certain embodiments, SLC5A8 activities may also include, without limitation, complex formation between SLC5A8 and its associated proteins. SLC5A8 complex formation may be assessed by immunoprecipitation and analysis of co-immunoprecipiated proteins or affinity purification and analysis of co-purified proteins. Fluorescence Resonance Energy Transfer (FRET)-based assays may also be used to determine complex formation. Fluorescent molecules having the proper emission and excitation spectra that are brought into close proximity with one another can exhibit FRET. The fluorescent molecules are chosen such that the emission spectrum of one of the molecules (the donor molecule) overlaps with the excitation spectrum of the other molecule (the acceptor molecule). The donor molecule is excited by light of appropriate intensity within the donor's excitation spectrum. The donor then emits the absorbed energy as fluorescent light. The fluorescent energy it produces is quenched by the acceptor molecule. FRET can be manifested as a reduction in the intensity of the fluorescent signal from the donor, reduction in the lifetime of its excited state, and/or re-emission of fluorescent light at the longer wavelengths (lower energies) characteristic of the acceptor. When the fluorescent proteins physically separate, FRET effects are diminished or eliminated. (U.S. Pat. No. 5,981,200).

In general, where the screening assay is a binding assay (whether protein-protein binding, agent-protein binding, etc.), one or more of the molecules may be joined to a label, where the label can directly or indirectly provide a detectable signal. Various labels include radioisotopes, fluorescers, chemiluminescers, enzymes, specific binding molecules, particles, e.g., magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts and neutral proteins (e.g., albumin, detergents, etc) that are used to facilitate optimal protein-protein binding and/or reduce nonspecific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4° C. and 40° C. Incubation periods are selected for optimum activity, but may also be optimized to facilitate rapid high-throughput screening.

It is to be understood that the screening assays discussed above are applicable to identify therapeutic agents related to soluble SLC5A8 polypeptides and derivatives thereof. An exemplary derivative of soluble SLC5A8 polypeptides is a fusion protein containing soluble SLC5A8 polypeptide. Given the role of soluble SLC5A8 polypeptides in sodium transporting and/or tumor suppression, compositions that perturb the formation or stability of the protein-protein interactions between soluble SLC5A8 polypeptides and the proteins that they interact with, are candidate pharmaceuticals for the treatment of SLC5A8-associated diseases such as cancer.

IX. Predictive Medicine

The present invention also pertains to the field of predictive medicine in which diagnostic assays, prognostic assays, and monitoring clinical trials are used for prognostic (predictive) purposes to thereby treat an individual. Generally, the invention provides a method of determining if a subject is at risk for a disorder related to a lesion in or the misexpression of a gene which encodes SLC5A8, for example cancers (e.g., colon cancer, breast cancer, thyroid cancer, or stomach cancer).

The method includes one or more of the following: 1) detecting, in a tissue of the subject, the presence or absence of a mutation which affects the expression of the SLC5A8 gene, or detecting the presence or absence of a mutation in a region which controls the expression of the gene, e.g., a mutation in the 5' control region; 2) detecting, in a tissue of the subject, the presence or absence of a mutation which alters the structure of the SLC5A8 gene; 3) detecting, in a tissue of the subject, the misexpression of the SLC5A8 gene, at the mRNA level, e.g., detecting a non-wild type level of a mRNA; 4) detecting, in a tissue of the subject, the misexpression of the gene, at the protein level, e.g., detecting a non-wild type level of a SLC5A8 polypeptide; and 5) detecting, in a tissue of the subject, methylation of the SLC5A8 gene in the 5' SLC5A8 genomic nucleotide sequences (see detailed descriptions in the following section).

In preferred embodiments, the method may also include ascertaining the existence of at least one of: 1) a deletion of one or more nucleotides from the SLC5A8 gene; 2) an insertion of one or more nucleotides into the gene; 3) a point mutation, e.g., a substitution of one or more nucleotides of the gene; and 4) a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO: 3 or 4, or naturally occurring mutants thereof, or 5' or 3' flanking sequences naturally associated with the SLC5A8 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments, detecting the misexpression includes ascertaining the existence of at least one of: an alteration in the level of a messenger RNA transcript of the SLC5A8 gene; the presence of a non-wild type splicing pattern of a messenger RNA transcript of the gene; or a non-wild type level of SLC5A8.

Methods of the invention can be used prenatally or to determine if a subject's offspring will be at risk for a disorder. In preferred embodiments, the method includes determining the structure of a SLC5A8 gene, an abnormal structure being indicative of risk for the disorder.

In preferred embodiments, the method includes contacting a sample from the subject with an antibody to the SLC5A8 protein or a nucleic acid which hybridizes specifically with the gene. These and other embodiments are discussed below.

X. Diagnostic and Prognostic Assays

Diagnostic and prognostic assays of the invention include method for assessing the expression level of SLC5A8 molecules and for identifying variations and mutations in the sequence of SLC5A8 molecules. In certain embodiments, the invention provides methods by assaying the SLC5A8 expression level so as to determine whether a patient has or does not have a disease condition. Further, such a disease condition may be characterized by decreased expression of SLC5A8 nucleic acid or protein described herein. In certain embodiments, the invention provides methods for determining whether a patient is or is not likely to have a SLC5A8-associated disease by detecting the expression of the SLC5A8 nucleotide sequences. In further embodiments, the invention provides methods for determining whether the patient is having a relapse or determining whether a patient's cancer is responding to treatment.

The presence, level, or absence of SLC5A8 protein or nucleic acid in a biological sample can be evaluated by obtaining a biological sample from a test subject and contacting the biological sample with a compound or an agent capable of detecting SLC5A8 protein or nucleic acid (e.g., mRNA, genomic DNA) that encodes SLC5A8 protein such that the presence of SLC5A8 protein or nucleic acid is detected in the biological sample. The level of expression of the SLC5A8 gene can be measured in a number of ways, including, but not limited to: measuring the mRNA encoded by the SLC5A8 genes; measuring the amount of protein encoded by the SLC5A8 gene; or measuring the activity of the protein encoded by the SLC5A8 gene. The level of mRNA corresponding to the SLC5A8 gene in a cell can be determined both by in situ and by in vitro formats.

The isolated mRNA can be used in hybridization or amplification assays that include, but are not limited to, Southern or Northern analyses, polymerase chain reaction (PCR) analyses and probe arrays. One preferred diagnostic method for the detection of mRNA levels involves contacting the isolated mRNA with a nucleic acid molecule (probe) that can hybridize to the mRNA encoded by the SLC5A8 gene. The nucleic acid probe can be, for example, a full-length SLC5A8 nucleic acid, such as the nucleic acid of SEQ ID NO: 3 or 4, or a portion thereof, such as an oligonucleotide of at least 7, 15, 30, 50, 100, 250 or 500 nucleotides in length and sufficient to specifically hybridize under stringent conditions to SLC5A8 mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example, by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the SLC5A8 gene.

The level of SLC5A8 mRNA in a sample can be evaluated with nucleic acid amplification, e.g., by RT-PCR (Mullis (1987) U.S. Pat. No. 4,683,202), ligase chain reaction (Barany (1991) Proc. Natl. Acad. Sci. USA 88:189-193), self sustained sequence replication (Guatelli et al., (1990) Proc. Natl. Acad. Sci. USA 87:1874-1878), transcriptional amplification system (Kwoh et al., (1989), Proc. Natl. Acad. Sci. USA 86:1173-1177), Q-Beta Replicase (Lizardi et al., (1988) Bio/Technology 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the SLC5A8 gene being analyzed.

In another embodiment, the methods further contacting a control sample with a compound or agent capable of detecting SLC5A8 mRNA, or genomic DNA, and comparing the presence of SLC5A8 mRNA or genomic DNA in the control sample with the presence of SLC5A8 mRNA or genomic DNA in the test sample.

A variety of methods can be used to determine the level of protein encoded by SLC5A8. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect SLC5A8 protein in a biological sample in vitro as well as in vivo. In vitro techniques for detection of SLC5A8 protein include enzyme linked immunosorbent assays (ELISAs), immunoprecipitations, immunofluorescence, enzyme immunoassay (EIA), radioimmunoassay (RIA), and Western blot analysis. In vivo techniques for detection of SLC5A8 protein include introducing into a subject a labeled anti-SLC5A8 antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-SLC5A8 antibody positioned on an antibody array (as described below). The sample can be detected, e.g., with avidin coupled to a fluorescent label.

In another embodiment, the methods further include contacting the control sample with a compound or agent capable of detecting SLC5A8 protein, and comparing the presence of SLC5A8 protein in the control sample with the presence of SLC5A8 protein in the test sample.

The invention also includes kits for detecting the presence of SLC5A8 in a biological sample. For example, the kit can include a compound or agent capable of detecting SLC5A8 protein or mRNA in a biological sample; and a standard. The compound or agent can be packaged in a suitable container. The kit can further comprise instructions for using the kit to detect SLC5A8 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted SLC5A8 expression or activity. As used herein, the term "unwanted" includes an unwanted phenomenon involved in a biological response such as pain or deregulated cell proliferation.

In one embodiment, a disease or disorder associated with aberrant or unwanted SLC5A8 expression or activity is identified. A test sample is obtained from a subject and SLC5A8 protein or nucleic acid (e.g., mRNA or genomic DNA) is evaluated, wherein the level, e.g., the presence or absence, of SLC5A8 protein or nucleic acid is diagnostic for a subject having or at risk of developing a disease or disorder associated with aberrant or unwanted SLC5A8 expression or activity.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted SLC5A8 expression or activity. For example, such methods can be used to determine whether a subject can be effectively treated with an agent for a pain or solute transport disorder.

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of SLC5A8 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

XI. Methods of Assaying Methylation of SLC5A8 Nucleotides

In certain aspects, the invention provides assays and methods using the SLC5A8 nucleotide sequences as molecular markers that distinguish between healthy cells and SLC5A8-associated diseased cells (cells of colon cancer, breast cancer, thyroid cancer or stomach cancer). In one aspect, a molecular marker of the invention is a differentially methylated SLC5A8 nucleotide sequence.

Accordingly, in certain embodiments, the invention provides assays for detecting differentially methylated SLC5A8 nucleotide sequences, such as the differential methylation patterns in nucleic acid sequence of SEQ ID NO: 12, 13 or 14. Thus, a differentially methylated SLC5A8 nucleotide sequence, in its methylated state, can be a SLC5A8-associated cancer-specific modification that serves as a target for detection using various methods described herein and the methods that are well within the purview of the skilled artisan in view of the teachings of this application.

In certain aspects, such methods for detecting methylated SLC5A8 nucleotide sequences are based on treatment of SLC5A8 genomic DNA with a chemical compound which converts non-methylated C, but not methylated C (i.e., 5mC), to a different nucleotide base. One such compound is sodium bisulfite, which converts C, but not 5mC, to U. Methods for bisulfite treatment of DNA are known in the art (Herman, et al., 1996, Proc Natl Acad Sci USA, 93:9821-6; Herman and Baylin, 1998, Current Protocols in Human Genetics, N. E. A. Dracopoli, ed., John Wiley & Sons, 2:10.6.1-10.6.10; U.S. Pat. No. 5,786,146). To illustrate, when an DNA molecule that contains unmethylated C nucleotides is treated with sodium bisulfite to become a compound-converted DNA, the sequence of that DNA is changed (C→U). Detection of the U in the converted nucleotide sequence is indicative of an unmethylated C.

The different nucleotide base (e.g., U) present in compound-converted nucleotide sequences can subsequently be detected in a variety of ways. In a preferred embodiment, the present invention provides a method of detecting U in compound-converted SLC5A8 DNA sequences by using "methylation sensitive PCR" (MSP) (see, e.g., Herman, et al., 1996, Proc. Natl. Acad. Sci. USA, 93:9821-9826; U.S. Pat. Nos. 6,265,171; 6,017,704; and 6,200,756). In MSP, one set of primers (i.e., comprising a forward and a reverse primer) amplifies the compound-converted template sequence if C bases in CpG dinucleotides within the SLC5A8 DNA are methylated. This set of primers is called "methylation-specific primers." Another set of primers amplifies the compound-converted template sequence if C bases in CpG dinucleotides within the SLC5A8 5' flanking sequence are not methylated. This set of primers is called "unmethylation-specific primers."

In MS-PCR, the reactions use the compound-converted DNA from a sample in a subject. In assays for SLC5A8 methylated DNA, methylation-specific primers are used. In the case where C within CpG dinucleotides of the target sequence of the DNA are methylated, the methylation-specific primers will amplify the compound-converted template sequence in the presence of a polymerase and an MSP product will be produced. If C within CpG dinucleotides of the target sequence of the DNA are not methylated, the methylation-specific primers will not amplify the compound-converted template sequence in the presence of a polymerase and an MSP product will not be produced It is often also useful to run a control reaction for the detection of unmethylated SLC5A8 DNA. The reactions uses the compound-converted DNA from a sample in a subject and unmethylation-specific primers are used. In the case where C within CpG dinucleotides of the target sequence of the DNA are unmethylated, the unmethylation specific primers will amplify the compound-converted template sequence in the presence of a polymerase and an MSP product will be produced. If C within CpG dinucleotides of the target sequence of the DNA are methylated, the unmethylation-specific primers will not amplify the compound-converted template sequence in the presence of a polymerase and an MSP product will not be produced. Note that a biologic sample will often contain a mixture of both neoplastic cells that give rise to a signal with methylation specific primers, and normal cellular elements that give rise to a signal with unmethylation-specific primers. The unmethyl specific signal is often of use as a control reaction, but does not in this instance imply the absence of cancer (e.g., colon cancer, breast cancer, thyroid cancer, or stomach cancer) as indicated by the positive signal derived from reactions using the methylation specific primers.

Primers for an MSP reaction are derived from the compound-converted SLC5A8 template sequence. Herein, "derived from" means that the sequences of the primers are chosen such that the primers amplify the compound-converted template sequence in an MSP reaction. Each primer comprises a single-stranded DNA fragment which is at least 8 nucleotides in length. Preferably, the primers are less than 50 nucleotides in length, more preferably from 15 to 35 nucleotides in length. Because the compound-converted SLC5A8 template sequence can be either the Watson strand or the Crick strand of the double-stranded DNA that is treated with sodium bisulfite, the sequences of the primers is dependent upon whether the Watson or Crick compound-converted template sequence is chosen to be amplified in the MSP. Either the Watson or Crick strand can be chosen to be amplified.

The compound-converted SLC5A8 template sequence, and therefore the product of the MSP reaction, can be between 20 to 3000 nucleotides in length, preferably between 50 to 500 nucleotides in length, more preferably between 80 to 150 nucleotides in length. Preferably, the methylation-specific primers result in an MSP product of a different length than the MSP product produced by the unmethylation-specific primers.

A variety of methods can be used to determine if an MSP product has been produced in a reaction assay. One way to determine if an MSP product has been produced in the reaction is to analyze a portion of the reaction by agarose gel electrophoresis. For example, a horizontal agarose gel of from 0.6 to 2.0% agarose is made and a portion of the MSP reaction mixture is electrophoresed through the agarose gel. After electrophoresis, the agarose gel is stained with ethidium bromide. MSP products are visible when the gel is viewed during illumination with ultraviolet light. By comparison to standardized size markers, it is determined if the MSP product is of the correct expected size.

Other methods can be used to determine whether a product is made in an MSP reaction. One such method is called "real-time PCR." Real-time PCR utilizes a thermal cycler (i.e., an instrument that provides the temperature changes necessary for the PCR reaction to occur) that incorporates a fluorimeter (i.e. an instrument that measures fluorescence). The real-time PCR reaction mixture also contains a reagent whose incorporation into a product can be quantified and whose quantification is indicative of copy number of that sequence in the template. One such reagent is a fluorescent dye, called SYBR Green I (Molecular Probes, Inc.; Eugene, Oreg.) that preferentially binds double-stranded DNA and whose fluorescence is greatly enhanced by binding of double-stranded DNA. When a PCR reaction is performed in the presence of SYBR Green I, resulting DNA products bind SYBR Green I and fluorescence. The fluorescence is detected and quantified by the fluorimeter. Such technique is particularly useful for quantification of the amount of the product in the PCR reaction. Additionally, the product from the PCR reaction may be quantitated in "real-time PCR" by the use of a variety of probes that hybridize to the product including TaqMan probes and molecular beacons. Quantitation may be on an absolute basis, or may be relative to a constitutively methylated DNA standard, or may be relative to an unmethylated DNA standard. In one instance the ratio of methylated SLC5A8 derived product to unmethylated derived SLC5A8 product may be constructed.

Methods for detecting methylation of the SLC5A8 DNA in this invention are not limited to MSP, and may cover any assay for detecting DNA methylation. Another example method for detecting methylation of the SLC5A8 DNA is by using "methylation-sensitive" restriction endonucleases. Such methods comprise treating the genomic DNA isolated from a subject with an methylation-sensitive restriction endonuclease and then using the restriction endonuclease-treated DNA as a template in a PCR reaction. Herein, methylation-sensitive restriction endonucleases recognize and cleave a specific sequence within the DNA if C bases within the recognition sequence are not methylated. If C bases within the recognition sequence of the restriction endonuclease are methylated, the DNA will not be cleaved. Examples of such methylation-sensitive restriction endonucleases include, but are not limited to HpaII, SmaI, SacII, EagI, MspI, BstUI, and BssHII. In this technique, a recognition sequence for a methylation-sensitive restriction endonuclease is located within the template DNA, at a position between the forward and reverse primers used for the PCR reaction. In the case that a C base within the methylation-sensitive restriction endonuclease recognition sequence is not methylated, the endonuclease will cleave the DNA template and a PCR product will not be formed when the DNA is used as a template in the PCR reaction. In the case that a C base within the methylation-sensitive restriction endonuclease recognition sequence is methylated, the endonuclease will not cleave the DNA template and a PCR product will be formed when the DNA is used as a template in the PCR reaction. Therefore, methylation of C bases can be determined by the absence or presence of a PCR product (Kane, et al., 1997, Cancer Res, 57:808-11). No sodium bisulfite is used in this technique.

Yet another exemplary method for detecting methylation of the SLC5A8 DNA is called the modified MSP, which method utilizes primers that are designed and chosen such that products of the MSP reaction are susceptible to digestion by restriction endonucleases, depending upon whether the compound-converted template sequence contains CpG dinucleotides or UpG dinucleotides.

Yet other methods for detecting methylation of the SLC5A8 DNA include the MS-SnuPE methods. This method uses compound-converted SLC5A8 DNA as a template in a primer extension reaction wherein the primers used produce a product, dependent upon whether the compound-converted template contains CpG dinucleotides or UpG dinucleotides (see e.g., Gonzalgo, et al., 1997, *Nucleic Acids Res.*, 25:2529-31).

Another exemplary method for detecting methylation of the SLC5A8 DNA is called COBRA (i.e., combined bisulfite restriction analysis). This method has been routinely used for DNA methylation detection and is well known in the art (see, e.g., Xiong, et al., 1997, *Nucleic Acids Res*, 25:2532-4).

In certain embodiments, the invention provides methods that involve directly sequencing the product resulting from an MSP reaction to determine if the compound-converted SLC5A8 template sequence contains CpG dinucleotides or UpG dinucleotides. Molecular biology techniques such as directly sequencing a PCR product are well known in the art.

XII. SLC5A8 Oligonucleotides for Methylation Detection

In yet other aspects, the application provides oligonucleotide primers for amplifying a region within the SLC5A8 nucleic acid sequence of any one of SEQ ID NOs: 5-11. In certain aspects, a pair of the oligonucleotide primers (for example, SEQ ID NOs: 5-7) can be used in a detection assay, such as the HpaII assay. In certain aspects, primers used in an MSP reaction can specifically distinguish between methylated and non-methylated SLC5A8 DNA, for example, SEQ ID NOs: 8-11.

The primers of the invention have sufficient length and appropriate sequence so as to provide specific initiation of amplification of SLC5A8 nucleic acids. Primers of the invention are designed to be "substantially" complementary to each strand of the SLC5A8 nucleic acid sequence to be amplified. While exemplary primers are provided in SEQ ID NOs: 5-11, it is understood that any primers that hybridizes with the bisulfite-converted SLC5A8 sequence of SEQ ID NOs: 12-14 are included within the scope of this invention and is useful in the method of the invention for detecting methylated nucleic acid, as described. Similarly, it is understood that any primers that would serve to amplify a methylation sensitive restriction site or sites within the differentially methylated region of SEQ ID NOs: 12-14 are included within the scope of this invention and is useful in the method of the invention for detecting nucleic methylated nucleic acid, as described.

The oligonucleotide primers of the invention may be prepared by using any suitable method, such as conventional phosphotriester and phosphodiester methods or automated embodiments thereof. In one such automated embodiment, diethylphosphoramidites are used as starting materials and may be synthesized as described by Beaucage, et al. (*Tetrahedron Letters*, 22:1859-1862, 1981). One method for synthesizing oligonucleotides on a modified solid support is described in U.S. Pat. No. 4,458,066.

In particular, a pair of primers are selected to amplify the SLC5A8 methylation target region or a DNA segment thereof. The targeted DNA segment that is amplified by the primers contains a plurality of sites that are recognized by the methylation sensitive restriction enzyme and is located between base pairs 82200 to 83267 of GenBank entry AC063951. In one preferred embodiment, the targeted DNA segment comprises at least four HpaII sites and the primers amplify a region including base pair 82638 through base pair 83080 of GenBank entry AC063951. In another highly preferred embodiment, the targeted DNA segment comprises at least six HpaII sites and the primers amplify a region including base pair 82430 through base pair 83080 of GenBank entry AC063951.

For example, each primer comprises a single-stranded DNA fragment which is at least 8 nucleotides in length. Preferably, the primers are less than 50 nucleotides in length, more preferably from 15 to 35 nucleotides in length. The sequences of the primers are derived from the sequence of the targeted DNA segment, i.e., the segment that is to be amplified. The sequence of the forward primer is identical to a sequence at the 5' end of the targeted DNA segment. The sequence of the reverse primer is the reverse complement of a sequence at the 3' end of targeted DNA segment.

XIII. Subjects and Samples

In certain aspects, the invention relates to a subject suspected of having or has a SLC5A8-associated disease, such as colon cancer, breast cancer, thyroid cancer, or stomach cancer. Alternatively, a subject may be undergoing routine screening and may not necessarily be suspected of having such a SLC5A8-associated disease or condition. In a preferred embodiment, the subject is a human subject, and the SLC5A8-associated disease is colon neoplasia.

Assaying for SLC5A8 markers discussed above in a sample from subjects not known to have a cancer (e.g., colon cancer, breast cancer, thyroid cancer, or stomach cancer) can aid in diagnosis of such a cancer in the subject. To illustrate, detecting the methylation status of the SLC5A8 nucleotide sequence by MSP can be used by itself, or in combination with other various assays, to improve the sensitivity and/or specificity for detecting a cancer. Preferably, such a detection is made at an early stage in the development of cancer, so that treatment is more likely to be effective.

In addition to diagnosis, assaying of a SLC5A8 marker in a sample from a subject not known to have a cancer (e.g., colon cancer, breast cancer, thyroid cancer, or stomach cancer) can be prognostic for the subject (e.g., indicating the probable course of the disease). To illustrate, subjects having a predisposition to develop colon neoplasia may possess methylated SLC5A8 nucleotide sequences. Assaying of SLC5A8 markers in a samples from subjects can also be used to select a particular therapy or therapies which are particularly effective against the colon neoplasia in the subject, or to exclude therapies that are not likely to be effective.

Assaying of SLC5A8 markers in samples from subjects that are known to have, or to have had, a cancer associated with silencing of the SLC5A8 gene is also useful. For example, the present methods can be used to identify whether therapy is effective or not for certain subjects. One or more samples are taken from the same subject prior to and following therapy, and assayed for the SLC5A8 markers. A finding that the SLC5A8 marker is present in the sample taken prior to therapy and absent (or at a lower level) after therapy would indicate that the therapy is effective and need not be altered. In those cases where the SLC5A8 marker is present in the sample taken before therapy and in the sample taken after therapy, it may be desirable to alter the therapy to increase the likelihood that the cancer will be eradicated in the subject. Thus, the present method may obviate the need to perform more invasive procedures which are used to determine a patient's response to therapy.

Cancers frequently recur following therapy in patients with advanced cancers. In this and other instances, the assays of the invention are useful for monitoring over time the status of an cancer associated with silencing of the SLC5A8 gene. For subjects in which a cancer is progressing, a SLC5A8 marker may be absent from some or all samples when the first sample is taken and then appear in one or more samples when the second sample is taken. For subjects in which cancer is regressing, a SLC5A8 marker may be present in one or a number of samples when the first sample is taken and then be absent in some or all of these samples when the second sample is taken.

Samples for use with the methods described herein may be essentially any biological material of interest. For example, a sample may be a bodily fluid sample from a subject, a tissue sample from a subject, a solid or semi-solid sample from a subject, a primary cell culture or tissue culture of materials derived from a subject, cells from a cell line, or medium or other extracellular material from a cell or tissue culture, or a xenograft (meaning a sample of a cancer from a first subject, e.g., a human, that has been cultured in a second subject, e.g., an immuno-compromised mouse). The term "sample" as used herein is intended to encompass both a biological material obtained directly from a subject (which may be described as the primary sample) as well as any manipulated forms or portions of a primary sample. A sample may also be obtained by contacting a biological material with an exogenous liquid, resulting in the production of a lavage liquid containing some portion of the contacted biological material. Furthermore, the term "sample" is intended to encompass the primary sample after it has been mixed with one or more additive, such as preservatives, chelators, anti-clotting factors, etc.

In certain embodiments, a bodily fluid sample is a blood sample. In this case, the term "sample" is intended to encompass not only the blood as obtained directly from the patient but also fractions of the blood, such as plasma, serum, cell fractions (e.g., platelets, erythrocytes, and lymphocytes), protein preparations, nucleic acid preparations, etc. In certain embodiments, a bodily fluid sample is a urine sample or a colonic effluent sample. In certain embodiments, a bodily fluid sample is a stool sample.

A subject is preferably a human subject, but it is expected that the molecular markers disclosed herein, and particularly their homologs from other animals, are of similar utility in other animals. In certain embodiments, it may be possible to detect a SLC5A8 marker directly in an organism without obtaining a separate portion of biological material. In such instances, the term "sample" is intended to encompass that portion of biological material that is contacted with a reagent or device involved in the detection process.

In certain embodiments, DNA which is used as the template in an MSP reaction is obtained from a bodily fluid sample. Examples of preferred bodily fluids are blood, serum, plasma, a blood-derived fraction, stool, colonic effluent or urine. Other body fluids can also be used. Because they can be easily obtained from a subject and can be used to screen for multiple diseases, blood or blood-derived fractions are especially useful. For example, it has been shown that DNA alterations in colorectal cancer patients can be detected in the blood of subjects (Hibi, et al., 1998, Cancer Res, 58:1405-7). Blood-derived fractions can comprise blood, serum, plasma, or other fractions. For example, a cellular fraction can be prepared as a "buffy coat" (i.e., leukocyte-enriched blood portion) by centrifuging 5 ml of whole blood for 10 min at 800 times gravity at room temperature. Red blood cells sediment most rapidly and are present as the bottom-most fraction in the centrifuge tube. The buffy coat is present as a thin creamy white colored layer on top of the red blood cells. The plasma portion of the blood forms a layer above the buffy coat. Fractions from blood can also be isolated in a variety of other ways. One method is by taking a fraction or fractions from a gradient used in centrifugation to enrich for a specific size or density of cells.

DNA is then isolated from samples from the bodily fluids. Procedures for isolation of DNA from such samples are well known to those skilled in the art. Commonly, such DNA isolation procedures comprise lysis of any cells present in the samples using detergents, for example. After cell lysis, proteins are commonly removed from the DNA using various proteases. RNA is removed using RNase. The DNA is then commonly extracted with phenol, precipitated in alcohol and dissolved in an aqueous solution.

XIV. Therapeutic methods for SLC5A8-associated diseases.

Yet another aspect of this application pertains to methods of treating a SLC5A8-associated disease (e.g., a proliferative disease such as cancer) which arises from reduced expression or over-expression of the SLC5A8 gene in cells. In certain cases, such SLC5A8-associated diseases (for example, colon cancer, breast cancer, thyroid cancer, or stomach cancer) can result from a wide variety of pathological cell proliferative conditions. In certain embodiments, treatment of a SLC5A8-associated disorder includes modulation of the SLC5A8 gene expression or SLC5A8 activity. The term "modulate" envisions the suppression of expression of SLC5A8 when it is over-expressed, or augmentation of SLC5A8 expression when it is under-expressed.

In an embodiment, the present invention provides a therapeutic method by using a SLC5A8 gene construct as a part of a gene therapy protocol, such as to reconstitute the function of a SLC5A8 protein (e.g., SEQ ID NO: 1) in a cell in which the SLC5A8 protein is mis-expressed or non-expressed. To illustrate, cell types which exhibit pathological or abnormal growth presumably depend at least in part on a function of a SLC5A8 protein. For example, gene therapy constructs encoding the SLC5A8 protein can be utilized in a cancer that is associated with silencing of the SLC5A8 gene, such as colon cancer, breast cancer, thyroid cancer, or stomach cancer.

In certain embodiments, the invention provides therapeutic methods using agents which induce re-expression of SLC5A8. Loss of SLC5A8 gene expression in a SLC5A8- associated diseased cells may be due at least in part to methylation of the SLC5A8 nucleotide sequence, methylation suppressive agents such as 5-deoxyazacytidine or 5-azacytidine can be introduced into the diseased cells. Other similar agents will be known to those of skill in the art. In a preferred embodiment, the SLC5A8-associated disease is colon neoplasia associated with increased methylation of SLC5A8 nucleotide sequences.

The present invention also provides gene therapy for the treatment of proliferative or immunologic disorders which are associated with SLC5A8. Such therapy would achieve its therapeutic effect by introduction of the SLC5A8 polynucleotide encoding full-length SLC5A8 into diseased cells.

Delivery of the SLC5A8 polynucleotide or the SLC5A8 gene can be achieved using a recombinant expression vector such as a chimeric virus or a colloidal dispersion system. Especially preferred for therapeutic delivery of antisense sequences is the use of targeted liposomes. Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a SLC5A8 sequence of interest into the viral vector, along with another gene which encodes the ligand for a receptor on a specific target cell, for example, the vector is target-specific. Retroviral vectors can be made target-specific by attaching, for example, a sugar, a glycolipid or a protein. Preferred targeting is accomplished by using an antibody to target the retroviral vector. Those skilled in the art will know of, or can readily ascertain without undue experimentation, specific polynucleotide sequences which can be inserted into the retroviral genome or attached to a viral envelope to allow target-specific delivery of the retroviral vector containing the SLC5A8 gene.

The invention also relates to a medicament or pharmaceutical composition comprising a SLC5A8 5' flanking polynucleotide or a SLC5A8 5' flanking polynucleotide operably linked to the SLC5A8 structural gene, respectively, in a pharmaceutically acceptable excipient or medium wherein the medicament is used for therapy of SLC5A8-associated diseases, such as colon cancer, breast cancer, thyroid cancer, or stomach cancer.

Exemplification

The invention now being generally described, it will be more readily understood by reference to the following examples, which are included merely for purposes of illustration of certain aspects and embodiments of the present invention, and are not intended to limit the invention.

Abstract:

We identify a new gene, SLC5A8, and show it is a candidate tumor suppressor gene whose silencing by aberrant methylation is a common and early event in human colon neoplasia. Aberrant DNA methylation has been implicated as a component of an epigenetic mechanism that silences genes in human cancers. Using restriction landmark genome scanning, we performed a global search to identify new genes that would be aberrantly methylated at high frequency in human colon cancer. From among 1,231 genomic Not1 sites assayed, site 3D41 was identified as methylated in 11 of 12 colon cancers profiled. Site 3D41 mapped to exon 1 of SLC5A8, a novel transcript that we assembled. In normal colon mucosa we found SLC5A8 exon 1 is unmethylated, and SLC5A8 transcript is expressed. In contrast, SLC5A8 exon 1 proved aberrantly methylated in 59% of primary colon cancers and 52% of colon cancer cell lines. SLC5A8 exon 1 methylated cells were uniformly silenced for SLC5A8 expression, but reactivated expression upon treatment with a demethylating drug, 5-azacytidine. Transfection of SLC5A8 suppressed colony growth in each of three SLC5A8 deficient cell lines, but showed no suppressive effect in any of three SLC5A8 proficient cell lines. SLC5A8 exon 1 methylation is an early event, detectable in colon adenomas, and in even earlier microscopic colonic aberrant crypt foci. Structural homology and functional testing demonstrated SLC5A8 is a novel member of the family of sodium solute symporters, which are now added as a new class of candidate colon cancer suppressor genes.

Introduction:

Cytosine methylation within CpG dinucleotides is a recognized epigenetic DNA modification, which in normal human tissues is excluded from CpG rich "islands" that mark the promoters of certain genes (Baylin, et al., 1998, Adv Cancer Res 72:141-96; Jones, et al., 1999, Trends Genet 15: 34-7; Baylin, et al., 2002, Cancer Cell 1: 299-305). Global hypomethylation accompanied by aberrant focal CpG island hypermethylation has emerged as one of the signature alterations evidenced by the cancer genome (Baylin, et al., 1998, Adv Cancer Res 72:141-96; Jones, et al., 1999, Trends Genet 15:34-7; Baylin, et al., 2002, Cancer Cell 1:299-305; Feinberg, et al., 1983, Nature 301:89-92). Moreover, silencing of gene expression as marked by aberrant methylation of CpG island promoter regions has emerged as a novel mechanism for the inactivation of tumor suppressor genes that provides an alternative to either mutation or to allelic loss (Baylin, et al., 1998, Adv Cancer Res 72:141-96; Jones, et al., 1999, Trends Genet 15:34-7; Kane, et al., 1997, Cancer Res 57:808-11; Veigl, et al., 1998, Proc Natl Acad Sci USA 95:8698-702). Additionally, aberrant methylation of defined genomic sequences can serve as a potentially useful diagnostic marker for detection of human cancers (Grady, et al., 2001, Cancer Res 61:900-2; Usadel, et al., 2002, Cancer Res 62S:371-5).

Restriction landmark genome scanning (RLGS) provides a global analysis of methylation events in a cancer cell by providing a two dimensional display of the methylation status of genomic Not1 sites (Costello, et al., 2000, Nat Genet 24:132-8). To identify new tumor suppressor genes and/or identify new genes targeted for methylation in human colon cancer, we carried out RLGS analysis of 12 colon cancer cell lines. This analysis lead to the identification of a novel transcript SLC5A8, whose aberrant methylation and transcriptional silencing was found to be a common and early event in human colon cancers, and that was found to encode a novel sodium symporter whose restoration can markedly suppress colony forming ability of colon cells in which endogenous SLC5A8 has been inactivated.

Significance:

This study demonstrates the application of restriction landmark genome scanning to identify a novel high frequency aberrant methylation event in human colon cancer. We extend that observation to identify a novel sodium transporter, SLC5A8, silenced by the methylation event. SLC5A8 methylation is among the most frequent molecular alterations in colon cancer, and finding SLC5A8 is a growth suppressor adds sodium transporters as a new functional class that can act as tumor suppressors. Moreover, detecting SLC5A8 methylation in aberrant crypt foci demonstrates this event as one of the earliest molecular changes in colon neoplasia, and adds further molecular support to the model in which at least some aberrant crypt foci are able to progress to more advanced colon adenomas and cancers.

EXAMPLE 1

FIG. 3 depicts certain aspects of the present invention. The numerical coordinates are those of genomic clone AC063951. Lollipops designate CpG sites that are potential acceptors of aberrant methylation. Asterisks designate sites recognized by the HpaII restriction enzyme that cut these sites if unmethylated, but not if methylated. Shown are the positions of PCR primers that amplify regions crossing 6 HpaII sites, or regions crossing 4 HpaII sites. Also shown is the position of PCR primers designed for a methyl-specific PCR (MS-PCR) assays that amplify sodium bisulfite converted DNA specifically derived from templates that are either methylated or unmethylated at CpG dinucleotides interrogated by the PCR primers. Also shown in the gray bar is the 5' end of exon 1 of the SLC5A8 transcript which overlaps with the methylation sites detected in both MS-PCR and HpaII based assays. Lastly indicated is a site corresponding to methylation site 2D41 detected in Restriction Landmark Genome Scanning assay as methylated in colon cancer cell lines, though not in primary tumors.

Colon cancers that are aberrantly methylated can be detected as they are resistant to cutting by the HpaII enzyme. That is methylation in a colon cancer can be assayed by showing PCR amplification of a DNA product using the primers and conditions shown from DNA that has first been digested with the HpaII restriction enzyme. The assay is diagrammed in FIG. 4 that provides the sequence of AC063951 between base pairs 82200-83267, and designates every CpG site with a gray lollipop, and shows the HpaII sites in the assay as black lollipops, and also shows the location of the PCR primers used in this assay. In this figure, the base pairs have been renumbered sequentially from 1-1068, with basepair 82200 being renumbered as basepair 1.

FIG. 5 tabulates the correspondence of assay for methylation over 4 and 6 HpaII sites with silencing of expression of the SLC5A8 transcript. As noted, assay of methylation over 4 HpaII sites detects 100% of colon cancer cell lines that silence the SLC5A8 transcript, but also detects some colon cancer cell lines that express SLC5A8. Assay of methylation over 6 HpaII sites has 100% specificity and detects only cell lines that have silenced SLC5A8, with a sensitivity of 68%.

FIG. 6 tabulates the results of this assay in actual colon cancer tumors. In a group of 34 human colon cancers 76% are detected by resistance to cutting at 4 HpaII sites whereas 50% are detected by resistance to cutting at 6 HpaII sites. Both assays detect methylation in some normal tissues accompanying methylated cancers, suggesting the detection of microscopic colon cancer cells. No methylation is detected in any normal tissue in which the accompanying tumor is unmethylated. Because of its high specificity, the assay which employs methylation over 6 HpaII sites is preferred.

Figure 4:
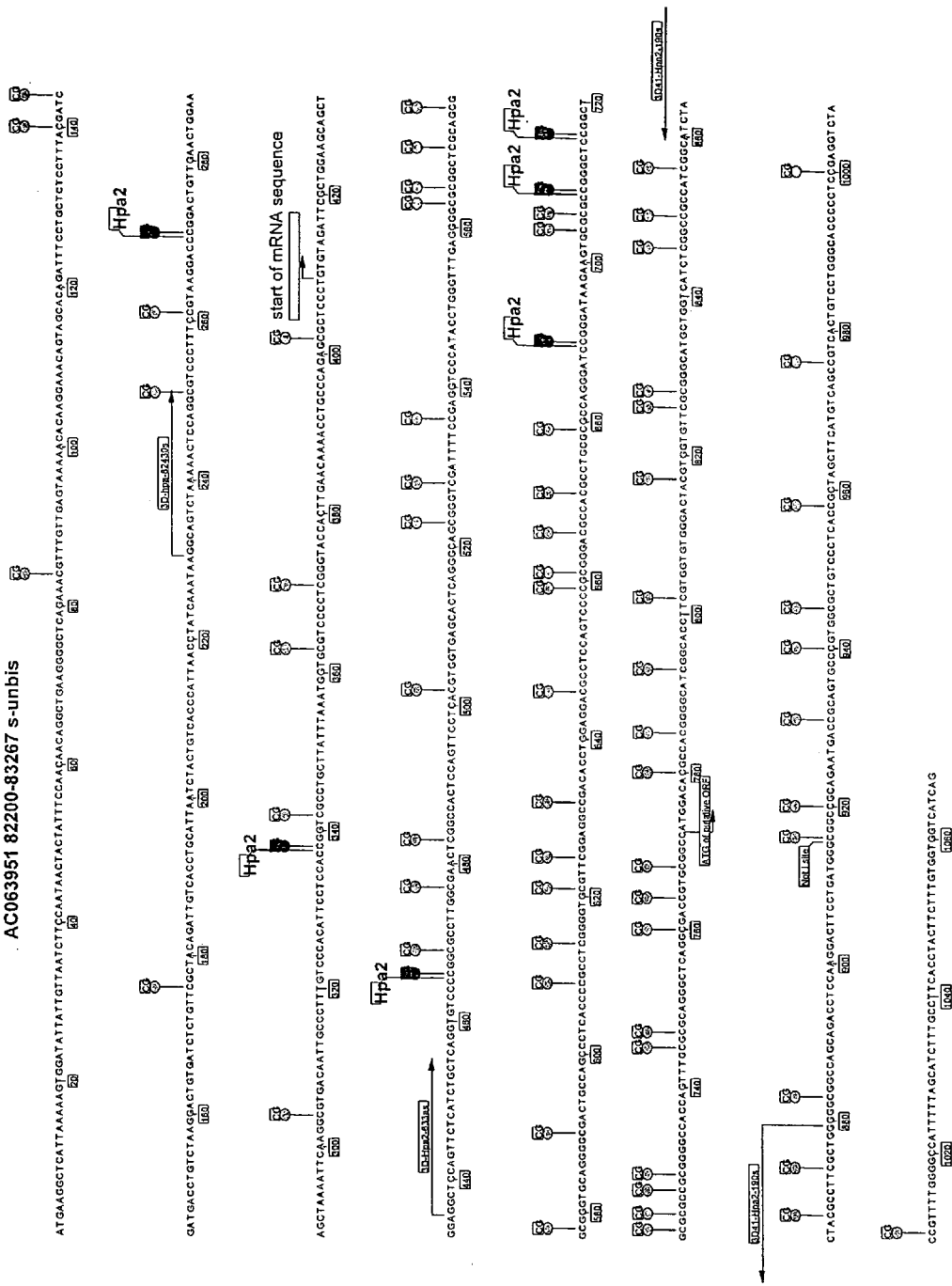
FIG. 4 provides the sequence of AC063951 between nucleotides 82200-83267 (SEQ ID NO: 12), and designates every CpG site with a gray lollipop, and shows the HpaII sites in the assay as dark lollipops, and also shows the location of the PCR primers used in the assay. In this figure, the base pairs have been renumbered sequentially from 1-1068, with nucleotide 82200 being renumbered as nucleotide 1.
Figure 7:
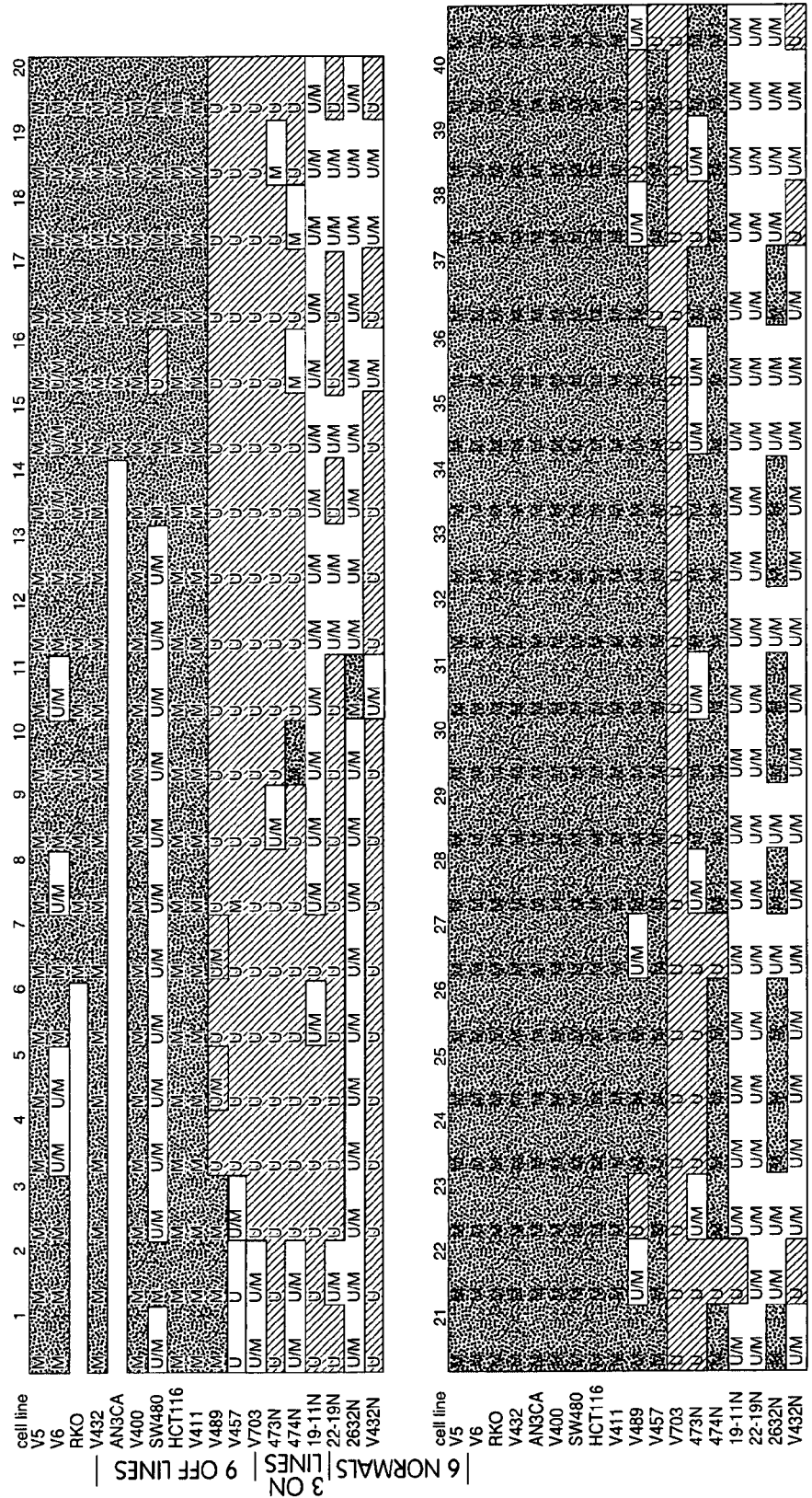
FIG. 7 shows the results of assay for methylation at 61 CpG sites enumerated in FIG. 4 with site 1 corresponding to basepair 466 in FIG. 4 and site 61 corresponding to basepair 1010. The bold arrows correspond to 4 of the HpaII sites at respectively basepairs 466, 691, 709, and 716 in FIG. 4. Methylation was assayed by sequencing DNA from samples following sodium bisulfite treatment of DNA that converts cytosine to uracil but leaves methyl-cytosine unchanged. Bases that are methylated are coded black, unmethylated bases are coded dark gray, and samples with both methylated and unmethylated bases are coded light gray.
Figure 7:
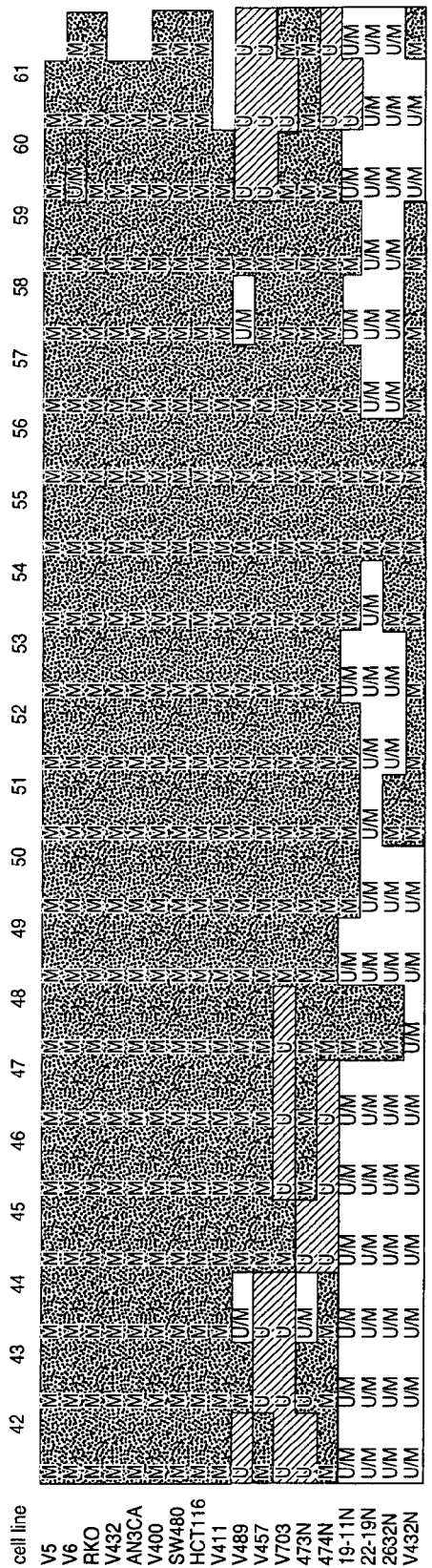

FIG. 7 shows the results of assay for methylation at 61 CpG sites enumerated in FIG. 4 with site 1 corresponding to basepair 466 in FIG. 4 and site 61 corresponding to basepair 1010. The bold arrows correspond to 4 of the HpaII sites at respectively basepairs 466, 691, 709 and 716 in FIG. 4. Methylation was assayed by sequencing DNA from samples following sodium bisulfite treatment of DNA that converts cytosine to uracil but leaves methyl-cytosine unchanged. Bases that are methylated are coded black, unmethylated bases are coded darker gray, and samples with both methylated and unmethylated bases are coded lighter gray. Samples analyzed included 9 colon cancer cell lines that do not show SLC5A8 transcript expression, 3 colon cancer cell lines that express SLC5A8 transcript, and 6 normal colon tissues. Clearly most colon cancers show substantially more methylation across this region than do normal colon tissues.

To detect the methylation associated with colon cancer a set of methylation specific PCR primers were fashioned. DNA from the assayed tissues was first treated with sodium bisulfite to convert cytosine to uracil, leaving methyl-cytosine unchanged. PCR primers were designed specific for the bisulfite converted sequences arising from methylated or unmethylated templates from the anti-sense strand of the target region (note that after bisulfite conversion the sense and anti-sense strands are no longer complementary to one another).

Figure 8:
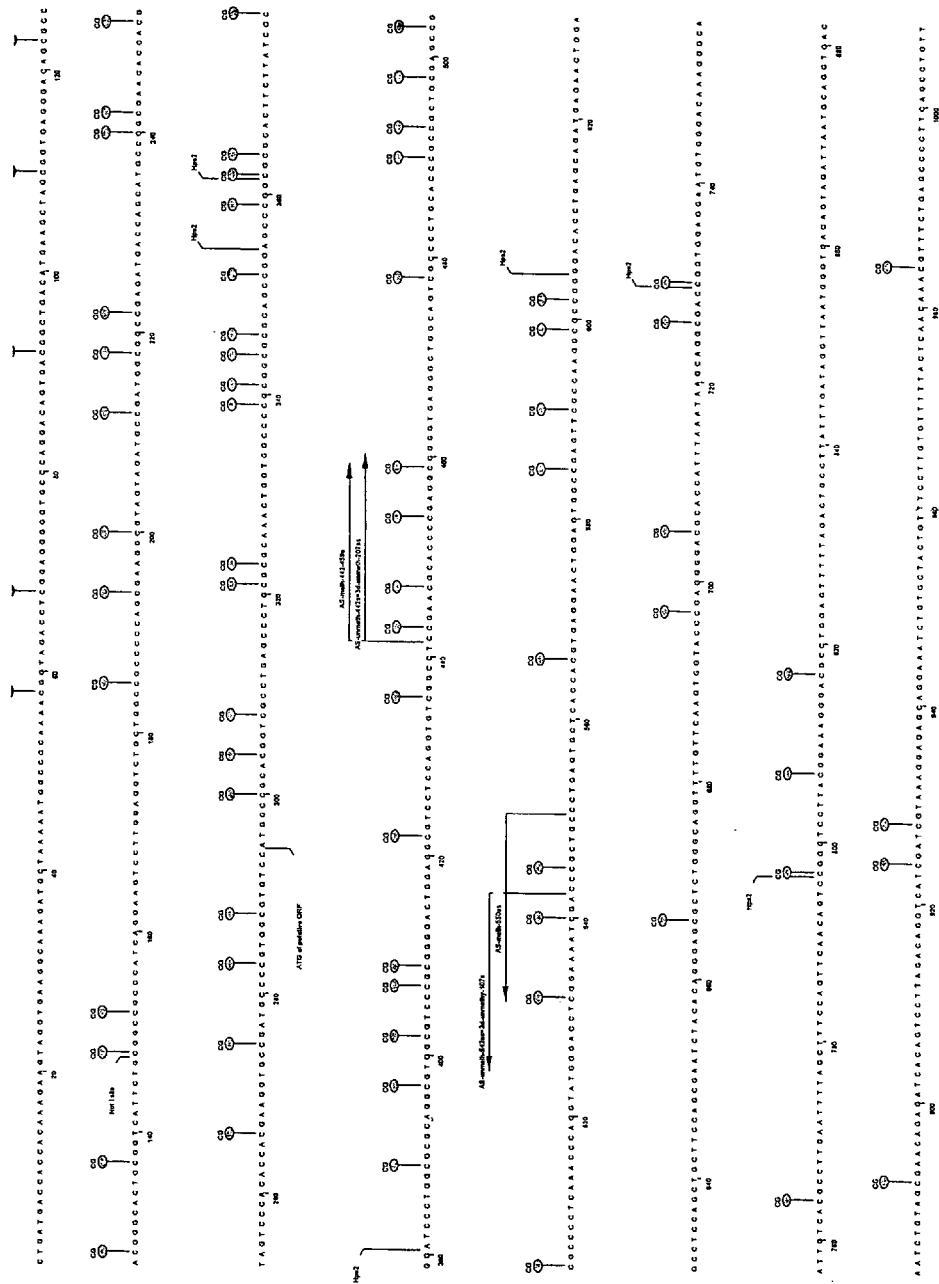
FIG. 8 shows the wild-type sequence of the anti-sense strand of AC063951 between bases 82200-83267 (SEQ ID NO: 13). Note that the sequence is the reverse complement of that shown in FIG. 4, and therefore base number 1 on this diagram corresponds to basepair 83267 in AC063951, and to basepair 1068 in FIG. 4. Indicated on this diagram is the position of the MS-PCR1 primers (AS-meth) and the UMS-PCR1 primers (AS-unmethy). The methyl specific MS-PCR1 primers amplify a CpG sites numbered 6, 7, 8 and 15, 16, 17, 18 respectively in FIG. 7. The UMS-PCR1 primers interrogate CpG sites 7, 8 and 15, 16, 17, 18 respectively.

FIG. 8 shows the wild-type sequence of the anti-sense strand of AC063951 between bases 82200-83267. Indicated on this diagram is the position of the MS-PCR1 primers (AS-meth) and the UMS-PCR1 primers (AS-unmethy). The methyl specific MS-PCR1 primers amplify a CpG sites numbered 6, 7, 8 and 15, 16, 17, 18 respectively in FIG. 7. The UMS-PCR1 primers interrogate CpG sites 7, 8 and 15, 16, 17, 18 respectively.

FIG. 9 shows a blow up of the region and the sequences of the antisense strand that are amplified by the methyl-specific and unmethyl-specific PCR primers.

FIG. 10 corresponds to FIG. 8, but does not show the wild-type sequence of the anti-sense strand, but the bisulfite converted sequence of a uniformly methylated antisense strand. Indicated again are the position of the methylation specific PCR primers for the MS-PCR1 assay.

FIG. 11 also corresponds to FIG. 8, but does not shows the wild-type sequence of the antisense strand, but the bisulfite converted sequence of a uniformly unmethylated antisense strand. Indicated are the position of the unmethylation specific PCR primers for the UMS-PCR1 assay.

FIG. 12 discloses the bisulfite converted sequence of the unmethylated sense strand of nucleotides 82200-83267 of AC063951, renumbered such that basepair 82200 is designated as nucleotide 1.

FIG. 13 similarly discloses the bisulfite converted sequence of a uniformly methylated sense strand of nucleotides 82200-83267. To one skilled in the art these disclosures would permit design of methylation specific PCR primers directed against the bisulfite converted sequences of either the sense or antisense strands of the region 82200-83267 demonstrated herein as enabling the detection of human colon cancers.

FIG. 14 shows the tabular results of MS-PCR1 assay performed on 31 colon cancer cell lines that do or do not express the SLC5A8 transcript. 70% of cell lines that do not express SLC5A8 score as methylated in the MS-PCR1 assay. No methylation is detected in any cell line that expresses SLC5A8 (100% specificity for prediction of SLC5A8 expression).

FIG. 15 shows the tabular results of MS-PCR1 assay performed on 63 matched sets of primary colon cancer tumor tissue and accompanying normal colon tissue. The assay detects 59% of all colon cancers. No methylation was detected in any of 26 normal tissues from patients with unmethylated colon cancers. 3 individuals with MS-PCR1 positive methylation assays in their cancers also showed positivity in their normal colon tissue. It is likely that this represents detection of microscopic contamination of these tissues by tumor cells.

To further test that assertion, FIG. 16 gives the results of testing 12 normal colon tissues from individuals without colon cancer. None of the tissues test positive in the MS-PCR1 test. We therefore estimate the sensitivity of MS-PCR1 for detecting colon cancer at 59% and the specificity at 100%.

Figure 17:
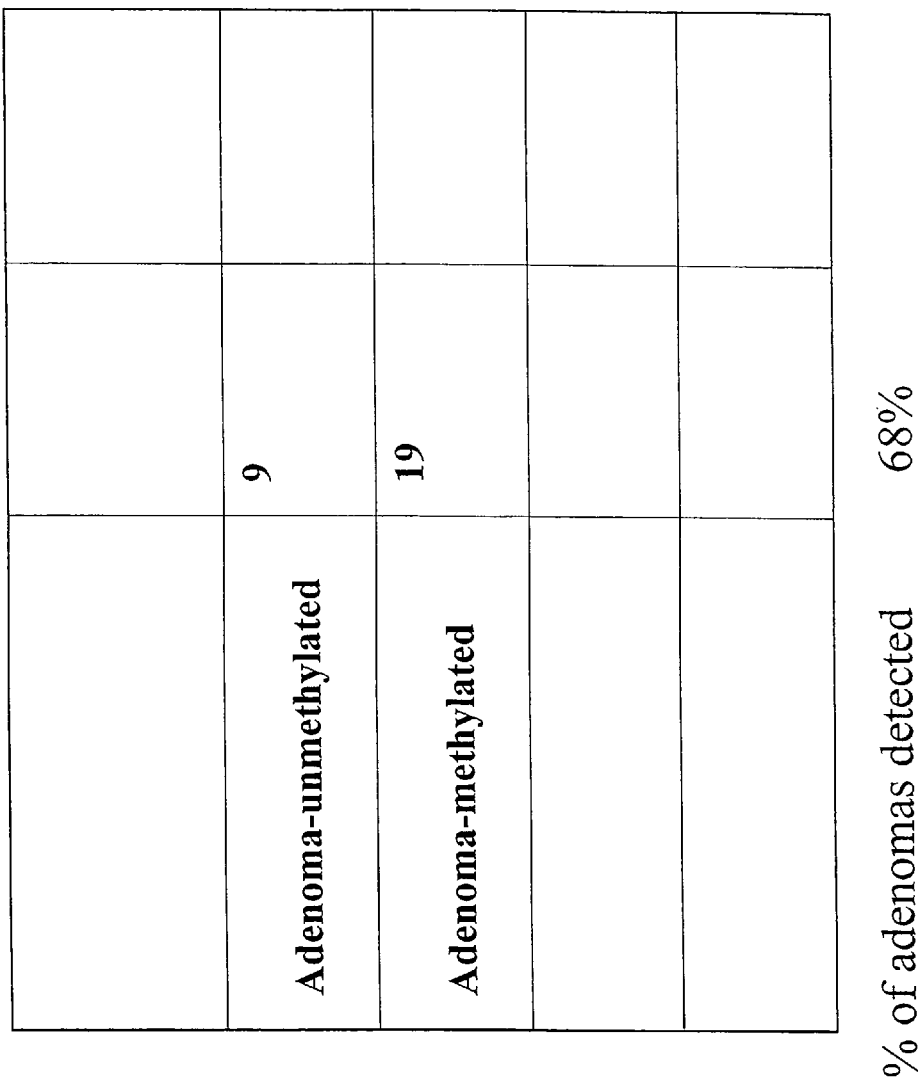
FIG. 17 shows the tabular results of the MS-PCR1 assay of 28 premalignant colon adenomas, 68% of which are detected.

FIG. 17 gives the tabular results of the MS-PCR1 assay of 28 premalignant colon adenomas, 68% of which are detected.

Figure 19:
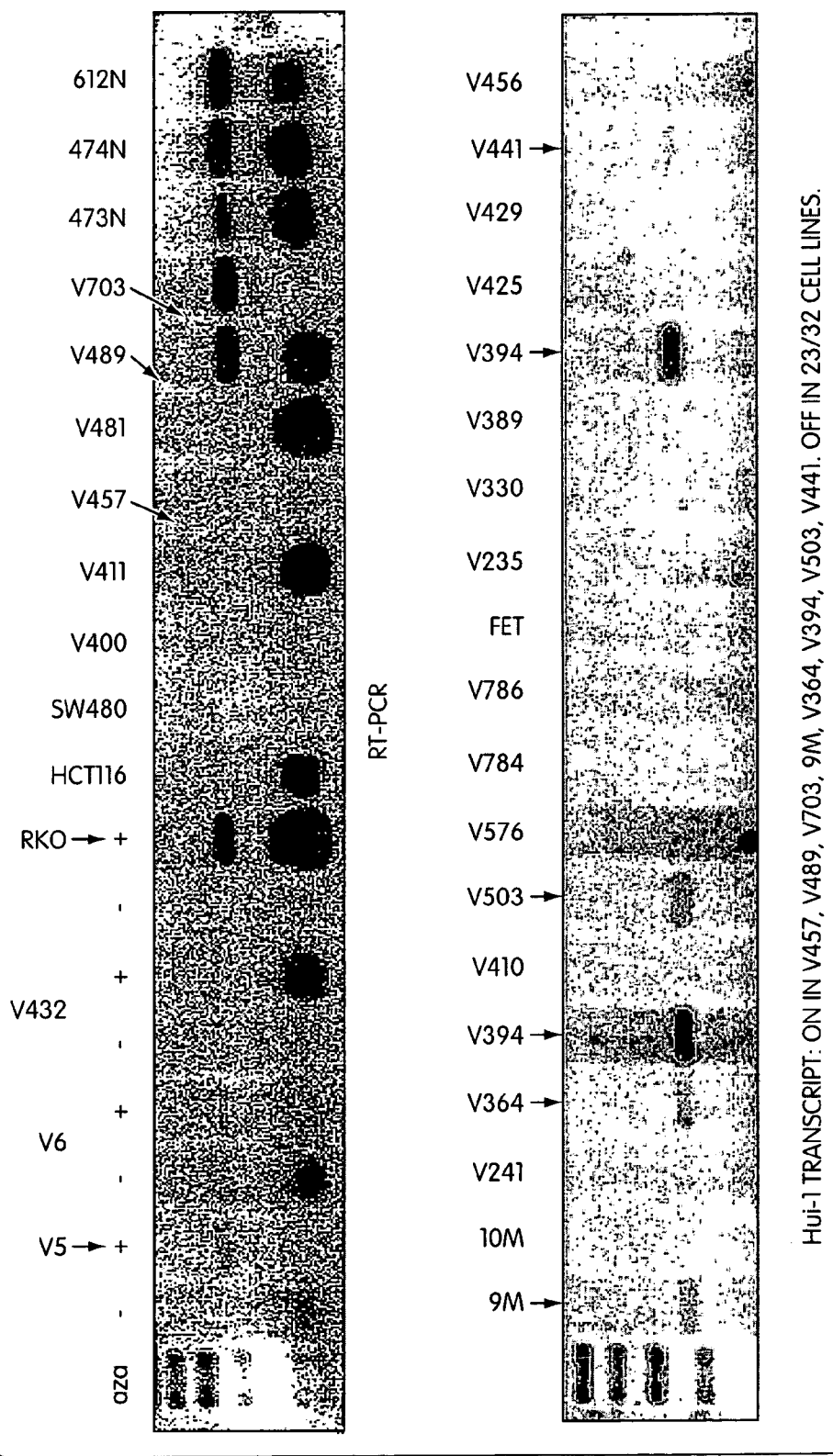
FIG. 19 shows RT-PCR detection of the SLC5A8 transcript in normal colon and in a minority subset of colon cancer cell lines.

FIG. 19 shows RT-PCR detection of the SLC5A8 transcript in normal colon and in a minority subset of colon cancer cell lines, but also demonstrates that 23 of 31 colon cancer cell lines do not express SLC5A8.

Figure 20:
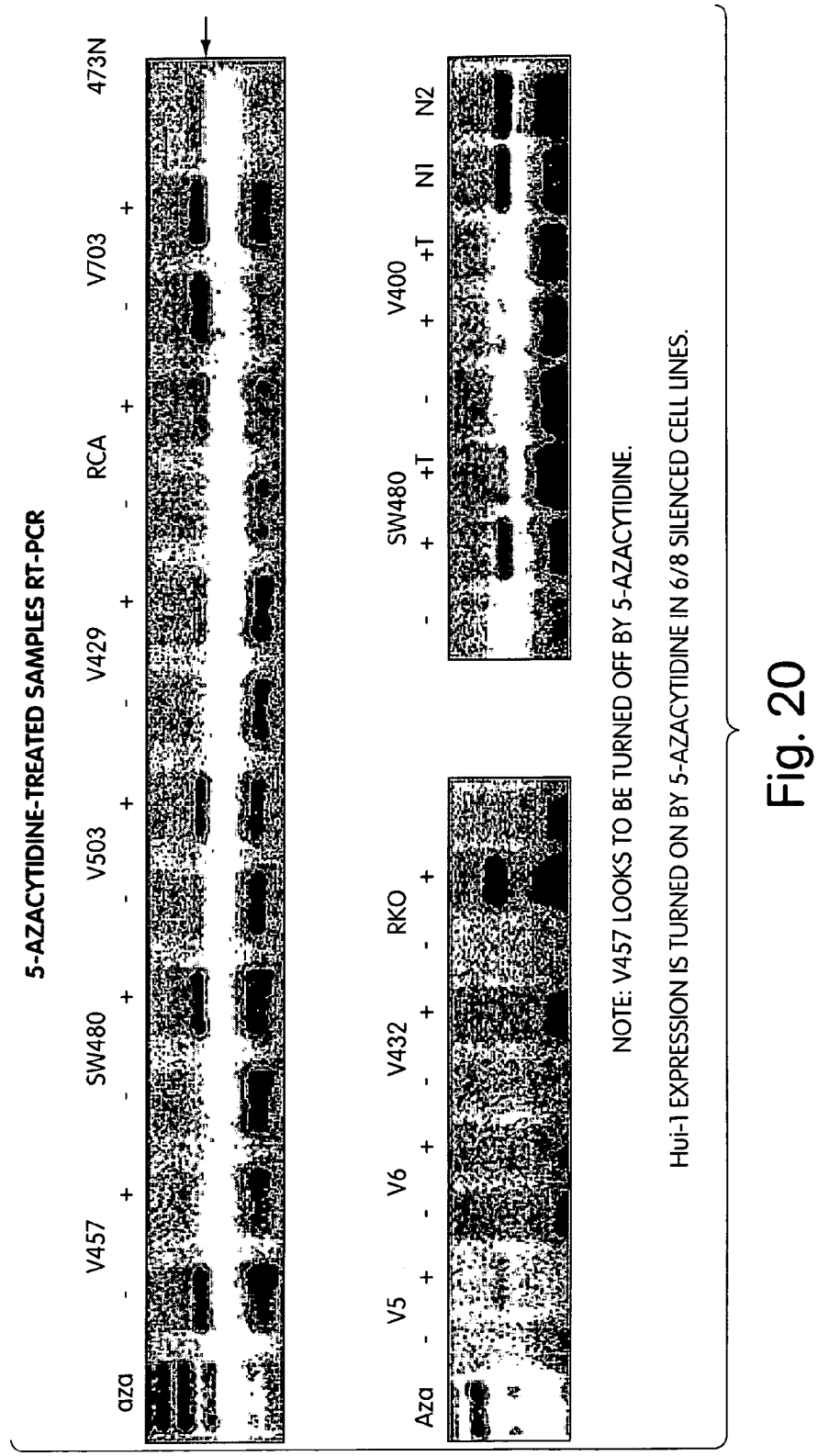
FIG. 20 shows RT-PCR detection of SLC5A8 transcript in colon cancer cell lines that have been treated with the DNA-demethylating agent 5-azacytidine. 5-azacytidine reactivates expression of the SLC5A8 gene in 6 of 8 colon cancer cell lines.

FIG. 20 shows RT-PCR detection of SLC5A8 transcript in colon cancer cell lines that have been treated with the DNA-demethylating agent 5-azacytidine. 5-azacytidine reactivates expression of the SLC5A8 gene in 6 of 8 colon cancer cell lines, strongly consistent with DNA methylation as the cause of silencing of the SLC5A8 transcript.

Figure 21:
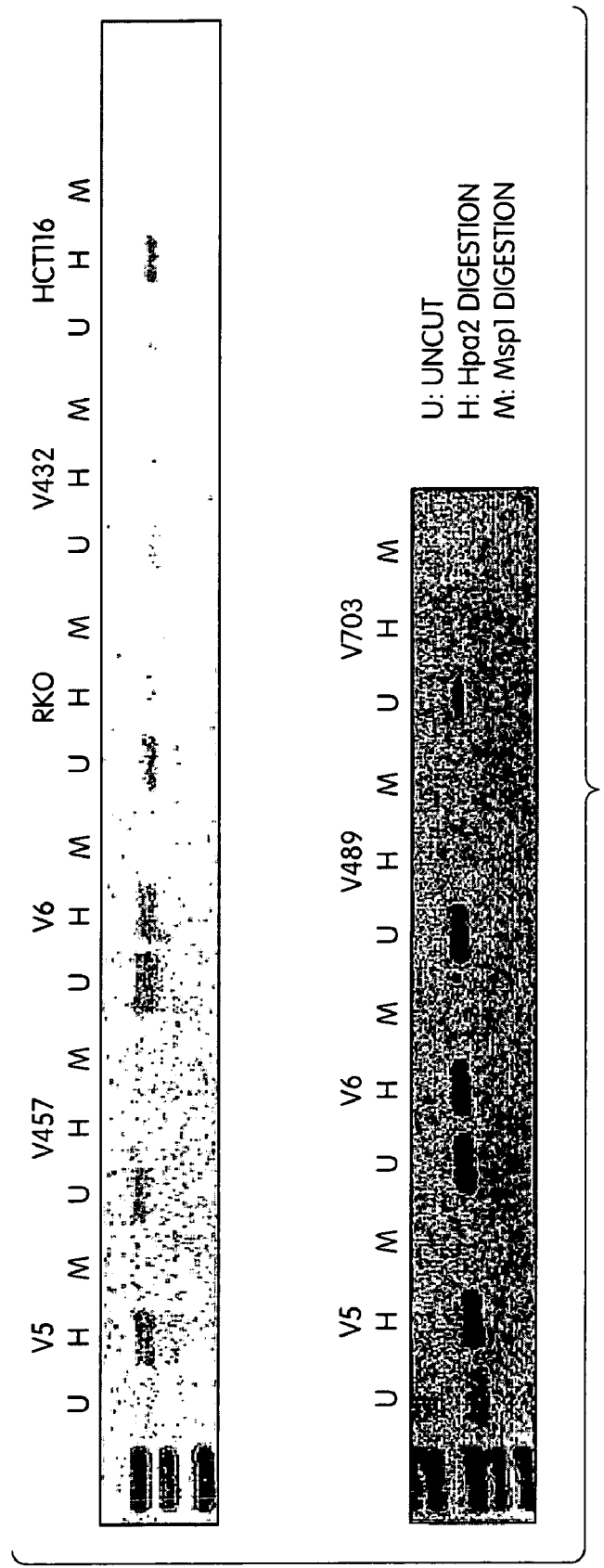
FIG. 21 demonstrates detection of methylation of the SLC5A8 locus by showing resistance of the locus to HpaII digestion. The 4 HpaII assay (as described in the invention disclosure) is based on PCR amplification of a portion of the SLC5A8 locus. Lanes labeled U show control amplification of undigested SLC5A8 DNA. Lanes labeled M show amplification of DNA that has first been cut with the restriction enzyme Msp1.

FIG. 21 demonstrates detection of methylation of the SLC5A8 locus by showing resistance of the locus to HpaII digestion. The 4 HpaII assay (as described in the invention disclosure) is based on PCR amplification of a portion of the SLC5A8 locus. Lanes labeled U show control amplification of undigested SLC5A8 DNA. Lanes labeled M show amplification of DNA that has first been cut with the restriction enzyme Msp1. Msp1 digestion of the DNA eliminates the ability to amplify the locus. Lanes labeled H show amplification of DNA that has first been cut with the restriction enzyme HpaII. HpaII cuts the same sequence as Msp1, but unlike Msp1, HpaII is blocked by DNA methylation. The presence of amplified HpaII cut DNA indicates methylation of the DNA in cell lines V5, V6, RKO, V432, HCT116, V5, V6, V489.

Figure 22:
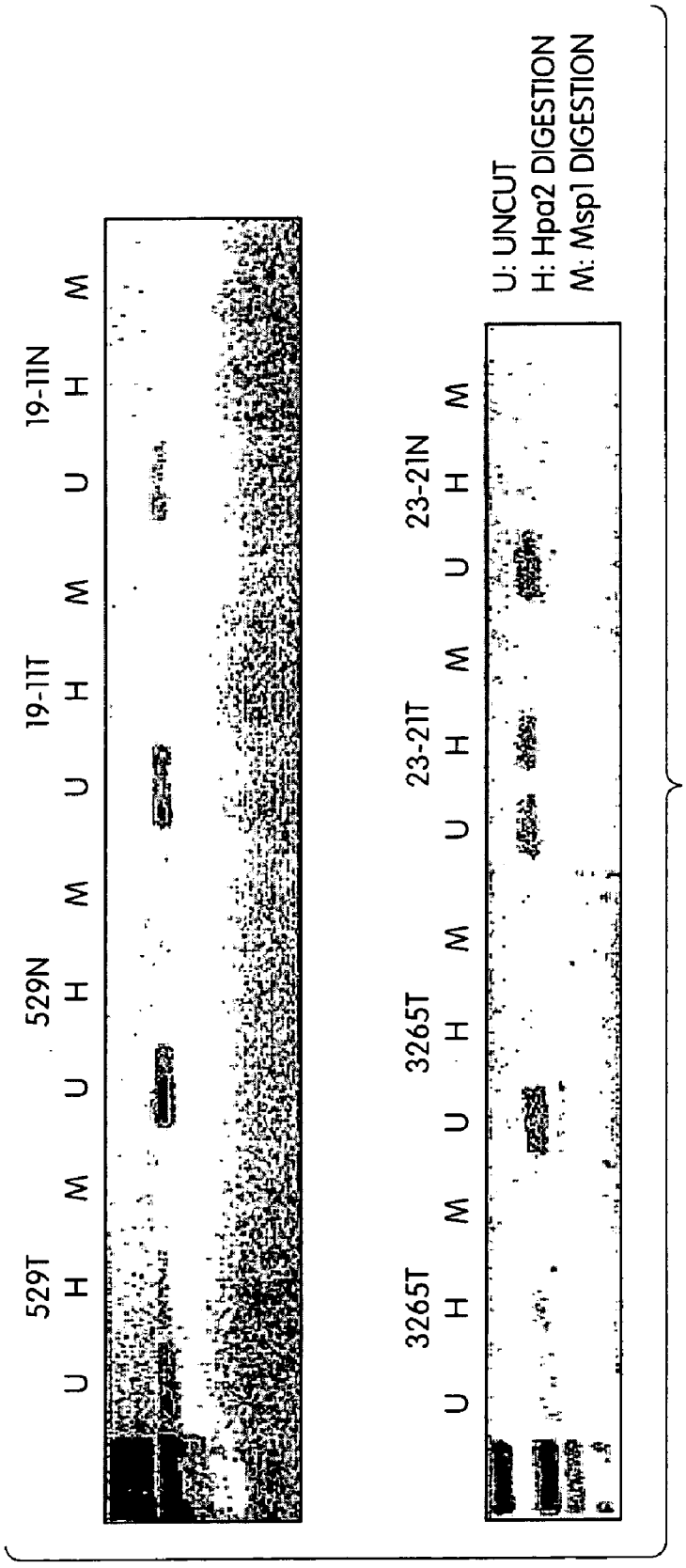
FIG. 22 demonstrates detection of SLC5A8 DNA methylation in primary colon cancer tumors but not in matched normal tissue from the same patients. Samples labeled T represent colon cancer tumor tissue; whereas samples labeled N represent the matched normal tissue.

FIG. 22 demonstrates detection of SLC5A8 DNA methylation in primary colon cancer tumors but not in matched normal tissue from the same patients. Samples labeled T represent colon cancer tumor tissue; whereas samples labeled N represent the matched normal tissue. Detecting a PCR amplified band after HpaII digestion (lanes labeled H) indicates methylation of the SLC5A8 locus. Methylation of tumor but not normal tissue is seen in samples 529, 365, and 23-21.

EXAMPLE 2

A. Identification of the SLC5A8 Gene

Figures 23A, 23B:
FIGS. 23A-23B show the identification of SLC5A8. (A) Shown is the genomic structure of the SLC5A8 gene. Black boxes represent exons, and arrows the start codon and stop codons respectively. (B) The nucleotide sequence of the SLC5A8 coding region (SEQ ID NO: 4).
Figure 28:
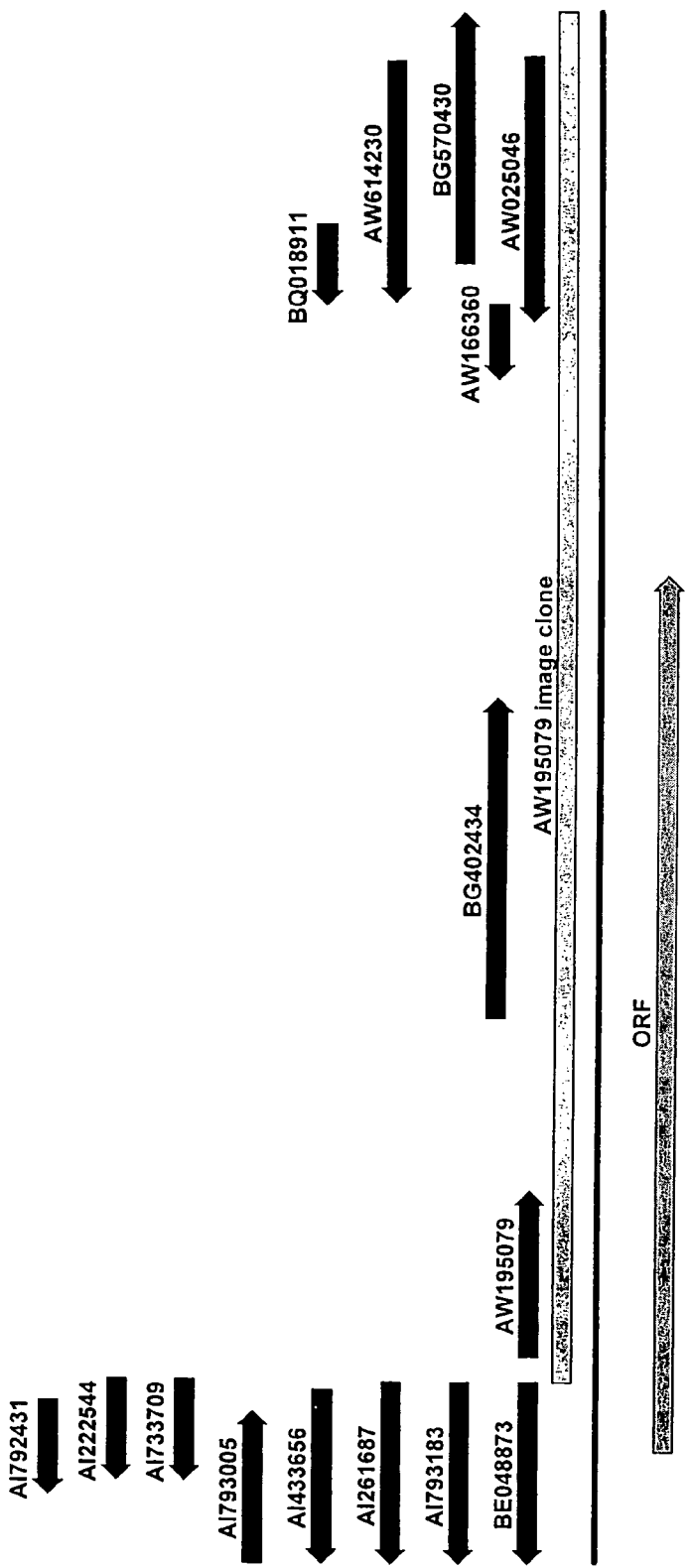
FIG. 28 shows the cloning of SLC5A8 transcript. Black bars indicate representative ESTs. The lighter gray bar indicates sequence generated from an image clone. The dark gray bar indicates open reading frame encoding SLC5A8 protein.
Figure 29:
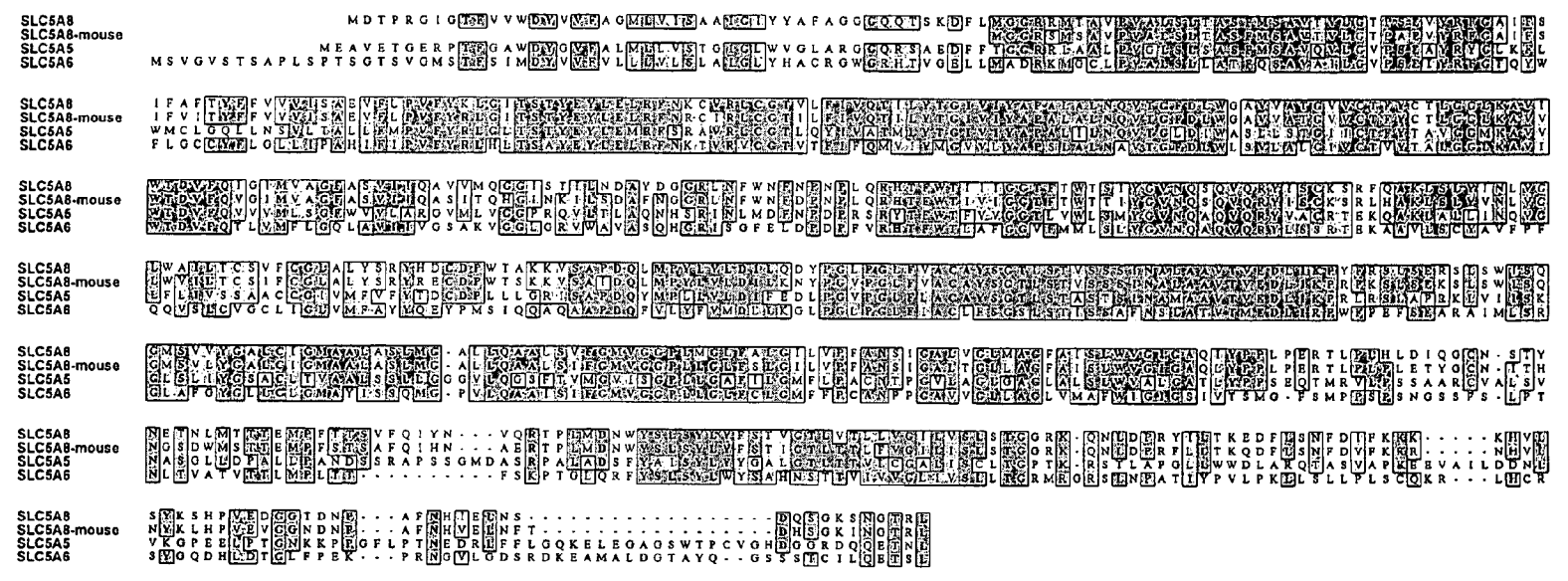

Methylation events in genomic DNA from 12 colon cancer cell lines were profiled by restriction landmark genomic scanning. Out of 1,231 unselected CpG islands visualized, spot 3D41 was detected as absent and presumptively methylated in 11 of the 12 colon cancer cell lines. A 510 base pair genomic fragment surrounding the 3D41 site was cloned and shown to correspond to genomic sequence on human chromosome 12q22-23. RNA from normal human colon mucosa was used for connection RT-PCR that linked together over 10 EST sequences mapping to this genomic region. New sequence was generated both by sequencing of these RT-PCR amplified products, as well as by sequencing image clones corresponding to these ESTs (FIG. 28). This established that the 3D41 site was included within a new transcript encoded by a novel gene (FIG. 23B). This gene, located on chromosome 12q22-23 gene, is comprised of 15 exons, with the site from RLGS located in exon 1 (FIG. 23A). The newly identified transcript includes an in frame TAA stop codon 5' to the presumptive ATG start codon, which additionally is embedded within a GCCATGG sequence that conforms to the standard for a good Kozak sequence. BLAST alignment of the predicted protein product of this novel transcript showed the most closely related proteins to be the human sodium iodide symporter—SLC5A5 (46% homology) and the human sodium-dependent multivitamin transporter—SLC5A6 (43% homology), both of which belong to the solute carrier 5 family (SLC5) of sodium coupled transporters (FIG. 29). Moreover, analysis of the predicted novel protein by the TMHMM prediction program identified 13 transmembrane fragments, which is consistent with structural features of the sodium iodide symporter. Thus structurally, this new transcript encodes a novel member of the SLC5 sodium solute symporter family (SSF) family, and HUGO assigned the encoded protein the name of SLC5A8. A mouse protein of unknown function shows 77% identity to SLC5A8, and is likely the mouse homologs of the human protein (FIG. 29). RT-PCR confirmed SLC5A8 transcript was expressed by normal colon mucosa, as well as by kidney, lung, esophagus, small bowel, stomach, thyroid, and uterus, with greatest expression seen in kidney.

B. SLC5A8 is frequently silenced and methylated in colon cancer cell lines.

Figure 24:
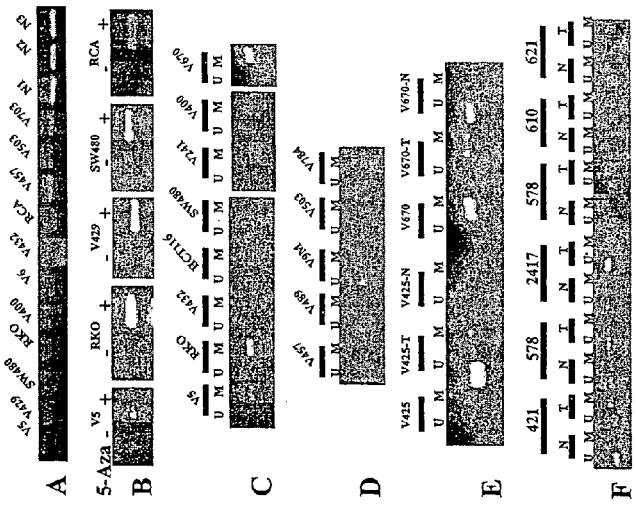
FIGS. 24A-24F show SLC5A8 expression. (A) Shown is RT-PCR analysis demonstrating SLC5A8 transcript expression in three normal colon mucosa samples (N1, N2, N3), but absence of SLC5A8 transcript in most colon cancer cell lines (remaining samples). (B) Shown is RT-PCR analysis demonstrating reactivation of SLC5A8 expression in cell lines treated with 5-azacytidine (+) compared to untreated (−) controls. (C) Methylation specific PCR (MS-PCR) assay for methylated (M) or unmethylated (U) SLC5A8 exon 1 sequences detects exclusively methylated templates in SLC5A8 silenced cell lines. (D) MS-PCR detects only unmethylated SLC5A8 templates in SLC5A8 expressing cell lines. (E) MS-PCR detection of methylated SLC5A8 templates in colon cancer tumors (T) antecedent to SLC5A8 methylated cell lines (V425, V670). Matched normal colon tissue (N) shows only unmethylated templates. Unmethylated templates in tumor tissue presumptively arise from contaminating non-malignant cells. (F) MS-PCR analysis of colon cancer tumors (T) and matched normal (N) colon tissues. Methyl specific bands are seen in each of the tumor samples, but none of the normal controls.

RT-PCR was used to further characterize SLC5A8 expression in normal colon mucosa compared to a collection of 31 colon cancer cell lines. Whereas the SLC5A8 transcript was well expressed in normal colon, it proved absent in 23 of the 31 colon cancer cell lines (FIG. 24A). The methylation of SLC5A8 exon 1 detected by RLGS suggested the hypothesis that aberrant methylation might be the mechanism for silencing of SLC5A8 expression. Consistent with this hypothesis, treatment of SLC5A8 silenced cell lines with the demethylating agent 5-azacytidine reactivated SLC5A8 expression in 6 of 8 colon cancer cell lines tested (FIG. 24B and data not shown). Sequencing of the SLC5A8 transcript in the 8 colon cancer cell lines in which it was expressed showed only wild-type sequence with no mutations. Thus methylation, but not mutation, appeared to be the putative mechanism for inactivating SLC5A8 in colon cancer.

Figure 30:
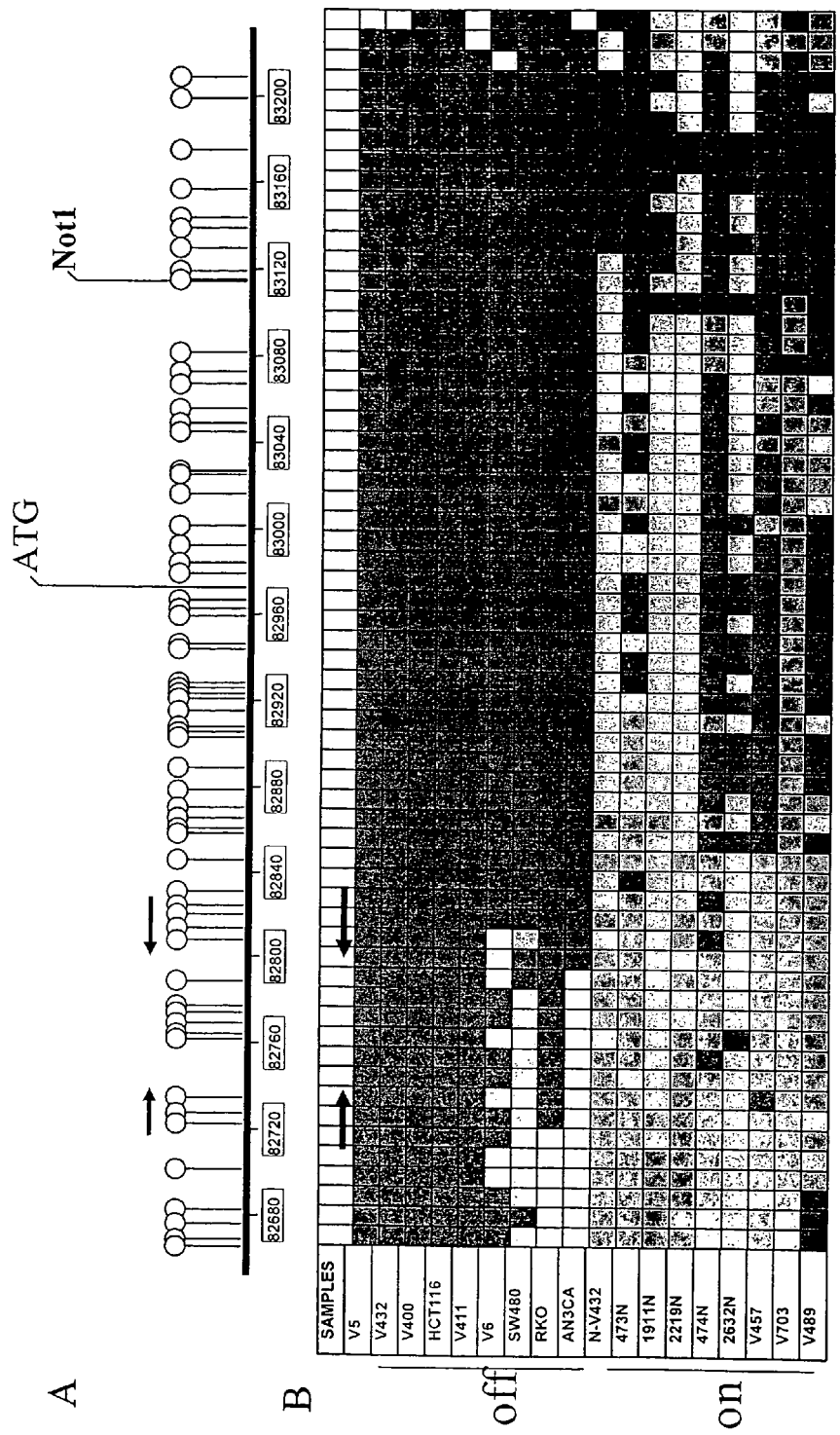
FIGS. 30A-30B show methylation in SLC5A8 exon 1. (A) Diagrammatic representation of the CpG island in SLC5A8 exon 1. Balloons represent CpG dinucleotides. Coordinates represent nucleotide positions numbered as per GenBank entry AC063951. Positions of the ATG and NotI site are indicated. Arrows cover the regions interrogated by primers for MS-PCR. (B) Diagrammatic summary of methylation status of the 62 CpG sites in SLC5A8 exon 1 as determined by sequencing of bisulfite converted genomic DNA. Each site is sequentially represented by one shaded block. Black represents sites that are fully methylated. Darker gray represents sites that are fully unmethylated. And lighter gray represents sites that are partially methylated. Samples include 9 SLC5A8 silenced cell lines (Off samples), 6 SLC5A8 expressing normal colonic mucosa (On samples designated N), and 3 SLC5A8 expressing cell lines (On samples designated V). Arrows indicate sites that are interrogated by MS-PCR primers and bracket a differentially methylated region that is unmethylated in SLC5A8 expressing samples and is methylated in SLC5A8 silenced samples.

To identify target sequences for aberrant SLC5A8 methylation in colon cancer, we investigated a dense CpG island (G+C %=70%, CG/GC=0.9) located in SLC5A8 Exon 1, and surrounding the 3D41 site. This region covered 573 base pairs and included 62 CpG dinucleotides (FIG. 30A). In contrast, the region immediately 5' of exon 1 showed only a 46% G+C content. We used sodium bisulfite treatment of genomic DNA to convert unmethylated cytosines to uracil; while leaving methylated cytosines unchanged (Herman and Baylin, 1998, Current Protocols in Human Genetics, N. E. A. Dracopoli, ed., John Wiley & Sons, 2:10.6.1-10.6.10). Sequencing of PCR amplified bisulfite converted SLC5A8 exon 1 genomic DNA was then used to determine the methylation status of each of the 62 target cytosines within the CpG island domain. Comparing the findings in nine SLC5A8-silenced cell lines versus those in three SLC5A8-expressing cell lines and in six samples of SLC5A8 expressing normal colon mucosa defined a 182 bp subregion. In the nine SLC5A8-silenced cell lines this subregion demonstrated uniform methylation of all CpG cytosines; whereas, these cytosines were uniformly unmethylated in the three SLC5A8 expressing cell lines and six normal colon mucosa samples (FIG. 30B). Primers for assay of this subregion by methylation specific PCR (MS-PCR) were designed, such that following bisulfite conversion amplification products would selectively be derived from either methylated (M) or unmethylated (U) genomic templates (Herman and Baylin, 1998, Current Protocols in Human Genetics, N. E. A. Dracopoli, ed., John Wiley & Sons, 2:10.6.1-10.6.10). MS-PCR assay of 31 total colon cancer cell lines demonstrated SLC5A8 exon 1 methylation was present in 16 cases (52%), and in each of these methylated cell lines, no SLC5A8 transcript was detectable (FIG. 24C). In contrast, in each of the 8 SLC5A8 expressing cell lines MS-PCR assayed exon 1 as unmethylated (FIG. 24D). In 7 remaining instances, SLC5A8 expression was absent, but aberrant methylation was not detected as the reason. Moreover, in the case of two of the SLC5A8-methylated cell lines (V425 and V670), DNA from antecedent tumor and matched patient normal tissue was also available. In each of these cases, MS-PCR confirmed that SLC5A8 methylation was present in the primary tumor tissues, but was absent in the matched normal tissues (FIG. 24F). Thus the SLC5A8 methylation and silencing detected in colon cancer cell lines reflects somatic aberrations present in primary colon cancer tissues. We note that the finding of gene silencing associated with aberrant methylation in a first exon region corresponding to 5' untranslated sequences has existing precedent at other loci (Attwood et al, 2002, Cell Mol Life Sci 59: 241-257; Jones, P. A. 1999, Trends Genet 15: 34-37).

In previous studies our group has noted that in colon cancers aberrant methylation of hMLH1 and of HLTF commonly silences both maternal and paternal alleles in the same tumor Veigl, et al., 1998, Proc Natl Acad Sci USA 95:8698-702; Moinova, et al., 2002, Proc Natl Acad Sci USA 99:4562-7). Consistent with this mechanism, testing of microsatellite markers D12S1041 and D12S1727, that flank SLC5A8, showed the presence of two distinguishable parental SLC5A8 chromosomal regions in 10 of 10 colon cancer cell lines that showed the presence of only methylated SLC5A8 exon 1.

C. SLC5A8 methylation is commonly present in primary colon cancers and in colon adenomas.

To further establish the frequency of SLC5A8 exon 1 methylation in primary colon cancer tumors, we analyzed by MS-PCR an additional 64 pairs of primary colon cancer tumor tissues as well as their accompanying matched normal colon tissues. SLC5A8 methylation was detected in 38 of 64 (59%) primary colon cancers (FIG. 24F and Table 2 below). In 35 of 38 cases (92%) in which colon tumors showed SLC5A8 methylation, this methylation was not detected in the same individuals' normal colon tissues. SLC5A8 exon 1 methylation thus substantially arose in these individuals' cancers as part of and during the neoplastic process. In 3 cases in which SLC5A8 methylation was detected in both an individuals' cancerous and normal colon tissues, these findings likely indicate either the presence of some cancer cells within the grossly normal resected tissue, or the possibility that the cancer arose from a field of SLC5A8 methylated cells. The rarity of detecting SLC5A8 methylation in normal colon tissues is highlighted by noting that no SLC5A8 methylation was detected in any of the 26 normal colon tissues in which the accompanying colon cancer was also unmethylated (Table 2 below), and moreover, that no SLC5A8 methylation was detected in any of 12 additional normal colon tissues from resections done for non-cancer diagnoses.

TABLE 2

SLC5A8 Methylation in Colon Tumors and Matched Normal Mucosa. Shown is the characterization of 64 pairs of colon cancer tumors and matched normal colon tissues assayed for methylation of SLC5A8 exon 1 by MS-PCR. Indicated are the numbers (and percentages) of tissue pairs with each of the four possible methylation phenotypes.

|  |  | NORMAL TISSUE | |
| --- | --- | --- | --- |
|  |  | Methylated | Unmethylated |
| TUMOR TISSUE | Methylated | 3 (5%) | 35 (54%) |
|  | Unmethylated | 0 (0%) | 26 (41%) |

Among all primary cancers and cell lines analyzed, the finding of SLC5A8 methylation in colon cancer tumors and cell lines was not significantly correlated with either patients' sex (P=0.39) or age (P=0.52), with a median age of 69 in persons with SLC5A8-methylated cancers versus 67 in those with SLC5A8 unmethylated cancers. Moreover, the distribution by tumor stage (Dukes' stage B, C, D primary tumor; or metastatic cancer deposit) was not significantly different between SLC5A8-methylated and nonmethylated colon cancers (P=0.77) (Table 3 below). SLC5A8 methylated and unmethylated cancers also showed no significant difference with respect to site of origin in the rectum, left colon, or right colon (P=0.47) (Table 4 below).

TABLE 3

Distribution of SLC5A8 methylation by tumor stage. Shown are numbers (and %) of colon neoplasms (tumor and cell lines) in each category defined by clinical stage and SLC5A8 methylation status.

| Tumor Stage | SLC5A8 Methylated | SLC5A8 Unmethylated |
| --- | --- | --- |
| Adenoma | 17 (24%) | 12 (23%) |
| Duke's B | 24 (34%) | 16 (30%) |
| Duke's C | 15 (21%) | 13 (25%) |
| Duke's D | 6 (8%) | 5 (9%) |
| Metastatic lesion | 7 (10%) | 7 (13%) |

TABLE 4

Distribution of SLC5A8 methylation by tumor site. Shown are numbers (and %) of colon neoplasms (tumor and cell lines) in each category defined by location in the colon and SLC5A8 methylation status.

| Tumor site | SLC5A8 Methylated | SLC5A8 Unmethylated |
| --- | --- | --- |
| Right colon | 12 (23%) | 13 (35%) |
| Left colon | 30 (59%) | 20 (54%) |
| Rectal | 9 (18%) | 4 (11%) |

To determine the timing of onset of SLC5A8 silencing during colon carcinogenesis, we additionally analyzed a group of 29 adenomas for SLC5A8 exon 1 methylation. SLC5A8 methylation was detected in 17 of the 29 (59%) adenoma cases. SLC5A8 methylation thus appears to be an early event that is already established in colon neoplasia by the adenoma stage.

D. Quantitative assay of SLC5A8 exon 1 methylation.

Figure 25:
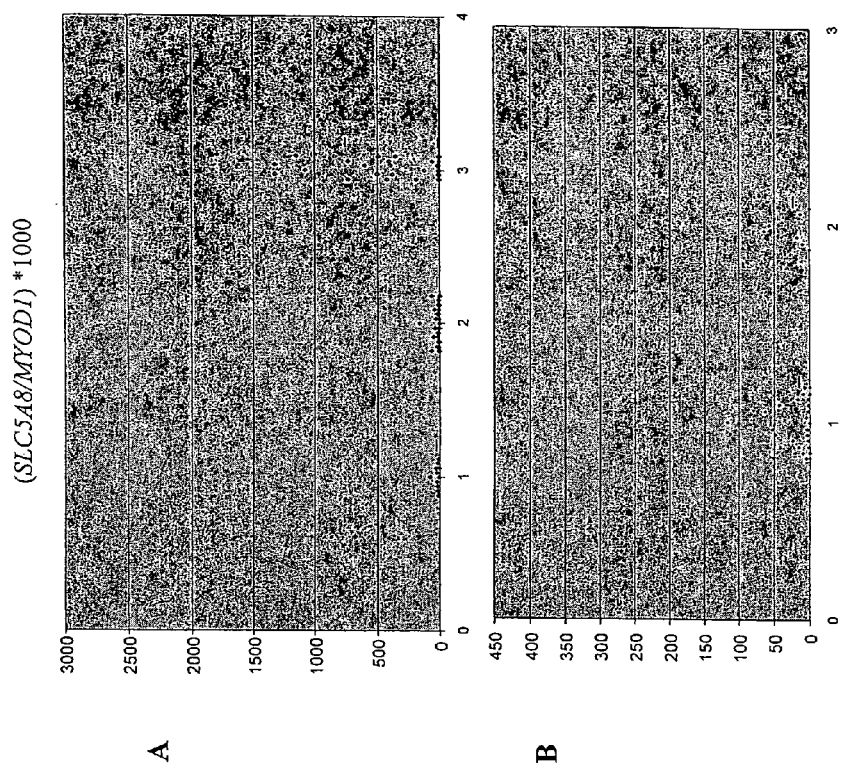
FIGS. 25A-25B show real time MS-PCR analysis of SLC5A8 methylation. Plotted are 1000 times the ratio of measured SLC5A8 methylated product to the control MYOD1 derived product. (A) Detection of SLC5A8 methylation in primary colon cancer tissues. Column 1 displays values for normal colon tissues harvested from non-cancer resections (dark diamonds). Column 2 displays values for normal colon tissues harvested from colon cancer resections (dark diamonds). Column 3 displays values for colon cancer tissues divided into unmethylated samples falling within the normal tissue range (dark diamonds at the bottom), versus methylated samples showing values greater than the normal tissue range (light diamonds at the top). Adjacent bars indicate population means. (B) Real time MS-PCR analysis of SLC5A8 methylation in aberrant crypt foci. Column 1 displays values for 24 normal colon tissues harvested from colon resections from 11 individuals (dark diamonds). Column 2 displays values for 15 aberrant crypt foci harvested from the same 11 individuals' resections. Dark diamonds (at the bottom) indicate unmethylated samples within the normal range, and light diamonds (at the top) indicate methylated samples falling within the range previously demonstrated by methylated cancers. Adjacent bars indicate the mean value for each group.

To derive a quantitative measure of SLC5A8 methylation, we employed a real time MS-PCR assay whose results were expressed as 1000 times the ratio of methylated SLC5A8 reaction product to a control MYOD1 reaction product (Usadel, et al., 2002, Cancer Res 62:371-5). In this assay, 0 methylation was detected in the Vaco9 SLC5A8 expressing colon cancer cell line, and a methylation value of 1000 was detected in the SLC5A8 methylated and silenced RKO colon cancer cell line. As shown in FIG. 25A, assay for SLC5A8 exon 1 methylation in 11 normal colon mucosal samples derived from non-cancer resections yielded only barely detectable methylation values (mean value=24; range=4-82) and defined an "unmethylated normal range" of values all <100. Analysis of 29 normal colon samples derived from colon cancer resections gave similarly low values with a mean value=22 and with a single outlier sample (value=159) falling outside the range defined by the non-cancer derived normal tissues. This observation essentially replicated our previous observation of rare faint methylation events detected in some cancer associated normal tissue. In contrast, analysis of colon cancer samples clearly distinguished two populations of tumors. Twelve cancers were deemed unmethylated, as they showed methylation values falling well within the population normal range (mean value =12; range=0-58) (FIG. 25A), and hence were indistinguishable from unmethylated normal tissues. In contrast, 17 cancers with methylation values greater than the normal range comprised a distinct "methylated" group of cancers that was characterized by a mean methylation value of 747 and a range=(121-2549) (FIG. 25A). The mean methylated colon cancer thus displayed 75% the level of methylation as was measured in a pure cell line population of methylated RKO cells. The heterogeneity in measured methylation values among the methylated colon cancers may in part derive from differences among the tumors in levels of contaminating and infiltrating non-cancer cells. The methylated and unmethylated cancer populations defined by real time MS-PCR respectively corresponded to the tumors classified as unmethylated and methylated in the previous non-quantitated MS-PCR reaction.

E. Detection of SLC5A8 methylation in aberrant crypt foci.

The finding of SLC5A8 methylation in colon adenomas prompted us to consider that SLC5A8 methylation might be an early event in human colon neoplasia. The earliest morphologically identifiable colon neoplasias putatively are aberrant crypt foci (ACF) (Siu et al., 1999, Cancer Res 59: 63-66). These microscopic morphologically aberrant multicrypt structures are recognizable in unembedded colon under low power magnification. Moreover, a subset of ACF lesions demonstrate both histologic dysplasia and mutations of the APC tumor suppressor gene (Bird, 1987, Cancer Lett 37:147-51; Pretlow, et al., 1991, Cancer Res 51:1564-7), suggesting that at least some ACF have potential to progress to colon adenomas and cancers. To assess a possible role of SLC5A8 methylation in ACF development, 15 ACF, composed of from 17 to 155 crypts (48±36 crypts, mean ± standard deviation), were dissected from 11 different patients' colons bearing either cancer or adenomas. From these same 11 cases, 24 similarly sized tissue samples were dissected from mucosal regions that appeared normal under low power magnification. Real time MS-PCR analysis of SLC5A8 methylation in the 24 control normal samples gave results similar to those obtained in previous normal mucosal samples, with a mean SLC5A8 methylation value of 12, and with only one of these 24 new samples (methylation value of 117) falling just outside of the previously determined normal limit of 100 (FIG. 25B). In contrast, analysis of DNA from the ACF revealed two distinct populations, with 8 of 15 ACF falling within the normal range (mean=34, and range=0-113), and with 7 of 15 ACF samples demonstrating SLC5A8 values that fell well within the range of methylated cancers (mean=355, range=287-420) (FIG. 25B). In contrast, none of these 15 aberrant crypt foci demonstrated aberrant methylation of hMLH1, which thus likely arises later during colon carcinogenesis. These findings suggest that SLC5A8 methylation is indeed an early aberration that precedes adenoma formation and is detectable in aberrant crypt foci. This finding also further strengthens the model that suggests a subset of aberrant crypt foci are likely to progress to more advanced colonic neoplasms.

F. SLC5A8 methylation as a serologic marker of colon cancer.

Figure 26:
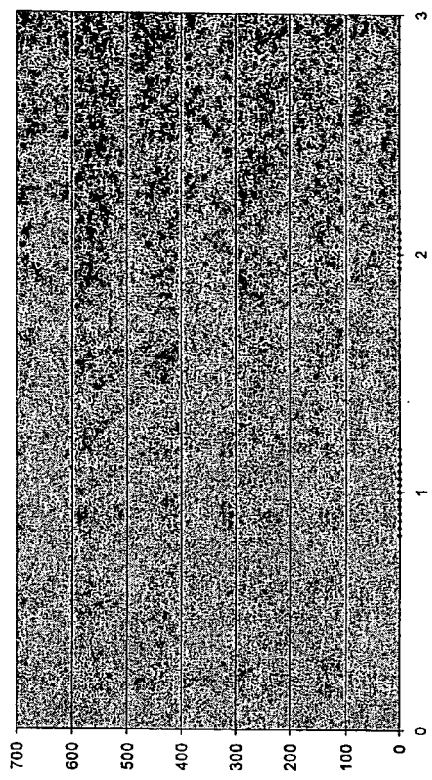
FIG. 26 shows real time MS-PCR analysis of SLC5A8 methylation in DNA precipitated from the serum of colon cancer patients. Plotted are 1000 times the ratio of measured SLC5A8 methylated product to the control MYOD1 derived product. Column 1 displays absence of detectable SLC5A8 methylation in serum of 13 individuals whose colon cancer tumors assayed as unmethylated by MS-PCR (dark diamonds at the bottom). Column 2 displays values of SLC5A8 methylation in the serum of 10 individuals whose colon cancer tumors assayed as methylated by MS-PCR. Dark diamonds (at the bottom) indicate 6 sera without detectable methylation, and light diamonds (at the top) indicate 4 sera in which SLC5A8 methylation was detectable.
Figure 31:
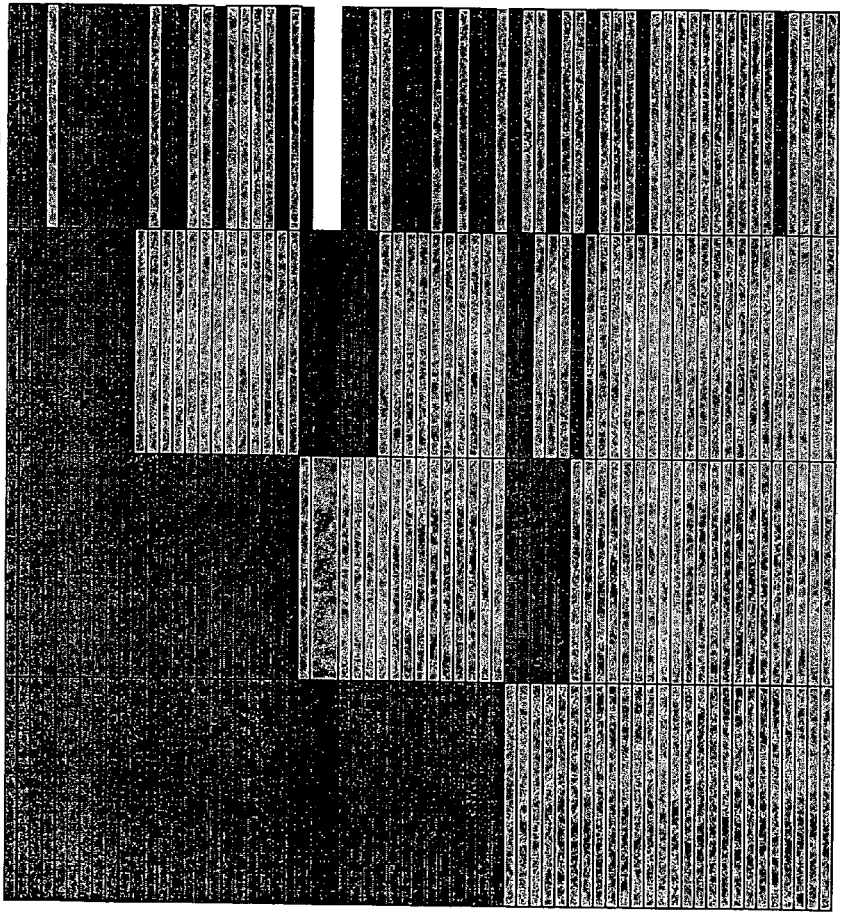
FIG. 31 shows methylation events in primary colon cancers. Shown is analysis of 64 primary colon cancers for aberrant methylation at 4 genomic loci, SLC5A8, HLTF, hMLH1, and p16. Black bars represent positive assays for methylation in tumor tissue, and gray bars represent detection only of unmethylated alleles.

SLC5A8 methylation was detected in 59% of our primary colon samples. In these same samples we had previously noted a 44% frequency of methylation of HLTF, a SWI/SNF family gene (Moinova et al., 2002, Proc Natl Acad Sci USA 99: 4562-4567), and had also found a 44% frequency of methylation of p16 (FIG. 31) (Herman et al., 1995, Cancer Res 55: 4525-4530; Gonzalez-Zulueta et al., 1995, Cancer Res 55: 4531-4535). These data suggest SLC5A8 methylation might be a high quality marker of colon cancer presence. In this regard, we and others have shown that aberrantly methylated genomic DNA from specific loci can be detected in the serum of some cancer patients (Grady et al., 2001, Cancer Res 61: 900-902; Hibi et al., 1998, Cancer Res 58: 1405-1407; Jeronimo et al., 2001, J Natl Cancer Inst 93: 1747-1752; Usadel et al., 2002, Cancer Res 62: 371-375). Accordingly, we characterized the level of SLC5A8 methylation in ethanol precipitable DNA prepared from the serum of colon cancer patients (Grady et al., 2001, Cancer Res 61: 900-902). SLC5A8 methylation was totally undetectable with a measured value of 0 in DNA extracted from each of 13 serum samples from individuals with colon cancers in which SLC5A8 assayed as unmethylated (FIG. 26). In contrast, SLC5A8 methylation was detectable in serum DNA from 4 of 10 patients in which the underlying colon cancer assayed as SLC5A8 methylated (FIG. 26). A positive signal for MYOD1 verified the presence of input DNA into each of these assays. While serologic assays for methylated DNA as a marker of cancer are clearly in the early stages of investigation, we note that a panel of methylated genes that included SLC5A8, HLTF, p16 and hMLH1 provided greater sensitivity than any single locus alone for detecting an aberrant methylation event in our set of 64 primary colon cancers (FIG. 31).

G. SLC5A8 suppression of colon cancer colony formation.

Figure 27A:
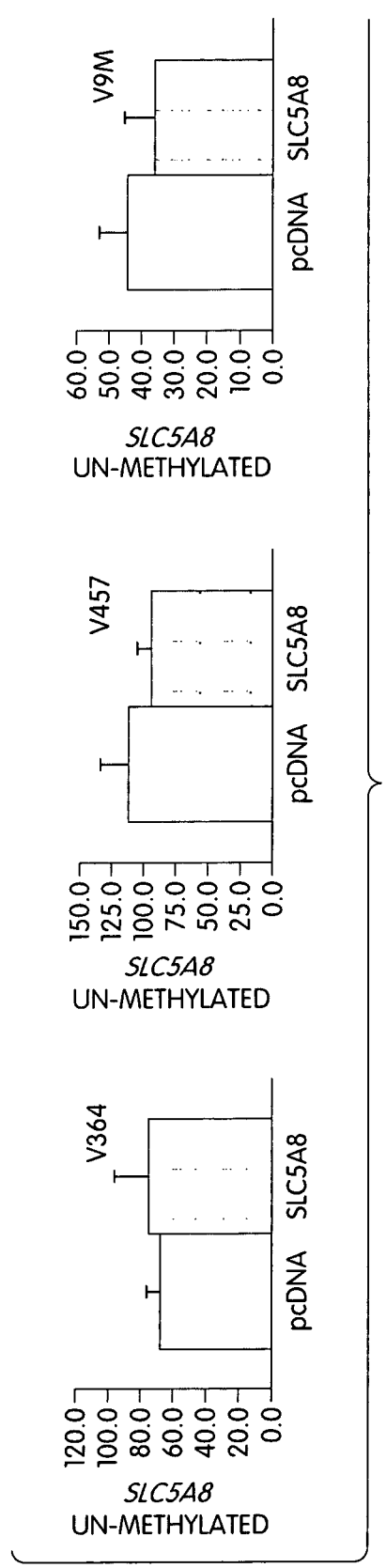
FIGS. 27A-27B show SLC5A8 suppression of colon cancer colony formation. Shown are the number of G418 resistant colonies arising from transfection with a SLC5A8 expression vector (SLC5A8) or a control empty expression vector (pcDNA) in SLC5A8 unmethylated and expressing V364, V457, and V9M cells (panel A) as compared to SLC5A8 methylated and deficient FET, V400, and RKO cells (panel B).
Figure 27B:
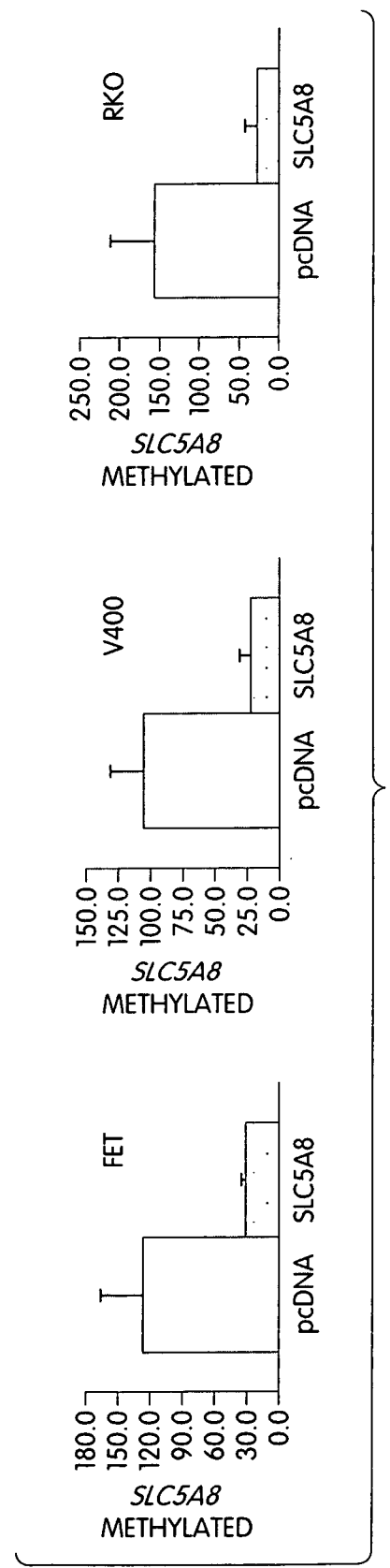

The high frequency of SLC5A8 methylation observed in colon cancer suggested that inactivation of this gene might confer a selective advantage. To assay for such an advantage, we examined the effect of SLC5A8 transfection in three colon cancer cell lines (V400, RKO and FET) in which the endogenous SLC5A8 gene was methylated and silenced, as compared with three colon cancer cell lines (V457, V9M and V364) in which the endogenous SLC5A8 gene remained unmethylated and expressed. Reconstitution of SLC5A8 expression in SLC5A8-methylated cells suppressed colony-forming ability by at least 75% in each of the three lines tested (P<0.01) (FIG. 27B). In contrast, transfection of SLC5A8 did not show significant colony suppression in the any of the three cell lines that already expressed an endogenous SLC5A8 allele (FIG. 27A) (P<0.01 for the difference in effect of SLC5A8 transfection in SLC5A8-methylated versus unmethylated cell lines). Transient transfection showed that both SLC5A8-methylated and unmethylated cells were able to express comparable levels of exogenous SLC5A8, as determined by western analysis for a V5 epitope tag attached to the SLC5A8 cDNA. These findings suggest that SLC5A8 methylation and silencing confers a specific growth advantage in the subset of colon cancers in which this locus is inactivated.

Figure 32:
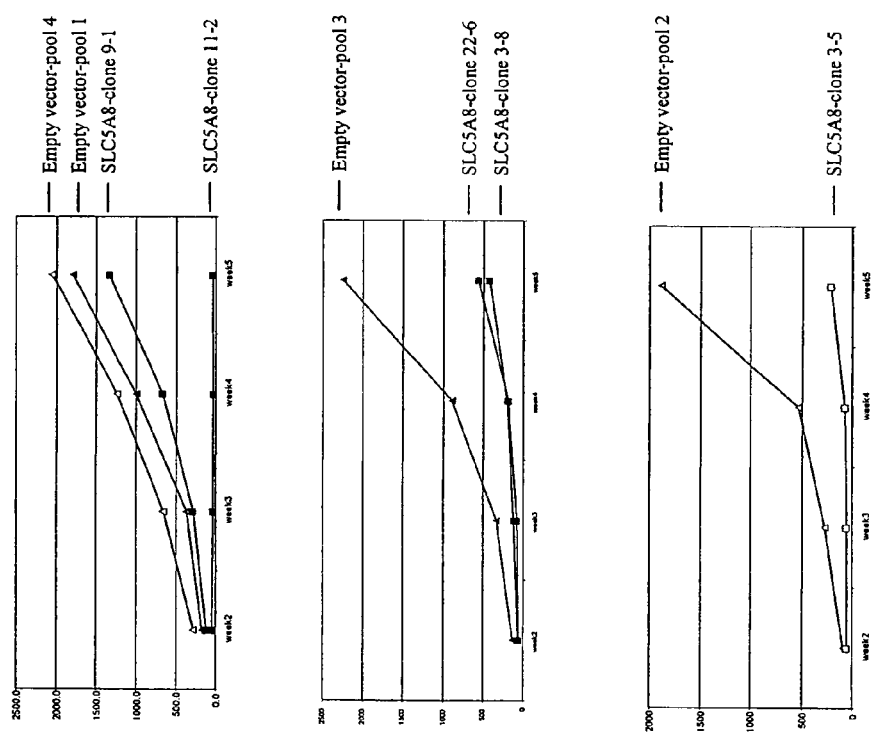
FIG. 32 shows suppression of xenograft growth in 4 of 5 SLC5A8 expressing V400 transfected clones (square symbols, gray lines) as compared with control pools of V400 cells transfected with an empty expression vector (triangular symbols, black lines).

Consistent with this interpretation, we found that 4 of 5 of the rare SLC5A8 expressing clones that grew out following transfection of the SLC5A8 methylated V400 colon cancer cell lines were markedly suppressed in their ability to form xenograft tumors in athymic mice (FIG. 32).

H. Discussion.

In this study, we have identified a novel gene, SLC5A8, that we demonstrate is a new candidate colon cancer suppressor gene. We find that SLC5A8 encodes a sodium transporter and is a new member of the sodium solute symporter family (SLC5). SLC5A8 is frequently targeted for methylation and silencing in human colon cancer, with aberrant SLC5A8 exon 1 methylation was detected in 52% of colon cancer cell lines and in 59% of primary colon cancers. All colon cancer cell lines showed that SLC5A8 exon 1 methylation were silenced for SLC5A8 expression, and SLC5A8 expression could be restored by treatment with a demethylating agent 5-azacytidine. We therefore conclude that epigenetic gene silencing, which is reflected by aberrant SLC5A8 methylation represents the principal mechanism for inactivating this gene in colon cancer. Moreover, our finding that exogenous SLC5A8 specifically suppresses colony forming activity in colon cells that have inactivated this allele supports the hypothesis that SLC5A8 inactivation confers a selectable advantage in neoplastic colon epithelial cells. Colon cells that retain SLC5A8 are insensitive to the introduction of an exogenous allele, and presumably bear a mutation elsewhere that renders them tolerant to continued SLC5A8 expression. Also supporting that SLC5A8 methylation is a pathogenetic event in colon neoplasia is our finding that SLC5A8 methylation is a highly early event that is detectable in 47% of aberrant crypt foci, which are the earliest detectable morphologic abnormality of the colon epithelium.

SLC5A8 methylation may also play an etiologic role in malignancies additional to colon cancer. In earlier studies, we note that SLC5A8 methylation is present in a subset of cancers of the breast and stomach cancers (Table 5 below).

TABLE 5

SLC5A8 methylation in additional cancers. Shows are the results of MS-PCR assay for SLC5A8 exon 1 methylation in primary human tumors. In each case, paired normal tissue assayed as unmethylated.

| Cancer Types | Breast | Stomach | Kidney |
|---|---|---|---|
| SLC5A8 methylated | 4 | 4 | 0 |
| SLC5A8 unmethylated | 16 | 2 | 7 |

Both molecular homology and functional data suggest that SLC5A8 functions as a sodium solute symporter. There are 109 currently known members of the sodium solute symporter family which functions to co-transport sodium coupled to solutes as diverse as iodine (NIS/SLC5A5), glucose (SGLT1/SLC5A1; SGLT2/SLC5A2), inositol (SMIT/SLC5A3), and water soluble vitamins (SMVT/SLC5A6) (Smanik et al., 1996, Biochem Biophys Res Commun 226: 339-345; Prasad et al., 1998, J Biol Chem 273: 7501-7506; Wright et al., 1994, J Exp Biol 196: 197-212). Elucidating the putative solute cotransported by SLC5A8 may provide future insight both into the mechanism of SLC5A8 growth suppression, as well as leads for potential development of novel agents useful for colon neoplasia prevention and treatment.

Materials And Methods

Sequences. Human SLC5A8 mRNA and gene sequence accession numbers as deposited by our group are AF53621 and AF536217. The SLC5A8 murine homolog is accession number is BC017691. Contemporaneously with our Genbank entry, SLC5A8 mRNA sequence was also independently deposited under accession number AY081220 (Rodriguez et al., 2002, J Clin Endocrinol Metab. 87:3500-3).

Restriction Landmark Genomic Scanning (RLGS). RLGS was performed as previously described (Costello et al., 2000, Nat Genet 24: 132-138).

Amplification and Sequencing of SLC5A8. The primers used for RT-PCR assay of a SLC5A8 fragment are 5'-TCCGAGGTCTACCGTTTTG-3', and 5'-GGGCA GGGGC ATAAA TAAC-3'. The PCR parameters were 35 cycles of 95° C. (45s), 54° C. (45s), 72° C. (60s), 72° C. (10 min), and 4° C. to cool. The full length SLC5A8 ORF was amplified using primers: 5'TCCGGGATAAGAAGTGCG-3' and 5'-TAG-TATCAGAGCAGCTTCACAAAC-3'. GC-rich cDNA polymerase kit (Clonetech) was used and PCR parameters were 35 cycles of 95° C. (45s), 62° C. (45s), 72° C. (90s), 72° C. (10 min), and 4° C. to cool. Sequencing primers were: 5'-TTTGT GGTGGTCA TCAGCG-3',5'-GGGCAGGGGCAT-AAATAAC-3',5'-AGGCTGTG GTGATGCAAGGT-3',5'-TTAATGCCTTAGCAGCAG-3', and 5'-CCTCCACTT CCTGAGAGAAC-3'.

Constructs. To construct the V5 tagged SLC5A8 expression vector, the following PCR primers were used: 5'-TCCGGGATAAGAAGTGCG-3' and 5'-TCTAGTATCA GAGCAGCTACACAA-3'. The PCR conditions were the same as employed for amplification of the full length ORF. PCR products were cloned into pcDNA3.1/V5-His-TOPO vector (Invitrogen).

Serum DNA purification. Blood was drawn into red/grey vacutainer collection tubes and allowed to clot for 2 hours. It was then spun in a clinical table top centrifuge for 15 min at 3000 rpm at room temperature. Serum was collected using a sterile pipette, divided into 1 ml aliquots, and stored at −80° C. Serum DNA from patients was purified as described previously (Grady et al., 2001, Cancer Res 61:900-902).

Western Analysis. Approximately $10^7$ cells were lysed in cell lysis buffer [50 mM Tris.HCl (pH 7.4)/1 mM EGTA/1% Nonidet P-40/0.25% sodium deoxycholate/150 mM NaCl]. Equal amounts of protein were subjected to SDS polyacrylamide gel electrophoresis and then transferred to a PVDF nylon membrane (Millipore), which was probed with 1:200 dilution of mouse anti-V5 monoclonal antibody (Invitrogen). Immune complexes were visualized with ECL+Plus Western blotting detection kit (Amersham) after incubation with horseradish peroxidase-coupled secondary antibody (Santa Cruz).

Sodium Bisulfite Treatment: Flanking PCR and MS-PCR. Sodium bisulfite treatment to convert unmethylated cytosine to thymidine was performed similarly as described (Grady et al., 2001, Cancer Res 61:900-902). Primers that flank the SLC5A8 exon 1 CpG island are 5'-CGTGAA GGTAAA GATGTT AAAAATG-3' and 5'-ACAACT AAAAAC TCCAAT TCTCATC-3'. PCR were carried out by using a hot start at 95° C. (7 min) and following cycling parameters: 35 cycles of 95° C. (45s), 56° C. (45s), 72° C. (45s), 72° C. (10 min), and 4° C. to cool. Primers to amplify the methylated allele are AS-meth-442-459s: 5'-TCGAAC GTATTT CGAGGC-3' and AS-meth-550 as: 5'-ACAACG AATCGA TTTTCCG-3'. PCR parameters are 31 cycles of 95° C. (45s), 56° C. (45s), 72° C. (45s), 72° C. (10 min), and 4° C. to cool. Primers to amplify the unmethylated allele are AS-unmeth-442s: 5'-TTGAAT GTATTT TGAGGTG-3' and AS-unmeth-542 as: 5'-TCAATT TTCCAA AATCCC-3'. PCR parameters are 31 cycles of 95° C. (45s), 46° C. (45s), 72° C. (45s), 72° C. (10 min), and 4° C. to cool.

Methylation-Specific Real-time PCR. The same MS-PCR primers as above (As-meth-442-459s and As-meth-550 as), were first used to amplify a bisulfite converted methylated SLC5A8 exon 1 template. A fluorogenic hybridization probe was designed using sequences specific for the sodium bisulfite converted SLC5A8 methylated template. The sequence was the following: 5'-6FAM-CAACGACGAAT ACAAAAACG ACTACCAAC-BHQ-2-3'. Bisulfite converted sequences from the MYOD1 gene were used as an internal reference as described by (Usadel et al., 2002, Cancer Res 62: 371-375). Primers and probes for MYOD1 were: forward primer: 5'-CCAACTCCA AATCCCCTC TCTAT-3'; reverse primer: 5'-TGATIAATT TA GATTGGGTTT AGAGAAGGA-3'; and probe: 5'-6FAM-TCCCTTCCT ATICCTAAA TCCAACCTAAATACCTCC-BH-2-3'. All the above primers and probes were synthesized by Integrated DNA Technologies, Inc. For the gene of interest, SLC5A8, the reaction mix contained 600 nM primer, 200 nM probe, 5.5 mM-$Mg^{2+}$, 1× Supermix from Bio-Rad. The total volume was 25 μl. For the MYOD1 gene, the reaction mix contained 400 nM primer, 200 nM probe, 3 mM-$Mg^{2+}$, 1× Supermix from Bio-Rad. The total volume was also 25 μl. Thermal cycling was initiated with 50° C. for 2 min, then 95° C. for 10 min, followed by 55 cycles of 95° C. for 15 sec and 60° C. for 1 min. PCR was performed in separate wells for each probe/primer set. Each plate contained multiple positive controls, negative controls and water blanks. Colon cancer cell line RKO was used for a positive control, and V9M as a negative control. Serial dilutions of RKO DNA were used to create a standard curve. SLC5A8 methylation was determined as the ratio of SLC5A8:MYOD1=2 exp-($CT_{SLC5A8}$-$CT_{MYOD1}$).

Aberrant Crypt Foci. Aberrant crypt foci (ACF) (Bird, 1987, Cancer Lett 37: 147-151; Pretlow et al., 1991, Cancer Res 51: 1564-1567; Siu et al., 1999, Cancer Res 59: 63-66) were isolated from grossly normal human colonic mucosa according to the method of Bird et al. (Bird et al., 1997, Cancer Lett 116: 15-19). Strips of human colonic mucosa, stored over liquid nitrogen, were thawed rapidly in 1% paraformaldehyde and fixed flat in 70% ethanol for 30 min at 4° C. (Bird et al., 1997, Cancer Lett 116: 15-19). The colonic strips were stained for 2 min in 0.2% methylene blue (Chroma-Gesellschaft Schmid & Co, distributed by Roboz Surgical Instrument Co, Washington, D.C.) in 0.1 M sodium phosphate buffer (pH 7.4), rinsed in 1% paraformaldehyde for 15 min, transferred mucosal side up to a glass slide and viewed at 30× magnification under a dissecting microscope. The ACF were teased from the mucosa with microdissection forceps (FWR #55 Dumont Bio Inox Forceps, 0.05×0.02 mm tips), placed in microfuge tubes, and stored over liquid nitrogen. The control for each ACF was a similar number of microscopically normal crypts teased from the same mucosa.

Cell Culture and Clonogenic Assays. Vaco cell lines were cultured as previously described (Veigl et al., 1998, Proc Natl Acad Sci USA 95: 8698-8702; Markowitz et al., 1995, Science 268: 1336-1338; Willson et al., 1987, Cancer Res 47: 2704-2713). FET and RKO were the kind gift of Dr. M. Brattain (Roswell Cancer Institute, Buffalo, N.Y.). Colony formation assays were performed as described (Moinova et al., 2002, Proc Natl Acad Sci USA 99: 4562-4567). Briefly, colon cancer cells were plated on a rat tail collagen matrix (Willson et al., 1987, Cancer Res 47: 2704-2713) (which was found necessary for proper membrane localization of SLC5A8 protein). Cells were then transfected with either a SLC5A8 expression vector or a control empty vector, and the number of stable colonies arising after selection in G418 was respectively counted.

5-Azacytidine Treatment. The treatment was performed as described previously (Veigl et al., 1998, Proc Natl Acad Sci USA 95: 8698-8702). Briefly, cells were treated for 24 h on day 2 and day 5 with 5-azacytidine (Sigma) at 1.5 μg/ml. The medium was changed 24 h after addition of the 5-azacytidine (i.e., on day 3 and day 6).

Statistical Methods. Association of SLC5A8 methylation with sex was analyzed by using two-tailed Fishers' exact tests. Association of SLC5A8 methylation status with tumor site or stage was analyzed by using Pearson's $\chi^2$ statistics. Comparisons of age distributions based on SLC5A8 methylation were done by using Wilcoxon nonparametric tests. Comparisons of colony counts after transfection with different vectors were done by t tests and linear models.

Hap2 site assays. (1) For 4 Hpa2 site assays, the following primers were used: 5'-CCAGCGAAGGCGTAGTAGAT-3' (3D41-Hpa2-190R) and 5'-GGCTCCAGTTCTCA TCT-GCT-3' (3D41-Hpa2-633F). The Advantage-GC-genomic DNA polymerase kit was used. Thermal cycling was performed at 95° C. for 1 min, 95° C. for 45 sec, 63° C. for 45, 72° C. for 90 sec, then followed by 26 cycles, and finally 72° C. for 5 min. (2) For 6 Hpa2 site assays, the following primers were used: 5'-CCAGCGAAGGCGTAGTAGAT-3' (3D41-Hpa2-190R) and 5'-GGCAGTCTAAAAACTCCAGGC-3' (3D41-Hpa2-82430F). The Advantage-GC-genomic DNA polymerase kit was used. Thermal cycling was performed at 95° C. for 7 min, 95° C. for 45 sec, 64° C. for 45, 72° C. for 90 sec, then followed by 29 cycles, and finally 72° C. for 5 min. In both assays, aberrant methylation of colon cancer cells is indicated by recovery of a PCR product from DNA that has been digested with the restriction enzyme Hpa2.

Incorporation by Reference

All publications and patents mentioned herein are hereby incorporated by reference in their entirety as if each individual publication or patent was specifically and individually indicated to be incorporated by reference. In case of conflict, the present application, including any definitions herein, will control.

Equivalents

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

I claim:

1. A method for detecting differential methylation patterns in the SLC5A8 gene, comprising:
   a) obtaining a sample from a patient;
   b) performing an assay of said sample for the presence of methylation within a nucleotide sequence selected from the group consisting of SEQ ID NOs: 12-13;
   c) obtaining a sample from a healthy subject;
   d) performing an assay for the presence of methylation within a nucleotide sequence selected from the group consisting of SEQ ID NOs: 12-13; and
   e) comparing the methylation patterns in the sample from the patient to the methylation patterns in the normal sample to detect differential methylation patterns.

2. A method for detecting an SLC5A8-associated cancer, comprising:
   a) obtaining a sample from a patient; and
   b) performing an assay of said sample for the presence of methylation within a nucleotide sequence as set forth in any one of SEQ ID NOs: 12-13;
      wherein methylation of said nucleotide sequence is indicative of a SLC5A8-associated cancer.

3. The method of claim 1 or 2, wherein the sample is a bodily fluid selected from the group consisting of blood, serum, plasma, a blood-derived fraction, stool, urine, and a colonic effluent.

4. The method of claim 3, wherein the bodily fluid is obtained from a subject suspected of having or is known to have an SLC5A8-associated cancer.

5. The method of claim 4, wherein said SLC5A8-associated cancer is colon cancer.

6. The method of any one of claims 1 and 2, comprising assaying for the presence of methylation within the SLC5A8 sequence as set forth in SEQ ID NO: 14.

7. The method of any of claim 1 or 2, wherein the assay is methylation-specific PCR.

8. The method of claim 7, wherein the methylation-specific PCR comprises:
   a) treating DNA from the sample with a compound that converts non-methylated cytosine bases in the DNA to a different base;
   b) amplifying a region of the compound-converted SLC5A8 nucleotide sequence with a forward primer and a reverse primer; and
   c) analyzing the methylation patterns of said SLC5A8 nucleotide sequences.

9. The method of claim 7, wherein the methylation-specific PCR comprises:
   a) treating DNA from the sample with a compound that converts non-methylated cytosine bases in the DNA to a different base;
   b) amplifying a region of the compound-converted SLC5A8 nucleotide sequence with a forward primer and a reverse primer; and
   c) detecting the presence and/or amount of the amplified product.

10. The method of claim 7, wherein a forward primer is selected from the group consisting of SEQ ID NOs: 8 and 10.

11. The method of claim 7, wherein a reverse primer is selected from the group consisting of SEQ ID NOs: 9 and 11.

12. The method of claim 8, wherein the compound used to treat DNA is a bisulfite compound.

13. The method of any of claims 1 and 2, wherein the assay comprises using a methylation-specific restriction enzyme.

14. The method of claim 13, wherein said methylation-specific restriction enzyme is selected from the group consisting of HpaII, SmaI, SacII, EagI, MspI, BstUI, and BssHII.

15. The method of claim 13, further comprising a pair of primers selected from SEQ ID NOs: 5-7.

16. A method for monitoring over time an SLC5A8-associated cancer comprising:
   a) detecting the methylation status within a nucleotide sequence of the SLC5A8 gene selected from the group consisting of SEQ ID NOs: 12-13 in a sample from the subject for a first time; and
   b) detecting the methylation status within a nucleotide sequence of the SLC5A8 gene selected from the group consisting of SEQ ID NOs: 12-13 in a sample from the same subject at a later time;
   wherein the absence of methylation in said nucleotide sequence of the SLC5A8 gene taken at a later time and the presence of methylation in said nucleotide sequence of the SLC5A8 gene taken at the first time is indicative of cancer regression;
   wherein the presence of methylation in said nucleotide sequence of the SLC5A8 gene taken at a later time and the absence of methylation in said nucleotide sequence of the SLC5A8 gene taken at the first time is indicative of cancer progression.

17. The method of claim 16, wherein the sample is a bodily fluid selected from the group consisting of blood, serum, plasma, a blood-derived fraction, stool, urine, and a colonic effluent.

18. The method of claim 16, wherein the SLC5A8-associated cancer is colon cancer.

* * * * *